US012559789B2

(12) United States Patent
Verhaak et al.

(10) Patent No.: US 12,559,789 B2
(45) Date of Patent: Feb. 24, 2026

(54) METHOD OF TARGETING PATIENT-SPECIFIC ONCOGENES IN EXTRACHROMOSOMAL DNA TO TREAT GLIOBLASTOMA

(71) Applicants: The Jackson Laboratory, Bar Harbor, ME (US); Henry Ford Health System, Detroit, MI (US)

(72) Inventors: Roel Verhaak, West Hartford, CT (US); Hoon Kim, West Hartford, CT (US); Ana Decarvalho, Detroit, MI (US); Tom Mikkelsen, Detroit, MI (US)

(73) Assignees: The Jackson Laboratory, Bar Harbor, ME (US); Henry Ford Health System, Detroit, MI (US)

( * ) Notice: Subject to any disclaimer, the term of this patent is extended or adjusted under 35 U.S.C. 154(b) by 158 days.

(21) Appl. No.: 16/479,427

(22) PCT Filed: Jan. 19, 2018

(86) PCT No.: PCT/US2018/014588
§ 371 (c)(1),
(2) Date: Jul. 19, 2019

(87) PCT Pub. No.: WO2018/136837
PCT Pub. Date: Jul. 26, 2018

(65) Prior Publication Data
US 2019/0360029 A1      Nov. 28, 2019

Related U.S. Application Data

(60) Provisional application No. 62/576,681, filed on Oct. 25, 2017, provisional application No. 62/448,625, filed on Jan. 20, 2017.

(51) Int. Cl.
*C12Q 1/68* (2018.01)
*A61K 31/4545* (2006.01)
(Continued)

(52) U.S. Cl.
CPC ........ *C12Q 1/6841* (2013.01); *A61K 31/4545* (2013.01); *A61K 31/53* (2013.01);
(Continued)

(58) Field of Classification Search
None
See application file for complete search history.

(56) References Cited

U.S. PATENT DOCUMENTS

2017/0224692 A1 * 8/2017 Hao ..................... C07D 487/04

FOREIGN PATENT DOCUMENTS

WO            99/35292 A1        7/1999

OTHER PUBLICATIONS

Nikolaev et al. Extrachromosomal driver mutations in glioblastoma and low-grade glioma. Nature Communications; 2014; 5: 5690; DOI: 10.1038/ncomms6690: p. 1-17. (Year: 2014).*
(Continued)

*Primary Examiner* — Juliet C Switzer
(74) *Attorney, Agent, or Firm* — McDonnell Boehnen Hulbert & Berghoff LLP

(57) ABSTRACT

Provided are methods of targeting patient-specific oncogenes in extrachromosomal DNA (ecDNA) to treat glioma in a human. The present methods include identifying a drug that targets against an oncogene present in ecDNA of a human suffering from glioma, such as glioblastoma. The identified oncogenes present in ecDNA include MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1. The present methods include identifying a drug targeted against the ecDNA oncogene, which drug inhibits the function of the identified oncogene, so as to inhibit tumor growth or progression of the glioma in the human. Also provided are PDX mouse models to further identify and/or
(Continued)

confirm patient-specific drugs that target the identified onco-gene(s) present in ecDNA. Also provided are methods of diagnosing gliomas or recurrent gliomas and methods of screening or monitoring for recurrence of gliomas. Further provided are methods of validating a predicted presence of ecDNA in a brain tumor using fluorescence in situ hybrid-ization (FISH). Also provided are methods of screening drug candidates for a patient by implanting different identified drugs that target an identified oncogene into PDX mouse models.

8 Claims, 175 Drawing Sheets

(51 of 175 Drawing Sheet(s) Filed in Color)

Specification includes a Sequence Listing.

(51) Int. Cl.

| | | |
|---|---|---|
| A61K 31/53 | (2006.01) | |
| A61K 49/00 | (2006.01) | |
| A61P 35/00 | (2006.01) | |
| C12Q 1/6841 | (2018.01) | |
| C12Q 1/6886 | (2018.01) | |

(52) U.S. Cl.

CPC .......... *A61K 49/0008* (2013.01); *A61P 35/00* (2018.01); *C12Q 1/6886* (2013.01)

(56) References Cited

OTHER PUBLICATIONS

Nathanson et al. Targeted Therapy Resistance Mediated by Dynamic Regulation of Extrachromosomal Mutant EGFR DNA. Science; 2014; 343: 72-76. (Year: 2014).*

Vogt et al. Amplicon rearrangements during the extrachromosomal and intrachromosomal amplification process in a glioma. Nucleic Acids Research; 2014; vol. 42; No. 21: 13194-13205. (Year: 2014).*

Nikolaev et al. Extrachromosomal driver mutations in glioblastoma and low-grade glioma. Nature Communications; 2014; 5: 5690: p. 1-7. (Year: 2014).*

Gupta et al. Editorial: Targeted Therapies for Glioblastoma: A Critical Appraisal. Frontiers in Oncology; 2019; 9: 1-4. (Year: 2019).*

Nathanson et al. Science; 2014; 343: 72-76, cited in IDS. (Year: 2014).*

Vogt et al. Nucleic Acids Research; 2014;, vol. 42; No. 21: 13194-13205, cited in IDS. (Year: 2014).*

Nathanson et al. Science; 2014; 343: 72-76, cited in IDS. Supple-mental Information. (Year: 2014).*

Stathias et al. PLOS ONE: 2014: DOI: 10.1371/journal.pone.0115842: p. 1-14. (Year: 2014).*

Favero et al. Annals of Oncology;2015; 26: 880-887. (Year: 2015).*

Favero et al. Annals of Oncology;2015; 26: 880-887. Supplemental Information. (Year: 2015).*

Bai et al. Trends in Molecular Medicine; 2011, vol. 17, No. 6: p. 301-312. (Year: 2011).*

Joo et al. Cell Reports; 2013;6: 260-273. (Year: 2013).* deCarvalho et al. (bioRxiv preprint doi: https://doi.org/10.1101/081158; this version posted Jun. 27, 2017; 30 pages) (Year: 2017).*

Joo et al. (Cell Reports 3, 260-273, Jan. 31, 2013) (Year: 2013).*

Favero (Favero et al. Annals of Oncology;2015; 26: 880-887) (Year: 2015).*

Hasselbach et al. (Hasselbach et al. J. Vis. Exp. (83), e51088, doi:10.3791/51088 (2014) (Year: 2014).*

Chi et al. (2012. Journal of Oncology, vol. 30, No. 3, p. e30-e33 (Year: 2012).* deCarvalho (bioRxiv preprint doi: https://doi.org/10.1101/081158; this version posted Oct. 14, 2016, pp. 1-23 and supplemental information, pp. 1-11) (Year: 2016).*

Malaney et al. (Cancer Letters 344 (2014) 1-12) (Year: 2014).*

Andor, et al., "Pan-cancer analysis of the extent and consequences of intratumor heterogeneity." Nat Med. Jan. 2016 ; 22(1): 105-113.

Annibali, D. et al., "Myc inhibition is effective against glioma and reveals a role for Myc in proficient mitosis." Nat Commun 5, 4632(2014).

Aparicio, et al., "The implications of clonal genome evolution for cancer medicine." N Engl J Med 2013; 368:842-851.

Bao, Z.S. et al.: "RNA-seq of 272 gliomas revealed a novel, recurrent PTPRZI-MET fusion transcript in secondary glioblastomas." Genome Res 24, 1765-73 (2014).

Berezovsky, A.D. et al., "Sox2 Promotes Malignancy in Glioblastoma by Regulating Plasticity and astrocytic differentiation." Neoplasia 16, Issue 3, 193-206.e25 (2014).

Berlin, K. et al., "Assembling Large Genomes with Single-Molecule Sequencing and Locality Sensitive Hashing." Nat Biotechnol 33, 623-30 (2015).

Brennan, C.W. et al., "The Somatic Genomic Landscape of Glioblastoma." Cell 155, 462-477, Oct. 10, 2013.

Ceccarelli, M. et al. "Molecular Profiling Reveals Biologically Discrete Subsets and Pathways of Progression in Diffuse Glioma." Cell 164, 550-63 (2016).

Chi, A.S. et al., "Rapid Radiographic and Clinical Improvement After Treatment of a MET-Amplified Recurrent Glioblastoma With a Mesenchymal-Epithelial Transition Inhibitor." Journal of Clinical Oncology, vol. 30, Issue 3, e30-e33.

Chiang, C. et al. "SpeedSeq: ultra-fast personal genome analysis and interpretation." Nat Methods. (2015), 12(10): 966-968. (2015).

Cibulskis, K. et al., "Sensitive detection of somatic point mutations in impure and heterogeneous cancer samples." Nat Biotechnol 31, 213-219 (2013).

Conway, T. et al., "Xenome—a tool for classifying reads from xenograft samples." Bioinformatics vol. 28 ISMB 2012, pp. 172-178 (2012).

Decarvalho, et al., "Discordant Inheritance of Chromosomal and Extrachromosomal DNA Elements contributes to Dynamic Disease Evolution in Glioblastoma." bioRxiv, Oct. 14, 2016 (Oct. 14, 2016), XP002780079, DOI: 10.1101/081158.

Decarvalho, et al., "Gliosarcoma Stem Cells Undergo Glial and Mesenchymal Differentiation In Vivo." Stem Cells, 2010;28:181-190.

Delcher, A.L. et al., "Alignment of whole genomes." Nucleic Acids Research, 1999, vol. 27, No. 11. p. 2369-76.

Dolecek, et al., "CBTRUS statistical report: primary brain and central nervous system tumors diagnosed in the United States in 2005-2009." Neuro Oncol 14 Suppl 5, vl-49 (2012).

Favero, F. et al., "Sequenza: allele-specific copy No. and mutation profiles from tumor sequencing data." Ann Oncol 26, 64-70 (2015).

Forbes, S.A. et al., "COSMIC: exploring the world's knowledge of somatic mutations in human cancer." Nucleic Acids Res 43, D805-11 (2015).

Gibaud, et al., "Characterization at nucleotide resolution of the omogeneously staining region sites of insertion in two cancer cell lines." Nucleic Acids Research, vol. 41, No. 17, Jul. 2, 2013 (Jul. 2, 2013), pp. 8210-8219.

Graveel, C. et al., "Activating MET mutations produce unique tumor profiles in mice with selective duplication of the mutant allele." PNAS, vol. 101, No. 49, 17198-17203 (2004).

Hasselbach, L.A. et al., "Optimization of High Grade Glioma Cell Culture fom Surgical Specimens for Use in Clinically Relevant Animal Models and 3D Immunochemistry" Journal of Visualized Experiments, Jan. 2014, 83, e51088, p. 1-9.

International Search Report and Written Opinion from correspond-ing PCT Appl. No. PCT/US18/14588 mailed Feb. 5, 2018.

Kim, et al., "Whole-genome and multisector exome sequencing of primary and post-treatment glioblastoma reveals patterns of tumor evolution." Genome Research, 25:316-327 (2015).

Kim, H.P. et al., "Novel fusion transcripts in human gastric cancer revealed by transcriptome analysis." Oncogene vol. 33, pp. 5434-5441 (2014).

(56)                    References Cited

OTHER PUBLICATIONS

Kim, J. et al., "Spatiotemporal Evolution of the Primary Glioblastoma Genome." Cancer Cell 28, 318-328 (2015).

Kohl, N.E. et al., "Transposition and Amplification of Oncogene-Related Sequences in Human Neuroblastomas." Cell vol. 35, Issue 2, Part 1, Dec. 1983, 359-367.

Li, H. et al., "Fast and accurate short read alignment with Burrows-Wheeler transform." Bioinformatics, vol. 25 No. 14 2009, pp. 1754-1760.

Liu, X. et al., "A Novel Kinase Inhibitor, INCB28060, Blocks c-MET-Dependent Signaling, Neoplastic Activities, and Cross-Talk with EGFR and HER-3." Clin Cancer Res; (2011); 17(22); 7127-38.

Lundberg, G. et al., "Binomial Mitotic Segregation of MYCN-Carrying Double Minutes in Neuroblastoma Illustrates the Role of Randomness in Oncogene Amplification." PLoS One, vol. 3, Issue 8, e3099. (2008).

Mckenna, et al. "The Genome Analysis Toolkit: a MapReduce framework for analyzing next-generation DNA sequencing data. "Genome Res 20, 1297-303 (2010).

Mueller, H.W. et al., "Identification of an amplified gene cluster in glioma including two novel amplified genes solated by exon trapping." Hum Genet 101, 190-7 (1997).

Nathanson, et al., "Targeted Therapy Resistance Mediated by Dynamic Regulation of Extrachromosomal Mutant EGFR DNA." Science, vol. 343, No. 6166, Jan. 2014, pp. 72-76.

Nikolaev S., et al., "Extrachromosomal driver mutations in glioblastoma and low-grade glioma." Nat Comm 5, 5690 (2014) p. 1-7.

Organ, S.L. et al., "An overview of the c-MET signaling pathway." Ther. Adv. Med, Oncol. 3, S7-S19 (2011).

Ozawa, T. et al., "Most human non-GCIMP glioblastoma subtypes evolve from a cornmon proneural-like precursor glioma." Cancer Cell 26, 288-300 (2014).

Robinson, J.T., et al., "Integrative genomics viewer." Nat Biotechnol 29, 24-6 (2011).

Roos, W.P. et al., "DNA damage and the balance between survival and death in cancer biology." Nature Reviews, vol. 16, (2016).

Roth, A. et al., "PyClone: Statistical inference of clonal population structure in cancer." Nat Methods. Apr. 2014 ; 11(4): 396-398.

Rubio-Perez, C. et al., "In Silico Prescription of Anticancer Drugs to Cohorts of 28 Tumor Types Reveals Targeting Opportunities." Cancer Cell 27, 382-396, 2015.

Sanborn, J.Z. et al., "Double Minute Chromosomes in Glioblastoma Multiforme Are Revealed by Precise Reconstruction of Oncogenic Amplicons." Cancer Res; 73(19); 6036-45, (2013).

Sequist, et al., "Genotypic and Histological Evolution of Lung Cancers Acquiring Resistance to EGFR Inhibitors." Sci Transl Med. Mar. 23, 2011; 3(75): 75ra26.

Singh, D. et al., "Transforming Fusions of FGFR and TACC Genes in Human Glioblastoma." Science. Sep. 7, 2012; 337(6099): 1231-1235.

Snuderl, M. et al., "Mosaic Amplification of Multiple Receptor Tyrosine Kinase Genes in Glioblastoma." Cancer Cell 20, 810-817, Dec. 13, 2011.

Sottoriva, A. et al., "Intratumor heterogeneity in human glioblastoma reflects cancer evolutionary dynamics." PNAS, vol. 110, No. 10, 4009-4014 (2013).

Storlazzi, C.T. et al., Gene amplification as doubleminutes or homogeneously staining regions in solid tumors: Origin and structure, Genome Res 20, 1198-1206 (2010).

Szerhp, NJ. et al., "Intratumoral heterogeneity of receptor tyrosine kinases :GFR and PDGFRA amplification in glioblastoma defines subpopulations with distinct growth factor response." Proc Natl Acad. Sci. USA 109, 3041-6 (2012).

Thomas, et al., "Glioblastoma-related gene mutations and over-expression of functional epidermal growth factor receptors in SKMG-3 glioma cells." Acta Neuropathologica, vol. 101, 2001, 605-615.

Torres-Garcia, et al., "PRADA: pipeline for RNA sequencing data analysis." Bioinformatics, vol. 30 No. 15 2014, pp. 2224-2226.

Turner, K.M. et al., "Extrachromosomal oncogene amplification drives tumor evolution and genetic heterogeneity." Nature. Mar. 2, 2017; 543(7643): 122-125.

Verhaak, R.G. et al. "Integrated Genomic Analysis Identifies Clinically Relevant Subtypes of Glioblastoma Characterized by Abnormalities in PDGFRA, IDH1, EGFR, and NF1." vol. 17, Issue 1, Jan. 19, 2010, pp. 98-110.

Vogt, et al., "Amplicon rearrangements during the extrachromosomal and intrachromosomal amplification process in a glioma." Nucleic Acids Research, vol. 42, No. 21, Nov. 6, 2014, pp. 13194-13205.

Vogt, N et al., "Molecular structure of double-minute chromosomes bearing amplified copies of the epidermal growth factor receptor gene in gliomas." Proc Natl Acad Sci USA vol. 101, 11368-73 (2004).

Wang, J. et al., "c-Myc Is Required for Maintenance of Glioma Cancer Stem Cells." PLoS ONE 3(11): e3769 (2008).

Wang, K. et al., "ANNOVAR: functional annotation of genetic variants from high-throughput sequencing data." Nucleic Acids Res 38, el64 (2010).

Xi, R. et al., "Copy number variation detection in whole-genome sequencing data using the Bayesian information criterion." E1128-E1136, PNAS, Nov. 15, 2011, vol. 108, No. 46.

Yap et al., "Intratumor Heterogeneity: Seeing the Wood for the Trees." ScienceTranslationalMedicine.org, (2012) vol. 4 Issue 127 127ps10.

Ye, K. et al., "Pindel: a pattern growth approach to detect break points of large deletions and medium sized insertions from paired-end short reads." Bioinformatic, vol. 25 No. 21 2009, pp. 2865-2871.

Yoshihara, K., et al., The landscape and therapeutic relevance of cancer-associated transcript fusions. Oncogene 34, 4845-4854 (2015).

Zheng, S., et al., "A survey of intragenic breakpoints in glioblastoma identifies a distinct subset associated with poor survival." Genes & Development 27:1462-1472 (2013).

Zou H. et al., "Double minute amplification of mutant PDGF receptor a in a mouse glioma model." Scientific Reports, vol. 5, No. 1, Feb. 16, 2015.

* cited by examiner

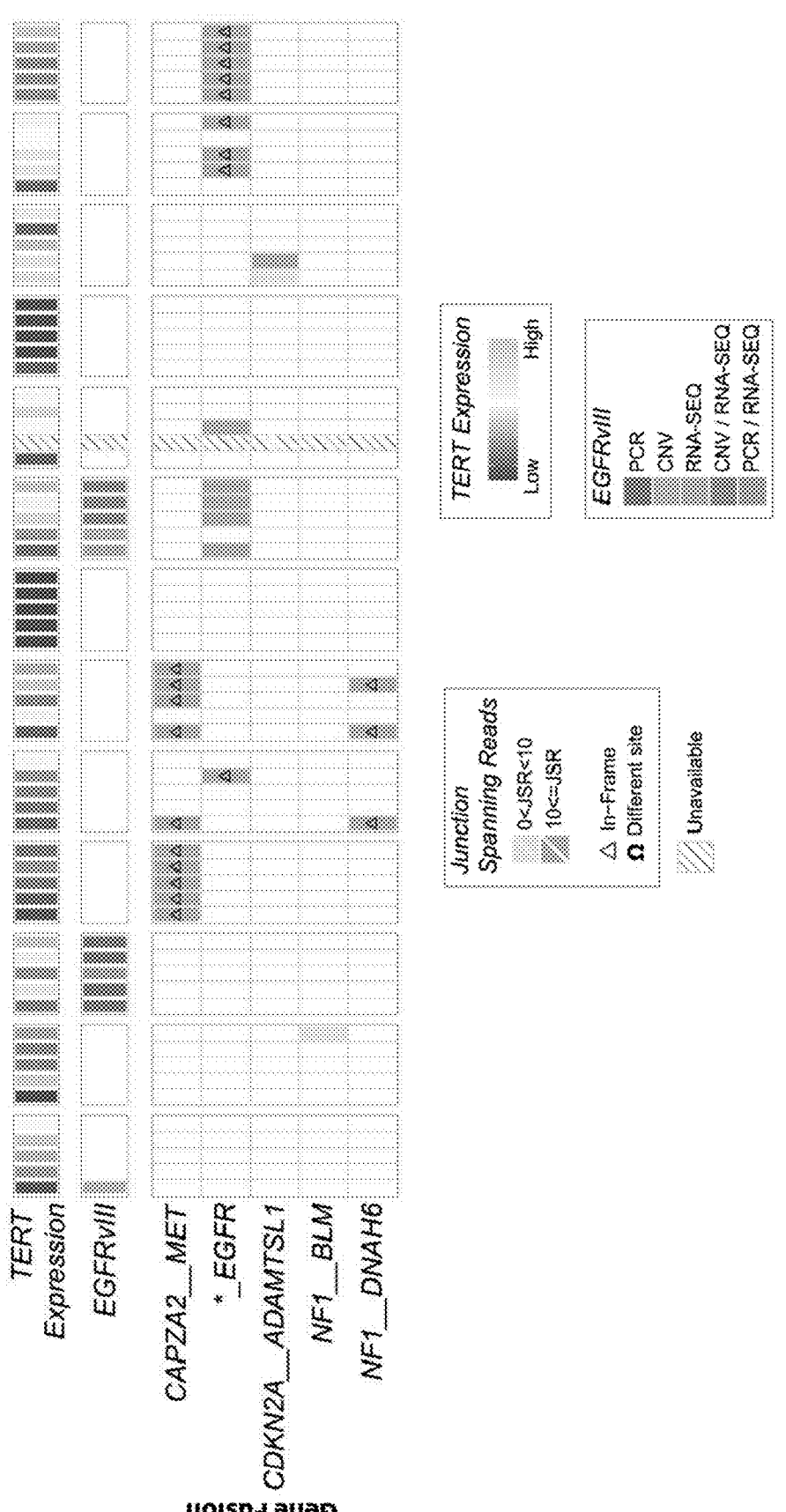
FIG. 1B (CONT'ED)

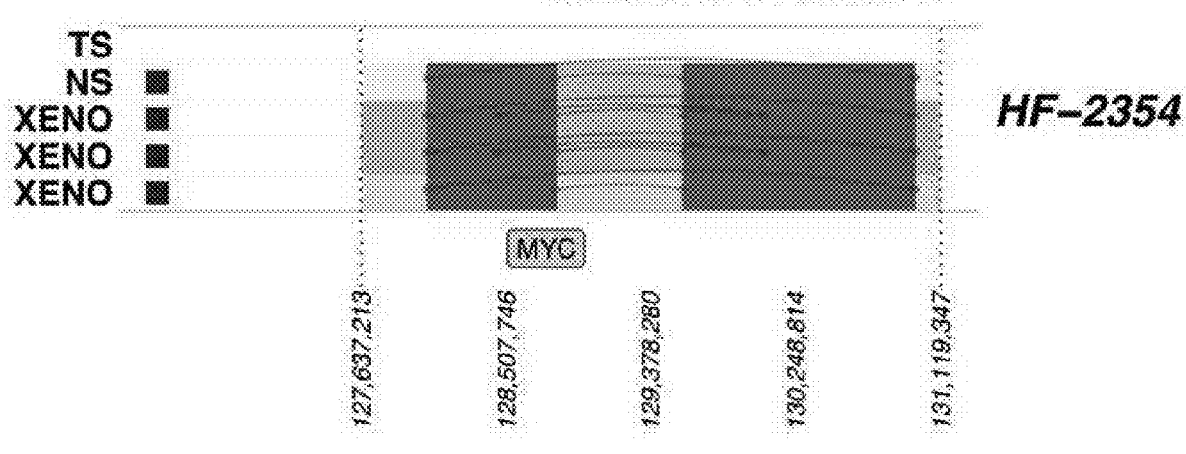
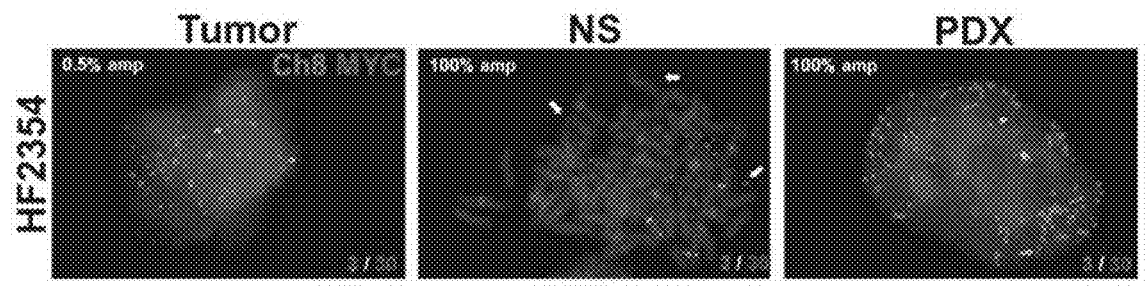
FIG. 2B

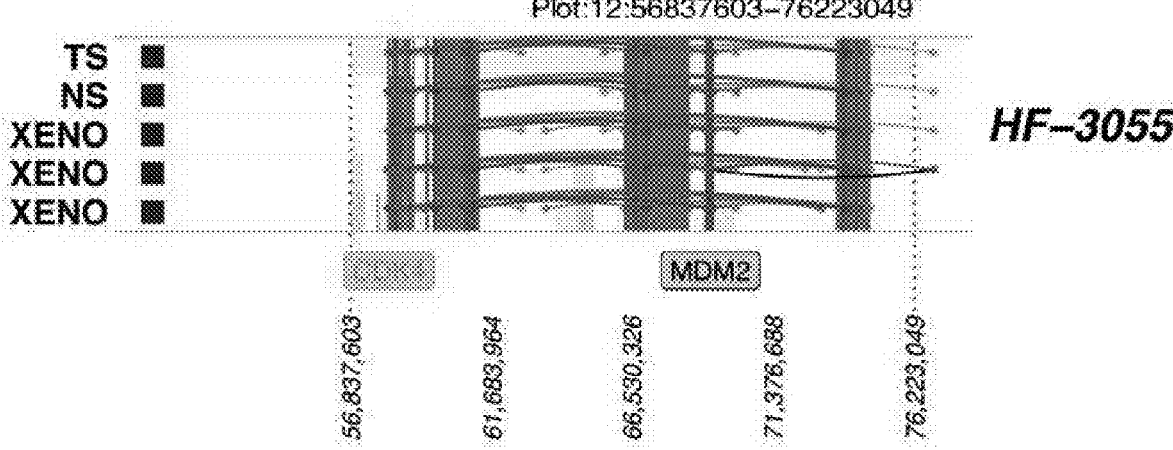
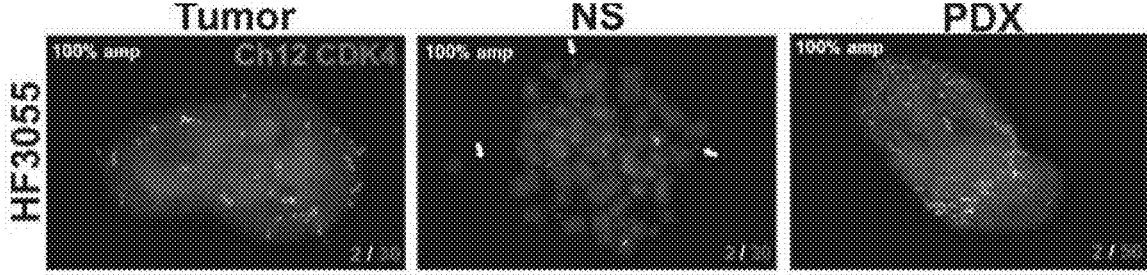
FIG. 2B (CONT'ED)

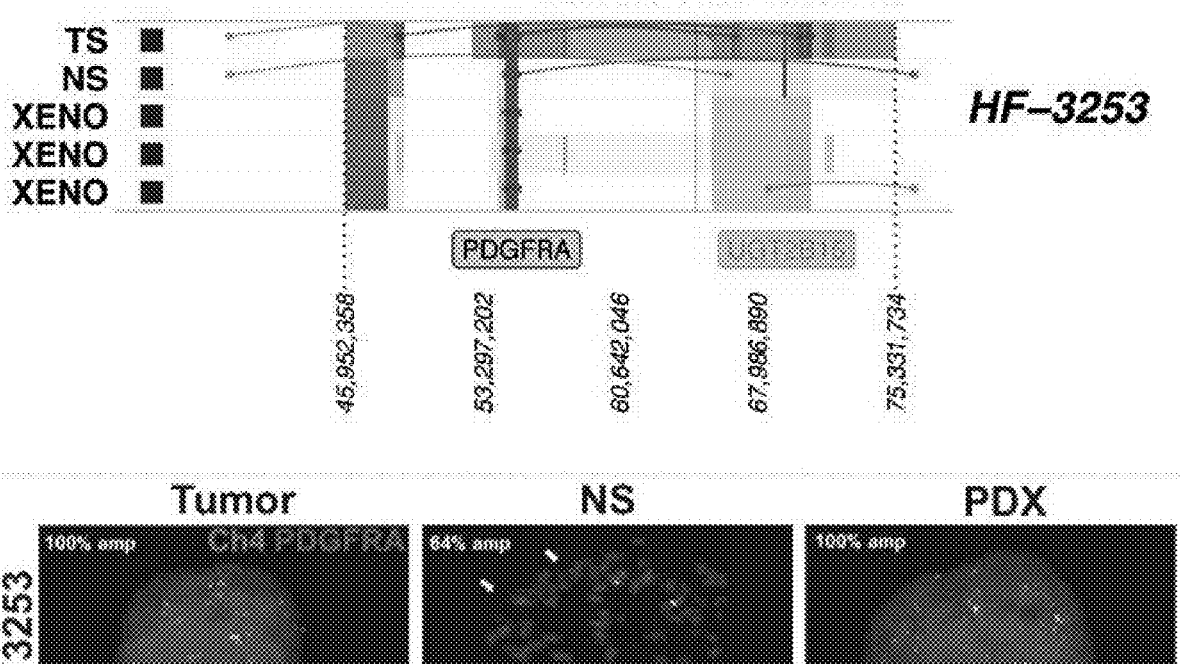
FIG. 2B (CONT'ED)

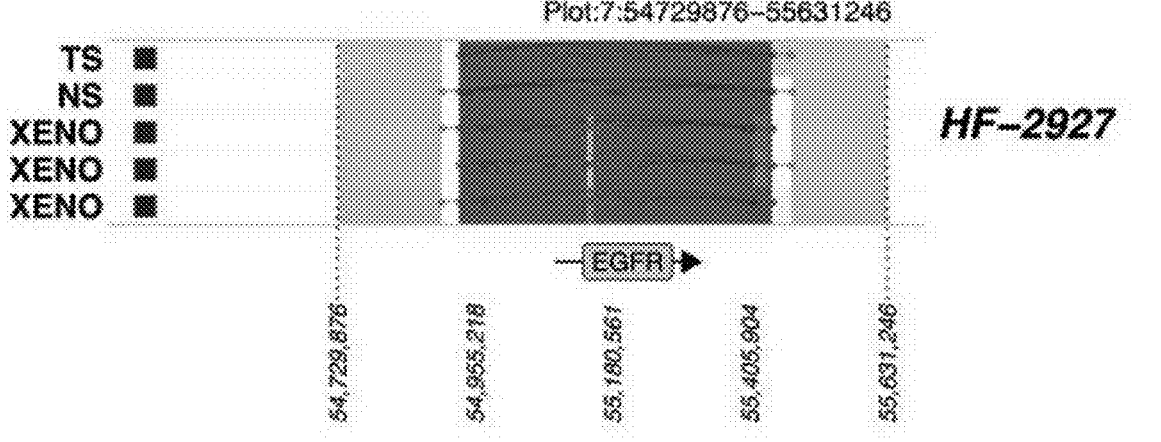
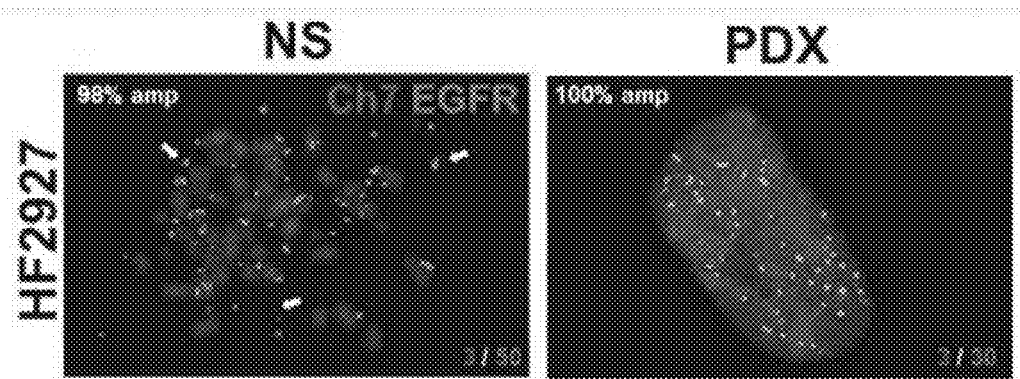
FIG. 2B (CONT'ED)

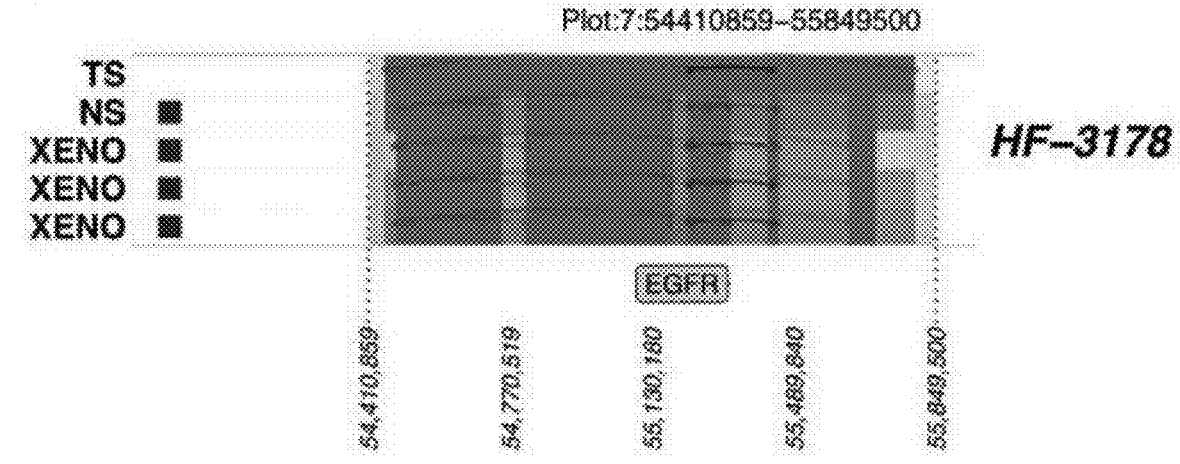
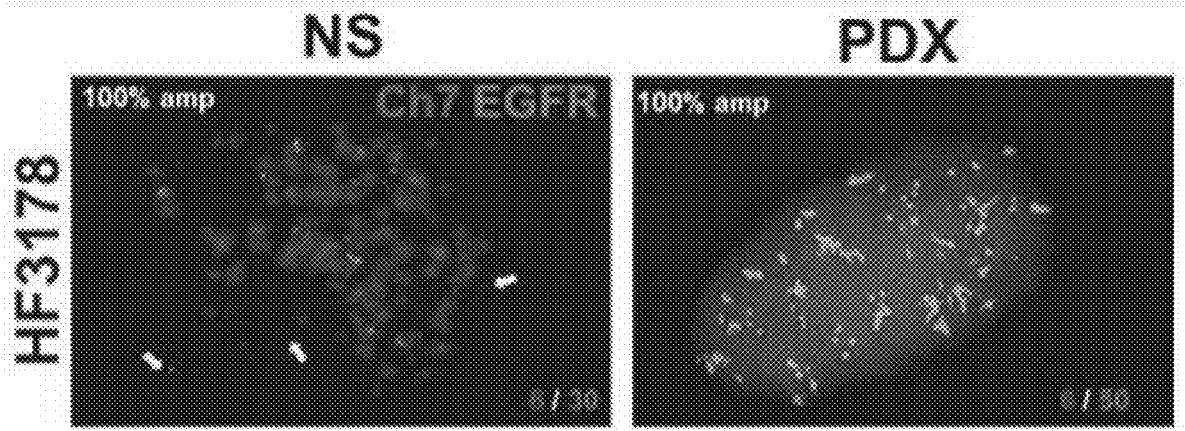
FIG. 2B (CONT'ED)

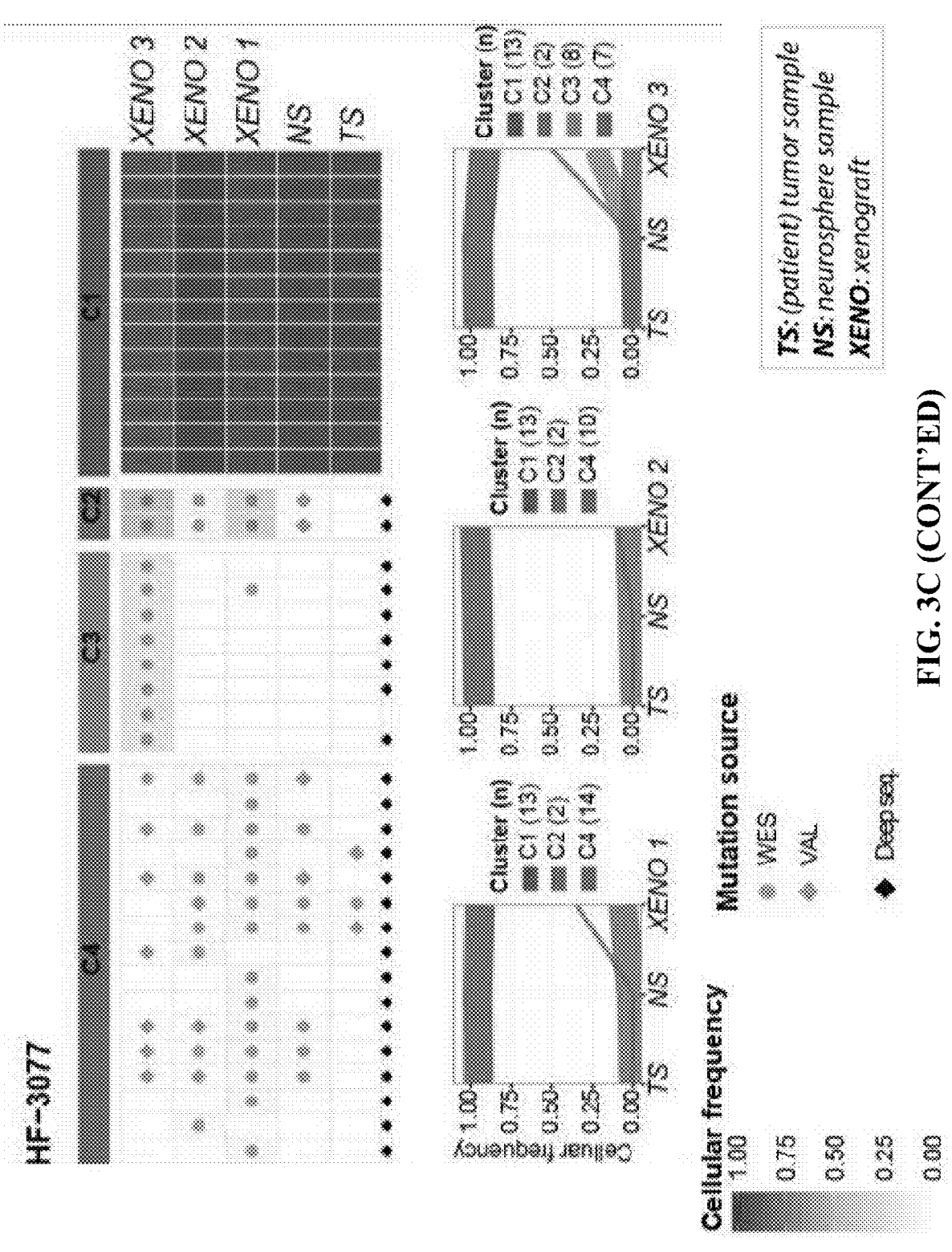
FIG. 3C (CONT'ED)

Note: All genomic coordinates are on chromosome 7.

NEUROSPHERE (CONT'ED)

(CONT'ED)

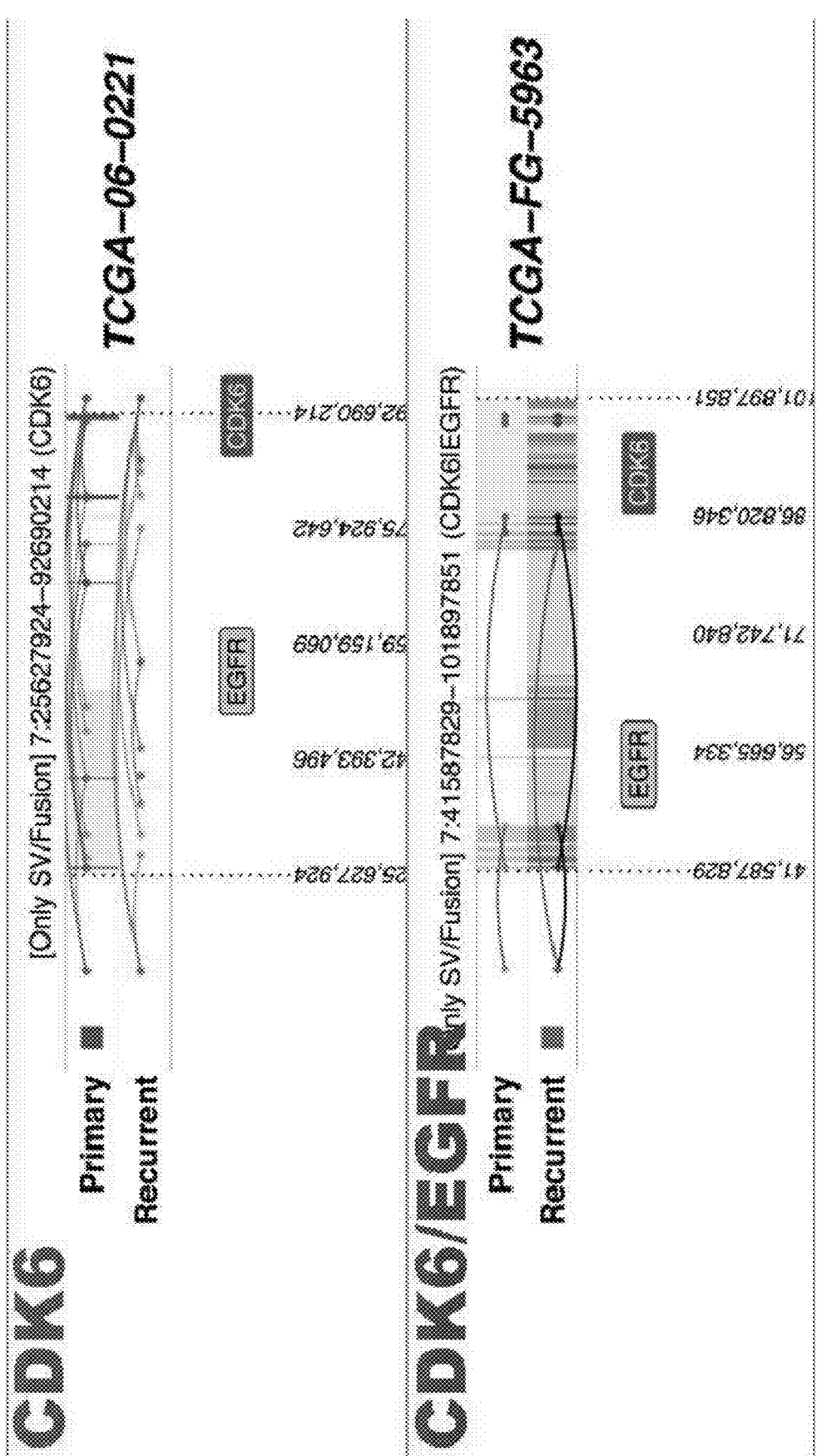
FIG. 5C (CONT'ED)

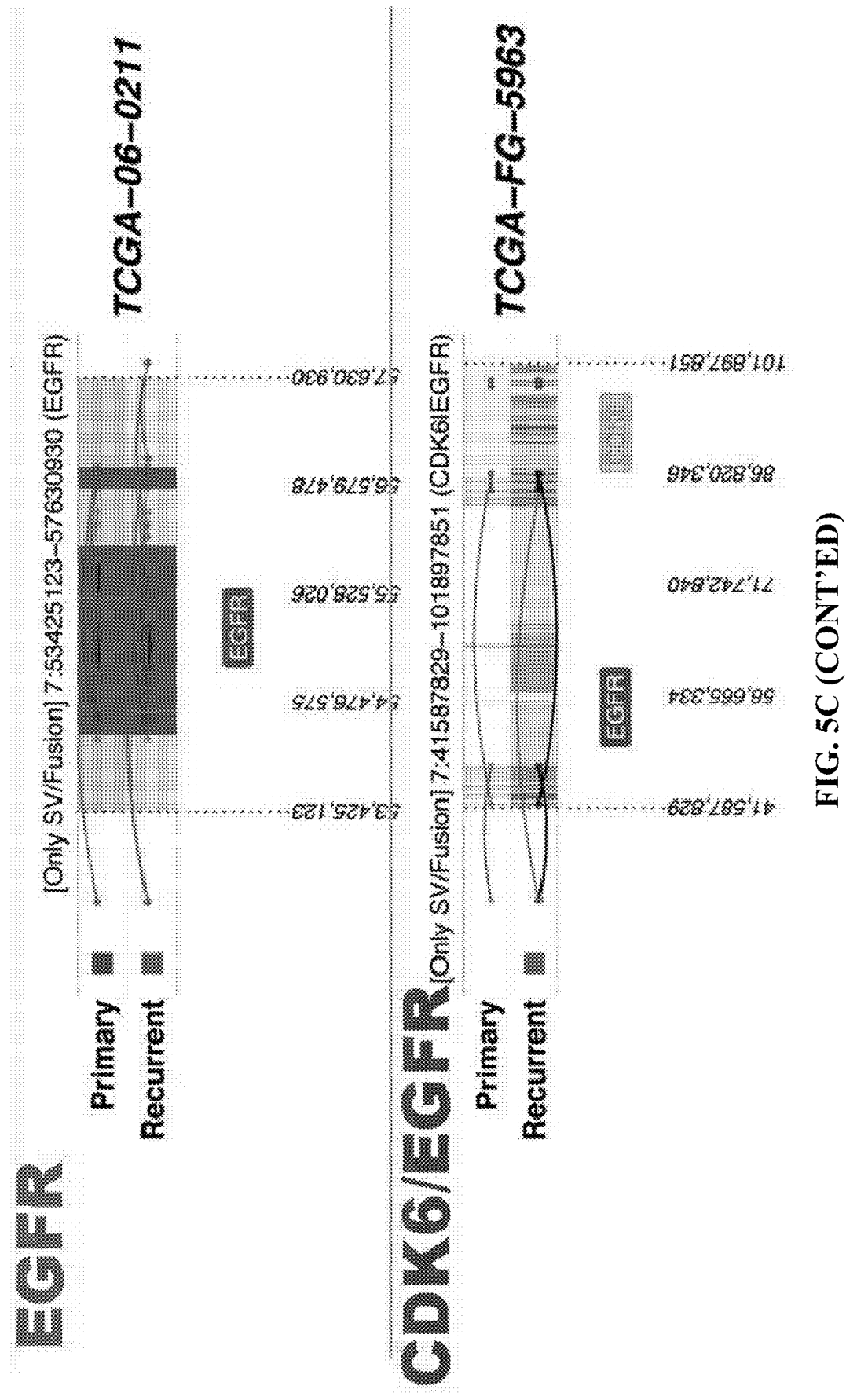
FIG. 5C (CONT'ED)

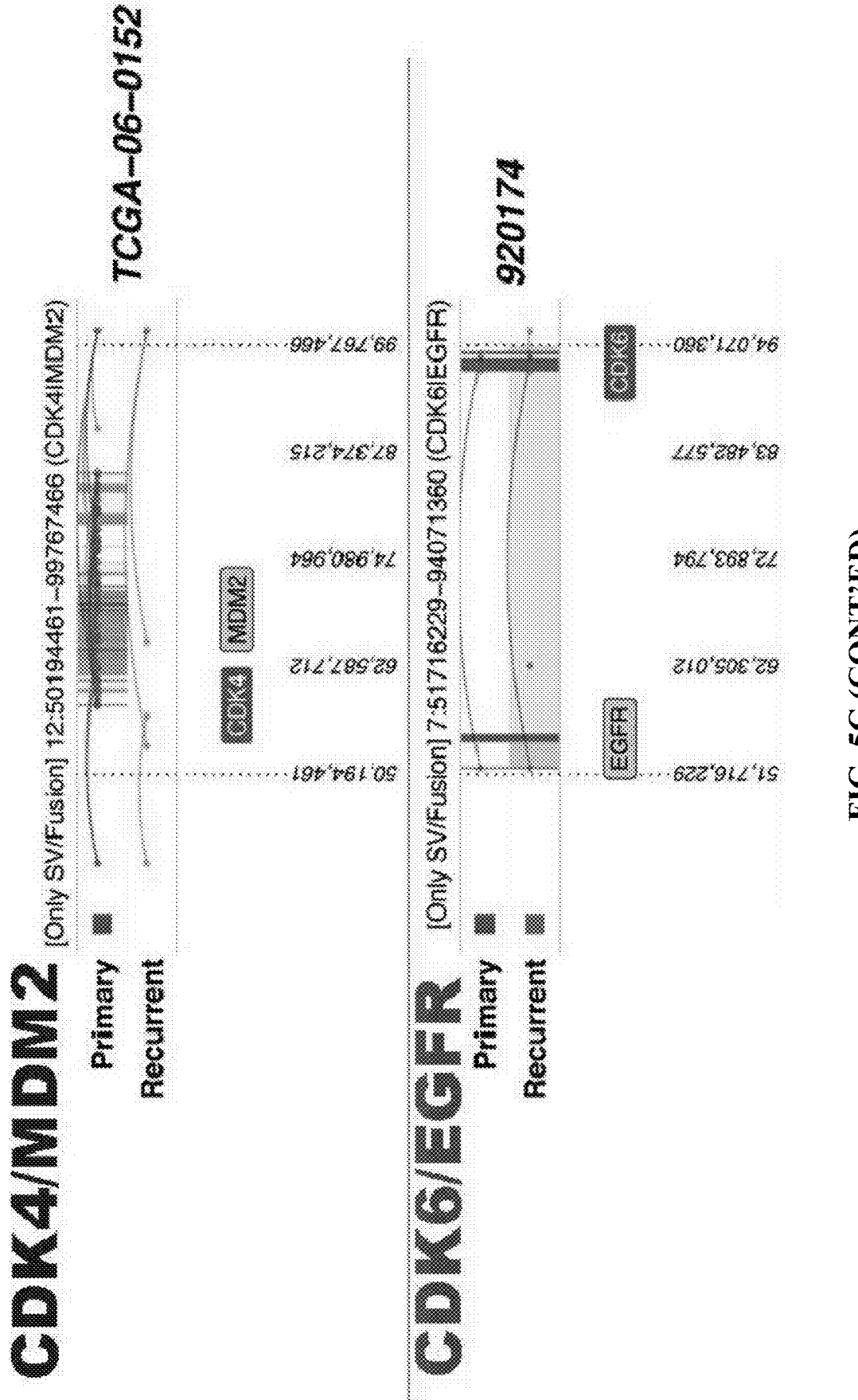
FIG. 5C (CONT'ED)

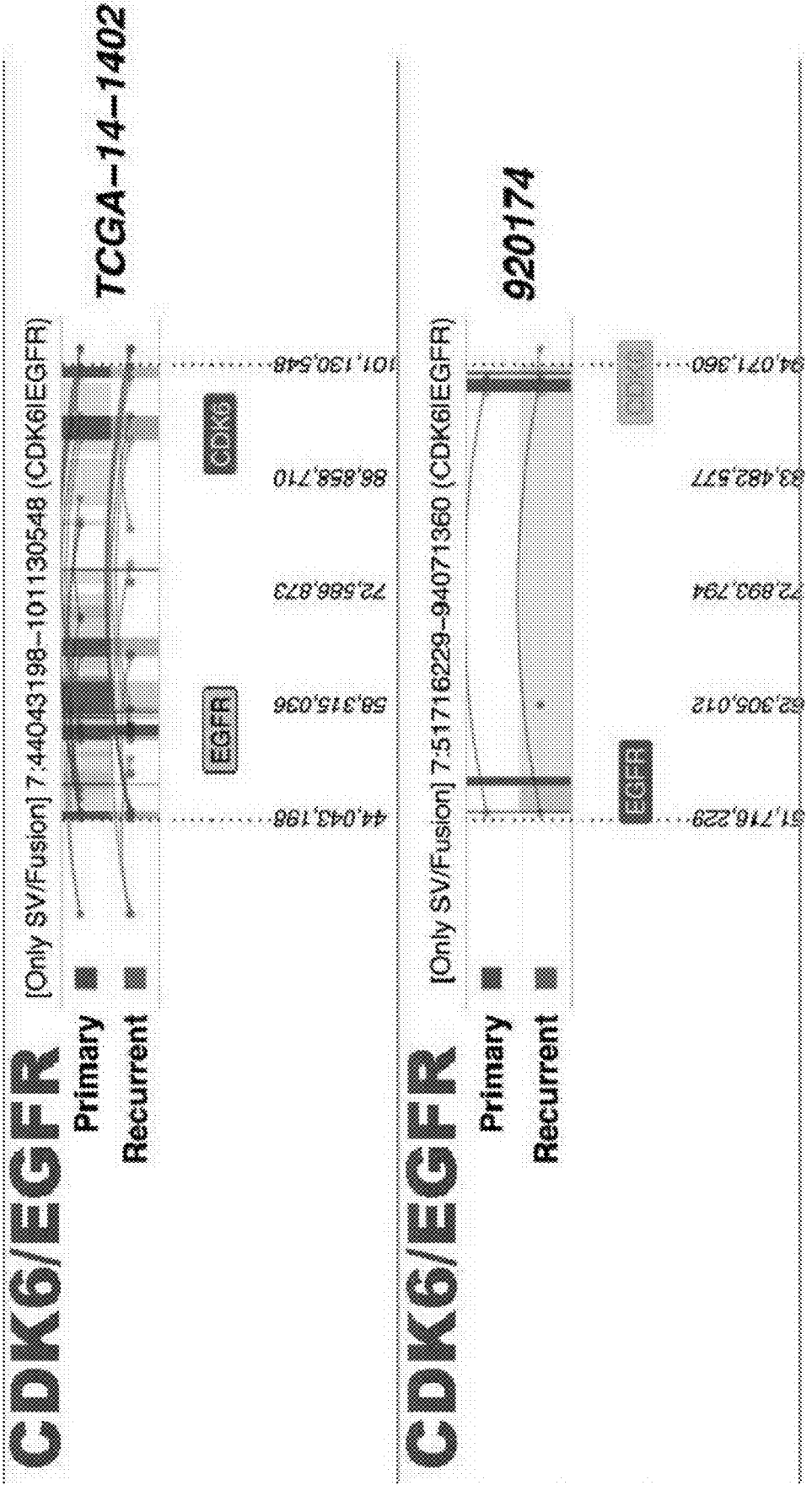
FIG. 5C (CONT'ED)

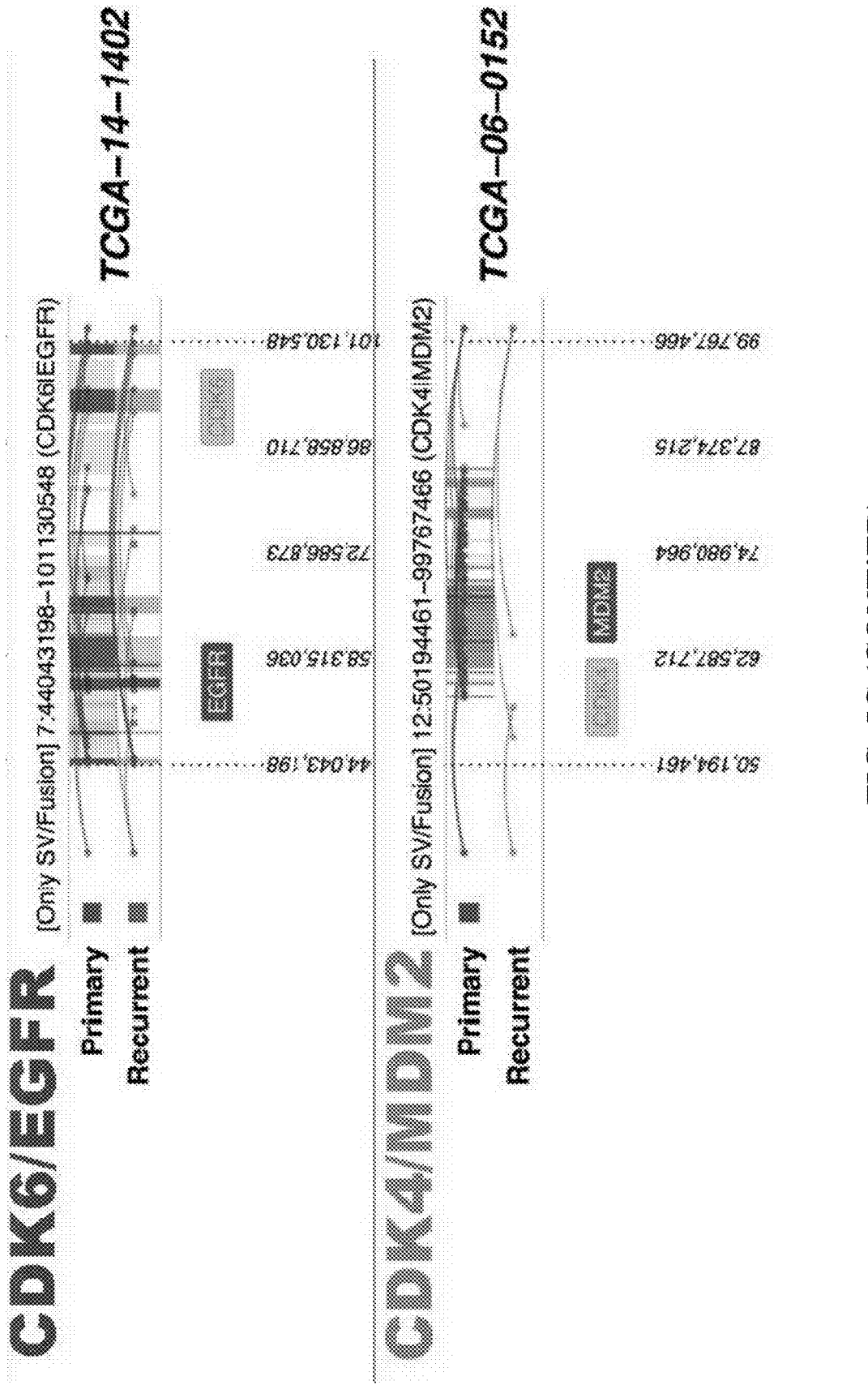
FIG. 5C (CONT'ED)

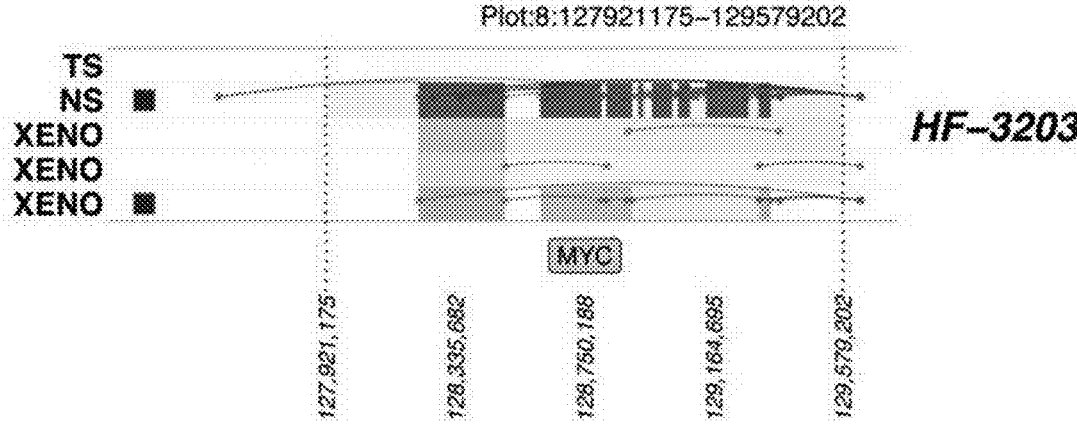
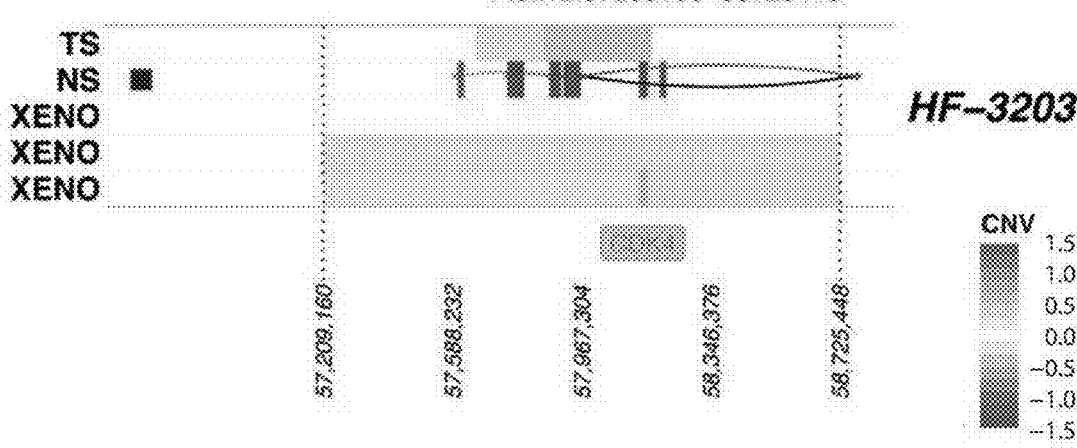
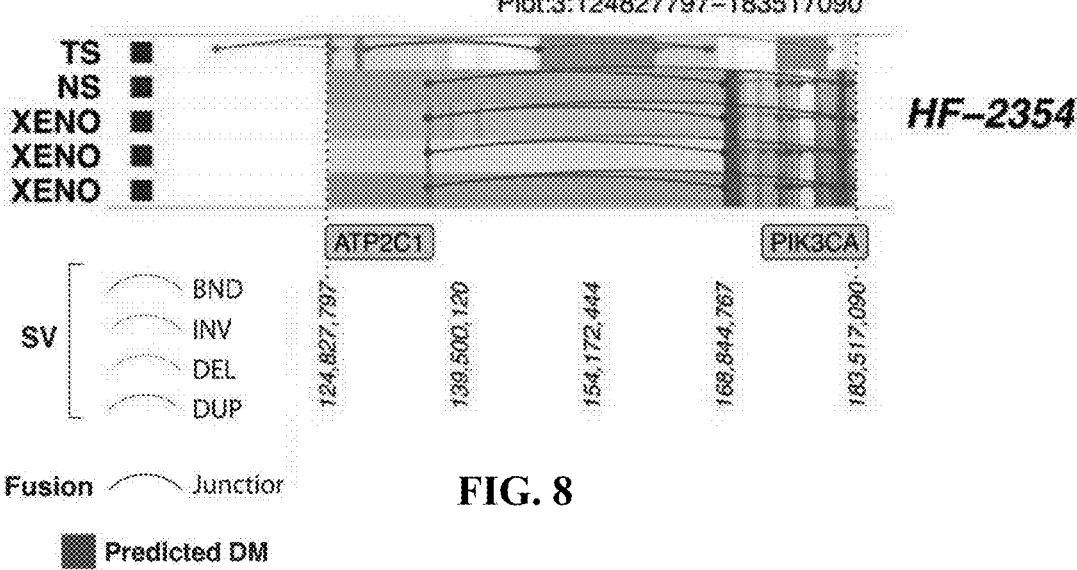
FIG. 8

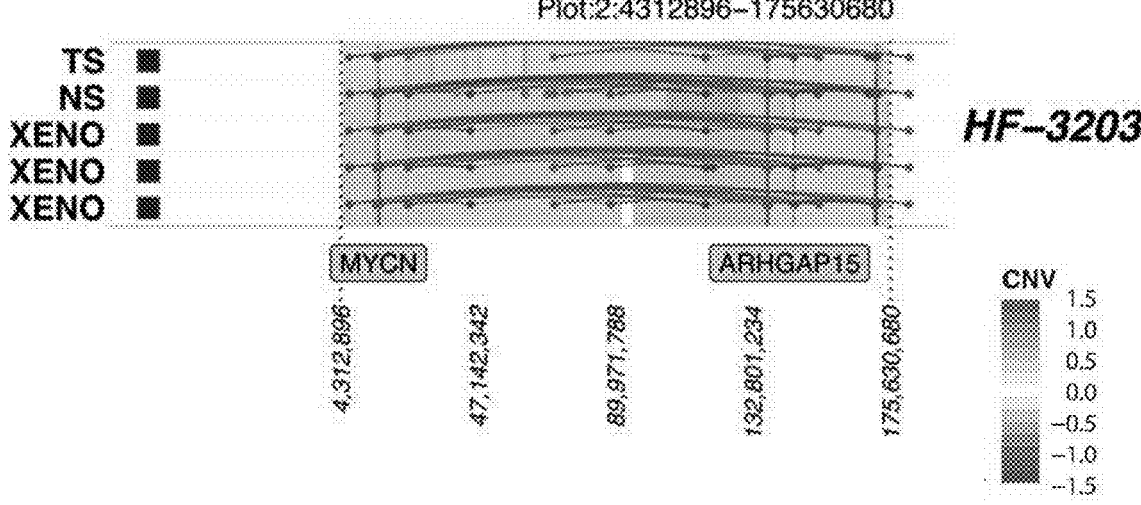
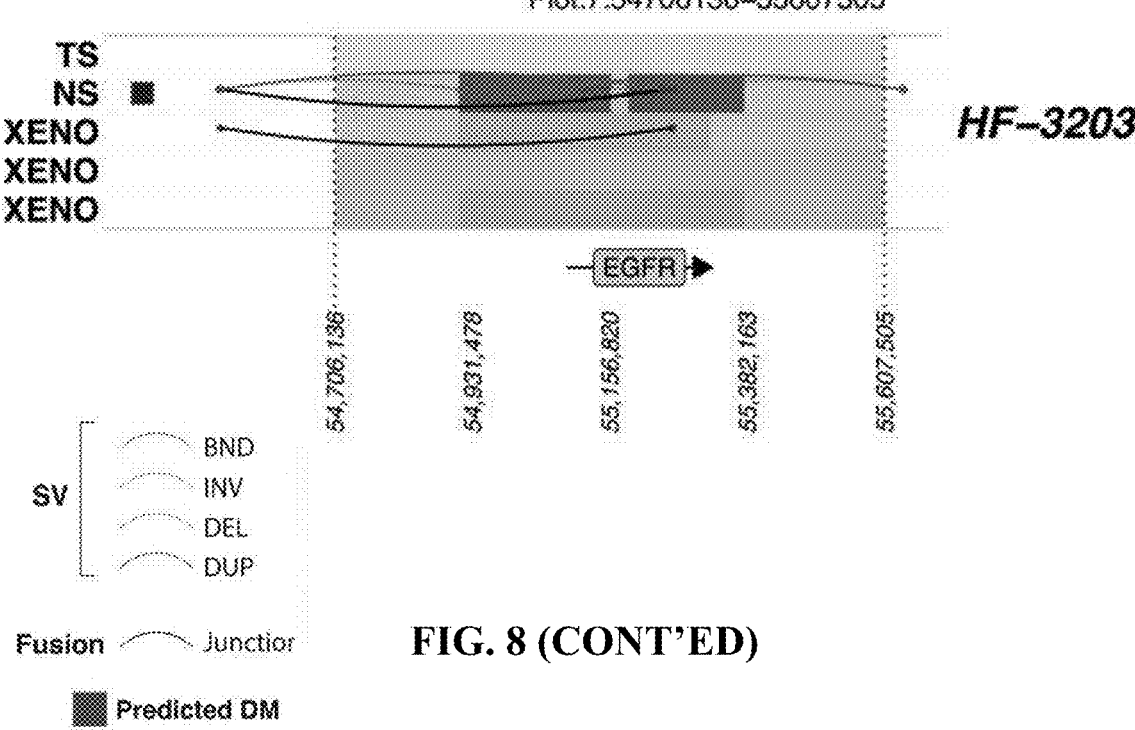
FIG. 8 (CONT'ED)

(CONT'ED)

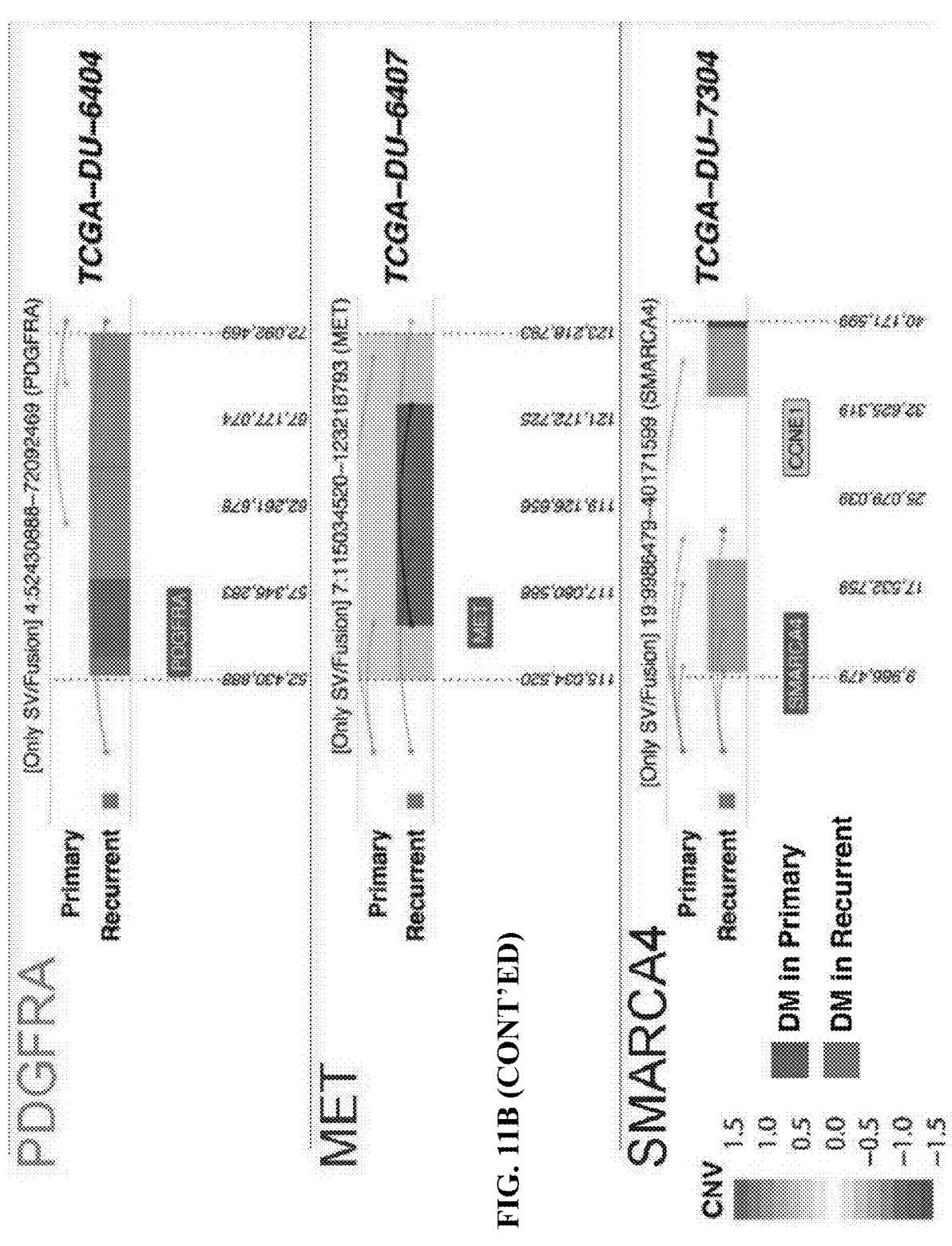
FIG. 11B (CONT'ED)

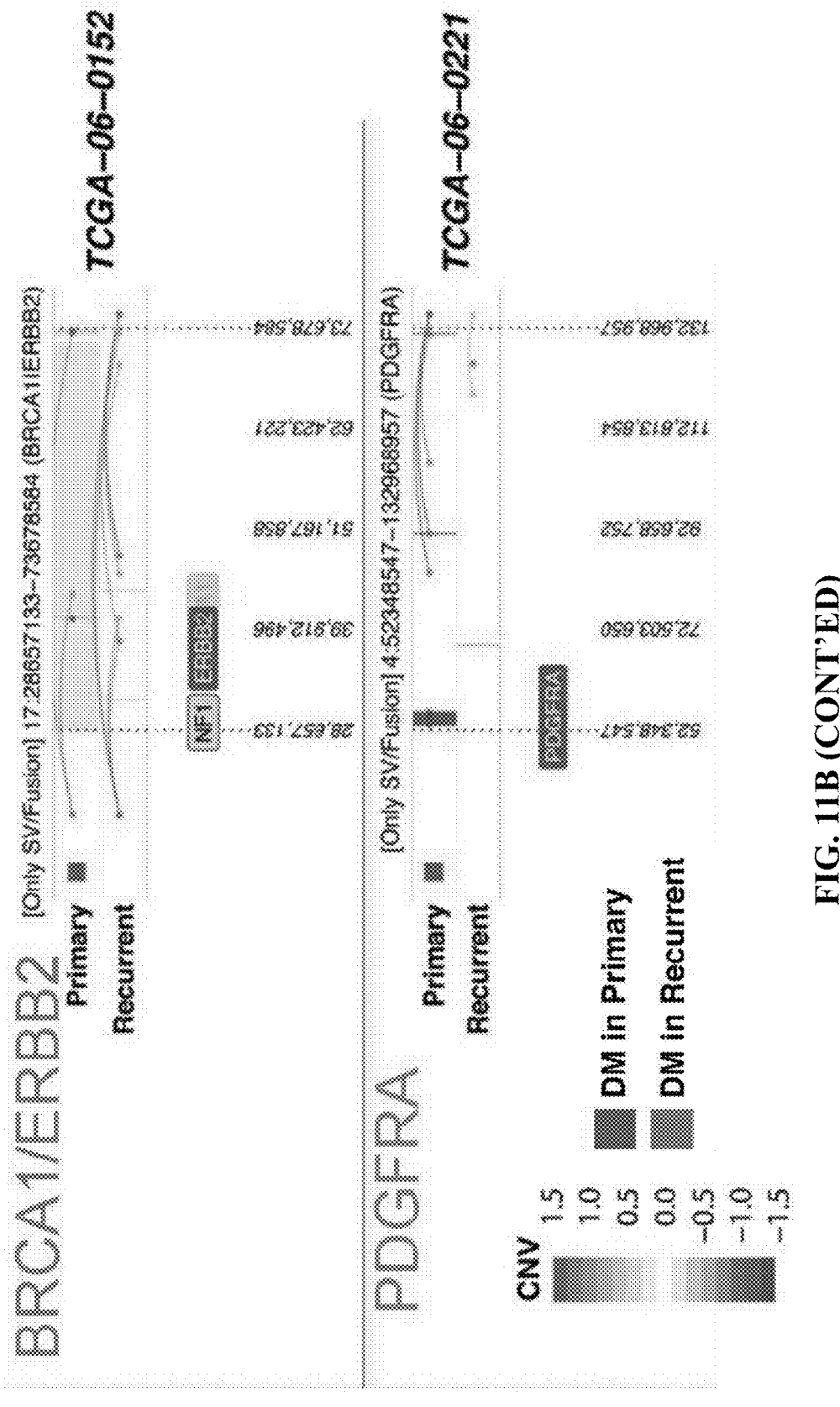
FIG. 11B (CONT'ED)

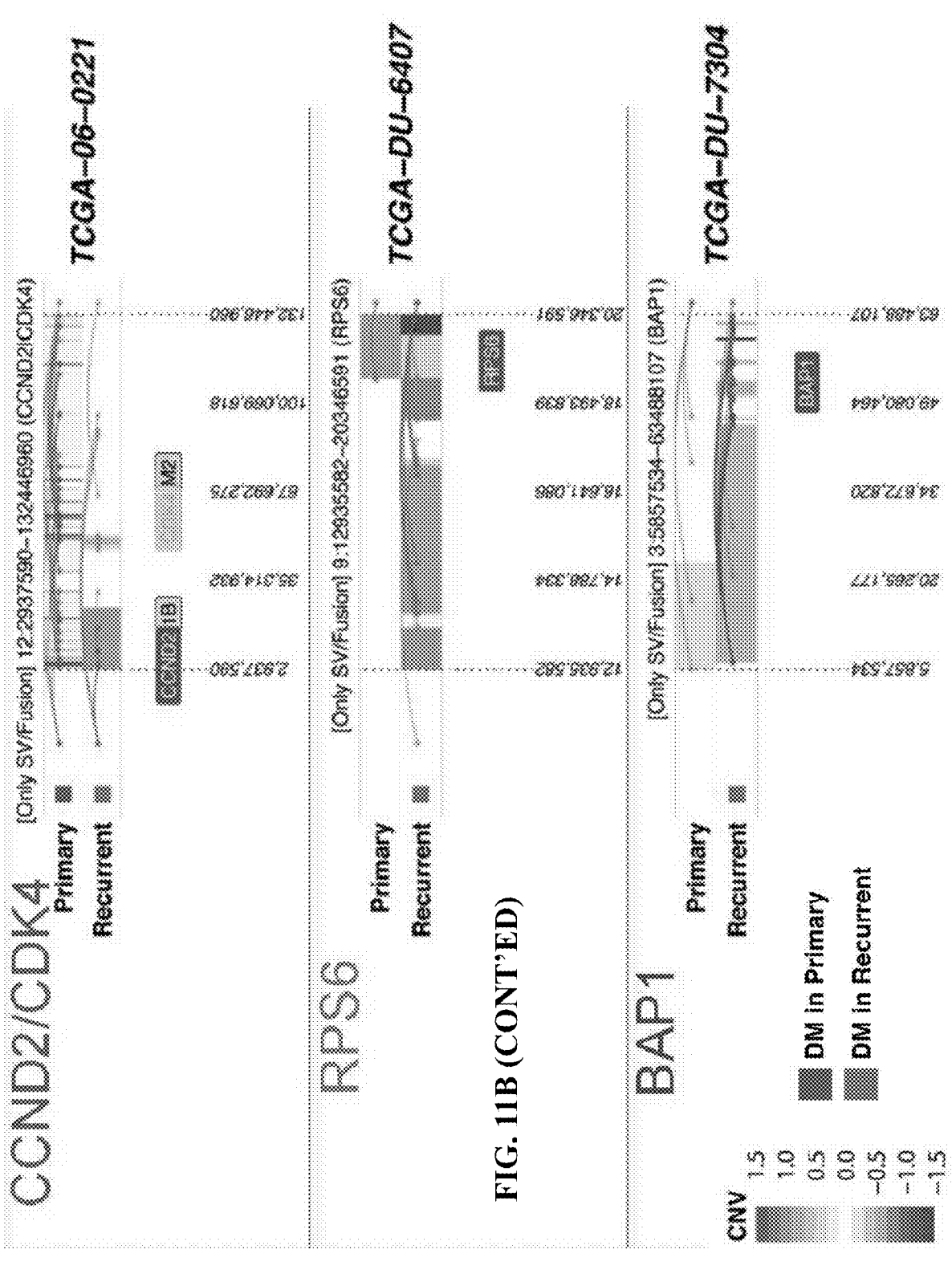
FIG. 11B (CONT'ED)

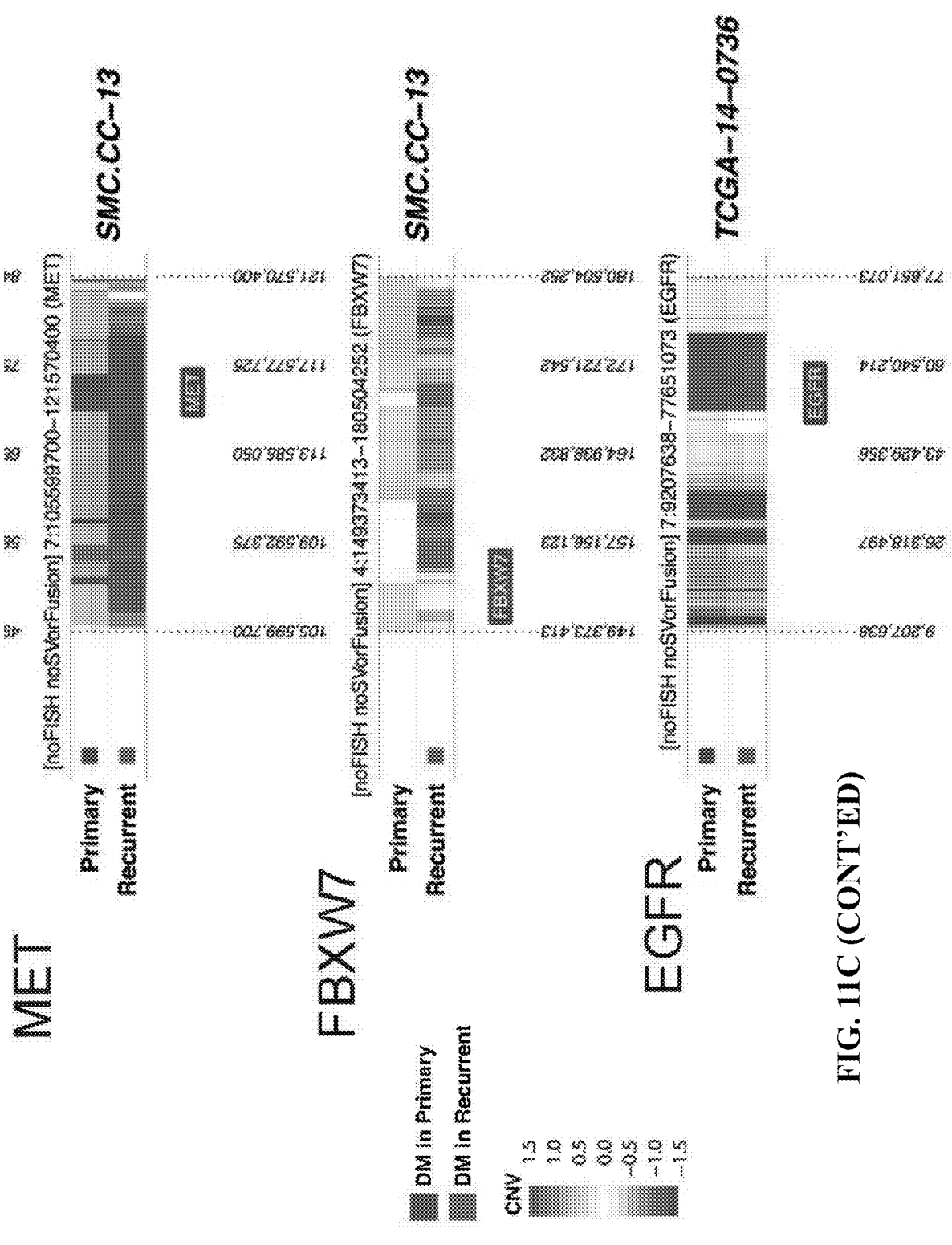
FIG. 11C (CONT'ED)

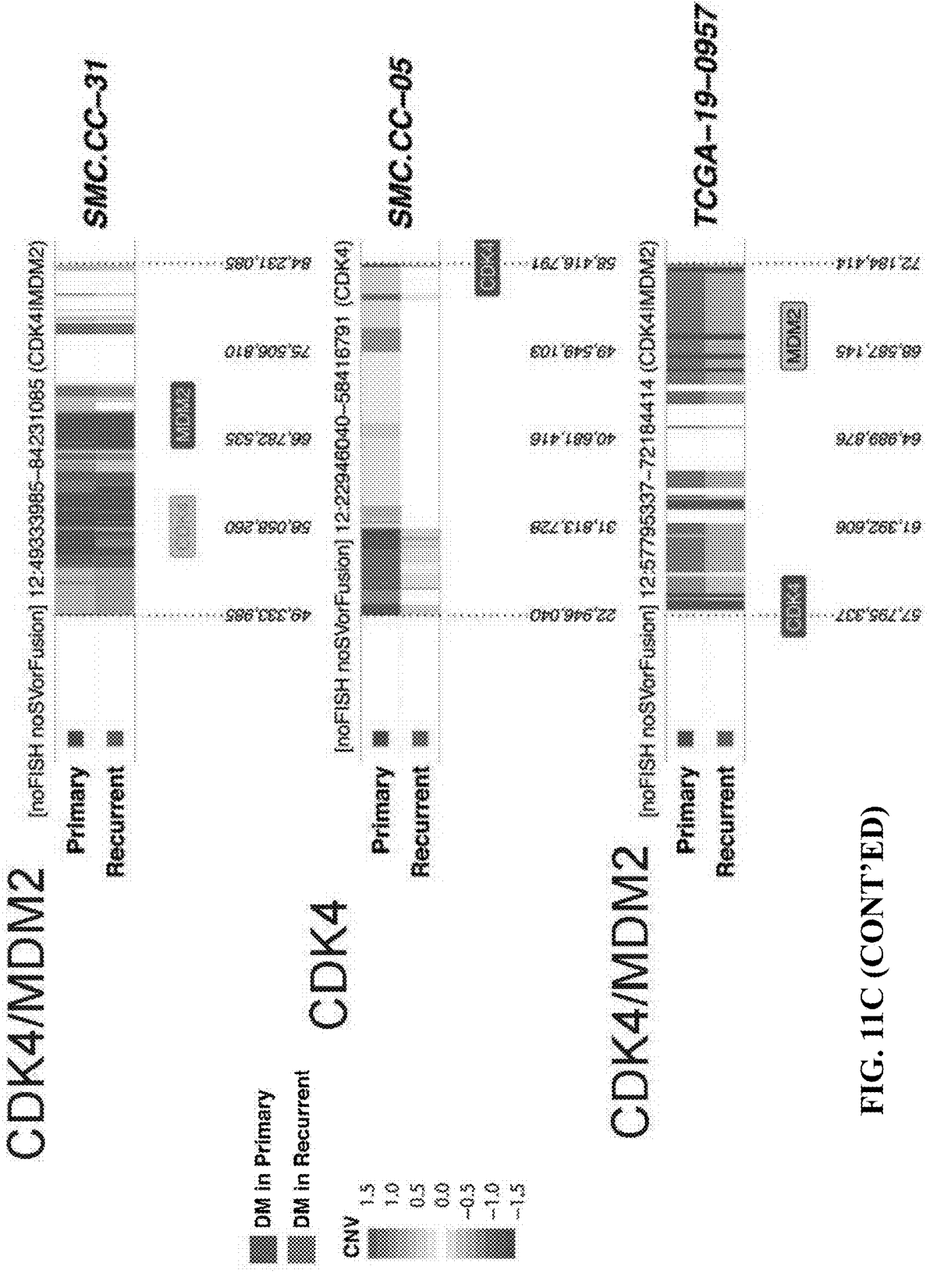
FIG. 11C (CONT'ED)

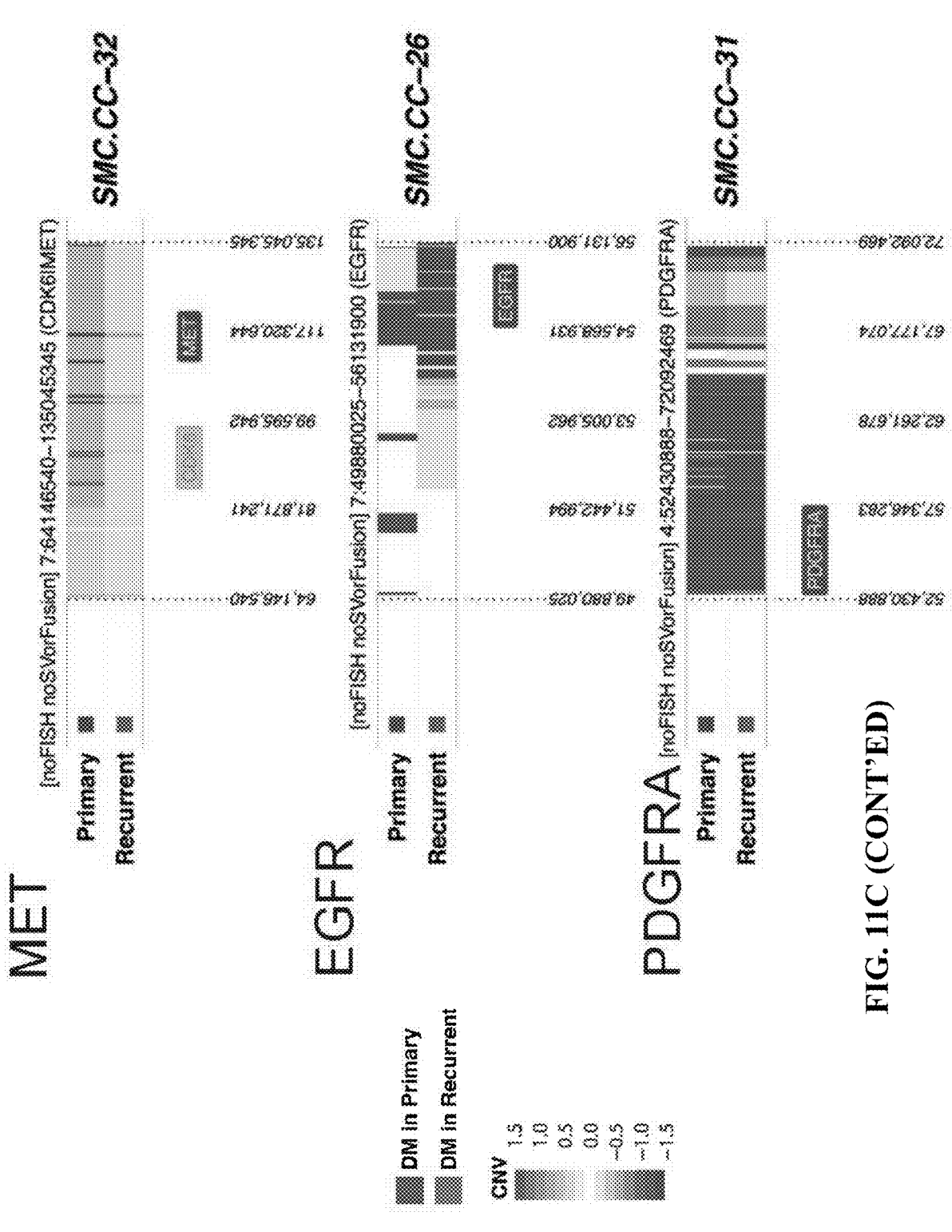
FIG. 11C (CONT'ED)

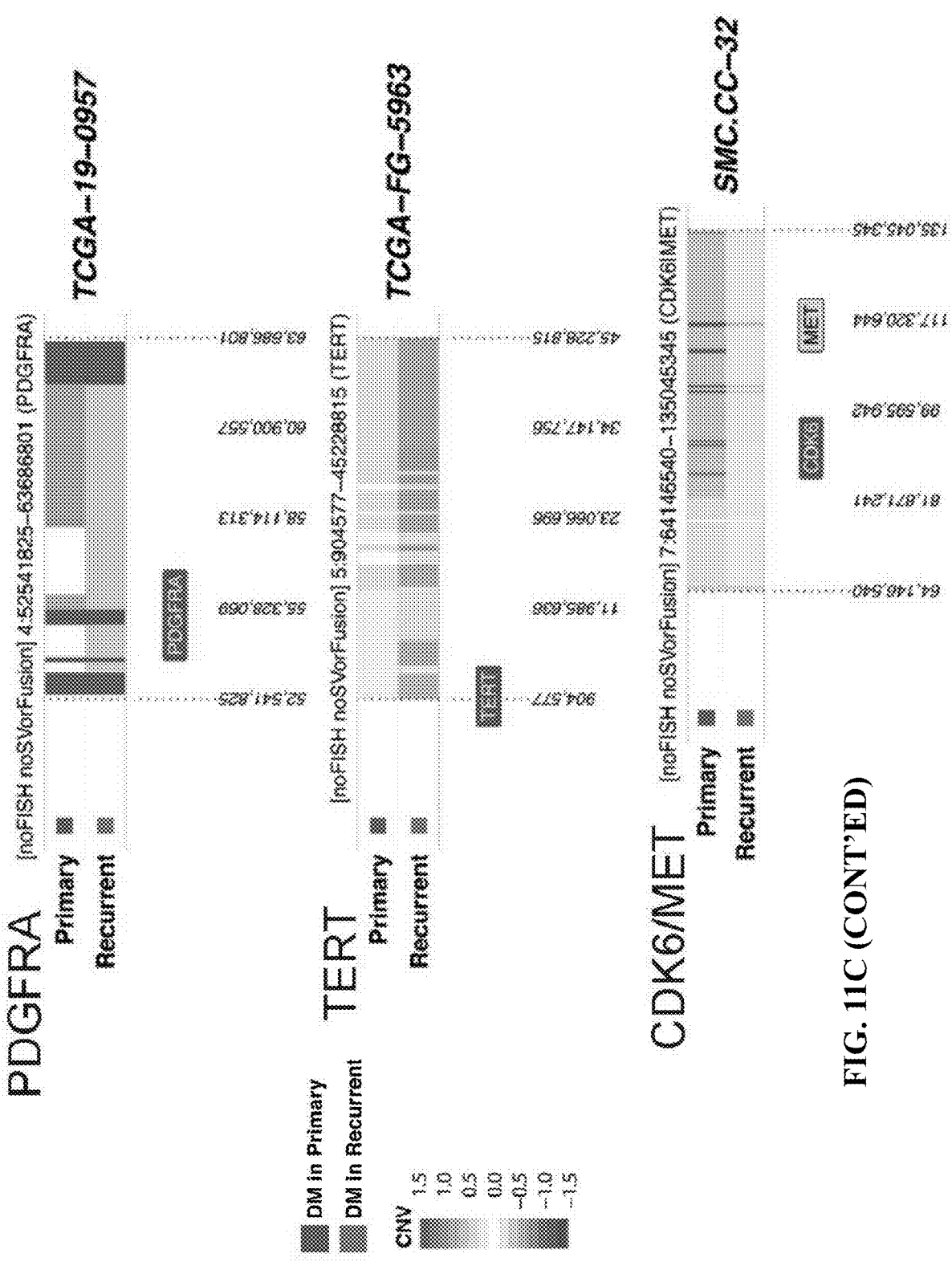
FIG. 11C (CONT'ED)

Days-To-Seconday Surgery vs. IDH1 status
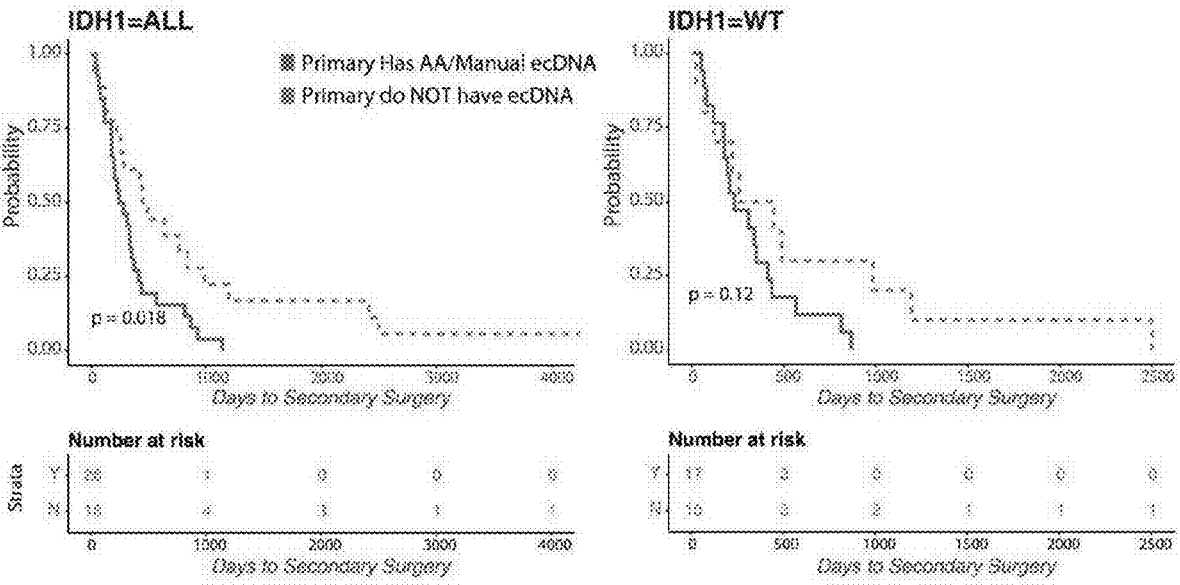
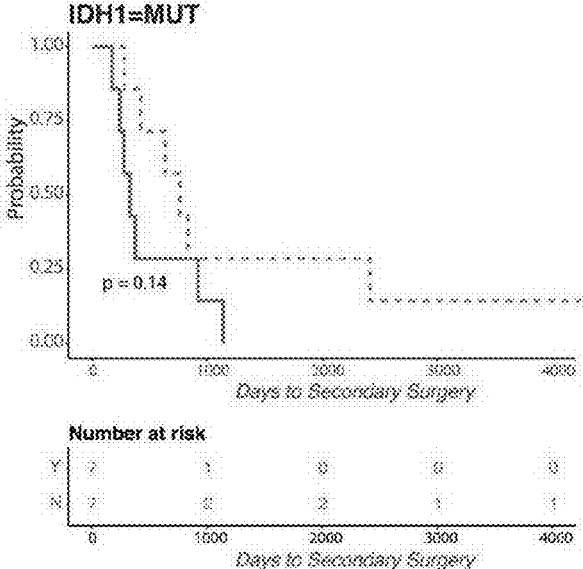
FIG. 11D

FIG. 14

TABLE 3A – SAMPLE INFO

*58 Longitudinal patients*

| | | AA run? | | | |
| | No WGS | WGS/Lowpass | | | Total |
| | NA | Failed | No Amp | Success | |
|---|---|---|---|---|---|
| HF | 20 | | | | 20 |
| IDH1-MUT | 2 | | | | 2 |
| IDH1-WT | 18 | | | | 18 |
| MDACC-GBM | | 2 | 4 | 8 | 14 |
| IDH1-WT | | 2 | 2 | 4 | 8 |
| NA | | | 2 | 4 | 6 |
| SMC | 28 | | | | 28 |
| IDH1-MUT | 4 | | | | 4 |
| IDH1-WT | 24 | | | | 24 |
| TCGA-GBM | 6 | | 1 | 19 | 26 |
| IDH1-MUT | | | | 2 | 2 |
| IDH1-WT | 6 | | 1 | 17 | 24 |
| TCGA-LGG | 2 | 1 | 9 | 16 | 28 |
| IDH1-MUT | | | 8 | 16 | 24 |
| IDH1-WT | 2 | 1 | 1 | | 4 |
| Total | 56 | 3 | 14 | 43 | 116 |

FIG. 15

TABLE 3B — KEY DESCRIPTION

| Key | Description |
|---|---|
| Cohorts | Longitudinal samples= HF, SMC, MDACC-GBM, TCGA-GBM, TCGA-LGG; hGBM samples=HGBM |
| ID | Sample ID |
| PatientID | Patient ID |
| SampleType | Sample Type= I (Initial or Primary), R (Recurrent), TS (Patient tumor), NS (Neurosphere), XENO (Xenograft) |
| isManualOrAA | MANUAL/AA= Detected in both Manual and AA, sharing overlapping regions between the two method; MANUAL/N=Detected only in Manual; N/AA=Detected only in AA |
| AA.Number_Amplified_Segments | # of the segmented copy number amplified regions (copy number>=1) that were used as inputs to AA. If this number is 0, AA did not run for the corresponding sample. NA means that the sample does not have WGS. |
| AA.Finished | success: AA run successfully; failed=AA failed to run; NA= AA did not run because of no amplified region or no WGS. |
| has.WGLP.or.WGS | whether or not the sample has WGS. |

Figure 15:
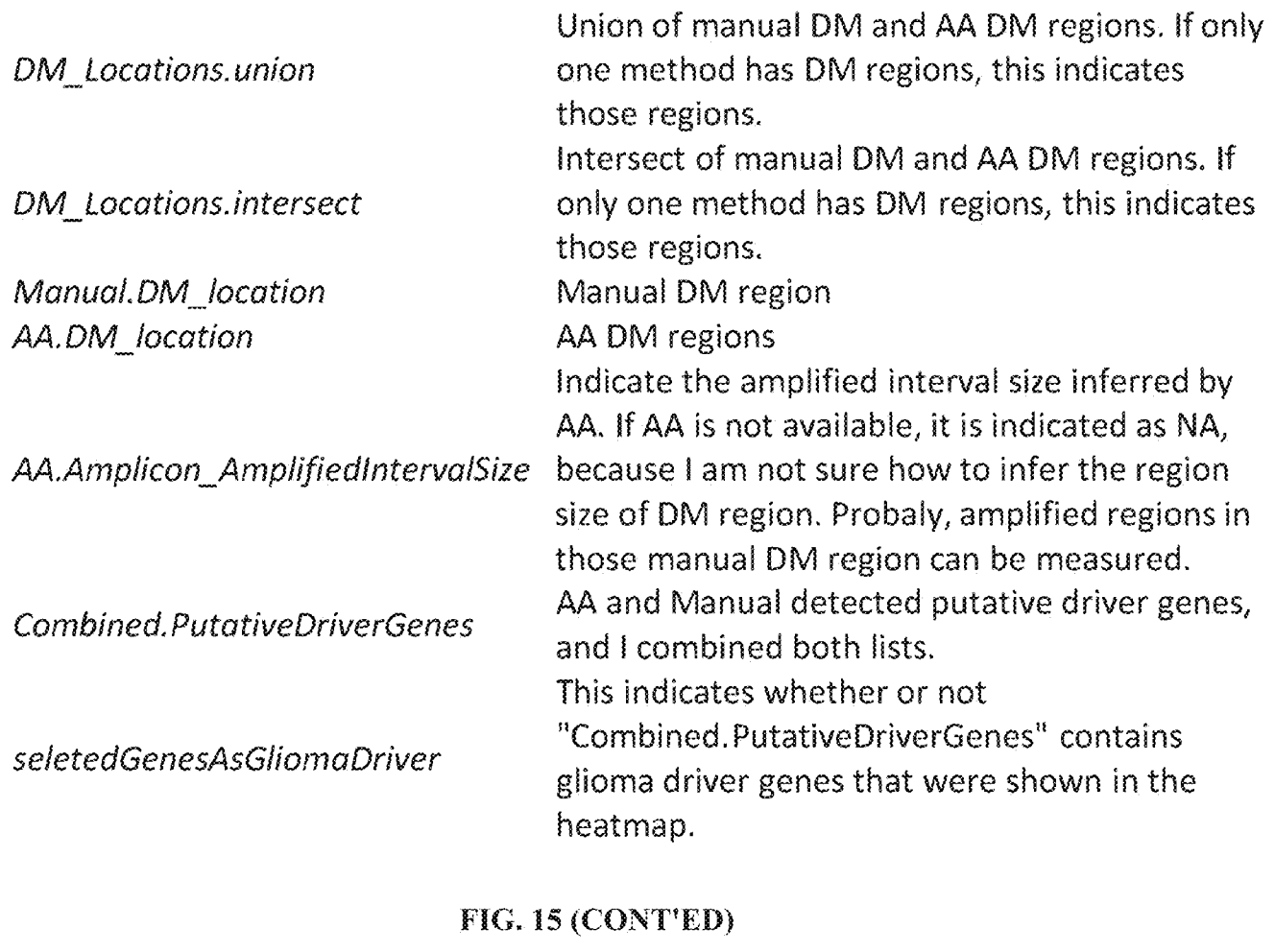

*DM_Locations.union*  Union of manual DM and AA DM regions. If only one method has DM regions, this indicates those regions.

*DM_Locations.intersect*  Intersect of manual DM and AA DM regions. If only one method has DM regions, this indicates those regions.

*Manual.DM_location*  Manual DM region

*AA.DM_location*  AA DM regions

*AA.Amplicon_AmplifiedIntervalSize*  Indicate the amplified interval size inferred by AA. If AA is not available, it is indicated as NA, because I am not sure how to infer the region size of DM region. Probaly, amplified regions in those manual DM region can be measured.

*Combined.PutativeDriverGenes*  AA and Manual detected putative driver genes, and I combined both lists.

*seletedGenesAsGliomaDriver*  This indicates whether or not "Combined.PutativeDriverGenes" contains glioma driver genes that were shown in the heatmap.

TABLE 3C

| Cohorts_Type | Cohorts | ID | PatientID | SampleType | AA.Number_Amplified_Segments | AA.Fished | has.WGLP.or.WGS | DM_Locations.union | DM_Locations.intersect | Manual.LDM_location | AA.DM_location | AA.Amplicon_Amplified_IntervalSize | isManual_CrA_A | isManual | isAA | Combined.PutativeDriverGenes | selectedGenesAsGliomaDriver | hasSelectedGenesAsGliomaDriver | IDH1 | Pathology |
|---|---|---|---|---|---|---|---|---|---|---|---|---|---|---|---|---|---|---|---|---|
| Longitudinal | HF | HF28-69-R | HF2869 | R | NA | NA | no | 7-1214799-56003260 1 | NA | 7-1214799- 56003760 1 | NA | NA | Manual/N | Manual | N | EGFR | EGFR | Y | WT | GBM |
| Longitudinal | HF | HF29-19-L | HF2919 | L | NA | NA | no | 14-85941092-98642754 | NA | 14-85941092- 98642754 | NA | NA | Manual/N | Manual | N | | | N | WT | GBM |
| Longitudinal | HF | HF29-19-R | HF2919 | R | NA | NA | no | 14-85941092-98642754 | NA | 14-85941092- 98642754 | NA | NA | Manual/N | Manual | N | | | N | WT | GBM |
| Longitudinal | HF | HF29-19-L | HF2919 | L | NA | NA | no | 5-1395964-1421477 | NA | 5-81996 4-1421477 | NA | NA | Manual/N | Manual | N | TERT | TERT | Y | WT | GBM |
| Longitudinal | HF | HF29-19-R | HF2919 | R | NA | NA | no | 5-1395964-1421477 | NA | 5-81996 4-1421477 | NA | NA | Manual/N | Manual | N | TERT | TERT | Y | WT | GBM |
| Longitudinal | HF | HF29-19-L | HF2919 | L | NA | NA | no | 7-52995605-1343871 34 | NA | 7-52995605- 1343871 34 | NA | NA | Manual/N | Manual | N | EGFR | EGFR | Y | WT | GBM |
| Longitudinal | HF | HF29-19-R | HF2919 | R | NA | NA | no | 7-52995605-1343871 34 | NA | 7-52995605- 1343871 34 | NA | NA | Manual/N | Manual | N | EGFR | EGFR | Y | WT | GBM |
| Longitudinal | HF | HF29-34-L | HF2934 | L | NA | NA | no | 7-548287 04-5533433 9 | NA | 7-548287 04-5533433 9 | NA | NA | Manual/N | Manual | N | EGFR | EGFR | Y | WT | GBM |
| Longitudinal | HF | HF29-34-R | HF2934 | R | NA | NA | no | 7-5469006 74-5544018 7 | NA | 7-54690 674-5544018 7 | NA | NA | Manual/N | Manual | N | EGFR | EGFR | Y | WT | GBM |
| Longitudinal | HF | HF30-81-L | HF3081 | L | NA | NA | no | 7-1351146 39-1418277 77 | NA | 7-13514 639-1418277 77 | NA | NA | Manual/N | Manual | N | MET | MET | Y | MUT | GBM |
| Longitudinal | HF | HF30-81-R | HF3081 | R | NA | NA | no | 7-1351146 39-1180751 53 | NA | 7-13514 639-1180751 53 | NA | NA | Manual/N | Manual | N | MET | MET | Y | MUT | GBM |

FIG. 16 (CONT'D)

| | | | | | | | | | | | | | | | |
|---|---|---|---|---|---|---|---|---|---|---|---|---|---|---|---|
| Longi tudin al | HF | HF 30 83- R | HF 308 1 | R | NA | NA | na | 8:279320 7- | NA | 8:27932 07- | NA | Manu al/N | Ma nua l | N | MYC | Y | M U T | GBM |
| Longi tudin al | HF | HF 31 18- L | HF 311 8 | L | NA | NA | na | 7:391330 84- | NA | 7:39133 084- | NA | Manu al/N | Ma nua l | N | EGFR | Y | W T | GBM |
| Longi tudin al | HF | HF 31 62- L | HF 316 2 | L | NA | NA | na | 1577720 14 | NA | 1577720 14 | NA | Manu al/N | Ma nua l | N | EGFR | Y | W T | GBM |
| Longi tudin al | HF | HF 31 62- L | HF 316 2 | L | NA | NA | na | 7:541213 55- 5659368 7 | NA | 7:54121 355- 5659368 7 | NA | Manu al/N | Ma nua l | N | EGFR | Y | W T | GBM |
| Longi tudin al | HF | HF 31 62- R | HF 316 2 | R | NA | NA | na | 7:470879 94- 55689745 4 | NA | 7:47087 994- 55689745 4 | NA | Manu al/N | Ma nua l | N | EGFR | Y | W T | GBM |
| Longi tudin al | HF | HF 31 62- L | HF 316 2 | L | NA | NA | na | 9:192251 69- 3466614 1 | NA | 9:19225 169- 3466614 1 | NA | Manu al/N | Ma nua l | N | RPS6 | Y | W T | GBM |
| Longi tudin al | HF | HF 31 62- R | HF 316 2 | R | NA | NA | na | 9:181906 62- 3826776 1 | NA | 9:18190 662- 3826776 1 | NA | Manu al/N | Ma nua l | N | RPS6 | N | W T | GBM |
| Longi tudin al | HF | HF 28 29- L | HF 282 9 | L | NA | NA | na | 17:30138 299- 7406738 6 | NA | 17:3013 8299- 7406738 6 | NA | Manu al/N | Ma nua l | N | | | W T | GBM |
| Longi tudin al | HF | HF 28 29- L | HF 282 9 | L | NA | NA | na | 4:526380 05- 5879931 6 | NA | 4:52638 005- 5879931 6 | NA | Manu al/N | Ma nua l | N | PDGFRA | Y | W T | GBM |
| Longi tudin al | HF | HF 28 29- L | HF 282 9 | L | NA | NA | na | 7:546239 91- 55309556 5 | NA | 7:54623 991- 55309556 5 | NA | Manu al/N | Ma nua l | N | EGFR | Y | W T | GBM |
| Longi tudin al | HF | HF 28 69- L | HF 285 9 | L | NA | NA | na | 12:50449 904- 7062986 4 | NA | 12:5044 9904- 7062986 4 | NA | Manu al/N | Ma nua l | N | MDM2 | Y | W T | GBM |
| Longi tudin al | HF | HF 28 69- L | HF 286 9 | L | NA | NA | na | 7:121247 99- 55632260 1 | NA | 7:12147 99- 55632260 1 | NA | Manu al/N | Ma nua l | N | EGFR | Y | W T | GBM |
| Longi tudin al | M DA CC | 19 16 84 4-1 | 101 684 4 | L | 7 | succ ess | WGS | 12:57699 728- 6448793 0 | NA 12:57802 773- 58628218 8:12:592 34812- 60099303 3:12:611 66617- 61688801 3:12:640 | 12:57801 07- 586281 88, 12:592348 12- 600993303, 12:611666 17- 61688313, 12:640901 | 1811946 | Manu al/AA | Ma nua l | A A | CDK4 | Y | W T | CJOB LASTO MA |

| | | | | | | | | | | | | | | | | |
|---|---|---|---|---|---|---|---|---|---|---|---|---|---|---|---|---|
| Longi tudin al | s M c | SM CC c- 18- L | SM CC c- 10 | - | NA | no | X:194296 16- 2480863 1 | NA | X:19429 616- 2480863 1 | NA | NA | Manu al/N | Ma nua l | M C T | GBM |
| Longi tudin al | s M c | SM CC c- 13- L | SM CC c- 13 | - | NA | no | 7:107598 445- 1215040 55 | NA | 7:10759 8445- 1215040 55 | NA | MET | Manu al/N | Ma nua l | N | R | M C T | SecAG A |
| Longi tudin al | s M c | SM CC c- 13- R | SM CC c- 13 | R | NA | no | 7:105599 700- 1215704 00 | NA | 7:10559 9700- 1215704 00 | NA | MET | Manu al/N | Mo nua l | N | MET | Y | M C T | GBM |
| Longi tudin al | s M c | SM CC c- 13- R | SM CC c- 13 | R | NA | no | 1:153280 226- 18588608 42 | NA | 1:15328 0226- 18588608 42 | NA | Manu al/N | Ma nua l | N | Y | M C T | GBM |
| Longi tudin al | s M c | SM CC c- 13- R | SM CC c- 13 | R | NA | no | 11:25552 7143- 1213366 18 | NA | 11:25517 142- 1213366 18 | NA | Manu al/N | Ma nua l | N | N | M C T | GBM |
| Longi tudin al | s M c | SM CC c- 13- R | SM CC c- 13 | R | NA | no | 3:772228 749- 1401008 69 | NA | 3:772287 49- 1401008 69 | NA | Manu al/N | Ma nua l | N | N | M C T | GBM |
| Longi tudin al | s M c | SM CC c- 13- R | SM CC c- 13 | R | NA | no | 4:24937 3413- 1805042 52 | NA | 4:149373 413- 1805042 52 | NA | Manu al/N | Ma nua l | N | N | M C T | GBM |
| Longi tudin al | s M c | SM CC c- 13- R | SM CC c- 13 | R | NA | no | 6:65543 182- 6939327 0 | NA | 6:655431 82- 6939327 0 | NA | FBXW7 | Manu al/N | Ma nua l | N | FBXW7 | Y | M C T | GBM |
| Longi tudin al | s M c | SM CC c- 13- L | SM CC c- 13 | R | NA | no | 8:805133 281- 9298035 9 | NA | 8:805132 81- 9298035 9 | NA | Manu al/N | Mo nua l | N | N | M C T | GBM |
| Longi tudin al | s M c | SM CC c- 13- L | SM CC c- 13 | - | NA | no | 11:77990 2914- 1197604 08 | NA | 11:77902 914- 1197604 08 | NA | Manu al/N | Ma nua l | N | N | M C T | GBM |
| Longi tudin al | s M c | SM CC c- 17- L | SM CC c- 17 | - | NA | no | 7:49880 025- 5613190 0 | NA | 7:498800 25- 5613190 0 | NA | EGFR | Manu al/N | Ma nua l | N | EGFR | Y | M T | GBM |

Figure 16:
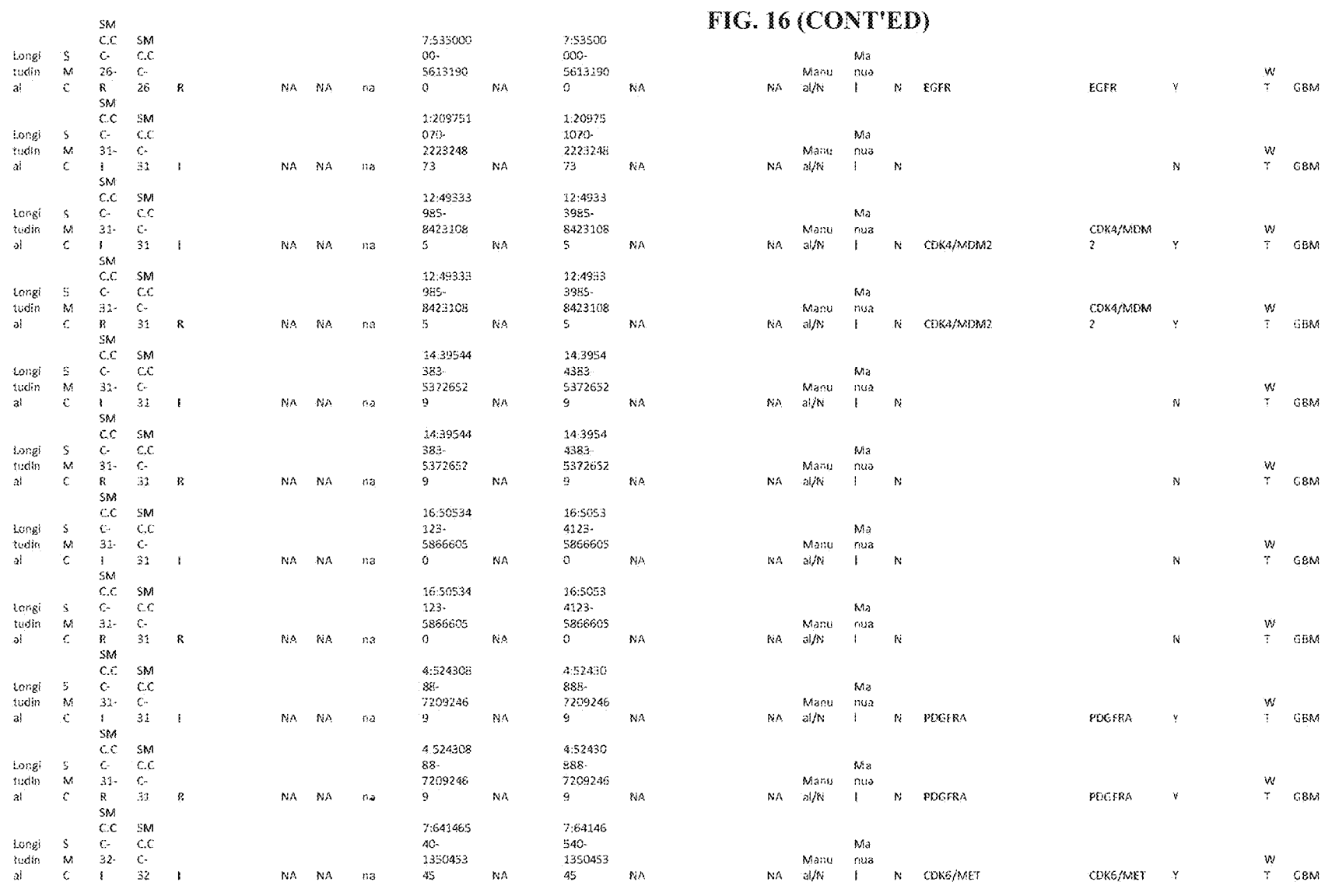

FIG. 16 (CONT'ED)

| | S M C | | R/I | NA | NA | na | | NA | | NA | | Manual NA | Manual NA | Ma nua l | N | | | | Y/N | | WT | GBM |
|---|---|---|---|---|---|---|---|---|---|---|---|---|---|---|---|---|---|---|---|---|---|---|
| Longitudinal | S M C | SM CC G 26- R | SM CC G 26 | R | NA | NA | na | 7.53500000- | NA | 7.53500 000- 5613190 0 | NA | | Manual NA | Manual N/A | Ma nua l | N | EGFR | EGFR | | Y | EGFR | WT | GBM |
| Longitudinal | S M C | SM CC G 31- R | SM CC G 31 | I | NA | NA | na | 1.2097751 070- 2223248 | NA | 1.209751 1070- 2223248i 73 | NA | | Manual NA | Manual N/A | Ma nua l | N | | | | N | | WT | GBM |
| Longitudinal | S M C | SM CC G 31- R | SM CC G 31 | I | NA | NA | na | 12.3933 985- 8423108 5 | NA | 12.4933 3985- 8423108 5 | NA | | Manual NA | Manual N/A | Ma nua l | N | CDK4/MDM2 | CDK4/MDM 2 | | Y | CDK4/MDM 2 | WT | GBM |
| Longitudinal | S M C | SM CC G 31- R | SM CC G 31 | I | NA | NA | na | 12.49333 985- 8423108 5 | NA | 12.4933 3985- 8423108 5 | NA | | Manual NA | Manual N/A | Ma nua l | N | CDK4/MDM2 | CDK4/MDM 2 | | Y | | WT | GBM |
| Longitudinal | S M C | SM CC G 33- R | SM CC G 33 | R | NA | NA | na | 14.39544 383- 5372652 9 | NA | 14.3954 4383- 5372652 9 | NA | | Manual NA | Manual N/A | Ma nua l | N | | | | N | | WT | GBM |
| Longitudinal | S M C | SM CC G 33- R | SM CC G 33 | I | NA | NA | na | 14.39544 383- 5372652 9 | NA | 14.3954 4383- 5372652 9 | NA | | Manual NA | Manual N/A | Ma nua l | N | | | | N | | WT | GBM |
| Longitudinal | S M C | SM CC G 31- R | SM CC G 31 | R | NA | NA | na | 16.50534 123- 5866605 0 | NA | 16.5053 4123- 5866605 0 | NA | | Manual NA | Manual N/A | Ma nua l | N | | | | N | | WT | GBM |
| Longitudinal | S M C | SM CC G 31- R | SM CC G 31 | I | NA | NA | na | 16.50534 123- 5866605 0 | NA | 16.5053 4123- 5866605 0 | NA | | Manual NA | Manual N/A | Ma nua l | N | | | | N | | WT | GBM |
| Longitudinal | S M C | SM CC G 31- R | SM CC G 31 | I | NA | NA | na | 4.5243088 88- 7209246 9 | NA | 4.524308 88- 7209246 9 | NA | | Manual NA | Manual N/A | Ma nua l | N | PDGFRA | PDGFRA | | Y | PDGFRA | WT | GBM |
| Longitudinal | S M C | SM CC G 31- R | SM CC G 31 | R | NA | NA | na | 4.524308 88- 7209246 9 | NA | 4:52430 888- 7209246 9 | NA | | Manual NA | Manual N/A | Ma nua l | N | PDGFRA | PDGFRA | | Y | PDGFRA | WT | GBM |
| Longitudinal | S M C | SM CC G 32- R | SM CC G 32 | I | NA | NA | na | 7.641465 40- 1350453 45 | NA | 7.641465 40- 1350453 45 | NA | | Manual NA | Manual N/A | Ma nua l | N | CDK6/MET | CDK6/MET | | Y | CDK6/MET | WT | GBM |

Figure 16:
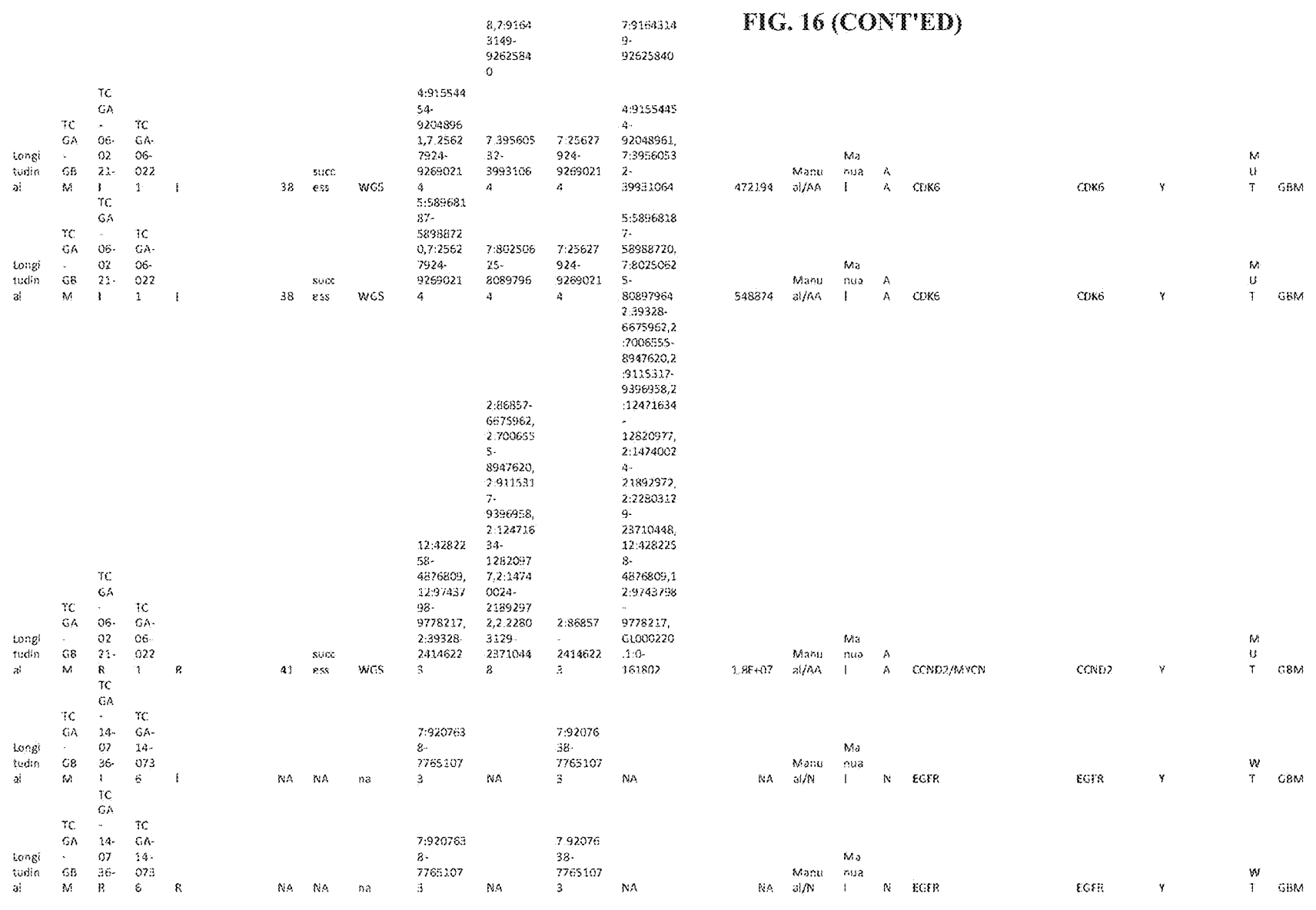

| | | | | | | | | | | | | | |
|---|---|---|---|---|---|---|---|---|---|---|---|---|---|
| Longi tudinal | TCGA | TCGA-06-02 | GBM | R | 1 | 38 | succ ess | WGS | 4915544 54- 9204896 17.25627 7924- 9269021 4 | 8,79164 3149- 9262584 0 | 7.915433.4 9- 9262584 0 | | | M U T GBM |
| | TCGA | TCGA-06-02 21- | GBM | R | TCGA-06-022 1 | | | | 7.25627 924- 9269021 4 | 7.395605 32- 3993106 4 | 4.9155445 4- 92048961, 7:3956053 2- 3993106 4 | 472194 | Manu al/AA | Ma nua l | A A | CDK6 | CDK6 | Y | | | CDK6 |
| Longi tudinal | TCGA | TCGA-06-02 | GBM | M | 1 | 38 | succ ess | WGS | 5898872 7924- 9269021 4 | 7.8025056 15- 80899796 4 | 5.5896818 7- 58988720, 7.8025052 5- 80899796 4 | 548874 | Manu al/AA | Ma nua l | A A | CDK6 | CDK6 | Y | | | M U T GBM |
| | | | | | | | | | 2.86857- 66759962, 2.70069655 5- 89947620, 2.9115331 7- 93969358,2 34- 1282097 7.2.4474 0024- 21892917 | 2.86857- 66759962, 2.7006655 5- 89947620, 2.9115331 7- 9396958, 2.124716 34- 1282097 7.2.4474 0024- | 80897964 2.39328- 66759962.2 .70006555- 8947620.2 .9115317- 9396938.2 .12471634 12820977, 2.1474002 4- 21892972, 2.2280312 9- 23710448, 12.428225 8- 4876809,1 2.9743798 . | | | | | | | | | | |
| Longi tudinal | TCGA | TCGA-06-02 21- | GBM | R | TCGA-06-022 1 | 41 | succ ess | WGS | 9778217, 2.39328- 2414622 3 | 2.2.2280 3129. 23710449 8 | 9778217, 01000220 .10- 161802 | 1.9E-07 | Manu al/AA | Ma nua l | A A | CCND3/MYCN | CCND3/MYCN | Y | | | M U T GBM |
| Longi tudinal | TCGA | TCGA-14-07 36- | GBM | R | TCGA-14-073 6 | NA | NA | na | 7.920763 8- 7765107 3 | NA | NA | NA | Manu al/N | Ma nua l | A N | EGFR | EGFR | Y | | | W T GBM |
| Longi tudinal | TCGA | TCGA-14-07 36- | GBM | R | TCGA-14-073 6 | NA | NA | na | 7.920763 8- 7765107 3 | NA | NA | NA | Manu al/N | Ma nua l | A N | EGFR | EGFR | Y | | | W T GBM |

Figure 16:
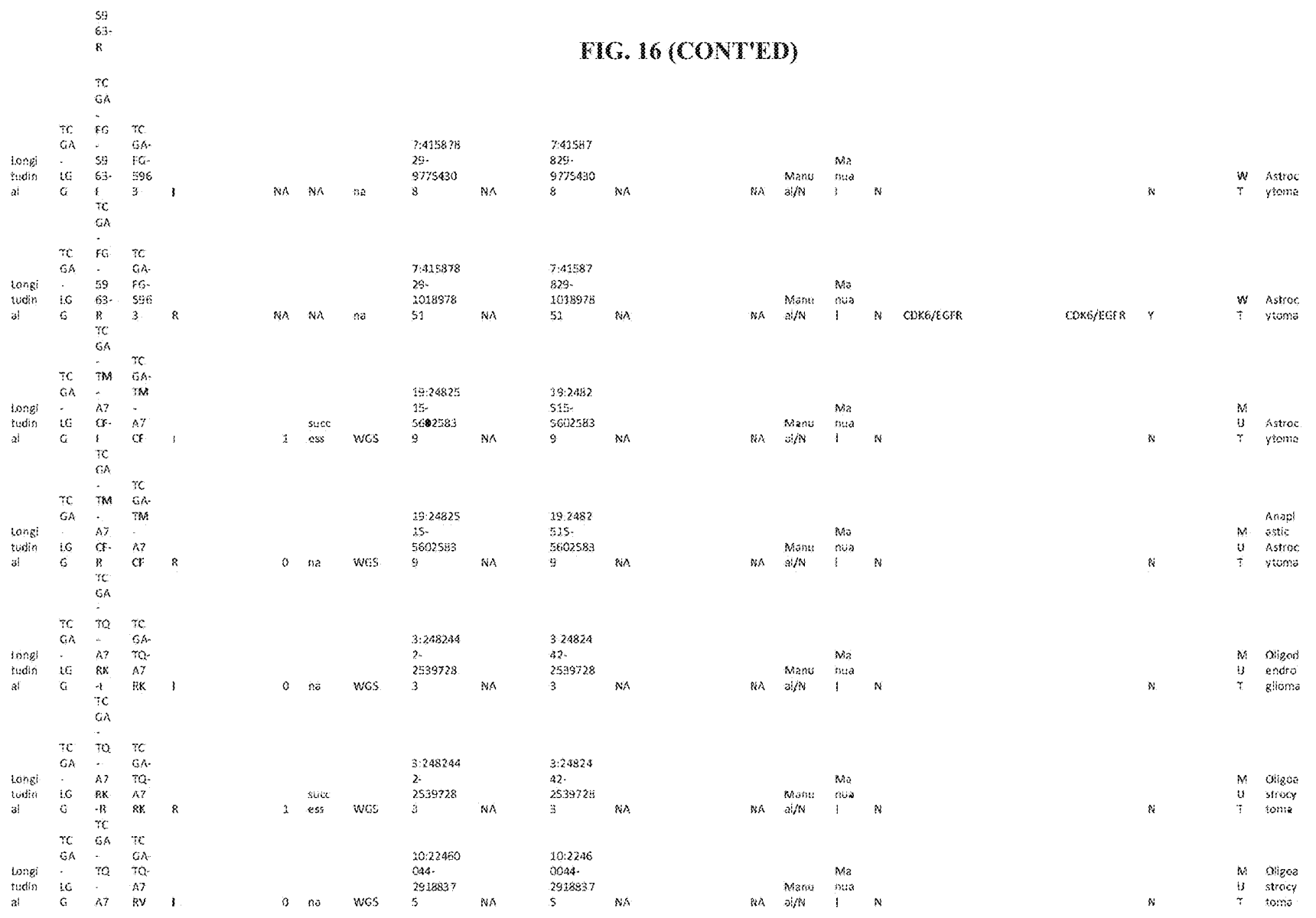

| | | | | | | | | | | | | | |
|---|---|---|---|---|---|---|---|---|---|---|---|---|---|
| longitudinal | TCGA, TCGA-59-R, FG-5963 | 1 | NA | NA | NA | 7:41587825-9775430 8 | NA | NA | 7:41587825-9775430 8 | NA | Manual NA | Manual NA | Ma nua l | N | | | WT Astrocytoma |
| longitudinal | TCGA, TCGA-FG-59-R, FG-5963 | R | NA | NA | NA | 7:415878 26-9775430 8 | NA | NA | 7:41587829-1038978 51 | NA | Manual NA | Manual al/N | Ma nua l | N | CDK6/EGFR | Y CDK6/EGFR | WT Astrocytoma |
| longitudinal | TCGA, TCGA-TM, A7-CF | 1 | succ ess | WGS | 19:24825 15-5602583 9 | NA | 19:2482 S15-5602583 9 | NA | Manual al/N | Ma nua l | N | | N | MUT Astrocytoma |
| longitudinal | TCGA-TM, A7-A7-CF | R | na | WGS | 19:24825 15-5602583 9 | NA | 19:2482 S15-5602583 9 | NA | Manual al/N | Ma nua l | N | | N | MUT Anaplastic Astrocytoma |
| longitudinal | TCGA, TCGA-TQ, A7-RK | 1 | na | WGS | 3:248244 2-2539728 3 | NA | 3:24824 42-2539728 3 | NA | Manual al/N | Ma nua l | N | | N | MUT Oligodendro glioma |
| longitudinal | TCGA, TCGA-TQ-A7, RK-TC | R | succ ess | WGS | 3:248244 2-2539728 3 | NA | 3:24824 42-2539728 3 | NA | Manual al/N | Ma nua l | N | | N | MUT Oligo astrocytoma |
| longitudinal | TCGA, TCGA-TQ, A7-RV | 1 | na | WGS | 10:22460 044-2918837 5 | NA | 10:2246 0044-2918837 5 | NA | Manual al/N | Ma nua l | N | | N | MUT Oligo astrocytoma |

Figure 16:
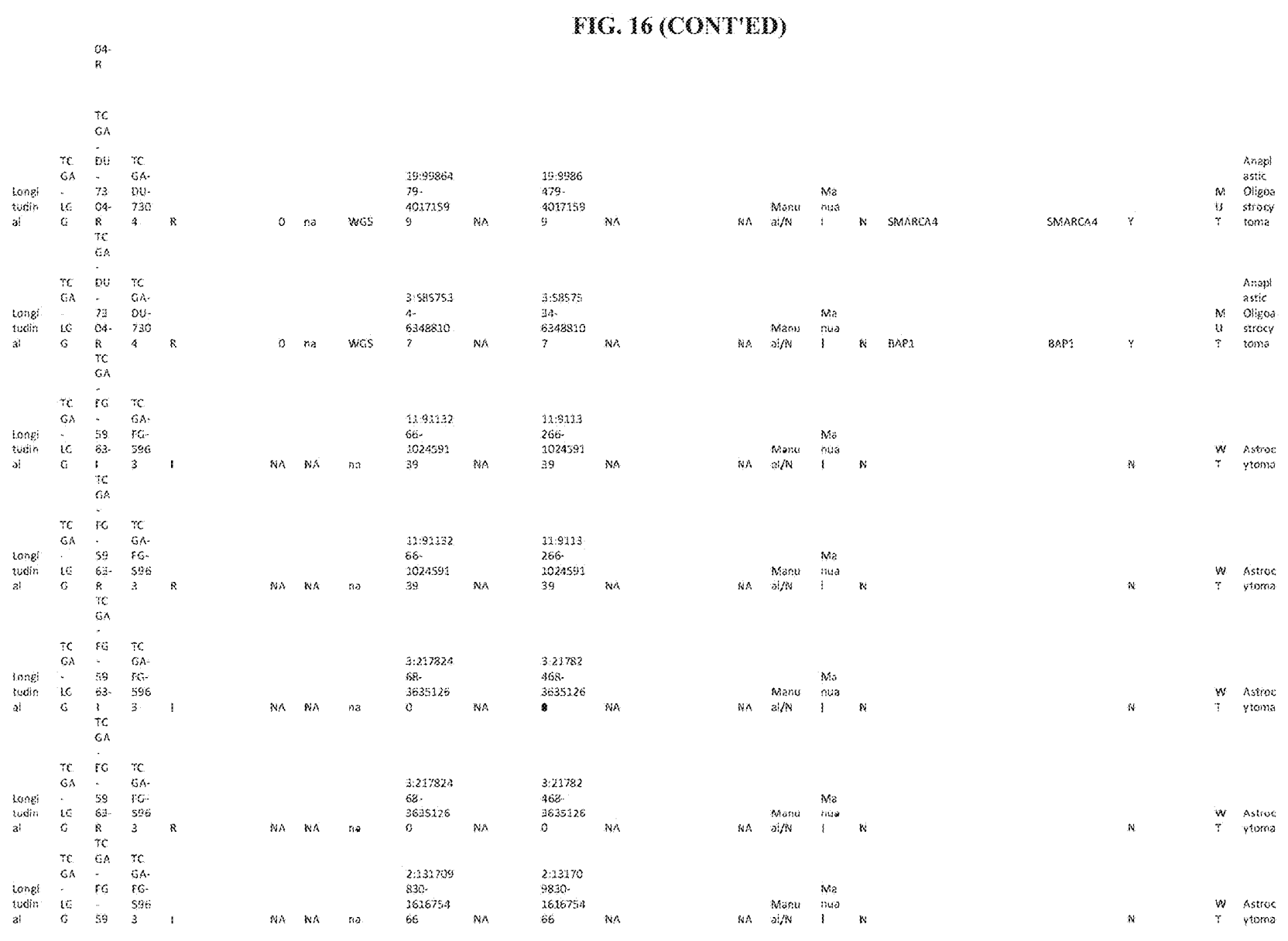

| | | | | | | | | | | | | | |
|---|---|---|---|---|---|---|---|---|---|---|---|---|---|
| Longitudinal | TC GA , LG G | TC GA . LG G | 04- R | R | na | NA | na | WGS | 19.958864 79- 4017159 9 | NA | NA | Manual/N | Ma nual | N | SMARCA4 | SMARCA4 | Y | MD T | Anaplastic Oligoastrocytoma |
| Longitudinal | TC GA , LG G | TC GA . LG G | TC GA . LG G , TC GA . DU- 730 4 | R | na | NA | na | WGS | 19.958 64 79- 4017159 9 | NA | NA | Manual/N | Ma nual | N | | | | | |
| Longitudinal | TC GA , LG G | TC GA . LG G | TC GA . DU- 730 4 | R | na | NA | na | 3.585753 4- 6348810 7 | NA | NA | Manual/N | Ma nual | N | BAP1 | BAP1 | Y | MD T | Anaplastic Oligoastrocytoma |
| Longitudinal | TC GA , FG | TC GA . FG , TC GA . FG- 596 3 | TC GA . FG- 596 3 | - | NA | na | 11.91132 66- 1024591 39 | NA | NA | NA | Manual/N | Mo nual | N | | | N | WT | Astrocytoma |
| Longitudinal | TC GA , FG | TC GA . FG , TC GA . FG- 596 3 | TC GA . FG- 596 3 | R | NA | na | 11.91132 66- 1024591 39 | NA | NA | 11.9113 266- 1024591 39 | NA | Manual/N | Ma nual | N | | | N | WT | Astrocytoma |
| Longitudinal | TC GA , FG | TC GA . FG , TC GA . FG- 596 3 | TC GA . FG- 596 3 | - | NA | na | 3.217824 68- 3635126 0 | NA | NA | 3.21782 468- 3635126 6 | NA | Manual/N | Ms nual | N | | | N | WT | Astrocytoma |
| Longitudinal | TC GA , FG | TC GA . FG , TC GA . FG- 596 3 | TC GA . FG- 596 3 | R | NA | na | 3.217824 68- 3635126 0 | NA | NA | 3.21782 468- 3635126 0 | NA | Manual/N | Ma nual | N | | | N | WT | Astrocytoma |
| Longitudinal | TC GA , FG | TC GA . FG , TC GA . FG- 596 3 | TC GA . FG- 596 3 | - | NA | na | 2.131709 830- 1616754 66 | NA | NA | 2.13170 9830- 1616754 66 | NA | Manual/N | Ma nual | N | | | N | WT | Astrocytoma |

FIG. 16 (CONT'D)

| | | | | | | | | | | | | | | |
|---|---|---|---|---|---|---|---|---|---|---|---|---|---|
| Longitudinal | TCGA-59-63-R, TCGA | TCGA-59-63-R, LG G | R | NA | na | 2:131709830-16167546 | 2:131709830-16167546 | NA | NA | NA | | | WT | Astrocytoma |
| Longitudinal | TCGA-59-63-R, TCGA | TCGA-59-63-R, LG G | I | NA | na | 5:904577 | 5:904577, 4522881 5 | NA | NA | NA | | | WT | Astrocytoma |
| Longitudinal | TCGA-59-63-R, TCGA | TCGA-59-63-R, LG G | R | success | WGS | X:540089 97-54237966 | NA | NA | NA | TERT | TERT | N | Anaplastic Oligodendroglioma |
| hGBM | 29-27-01-03 HF, HF-292 7 | HG 8 M | T5 | 1 | WGS | 7:547298 76-55563124 6 | 7:548292 91-55554176 5 | 228969 | N/AA | EGFR | A A | | N | NA |
| hGBM | 29-27-61-31 HF, HF-292 7 | HG 8 M | NS | 1 | WGS | 7:547298 76-55563124 6 | 7:548292 91-55554176 5 | 712451 | Manual/AA | EGFR | A A | EGFR | Y | NA |
| hGBM | 29-27-60-19 HF, HF-292 7 | HG 8 M | XEN O_3 | 5 | WGS | 7:547298 76-55573843 4 | 7:547932 61-55563124 6 | 683880 | Manual/AA | EGFR | A A | EGFR | Y | NA |
| hGBM | 29-27-60-43 HF, HF-292 7 | HG 8 M | XEN O_2 | 5 | WGS | 7:546994 92-55738843 4 | 7:547298 76-55563124 6 | 947146 | Manual/AA | EGFR | A A | EGFR | Y | NA |
| hGBM | 29-27-60-42 HF, HF-292 7 | HC 8 M | XEN O_3 | 5 | WGS | 7:545695 93-55738843 4 | 7:547298 76-54770025, 7.5.5479 1262- | 1038877 | Manual/AA | EGFR | A A | EGFR | Y | NA |

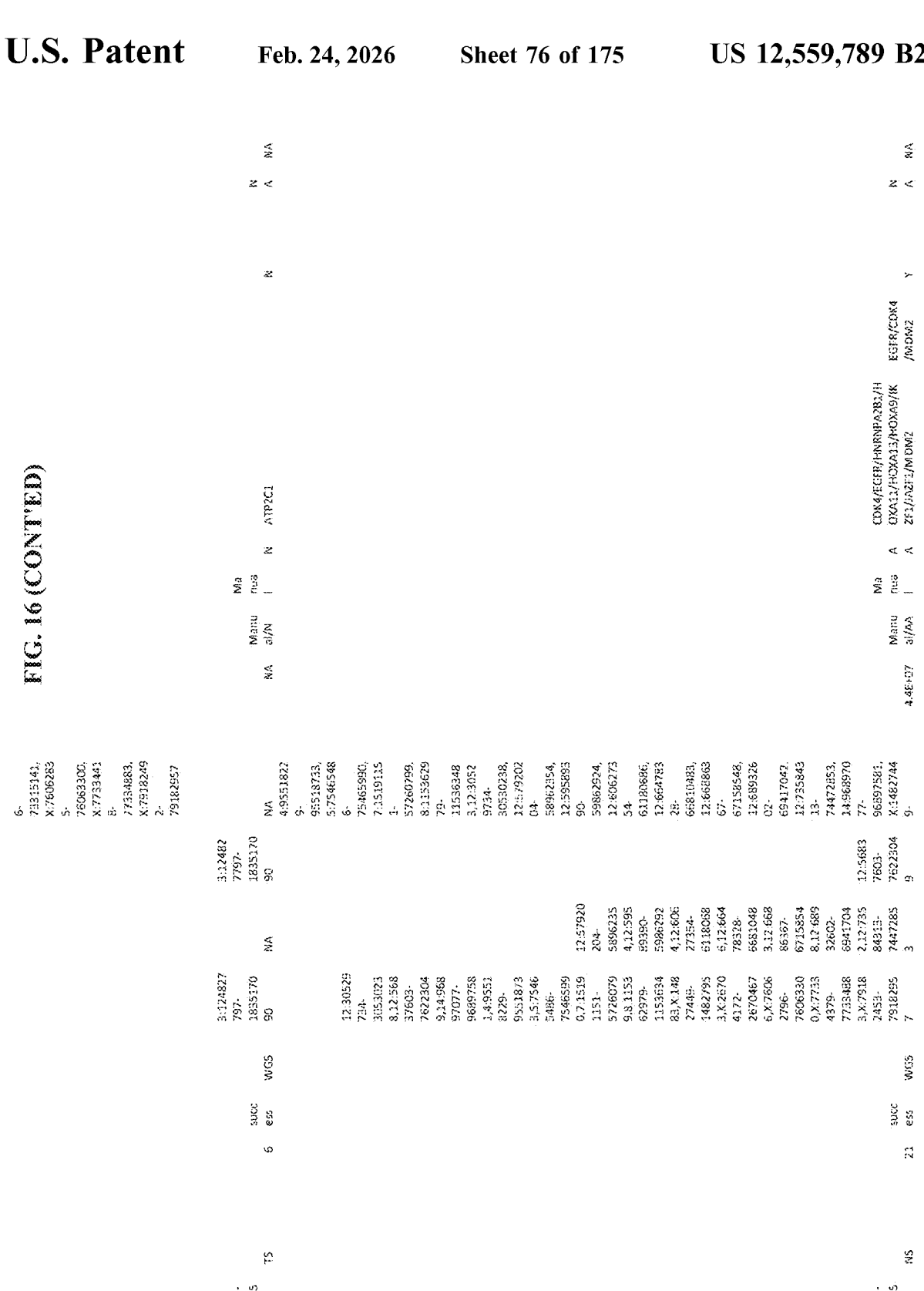
FIG. 16 (CONT'ED)

FIG. 16 (CONT'ED)
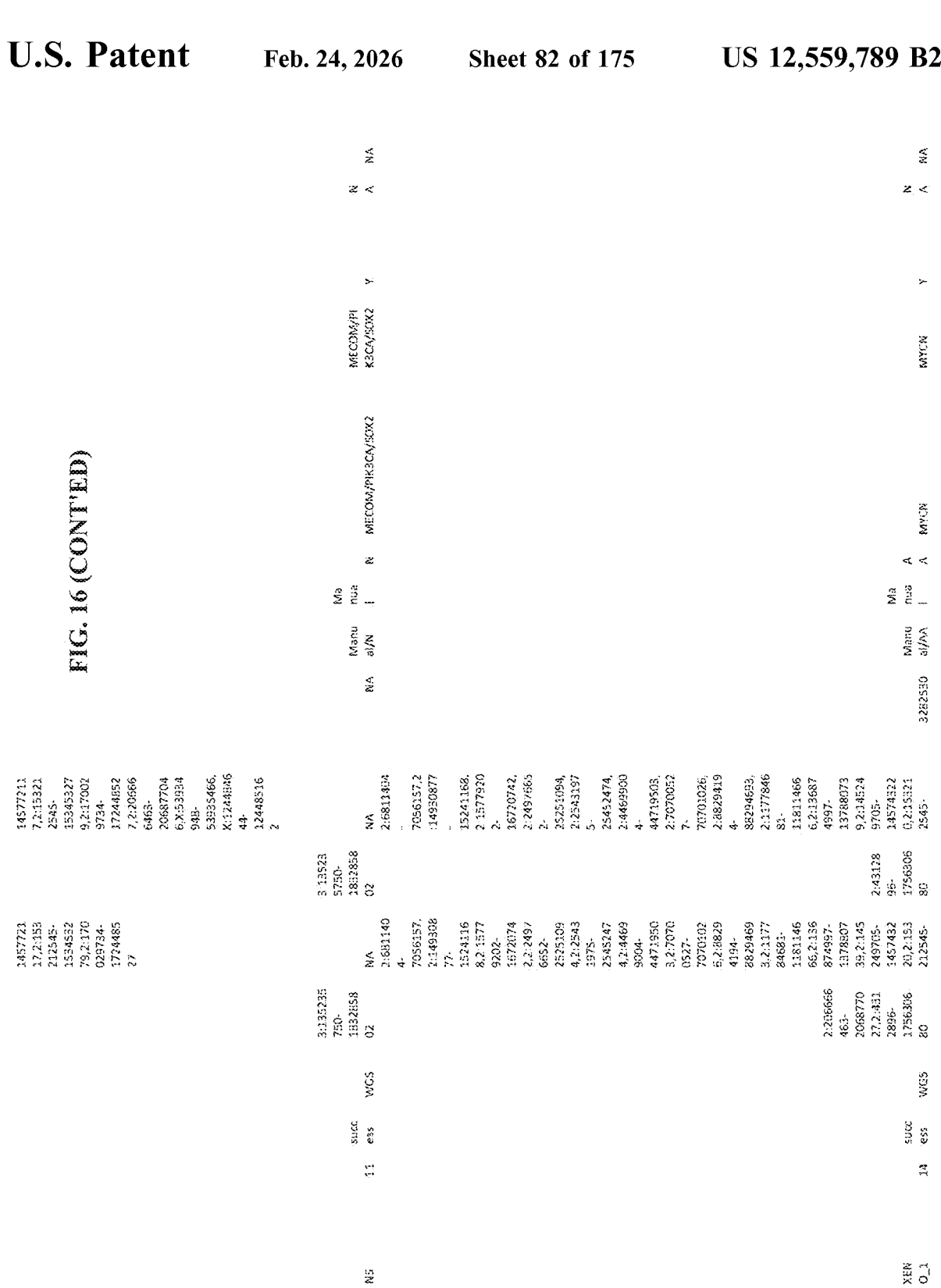

hGBM

| | | | | | | | | | | | | | | |
|---|---|---|---|---|---|---|---|---|---|---|---|---|---|
| H G B M | HF-3016-61-12 | HF-3016 | N 5 | 2 8 | succ ess | W GS | 12:57502937-585625513,12:70496679-70497179,3:117162167-11716767,5:57853483-57853983,7:54728544-55629913,7:57869211-5787428,8:126581168-126601667,8:127009013 | 7.5480910 6-55477598 | 7.547285 44-55629913 | 3:117162167-11716767,5:57853483-57853983,7:54809106-55477598,8:126581168, 1266116676,8:127009013, 132643908,8:13511916 0-136243156,12:5750293 7- | Ma nua l/A A | Man ual | A A | CDK4/DDIT3/EGF R/MYC | MYC/EGFR/CDK 4 | Y | N A A |

132643908,8:135119160
-136243156    585625513,12:70496679
-70497179
3:117162177-
11716767,3:111174081
-
1112745 70,5:57853493    57088
52 hGBM

| HF-3016-60-20 | HF-3016 | XE N O -1 | 1 0 | succ ess | W GS | 12:57503752-585625513,21:233357595-23358085,3:111174081-1112745 70,3:117716277-11716767,5:57853493-57853983,7:54728544-55629913,8:105882036-105882526,8:127399968-13251961689,8:135119160 | 7.5480910 6-55477598 | 7.547285 44-55629913 | 57853983,7:54809106-55477598,8:105882036-105882526,8:127399996 8-132519689,8:13511916 0-136243156,12:5750375 2-585625513,21:233575695-233560085,X:116866170-116866660 | Ma nua l/A A | Man ual | A A | CDK4/DDIT3/EGF R/MYC | MYC/EGFR/CDK 4 | Y | N A A |

13624315 6,X:116866170
-116866660    57088
15 hGBM

| HF-3016-60-41 | HF-3016 | XE N O -2 | 2 0 | succ ess | W GS | 12:57503752-585625513,3:111174081-1112745 83,3:117162261-11716764,7:54728544-55629913,8:126238838-1323086 54,8:135119160-136243156 | 7.5479320 2-555480745 | 7.547285 44-55629913 | 3:117162261-11716764,3:111174081-1112745 83,7:54793202-55548745,8:126238838-1323086 54,8:13511916 0-136243156,12:5750375 2-585625513 | Ma nua l/A A | Man ual | A A | CDK4/DDIT3/EGF R/MYC | MYC/EGFR/CDK 4 | Y | N A A |

Figure 16:
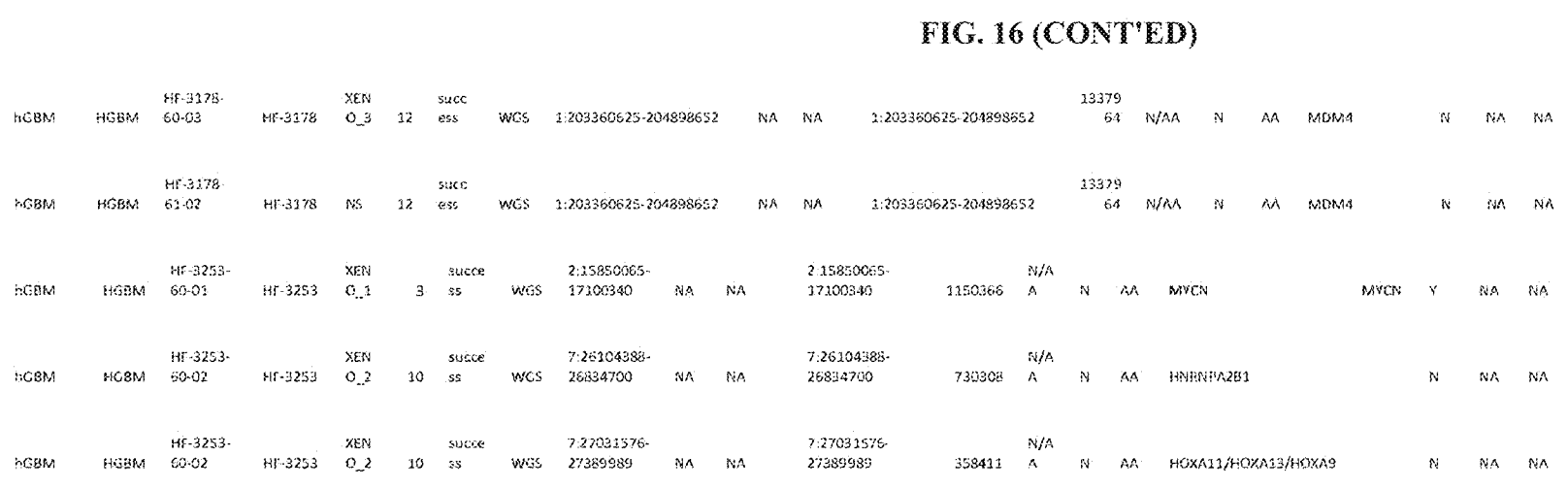

| | | | | | | | | | | | | | | | | | |
|---|---|---|---|---|---|---|---|---|---|---|---|---|---|---|---|---|---|
| HGBM | HF-3178-60-03 | HF-3178 | XEN O_3 | 12 | success | WGS | 1:203360625-204898652 | NA | NA | 1:203360625-204898652 | 13379 64 | N/AA | N | AA | MDM4 | N | NA |
| HGBM | HF-3178-60-02 | HF-3178 | NS | 12 | success | WGS | 1:203360625-204898652 | NA | NA | 1:203360625-204898652 | 13379 64 | N/AA | N | AA | MDM4 | N | NA |
| HGBM | HF-3253-60-01 | HF-3253 | XEN O_1 | 3 | success | WGS | 2:15850065-17100340 | NA | NA | 2:15850065-17100340 | N/A A | N | AA | MYCN | MYCN | Y | NA |
| HGBM | HF-3253-60-02 | HF-3253 | XEN O_2 | 10 | success | WGS | 7:26104388-268347000 | NA | NA | 7:26104388-268347000 | N/A A | N | AA | HNRNPA2B1 | N | NA | |
| HGBM | HF-3253-60-02 | HF-3253 | XEN O_2 | 10 | success | WGS | 7:27031576-273859989 | NA | NA | 7:27031576-273859989 | N/A A | N | AA | HOXA11/HOXA13/HOXA9 | N | NA | |

FIG. 17

TABLE 30 — SAMPLE MAP

| Cohorts_Type | Cohorts | ID | PatientID | SampleType | AA. Number_amp_region | AA.ov_finished | CNV. Data Type | Data Avail. WGL. CNL. WGS | Clinic. Age | Clinic. Censor | Clinic. OS_days | Clinic. PFS_days | Clinic. Time To Secondary Surgery_days | Clinic. Sample Type_Origin of | Clinic. IDH1 | Clinic. Pathology |
|---|---|---|---|---|---|---|---|---|---|---|---|---|---|---|---|---|
| Longitudinal | TCGA-GBM | TCGA-06-0125-I | TCGA-06-0125 | I | 11 | success | CNV-SNP6 | WGS | 63.9 | DEATH | 1448 | 797 | 812 | I | WT | GBM |
| Longitudinal | TCGA-GBM | TCGA-06-0125-R | TCGA-06-0125 | R | 5 | success | CNV-SNP6 | WGS | 63.9 | DEATH | 1448 | 797 | 812 | R | WT | GBM |
| Longitudinal | TCGA-GBM | TCGA-06-0152-I | TCGA-06-0152 | I | 14 | success | CNV-SNP6 | WGS | 68 | DEATH | 373 | 53 | 173 | I | WT | GBM |
| Longitudinal | TCGA-GBM | TCGA-06-0152-R | TCGA-06-0152 | R | 9 | success | CNV-SNP6 | WGS | 68 | DEATH | 373 | 53 | 173 | R | WT | GBM |
| Longitudinal | TCGA-GBM | TCGA-06-0171-I | TCGA-06-0171 | I | 1 | success | CNV-SNP6 | WGS | 65.9 | DEATH | 399 | 117 | 119 | I | WT | GBM |
| Longitudinal | TCGA-GBM | TCGA-06-0171-R | TCGA-06-0171 | R | 0 | na | CNV-SNP6 | WGS | 65.9 | DEATH | 399 | 117 | 119 | R | WT | GBM |
| Longitudinal | TCGA-GBM | TCGA-06-0190-I | TCGA-06-0190 | I | 3 | success | CNV-SNP5 | WGS | 62.5 | DEATH | 317 | 88 | 221 | I | WT | GBM |
| Longitudinal | TCGA-GBM | TCGA-06-0190-R | TCGA-06-0190 | R | 1 | success | CNV-SNP5 | WGS | 62.5 | DEATH | 317 | 88 | 221 | R | WT | GBM |
| Longitudinal | TCGA-GBM | TCGA-06-0210-I | TCGA-06-0210 | I | 13 | success | CNV-SNP5 | WGS | 72.8 | DEATH | 225 | 67 | 67 | I | WT | GBM |
| Longitudinal | TCGA-GBM | TCGA-06-0210-R | TCGA-06-0210 | R | 2 | success | CNV-SNP5 | WGS | 72.8 | DEATH | 225 | 67 | 67 | R | WT | GBM |
| Longitudinal | TCGA-GBM | TCGA-06-0211-I | TCGA-06-0211 | I | 27 | success | CNV-SNP5 | WGS | 48 | DEATH | 360 | 53 | 53 | I | WT | GBM |
| Longitudinal | TCGA-GBM | TCGA-06-0211-R | TCGA-06-0211 | R | 10 | success | CNV-SNP5 | WGS | 48 | DEATH | 360 | 53 | 53 | R | WT | GBM |
| Longitudinal | TCGA-GBM | TCGA-06-0221-I | TCGA-06-0221 | I | 38 | success | CNV-SNP5 | WGS | 31 | DEATH | 603 | 260 | 280 | I | MUT | GBM |
| Longitudinal | TCGA-GBM | TCGA-06-0221-R | TCGA-06-0221 | R | 41 | success | CNV-SNP5 | WGS | 31 | DEATH | 603 | 260 | 280 | R | MUT | GBM |
| Longitudinal | TCGA-GBM | TCGA-14-0736-I | TCGA-14-0736 | I | NA | NA | CNV-SNP5 | na | 49.9 | DEATH | 459 | 127 | 206 | I | WT | GBM |
| Longitudinal | TCGA-GBM | TCGA-14-0736-R | TCGA-14-0736 | R | NA | NA | CNV-SNP5 | na | 49.9 | DEATH | 459 | 127 | 206 | R | WT | GBM |
| Longitudinal | TCGA-GBM | TCGA-14-1034-I | TCGA-14-1034 | I | 1 | success | CNV-SNP5 | WGS | 60.3 | DEATH | 485 | 274 | 448 | I | WT | GBM |
| Longitudinal | TCGA-GBM | TCGA-14-1034-R | TCGA-14-1034 | R | 4 | success | CNV-SNP5 | WGS | 60.3 | DEATH | 485 | 274 | 448 | R | WT | GBM |

FIG. 17 (CONT'ED)

| Type | Cohort | Patient | Sample | P/R | NA | N | Status | Assay | WGS | Age | Event | n1 | n2 | n3 | P/R | Mut | Dx |
|---|---|---|---|---|---|---|---|---|---|---|---|---|---|---|---|---|---|
| Longitudinal | TCGA-GBM | TCGA-14-1402 | TCGA-14-1402-I | ~ | | 13 | success | CNV-SNP6 | WGS | 58.6 | DEATH | 97 | 333 | 867 | ~ | WT | GBM |
| Longitudinal | TCGA-GBM | TCGA-14-1402 | TCGA-14-1402-R | R | | 6 | success | CNV-SNP6 | WGS | 58.6 | DEATH | 4 | 333 | 867 | R | WT | GBM |
| Longitudinal | TCGA-GBM | TCGA-19-0957 | TCGA-19-0957-I | ~ | NA | | NA | CNV-SNP6 | na | 48.5 | DEATH | 66 | 50 | 413 | ~ | WT | GBM |
| Longitudinal | TCGA-GBM | TCGA-19-0957 | TCGA-19-0957-R | R | NA | | NA | CNV-SNP6 | na | 48.5 | DEATH | 5 | 50 | 413 | R | WT | GBM |
| Longitudinal | TCGA-GBM | TCGA-19-1389 | TCGA-19-1389-I | ~ | | 1 | success | CNV-SNP6 | WGS | 51.1 | DEATH | 65 | 81 | 81 | ~ | WT | GBM |
| Longitudinal | TCGA-GBM | TCGA-19-1389 | TCGA-19-1389-R | R | | 3 | success | CNV-SNP6 | WGS | 51.1 | DEATH | 5 | 81 | 81 | R | WT | GBM |
| Longitudinal | TCGA-GBM | TCGA-19-4065 | TCGA-19-4065-I | ~ | NA | | NA | CNV-SNP6 | na | 36 | DEATH | 14 | 70 | 70 | ~ | WT | GBM |
| Longitudinal | TCGA-GBM | TCGA-19-4065 | TCGA-19-4065-R | R | NA | | NA | CNV-SNP6 | na | 36 | DEATH | 1 | 70 | 70 | R | WT | GBM |
| Longitudinal | HF | HF2548 | HF2548-R | R | NA | | NA | CNV-SNP6 | na | 52.5 | DEATH | 14 | 697 | 984 | R | WT | GBM |
| Longitudinal | HF | HF2919 | HF2919-I | ~ | NA | | NA | CNV-SNP6 | na | 64 | DEATH | 1 | 259 | 352 | ~ | WT | GBM |
| Longitudinal | HF | HF2934 | HF2934-I | ~ | NA | | NA | CNV-SNP6 | na | 46.4 | DEATH | 43 | 93 | 196 | ~ | WT | GBM |
| Longitudinal | HF | HF2829 | HF2829-R | R | NA | | NA | CNV-SNP6 | na | 44.5 | DEATH | 0 | 328 | 339 | R | WT | GBM |
| Longitudinal | HF | HF2869 | HF2869-R | R | NA | | NA | CNV-SNP6 | na | 35 | DEATH | 43 | 2314 | 310 | R | WT | GBM |
| Longitudinal | HF | HF2998 | HF2998-I | ~ | NA | | NA | CNV-SNP6 | na | 67 | DEATH | 0 | 39 | 24 | ~ | WT | GBM |
| Longitudinal | HF | HF2998 | HF2998-R | R | NA | | NA | CNV-SNP6 | na | 67 | DEATH | 12 | 39 | 24 | R | WT | GBM |
| Longitudinal | HF | HF2934 | HF2934-R | R | NA | | NA | CNV-SNP6 | na | 46.4 | DEATH | 27 | 93 | 196 | R | WT | GBM |
| Longitudinal | HF | HF3050 | HF3050-I | ~ | NA | | NA | CNV-SNP6 | na | 63.7 | DEATH | 56 | 465 | 490 | ~ | WT | GBM |
| Longitudinal | HF | HF2919 | HF2919-R | R | NA | | NA | CNV-SNP6 | na | 64 | DEATH | 1 | 259 | 352 | R | MUT | GBM |
| Longitudinal | HF | HF3081 | HF3081-I | ~ | NA | | NA | CNV-SNP6 | na | 62 | DEATH | 50 | 711 | 242 | ~ | WT | GBM |
| Longitudinal | HF | HF3118 | HF3118-I | ~ | NA | | NA | CNV-SNP6 | na | 67.1 | DEATH | 0 | 151 | 176 | ~ | WT | GBM |
| Longitudinal | HF | HF3162 | HF3162-I | ~ | NA | | NA | CNV-SNP6 | na | 52.3 | DEATH | 40 | 208 | 232 | ~ | WT | GBM |
| Longitudinal | HF | HF3081 | HF3081-R | R | NA | | NA | CNV-SNP6 | na | 62 | DEATH | 3 | 711 | 242 | R | MUT | GBM |
| Longitudinal | HF | HF3118 | HF3118-R | R | NA | | NA | CNV-SNP6 | na | 67.1 | DEATH | 42 | 151 | 176 | R | WT | GBM |
| Longitudinal | HF | HF3162 | HF3162-R | R | NA | | NA | CNV-SNP6 | na | 52.3 | DEATH | 56 | 208 | 232 | R | WT | GBM |
| Longitudinal | HF | HF3050 | HF3050-R | R | NA | | NA | CNV-SNP6 | na | 63.7 | DEATH | 13 | 465 | 490 | R | WT | GBM |

FIG. 17 (CONT'ED)

| Type | Group | ID | Accession | Marker | NA/Count | Result | CNV method | WGS | Age | Status | A | B | C | D | Marker | Mut | Diagnosis |
|---|---|---|---|---|---|---|---|---|---|---|---|---|---|---|---|---|---|
| Longitudinal | HF | HF2548-1 | | - | NA | NA | CNV-SNP6 | na | 52.5 | DEATH | 12 | 27 | 697 | 984 | - | WT | GBM |
| Longitudinal | HF | HF2829-1 | | - | NA | NA | CNV-SNP6 | na | 44.5 | DEATH | 40 | 3 | 328 | 339 | - | WT | GBM |
| Longitudinal | HF | HF2869-1 | | - | NA | NA | CNV-SNP6 | na | 35 | DEATH | 42 | 56 | 2314 | 310 | - | WT | GBM |
| Longitudinal | MDACC-GBM | 1016844-R | 1016844 | R | 7 | success | CNV-WGLP | WGS | 49 | ALIVE | 30 | 0 | NA | 118 | R | WT | Recurrent Glioblastoma |
| Longitudinal | MDACC-GBM | 1016844-1 | 1016844 | - | 7 | success | CNV-WGLP | WGS | 49 | ALIVE | 30 | 0 | NA | 118 | - | WT | GLIOBLASTOMA |
| Longitudinal | MDACC-GBM | 648849-R | 648849 | R | 2 | failed | CNV-WGLP | WGS | 42 | ALIVE | 31 | 81 | NA | 2500 | R | WT | Recurrent Glioblastoma |
| Longitudinal | MDACC-GBM | 648849-1 | 648849 | - | 2 | failed | CNV-WGLP | WGS | 42 | ALIVE | 31 | 81 | NA | 2500 | - | WT | GLIOBLASTOMA |
| Longitudinal | MDACC-GBM | 853595-1 | 853595 | - | 2 | success | CNV-WGLP | WGS | 45 | ALIVE | 11 | 83 | NA | 566 | - | WT | GLIOBLASTOMA |
| Longitudinal | MDACC-GBM | 853595-R | 853595 | R | 1 | success | CNV-WGLP | WGS | 45 | ALIVE | 11 | 83 | NA | 566 | R | WT | Recurrent Glioblastoma and necrosis |
| Longitudinal | MDACC-GBM | 917962-1 | 917962 | - | 0 | na | CNV-WGLP | WGS | 60 | DEATH | 57 | 6 | NA | 258 | - | WT | GLIOBLASTOMA |
| Longitudinal | MDACC-GBM | 917962-R | 917962 | R | 0 | na | CNV-WGLP | WGS | 60 | DEATH | 57 | 6 | NA | 258 | R | WT | GLIOBLASTOMA |
| Longitudinal | MDACC-GBM | 920174-R | 920174 | R | 4 | success | CNV-WGLP | WGS | 49 | ALIVE | 68 | 1 | NA | 38 | R | na | GLIOBLASTOMA |
| Longitudinal | MDACC-GBM | 920174-1 | 920174 | - | 4 | success | CNV-WGLP | WGS | 49 | ALIVE | 68 | 1 | NA | 38 | - | na | GLIOBLASTOMA |
| Longitudinal | MDACC-GBM | 921907-R | 921907 | R | 1 | success | CNV-WGLP | WGS | 59 | DEATH | 56 | 7 | NA | 113 | R | na | Recurrent Glioblastoma |
| Longitudinal | MDACC-GBM | 921907-1 | 921907 | - | 3 | success | CNV-WGLP | WGS | 59 | DEATH | 56 | 7 | NA | 113 | - | na | GLIOBLASTOMA |
| Longitudinal | MDACC-GBM | 927497-R | 927497 | R | 0 | na | CNV-WGLP | WGS | 53 | ALIVE | 35 | 6 | NA | 135 | R | na | necrosis with gliosis and infiltrating tumor cells |
| Longitudinal | MDACC-GBM | 927497-1 | 927497 | - | 0 | na | CNV-WGLP | WGS | 53 | ALIVE | 35 | 6 | NA | 135 | - | na | GLIOBLASTOMA |
| Longitudinal | SMC | SMC.CC-05-1 | SMC.CC-05 | - | NA | NA | CNV-aCGH | na | 70 | ALIVE | 14 | 90 | 1129 | NA | - | WT | GBM |

Figure 17:
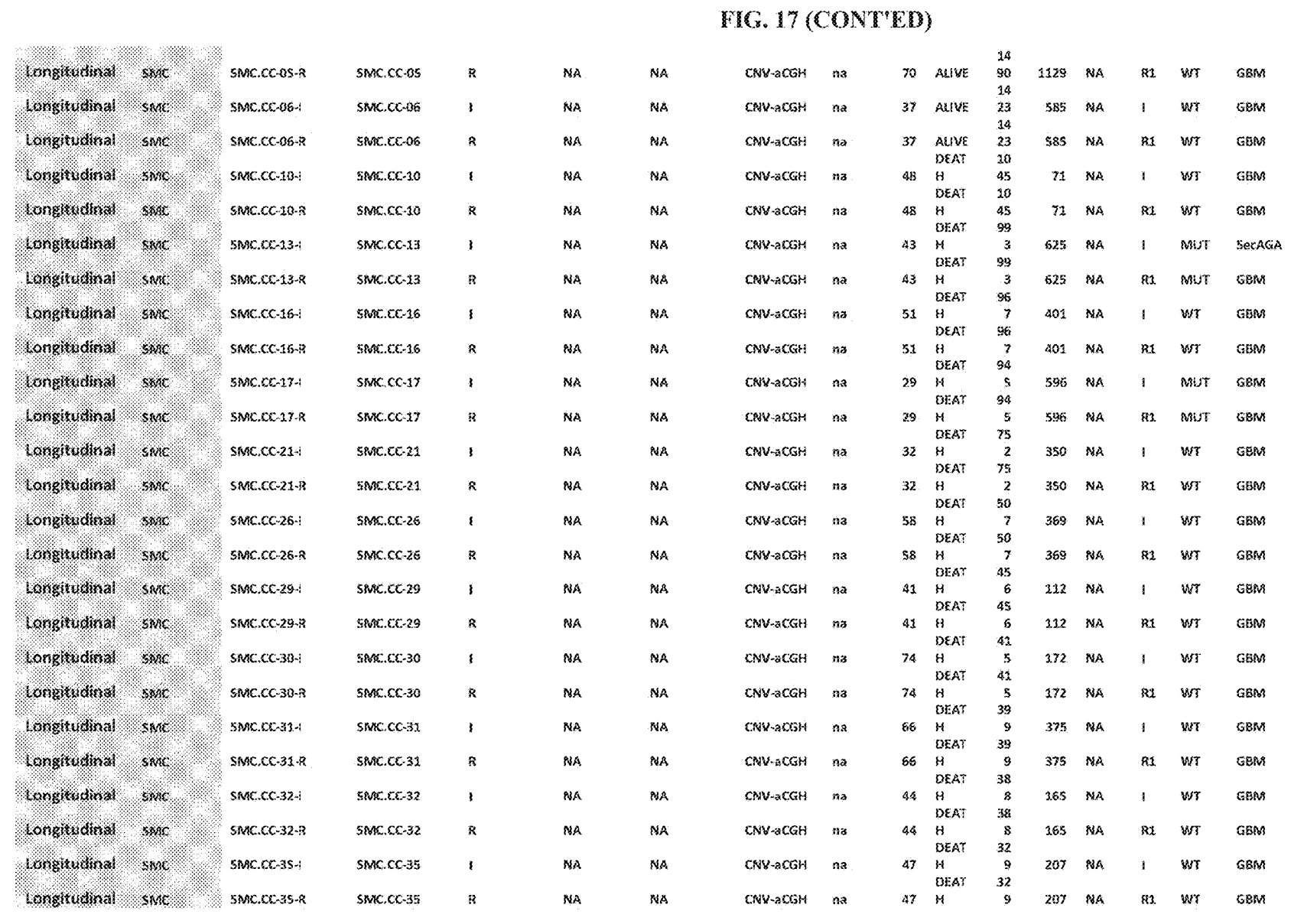

FIG. 17 (CONT'ED)

| | | | | | | | | | | | | | | | | |
|---|---|---|---|---|---|---|---|---|---|---|---|---|---|---|---|---|
| Longitudinal | SMC | SMC.CC-05-R | SMC.CC-05 | R | NA | NA | CNV-aCGH | na | 70 | ALIVE | 14 | 1129 | NA | R1 | WT | GBM |
| Longitudinal | SMC | SMC.CC-06-I | SMC.CC-06 | l | NA | NA | CNV-aCGH | na | 37 | ALIVE | 90 | 585 | NA | - | WT | GBM |
| Longitudinal | SMC | SMC.CC-06-R | SMC.CC-06 | R | NA | NA | CNV-aCGH | na | 37 | ALIVE | 14 | 585 | NA | R1 | WT | GBM |
| Longitudinal | SMC | SMC.CC-10-I | SMC.CC-10 | l | NA | NA | CNV-aCGH | na | 48 | DEATH | 23 | 71 | NA | - | WT | GBM |
| Longitudinal | SMC | SMC.CC-10-R | SMC.CC-10 | R | NA | NA | CNV-aCGH | na | 48 | DEATH | 14 | 71 | NA | R1 | WT | GBM |
| Longitudinal | SMC | SMC.CC-13-I | SMC.CC-13 | l | NA | NA | CNV-aCGH | na | 43 | DEATH | 23 | 625 | NA | - | MUT | SecAGA |
| Longitudinal | SMC | SMC.CC-13-R | SMC.CC-13 | R | NA | NA | CNV-aCGH | na | 43 | DEATH | 10 | 625 | NA | R1 | MUT | GBM |
| Longitudinal | SMC | SMC.CC-16-I | SMC.CC-16 | l | NA | NA | CNV-aCGH | na | 51 | DEATH | 45 | 401 | NA | - | WT | GBM |
| Longitudinal | SMC | SMC.CC-16-R | SMC.CC-16 | R | NA | NA | CNV-aCGH | na | 51 | DEATH | 10 | 401 | NA | R1 | WT | GBM |
| Longitudinal | SMC | SMC.CC-17-I | SMC.CC-17 | l | NA | NA | CNV-aCGH | na | 29 | DEATH | 45 | 596 | NA | - | MUT | GBM |
| Longitudinal | SMC | SMC.CC-17-R | SMC.CC-17 | R | NA | NA | CNV-aCGH | na | 29 | DEATH | 99 | 596 | NA | R1 | MUT | GBM |
| Longitudinal | SMC | SMC.CC-21-I | SMC.CC-21 | l | NA | NA | CNV-aCGH | na | 32 | DEATH | 3 | 350 | NA | - | WT | GBM |
| Longitudinal | SMC | SMC.CC-21-R | SMC.CC-21 | R | NA | NA | CNV-aCGH | na | 32 | DEATH | 75 | 350 | NA | R1 | WT | GBM |
| Longitudinal | SMC | SMC.CC-26-I | SMC.CC-26 | l | NA | NA | CNV-aCGH | na | 58 | DEATH | 2 | 369 | NA | - | WT | GBM |
| Longitudinal | SMC | SMC.CC-26-R | SMC.CC-26 | R | NA | NA | CNV-aCGH | na | 58 | DEATH | 50 | 369 | NA | R1 | WT | GBM |
| Longitudinal | SMC | SMC.CC-29-I | SMC.CC-29 | l | NA | NA | CNV-aCGH | na | 41 | DEATH | 7 | 112 | NA | - | WT | GBM |
| Longitudinal | SMC | SMC.CC-29-R | SMC.CC-29 | R | NA | NA | CNV-aCGH | na | 41 | DEATH | 50 | 112 | NA | R1 | WT | GBM |
| Longitudinal | SMC | SMC.CC-30-I | SMC.CC-30 | l | NA | NA | CNV-aCGH | na | 74 | DEATH | 7 | 172 | NA | - | WT | GBM |
| Longitudinal | SMC | SMC.CC-30-R | SMC.CC-30 | R | NA | NA | CNV-aCGH | na | 74 | DEATH | 45 | 172 | NA | R1 | WT | GBM |
| Longitudinal | SMC | SMC.CC-31-I | SMC.CC-31 | l | NA | NA | CNV-aCGH | na | 66 | DEATH | 6 | 375 | NA | - | WT | GBM |
| Longitudinal | SMC | SMC.CC-31-R | SMC.CC-31 | R | NA | NA | CNV-aCGH | na | 66 | DEATH | 45 | 375 | NA | R1 | WT | GBM |
| Longitudinal | SMC | SMC.CC-32-I | SMC.CC-32 | l | NA | NA | CNV-aCGH | na | 44 | DEATH | 6 | 165 | NA | - | WT | GBM |
| Longitudinal | SMC | SMC.CC-32-R | SMC.CC-32 | R | NA | NA | CNV-aCGH | na | 44 | DEATH | 41 | 165 | NA | R1 | WT | GBM |
| Longitudinal | SMC | SMC.CC-35-I | SMC.CC-35 | l | NA | NA | CNV-aCGH | na | 47 | DEATH | 5 | 207 | NA | - | WT | GBM |
| Longitudinal | SMC | SMC.CC-35-R | SMC.CC-35 | R | NA | NA | CNV-aCGH | na | 47 | DEATH | 41 | 207 | NA | R1 | WT | GBM |

FIG. 17 (CONT'D)

| | | | | | | | CNV type | | age | vital | | | | | mut | tumor type |
|---|---|---|---|---|---|---|---|---|---|---|---|---|---|---|---|---|
| Longitudinal | SMC | SMC.CC-3B | SMC.CC-3B-I | - | NA | NA | CNV-aCGH | na | 52 | DEATH | 21 06 | 175 | NA | - | WT | GBM |
| Longitudinal | SMC | SMC.CC-3B | SMC.CC-3B-R | R | NA | NA | CNV-aCGH | na | 52 | DEATH | 21 06 | 175 | NA | R1 | WT | GBM |
| Longitudinal | TCGA-LGG | TCGA-DH-A669 | TCGA-DH-A669-I | - | | success 1 | CNV-SNP6 | WGS | 70 | DEATH | 91 09 | 425 | 425 | - | MUT | Oligodendroglioma |
| Longitudinal | TCGA-LGG | TCGA-DH-A669 | TCGA-DH-A669-R | R | | success 3 | CNV-SNP6 | WGS | 70 | DEATH | 91 09 | 425 | 425 | R | MUT | Anaplastic oligo |
| Longitudinal | TCGA-LGG | TCGA-DU-5870 | TCGA-DU-5870-I | - | | success 9 | CNV-SNP6 | WGS | 34 | ALIVE | 67 48 | 4437 | 4437 | - | MUT | Oligodendroglioma |
| Longitudinal | TCGA-LGG | TCGA-DU-5870 | TCGA-DU-5870-R | R | | success 3 | CNV-SNP6 | WGS | 34 | ALIVE | 67 48 | 4437 | 4437 | R | MUT | Anaplastic oligodendroglioma |
| Longitudinal | TCGA-LGG | TCGA-DU-5872 | TCGA-DU-5872-I | - | | na 0 | CNV-SNP6 | WGS | 43 | ALIVE | 16 30 | 283 | 283 | - | MUT | Oligoastrocytoma |
| Longitudinal | TCGA-LGG | TCGA-DU-5872 | TCGA-DU-5872-R | R | | success 1 | CNV-SNP6 | WGS | 43 | ALIVE | 16 30 | 283 | 283 | R1 | MUT | Oligodendroglioma |
| Longitudinal | TCGA-LGG | TCGA-DU-6397 | TCGA-DU-6397-I | ~ | | success 2 | CNV-SNP6 | WGS | 45 | DEATH | 14 01 | 837 | 837 | - | MUT | Anaplastic oligodendroglioma |
| Longitudinal | TCGA-LGG | TCGA-DU-6397 | TCGA-DU-6397-R | R | | success 9 | CNV-SNP6 | WGS | 45 | DEATH | 14 01 | 837 | 837 | R | MUT | Oligodendroglioma |
| Longitudinal | TCGA-LGG | TCGA-DU-6404 | TCGA-DU-6404-I | - | | na 0 | CNV-SNP6 | WGS | 24 | DEATH | 40 68 | 1194 | 1194 | - | WT | Atypical Oligodendroglioma |
| Longitudinal | TCGA-LGG | TCGA-DU-6404 | TCGA-DU-6404-R | R | | failed 10 | CNV-SNP6 | WGS | 24 | DEATH | 40 68 | 1194 | 1194 | R1 | WT | Oligodendroglioma |
| Longitudinal | TCGA-LGG | TCGA-DU-6407 | TCGA-DU-6407-I | - | | na 0 | CNV-SNP6 | WGS | 35 | DEATH | 28 75 | 2415 | 2415 | - | MUT | Oligodendroglioma |
| Longitudinal | TCGA-LGG | TCGA-DU-6407 | TCGA-DU-6407-R | R | | success 4 | CNV-SNP6 | WGS | 35 | DEATH | 28 75 | 2415 | 2415 | R1 | MUT | Oligoastrocytoma |
| Longitudinal | TCGA-LGG | TCGA-DU-7304 | TCGA-DU-7304-I | - | | success 1 | CNV-SNP6 | WGS | 43 | DEATH | 70 09 | 332 | 332 | - | MUT | Oligoastrocytoma |
| Longitudinal | TCGA-LGG | TCGA-DU-7304 | TCGA-DU-7304-R | R | NA | na 0 | CNV-SNP6 | WGS | 43 | DEATH | 70 09 | 332 | 332 | R | MUT | Anaplastic Oligoastrocytoma |
| Longitudinal | TCGA-LGG | TCGA-FG-5963 | TCGA-FG-5963-I | - | NA | NA | CNV-SNP5 | na | 23 | DEATH | 81 06 | 436 | 436 | - | WT | Astrocytoma |
| Longitudinal | TCGA-LGG | TCGA-FG-5963 | TCGA-FG-5963-R | R | NA | NA | CNV-SNP6 | na | 23 | DEATH | 81 06 | 436 | 436 | R1 | WT | Astrocytoma |
| Longitudinal | TCGA-LGG | TCGA-FG-5965 | TCGA-FG-5965-I | - | | na 0 | CNV-SNP6 | WGS | 39 | DEATH | 11 20 | 765 | 765 | - | MUT | Oligoastrocytoma |

Figure 17:
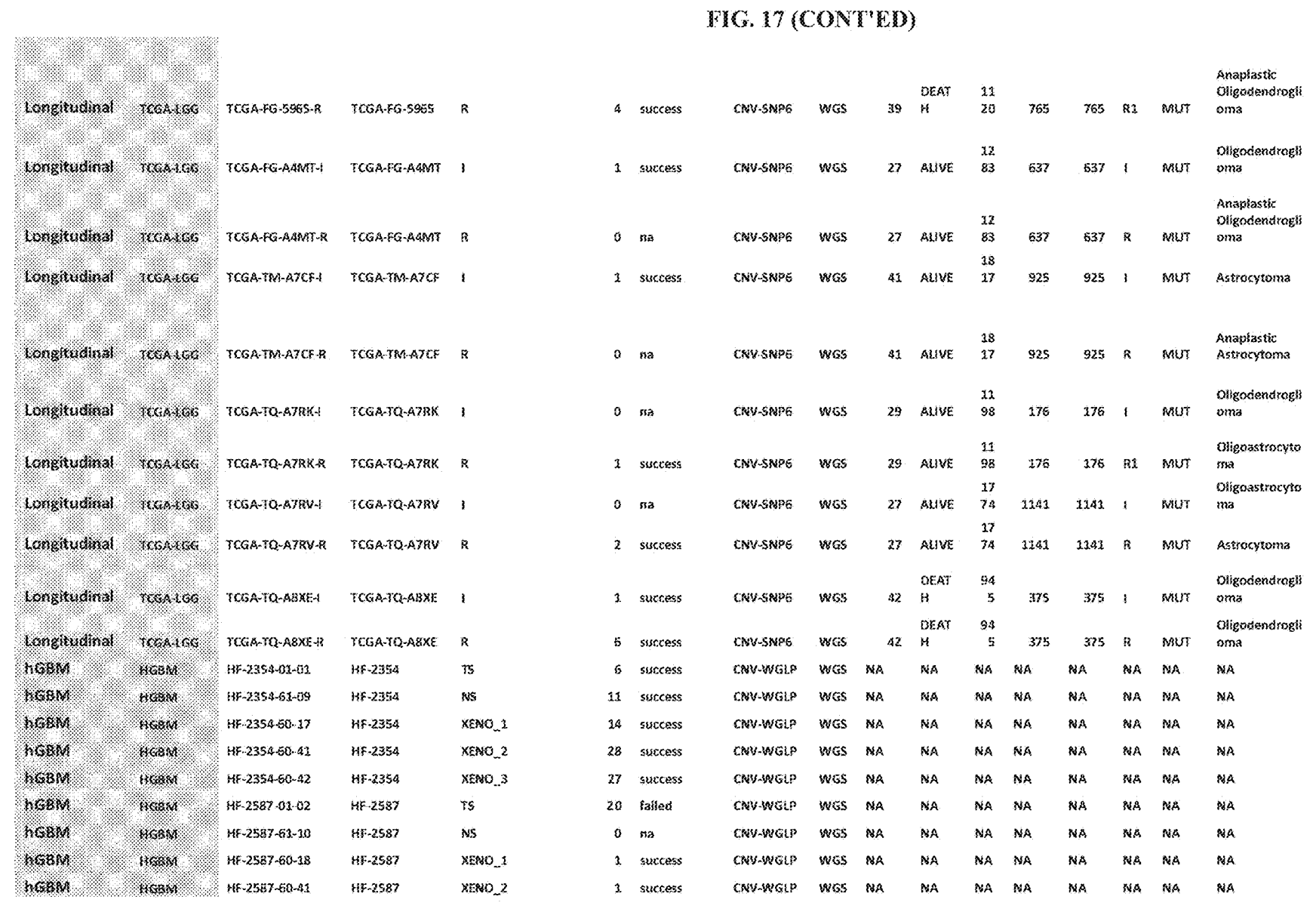

FIG. 17 (CONT'ED)

| Type | Cohort | Sample | | Sample ID | # | Status | CNV | WGS | # | Vital | # | # | # | | MUT | Diagnosis |
|---|---|---|---|---|---|---|---|---|---|---|---|---|---|---|---|---|
| Longitudinal | TCGA-LGG | TCGA-FG-5965 | R | TCGA-FG-5965-R | 4 | success | CNV-SNP6 | WGS | 39 | DEATH | 11/20 | 765 | 765 | R1 | MUT | Anaplastic Oligodendroglioma |
| Longitudinal | TCGA-LGG | TCGA-FG-A4MT | - | TCGA-FG-A4MT-I | 1 | success | CNV-SNP6 | WGS | 27 | ALIVE | 12/83 | 637 | 637 | - | MUT | Oligodendroglioma |
| Longitudinal | TCGA-LGG | TCGA-FG-A4MT-R | R | TCGA-FG-A4MT-R | 0 | na | CNV-SNP6 | WGS | 27 | ALIVE | 12/83 | 637 | 637 | R | MUT | Anaplastic Oligodendroglioma |
| Longitudinal | TCGA-LGG | TCGA-TM-A7CF | - | TCGA-TM-A7CF-I | 1 | success | CNV-SNP6 | WGS | 41 | ALIVE | 18/17 | 925 | 925 | - | MUT | Astrocytoma |
| Longitudinal | TCGA-LGG | TCGA-TM-A7CF-R | R | TCGA-TM-A7CF-R | 0 | na | CNV-SNP6 | WGS | 41 | ALIVE | 18/17 | 925 | 925 | R | MUT | Anaplastic Astrocytoma |
| Longitudinal | TCGA-LGG | TCGA-TQ-A7RK | - | TCGA-TQ-A7RK-I | 0 | na | CNV-SNP6 | WGS | 29 | ALIVE | 11/98 | 176 | 176 | - | MUT | Oligodendroglioma |
| Longitudinal | TCGA-LGG | TCGA-TQ-A7RK-R | R | TCGA-TQ-A7RK-R | 1 | success | CNV-SNP6 | WGS | 29 | ALIVE | 11/98 | 176 | 176 | R1 | MUT | Oligoastrocytoma |
| Longitudinal | TCGA-LGG | TCGA-TQ-A7RV | - | TCGA-TQ-A7RV-I | 0 | na | CNV-SNP6 | WGS | 27 | ALIVE | 17/74 | 1141 | 1141 | - | MUT | Oligoastrocytoma |
| Longitudinal | TCGA-LGG | TCGA-TQ-A7RV-R | R | TCGA-TQ-A7RV-R | 2 | success | CNV-SNP6 | WGS | 27 | ALIVE | 17/74 | 1141 | 1141 | R | MUT | Astrocytoma |
| Longitudinal | TCGA-LGG | TCGA-TQ-A8XE | - | TCGA-TQ-A8XE-I | 1 | success | CNV-SNP6 | WGS | 42 | DEATH | 94/5 | 375 | 375 | - | MUT | Oligodendroglioma |
| Longitudinal | TCGA-LGG | TCGA-TQ-A8XE-R | R | TCGA-TQ-A8XE-R | 5 | success | CNV-SNP6 | WGS | 42 | DEATH | 94/5 | 375 | 375 | R | MUT | Oligodendroglioma |
| hGBM | hGBM | HF-2354 | TS | HF-2354-01-01 | 6 | success | CNV-WGLP | WGS | NA | NA | NA | NA | NA | NA | NA | NA |
| hGBM | hGBM | HF-2354 | NS | HF-2354-61-09 | 11 | success | CNV-WGLP | WGS | NA | NA | NA | NA | NA | NA | NA | NA |
| hGBM | hGBM | HF-2354 | XENO_1 | HF-2354-60-17 | 14 | success | CNV-WGLP | WGS | NA | NA | NA | NA | NA | NA | NA | NA |
| hGBM | hGBM | HF-2354 | XENO_2 | HF-2354-60-41 | 28 | success | CNV-WGLP | WGS | NA | NA | NA | NA | NA | NA | NA | NA |
| hGBM | hGBM | HF-2354 | XENO_3 | HF-2354-60-42 | 27 | success | CNV-WGLP | WGS | NA | NA | NA | NA | NA | NA | NA | NA |
| hGBM | hGBM | HF-2587 | TS | HF-2587-01-02 | 20 | failed | CNV-WGLP | WGS | NA | NA | NA | NA | NA | NA | NA | NA |
| hGBM | hGBM | HF-2587 | NS | HF-2587-61-10 | 0 | na | CNV-WGLP | WGS | NA | NA | NA | NA | NA | NA | NA | NA |
| hGBM | hGBM | HF-2587 | XENO_1 | HF-2587-60-18 | 1 | success | CNV-WGLP | WGS | NA | NA | NA | NA | NA | NA | NA | NA |
| hGBM | hGBM | HF-2587 | XENO_2 | HF-2587-60-41 | 1 | success | CNV-WGLP | WGS | NA | NA | NA | NA | NA | NA | NA | NA |

FIG. 17 (CONT'ED)

| | | | | | | | | | | | | | | | | | |
|---|---|---|---|---|---|---|---|---|---|---|---|---|---|---|---|---|---|
| HGBM | HGBM | HF-2587-60-42 | HF-2587 | XENO_3 | 1 | success | CNV-WGLP | WGS | NA | NA | NA | NA | NA | NA | NA | NA | NA |
| HGBM | HGBM | HF-2927-01-03 | HF-2927 | TS | 1 | success | CNV-WGLP | WGS | NA | NA | NA | NA | NA | NA | NA | NA | NA |
| HGBM | HGBM | HF-2927-61-11 | HF-2927 | NS | 1 | success | CNV-WGLP | WGS | NA | NA | NA | NA | NA | NA | NA | NA | NA |
| HGBM | HGBM | HF-2927-60-19 | HF-2927 | XENO_1 | 5 | success | CNV-WGLP | WGS | NA | NA | NA | NA | NA | NA | NA | NA | NA |
| HGBM | HGBM | HF-2927-60-41 | HF-2927 | XENO_2 | 5 | success | CNV-WGLP | WGS | NA | NA | NA | NA | NA | NA | NA | NA | NA |
| HGBM | HGBM | HF-2927-60-42 | HF-2927 | XENO_3 | 5 | success | CNV-WGLP | WGS | NA | NA | NA | NA | NA | NA | NA | NA | NA |
| HGBM | HGBM | HF-3035-01-06 | HF-3035 | TS | 3 | success | CNV-WGLP | WGS | NA | NA | NA | NA | NA | NA | NA | NA | NA |
| HGBM | HGBM | HF-3035-61-14 | HF-3035 | NS | 0 | na | CNV-WGLP | WGS | NA | NA | NA | NA | NA | NA | NA | NA | NA |
| HGBM | HGBM | HF-3035-60-22 | HF-3035 | XENO_1 | 4 | success | CNV-WGLP | WGS | NA | NA | NA | NA | NA | NA | NA | NA | NA |
| HGBM | HGBM | HF-3035-60-41 | HF-3035 | XENO_2 | 4 | success | CNV-WGLP | WGS | NA | NA | NA | NA | NA | NA | NA | NA | NA |
| HGBM | HGBM | HF-3035-60-42 | HF-3035 | XENO_3 | 3 | success | CNV-WGLP | WGS | NA | NA | NA | NA | NA | NA | NA | NA | NA |
| HGBM | HGBM | HF-3055-01-37 | HF-3055 | TS | 21 | success | CNV-WGLP | WGS | NA | NA | NA | NA | NA | NA | NA | NA | NA |
| HGBM | HGBM | HF-3055-61-15 | HF-3055 | NS | 21 | success | CNV-WGLP | WGS | NA | NA | NA | NA | NA | NA | NA | NA | NA |
| HGBM | HGBM | HF-3055-60-23 | HF-3055 | XENO_1 | 22 | success | CNV-WGLP | WGS | NA | NA | NA | NA | NA | NA | NA | NA | NA |
| HGBM | HGBM | HF-3055-60-41 | HF-3055 | XENO_2 | 37 | success | CNV-WGLP | WGS | NA | NA | NA | NA | NA | NA | NA | NA | NA |
| HGBM | HGBM | HF-3055-60-42 | HF-3055 | XENO_3 | 61 | success | CNV-WGLP | WGS | NA | NA | NA | NA | NA | NA | NA | NA | NA |
| HGBM | HGBM | HF-3077-01-08 | HF-3077 | TS | 1 | success | CNV-WGLP | WGS | NA | NA | NA | NA | NA | NA | NA | NA | NA |
| HGBM | HGBM | HF-3077-61-16 | HF-3077 | NS | 1 | success | CNV-WGLP | WGS | NA | NA | NA | NA | NA | NA | NA | NA | NA |
| HGBM | HGBM | HF-3077-60-24 | HF-3077 | XENO_1 | 3 | success | CNV-WGLP | WGS | NA | NA | NA | NA | NA | NA | NA | NA | NA |
| HGBM | HGBM | HF-3077-60-41 | HF-3077 | XENO_2 | 2 | success | CNV-WGLP | WGS | NA | NA | NA | NA | NA | NA | NA | NA | NA |
| HGBM | HGBM | HF-3077-60-42 | HF-3077 | XENO_3 | 4 | success | CNV-WGLP | WGS | NA | NA | NA | NA | NA | NA | NA | NA | NA |
| HGBM | HGBM | HF-3160-01-01 | HF-3160 | TS | 4 | success | CNV-WGLP | WGS | NA | NA | NA | NA | NA | NA | NA | NA | NA |
| HGBM | HGBM | HF-3160-61-01 | HF-3160 | NS | 1 | success | CNV-WGLP | WGS | NA | NA | NA | NA | NA | NA | NA | NA | NA |
| HGBM | HGBM | HF-3160-60-01 | HF-3160 | XENO_1 | 1 | success | CNV-WGLP | WGS | NA | NA | NA | NA | NA | NA | NA | NA | NA |
| HGBM | HGBM | HF-3160-60-02 | HF-3160 | XENO_2 | 3 | success | CNV-WGLP | WGS | NA | NA | NA | NA | NA | NA | NA | NA | NA |
| HGBM | HGBM | HF-3160-60-03 | HF-3160 | XENO_3 | 4 | success | CNV-WGLP | WGS | NA | NA | NA | NA | NA | NA | NA | NA | NA |
| HGBM | HGBM | HF-3178-01-01 | HF-3178 | TS | 3 | success | CNV-WGLP | WGS | NA | NA | NA | NA | NA | NA | NA | NA | NA |
| HGBM | HGBM | HF-3178-61-02 | HF-3178 | NS | 12 | success | CNV-WGLP | WGS | NA | NA | NA | NA | NA | NA | NA | NA | NA |
| HGBM | HGBM | HF-3178-61-01 | HF-3178 | XENO_1 | 8 | success | CNV-WGLP | WGS | NA | NA | NA | NA | NA | NA | NA | NA | NA |
| HGBM | HGBM | HF-3178-60-02 | HF-3178 | XENO_2 | 9 | success | CNV-WGLP | WGS | NA | NA | NA | NA | NA | NA | NA | NA | NA |
| HGBM | HGBM | HF-3178-60-03 | HF-3178 | XENO_3 | 12 | success | CNV-WGLP | WGS | NA | NA | NA | NA | NA | NA | NA | NA | NA |

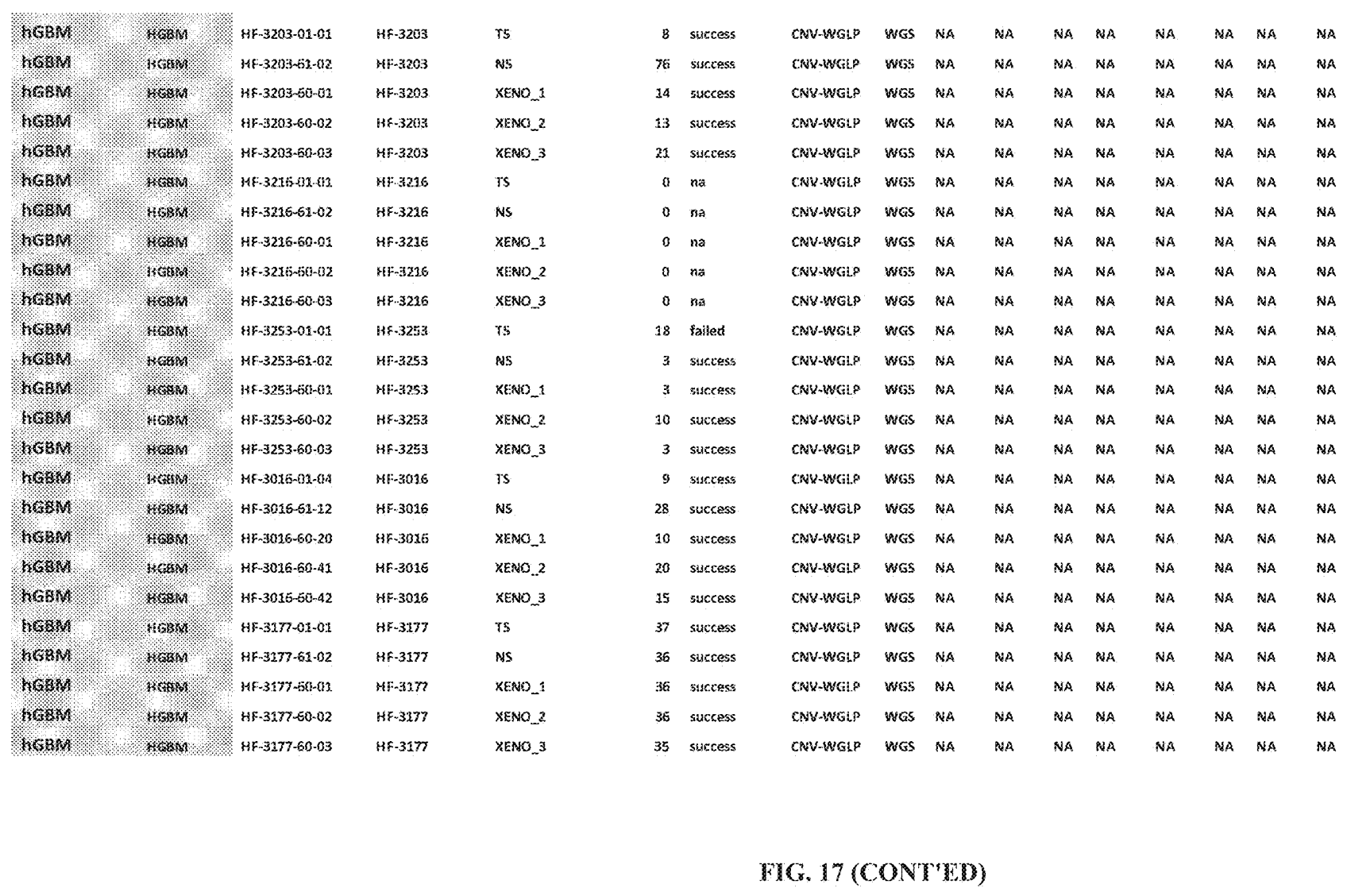

| | | | | | | | | | | NA | NA | NA | NA | NA | NA | NA | NA | NA |
|---|---|---|---|---|---|---|---|---|---|---|---|---|---|---|---|---|---|---|
| hGBM | hGBM | HF-3203-01-01 | HF-3203 | TS | 8 | success | CNV-WGLP | WGS | NA | NA | NA | NA | NA | NA | NA | NA | NA | NA |
| hGBM | hGBM | HF-3203-61-02 | HF-3203 | NS | 76 | success | CNV-WGLP | WGS | NA | NA | NA | NA | NA | NA | NA | NA | NA | NA |
| hGBM | hGBM | HF-3203-60-01 | HF-3203 | XENO_1 | 14 | success | CNV-WGLP | WGS | NA | NA | NA | NA | NA | NA | NA | NA | NA | NA |
| hGBM | hGBM | HF-3203-60-02 | HF-3203 | XENO_2 | 13 | success | CNV-WGLP | WGS | NA | NA | NA | NA | NA | NA | NA | NA | NA | NA |
| hGBM | hGBM | HF-3203-60-03 | HF-3203 | XENO_3 | 21 | success | CNV-WGLP | WGS | NA | NA | NA | NA | NA | NA | NA | NA | NA | NA |
| hGBM | hGBM | HF-3216-01-01 | HF-3216 | TS | 0 | na | CNV-WGLP | WGS | NA | NA | NA | NA | NA | NA | NA | NA | NA | NA |
| hGBM | hGBM | HF-3216-61-02 | HF-3216 | NS | 0 | na | CNV-WGLP | WGS | NA | NA | NA | NA | NA | NA | NA | NA | NA | NA |
| hGBM | hGBM | HF-3216-60-01 | HF-3216 | XENO_1 | 0 | na | CNV-WGLP | WGS | NA | NA | NA | NA | NA | NA | NA | NA | NA | NA |
| hGBM | hGBM | HF-3216-60-02 | HF-3216 | XENO_2 | 0 | na | CNV-WGLP | WGS | NA | NA | NA | NA | NA | NA | NA | NA | NA | NA |
| hGBM | hGBM | HF-3216-60-03 | HF-3216 | XENO_3 | 0 | na | CNV-WGLP | WGS | NA | NA | NA | NA | NA | NA | NA | NA | NA | NA |
| hGBM | hGBM | HF-3253-01-01 | HF-3253 | TS | 18 | failed | CNV-WGLP | WGS | NA | NA | NA | NA | NA | NA | NA | NA | NA | NA |
| hGBM | hGBM | HF-3253-61-02 | HF-3253 | NS | 3 | success | CNV-WGLP | WGS | NA | NA | NA | NA | NA | NA | NA | NA | NA | NA |
| hGBM | hGBM | HF-3253-60-01 | HF-3253 | XENO_1 | 3 | success | CNV-WGLP | WGS | NA | NA | NA | NA | NA | NA | NA | NA | NA | NA |
| hGBM | hGBM | HF-3253-60-02 | HF-3253 | XENO_2 | 10 | success | CNV-WGLP | WGS | NA | NA | NA | NA | NA | NA | NA | NA | NA | NA |
| hGBM | hGBM | HF-3253-60-03 | HF-3253 | XENO_3 | 3 | success | CNV-WGLP | WGS | NA | NA | NA | NA | NA | NA | NA | NA | NA | NA |
| hGBM | hGBM | HF-3016-01-04 | HF-3016 | TS | 9 | success | CNV-WGLP | WGS | NA | NA | NA | NA | NA | NA | NA | NA | NA | NA |
| hGBM | hGBM | HF-3016-61-12 | HF-3016 | NS | 28 | success | CNV-WGLP | WGS | NA | NA | NA | NA | NA | NA | NA | NA | NA | NA |
| hGBM | hGBM | HF-3016-60-20 | HF-3016 | XENO_1 | 10 | success | CNV-WGLP | WGS | NA | NA | NA | NA | NA | NA | NA | NA | NA | NA |
| hGBM | hGBM | HF-3016-60-41 | HF-3016 | XENO_2 | 20 | success | CNV-WGLP | WGS | NA | NA | NA | NA | NA | NA | NA | NA | NA | NA |
| hGBM | hGBM | HF-3016-60-42 | HF-3016 | XENO_3 | 15 | success | CNV-WGLP | WGS | NA | NA | NA | NA | NA | NA | NA | NA | NA | NA |
| hGBM | hGBM | HF-3177-01-01 | HF-3177 | TS | 37 | success | CNV-WGLP | WGS | NA | NA | NA | NA | NA | NA | NA | NA | NA | NA |
| hGBM | hGBM | HF-3177-61-02 | HF-3177 | NS | 36 | success | CNV-WGLP | WGS | NA | NA | NA | NA | NA | NA | NA | NA | NA | NA |
| hGBM | hGBM | HF-3177-60-01 | HF-3177 | XENO_1 | 36 | success | CNV-WGLP | WGS | NA | NA | NA | NA | NA | NA | NA | NA | NA | NA |
| hGBM | hGBM | HF-3177-60-02 | HF-3177 | XENO_2 | 36 | success | CNV-WGLP | WGS | NA | NA | NA | NA | NA | NA | NA | NA | NA | NA |
| hGBM | hGBM | HF-3177-60-03 | HF-3177 | XENO_3 | 35 | success | CNV-WGLP | WGS | NA | NA | NA | NA | NA | NA | NA | NA | NA | NA |

FIG. 17 (CONT'D)

TABLE 4A - FISH signal per nucleus - HF3035

| # signal per nucleus 7q11 (control) / 7q31 (MET) | 2/2 | 3/3 | 3/7-9 | 3/10 | 3/20 | 3/30 | 3/50 | 3/100 | 6/6 | 6/20 | 6/50 | 6/100 | nuclei with >5 signals (%) | total counted |
|---|---|---|---|---|---|---|---|---|---|---|---|---|---|---|
| HF3035 Tumor | 32.5 | 4.0 | - | 6.0 | 26.0 | 20.5 | 8.5 | 2.5 | - | - | - | - | 63.5 | 200 |
| HF3035 NS (P5) | | 78.0 | 7.0 | 5.5 | 1.0 | 0.5 | | | 6.5 | 1.0 | 0.5 | - | 15.5 | 200 |
| HF3035 NS (P7) | | 99.5 | - | - | 0.5 | - | | - | - | - | - | - | 0.5 | 200 |
| HF3035 PDX3 | - | 20.5 | - | 0.5 | 14.5 | 27.5 | 19.5 | 12.0 | - | - | 2.0 | 3.5 | 79.5 | 200 |
| HF3035 PDX4 | - | 13.5 | - | 24.0 | 27.5 | 21.0 | 11.0 | 3.0 | - | - | - | - | 86.5 | 200 |
| HF3035 PDXNS1 (P13) | - | 83.0 | 4.0 | 10.0 | 1.0 | 2.0 | - | - | - | - | - | - | 17.0 | 200 |
| HF3035 PDXNS2 (P8) | - | 95.5 | 2.0 | 1.5 | 1.0 | - | - | - | - | - | - | - | 4.5 | 200 |

(%) METAPHASE NUCLEI (**)

| # signal per nucleus 7q11 (control) / 7q31 (MET) | 3/3(^) | 6/6 | 3/7-9 | 3/10 | 3/20 | 3/30 | total metaphase nuclei | extrachromosomal amplification |
|---|---|---|---|---|---|---|---|---|
| HF3035 NS (P5) | 86.0 | 6.0 | 5.0 | | | | 100 | Yes |
| HF3035 NS (P7) | 100.0 | | - | - | - | - | 100 | Yes |
| HF3035_PDXNS1 (P13) | 93.0 | | 3.0 | - | 2.0 | 2.0 | 100 | Yes |
| HF3035_PDXNS2 (P8) | 99.0 | | 1.0 | - | - | - | 100 | Yes |

(^) 3 7qCtr, 2MET + 2SM

FIG. 18

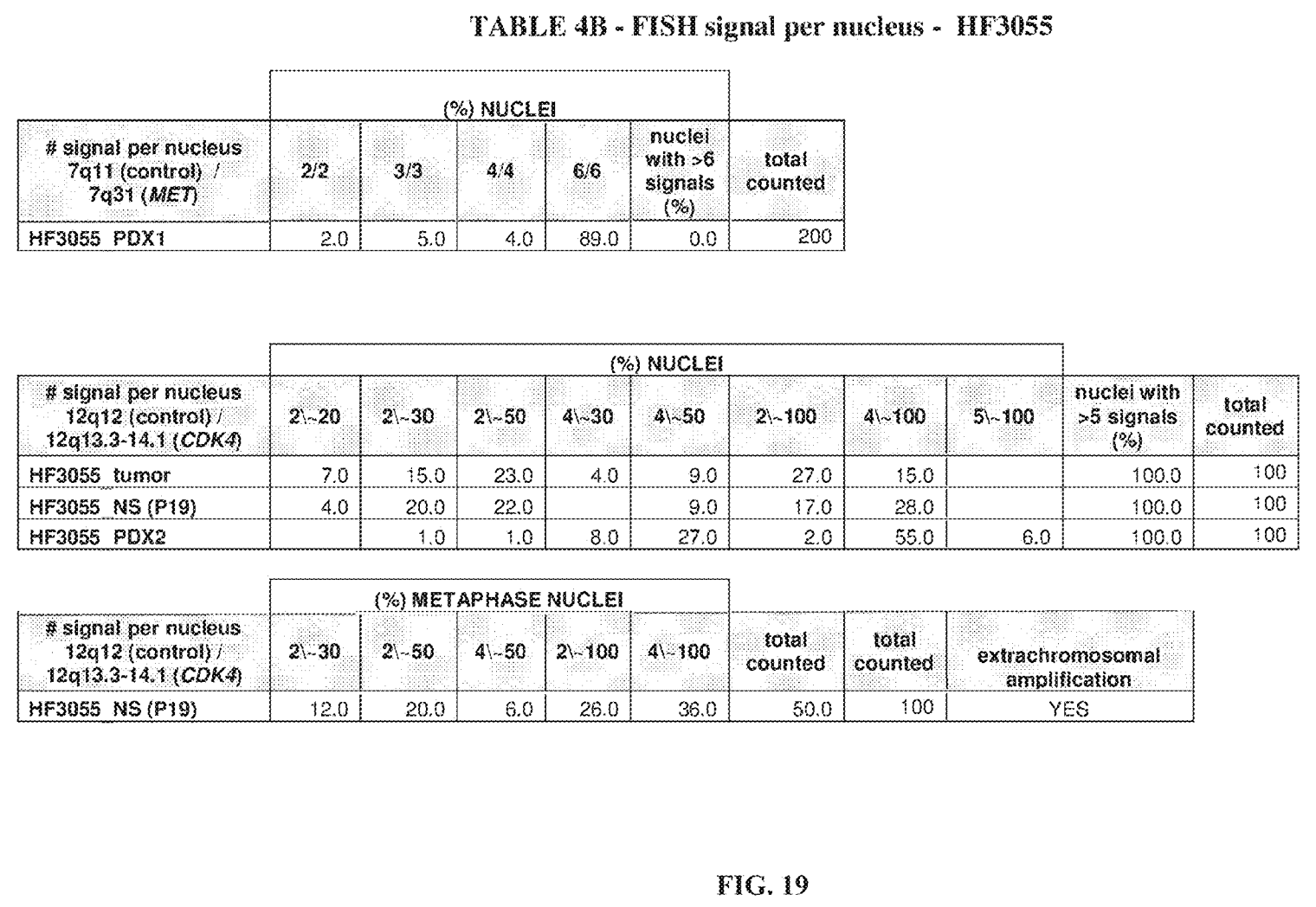

TABLE 4B - FISH signal per nucleus - HF3055

| # signal per nucleus 7q11 (control) / 7q31 (MET) | (%) NUCLEI | | | | | |
|---|---|---|---|---|---|---|
| | 2/2 | 3/3 | 4/4 | 6/6 | nuclei with >6 signals (%) | total counted |
| HF3055 PDX1 | 2.0 | 5.0 | 4.0 | 89.0 | 0.0 | 200 |

| # signal per nucleus 12q12 (control) / 12q13.3-14.1 (CDK4) | (%) NUCLEI | | | | | | | | | |
|---|---|---|---|---|---|---|---|---|---|---|
| | 2~20 | 2~30 | 2~50 | 4~30 | 4~50 | 2~100 | 4~100 | 5~100 | nuclei with >5 signals (%) | total counted |
| HF3055_tumor | 7.0 | 15.0 | 23.0 | 4.0 | 9.0 | 27.0 | 15.0 | | 100.0 | 100 |
| HF3055 NS (P19) | 4.0 | 20.0 | 22.0 | | 9.0 | 17.0 | 28.0 | | 100.0 | 100 |
| HF3055 PDX2 | | 1.0 | 1.0 | 8.0 | 27.0 | 2.0 | 55.0 | 6.0 | 100.0 | 100 |

| # signal per nucleus 12q12 (control) / 12q13.3-14.1 (CDK4) | (%) METAPHASE NUCLEI | | | | | | |
|---|---|---|---|---|---|---|---|
| | 2~30 | 2~50 | 4~50 | 2~100 | 4~100 | total counted | extrachromosomal amplification |
| HF3055 NS (P19) | 12.0 | 20.0 | 6.0 | 26.0 | 36.0 | 50.0 | YES |

FIG. 19

TABLE 4C - FISH signal per nucleus - HF3077

| # signal per nucleus 7q11 (control) / 7q31 (MET) | (%) NUCLEI | | | | | | | | | | | nuclei with >5 signals (%) | MET del (%) | total counted |
|---|---|---|---|---|---|---|---|---|---|---|---|---|---|---|
| | 2/2 | 3/2 | 3/3 | 3/6-9 | 3/10 | 3/20 | 3/30 | 3/50 | 6/4 | 6/6 | 6/40 | | | |
| HF3077 Tumor | 6.5 | 2.0 | 8.5 | 10.5 | 44.0 | 21.0 | 6.5 | 0.5 | 2.5 | - | 0.5 | 83.0 | 4.5 | 200 |
| HF3077 NS (P11) | - | 36.5 | 2.5 | 0.5 | - | 1.0 | - | - | 59.5 | - | - | 1.5 | 96.0 | 200 |
| HF3077 PDX1 | 1.0 | 27.0 | 4.0 | 13.0 | 33.0 | 16.0 | 1.0 | 1.0 | 4.0 | - | - | 64.0 | 31.0 | 100 |
| HF3077 PDX2 | 0.5 | 44.5 | - | 3.0 | 25.5 | 13.5 | 3.0 | - | 8.0 | - | 2.0 | 47.0 | 52.5 | 200 |

| # signal per nucleus 7q11 (control) / 7q31 (MET) | (%) METAPHASE NUCLEI | | | total counted |
|---|---|---|---|---|
| | 3/2 | 3/3 | 6/4 | |
| HF3077 NS (P11) | 24.0 | 3.0 | 73.0 | 100 |

FIG. 28

TABLE 4D - FISH signal per nucleus - HF2354

(%) NUCLEI

| # signal per nucleus 8q11 (control) / 8q14 (MYC) | 2\2 | 4\4 | 3\6~9 | 2\~10 | 3\~10 | 3\~20 | 2\~30 | 3\~30 | 3\~50 | 3\~100 | 6\~100 | nuclei with >5 copies (%) | total counted |
|---|---|---|---|---|---|---|---|---|---|---|---|---|---|
| HF2354Tumor | 96.0 | 3.5 | - | - | - | - | 0.5 | - | - | - | - | 0.5 | 100 |
| HF2354 NS (P14) | - | - | 6.0 | - | 14.0 | 20.0 | 6.0 | 33.0 | 14.0 | 7.0 | - | 100.0 | 100 |
| HF2354 PDX1 | - | - | 3.0 | 2.0 | 7.0 | 15.0 | 4.0 | 35.0 | 19.0 | 11.0 | 4.0 | 100.0 | 200 |

(%) METAPHASE NUCLEI

| # signal per nucleus 8q11 (control) / 8q14 (MYC) | 3\3 | 3\6~9 | 2\~10 | 3\~10 | 3\~20 | 2\~30 | 3\~30 | 3\~50 | 3\~100 | total metaphase nuclei | extrachromosomal amplification |
|---|---|---|---|---|---|---|---|---|---|---|---|
| HF2354 NS (P14) | 4.0 | 4.0 | 4.0 | 16.0 | 16.0 | 4.0 | 28.0 | 18.0 | 6.0 | 50 | Yes |

FIG. 21

TABLE 4E - FISH signal per nucleus - HF3016 / HF3016-R (HF3177)

| # signal per nucleus 8q11 (control) / 8q14 (MYC) | (%) NUCLEI | | | | | | | | | | | | | | nuclei with >5 signals (%) | total counted |
|---|---|---|---|---|---|---|---|---|---|---|---|---|---|---|---|---|
| | 2\2 | 3\3 | 6\6 | 2\6~9 | 2\~10 | 1\~20 | 2\~20 | 1\~30 | 2\~30 | 1\~50 | 2\~50 | 1\~100 | 2\~100 | 3\~100 | | |
| HF3016 Tumor | 5.0 | 89.0 | 4.0 | - | - | - | 1.5 | - | 0.5 | - | - | - | - | - | 2.0 | 100 |
| HF3016_NS (P16) | - | - | - | 3.0 | 19.0 | - | 35.0 | - | 21.0 | - | 10.0 | - | 10.0 | 2.0 | 100.0 | 100 |
| HF3016_PDX1 | - | - | - | 2.0 | 17.0 | - | 35.0 | - | 29.0 | - | 13.0 | - | 4.0 | - | 100.0 | 200 |
| HF3177 Tumor | - | - | - | 3.0 | 2.0 | 5.0 | 12.0 | 12.0 | 23.0 | 16.0 | 11.0 | 7.0 | 9.0 | - | 100.0 | 100 |
| HF3177_NS (P18) | - | - | - | - | 15.0 | - | 31.0 | - | 24.0 | - | 21.0 | - | 9.0 | - | 100.0 | 100 |
| HF3177_PDX1 | - | - | - | - | 5.0 | - | 34.0 | - | 35.0 | - | 20.0 | - | 6.0 | - | 100.0 | 100 |

| # signal per nucleus 8q11 (control) / 8q14 (MYC) | (%) METAPHASE NUCLEI | | | | | | | total metaphase nuclei | extrachromosomal amplification |
|---|---|---|---|---|---|---|---|---|---|
| | 2\6~9 | 2\~10 | 2\~20 | 2\~30 | 2\~50 | 2\~100 | 3\~100 | | |
| HF3016_NS (P16) | 2.0 | 6.0 | 14.0 | 22.0 | 30.0 | 24.0 | 2.0 | 50 | Yes |
| HF3177_NS (P18) | - | 6.0 | 18.0 | 30.0 | 26.0 | 20.0 | - | 50 | Yes |

FIG. 22

TABLE 4E (CONTINUED)

(%) NUCLEI

| # signal per nucleus 7p11.2 (EGFR) / 12q13.3-14.1 (CDK4) | 6~9\|6~9 | ~10\|~10 | ~20\|~20 | ~30\|~30 | ~50\|~50 | ~100\|~100 | nuclei with >5 signals (%) | total counted |
|---|---|---|---|---|---|---|---|---|
| HF3016 Tumor | - | 8.0 | 36.0 | 39.0 | 14.0 | 3.0 | 100.0 | 100 |
| HF3016 NS (P16) | - | 9.0 | 20.0 | 42.0 | 21.0 | 8.0 | 100.0 | 100 |
| HF3016 PDX1 | - | 9.0 | 34.0 | 38.0 | 17.0 | 2.0 | 100.0 | 100 |
| HF3177 Tumor | - | 13.0 | 38.0 | 25.0 | 15.0 | 9.0 | 100.0 | 100 |
| HF3177 NS (P18) | 8.0 | 26.0 | 38.0 | 24.0 | 3.0 | 1.0 | 100.0 | 100 |
| HF3177 PDX1 | 2.0 | 16.0 | 56.0 | 24.0 | 2.0 | - | 100.0 | 100 |

(%) METAPHASE NUCLEI

| # signal per nucleus 7p11.2 (EGFR) / 12q13.3-14.1 (CDK4) | 6~9\|6~9 | ~10\|~10 | ~20\|~20 | ~30\|~30 | ~50\|~50 | ~100\|~100 | total metaphase nuclei | extrachromosomal amplification |
|---|---|---|---|---|---|---|---|---|
| HF3016 NS (P16) | - | 4.0 | 14.0 | 52.0 | 20.0 | 10.0 | 50.0 | Yes |
| HF3177 NS (P18) | 10.0 | 20.0 | 36.0 | 28.0 | 4.0 | 2.0 | 50.0 | Yes |

TABLE 4F – FISH signal per nucleus – HF2927

(%) NUCLEI

| # signal per nucleus 7q11.22 (control)/ 7p11.2 (EGFR) | 3/2 | 3/6~9 | 3/~10 | 3/~20 | 3/~30 | 3/~50 | 3/100+ | 6/100+ | nuclei with >5 copies (%) | total counted |
|---|---|---|---|---|---|---|---|---|---|---|
| HF2927 p18 | 2.0 | 9.0 | 16.0 | 21.0 | 34.0 | 10.0 | 7.0 | 1.0 | 98.0 | 100 |
| HF2927 PDX1 | 4.0 | 4.0 | 21.0 | 43.0 | 20.0 | 6.0 | 6.0 | | 100.0 | 100 |

(%) METAPHASE NUCLEI

| # signal per nucleus 7q11.22 (control)/7p11.2 (EGFR) | 2\3 | 3/6~9 | 3/~10 | 3/~20 | 3/~30 | 3/~50 | 6/~50 | 3/100+ | total metaphase nuclei | extrachromosomal amplification |
|---|---|---|---|---|---|---|---|---|---|---|
| HF2927 p18 | 2.0 | 2.0 | 22.0 | 20.0 | 24.0 | 22.0 | 4.0 | 4.0 | 50 | Yes |

FIG. 24

TABLE 4G – FISH signal per nucleus – HF3178

(%) NUCLEI

| # signal per nucleus 7q11.22 (control)/7p11.2 (EGFR) | 6/6~9 | 6/~10 | 6/~20 | 6/~30 | 6/~50 | 6/100+ | nuclei with >5 copies (%) | total counted |
|---|---|---|---|---|---|---|---|---|
| HF3178 p15 | 11.0 | 6.0 | 10.0 | 14.0 | 14.0 | 45.0 | 100.0 | 100 |
| HF3178 PDX1 | 9.0 | 9.0 | 18.0 | 33.0 | 22.0 | 18.0 | 100.0 | 100 |

(%) METAPHASE NUCLEI

| # signal per nucleus 7q11.22 (control)/7p11.2 (EGFR) | 6/6~9 | 6/~10 | 6/~20 | 6/~30 | 6/~50 | 6/100+ | total metaphase nuclei | extrachromosomal amplification |
|---|---|---|---|---|---|---|---|---|
| HF3178 p15 | 5.0 | 10.0 | 15.0 | 30.0 | 35.0 | 5.0 | 20 | Yes |

TABLE 5. FISH RESULTS FOR PREDICTED DM AND NON-AMPLIFIED CONTROL GENES IN PRIMARY-RECURRENT GBM PAIRS (genes in primary-recurrent GBM pairs (50 cells counted))

|  | Rx prior to resection | MYC amp | OBS | MET amp | OBS | EGFR amp | MET amp |
|---|---|---|---|---|---|---|---|
| HF3081 | RT | 0% |  |  |  | 0% | 0% |
| HF3174 (R) | RT/TMZ | 92% | evidence for ecDNA | 100% | evidence for ecDNA | 0% | 0% |

|  | Rx prior to resection | EGFR amp /vIII mut | OBS | PDGFRA amp | OBS | MYC amp |
|---|---|---|---|---|---|---|
| HF2829 | untreated | 84% vIII(+) | 38% CEN7 amp, evidence for ecDNA | 0% |  | 0% |
| HF2959 (R) | RT/TMZ | 0% vIII (-) | vIII | 0% |  | 0% |

|  | Rx prior to resection | EGFR amp | OBS | MET amp | OBS | TERT amp |
|---|---|---|---|---|---|---|
| HF2934 | untreated | 86% vIII(+) | evidence for ecDNA | 0% |  | 0% |
| HF3041 (R) | RT/TMZ/Dacomitinib | 96% vIII(+) | evidence for ecDNA | 0% |  | 0% |

|  | Rx prior to resection | EGFR amp | OBS | CDK4 amp | OBS | MYC amp |
|---|---|---|---|---|---|---|
| HF2869 | untreated | 86% vIII(-) | evidence for ecDNA | 0% |  | 0% |
| HF2990 (R) | RT/TMZ/CCNU | 86% n/d | evidence for ecDNA | 0% |  | 0% |

FIG. 25

TABLE 5 (CONTINUED)

| | EGFR amp | OBS | TERT amp | OBS | CDK4 amp | PDGFRA amp |
|---|---|---|---|---|---|---|
| HF2919 untreated | 96% vIII(-) | evidence for ecDNA | 72% | evidence for ecDNA | 0% | 0% |
| HF3058 (R) RT/TMZ | 96% n/d | evidence for ecDNA | 40% | evidence for ecDNA | 0% | 0% |

| | EGFR amp | OBS | MET amp | OBS | MYC amp |
|---|---|---|---|---|---|
| HF3118 untreated | 94% vIII(-) | evidence for ecDNA | 0% | OBS | 0% |
| HF3186 (R) RT/TMZ/BSI-201 | N/A | | N/A | | N/A |

| | EGFR amp | OBS | RPS6 amp | OBS | CDK4 amp | PDGFRA amp |
|---|---|---|---|---|---|---|
| HF3162 untreated | 92% vIII(+) | evidence for ecDNA | N/A | | N/A | 0% |
| HF3205 (R) RT/TMZ | 86% vIII(+) | evidence for ecDNA | 84% | evidence for ecDNA | 0% | 0% |

RT, radiation therapy
TMZ, temozolomide

FIG. 25 (CONT'ED)

TABLE 6 – Alignment of the selected contigs on the hg19 chromosome 7 – HF3035_X2154C_gDNA_z1

| Ref.chr | Ref.start | Ref.end | Query.name | Query.length | Query.start | Query.end | Ref.hit.length | Query.hit.length | perc.IDY | mouseblast.identity | mouseblast.alignmentlength |
|---|---|---|---|---|---|---|---|---|---|---|---|
| 7 | 116393121 | 116402898 | tig00000023 | 18051 | 9779 | 1 | 9778 | 9779 | 99.67 | 84.1 | 478 |
| 7 | 145874783 | 145883054 | tig00000023 | 18051 | 9779 | 18051 | 8272 | 8273 | 99.89 | NA | NA |
| 7 | 116426115 | 116441629 | tig01170325 | 17844 | 1 | 15501 | 15515 | 15501 | 99.68 | 76.231 | 1401 |
| 7 | 116441590 | 116442739 | tig01170325 | 17844 | 15502 | 16646 | 1150 | 1145 | 99.9 | 78.902 | 346 |
| 7 | 116441583 | 116442787 | tig01170325 | 17844 | 17844 | 16647 | 1205 | 1198 | 99.17 | 77.465 | 426 |
| 7 | 145877922 | 145913731 | tig01170337 | 135621 | 1 | 35792 | 35810 | 35792 | 99.87 | 84.462 | 502 |
| 7 | 145643321 | 145646168 | tig01170337 | 135621 | 35794 | 38635 | 2848 | 2842 | 99.72 | NA | NA |
| 7 | 145902832 | 145906319 | tig01170337 | 135621 | 42092 | 38631 | 3488 | 3462 | 99.17 | 84.263 | 502 |
| 7 | 145649581 | 145651149 | tig01170337 | 135621 | 42091 | 43659 | 1569 | 1569 | 100 | NA | NA |
| 7 | 116312408 | 116314501 | tig01170337 | 135621 | 45746 | 43660 | 2094 | 2089 | 99.62 | 80.438 | 593 |
| 7 | 116503351 | 116508625 | tig01170337 | 135621 | 51014 | 45749 | 5275 | 5266 | 99.68 | 81.755 | 170 |
| 7 | 145910877 | 145912490 | tig01170337 | 135621 | 52624 | 51015 | 1614 | 1610 | 99.57 | NA | NA |
| 7 | 116501472 | 116501729 | tig01170337 | 135621 | 52882 | 52625 | 258 | 258 | 100 | NA | NA |
| 7 | 116418570 | 116501382 | tig01170337 | 135621 | 135621 | 52883 | 82813 | 82739 | 99.65 | 76.231 | 1401 |
| 7 | 116365529 | 116366232 | tig01170640 | 6466 | 1 | 755 | 704 | 755 | 98.9 | NA | NA |
| 7 | 116366188 | 116371911 | tig01170640 | 6466 | 756 | 6466 | 5724 | 5711 | 99.76 | NA | NA |
| 7 | 116314564 | 116334524 | tig01170699 | 108627 | 19846 | 1 | 19661 | 19846 | 99.82 | 80.236 | 678 |
| 7 | 145816805 | 145849583 | tig01170699 | 108627 | 19845 | 52618 | 32779 | 32774 | 99.9 | NA | NA |
| 7 | 145839124 | 145839902 | tig01170699 | 108627 | 53382 | 52619 | 779 | 764 | 99.8 | NA | NA |
| 7 | 145850348 | 145873704 | tig01170699 | 108627 | 53383 | 76688 | 23357 | 23306 | 99.7 | 96.875 | 32 |
| 7 | 116363943 | 116366223 | tig01170699 | 108627 | 76695 | 78977 | 2281 | 2283 | 99.69 | NA | NA |
| 7 | 116366192 | 116395855 | tig01170699 | 108627 | 79050 | 108627 | 29664 | 29578 | 99.43 | 82.391 | 460 |
| 7 | 116387044 | 116409224 | tig01170706 | 46254 | 1 | 22110 | 22181 | 22110 | 99.19 | 84.583 | 480 |
| 7 | 116393414 | 116398057 | tig01170706 | 46254 | 26740 | 22111 | 4644 | 4630 | 99.12 | 83.495 | 206 |
| 7 | 116413872 | 116432424 | tig01170706 | 46254 | 26741 | 45278 | 18553 | 18538 | 99.83 | 86.757 | 370 |
| 7 | 116431480 | 116432458 | tig01170706 | 46254 | 46254 | 45279 | 979 | 976 | 99.4 | NA | NA |
| 7 | 116331348 | 116361056 | tig01171467 | 29652 | 1 | 29652 | 29709 | 29652 | 99.63 | 83.985 | 1817 |

FIG. 26

HF3077_X2204C_gDNA_z1

| Ref.chr | Ref.start | Ref.end | Query.name | Query. length | Query. start | Query. end | Ref.hit. length | Query.hit. length | perciDY | mouseblast. identity | mouseblast. alignment.length |
|---|---|---|---|---|---|---|---|---|---|---|---|
| 7 | 116390764 | 116516562 | tig01141776 | 183455 | 1 | 125661 | 125799 | 125661 | 99.66 | 76.143 | 1400 |
| 7 | 116310078 | 116366223 | tig01141776 | 183455 | 125659 | 181683 | 56146 | 56025 | 99.48 | 83.976 | 1816 |
| 7 | 116366196 | 116367910 | tig01141776 | 183455 | 181683 | 183455 | 1715 | 1772 | 98.4 | NA | NA |
| 7 | 116367290 | 116389987 | tig01141835 | 22628 | 1 | 22628 | 22698 | 22628 | 99.52 | 82.391 | 460 |

FIG. 26 (CONT'ED)

TABLE 7- Mutation count and tumor purity estimates.

| Patient | Mutation count | | | | | | Purity |
|---|---|---|---|---|---|---|---|
| | Patient tumor | Low passage neurosphere | High passage neurosphere | Xenograft 1 | Xenograft 2 | Xenograft 3 | Patient tumor |
| HF-2354 | 53 | 81 | | 107 | 103 | 129 | 0.78 |
| HF-2587 | 40 | 30 | | 36 | 37 | 39 | 0.61 |
| HF-2927 | 61 | 53 | 74 | 83 | 87 | 79 | 0.89 |
| HF-3035 | 42 | 38 | 57 | 56 | 58 | 51 | 0.42 |
| HF-3055 | 33 | 39 | | 46 | 37 | 37 | 1 |
| HF-3077 | 46 | 50 | 64 | 68 | 56 | 62 | 0.84 |
| HF-3160 | 32 | 52 | | 36 | 37 | 26 | 0.76 |
| HF-3178 | 45 | 46 | | 50 | 50 | 53 | 0.66 |
| HF-3203 | 45 | 48 | | 67 | 52 | 89 | 0.81 |
| HF-3216 | 37 | 49 | | 40 | 56 | 45 | 0.4 |
| HF-3253 | 55 | 74 | 54 | 58 | 52 | 58 | 0.68 |
| HF-3016 | 42 | 48 | | 48 | 44 | 54 | 0.91 |
| HF-3177 | 77 | 89 | | 86 | 84 | 89 | 0.86 |

Sequence of ecDNA MET/CAPZA2 fusion (SEQ. ID NO. 8)

ggccatatctcattacttactataaagtgctatctacatagttataaattatgacagctaagagaaaaattaatccctaaagaaagcaaaattacctatgtcacggtttagaaagtcttctctcttaagaagaaaaacttattcttattgcctctgttggttttttc
ctgaggaatcggtgtttgaatgcaatatacatttttgtaggctctgcaatgttttatgatgaggacagtgagtgttgacaattacctcaatgatacttagcgatttgaatgtatcgctagatttctggaaagtatcctagaaagaccaatgtaagct
agttgaatgagaaaaccagagttggcagaaccagaggtggcagatgggttggcagaattagtcgctggttaactattaataacagccatcttcttaaaggagtactcctaaatatcaatagtttagtggccaaggtgcc
attggatgatcactcccaggaaatgttttgccagtgattacccttaactttcatctgaaaagaaataacagaaacagtgaaaagcacaaagaaagccaatccttcaccgatagtgcacaacattttaagagaatgaattagtcagtctgtttgaatcatctt
tacgttcctttagcaggggactcaagttggttacactggtctcattcgaataatgcctagctcgtctcattcttcattcagagaaaatctgaaaagcaaagatctatagaaaatatatcaggacaaaaatat
atgaaaagtgaaagtattgtattctggagtattcactaccaataataaataatgctcacacagccagatctggccaagtacatagatgaggaagtgaaagcaataatatgccaagtcaatggccatggctgtaaaatgtaatcatagaggaa
caatctcagagttgaaaattattagaattggaaaacactttgagagtcttagttccacccaggagtatgccattaaatatttaataacaagccctgattttgtagttgtttgccaattctatggtcaatac
agccaccatggctgatttaggctaccaagatgagagtcactgcacaactaaactaggccctctccagtgtttgacctgagaagaaggatgccacagttgggaagaagatgcacagcaggaagaagcagttgacttcagaggagtgg
gtgacttgcctgggtcatacaaataattagctgcactgccacaactaaactaggccctctccagtgtttgaatgcattggaagaaagcaccatgattgattggtaagcccagtgacttttctgtcctgttaagt
cccctttgagggcctccatagacattctacattggtttaaactatagtctgcctctatctccactactggccactactaactatagtctcgatctcgatctggcctcactagatgcttataa
gtgtttgtttggggccatgcaacaatagagaacatgcattgactgacctgctatgtgccagccagtgttgttcttagtgattggcaggggtttaaacctaaaatctggcagtgggtttatcatcatagtgccactcattattaga
tgagaaaatacaggcttagacttactgccctaaggtaacatggacagtgattgaagcctcttagttttaaacccttgatctggccagtgtctcattaactagcagttgtcactcattaatctagtagccatcatttct
acttctaaaagtctccctccttcttaggaaggacacaaaacgttccagaaagatctgatctgaccaacacaccttgtttattaatggggaaggccttattaatgggaatgatcaagaaatggcatcaccatatggtaacagataatgtaa
cattatctgaggttttaaacagaaaacctcttagtttaattaaatttctgtgctgacaataggccctagtccattttttcttaattaaaaagttaactttttgatgtattcacttgagaaaatggcatcacacatatgtgtaacagataatgtaa
agaaggtaggagattaagtactaactccaactgttctgtggaggtttttcttttaaatagaaaatatatctctctctccactgatttccatttcatcaaatgaagtaacaaaaagcctatttctacatgtacattttctggattcttgtc
cactgagatttagtacagtgtgtgacttatgtgcgaacctttaagatatgcaaatcttattttttgttctttttttttgttggtctgtctgcttcatcaggctggagtgcagtggcgca
attcaactcactgaccactctcaatctccctggttcaagagattctcctgcctcagcctcccaagtagctggggattacaggcgcgccaccacaccccagaaaatcaaaatatattttcacataatatttattttccc
gatctcctgaccacgtgatccaccctctgcctcccaagtgctaggattacagattatttttgaggcctccttctttcattattctttcattataaattctacagaaaatacagcaatacaattatatattctatggaatgttacagttaacatttc
attgtgctctagatggtttagatacatatttgcagtttgattttttacagttcctaagcaccaatatttcctttccttccttagtacaacaaaattgctagtacattgcaaaaacaatgagaatt
acagtaaaatagcagcagcattataatactctatatatgtctatataaagtgcttcagagagtgagtctttttttgatctcagaggttatgcctgagaatatcaccacagccatagaagg
gaaagggctagaatcagagggctgattgtcgacttcgttctctgggagctgcatgtccacctgcttttggaagctggcatggatggttttggttcagtgaggtagcatttggttcaactggttcaactgtgtg
atttagcaagttgcttactcttagagaggaagtgaaatacaatacttcctttcactccttcctggctatcctttcataaaccttgctcactacaaaccttgctcactacacgtcttttgtttatttattattacatggctttgc
cttactgaggctttattcttgctctctggtccaactacagttttctggctattgtcaacctggctataacaatctatgctgcatttcaagcaatctcgctccaagttcaagcaatcttctgcctcagctctccaagtagctag
gattacaggcacctgtacccccacaccggtttttgcctctggtccaactacagtttttgtagtagagatgggggtttcaccatgttggtcaggctggtctcgaacctcctgatctcaggttgatccacccgcg
ctcagccaggaaatttcattcttttatccctcctttgagactggctcggcatcattcccagtgcagttgtcaggggtttcctctgccagttcctgtgaactgttaaccatcaagtgactgagctgccaccaagtactttgtgatcatccaat
aaatgttagtagaagaaagggggtcctgccaataatcatgtctcttccccatctcttcatgtttcttgatggtctcttttgctctcaatttaaactccttttgctttcctttcatcacccatttcctttctttgataaacattctaacatctgatactacta
tagaaactactgcctgagatcaacaaacgggttcatgtggaccaaggtcctcctggaccaccaccatccggatggtttttgcacagtgcaatattgctctttgacctcactggatttctcaactgt
gggtatcccctaagattaggccatttgcctttctctcttctctcatctagtccattcatgaacacaccatcctggtttaaccatcaccctgtgcagataatgtgcaaagtttattctgtagtcgggagtgcaagtctcctttactctgccaatcaagttc
taaattttattccttttagtgcagcagtggcaaatccctgacacctgaaatcagtgttcacccaagctgatcctcttcagagctcttcaggcttctcagaatcttcagatctgcctctgtccttggcac
taatgctctgtctgcccagagtttcattcttcacttgttccagcacctgttcactttcctcagtgatattacttttgtttgtcttgatatattaggagtatccagataaatgttaaaaccagctgcctactttccaccaccatt
cccatatattcagcctaaccactgtctccagtgcagtctcagtcactccaggtttattaactttgtctctagtttttttcagataaattggactgttgatatattaggctcttttgcctgttttgataatattacatctacttcctattgctccagatactct
attcattcctttatcctttggtgctaccatattgtctggctcttcattatgggataacatagctcgtaactggtcttttccattgccacccctgttctcagctccagggctcgtctcttcctttgtgtacacttaactactttatgtaacttc
ttgtatgacggctctagctcaaaattcctaatgattattatcaccttcttaaagtcccaattcttagctttgagctattagagaatatcactcttagatattggagtcaaaaaatttggacgcaaatacttctaaaaacctcttca

```
gtgggagtgacccgattttccaggttgcgtctgtcaccctttcttgatccctgacccctggcttcccaagtgaggcaatgcctggccctgcttcggctcggcacggtgcacgcaccccactgacctggcccactgtctggcactcctagtgag
atgaaccgtacctcagatggaaatgcagaaatcaccgtcttctgtccgctggagctgtagacgagcgctgttcctcattcgcatcttggtccgtggataagcttaaaggcttaaaaattcctataaaatcca
gaatctatctagattttgagcagcctgagtggttggaggaccatgattttactacattggtcagtctaaacatcccaagcaatgattgttctgacagcagactgatcagatttttactcctggaatcggcaaaaaaaatcacaaggg
aagctttgggagccaccccggtagagctgagagagaattcgaaatcaattcgcaacctctccttacggcaagaaaatgtgctagattggaggtgaagacggagcagagagcctaggcttatcctagcctgactgaaggtaatg
tgaacactcagtgcctcagtttccttctaggcttctgttctgagattcatgaattaatattttgtaaatgcttagaactgtctaacacattgtaaatactaggaacaaatgtcaaggtcatgcaacttcatcaatgctccctgggtgaaacgc
agcctttgcccatgggcattgcctcattcttttagacaaggccttagcatcctagagtgtgggttcctcctatgcctgctacgttaaatgtaaatgtaaggatataggattcaaaatcaacaattaggattcaaatgctaaat
attattgactcaactctcgatctgtagttttctccatcgtaaaattataatgatcatcaaaaccaagtcacagactgttcagaggaggcaaatgagataatgtactttgaaaccaataatctactctgcaaatgttatgtaacaattattgtgag
ttcagcaaagccatgagaatgtttcaaactgctgaatagcaacttttaataggtttctccatatcctcatttttcattttctatgtgatatacatatatatatatatatataatatat
acacacacacaaaagaattatgttacggtcctgcattcttgcattgttcattgtcaaaacatagagttgactatactaaccctggtgatatagcctactacacactaggctgtatggtatg
acctttgtcctaggcacaaacctgtaaggcaatgttactctgcttgaatactgtaacacaatggtaagtatttgtatctaaatatatcttaaagatataacaatatatcttaatatactagtat
atattttatagatacaaatgtataaatatctatagatgtactagtctatatttatagactagaaaaggcacagtacaaatgtggttgttattcatgcctaatcccagcactttggaggtcaaggtgggaggaat
tgcttgagccctggagtttgaggttacagttacgtgagctacgaacaacattcactgacttactcagtctatca
ctgattgaaagtcattcagcacatgcagcacatgtatatatatgtatataaaaaatatcatctttccaccaggtcaaaagaatctttattgatgcatggttcctttcactgagtcatg
atatataataatctatatatatatatggatataaaaaatatcatctttccaccaggtcaaaagaatctttattgatgcatggttcctttcactgagtcatg
tgtttgtcttttcctttgcctgtagttgcgtcacacagtgtgtgcccagaaatattctttatcagactgtaaagaagtggagcacagctgccagaggaccaa
tccagcaataagcacattacctgtcattcaatgaactgtaaagagagatttagaaaagagcttagaaacctgcctgagttcacctcaggttcactcacccttacaccttaaggagaaaagatagaagccaatggcttagacttttcctgcaggcct
gaaatggggggtctttgactggggataaccatcactctgagattcattggatgtcctacctgtcacctgcctacaccttaaggagaaaagataagcagcaatggcttagacttttcctgcaggcct
ttggggagcaactgaggcttgagaggaagaatgacagcttgagactgttcaggcagagagaggccagaagcccagtggcctgctcctgctgtgg
tggaccaggctgagcaggctgagtgagtgattggtagatataggaagaaagagagattaatttcagcctttaagtgggacttaaatgagatgatctccgaagccttcattttgtaattgtgcaatcctcagaacgttgcccagaatca
ccaaagctgattagtacagaatgcgagttgttattcgtgtgtttcagaaaataaagattaatttcagccttaagtgggacttaaatgagatgatctccgaagccttcattttgtaattgtgcaatcctcagaacgttgcccagaatca
gtaagcagaagcaagaaattcggagttgaacattcaggagagctgtttctcgatgcctgctcccaatgaactggcactgtttggactgagcctggctccttctggctcctgtctcctgaggagtgtgataagaaacctcacaggggctgctgtgg
gtcttattatgcatgaaaatacccacctcagtgcctggcacatctgtgcagaaaagttgattctcctctccctccttgttaccagtaggaggagtcaggcggcttggttcctgtggggtgctggtgtgaa
acctgctcttagactctttgcagttcccaaagcgctactgtcccagagaactgcttctgccagcaatgctcagtttctgccagcaatgctcagttttgccagagataactcctggcttgaggaggaagcacagagagcagtgcagggtggtagtgt a
gttgttcttccagctaggcccccaccccaccttaaatgccaccagtccagacacttaaatccaaaaatgagcagcaaacatattgctgattatctttgaggggacataa
```

FIG. 29

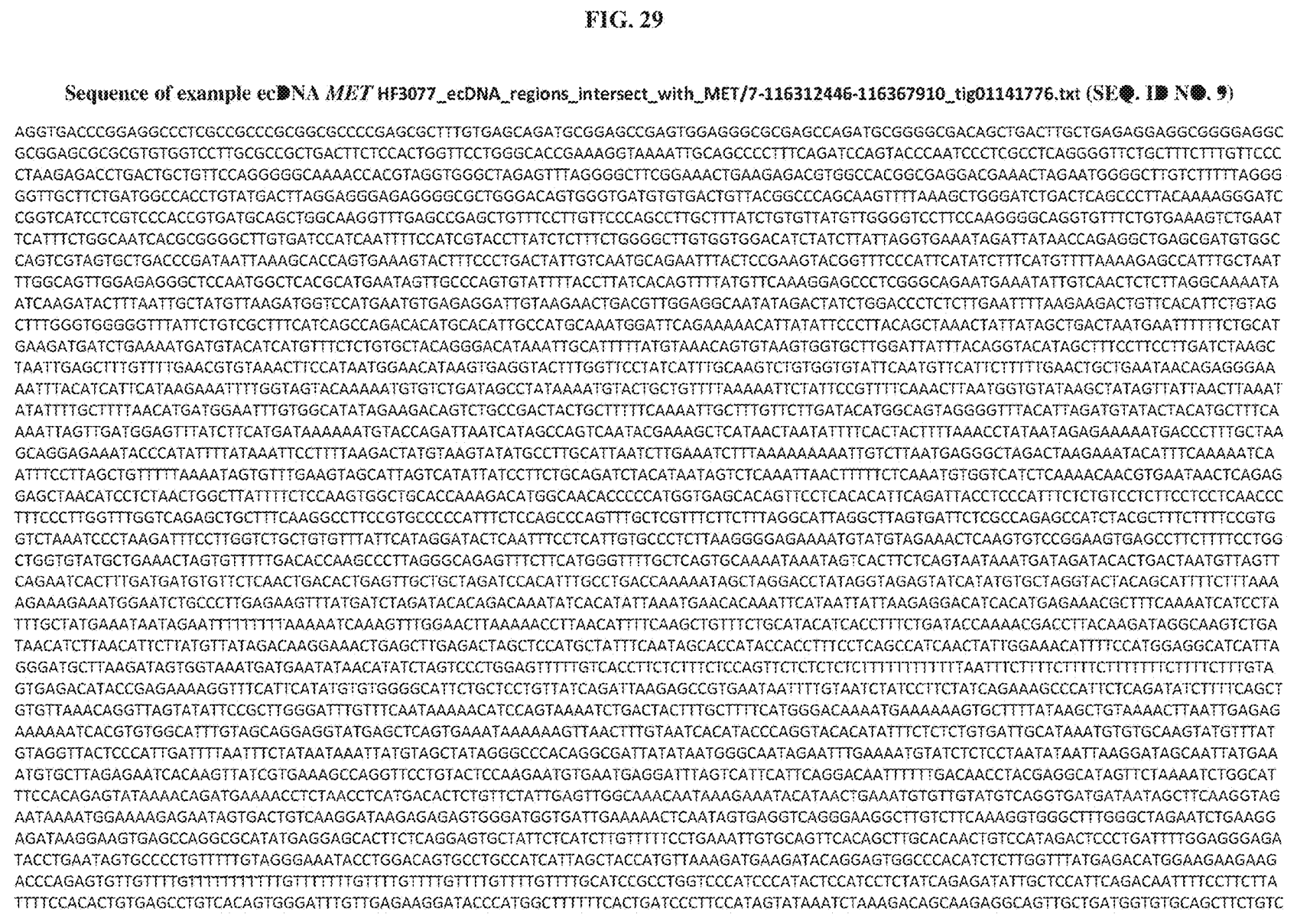

Sequence of example ecDNA. *MET* HF3077_ecDNA_regions_intersect_with_MET/7-116312446-116367910_tig01141776.txt (SEQ. ID NO. 9)

ATCCATGTCCCTGCAAAAGACATGATCTGTTCCTTTTATGGCTGCATACAACCATTTTAAATACACAGTACAGTATTGTTAACTATGTGAAACATTGTTGTGCAATAGATTCCTAGAAACTTTTCATCTTA

GCAAAACTGAAACTCTATATCCATTAAACAATTCTCTCTCTCTCCCCAGGCCCTGGCAACACAATTCTACTTTGTCTAAGGAGTTTGACTACTCAGATACCTCATATAAGTGGAATCACGCAGTATTTGTCTT

TTTAGGACCGACTTATTCATTTAGCAAAAATATTCTCAAGCTTCAGTGTTCTAGTATATGACAAGATTCCTTCTTTTAAAGGCAGAATAATATTCCATTGTACATATATGCCACATTTCTTTATCCAT

TCATCTGTCAATGGACATTTAGGTTTCTTTATACCTCTTGGCTATTTGAATAGTGCCGCAGTGGCCATTTGGGGGACCTCTTCTACTGTTTTCAAATTTTGGGGAATCCTTTTCAAATTTCATCTTTTATCC

ATTGCTGGATCATATGGTAATTTTCAAATTTCAAGATTTGGGGAGAGGTGGCTCACGCCTGTAATCCCAGCAGTAGTCATCTTTGAGTAGTGTTAGGAGTTCGAGACCAGCCTGGCCAACATGGTA

AAACCCATCTCCACTAAAATACAAAAAATTAGCCGGGCATGGTGGCACAGCCTGTAATCCCAACTATTCAGGAGGCTGCGGCAGGAGAATCGCTTGAACCCTGGAGGTAGAGGTTGCAGTGAGCT

GAGATCATGCCACTGCCACTGTACTCCAGCCTGGGATGACAGAGTGAGACCCTGTCTCAAAAAATAATAAATAATAATAATAAGAAACATTGAGTTCTTCAGGCAATTACTTATCAAATTGTAATGGCTATGACAT

TTGCTTGAAGGTTTTCTGTGAACGTAATTTTATTTCTTGGGTGAATATCTAAGAGTTAAACTGGGGTTGTAAGATAAGTGTACATTCAACTTATGAGAAACTGCCAACTATTTTCAAAG

TGGCTGTATCATTTTATGTCCCACCAGCGATCCATAAGAGTTCAGTGTTCAGCTTCTGATTGTCGAGCCTCTCATTCTTATCACCTTAGTATAAACTCTTTGCCTATTTTAAGTATTTATTATAATAATATTAAT

TTTAATCTTTATTTCCATGGCTAGTGATGTCGAGACCTCTGATGCCTCATCCTTATATCACTTTAGTAAGTGTCTACTCAAATCTTTGCCATTTTAAGTATTTATTATAATAATATTAAT

TTAGTTAGGGTTTATTTATTGGCTTGTTTGTTCTTATTGAATTGTTCACTGTCAGTGGTGCAGTCGATTGGGTGTCTTGGGATTCTTTTGTATTGTTGGGACGAAGT

CTCACTCTGTCACCCAGCCTGAAGTGCAGTGGTGCAGTGGTTCACCATGTTCACCATGTTGGCCAATCTTGGCTCAATCTTGGCTCCTCGCCCAGTAGCTGCAGGCATGGGATCTGGGAGCCACCATGC

CCAGTAATTTTGTATTTTAGTAGAGACAGGGTTTCACTGTGTTGGCCAGGCTGGTCTCGAAACTTTATCAGTTTACCAATTGATAAAACTTATCAATTATT

GGCCCACAAATGCATTTTCTAGTCTGTGGATTACCTTTCATTTATTTAATTGTTCTTGCTCCTGCTCACTTACCTCAGTAGCAACCCTGTCTCATCACTTTCATAGCTTACAA

CCATTTTCACATTTAATCAATCCTGGTGTTGTTGTGATGTGTATCTCACGTGTTACCCAGTAAAGTTAGGCCAGATATTCTCCAGATGAGCTTATTCTGTGGTGCCAAATGGCTTGGACCAAATGCCATCACACACACAC

ACACACACACACACCAGCTTCTTCTTCTTGGTCATCATCACCTCCTCTTCACTGTCCCTGCTGGAGTTATGTCCCTGTAATCCTGCCACGTGTTCAGGGGAGTGTGGAGTGCAGACAA

TACAATGCTCTCTCTGGAAACCTTCTTCCTTACCTCCCGTGTCCCTGAGTCTGATACCCAGTTATTGCCCACGTCCTTAATTCCTTGGAAAATTACCCAACTCATCCCCTTTATG

TGACTTTGTCTCCAGACAAATCTACATGTAGCGTAGACTGTCAGATAGGGAGACCTGAATCATTATATATGATGAATCATTATATGATGAATTCCAGAGAAAAGCCTCATAAAACCAATCATCACAGGATTGTAACCAAGTACAATCCAT

TATAAGGATTAAATAAGATGTTTGTAAAGGAATATAATGCCATGAATCAGTTGTAAACTGGCCTTCCTTGTGTCTTAAGGTTGGCGTTACAGCTTCCGTATTTGTAGGTATGGCAG

GAGTGTCCCTCACCTATTCTTATTCAGAAACCTCCTAACTGGCCTCCATTGTGAATCAGTCTCACTCACTTCTTTTTTTTTGAGACGGAGTCTCACTCCATGCTCACTCCCAGGTTCAAGCGA

GTCCATTGATTCAGTCTAACGCACTTCTTTTTTTTTGAGACGGAGTCTCACTCACTTCTCTCAGCCTCCCAAGTCCTCGGGTTGTTGTTGGGATCAAGGCA

TTGTCCTGCTTCAGCCTCCCAAGTAGCTGGGATTACAGGTGCACACCACCATGCCTGGCTAATTTTGTATTTTGTAGTAGAGACAGGGTTTCACCATGTTGGCCAGGCTGGTCCCGAACTCTTGACCTCAA

GTGATCTGCCCACCCCGCCTCACTCCAAAGTGCTGGGATTACAGGTGGGATTACAGATGTGAACCACTGTTCCCGTCCTGTCTAATAAGAACACATATGCAGGTCCGTGGCTCATGGTGGCAGGCCTATAATCCCAGCTACTCAGGGAGGCTG

AGGCAGGAGAATCGCTTGAACCCGGGAGGCGGAGGTTGCAGTGAGCCGAGATTGCACCACTGCACTCCAGCCTGGGCAAAGAGCGAAACTCCATCCAAAAAGAAAGGAAAGAAACACA

TGTGTACTGTTACTCCTGGCCCACCCCTCCACCCAAAACTCTCCACCCAAAACTGTACCTTGGCAACCTTGGCAACCTTGCTCTTGCTCAATTCTCTTAACCCTGTTCATTC

CTCAGTACCCTACTATTATCTCTTGACTTTGGCAACCTTGTACCTTGTATCCGTATGTGATCAAGGGTCAAAGTTCTGGCAGTATTCTGGCAGTATTCTGGGACTTAACACGATGATGTTG

AGCCCTGGGACCTATCTAGTAACTTGAACAGTAACCTACTCGTATGTGATCAAGGTCAAAGTGTAAAGGTCAAAGTTCTGCAAAGTCTGAATTAGCAGCAAAGTTCTGATCAAGGCA

TCAGAAGTGATTGTTGATTGTTAAGATTTTCAGACTTTGAAAACTTCACTTGAAAACTTGTACTTTGTATCAGCAATTACACGCATCTACCTCATTTCTTTCTTCAGTCGCAGCGTTCAAAGGCAGCTTTATTCTCCTTCT

TGCTGGGTACTGCAAGCTACACTGCCTCTCAGTTTATGTCTCCTATCTCAGCGTGTGGATTTTTCCTTGTCCTTGTCCTTAGTCTCCTTATCTCTTAGCTTCCTACTCTTAGAGTTGGCCTG

GAAGTGTTGCTGAGCACAGTGTTTAAATCAAGAAATTGCATGTTATTGAAGTCAGTAACGGCTATTTTATTGTATCCAGTGTGACTGGACTTTATTCAAATGTTCAATAAATTTCAATAGAGAAACT

AGCAAGTCACTTAACCTCTCCGTGTCCGTGTCCCTGATCTTCGATTTTAATATGTATTTACAAGTAATGTAAAATTGTGAAGCTATTCTGAAGCTATTCTGGGTGGTTACATTCTTAAAGAGTTATGTTCAGTTGAAACC

TGTTGCCTTGCAGTTTTTATTTCTGATTTAAATATGTATTTTACAAGTAATGTAAAATTGTGAAGCTATTAATCTAAACCTTACTTGTTTAAACAAGTCATGAAAGTGTATAGCTTAATAAT

ACACAAATTTAAATTTGGGAGGCTTTCTTCTTCATCATCACTGAGAATCTTACTTGTTTAAACAAGTCATGAAAGTGTATAGCTTAATAAT

AGATATTCTACCAACTACAGATGGAATCTTCATCATCACTGAGAATCTTACTTTACTTTACATTTACAATTTACATTTTTAGAAAAACTTACTTGTTTAAACAAGTCATGAAAGTGTATAGCTTAATAAT

FIG. 29 (CONT'ED)

TGCCTTTAAGAAAATTGTTGCCCAAAACAGAAACCGTATTGAGTATGTAAAGCCAAGTTAGTTACCAAGACCTACTGATTCCTTTCATATATGTAGGTCACATCTCTCACCTCATCTGTCCTGTTTCTTG
TTTTACTTAGTGGTCCCTTGGCGTGCTCCTCTGGGAGCTCTTGTACCTTCTTTACTTTGTGTACCTTTGATAAACACTTTGATATAAACTGTTTACTGTTGCAAGGGGAGAAGACTCCTACAACCCGAATA
CTGCCCAGACCCCTGTAAGTAGTCTTTCTGTACCTTACGTTCTTTACAGAAATGCCTGCCTTCAAAGGGTCTCTTCACGCATGTCTTCTTTTTGGAACAGATATGAAGTAATGCTAAAATGCT
GGCACCCTAAAGCCGAAATGCGCCCATCCTTTTCTGAACTGGTGTCCCGGATATCAGCGATCTTCTCTACTTCATTGGGGAGCACTATGTCATGTGTGAACGCTACTTATGTGAACGTAAAATGTGTCGCT
CCGTATCCTTCTTCTGTTGTCATCAGAAGATAACGCTGATGATGAGGTGGACACAGACCAGCCTCCTCCTTCTCGTGGGAGACATCATAGTGCTAGTACTATGTCAAAGCAACAGTCCACACTTGTCCAATGGTT
TTTCACTTGCCTGACCTTTAAAAAGGCCATCGATATTCTTTGCTTGCCAAAATTGCACTATTATAGGACTTGTATTGTTATTTAAATTACTGGATTCAAGGAATTTCTTATCTGACAGAGCATCAGAACCAG
AGGCCTGGTCCCACAGGCCACGGACCACGGACGCAATGGCCTGACCGTGACAACACTCCTGTCATGGAGTCCAAAACTTGAATTCTGGGTTGAATTTTAAAAATCAGGTACCACTTGATTTCATATGGGAA
ATTGAAGCAGGAAATATTGAGGGCTTCTTGATCACAGAAAACTCAGAAGAGATAGTAATGCTCAGGACGAGGCGGCAGCCCAGAACAGGCCACTCATTAGAATTCTAGTGTTCAAAACACTTTG
TGTGTTGTATGGTCAATAACATTTTCATTACTGATGGTCATTCACCCATTAGGTAAACATTCCCTTTAAATGTTGTTTGTTTTGTAGAGACGGGGTTTGCCATGTTGCC
TGTGATCATAGCTCACTGCAACCTCCACCTCCCAGGCTCAAGCCTCCGAATAGCTGGGACTACAGGCGCCACCACCATCCCGGCTAATTTTTGTATTTTTGTAGACACTCCTTGGTTGGAAG
AAGGCTGGTTTCAAACTCCTGACCTCAAGTTTCAAAATAGCATCACAAAATGTTTATAAGTGAACATGTACTCTGATCTAAATGGTAGTAATAAGACAAGTAATTGTTGATAAA
AATATTTATAGGCAATACAGTCAAGTTCAAAATAGCATCACAAAATGTTTATAAAGTGTGATATTTTTAAATGAAAACTCAAAATAAGACAAGTAATTGTTGATAAA
ATTTAGTTGCATATAAAAACCCACTGTTTGAGAATGATGCTACTTCTGATCTAATGAACATGTACTCTGTGTATTTTTGTGTGTATTTTTAAATGAAAACTCAAAATAAGACAAGTAATTGTTGATAAA
TATTTTAAAGATAACTCAGCATGTTTGTAAAGCAGGATACAATTTACTAAAAGGTCATTGGTTCAATCACAGCTCATAGGGGGGGATTGAAAAGATTAGCCTCTGTCTC
GGTGGCAGGTTCCCACCTCGCAAGCAATTGGAAACAAAACTTTGGGGAGTTTATTTGCATTGTGGGAGTTCATTCTGTCTACTGTATAGTGCATCTAACTGGTTTGTCGACGTAAACAT
GCTATTCACCTAGATGGAATAGCCACCCTGAGCAGAACTTTGTGATGCTTCATTCTGTGGAATTTGTGGTTACTCTAACTGGTTTGTCGACGTAAACAT
TTAAAGTGTTATATTTTTATAAAAATGTTTATTTTAATGTACTGTTTAATGATATGGAAAAATTTTGTTAGGCCACAAAAACACTGCACTGTGAACATTTAGAAAAGTATGTGAACGATGAT
TTCAATGACTGTAAATTGCGATAAGGAAATGTACTGATTGCCAATACACCCACCCTATTACATCATCAGGGACTTGAAGCCAAGGGGGTGTGTCACACTGAAACT
CAATAGTTGAGTTTGGCTGTTGTTGCAGGAAAATGATTATAACTAAAAGCTCTCTGATAGTGCAGAAGACACAAGGAATTGTACTGACAGAAGAAAGAAAGAAAAC
TAAAAGTAATAAGTAATACTAATTCACAGAGTATTGTAAAATGGTGGATGACAAAAGAAAAATCTGCTCTGTGTGGAAAGAAGAAATCACGTTGCTATTTATAAAACTTGTCCTTAGATTAAATGTGTCTGGACAGATTGTGGGAGTA
TCGGGGAAACATCCCATCAACAGGACTACACACTTGTATATACATTCTTGAGAACACTGCAAATGCAAATGTGAAAATCACGTTGCTATTTATAAAACTTGTCCTTAGATTAAATGTGTCTGGACAGATTGTGGGAGTA
AGTGATTCTTCTAAGAATTAGATACTTGTCACTGCCTATACCTGCAGCTGAACTGAATGGTACTTCGTATGTTAATAGTTGTTCTGATAAATCATGCAATTAAAGTAAAGTGATGCAACATCTTGTA

```
                            SEQUENCE LISTING

<160> NUMBER OF SEQ ID NOS: 9

<210> SEQ ID NO 1
<211> LENGTH: 22
<212> TYPE: DNA
<213> ORGANISM: Homo sapiens

<400> SEQUENCE: 1
agcaatgggg agtgtaaaga gg                                          22

<210> SEQ ID NO 2
<211> LENGTH: 21
<212> TYPE: DNA
<213> ORGANISM: Homo sapiens

<400> SEQUENCE: 2
gtaagtaaag tgccaccagc c                                           21

<210> SEQ ID NO 3
<211> LENGTH: 21
<212> TYPE: DNA
<213> ORGANISM: Homo sapiens

<400> SEQUENCE: 3
gtaagtaaag tgccaccagc c                                           21

<210> SEQ ID NO 4
<211> LENGTH: 21
<212> TYPE: DNA
<213> ORGANISM: Homo sapiens

<400> SEQUENCE: 4
gcagcgatgc gaccctccgg g                                           21

<210> SEQ ID NO 5
<211> LENGTH: 23
<212> TYPE: DNA
<213> ORGANISM: Homo sapiens

<400> SEQUENCE: 5
ctattccgtt acacactttg cgg                                         23

<210> SEQ ID NO 6
<211> LENGTH: 20
<212> TYPE: DNA
<213> ORGANISM: Homo sapiens

<400> SEQUENCE: 6
ccgacaggat gcagaaggag                                             20

<210> SEQ ID NO 7
<211> LENGTH: 20
<212> TYPE: DNA
<213> ORGANISM: Homo sapiens

<400> SEQUENCE: 7
catctgctgg aaggtggaca                                             20

<210> SEQ ID NO 8
```

-continued

```
<211> LENGTH: 183455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
aggaacttaa acaaatttac aaggaaaaaa aaccatccaa aaagtgcggc caaggatata      60
aacagacact tctcaaaaga agacatttag tggccaaaaa aacatatgaa aaaaagctca     120
tcatcactgg ttattagaga aatgcaatca aaaaccacaa tgagatccca tctccacacc     180
agttagaatg gtgatcatta aaaagtcagg aacaatatgt gctggagagg ctgtggagaa     240
ataggaatgc tttacactgt tggtgggagt gtaaattagt tcaaccattg tggaagacag     300
tggcgattcc tcaaggatct agaaatcaga aataccattt gacccagcaa tcccattact     360
gggtatatac ccaaaggatt ataatcattc tatataaaga tacatgcaca cgtatgttta     420
ttgcagcact atcacaatag caaagacttg gaaccaaccc aaatgcccat caatgataga     480
ctggataaag aaaatgtggc acatatacca tggaatacta tgcagccata aaaaaggatg     540
agttcatgtc ctttgcaggg acatggatga agctggaaac cgtaattcca gcaagctaac     600
acaggaacag aaaccagaca ctgcatgttc tcacttcata agtgggagtt tgaaccatga     660
gaacacatgg accacaagga gggaaacatc acacataggg gcctgtcggg tggcgggggt     720
ctaggggagg gatagcatta ggagaaatac ctaatgtaga tgacagataa tcttatgtgt     780
cttaaacctt gcaggcacaa aatccagcta atgtatggag tttcactttc taatacatgc     840
aagttaacct gcttttcaag gtacatgatg ttcagtggct aaaatcttta cagttctaga     900
tatgagagat ttcaggactg taagccccat tattttgctt caaacattgg tatctgatct     960
catacttaaa gagcaatgag aaatgcttca gaaaagggag agcacttttt aatatattct    1020
gaatgtatta ggatgcagtt atcatatctt gtaaggttga aaattcaggc cgggcgtggt    1080
ggctcatgtc tgtaatccca gcactttggg gaggccgagg tgggcagatc acgaggtcag    1140
gagatcgaga ccatcctggc taacacggtg aaaccctgtc tccactaaaa aataggaaaa    1200
attagctagg catggtggca ggtgcctgta gtaccagcta ctcggaggct gaggcaggag    1260
aatggcgtga acctgggtgg cggagcttgc agtgagccaa gattgctcca ctgcactcca    1320
gcctggatga cagaacgaga ctctgtctca ataaaaaaaa aagaaagaaa gaaagaaaat    1380 tcaacccctag tgagacaaca gaactattca ttgatcagaa tactcagaaa agcagtatta    1440
tatagggata ggagggtagg caggcagtat actgccacca gtaaatatat ttgtgagttc    1500
tactaaagag gaaaggagac cccttttgga gtttttttgt tctgtttttgt ttttgttttt    1560 tagtttctc atgtttttatc ctaatgggtt ttgaaagcat gatcatttaa aatactgttg    1620
gaatgggccc atcagtgatg tgatctttca cctgtgaaaa gacaagggct acttttgtgg    1680
ctgtatctcc cctatccaga caggtaggag acccagcctc tgtggcttta tgccggacgc    1740
tcatttcctg cccacagagt ttctctgccc ttcaggataa ctcagagttt gccagccatt    1800
gttgggtcta tccaagggtg tgtagttcac aactgcttcc ttccttttttc cctagaaggg    1860 taaaggttac cccataagct aaggggaaaa tgcccagccc agagagaaaa gctaagcaga    1920
gcgagcctct tggatcctga gggtctagca gagggcttat aatatctctt cctattgcca    1980
gtgccccagt tgcgcagctc tctgcgtctt ttctcaaatc atcacccaat ccgtttgcct    2040
tttatagaaa gtgatggtaa tgatgtgtgt agagtgacag acttcagttt ttacatagaa    2100
```

-continued

```
agacgggatg taggcagtgg gatcaggcca acatcagcct tgggcagcgt tttcagtggg     2160
gaagcctcct cattagaaga gccggcagca gctgtgtgac tgcctcaggc tgaagagagt     2220
cctgggaggg ttggatgtct tgttctctcc tactggattt ctaccataat aataataaac     2280
agatttattt ttctagtagt tctcatttga ctagacatgg atgaggtaaa ttttcaggaa     2340
aggcacaaca gtgtaatgga tttttatggg taaaatggct atcataaaag ctttaagcta     2400
aactttaaag gggtttgata acgagggtac attaagactt tggtttgcaa ttatttactt     2460
aggaaggatg gaaatgtttg caagtttgaa tttggctaaa agcccttctt aattgtaaaa     2520
gaatcacttt tagatgttca caagctgagc tttagcaaat accttactgg ttcttgagtt     2580
gcctctatct tagttttccc accattgtac tttacagcac aatttacaat atgtccccac     2640
ccccaaaaga gcatttcctt tctcaattgt cacaaagctg ctgagaagaa gcttattttt     2700
aacttggaaa tgtgttttgt tttaatagtt ttagcctgag agcaattatc ttacacactt     2760
tataggtgcc taatgcggtc ttaaatcatg actgaccaag gtttatcaat aaatccattg     2820
ataacatacc agaaatgagt ctgcaataac aaaatgagtc tgttatttgc ttaacatcaa     2880
ccatcagggg gaaaaattta atcctaaaaa tgagatataa aacaatacca atgaagataa     2940
ttaggaaaaa ttgttacaat actgattttg ggccctctct ggttccgttt ttatctattt     3000
ctaaaagaaa caacataaca catgtattaa atattacata atttttaaaa ggctgagtgt     3060
gtcaactaac cagcctggta tacatcaaat agtgaccata tttaaagaac aaggaaaaat     3120
cttcagtcat taataaatgt gaaactaata ggtaaaaaga agtagattca cttttcattt     3180
gttagtgcct ggtgcatagg aggtgcttta ttaagaaata attaatgaaa ctgggcagca     3240
taacaagacc ccgtctctac agaaatttaa aaattagctg ggtgaggtgg cgcacacctg     3300
tagtcctgtc tactagagag gctgaggcgg gaggattgct tgagcccagg agtttgaggc     3360
tgcagtgagc taggactatg ccactgcact gcagactggg caagagtgag accccccatct     3420 ctaaaagtaa ataagtaaat aatgaatgaa tgaatgaatg aatgaattat tggcagatat     3480
gtgttccaaa accatctata tgtttcatat tatgctagct gctgaatgca actgggcaaa     3540
cactggatac caaatgaggt attttttactg tgcaactttt gtctctgggt ggggaatacc     3600
atagcaacca gaatgtagtg cacgcagcca gtgcacagag caaggcgtat aatggctgga     3660
ccttggctta tagagcacat gaaggagttt gataagagct cagtccgaag gctgatgaag     3720
agttacaatc agagttatga gcaagtaaaa gtctgggcca acgtgtttct actcctaccc     3780
taaagagccc tagaagatga attcacttca gaatggccca aaaagggcca ggtccaatgg     3840
ctcatgcttg taatcctagc actttgggag gccaaggcag gaggatcact tgagcccagg     3900
agtttgagac cagctgggca acgtagtgag accctgtctc tagaaaaaaa aaaaatagcc     3960
aagcatggtg gcccacgcct gtgatcccag ctactcagga ggctaatgtg ggaggattgc     4020
ttgagctcaa gaggttgagg ctgcagtgag ccatgatcac gccactgcac tccagcctga     4080
acaacagagc cagactctgt ctgaaaaaga aagaaaaga aagaaggaag aaaggaaggg     4140
agggaaagaa aaagaaagaa agagagagag agagaaagag agaaagaaag aaagaaagaa     4200
agaaagaaag aaagaaagaa agaaagagaa agaaagagaa ggaaggaagc agagaaagga     4260
aagaaagaaa gaaagaaaga aagaaagaaa gaaagaaaga aagaaagaaa gaaagaaaga     4320
aagaaagaaa gaaagaaaag aaagaacgga aggactcgaa aagccccttt attcctacca     4380
agctgcatct gctctttgtc ccatctttgg atctcctgaa aacaacttgt ttcattaaca     4440
```

-continued

```
tgtcatgtag ttttaatgtt tgttccagat gctctgaaat ttgtgaccct tttttccttta    4500 gtgaaaatta aatttttact aaattgtggg aaaatgaaag aatttcagac tatttaagga    4560
tatacatttt gtttgttcgt tttccatata tgtgaaaaat tataatatat tgggtttttt    4620
taaaagttct atgttgtcct tgtaggtttt cccaaatagt gcaccccttg aaggagggac    4680
aaggctgacc atatgtggct gggactttgg atttcggagg aataataaat ttgatttaaa    4740
gaaaactaga gttctccttg gaaatgagag ctgcaccttg actttaagtg agagcacgat    4800
gaatacgtaa ggatcttaaa atgctttgct ggggtgtgct tggaaaatag gttttgtttt    4860
tgaatgaata tttcttttaa aattgctcaa gaagctcatc tcttgaatta aaaagggtct    4920
tggcctgtca catgccttgt gggtctgttc tgttttgttc ttgtaatccc atttactcat    4980
tggatttgaa gagagagaaa ggtgacatgg cctaggtgaa gagaagaggc cagaaatggg    5040
agtttctcaa ccatttatgc gacaagtctt caggtgttgt ctgagtagat ttgcaagagt    5100
agcactagtt gggatcactt catccttgga gtcttcaaat gtagagtctc caaaggcttt    5160
ttctacagaa atcagtaaac agctcagcat ggatcctctc ttttaaattc actttctaaa    5220
cctcagaaat gtagtgaggc agctgaatca cgtgtttgag acttttttag atgagttaaa    5280
atttatattc agcttatatt tactggcact gcaatatatg ggctgtatct cactgaacca    5340
tccccacggt cctgggaggg agcagtatca ttcctataat ataaaagagg tacctgaagt    5400
tcagagagat gaagtgtggc ttcacagagg taatccagag agtaagagct gaacaagcct    5460
tcagctcagc tctgatcatc ttctgatcca agacccgtgc tagttctact gtattctaca    5520
tgtacccttc tacaagcttt gaattccata atcatcagag aatccagaaa ttattcatta    5580
tcacataata acaacactca aatatttaaa gttttatggt tgaatcttta tgattgaacc    5640
cattctatca ggtggttatt ttatatctaa tagaattcat ttcagggtta cacaaaggtc    5700
cgaatctatc cattttactg agaccaaaac actaatgaag gtaatatttg ttagctgaat    5760
ggcaaaacaa attttttcta gaaatctccc ttgtaaaatc tccaaaactc ttaatcattg    5820
catataaatc aggacctgta aaagtaaagc ataattcatt ctctccttta aaaagttatt    5880
taataaatca aattgtattt aaattttctc agaactatat gattattcat tcagaaataa    5940
ttctatggaa agccatcaca atttcattat catttaagta atttaaataa gcatgtacaa    6000
gtataaccac agaaatgtac ctgttgacat actttaatga agagattggc ctatttgtag    6060
ttagcccatt gtttcatatg catctgaagt ggaccaaaga ttatccccaa atattaatat    6120
tatccaaact tagattatta tgcactattc aactggtgag gtctttatgg ataaggtctg    6180
atatttcctg tttgtctgta taagtgctat agtaccatta atgtaaagtt tagtataagc    6240
agggtgcagt ggcttacgcc tgtgatccca gcactttggc agaccaaggc aggaggatca    6300
cctgagccca ggaattcaag accagcctgg gcaacgtagt gagactccat ctctaccaaa    6360
aaaaaaaaaa attttttta attaaccaga tgccgtggca tgcacctcta gttccaactc    6420
ctgagtccag aggatccctt gagcccagga gttcaaggct gcagtgagct atgactatgc    6480
cactgccctc cagcctgggt gacagagcaa gatcctgtct cttttttacat aaaaataaaa    6540 gttaagttta tcatagtata gaaataggat tatataattt ttggccttaa tgcttatctt    6600
gaaactctgc ttgctattca aagcagtcag ctcaccattt agagttaatg tcacttccta    6660
taaaacaacc taaccagaaa attccttgga tttgtcatgt attaaacttt gggtttttttt    6720 tccagattga aatgcacagt tggtcctgcc atgaataagc atttcaatat gtccataatt    6780
atttcaaatg gccacgggac aacacaatac agtacattct cctatgtggt aaggaagatt    6840
```

```
ctatcctatc atgtttgatt tttacttaat ctatttaaat tataagatga acaagttact    6900
ttgttttgtt tttatctccc ctccaggatc ctgtaataac aagtatttcg ccgaaatacg    6960
gtcctatggc tggtggcact ttacttactt taactggaaa ttacctaaac agtgggaatt    7020
ctagacacat ttcaattggt ggaaaaacat gtactttaaa aaggtgttgt aaatttattt    7080
tttgttgcat ctgtcaattt gaattaatat ctgtacctta aaaattaagc agattgtttt    7140
gtgtgtgtgt gtggagaaga aaaatcaaga tgtttatttg tttactctcc tactgacaaa    7200
acttcctcct tccaaaattc atctactcct tttgctgatt tttcttcctt tctcttgttt    7260
tttagcaatc ctacttttca gttttgtctt cccatccacc ctctttattg ttatagctta    7320
ggatcttagc tatactatga gctgtgagag tctggtcatt gataataatt taaaataaac    7380
attttcatca agatttgtaa ttagactaag tcactctggg gaaggaagaa atggggaaaa    7440
ttgggtctgg aagacagtta tgtttctgct tcttagagtt ggaagagctc agtttaatca    7500
agtaccaaaa gtactttaaa ggttttttttt tcaaatctca aatgtttttcc agtcaaggat    7560 agcttgtcca caacaaaggt aagtttgaga tccagtcaga ttaaacagcc tacactagaa    7620
aaggcttcca ctcaggaaat tcccacttag gaaccattga gttatatcct tttgatttgt    7680
ggatataatt ctaaaatatg tgtatctcta atagctaaaa ttcacttcct taattttttt    7740
tgttcagtgt gtcaaacagt attcttgaat gttatacccc agcccaaacc atttcaactg    7800
agtttgctgt taaattgaaa attgacttag ccaaccgaga gacaagcatc ttcagttacc    7860
gtgaagatcc cattgtctat gaaattcatc caaccaaatc ttttattagg taagtagaag    7920
cttctgatgg gtataagaaa acaatgaata caaggatgat tttgctgtag aatagtcaag    7980
aggaattgca gttttatctc tggctttgat gctgttatgt tgcttttgaa ggcttctttc    8040
caattcagga gagaaaacta tattcaggtt ctgagtgtag tttgacttat caatgctagt    8100
tcattccaag aagtatctta tcctgttcta ttacatttaa acagagtata gcaaaatagt    8160
ttaatgtggc attgtagtat acatgcactt acattatgta catatcaatt ctatactaac    8220
cttagtgccc agaagtggaa ttaccttttt tcttccattc tctagatatg tttttgtcct    8280
gcctgcttta cacacagctt ttctttatgc cagactctct ttgaattgat atctcattgg    8340
acccagttca atctgccttg tttccgttaa ttctatcagt ctagcaacaa tagttaagtt    8400 cggtttttctt tgtattttttt tcagaggtga aatatttatt ttgtgtaatt cggtgaataa    8460
aatacaaatg catttcttaa gcttatgaaa tatgcatttt aaaaatattt tcaagttaaa    8520
taagttgttt ccaaagaaca gttacccatg aacttccatt tgatgttgac tgtgcctctg    8580
acctgtaatc agtgcaggtg attaaattga atccctctct tacagtactt ggtggaaaga    8640
acctctcaac attgtcagtt ttctattttg ctttgccagt ggtgggagca caataacagg    8700
tgttgggaaa aacctgaatt cagttagtgt cccgagaatg gtcataaatg tgcatgaagc    8760
aggaaggaac tttacagtgg taagtccttt gagcaatggt tctactcaga gctctgcatc    8820
tttgcctcta accatgtggc tttcatggta cctgagacat ctcagtttcg cctttaaggt    8880
ttgctagtta atttccttgc agtgtagcca agtagtattt tttatttaat aactgaaatt    8940
atctagagtc ttgggctaac catgtggaaa aaatacatac acatacacac atgcacatat    9000
aatgtttaga caagaatgaa gattaccaat ttgagacagt gtttttttat gtttgttggt    9060
tggttggttt tgagggtttt tttgagacag tatctcaccc tgtcatccag gctggagtgc    9120
aagggcacga tctcagctca ctgcaatttc ccctcccag gttcaagcga ttctccacct    9180
```

-continued

```
cagcctccca agtagctgag actacaggca cgagccatca tgcctggcta attttttgtat    9240 ttttttggtag agacgaggtt tcaccatgtt ggccaggctg gtcttgaact cttgacctca    9300
aatgatctgc ccacctcggc ctcccaaagt gctgggatta caggcatgag ctactgtgcc    9360
tggcctgagg cagtgttttt acagacagtc agtacaaatg gaaatcacag catttcccta    9420
gtcccttttt aatgtgtcat agaacatgga ccctttttgct ctaataaaat ccttggaaaa    9480
ggttgctgat cttgcagcag tattcttgca tttctaagca gctgacgtat gctttcttac    9540 agcccctgt tcttcttatc attcttcttg tccctttgtt agctctttct tgaaagagct    9600
aacaaagaaa gagcattaga atatttatgt tatgtcctaa agtgtgaatg ttatttgctg    9660
tttctccacc tatccttatt ttatataggt cacattaaag tggtagtttt agtttagacc    9720
ttagaaagct tggagttatt tccaaagatt ccatacattt tgttgatgtt tttctctaat    9780
ataaaatacc ataatctagt aggacttgag cactcaactc agaatgaaag ttctaagtgc    9840
tcttgctcaa gcaaggtctt gattggtcag gtgatagatt gaattacagc acttcctttt    9900
agattctcca tccaatattt cttgaagact aaagccacaa tgttctttaa ttacaaaaac    9960
caatttgggg ctaaaaatgt caagccaaat caccaaataa taaggtcatt tcaaataaga    10020 ttttttcttgg ccttctcaat cagccacatt gcatcacctc tagagagtat tattagattt    10080
ttatcatatt cctgagagat tgtactctag ggagtcacca tatgaagcaa agcattttga    10140
aaccaatccc cacacatggc cacaaacaaa gttagagtac cactgctatt aatttaaagg    10200
acatcagttc tccacaacta agcataacaa tgtttcatta accaaataag aataatagtg    10260
accctctttg gtgttggtat gagacctttt aaagtagaaa tctgagaaat tattagttta    10320
tctaattaat gctgagcctc cattattaag ataatgactg aatttccttt cttctccctc    10380
attggcatta aagtgacact cagaatgcct tagcttcagt cattcatttg taatcaaata    10440
tttattaaaa actttttagg tgtcacacat gagagttaca tatcccaagg atgattcaaa    10500
caatggtaga cgataaaaat cttatttgtt tatatatctg gaaatataaa cttctgttgt    10560
tttagtgaca aacatgttag tacagtagaa ctgtacatta gaatcggaca agagtgaaaa    10620
attcagtgga tctattttac tatttactat ttattttact gtcgtttgtg aaaagtactt    10680
tataaggaga tatgtattca ttccatgttc cttgccactt atagaattta aagctgacca    10740
tgatgaattg aacccattta ttatttaaca aataaaaact cttggtcagg tctgatttag    10800
atatataggt ccagccacaa taactttaag tccaataaac ttgaatcctt tcaaaacaag    10860
aacaatcatc ttcataacaa aatgtatatt aaattgttaa catgtgcatt atgccctagg    10920
agcctgcagt ttattgtgta gttctcaaat ttcttgttat gtaaacaatt attgtgatga    10980
cagttaaatt gttcatgtcc atcaggaata aataacttttt agcattataa tattaatttt    11040
atataaaact aaatagtata attttatcca tattatatct ctatcagttt tatctgctgc    11100
ctatatacat ttttaatgta agatcatttt ttaaatgatt ttttaaagaa aatagcaaat    11160
aacaaattct gtttgtcctt tttatgtata tcctgagtcc tttttctatt gtgggcataa    11220
gtaattgttt tatctccaac tatacttgtc aaagaaagga aatctaaggg atgttgttgc    11280
ttgtttgtct tttccttggg ggaaaaatgc aaccgttaac cttagatgta ccactatgtg    11340
ttgctggttt agtctaagta caatcaagag gaagctacat tttccaaaat tccataaatc    11400
agaattccaa agaggaagat ttgaaatgag acatgaaagg gcatgaaata ataatagcag    11460
aggctttgta aaatagagag cataggaaaa ggtttcagta taaaatatgt catagacaaa    11520
aagatagcat gggagtgaag acactgaatt ttggagttaa tggcctagga tttatattcg    11580
```

-continued

```
ctattctgcc actccaagct gtgtgacctg gcctaatgac ataagtttgc aaagctcagt    11640
ttcttcattt gtaaactgtg ggtaatcata atacccacct ataggattat caggagaatt    11700
aaatgagacc aactttgtaa agtattttgc acagaacctg gcattcaata attaatagct    11760
taaaagacac taataagatt acctaacaac atagttaatt atcatgttca ccatatggtg    11820
cttggtgctt tacaaagcac tttaccatgt ggtatccaac atggtaaata gcattttcat    11880
cttaattcct aaatgaggaa actgagttat tcagtgtggg ccctacctta gttcccatag    11940
cttgggttaa agctaggaga tgagccaagg ccttctaacc ccacaaagct gagctcccag    12000
tctgcctgac tgcctcacac aacaaggggc agttcctcca ggtgactgtc ctgtcttctt    12060
aaggaaaata aaatgatgag atgaaggcca gcttcagata gatcagcaca gtttatgctg    12120
ggcaggtgga gctctgtgtt tctttgaagg gtgggttgtt tggataattt tgcatgtatc    12180
gtgtttccag aaatgtgtag tctaacatta ggaagttaaa tacagatttt ttcaaaaatt    12240
atatattttc aattgattgg ggtggtaaat tataaagttg ctatggatgt tgccaagctg    12300
tattctgttt acagtggata attgtgtctt tctctaggca tgtcaacatc gctctaattc    12360
agagataatc tgttgtacca ctccttccct gcaacagctg aatctgcaac tccccctgaa    12420
aaccaaagcc tttttcatgt tagatgggat cctttccaaa tactttgatc tcatttatgt    12480
acataatcct gtgtttaagc cttttgaaaa gccagtgatg atctcaatgg gcaatgaaaa    12540
tgtactggaa attaaggtaa gaaatgcttt aaacactgtc ttaaatcatc agctcaaact    12600
taattgactt catagctatg tgaatacaat tgttgtactt ggccattgta tcttatacaa    12660
caccagcaaa tatataaact ctgaaaaaca aatctttttg gcataaaact aaaagataag    12720
aataaccgtg gactgcattt taatgaagca ttaaaaaacc ctttcttgtg tatgtattaa    12780
aacgtagcaa atgtgggaca caaattatcc attaaagagg atccgcgtca tgcattatct    12840
tgctgatgtt atacatttcc ccggacatgt tacctaaatg tgctcattat aagataaaac    12900
ataagagctg tgaaagtaaa tgcatcaatt gtatctccgt tcttccttgt aatacttgga    12960
attttgtatc tgggtatggt catctctaag ctaatttgta aatggaacta gatatctgcc    13020
accttaggaa catattagct tctaaatgta atttaataga gaataacaga tcatcttttc    13080
taaagcaagc ctgttgcaaa caaagaacac taagacccag aaaggttaag tgattgacaa    13140
gtgacaaaat agtggcagaa taataaagac tagagtgcag cttttttatg tcccttcagt    13200
agtttctact tcaaataata acacaggcaa aatgctcaag acttgaatta ttcatagctc    13260
cagtcactag aaacagcaaa atatttatcc ttcaacatgt tgttaaaaca tttagaattt    13320
tttttcctga aagatgatct gaatgcaaat atgaacaaac ataaagcaat aggatagtct    13380
ttatttggtt gtaatatagg ctttcatggg tcatctccat ctaagtaata atatgtttcc    13440
attgaaattt ttctgacttt ttcaacaaaa atttaactgc agcccaactt atgcatatgt    13500
tcacgttcat acaagtttac taacctcatt attgtgtttt gtacaataat taagcaagcc    13560
cagcataaaa ttgaatggaa gcccgcttca atgaacagtg tgtttacaaa agcaaagttc    13620
tttcatctgc ttctttaatt agttttagaa agggagaaat aagctttttat cacttctttt    13680 ttttaataaa actaatctag tgtgaccttt tgctttcaac aattactgtg tttgccattt    13740
gaaagattcc atttggtttt tcttgatgat aacaaaggtt tatgtgcaaa tagtttttaca    13800 ctcacagaaa ctctattttt ctgttcctgt atctatgatg aagggattag agatataaacgg    13860 ttctttatct acccttccaa gcacagtctt tatggaagag aaaacttctc tttccataaa    13920
```

-continued

```
ttaaataccc attattcaac atcctacaaa attgttggac caagaaaaac ataatttggc   13980
atcatcctcg gcctgtcaat ggtattccca acatggcgaa agggtcttct agagactggc   14040
aaaaaacact ttattttctt gcctatatat ggaataactc tttctctaac aagtgtatag   14100
cacctgccac gtgacagaat agtaatctag tgggagcagt ggcaattcag ggagattatt   14160
ttagtatcat ggttcaatat ttttttcatac ttcatttttc ttatgtatga gaggaaagca   14220
aaggcataag agaatatttg ttgtgtcagc aatctaactc tttatcaata cgttaagttg   14280
atcacattaa aacttctacc tctcagccag gcacggtagc tcatacctgt aatcccagca   14340
ctttgggagg ccaaggcggg tgaatcactt gagatcagga gttcaagacc agcctggcca   14400
aaatggtgaa accccatctc cactaaaaat acaaaaatta gctgggcatg gtggtgggtg   14460
cctgtaatcc cagctactca ggaggctgag ggacggaggt gacctgagtc ctgaaggcgg   14520
aggttgcagt gagccaagat ggcaccactg cactccagcc tgggagacag agcaaaaaaa   14580
aaaaaaaaaa aaaaccacg tacttcatca atgaaagtgt tctggagaga atcatgtgtt   14640
tagaatgaga tatgctcttt attgccagga agatttcatg ctcctcatgc agccatgcat   14700
gcaagagttc ctagggtgaa aagagattgt gatcattccc tgccctagtt gtgagagtcc   14760
ctcaattcat agtaagccca gtgactacac catgggcaaa agggcgagcc aggtttggat   14820
gagggaacac aatagggggtc aagcataagt caccctcag aatgaatcct aagccccatg   14880
gatggagaag gaagtttttg gccaaggctt caagtccccc aagagcagtc gtagacagtg   14940
gtcatcaaaa gtaggtacct ctttgtgggt atacatgact ccccaaatgc ctctatcaac   15000
aacagctcat gtttgtatgg aattttacag ttgacactgt actttggcat attttattc   15060 atttgagtct catgtggacc catgaggttg ggaggtcagt gatgattatc cccatttata   15120
gataggtaaa caaaggttta ggaagattag ctgatttgtc ttgggtcacc caggaagcaa   15180
agagcagaac tggggctcac actcaggctt cttgattcca aatttggtct tctgtcactg   15240
catacactaa attacagtat ttcttatatt aactctcatt taatgtatac taaaatacca   15300
ttatagagac acttttctat catatgctat ttatatatct atgcagttct ttagagggaa   15360
tagctcttaa cttttttataa atatctaaaa atttattctg tttaaagaaa ctctgtattt   15420
ctccctgagt gtcttatttc tgactttttta tgcatgagca tatcttatga aaagtagaaa   15480
agtattctgt ttcatgctgg aacaaggact gcctgacatt gccttggggt ttatcttatt   15540
ctgcagcata taggaacata tgagaataaa gatgcttcaa atgttcaatc tggagaagtc   15600
aggtcaaaca ggaaaaagaa gcacaggaag atgagccagg gcagggagcg gggacttggt   15660
ctatgacact gtcatcacag gaacaaatgc tgagagctca ggaggaggtg aagcatcagt   15720
gtgtgggcat tggaaggatc aaaaaggaag catggttttg aaccatccta atccacctgc   15780
tgcccagagc cagccagatg ttgtccttct ccctttgaat aatttatgtg caactctacc   15840
cctcaatctc agtcaaaacc accatgaact cagttctgag tccagacagg ataaaagtga   15900
agggttcttt tttcagaggt tatttggccc agtgtcgaaa cctgttctta ttaatggtgc   15960
tcaacgctta ctctcaaact agtatttctt tgtgctgccc aggttaatgg gcattctgca   16020
aaatatatat atattctttt tccagggcag tttcatagta tctaataata aagatagtaa   16080
aaaatatatt cctgtggttt catggtacct agtagtaaag gtccccaact agccagcaaa   16140
gccaccagtt taattttggt ttgcccagct tttcccaaat ggccagggaa gttttcccca   16200
aaatgcctat taacatctgg tggaactcag ttctgaagct gtctgtgagg ttcgttgctt   16260
ggttcctaag ttgagggact tgtgtcctct atgtgaagtg taaatctcac cccctcacca   16320
```

-continued

```
ccacctcact aatttcctac tgctgatctc cctggacttt ggaccctcag cctggctgag   16380
tcctgctgcc aaactgtact gacttgccca gacccagcct gtggccacct gggtgtatga   16440
aaacttgaag gaccctcctc tcatagtgtt atttttcaga tcctacccac ttccactccc   16500
atctgctcgg ttctgtaacc atctcagaca tgagtccccg ggtgtgaata ctcaatagaa   16560
acatgtcaca cctggccagg gttggagagg aaagagacat ggtacatcct gatatagcac   16620
attgggagta attagttttc attttttgaaa tggatccatt ttgacattgc agtgagagga   16680
agaaatcctt actcatcttt atattctcag tgactagaac tgtgtctaac acacagtaga   16740
cggtaagtag attttgtgtc aaatggaatt tgatttgctt catgatctag cccctttctg   16800
gataatagtt ctccatatgt aaagcagaaa tgacaataat acctacttca gggggagtat   16860
ctttgcagga taatatgaga tgattataac taaattgctc tatgtctgtt ggagattaaa   16920
gatcagaaag ctctctctct tttgttgctt tatttttaaa cccacatatt accattttag   16980
tgactgaaat caccctgaag cagttgaatg acttttattt aataatagtt aatattcaat   17040
aataaatatt aatataatta atagtaaaat ttctaaatat aagttttta gcatctcaat   17100 aaagctatgt ttactttctt ttatttaaa tgacaaaaat tagcctatac cttttaaaat   17160
ttttcctttt ttgggcccca ttgttatata gaagtgagct accagtatca cttttgtaat   17220
atctgggact ttacgcttct aatatgcata tatatatata tgtgtgtgtg tgtgtgtgtg   17280
tgtgtgtgta tacatatgtg tgtgtgtgta tatatatata tataaactga tagtagttgc   17340
ttatataagt cactacttac catgtgtcct ttggtatcta catataaaat gagacacagt   17400
ggatgtgtga tctgtttttg ttttagagaa gcctttatgc aacaaccagg gagatcctaa   17460
gcctgaaacc ataagtattg gaaacacaaa tgttgtacat tcatcccttc ccccaacctt   17520
agttattatc taagcaagca agacacattt tagacctttt ctcataaatc aaatcctaca   17580
gctctttaat ctcttttctt tgtcattccc tgaattccct ccaatatgtg gataaggggtt   17640 ttatccccct tcagacctag ccaacaagtt gtcgtttgaa gccctaaagt catctcttag   17700
attgctgagc ttctgtgttg tgttggcctg tgtggctgac ctggttcaat ggactacaca   17760
tactgcttct agaagtatca taaggatagg gtttgtctat atccatttta tctgaaactc   17820
caacatcagg ttataaagaa gtattttctt cccacttctt ttcctagaat aataactgcc   17880
tgaccaatca atctattgag atccgtatga gaccatgtat gtgaatggag tttgccgagt   17940
attaaagatt atataaaaca aaggagcagc attttagcta ttatgggctg ctctttgtta   18000
gtaagaagaa tagtaatatg ctttgatata tgtcacctca aaataatagc ttgctcaata   18060
aataactgta ctcattaagt cttgatatga gaaattatac ctaggtttgc acttcttttcg   18120 caaggctaat tattggtttc tcaaacaaaa cgttgatatt tttaaaatgc ctgatggtaa   18180
cttcagttaa ctaaatatgc cacattaact aatttttaaa aaattttgtg taactatgta   18240
attgttcaaa ataatggaat tgtgctctca aattataata gtcatacagc atctcacata   18300
aatttctttt aaaatgaatt cacttatgta taggactcaa gtgtgcaaga aggatgaaag   18360
taaactaccc aactcaaaca aaaaagaat gtattaatat taacataaca taatacagtg   18420
ttaatacatt aacaactatt taacatcaga tctctggaga tgagacccgg acatcagtat   18480
tttttaaagt tttcacggtg attccaaaag caaagtcaag gctgagaatc tctgcattgg   18540
gcagtgttag atagtgcaac aactgaatct ctacattgcg tctttttttgc caaacattga   18600 taccctgag gacaatggtg aggtgatgat aggtaagaca tcattccaca tttaaggatg   18660
```

-continued

```
tgaagcaaga acctctttcc ttttctttaa ggtccaattt gatgcaaaag ctatatgcta   18720
taattcctaa ctaacacatg ccctgaaatg gtcatgctcc cctttagcca tcccaattcc   18780
catgaaaatt agtatcatag aatcgtgtgc cttggcaaac aacatggcct gtgtttgcag   18840
tatatttata ttcctttgcc attgttagca ttcctgcaga actgtgaagt gttaacaacc   18900
tttttttttt tttttccttt cagggaaatg atattgaccc tgaagcagtt aaaggtgaag   18960
tgttaaaagt tggaaataag agctgtgaga atatacactt acattctgaa gccgttttat   19020
gcacggtccc caatgacctg ctgaaattga acagcgagct aaatatagag gtgggattcc   19080
tgcattcctc tcatgatgta aataaggaag ccagtgtaat tatgttattc tcaggcttaa   19140
aataaatcat taaagctcat ttatgtgtgg gttttggctc atcaactcag cctgcattcc   19200
tagttgttat tttagaaata gtgagctttt tgccacattg tctccttccc caagcctggg   19260
aggtagatct caaaagttct ttctacccac actgcttctc catcacgcca cactcttccc   19320
aaaatttgct gtaattctca gaagaaataa ggatgcatcc aagagtgtcc ttctactgcc   19380
tcccaccacc ccaggaggcc agagccagtg ttccactgcc aaccactgtg atcactaatg   19440
catagagtcc cataaataaa ggaagatgca tgcatcaaac aaagtaaaat aaagattaaa   19500
ctactttaca gtaacttttt tcgtgtagac aactgaatca aacaagctag aaccaaagcg   19560
agtgatcttt ttcattcttt ttttagcagc tttattgtga tgtaattcac ataccatgca   19620
attcacccat tgaaagtgca cagttcaatg ggtttcagta tattatattg tcaatttctt   19680
tgaattgagg taaaatatac ataatgtaat gtttgccatt ttgaccattt ttaaatgtac   19740
aattaagttg cattaatttc attcacagtg ttgtataacc atcagcatta cctaattcca   19800
gaactttttc gtcaccccaa acagatactc tataaccaat aagcagcagc tccacatacc   19860
cttctctccc ccggctcctg ataacttcca atctactctt tctctctaga atttgcctat   19920
tctagatatt tcatgtgagt ggaatcatac aatatttgtc tttttatgtg tggcctattt   19980
tacttaacat aatgtttatc cacgtggatg aacataagat tcatccacgt tgtagcctgt   20040
gtcggtactt cattcctttt tgtggatgaa taatattcca ttgtatatat cccacattta   20100
tccaagagta agtgattttt aaagggttcc tgaagtcttc tgaagttata aaatggaaaa   20160
acacacaaaa attagaaaat caaaggctga atcatgagat cagagttgga atttcagaag   20220
gaccataaat cctaaaaatc ataaaatgtt agagccagaa gggacttcaa agatttctgc   20280
tgtgtatcaa aactgaagta aaaatattct gagactttat tgttccatca taacagtaca   20340
attatttacc tcttatggga agtcttctct gccctccacc ccaccgtcca ggacagaatt   20400
aatgtcccat tgtctctgtt gattactgtt tagtcctact tctatggtac ataccacact   20460
gtactggaat catttatta tatgtctgtc tccccttcta tacttcagtt cctgtttttt   20520
gtacatcttt ttatccctaa tacctagtta caaatacaaa cagctaagta ccacataagt   20580
acttaaggga tcagtgtccc ctaattattt gaacactgga gcataattga ggaatctctt   20640
attatcctga aggcagttat gccatttgta gaatggtaat aaccagttgg tatttgggac   20700
ccaaagtgct acaacctgtg tagtacaaat atctatcatg gctaaatgct gacttttctt   20760
tatttgtcat ttttagtgga agcaagcaat ttcttcaacc gtccttggaa aagtaatagt   20820
tcaaccagat cagaatttca caggattgat tgctggtgtt gtctcaatat caacagcact   20880
gttattacta cttgggtttt tcctgtggct gaaaaagaga aagcaaatta aaggtgcatt   20940
tttgttactg ttcattttag aagttacctt aagaacacag tcattacagt ttaagattgt   21000
cgtcgattct tgtgtgctgt cttatatgta gtccataaaa cccatgagtt ctgggcactg   21060
```

-continued

```
ggtcaaagtc tcctggggcc catgatagcc gtctttaaca agctctttct ttctctctgt 21120
tttaagatct gggcagtgaa ttagttcgct acgatgcaag agtacacact cctcatttgg 21180
ataggcttgt aagtgcccga agtgtaagcc caactacaga aatggtttca aatgaatctg 21240
tagactaccg agctactttt ccagaaggta tatttcagtt tattgttctg agaaatacct 21300
atacatatac ctcagtgggt tgtgacattg ttgtttattt ttggtttttgc atttatattt 21360 ttataaaaac ctaaaggaag tatttacctc tgccaagtaa gtatttgaca caaaattaca 21420
tggctcttaa tttttaaaaga acccatgtat atattacatt atgattttag agtccataag 21480
ctctcatttc acaaaaaggt taatttgagc aaaagtaatt tgtttatcat ctaagtgcaa 21540
tagtaagaaa ttgcgaagct ctcttttaca atccaggaag agttaagtta caaaatatac 21600
ttatttaaat gtaagttgga actgctacat tttttacctg ttgaagccca aacattgaaa 21660
ttatactgtt agtaattctt cgaagtgttt tcaatgaact gttagtacac agccttttc 21720 ccaccatatt ctaggacttg aatgtatttt gagacttagc caaggaaaac cttcaattat 21780
gccatgaaaa aaaggagggg tcaatatcat cagctttgta aaacactatg cctagtaatg 21840
ttcaggttaa tcagagtttt catgttgttt tatttaaatc tcctggtaaa agcaaaaggt 21900
ctgtattgta tcagctccat tatctttaga agttacagga tgtgagtcaa gtacaagcat 21960
ttccttggtt gaatatttac cattggacaa ataaaatgag tcacagatca ttgaggatac 22020
tggaaaagtt agaagttgct catccaaaca agttcaagag caatgaagca cttaacattt 22080
taacattttc aacacttact acctcttatg ttttgaagtt tatgttattt ctatggagat 22140
acacatagta aacattgtct ttgccctgat tccattcacc tttaaaaatc cattcgttta 22200
accgtgtgga aaaatcaaac ctagtttatt gttttgaaat ttagatctat ttagtatttt 22260
atgtgcacat ttagtgcatc tatttagtat tttatatgca catttcatag ttctaatctg 22320
agatcattaa aatttacaaa ttttctttga aaaaaaaact tacctaatct tctttgaacc 22380
tccttactca ccaaagctct gtcatcattg ctaagaaggt tgagtttcac actcttttct 22440
ccattgagcc tgctccttgg agacatgaaa agaaaacagg taaaagaggg tcatttagag 22500
agaatgagaa aataggtgca cagccaaaac ctaatgaaga ggcaactgca gagctttcct 22560
ctctacatct ggtggggaca gcattctcat cagactttttt cacggagacc tagagtgcta 22620
tgtggtgtga catcagggtg gcacactgat ggtttcaatt ggtttctgca catgttggaa 22680
tttagctgaa gagtcacgtt ttcatgccaa agggcttttta tccatgtctc accaaggatt 22740
tccctcaatc tgtgcaccct taagcattta gagccctgat ctccagatgc aaaggcttta 22800
ggaagtgaga atgaaagacc tgagtttaga gaggctgatt ggcattccca atccctgg 22860 gaaggtttag agaccctgac tccttggaat taagggagca agtacccagc taggctcctt 22920
ccttcctcac tcacccaaca tttcaggtac ttcactgatg ttccacatcc ttctttaaag 22980
gttgctcttg tctttttttct ggctagtgtc tactataact gtaattgatg cccaacgctt 23040
ttctggaacc acttttggcc aagttcattt attattaatc aaactgtcca ctgtagaaaa 23100
tactaaaaat gctcaagtgg gattaggaat agtcaaggta ctaacagcat tcttttttatg 23160 cccttctctc agattctgat tctcctgctt atttgcaaa aaatgataca ttttggtgct 23220
aatgaggaac cccacataac cttctccctg tgttacatac taatacattt caatactatg 23280
cctagtttat cttcatgtca gttgctgtgg ctatgatgcc ccctccttga tatgtgtgaa 23340
ttcccagtgg aaagagaaag ggaaagtgga aatgccctat ttggcattaa gaaattgact 23400
```

-continued

```
atcagcacca tttcttcccc tgaaataaaa aaaaaaattc tccttgcaaa agggaacttt   23460
gcctgaggtt cttacagagc tttggttata aagatcaact tataaagaat gcttacccct   23520
ttcatagtgt ccttaactaa acaacaagga tggtccacta accgagatct aacctgcctt   23580
ctctaaacaa cagtaacact aaatccagtg ccatcactgc acagtggaga atttaccact   23640
aatgtgaaaa gctttcagtt ttgggaatat agccattatt tatttctaat catatgtgta   23700 tttttcccctt ggccaggaat ccataggttt tgcacaatag taattaattc cattaacaaa   23760
tagtagtgtc tcaaaaggca tcttttttcat tttcttatat ttgagctgga tttttgtgag   23820
acgaggcaat tgctcaacta cctttgctgc taccactgct tccattctta aggacatagt   23880
atattcaaaa ataaaccata agcatggctt tttgctattg ataaagagag aaatgtctaa   23940
ggaaatgagg gtaaaaagct ttcaaaatta atacttagtc tacttaaatg aaaatctgta   24000
aacatctaat gaaatgcttg tatatataac ttagtatctt ttcccaattt attatcattt   24060
ttatcaaact aattccatta taaaagctct tcctgtttca gtccccatta aatgaggttt   24120
tactgttgtt ctttaataat tttccttcat cttacagatc agtttcctaa ttcatctcag   24180
aacggttcat gccgacaagt gcagtatcct ctgacagaca tgtccccatc ctaactagtg   24240
gggactctga tatatccagt ccattactgc aaaatactgt ccacattgac ctcagtgctc   24300
taaatccaga gctggtccag gcagtgcagc atgtagtgat tgggcccagt agcctgattg   24360
tgcatttcaa tgaagtcata ggaagaggta agtatttcca ctcagctttt tgttaaaatac   24420 gattttccag taagcatttt atctttggcc tttgcagatt aggaacttag acaatggtga   24480
aagcaactga cagagcagtg ataacaagtg tacttgattt ctgttctata gaaatgtagc   24540
cctgtaaatc atatccgtgg ggatttgccc ttgtgcatgg aagcaattgg ataatccccc   24600
aaatatatta gaactaaatc acaattcgtc ctcgtcctgt gtgtactagc aattatagtt   24660
tcttcaaagg tgccatttac tttcttctaa aactcagggc caggcgcagt ggctcacacg   24720
tgtaatccca gcactttggg aggccgaggc aggtggatca cctgaggtca ggagttcaaa   24780
accatcctgg ccaacatggc aaaaccccgt ctctactaaa aaaatacaaa aattagccag   24840
gcgtggtggc gggtgccttt aatcccaact actggggagg ctgaagcaag gagaattgct   24900
tgaacccagg aggtggaagt tgcagtgagc caaggttgtg ccacagcact ccagcctggg   24960
cagcagagcg agactccatg tcaaaaaaat aaatacttat aaataaataa atatcactcc   25020
tttaattttg agtattttta ttcaatctct ctccagtctt tctttaccct gagaacagtg   25080
acaaactcta tgaagcctgg tttatagcag tttgtacact gctggacagc atcagaagac   25140
agagaattta tagcattctc ctgatctaaa gcaacatata tcatctctac aatgcactcc   25200
aatttcttta tacaaagata aatgaatatt tgtaataagc tagccaaagc agcaataaca   25260
gctagcataa acagtatttg tggaaatatt tagcaggaaa agaaaccaat caaaaaccgg   25320
gaaatgaact tcattcttct tgttgttttt tttttctaaa aagcttttac ccttaatact   25380
aaatggcctc tgatcccttt tattctatat gtgctgcaag aggttgtaca ggcatctgcc   25440
agtgtgatac aagagaagct gatggcgtga tttcccttat atgaacacaa ggccttctca   25500
ctttcctgtg gtagcatcca cacattcttc tgtcaaacac cccagagcgt aatcctttgt   25560
gtgctccttc ttccccaaga gtggcttcac tgttaacaaa catctttcca tttctcttca   25620
gagtaatata tagttctgtc ataggcctat aaatcccagt aattgcatca attttagagt   25680
gtgtggactc actaattgtg ttctaattct acacatttgg aaaactagaa ttttttatca   25740
tgaaaggtac taaaatggca attatttctc ttttgaagtt ataatcatta acagctctat   25800
```

-continued

```
aaatattagc tactatgtat ttatatgttt ttctgcagga gaataggagc actcaaaagc   25860
ataagtttta ttttattctt ctttgcatta gtagagggca gcctaatgcc tgacactcac   25920
atactaggca ctcatggtgt cttggccagc tggatgaatt aattagtgaa tgacttacac   25980
agctatcaga catttggcac ctctgggtgga aattactgcc actggataaa aggctaccat   26040
tgggaaaatg atgtggttaa agccagagag aactggatga agtgagtcag ggtgaatttg   26100
cttcatctgg gcaactgcct ttcagtttct gccaacctgg attacgtatt aaccagtgac   26160
taatggggaa atccttattc tataatacta atcctatttt taatggtaac attttttattt   26220 catttcagct tattagaata tagagaactt attttattat agttcttcat gtgggttaac   26280 tttatttca tattttaaaa tactatgtca tcctttaaaa aaatttattt gatgaggccg   26340
atgttactca ccttttcagt ggttccactg tggttgaata ttttattagg ttaggcttta   26400
atatgagtca tatcatctac aacttattca tgaattaaat aatcacattg cttatatcct   26460
tgggtgaaat gtgttgcatc tacatatata tttacaaaca cacctacgta cctatagtgg   26520
tattgttaaa agtattttt aaatgtactc ttttgctgta tagaaagaag aaagaataaa   26580
atgaagctca taaagggttt gataaataat tatttcataa ttaaatgtta cgcagtgcta   26640
accaagttct ttctttttgca cagggcattt tggttgtgta tatcatggga ctttgttgga   26700
caatgatggc aagaaaattc actgtgctgt gaaatccttg aacagtaagt ggcattttat   26760
ttaaccatgg agtatacttt tgtggtttgc aacctaataa atagcttata ataaaacgtt   26820
gatttacact ttccccttgt ggaaaaatca gctaccactg aaattatggg cctaatcctg   26880
aaaatttgtt ttgttctaga cttttattga actacttccc ctgaaatgat ccctcagagc   26940
cctcattagt aaggggggtag gagaaatgag gttcttggat gaactgagta tcatttaact   27000
ataactatgt ttggtttata atatttgttt tgcaagtgac atttctggaa actattggaa   27060
gcatgttggc acctacagta gtaatgactc attttaccca gaggcattac tataattatt   27120
ttttaaccac aacttccatt aaaaagataa aaaatgaaat aagacaaaca ggagaaaact   27180
acgctggcca aaaattgaaa aatcataagt atggtaatac ctcatttatc cacatttttg   27240
gagagtgagg cattccacat acatgaactt cctaaataaa tgaaacctac cccttttaa   27300 tgctggaaca ttacttaaaa ttttagctgt tattgagaaa atcttttaa gatgaaatgc   27360 atactctgtt taagggaatg cttccaaata caaactaagt ctttattggt gacccaagcc   27420
ataattacag ccataaatta ctatattaca caaacagtgt actccacata catagtgttc   27480
ctggctccgc ctgtgttgac aggtctcaca tgcttgcgtt ttctactccc atttctcatt   27540
ttctgcttgc aaattgcagc agcctgaaaa atgttaacca gctctactac aaactttata   27600
tgggacttaa taagctttaa gtgcacaaat gaaagatttt cctgcaagat actttactgt   27660
cacaattatt tcagtctttt taaaatataa atcaacatgc taagtagtgt tctacatggt   27720
taattttgtt ggaagtctga ccatgaggga aataaatgga cagtctttat gaaacctaag   27780
tataaccttt gcactaagtt tataggagac aaactggtgg ctggttggac tctatcttgc   27840
aaaagtgggc ataggtggtg actggaaggc acagtgcacg gtggcatcat tcactcagat   27900
gtgatgtaaa aagaacactc tgcagtcaaa ccctcaggac aagatgctaa ctgtgtggtt   27960
taccatttca ttgctcttcc tatctaaatt tgacaaaagt attcactgtt ccataatgaa   28020
gttaatgtct ccaccactgg atttctcagg aatcactgac ataggagaag tttcccaatt   28080
tctgaccgag ggaatcatca tgaaagattt tagtcatccc aatgtcctct cgctcctggg   28140
```

```
aatctgcctg cgaagtgaag ggtctccgct ggtggtccta ccatacatga aacatggaga   28200
tcttcgaaat ttcattcgaa atgagactca tgtaagttga ctgccaagct tactaactgg   28260
caaactagct gtaagccagc catcccttca aaataggcct gctctgagtc tttaaaaagc   28320
tagtagccaa agatgcacat ttaaaatgtt agcatcattc aaatgcacct caaagtcttc   28380
tatcctggtg ggaaatagtg acacctggaa gggtttcctg gagcaatgat tcttacttgc   28440
tctgcaagca accttgctct accttccctc tgatagggac atttagtcat ctttgcatgt   28500
ctactatgtg ccagaaactg tgcacagcac aggagaagtg gaagcagagc aagcctcagc   28560
ccatatggaa tgttaactct acaaggcatt gaaaaattaa ctccagatgc gttccttgct   28620
gttccttgtc cttgccatcc actctcacac ctcaggaact ttgcacttgt gctccctcag   28680
cctggaacac tctccccgca aatagccacg tatctcactt cctcatcttc ttcagctttt   28740
ggccgtaatg ccatcttcaa cataagcctt ccctaatctg tttaaaattg caactgacca   28800
cccaccctca tggcttcaga ctcctcttcc ctgctctatt ttcccccatc acacttaact   28860
gtcatctgat acatgcatga agctgcctga agctgcccaa tactatggcc atgagccaca   28920
tgtaaaagga ggctagttcg aactgaaatg tgctgtacgg tgtagaatac atcccagatt   28980
ctgaatactt agtattaaaa aaaaagaagg tgaaatatct cactagtagt tgtttatatt   29040
gattacatgc tgaaatattt tggattttgg gggttgaaaa atacattgtg aaaattaatt   29100
tcacctgttt cttttttactt ttgagtatgg ctactagaaa attttatatt acatgtgtgt   29160
cttgctttat atttctattg aatagcactg tagtagataa taaacaaata aacaatagct   29220
atatagatgt atatgtatgc atatatatgt acacacaccc tcatcccatt agaatggaag   29280
ctcatgaggg taggattttt gtgtattttg ttcactgctg tggctccaac acctaaaaca   29340
gtgtttagca catagactcg cagtaaataa ttgttgaatg aatcagctaa gggttacaaa   29400
aaaaggttct tagcctcttg caagtggtag attttttttct tgacatttat gccaggacct   29460
aaaagtcacc aggccaggac cagggagggt gggaataaga atctcaagaa ctgaattcat   29520
agaaggcctc aagctccgtc tcggttcctg ctctccaagt ctctgtggga ggtaatgaag   29580
ttgatcaaaa gcaactttat aaatatgggg tcaaattatc agagaaaata agctctagga   29640
gagtaatgag atattactca gccaaaagaa taaaacattc cctggcagtg aacttttgca   29700
gataaggcga attgaccttta caaagcacac agctgccctg acagacccca ctttcccact   29760
tcaacttttg ttattaccct gatggattaa tgtggctgga ggtgctacct tctctagggt   29820
actgttaccc caggattaaa gcatgataga gatttcctgt tatccagaac ggaatagtgc   29880
catggccttt tttaatccaa ggagctgata ctgagagcaa ccacaaaccc agatgtgtct   29940
taaagagaaa cctaaaacca ggaactggcc tttctctatg ctgtgtgcat tgagtggggc   30000
tacagcccct ttgcagggtc cccactgact acatcttgca ctgacaaact cctcagtgac   30060
tgttgaaggg gaatacccca ttcctgattg ccagccagtg acatcaccag acttgacagc   30120
tgagtggttt ggggtgattt ctttctgagc ctcctctatt cactgtgctt ctgatgttct   30180
aaacatcttg ggccttacta accctggagg aactgtccct cccaaggcta gctaattcct   30240
gcaaatagta aacagcttgc cttcaaagca tacctgtcat gtgcaaacca accaatccag   30300
agcccttatc taacctcctc ctttatcagg ctcttacact ttgggctact atccacctgc   30360
cctaatcacc ccagggccca gttccagaca actagaacta tcctcggagc ctgctgaaat   30420
actccagatt ggccagctcc aaacctgctt accctgcctt accagtttct tcccaggaa    30480 actgcaatga aggctcttgc tcatgttttt cccctctctc tctctgcctc tagagcccag   30540
```

-continued

```
ggcttcccca tgtgaccctg catgacaggg tgtgcctcct cctcttgcaa actgtgaata    30600
gcaaactatc tttttcaatgg cagttgtctc ctgttctgtt ggcctcatca tacctggaaa    30660
ataataaaac tacattttaa aacacctcca tttttcccatc tggaaaatgg agcctgtaac    30720
acctgcctga cagaagtgta gaagtagctg taatttatga aaacaattag cctggtgtgt    30780
tgcatacaat aaatacttaa caaatggttg atctgtcaat ggggcacact ttttgttgtt    30840 gttgtttttgt tttttgtttt tggagacaag gtctctgtca cccaggctgg agtgcagtgg    30900
cacagtcata gtgcactgca gtatccaact cctgggctca agcaatcctc cttcctcaga    30960
ctcctaagca gctgggacta taggtgcaca ccaccacacc aggctaattt ttttgtgggc    31020
ggtggatggg agtaaagaca ggatctcact gtgttgccca ggctgatctc aaactcctgg    31080
cctcaagcca tcctctcgcc ttggcctctc aaagttctgg gattacaggc ttgagccatt    31140
aagaccaaac taatttttga dacaagataa ttttttataa ataaatattt cagaattcta    31200
aggtcaaaat tagaacagta gatgcttagt ttatgctttt ctaactctct ttgactgcag    31260
aatccaactg taaaagatct tattggcttt ggtcttcaag tagccaaagg catgaaatat    31320
cttgcaagca aaaagtttgt ccacagagac ttggctgcaa gaaactgtat gtaagtatca    31380
gaatctctgt gccacaatcc aaattaagtg acaaggagga atctgtttcc cactgttcaa    31440
tgctagttaa gctgttttct cttcttatgc aaaagtcctt tatttctgtt acaatcttaa    31500
atcgatgtgt aagccctggg gatgtgggtg ggactttcag actttatcca acagagaatt    31560
taaaaggatt ctccataggg ggtcttaaac agctgttgtg tacttttgct tttctcagtc    31620
cttccctcca gtagctctca atgttgtggt ttcacactgc attagtgttg gggaggggaga    31680 atttgatctt cagcatttga cagtgaaaag gagagggctg ggaacacaaa taccaacata    31740
ttgcaacttc ccaagagtgg atttgaagcc agcctgcaga agccctacca aaaatggtat    31800
ttggcaatga atatacaaag aactttattt gtgtctggct gcctggctat gtaatacaac    31860
agtcaacagt ttgtaattga gttcatgttt tcccttgcat agcactgatt catgacttat    31920
ggtatgtgtg aatgaaaaag ggtgtgctat taatttccta ccttggtttt ggtcactgta    31980
acaacataaa agccagctta aacagaggat gcatagcccc agatagcgga aattgatttt    32040
tgttgaactt cgctgttttt cttagatgct ttactgtgta tcctagttct ctattacctc    32100
agtggtggga tatatgagtt ttgtgtgcta acctagctca tttaagaatg aaaaagtaaa    32160
gtatcagtcc cctgtcatgc tctcccataa aactgagtat cgctaatcag ttgacaagcg    32220
aagattggta attgcttggg tagttaatta gcatacttca tttagcaacc aaagtaaacc    32280 cacagggggag acagccttac tactgcagat ctacattaaa gcaaaaagga ctttcttatg    32340
ccatacaatt catgatctct ttcctcagcc tgttgaattg gcaatgtcaa tgtcaagcat    32400
ttttattcaa gaattctgtt gtaatttagt gttagtcaat agaggccaga tgaaatactt    32460
ccttcagaag ttatggattt caaatactga agccacttgt ttaatctgta gatattcagc    32520
atcattgtaa attattctat ttcagccacg ggtaataatt tttgtccttt ctgtaggctg    32580
gatgaaaaat tcacagtcaa ggttgctgat tttggtcttg ccagagacat gtatgataaa    32640
gaatactata gtgtacacaa caaaacaggt gcaaagctgc cagtgaagtg gatggctttg    32700
gaaagtctgc aaactcaaaa gtttaccacc aagtcagatg tggtaatgta ttggttatct    32760
ctgagtttct cctctttttac tttcatatcc aactttttttt gaagtttttat cactacttaa    32820 tttttttaaaa aaattcaaca ccaccaattc cagtttttctt catatgtaaa aatggacttg    32880
```

-continued

```
tctgatacgt acacattgta tattttcata aattcactca tttgttcaaa aatatttgtt    32940 gagtgggggca acataccagc tccttaggaa gcccagagct gaaccaggca tgaaccctgt    33000
cggccaagaa ctttggctca gaagggaaga gatgagatgg tcaacaatga ctgtgacaca    33060
ggtggcctgg aatgggccct gattctcata gccccaggcg agcaagaatt ccacatcaag    33120
aaatctggaa gctgtaactg aggcagtcta gcagtgaggg catgatccct gggcctagct    33180
agtaaagtgc cttcccttat ctgcaaaggc catccttctt gcgcagaaca agctctcaaa    33240
aggcatgcac ctgagtgctg aggctgggag aaatactcac ctgggcagcc agattcacca    33300
cattcccctt ccaccatatg gagaagtggc atttgaattg ggttaaagga cagcaggttt    33360
ggagttgggc agctgggcaa tggaaatacc gatccaggtg tggcagaaga gcaggaaagt    33420
ataagcacct gtaaagttat aaggaaacag tacttagtta tttggcaaga acagaacaca    33480
gagagggaag ttatgagaat aaatggagaa aaatatactt atactaggtc atagagttcc    33540
ttgaaaactg aactagagag tatggaattt attctctggt aatgtggaaa caaaaaagta    33600
atcagattag actgcaatct ttcatcattg tattagtccg ttctcacact gctataaaga    33660
aatactgagc ctgggtaact tataaaaaga gatttaattg gctcacagtt ctgcagactc    33720
tacaggaagc atggctggag aggcctcagg gagctttac ccatagcaga aggcaaaata    33780
ggagcaggca ttttacatgg caggagcagg accaacgggg ctgtgggaag tgccatgcac    33840
ttttaaacaa ccagatctcc tgagaactct atcacaagaa cagcaccaaa ggaagaaatc    33900
tgcccccatg atccaatcac ctccaaccac gccctccct cagcattggg gattacaatt    33960
ttacatgaga gttgggtggg aacacagagt caaaccatat cattccgcct agttcctccc    34020
aaatctcacg tccttctcac atttcaaaac acaatcatgc cttcccaaca gtcccccaaa    34080
atcttaactc attccaacat cagctaaaaa gtccaagtcc aaagtctcat ctgagataag    34140
gcaagtccct tctgcctatg agcctgtaaa ataaaaaaac aagttagttg cttacaagat    34200
acaacggggg tacaggcatt gggtgaatgc tcccattcca aacgggagaa attggccaaa    34260
gcaaaggggc tccaggccct acacaagtcc gaggccctat gcaagtccaa aacccagcaa    34320
ggcagttatt aaatcttaaa gctccaaaat aattttttg actccatgtc tcatatccag    34380
ggcacgctga tgcaagggat gggctcccaa ggccttgggc agctctgctc ctgtggctct    34440
acagggctca gccccatggc tgctttcatc ggctggcatt gagtgcctgc agcttttcca    34500
ggcacacggt gcaaactgtc agtggatcta cctttctggg gtctagagga tggtggccct    34560
cttctcacag ccccacctgg caaagcccag cactaagggg aggtctcagg gagctttta    34620 cccatggcag aaggcaaagc aggagcaggc atcttgcatg gcaggagcag gaccaagtgg    34680
ggggaggggg agcatcttat atggcaggag caggaccaag gtggtgacaa gctttcacca    34740
aggggagagg tgccacacac ttttaaacaa ccagatctcc gtagaattct atcacgagaa    34800
cagcaccaaa gggagaaatc tacctccatg atgcagtcac ctcccaccag gcctcagctc    34860
ccacactggg gattataatt caacatgaga tttgaatggg gacacaaatc caaaccatat    34920
caatcattct ccaagacaac ttgaaggag tagaagcagg aagatgaagt gagaagtgga    34980
acttgaaata agacacaatg agaatggaaa ggaagagatg aaaggaggag catctccagag    35040 gtagaatcag aagtatttac caaggaattg ataaaaagtc aaagattagc aaagatatat    35100
gctcatgcaa taacacatat atgaagcaca gaagcaaaag ctggactcag aacaaaaata    35160
gcaagttgag ccttaaacac actgagtttg ccttgggagt agaatgtcca ggcagagaag    35220
tccatcaggc aattgaaaat gtgaatctgc aacttgtaaa aaatgtatta ttcagcctgg    35280
```

-continued

```
gctgtcatac aatagaccac agactggttg gcttaaacaa caaaaatgta tttctaacca   35340
ttctgaaggc tagaagtcca agatcaggat gtcagcatgg ttgggctcta ttgagggctc   35400
tcttcctggc ctatagatgg ccaccttctt gctgtgtcct cacatggcta aaagaataag   35460
agtcagttct ccagtatctc ttcttagaag ggcactaatc ccagcatgaa tgccaccctc   35520
atgaccttgt ctaaactgaa ttacctctaa atggccccat cattaaacat tgtcacagtg   35580
gggcttagag cttcaacata tgaatttccg gggaacacaa ttcagtccat agcagggtc    35640 aaggctggga atatgctttt gagagtccaa aagcaattat tcagtagtcc aaaagcaatt   35700
attcaactac atatataaag tgaaagagaa aagcagtgag gtaagggacc cagaagcaaa   35760
gaccaccatg aaagtcagag taagagaaag tttcaaggag aaattggatg ctcaacagag   35820
tccactgcta ctcagtacac cagaagggtc ttggaagctg agtaacttga gtgatttgga   35880
ggtctagagt gtgcttagga gcacaggtgt tgaatggaat ggagagtaca cttattctat   35940
tcacatgttg taagtcagag gactgtgatg tctgaagata gagaaacatt tgatgtttca   36000
gtccttaagg atgacaacta aaaaaggaaa atgtgcaaac aaagtagtca gaaaataatg   36060
ttcatggggg acatgcactt gaagagaaag ggttggtagc ttttgagaga tgatgggtca   36120
gagatctgag tgtggcatgg gaagcaagaa gtcatctcat ccacctctct gtgaatcagc   36180
aagagggaga ggtgtgaccc ctattggcaa gagttgcaaa gaaattgtga cttcaactga   36240
aagctgagtt tcagttcctg tgaggaggta ggggaactat tagagaataa gacgaggtga   36300
ctgggagttt gttttcaatg agtaagtagg tcataggtca tggtggagga ccaggacttc   36360
agcatgcatg agattggtaa gagaaagtga tagtgccatg tagagcttaa tgcctgggat   36420
tttgatcctg aaagattctg aaagaggtga aagaagtggg tgctagagag ggagactggg   36480
gacatgttag tgacagtggc aggtgaaggc aaaagatagg gagaattaac ccatcctcca   36540
agaacatact gttcattcag acttgagggt tagtctgcca ttaagaagcc agagccaacc   36600
cttacaactc aataataaga ctgtcttagt cgttttgtgc tgctataaca caataccaca   36660 aattgggggga tttataatga acagaaatgt atttggccca cagttctgga ggccaggaag  36720
tccaagatca aggggccaca tgtgctgaag gtcttcttgc tgtgtcataa catggtggaa   36780
ggcatcacat gggtgtgaga gagtgcaaga gagagcaaga ggtgaacaga ttctctaaca   36840 aacccottcc acaataatga actgactccc aagataatga cattaattca cccatgagag   36900
tagagcctca tgacctaatt acctcttaaa gatccctcct ctgaacactg ttgcattgga   36960
ggggattaag tgtccaacac atgaactttg gggacacatt caaaccatag caaaggcaat   37020
attactcaat tttttttaagt aagcagaaga tttgaataga cattttacca aagagacgta   37080
agaatagcta gctaatgagc acatgaaatg aaacatatgc ccacatgaag atttgtacat   37140
gaatgatcac agtagttttc ttcataatag ccaaaaacca gaagcaatct taatgtccat   37200
caacgggtga atggataaaa aaaaatgtgg tgtgtccata caatggacta aaccattcat   37260
caacataaag gaattactga tgcctactac agcatgataa acctcagaaa cattatgtta   37320
agtgaaaaaa aggcagataa aaaaattaca tgttgaatgg ttccatttat atgaaatttc   37380
tagaaagagg cagaactaca gagtcagaaa acaaatcagt ggttgcctgg ggccaagaga  37440
aggagtgaag ataaaccaca aatggacatg agggaatttt ctggaatgtt gagatgatct   37500
aaaactggac tgtgatgata tgatagctgc acgtctatat aaatttacta aacatcattt   37560 aatcactttta atttactaaa catcaccaat cacttaaaat tggtgagttt tatgatctat   37620
```

-continued

```
aaattatacc tcaacaaagc tgatttataa aaaaagagcc tgatgaaatt ttggatgttt   37680
agggcaagtg ttgggattct aagcttcttg acagccacat acatgcaaca atacccccac   37740
ctccccaaca aacacacaca gacagcacag aggccaaggc ttccaccata gccacagtca   37800
ctcagatact tgactggaaa tgtacataga tttctgcaga taggatggtg ctatttcttt   37860
ctcactctca tcgaaagaca ctattttgtg ctacataaag gctgaacctg aataatctgt   37920
acataatgct gctttgggaa atggttactg attgcatgga taaatttgca cagtgtttta   37980
cttccaggac agcgcaatct tgaatgttga catggaacat ttccaaaagc atgcaatgag   38040
ctatgtgtat gttgaaacct gcgaccaaaa acttgcctgc ttgtagattg ggtttctttt   38100
ctagaaaatg cccaaatgga gtttggctaa aatctgaata ctctttaagt ccattcaaac   38160
aaaatcggag tgtcactaca ctggaaatca ctcacaccct cctctgaacc cttttgcaat   38220
gggtgttgta attgtattat acgttgtttc acacttaata caagttcttc cattaaactg   38280
tgtattgact tccttgttct cagcccttat ctgcctcatc tttctgaagt gtttaacatt   38340
attgtaaccc tcattttttct tgaaatttcc tcttcctttg gtttctggga cactgaaact   38400
tccagttttc ctcctgcttc taggttgttt tctttatcct caatggcttc tcttccttct   38460
gtcttccttc tctcagatgt agctgtctcc caggatttt gtctttaggg gtcatcctcc   38520
accaacagtt ggaaccattc ccatcaataa ccacctttga ttctctctac ctggatgtca   38580
tcatcagtgt cacaaattta ccatgttcag aatcaaactc tttcctgcca aaccctcaat   38640
ttctcacctc ctggctttga ttaatggcat caccattgtg taatttaccc actcctcatt   38700
cttttcagtg ttcggttttt caggtttttga caaatgcatg cagttgtgta accaccaccc   38760
caacaatcag gacatagaac agttctatca tctcagaaaa tttccttatg ctcctttgta   38820
gtcaacctct acccctatccc caggacctgg aaatcagaaa accagattta ttttctgtct   38880
ctagagtttt acttttttcta aaatgtcata taaatggaat catgcagtca gtagtcttat   38940
gagtctgtct ccttttactt cgcatattac atttgagagc catccatgtt gtcgtatcag   39000
tagtagtaac gtatcagtaa ttcattcctt tcttattgtg gcaaaaaaat acataaaatt   39060
taccatctga acgattttta tttattttta agttccaggg tacatgtgca agatgtgcag   39120
atttgttacg taggtaaacg tgtgccatgg tggtttgctg cacctatcaa cccatcacct   39180
gggtattaag ctcggcatgc attagctgct tttcctgatg ctcctcccct ccctcgatag   39240
gccccagtgt gtgttgttcc cttccctgtg ttcatgtgct ctcattgttc agctcccact   39300
tagtgagaac ttgcggtatt tggtttttctg ttcctgcgtt agtttgctaa ggataacagc   39360
ttccagcttc atccatgtcc ctgcaaaaga catgatcttg ttccttttta tggctgcata   39420
caaccatttt taaatacaca gtacagtatt gttaactatg tgaacattgt tgtgcaatag   39480
attcctagaa cttttttcatc ttagcaaaac tgaaactcta tatccattaa acaattctct   39540 ctctcccca ggccctggca accacaattc tactttgtct aagagtttga ctacttcaga   39600
tacctcatat aagtggaatc atgcagtatt tgtctttta ggaccgactt atttcattta   39660
gcaaaatatt ctcaagcttc atccatgttc tagtatatga caagatttcc ttctttttaa   39720
aggcagaata atattccatt gtacatatat gccacatttt ctttatccat tcatctgtca   39780
atggacattt aggtttctta tacctcttgg ctattatgaa tagtgccgca gtggccatgg   39840
atgtaaaaat tctctttgag atccttttt tcaattcttt tgtatataca cacagagaca   39900
ggattgctgg atcatatggt aattttattt tcaaatttt ggggacctct ctactgtttt   39960
ccacagcaga gtagttcatc tcttttttatt tttgagtagt attccatcgt acagatgtac   40020
```

-continued

```
cacattttat ttatccattc accagttaaa gaacatttgg gccaggagag gtggctcacg   40080
cctgtaatcc cagcactttg gaggccgagg agggcagatc acttgatgtt aggagttcga   40140
gaccagccta gccaacatgg taaaacccca tctccactaa aaatacaaaa aattagccgg   40200
gagtggtggc acatgcctgt aatcccaact attcaggagg ctgcggcggg acagttgctt   40260
gaaccctgga tgcagaggtt gcagtgagct gagatcatgc cactgtactc cagcctggat   40320
gacagagtga gacccgtctc aaaaataata ataataaaga acatttgagt tctttccatt   40380
ttcaggcaat tacttataca taattgtaat ggctatgaca tttgcttgaa ggttttttctg   40440 tgaacgtaat ttttatttct cttgggtgaa tatctaggtg taagagtaac taactgggtt   40500
gtaagataag tgtacattca actttatgag aaactgccaa ctattttttca aagtggctgt   40560 atcattttat gtccccacca gcgatccata agagttccag ttgttcagca tcctctcccg   40620
cacttgacat tgtcagtttt ctgattgtta gtcattctaa ttggttgtag tgctgtctca   40680
ttttcttttt aatctttatt tcccaatggc tagtgatgtc gagcctcttt tcatgagctt   40740
atttgccatc cttatatcac ctttagtaaa gtgtctactc aaatcttttg cctattttta   40800
agtatttatt aataatatta atttagttag ggtttatttt attggcttgt ttttgtttct   40860
tattgaattg ttcgagttct ctgtatattg tggatacaag catatcttat gcgatacact   40920
tttgccaatg catttttttt ttcttttggg acgaagtctc actctgtcac ccagcctgaa   40980
gtgcagtggt gcaatcttgg ctcactgcta cctctgcttc ttgggttcaa gtgattcttt   41040
tacctcagcc tcgccagtag ctgggattgc aggcatgagc caccatgccc agctaatttt   41100 tgtatttttta gtagagacag ggtttcacca tgttggccag gctcctgact tcaagtgatc   41160
cgcctgcctt ggcctcccaa agtgctggga tcacaggcat gagccaccgg tgacacctgg   41220
cccacaaatg cattttttcta gtctgtggat tacctttttca tttatttaat ggtatccttc   41280
aaaaagcaaa agtttttgat tttgttgaaa attttatcag tttaccaatt gataaaactt   41340
tatcaattta tttttttttct tttatcaatc ctggtgttga tgttgtatct ccatgcatct   41400
actcttgaat gctcagattt gcctatcatc cttccttgct cacttacctc agtagcaacc   41460
ctgtctatca cttttcatag cttacaacca tctttcacat ttaatcattt ctttgatcat   41520
caccttcagt aaagttaggc cagatattct ccagatgagc ttattgctgg tgctcaaatg   41580
ctcaaaatgg cttgaccaat gccatacagt aagcacggat gatagcgctc tcatggcttg   41640
aaactaaaac tgacttgttt cctaatgcac atgaattgta cacctccctc ccctcacccc   41700 cgacccccc tcaacgacag acacacacac acacacacac acacacacac acaccagc   41760 ttctctcttc ttggtcatca tcctaatcag catcacctcc tctttcactg tccctcccct   41820
caccctgctg tcagcccac aatgctttca ggggagtgtg gagtgcagac aatacaatgc   41880
tcttcctgga aaccttcttc ctcttacctc cctgtcccgt gagtcctcca gctattttct   41940
gatacccagt tattgcccac gtcctttaat tccttggaaa attacccaac tccatccccc   42000
ttttatgtga ctttgtctcc agacaaatct acatgtagcg tagactgtca gatagggaga   42060
cctgatcaca gaactttggc ttcctcatcc taaaataaaa ccaattacat cacaggattg   42120
taacaagtac aatccattat aaggattaaa taagatgttt tgtaaaggat ataatgccta   42180
tgcatgaatc attatatgac aaatacactc tttcactacc ttaattccag agaaaagcct   42240
cataggcttc cgtattgtag gtatgcagga gtgtccctca cctattctta ttcagaaacc   42300
tcctaactgg cctccatatt gtgaatcagc ttctcctttc tgttctaagc ttggcgctta   42360
```

-continued

```
cagatgccat ctccctgagc acaactcaga actcagccat gtcccattga tttcagtcta   42420
acgcactttc tttttttttt ttttgagacg gagtctcact ctatcgccca agctggagtg   42480
caggggcgcg atctcagctc actgcaactt ccacctccca ggttcaagcg attgtcctgc   42540
ttcagcctcc caagtagctg gattacaggt gcacaccacc atgcctggct aattttttgta  42600 tttttagtag agacagggtt tcaccatgtt ggccaggctg gtcccgaact cttgacctca   42660
agtgatctgc ccaccccgc ctcccaaagt gctgggatta cagatgtgaa ccaccttgtc    42720
ccgccctgtc taacccactt tcaacattta aaaacctcca cagcacagtc ccatttcaat   42780
cttatgggtc cctaatccct tcccctactc caacatgtca agcaacatga actattatac   42840
tttatggttt aataagaaca catatgcagc caggcgccgt ggctcatgcc tgtaatccca   42900
gcactttggg aggccaagga ggtggatcac ctgaggtcag gagttagaga ccagcctggc   42960
caacatggag aaacccgtc tctactaaaa atacaaaaat tagcctggca tggtggcagg    43020
cgcctataat cccagctact caggaggctg aggcaggaga atcgcttgaa cccgggagga   43080
agaggttgca gtacaccaag attgcaccac ttcactccag cctgggcaaa agagcgaaac   43140
tccatctcaa aaaataaaaa aggaaagaaa gaacacatgt gtactgttac tcctggcccc   43200 acccctcca cccaaaactc tccctctgcc ctcatattac ctgcacctat aaaacaaagt     43260
ctccctgttc ctcaagaccc accttactgt cactctcttc ctgcagcctt tctcagtacc   43320
ctactattat ctctttgact tttggcaacc tttgtacctc tttgatatta ctgctctata   43380
ttacagctat tatcttattg tcctgtgtgg cagttatctg ctcaattctc ttaaccctgt   43440
tcattcagcc ctgggaccta tctagtaact tgaacagtaa cctactcgta tgtgatcaag   43500
ggtcaattga tacttgttaa attgattta aatattaatg catattctgg acttgaaagt    43560
taacacgatg atgttgtcag aagtgattgt tgattgttaa gattttcaga cttttgaaaac  43620 ttctactttg caaagctgaa ttagacagca aagttctgta gctccctcct ggcaaggggt   43680 ttgagtttc tgttgggatc aaggcagtca gcagccatca agggttcttg cacttgggca    43740
aagaagtcat taatggtaat ttgtatcagc aattacagca tctacctcat ttctttcttt   43800
cagtcgcagc gttcaaaggc aggcttattc tccttcttgc tgggtactgc aagctacact   43860
tgcctctcag ttttatgtct tcctactcca gctgtctggt gtggattttc cttctgctcc    43920
aagcttcctt catttcttcc tccttatgct tcctactctt agagtggcct ggaagtgttg   43980
ctgggcaaga actgcccccc tgggtcctgt ccacaggggc ggcctctgcc atgctgactc    44040
tcctcgtgtc attcttgcat gggcacatgt ccaggggag ataatatgta tgacctggtc     44100
tatcctgagc acagtgtttt aaatcaagaa attgcatgtt tattgaagtt cagtagacca   44160
aacaagacct aagggtcagg aactcttaaa tgtttatccc agtgtggact cagatgtatt   44220
ggggaatttt agcaagtcac ttaacctctc cgtgtccctg tgatcttcct atatagtact   44280
gatacggcta ttttatatga atctagtact ttcacatctt catgtgacag ttttattgaa   44340
attaattttc aatagagaaa cttgttgcct tgcagttttt tttatttctg attttttaata  44400 tgtattttac ttatgttgat ttagaccttc ccatttaata gtaacctttc aatgtggtta   44460
catttcttaa agagtattta tgttcagttt gaaaccacac aaatttaaat tttgggaggc   44520
tttcttcttc ttttacaagt aatgtaaaat tgtagtgaag ctattggaaa agaaaaggat   44580
agaaacatgt tagtgctttg acacagcagg agagaatttt ggaagagata ttctaccaac   44640
tacagatgga atcttcatca tcatgtagac ttcagatatt cttttagaaa actttacatt   44700
tacttataat ctaaacctta cttgtttaaa caagtcatga aatgtatagc ttaataattg   44760
```

-continued

```
cctttaagaa aattgttgcc caaaacagaa accgtattga gtatgtaaag ccaagtttag   44820
ttaccaagac ctactgattt cctttcatat atgtatggtc acatctctca cctcatctgt   44880
cctgtttctt gttttactag tggtcctttg gcgtgctcct ctgggagctg atgacaagag   44940
gagccccacc ttatcctgat gtaaacacct ttgatataac tgtttacttg ttgcaaggag   45000
aagactccta caacccgaat actgcccaga ccccttgtaa gtagtctttc tgtacctctt   45060
acgttcttta cttttacaga aatgcctgcc ttcaaagggt ctcttacagc atgtctttct   45120
ttttggaaca gatatgaagt aatgctaaaa tgctggcacc ctaaagccga aatgcgccca   45180 tcctttctg aactggtgtc ccggatatca gcaatcttct ctactttcat tggggagcac   45240
tatgtccatg tgaacgctac ttatgtgaac gtaaaatgtg tcgctccata tccttctctg   45300
ttgtcatcag aagataacgc tgatgatgag gtggacacac gaccagcctc cttctgggag   45360
acatcatagt gctagtacta tgtcaaagca acagtccaca ctttgtccaa tggtttttc   45420 actgcctgac ctttaaaagg ccatcgatat tctttgctct tgccaaaatt gcactattat   45480
aggacttgta ttgttattta aattactgga ttctaaggaa tttcttatct gacagagcat   45540
cagaaccaga ggcttggtcc cacaggccac ggaccaatgg cctgcagccg tgacaacact   45600
cctgtcatat tggagtccaa aacttgaatt ctgggttgaa ttttttaaaa atcaggtacc   45660
acttgatttc atatgggaaa ttgaagcagg aaatattgag ggcttcttga tcacagaaaa   45720
ctcagaagag atagtaatgc tcaggacagg agcggcagcc ccagaacagg ccactcattt   45780
agaattctag tgtttcaaaa cacttttgtg tgttgtatgg tcaataacat ttttcattac   45840
tgatggtgtc attcacccat taggtaaaca ttcccttta aatgtttgtt tgttttttga   45900
gacaggatct cactctgttg ccagggctgt agtgcagtgg tgtgatcata gctcactgca   45960
acctccacct cccaggctca agcctcccga atagctggac tacaggcgca caccaccatc   46020
cccggctaat ttttgtattt tttgtagaga cggggtttg ccatgttgcc aaggctggtt   46080
tcaaactcct ggactcaaga aatccaccca cctcagcctc ccaaagtgct aggattacag   46140
gcatgagcca ctgcgcccag cccttataaa tttttgtata gacattcctt tggttggaag   46200
aatatttata ggcaatacag tcaaagtttc aaaatagcat cacacaaaac atgtttataa   46260
atgaacagga tgtaatgtac atagatgaca ttaagaaaat ttgtatgaaa taatttagtc   46320
atcatgaaat atttagttgt catataaaaa cccactgttt gagaatgatg ctactctgat   46380
ctaatgaatg tgaacgtgta gatgttttgt gtgtattttt ttaaatgaaa actcaaaata   46440
agacaagtaa tttgttgata aatatttta aagataactc agcatgtttg taaagcagga   46500
tacattttac taaaaggttc attggttcca atcacagctc ataggtagag caaagaaagg   46560
gtggatggat tgaaaagatt agcctctgtc tcggtggcag gttcccacct cgcaagcaat   46620
tggaaacaaa actttgga gttttatttt gcattagggt gtgtttatg ttaagcaaaa   46680 catactttag aagcaaatga aaaaggcaat tgaaaatccc agctatttca cctagatgga   46740
atagccaccc tgagcagaac tttgtgatgc ttcattctgt ggaatttgt gcttactact   46800 gtatagtgca tgtgtgtagg ttactctaac tggtttttgtc gacgtaaaca tttaaagtgt   46860
tatattttta taaaaatgtt tatttttaat gatatgagaa aaattttgtt aggccacaaa   46920
aacactgcac tgtgaacatt ttagaaaagg tatgtcagac tgggattaat gacagcatga   46980
ttttcaatga ctgtaaattg cgataaggaa atgtactgat tgccaataca ccccaccctc   47040
attacatcat caggacttga agccaagggt taacccagca agctacaaag agggtgtgtc   47100
```

-continued

```
acactgaaac tcaatagttg agtttggctg ttgttgcagg aaaatgatta taactaaaag   47160
ctctctgata gtgcagagac ttaccagaag acacaaggaa ttgtactgaa gagctattac   47220
aatccaaata ttgccgtttc ataaatgtaa taagtaatac taattcacag agtattgtaa   47280
atggtggatg acaaaagaaa atctgctctg tggaaagaaa gaactgtctc taccagggtc   47340
aagagcatga acgcatcaat agaaagaact cggggaaaca tcccatcaac aggactacac   47400
acttgtatat acattcttga gaacactgca atgtgaaaat cacgtttgct atttataaac   47460
ttgtccttag attaatgtgt ctggacagat tgtgggagta agtgattctt ctaagaatta   47520
gatacttgtc actgcctata cctgcagctg aactgaatgg tacttcgtat gttaatagtt   47580
gttctgataa atcatgcaat taaaataaag tgatgcaaca tcttgtatac tgatagtggt   47640
tattgccagt catgcttgat tacctgcatt tgcataatga tagaggaagc ctaagattga   47700
tttcacctgg ctgcatagag ctcatccatg taggagagcc ttagtcaagt gaatgctgag   47760
gaagtagtaa aacagcatgc atccccgaat ctcaggaagt ctctgtcttt ccaagggttt   47820
ggtctaagtt gctgattacc cggatttttc tgacgatctt tcaactgcta gagcatctgg   47880
ttcctgtttt agcatggtgc tcttctccag caaggtgtgt ccttagacta gaagacacaa   47940
aaatggagca gcagccacac cattggcgca cagataccta ggtgtgggtt ggagagagag   48000
gccttcttgc cccatcaaaa ctactcttta tctacacagg tgcccaccct tttacccca   48060 gttaccagag aaattacctt caggttatct ccatgtatat tcttgtaatg gtaagggaat   48120
tcaaaggtga taatttcagc catctaagaa ttgtgtgaca cattgggggt aatctaattt   48180
taaaagaacc caatttaaaa taatgcctac aaaatacaat ggacactgat cctttactgg   48240
gagataattc aaccccgct cacggccaaa ctctctccca ctcaaaagat gcatttcccc   48300
agaaagttca atccaactct ctcccataag gagaacaacc tgtcatcttt acatctctag   48360
aatccggcac ttagtagatt ctcaaataat tgctgaactg aaacagcatt ttcttattcc   48420
ccatcacttt atttatttat ttatttattt atttatttat ttatttatttt ttgagacagg   48480 gtcccactct ggcccccag ctggagtgca gtggcatgat cttggctcac tgcaacctcc   48540
acctcctggg ttcaagccat tctcctgcct cagcctcctg agtagctgga attacaggca   48600
cacgccatca cgcccagctg attttttgtat tttagtagag acggggtctc gccatgttgg   48660
ccaggctggt ctcaaactcc tggcctcaag tgatccacct gcctcagcct cccaaagtgc   48720
tgggattaca ggcgtgagcc accacaccca gcctacttta aaccaccatg ggcagagtta   48780
ttgcctatgt agctcccatg atgtttggag aacactaata tggagaatgc agactttct   48840 ggggaaagag aaatagaaag atagacctt aagaagtttg gcttggtgct acgcattttt   48900
aattatcaca gggtttttcgc ttcacgatat aagcatcaat tatatttttg ctcgctgacc   48960
tacacagtgg attccatctt taaagaaata gggagaaggg atatataacg cgtagaaata   49020
catcaaatgc ttgaatgctg acatctggca ttgttaatct acctgattta gttcagaaaa   49080
tgagttagca ttatataaaa gaaattgatt agtattttat ttaactcaac gaatatttat   49140
caagcaccta tatatgtcag acactgctag gtaatgggga tataaaaata aacagtccct   49200
ctcaccccaa ggaatttgat gaaacagaca aaattacata attaatgaat attaaaaatt   49260
attcatttct tagatttgtg agttgtcttg aagagacacc acagtttaaa catacacaaa   49320
gtgcaggctc ctgggcaaca gaccaagccc taactcagat tgggcaacat attggacttc   49380
tctaaacctg tgttctcatc tgtcaaatac attaatcatg gttaccccca caaagttgtt   49440
tgaggacttt aaaaaaaaagt gtataaaggc acctggcaca ccatagttgt tcaataatca   49500
```

-continued

```
taatatcatt attatcttta gtcttagaca ataaaagccc atgtataggt agccttagtt   49560
ggctaaaggg aaatgaggct tggaggggca ttacagatgt ttaaatccaa attcttaccc   49620
cattcttttt gttttgtttt tttgtttgtt ttttggtttt tgttgttgtt tgtttgtttt   49680 gttttgaga cagagtctca ctctgttgcc caggctggag tgcagtggca tgatctttgc     49740
tcactgcaac ctccacctcc tgggttcaag cgattctcct gcctcagcct cctgagtagc    49800
tgggattaga ggtgtccacc accacaacag ctaatttttg tatttttagt agaaacgggg    49860
tttcaccatg ttggccaggc tggtcttgaa ctcctgacct caggggatct gcccgcctca     49920
ggctcccaaa gttctgagat tacaggcatg agccaccatg cccagccaac ttcttacccc    49980
attcttcacc tcacacctgc tttatataca gtagaaacag ctgtgattct gcctcatcct    50040
gcatatgaca gtgagggtga gagaggagaa aggtgacaag acagtggcac tggcaagaga    50100
actccctcac ttctttctct acactcccca ctatcacttt aattacttct cctgtgacag    50160
attccttttt tctgttttag cctttagacc tggaatacac aacagacatg gaagagaaca    50220
ttctgtctaa atgacaggca tgttgcatga aggtgcaaga ataagagcca tagtcttcag    50280
tattggtgtc tagaaattat tattgttcct cattttttgct caaatgttaa tagatggtta   50340
atgatcattc aggttgaaga aaaagtaaac taagtacagt attgtttttag ttatgtgcta  50400 tgtgtttgaa gatgaggaat acatgactag acacacatag caagttacac aggcacacat    50460
gactcactgt tgtagcactt cagacagttt caagacacag agaggtatgc agacgttatg   50520
ccccaaagga agaaatgctt attgctgttt ttctttttca tatttgaggg gttctttcag    50580
gactatctca attccttatc tatcaaagaa ttggaaagaa cttcagtcat aaaccaatga    50640
aatatttcag ttggtgaatt gaaggtaata aaatggatgc ttgcccaaac tgtcctttgt    50700
tgtaaattat tccagagaac tagattacgt cagccaaaga tattgatcac aatgctgaga    50760
ggtttataac tactattgac ttaccatgtg accccagggc agaaatctag gaaaattgca    50820
aaagcatatc tactgtaatg aaaagcccat cattaatagg acttactatc ttgtcatcca    50880
actagtacta tgttggcttc aaggcaaata tttaacaaac atttgaaaca gaaagcactt     50940
ctgtcttctc cctttatct tccattgatg ttcccgagct attctgatga atgtgttttt     51000
gttcttatca ataaaacatg taggttaaaa taagtgaata tatttataat tattagccta    51060
tataaattag catccaaata ttgaaatagc tcctactcct ttattattac tatcattatt    51120
ttaataagga gttagctcct catgtagacc agtttagaat acggctcaag tccaattctc    51180
ctgcgtagtt aaaccctacc tggttaagca ttctgaaaac tagttactct ttttttttttc   51240 tttttttgag atggagtctc tctctgtcac ccaggctgga gtgcagtggt cgatctcgg     51300 ctcactgcaa ccaccacctc ctgggttcaa gtgattctcc tgcctcaacc tcccaagtag    51360
ctggaattac aggcatgcat caccacaccc agctaatttt tgtattttca gtagagatgg     51420
gatttcgcca tgttggccag gctgatctcc agttcctggc ctcaaatgat tgccatctca    51480
gccttccaaa gtgctgggat tacaggtgtg agccaccaca cccggtggaa aacgaggtac    51540
tcttagagaa gcaattctga gatgaaaatg gccatattta gaatgcataa acagacatct    51600
ctgatttaaa ttaactacta atttaacgtt attttttgaag cactgggccc aaattacaat   51660
gagaattaat tcttattcct ttcttgaaaa gaagcccttt gtctttgtgc attcaatttt    51720
tcactgtcac atgagtacat tcttttcacc gcatgagtcc caggctggca gaaacatcca    51780
ctaatcctta gacctcttgg ctggaacgac aaaaatgcat aaaatcttac caggccaaaa    51840
```

-continued

```
gagatcaact ttaaaaatct ttggcatcca aacatgtcag aactgttttt cgctggttct   51900
gcaaaccatt tgtgttcttc atttatggtc caggggatct gtaatgtcag ttcctacttt   51960
tattgggcag cctggaattt ttaagcacca tatttccttt acctttcttg gtggtttata   52020
attttcaccg ctgtttttac gagtttttct ctctatgtct ctaagcctaa gtgtggagat   52080
gtggtaatag acagcctgct ctttgccaat caaagccctt actttgacgt tggccacttt   52140
gttcctgtga catctgctct ttccattata gacaaactgg ggctttcctt ctgcagaact   52200
gtgactaaac aaccaccata ttcatcagtg gcaacaattc ttgtaaacaa gaaacgctga   52260
attcaaaggc tttgtgaaat cctgccccca agaggccaca tgtctaaagt cagtcacgtg   52320
gtcctcagaa atgattttag aagtctcagt aaagaaaaat tacagagaca ctcaaatatc   52380
ctagtgtgat actgctgtaa aacttcttct aattttttgt taagctgtga gaaagggcct   52440
atggaaacac ctggatgaag cagcaaatca ctgtcccaaa gtcactaaaa atcatatttc   52500
agaaaggaaa tatctagcgt taaaacaaca tagatgcatt tttgaaaaca aattgaattg   52560
agaaaaataa taatgataac aataatgatc taatcccagg acatgtcaca ggaattaatg   52620
actgactaaa agctaatggt ctaaggtaat gctctcagga attagtcttg cttattgaac   52680
tgctattgtt ttagtaaacg aatgcttaaa ctgacagaaa gtaaaaaatc agggctgcca   52740
ttatggagcc tggttgattc atagtggggc aggggggagaa gctaaagcaa aaaaaaaaaa   52800
aatgcatcat ttgatcattt gctgttctta ctcaattttt taagttcgtt tgtcgttcac   52860
aaattataga ttctttatca tttttttctt tcatgtatct gtatgtactt ttacttttgt   52920
actttaagga tgtgtttact tatgcattgt tttattgaca gagaagtaat ctgataataa   52980
aaatgcaact ccctctagtg taggcatatc aaagatctaa cattctgttt gcctagaatc   53040
gttttatttt aaatactctg atctgaagaa aatgtggatc ctcggccggg cgcagtggtt   53100
cacgcctgta atcccagcac tttgggaggc cgaggtgggt ggatcacctg aggtcaggag   53160
tttgagacca gcctggccaa catggtgaaa ccctgtctcc tactaaaaat acaaacattg   53220
gctgggcgtg gtggcgggtg cctgtctgta atcctagcca ctcaggaggc tgaggcacga   53280
gaatcgcttg aacccggag gcagaggttg cagtgagccg agattgcacc gctgcactcc   53340
agctcgggca acagagtgag actttgtctc aaaacaaaaa aacaaaacaa aaaaaaagaa   53400
gtggatcttc catgtgggct ttagaatagt gcctcaaaat tatacttcac ttagaactta   53460
ttactcaaca tcttatttca agagtattct aacagctgac ttcttgattc tacctttccg   53520
tattgcctct tccttataac cccaaaacag ctaccaaaat tatatatctg atcacttcac   53580
tttcctgctt aaaaacctat gcccattcct agatgttctc tgtgcagatc ctttgttgtt   53640
tcattttgtt tattttttatt ataaaatata tttttgagga aaaaatttta aattggacaa   53700
aaagatataa agtgaacagg aaatatcctc cgaccacttt ctctcccct ccatcctcac   53760 tccccatggg tagctaatat taatgcactt tttcagaaat gttccactct gcatcagtgg   53820
aactgaacta aaccagacac tttagtacat ccttcaataa cctttgtctt attgaccgaa   53880
ctatgactcg gcacaccctt ccccagtcaa gaatattgtt cttctacctc tgtgactttg   53940
aactctcaac agaaatatcc cccttgggg tatgagccat ataaacaggg ctagaccaag   54000
ctctgtgaac tacccctcc cccactgact tataatttga tattgcttca aaccagtatc   54060 ctttacctt gttttgctca acttttattt aaatggagag gagattaaaa tgattttctc   54120
ttaataaaaa attaaagaaa gagattcact tgtttctatt tgccaaagca gaataaaatat   54180 attttttaatc aacaaaatag tatgcttttc taaaattcta gttctgtttt tcaatggaaa   54240
```

-continued

```
tttgcagtga aagtttccag atgcttggaa gttataaaaa gttttaaact taggtaataa   54300
aaataaatca cccatttatg ataagcagca ctctgtgaaa gattatttca gaatctcagc   54360
tgactgacaa cttttaggag actgaactgt acttaagtgt ggcaaacatg catcatagag   54420
atgggttgtt tactgtagca agttacttgc cttcggtcca actgtccttt tggcagaagc   54480
acaccaatct aattttgcct gttacataaa gagccacatg tggaaacctg agtcgcctga   54540
catcatgtta ctgacttaat ccagtcataa ttcagcgccc agagagcggc tggcaggccc   54600 acccacccc cactctcact ctcgatgtat tcatgatagc acagaggtta gctggacaca    54660
cttgggaatc agatatgcta ggtcagactc atttccacca cttatcagta gtgcgatttt   54720
ggaccaattg cgtaaccctc ctaagcctca gtttctgaat ccataaagta gaaatactaa   54780
cagtggcttc ctcataagat tgtgcaaaga ttgaatgaga caatgtgtgc aaagctctca   54840
aagggtggca gtcattattg ccggagacct tgattttact ttttaaattt ttattcaaga   54900
ctctagaata aaattacctc cacagatgtc caaagtttgg cacagttcag aaaagtctga   54960
aggtaaaaat catgaaaaca gacattgatt ttcttcatcc tttttggtag tatcaaccta   55020
atagaaactg gaccagggtc ctgatccagt ctgactttac tgcctatgtg accttccaca   55080
ttacttaaaa gttgtgcttt tcttgtctat aaaaaattaa gattatacct cacagcattg   55140
attgtaaata ttaaattgtg taagatttta cacaagtaca aggtgttatt atggttcatc   55200
agaatgtaat tttttacttt gaaaatctcc gtagaactca tctgattcac aaaattccct   55260
ctaaccaacc ccagcacttc atttgctccc acataattgc tggagttgtt tacacaaatc   55320
tgtactcaga atcaaagagc tcaaggctgg agaagtcagg gaatctggcc ctgggcctct   55380
gcttgaacat tctgggtgct ggtcgctagc tgacccttaa acaactccat gtcctctttg   55440
gagttcaaag tttgggggta aaatcactac cccctctcaa agataaacac aaatggagct   55500
ccaaggtggt gtccggtgct aacatgagac atgttgagtg tgaatctcat cagagcagtg   55560
tttttccaac ataataaact gccctttgtt caaatcagaa actgatttca ctcgattttc   55620
ccaaatcggc cctgccaggt ttccttgatt taattgtata ttttttgtct gctgacaatg   55680
gaaagcagaa gaaaatagtc tcgctaagga aatgaaatat taccaagaaa aaacaggcat   55740
tctcacactg tgtgaggtgg gtttttttttt cttcacattc aatttgtata agaaaaaggt   55800 ctctacccctt tgaaacaaca gcattattgc agtgactatt aggtcatatc tacatggccc   55860
aaaagaaaat gttggaaaga aaattaacta gttcataagg gtatgggcaa cattattttt   55920
aaaaggaaat ggttcttcat acatagagag aataataaat gggagcaaaa aaatgcaagt   55980
taggcaatta tttaaataat tccaatttta aaatatgtac ttaactaaag catccgtgga   56040
gttcaggtaa aatcatttag aggaacgaaa attaaccaaa tcactactga aattcttcac   56100 ttttttaagct aaaattgctt gttcttgctt taataccaga gaagacctga gtcctggttg   56160
actgttagtg aggagttgta tcaaaagaac aaaggtttga agccagttag ggccaggtgc   56220
ctatctcagc tctgccatct actcatcatt tgcccatcag caaattcaat ttttcattta   56280
tttggtttaa aaatattact gagacccttc tacgtgatag gtgctattgc aaagaaggaa   56340
gatacagcag gcaatatact agccaagcct gttgctccca aggggcattt attccaaagc   56400
agggagaaag aaagagagac aaaaggcagg ggagggagga aggaggggag aaaaggggaa   56460
aggaaggaaa gagaaaaaag agaaagataa gagataaaca acaaaactat caacatttgg   56520
tggtatgaag ccatggaacc agaatgagac tatctaggga tcggtaccag agagggccaa   56580
```

-continued

```
ggatgcagcc ttaggcacaa cagtgcctag aggtcaggga ggtgagattg aagaggcctt   56640
acttatctcg tcataaaatg ctaggttatc acctacaaag attttttttt tttttttgaga   56700 taaggtcttg ctatgtggcc caggctggag tgcaatggct tgatctcagc tcactgcagc   56760
ctccacctcc caggttcaag tgattctcct gcttcagcct cctgagctgg gattacaggt   56820
gtgcaccacc attcccagct aatttttttt tttttttttt ttagactgag tcttgctcta   56880
tcgccgaggc tggagtgcag tgatgtaatc tcggctcact gcaacctctg cctctcaggt   56940
tcaagcaatt ctcgcgcttc agcctcccga ggagctggat tacaggtgca cgccaccatg   57000
cctggctaat ttttgtattt ttagtagaga cggtgtttgg ccacgttggc caggctagtc   57060
tcgaactcct ggtttcaagt gatctgccca cctcagcctc ccaaagtgct gggattacaa   57120
gcatgagcca ctgtgcctgg ctgatttttt taaaattatg tacattttgc tactagccta   57180
ttaaagatac ccaacaaatg ttaatttctt cctttttttt ttttaaatcc tctccctcct   57240
caccaactcc caccatgcaa atataattaa tctctggttc taaaaaaaag acaactgagc   57300
tcctgcatac caaaggaata aaaaactaac acttcctta gctcaattta atctaggccc   57360
cactgaatgt aatagtgagc aaagaccata caatagcaaa tcattataga tcacaactag   57420
taatccaaat gacaggtctc ctctgttctg aatttcattt cattgaaatt gttccaaagt   57480
ttgcatctta aattacacaa attatattca ctcctgtctt ctattttaaa aggggaaaat   57540
tgtgcattca tttacctgtt ccctttaaac atcttaactc ctgcttacac ttgtatgaaa   57600
gcattgatct tatcataatt agagaaagtt cctaaaaaca aaaaaagcaa tgacacacaa   57660
ttaatctaca gtgtgtatat cagaattagg ttcagaaaat cccaaaacaa ctgtagctta   57720
caggagatga gctttttctc ttacacaaaa caggttggag gatgggcagt tggggctggt   57780
gtagaagctg caggatgttg gcagggaccc aggctcccat ccctctactc cactatccca   57840
aggcatgtct tctatcctca aggtcacctt gtggtccaga tggcttcctg cccttcagga   57900
aggaggaggg aaagcctgag tcaacacact ttacaaacct tccttataat agaaggggtt   57960
gaggaaggtt gtgtggaaga tgtttctgag ttggcccaga tggacaggta ggaaaggaca   58020
tcctccatag agtggatcat gtcagcaatg aagtcagaaa agtacaagta tggttaagga   58080
acaagaaaga ttcatctgaa tataataata tttgggaaaa atagtaatgc gtgtattgaa   58140
gatgagcctt ggtgtacaat tgactataag cctccccaca tataacgaaa tgattctctt   58200
attttctcat gatctgggga agtaggtctg gaaattcaag cctggggtgg agtaataggga   58260 aaatataatc agaataaaga ggatgagttt ttgttctttt ggtcttccag cccctcagct   58320
ctggccatgc caacgcaccc ctttccggga gtgagtccac ccagaaccct tcgtgcccat   58380
ggacatgctt caatgctgtg cactgggtta tctctcttgg aagaacacaa acacacaggc   58440
tggcgcacag taagcactgc agaaatattg tggatgaaga atctagaaac tagggtgcat   58500
gctccaggag tgtagagaga gcccaaatca agatgcacct ttaatatcac tctaaggtgt   58560
taggaaatgg ggaatgagga gaggctttca aaacagaggg caacaaaatc agaactatta   58620
tttggaatag taactccaac agcatgaatt ggaagaggaa ataccttaaa agatgagtta   58680
ggagactatt tcattcacac aggagggtct agataactaa aacagaaaca acagtcatat   58740
tgaagaagac tggcaagagg tcagcatcca tgatcgcgct gcactgttgc tttatatgat   58800
tgtgtttgat ggcacgattg tttacaaccc ttgactttct tcctgcttta tcattagcat   58860
tactttagaa taatgaagcc tgttccatcc attaactcca ctaacatttg atctccccat   58920
aggttgaggt taaaaattaa ttactcttcc aacatattga ttacatgact ataaatataa   58980
```

-continued

```
aaacagaact acagagtaac tacagggacc ctttgtttaa atagcatgtt tgctcttttt 59040
aaaggaggta attaatggca aaggactttg gaactggagg aacatgctag aaaagcaacc 59100
cttgagtgcc atctagtgtt gacaacacat ttaaatgtag tgtatcaaag aaaggtctgg 59160
tttcttacac tgtaggtgac ttaattgttg aaagcaggca atgtttgaat agtaaaaaac 59220
caaacttacc ctgcctttgt tgcttgccac ctgggtatta acatgaatct tcatttttga 59280
acttcagtgg gaggaagcct tcatttcagc ttctaggtca aggtgcgtta acagaattgg 59340
agggcattga gtttaactca cataactctt tcttttttgtc attccaggaa aaagttaccc 59400
ctaaggtaaa gctagcatgt aactcctcct tttcctccct tttaccagtt agtttcagac 59460
tatttcacct aattaaaaat gaactcataa tatttcatga attaaagaat ggagaacata 59520
gaagaggtta agaactggtg ttgaaatctc ctgccatgga aattcattgt tactgaggtg 59580
gctcatatat cagagcactg ccttctgcgg acattaaaat tcactttgtt tcgtgtccct 59640
aatactgccc agcccttggg aagcacgaag ctgacattgt attaggcaat tcacgctgac 59700
ctaataactc aaagcaatca tcactggtaa cttaaagtga ctacactcca aaagaaatag 59760
agcctaaggt cacagttata aatcttacca caggaaggcc aaagattata atctttatgc 59820
caagtgctgc agattccttt ctgcttagga gagtcatatt tcaaagactt tactaatctg 59880
aaacctatag gtggttgtga caatagcaga tatggcttac atgacatcaa acccacattt 59940
taaagaacac tgggtaaatc agtaaaaaag gggcaattat atttattata tctgcagcca 60000
agactgtata cttttacctt catactatgc tgaaatgcaa tatcataatt gtttttgaac 60060
tcaaaggcct aacatataat aaaagcatag ttaactaagg aggcgtgtga tcctcttatc 60120
agtgtatatt tgcataattt gcaagcagtc tctgagtttg ctatgatgat gtgtaaacag 60180
agggtatttg ttcagttgga actttgtgct gtggagacta aagtcaaagg tttgatccct 60240
aatcagggca gacagcttca ctgttgggtg actgaaagca ctttatcatt atgcttcctc 60300
aagatcgagg ggcttcagga cagtgaacat gtaagttgcc cactgctaaa gaaaaacatg 60360
ttttaaatgt ttttatttga ctttttttta tataaggaat gtatgccttc tttgtgcaaa 60420
ataagatgtg atttttttaa agctaacatt cttgcagact ctaacaatct cctcccgcat 60480
cccctctgtt cccatagctt ctctcacctc catatttaca agcctctcat ttttatagaa 60540
agatatacac atatgttgat tttagagttt aaataaaaat aggatcatgc tgtatacata 60600
atttgcaaca gtttattttg actttgcagc atatcacagg tattcctcca gtttataatt 60660
cagtctttct cattgctacc tgaccatctg tagaatggct gttacaatcc actcaggctg 60720
tttccagtat ttttttttgg tttattttgt ttactgttac aaacaatact acaaaaaaac 60780
ttttacgtat aatctaatat actggccttt tattctagga tacagtccca aaagtggggt 60840
cagtaaatca cacactgttt gtattttatt agatattagg caagttgttt tccccaaagg 60900
ctgcaccttt tcacactccc aacgatattt gaaaatactt atttccctat tttgtaccag 60960
cttgggacat cagcactctt tttcattact gccaaataag taaacaatgg tttcttactg 61020
ttgtcataat ttgctttttcc atgattaaca gagaagttga cttcctgtgt ttatgtgttt 61080
tgtagccatc tgcatttctt taaattgcct ttccacagcc tttgccccat tttattcttt 61140
cctctatttt ttattcaatt gtttgtcttt cagcaggtgg caaactcttc ttgtaaaata 61200
gatatattaa cccttttggct gggcgcagtg gctcacgctt gtaatcccag cactttggga 61260
ggctgaggca ggcagatcac ttgaggtcag gagattgaga ccaacctggc caacatggtg 61320
```

-continued

```
aaaacctgta actactaaaa atacaaaagt tagctggacg tggtggtgca tacctataaa   61380
cccagctact caggaggctg aggcaggaga attgcttgaa tccaggaggt ggaggttgca   61440
gtgagccgag atcacaccac tgtaatccag cctgggcagc agagtgagac tctgtctcaa   61500
aaaaaaaaaa aaaaaaaaaa aaagagaaag aaagattaaa cttttgtctt tacctttgtc   61560
tttattacaa attattttcc tgacaatcat ttatcctttg actatgttta tgtcttttgc   61620 catatataaaa ttttaaatct gtatgtaatc caaaatattt gtcttttctg gcattatgtc   61680 ctctacccctt aaaaggtctt agagagtctt cctggaccca atattgtaga aaaacaattt   61740
caagtacaca ccttaacgat ggtggacttt taactccagg gatctcaaac aaacaaccat   61800
agaagtctgg caggttatgg aaagttatga tacccaacca ataagaaaaa tagggtatac   61860
tgggggctgt gataaaatac agcatgtaca ccccatctaa aggagacagt cagtactgtc   61920
aacctcaaat aaccaaaagg atcagggttt aatttaaaga gagtttattc aagcacaaag   61980
tttgaagatg gcccacatgg aaacacaaac tccaaaggaa tggaatcagt gcttcaaaat   62040
agagaagtta aggtttcact tattcataca gaattagaga gttttttagca agattatgac   62100 attttttcata caaggttgat gcatagttac agcagtttaa tatgttacag gcagcatttc   62160
ttttgggaag atacatttaa cattttttac agagagtgta agagtcatga gattttttgtc   62220 atgtgttcta agcaaagtag gacaataaag ggaaagttaa tttgtaataa ggaccattaa   62280
ctaagaaagc aggaagtttt tgtccctgac gtcacttaat tctctccagt cactgtacag   62340
aacaagaaaa ataaaatagc aagttaatct ataatctgag aaacagaagt tgtaactaca   62400
tgtgactcag atcacagtcg catctctttc aagacttaaa gtgtttgagg gattccatca   62460 gcttttttt tttttagatgg agtttcactc ttgttgccca ggctggagtg cagtggtggg   62520
atcttggctt actgcaactt ccacctccca ggttcaagct gttctgcctc cgccctccaa   62580
gtagctggga ttgcccacca ccatacccag ctaattttgt gtattttttag agatgggggtt   62640 tcaccatatt ggctaggctg gttttgaact cctgatctca ggtgatctgc ctgccttggc   62700
ctcccaaagt gctggaatta caggcgtgag ccactgcgcc cagcctccag cagcttctaa   62760
gttatattta ttttcatagt tctaaactcc agtcaagatt ggcccttgag taattcaggc   62820
taaatgttac cacatcttct tgtttttctc tgagaaaagc cagctaacca gattttttata   62880 taaaatttcc caactttaaa atatatgtta ggcctttttta ttatttattt atttggaaca   62940
gggtctcact ctgtcaccca gactggaatg cagtggcacg atcatggctc actgcagcct   63000
tgacttacca ggctcaagtg accctctcac ttcagcctcc tgagtagcta gaaccacaga   63060
tgcatgccac cacacttggc tcattttttaa catgttttttg tagaggtgga gtttcactat   63120
attgcccagg ctggtctcaa actcctgggc tcaagggatc ctcctgccgt gacctcccaa   63180
agtgctaggt tcacaggcat gagccaccgt gcctggcctt aacccatttt tcccccctga   63240
gactgagtct tgcactatcg cccaggctgg agtgcagtgg cattgatctt ggcccactgc   63300
aacctctacc tcttgggttc gagcaattct cctgcctcag tctcccaagt cctgggatta   63360
caagtgcgca ccaccacacc cagctaattt ttgtattttt aatagatatg gggtttcacc   63420
atgttggcta ggctggtctc aaactcctga ccacatgatc cgcccgcctt ggcctcccaa   63480
agtgctggat tacaggcgtg agccaccgta cctggccaac ccattttttta aaaaataaaa   63540 ttgctcaggc cacaccaaat gtgtctgtga gcccctgaca taaagcttag ttcctcatgg   63600
tacttgcgct atgagagaaa aaaaagccaa ggatttacta tgcatcgggc attgaaactc   63660
atatacatca ttttttaatc ctcaaaatag cttaccactt agtgttagta tgatcatttt   63720
```

-continued

```
acagataaga aaactgaaat taaggatgga ttaaaaattt atccacgtta atcagctagt   63780
aacagagcca agatttcaac ccagtttttc cagctctaaa gagtagctct tccaatctta   63840
tcatgctata actctcacga aattccaaag tagaaggtca tctttatttt cccacttttt   63900
agaaagtgaa ccgtaaagat cttaaagggc atctccagca ttgtttgaaa tgtagaactc   63960
cgccgggcac agtggctcac gcctgtaatc ccagcacttt gggaggctga ggtgggtgga   64020
tcacttgagg tcaggaattc cagactagcc tggccaatat ggtgaaactc catctctact   64080
aaaaatacaa aaattagctg ggcatgatgg caggcgcctg gattccggct agtcaggaga   64140
ctgaggcagg agaatcgcct gcatccggga ggtggaggtt gcagtgagtc aagatcgagc   64200
cactgtactc cagcctgggc gaaagagcaa gactgtctca aaacaaaaaa ataaaaacta   64260
aaaacagaaa tataaaacta gatgagactt tgcacgtggc agagatgaag attactaccc   64320
aattcagtgt taacctcaaa attaaaattg tcactggaca tcagggaaga ctcttccagt   64380
gtgaagtagg ggaatggcat ggagttctct tgggataagg aggtggcagt ggctgaaaac   64440
tcaaaattaa ccagcgccaa cctcaagacc tagccttggt actgaggatc tgcccttcag   64500
cttcgtgctc ccataggaga gcctcagaaa gatgtgtggc cagataagct acagagattg   64560
cagacaaacc aaaaagagaa tagagtggca atcaaagcag ttcctttgag aaaggaatgt   64620
catttctctc cttctgagaa actgaaaacc catggcaaag attaagattt tgccaaacat   64680
gggaatttga agaaagcagt atctgctcca taagaacttt tgtttgaatg aagtaacctg   64740
ttaataagga cagataatat tgatttgttt tatgtgagtt tgcctgggga gttaaccacg   64800
gtcataataa tttttaagtt tccgggttct gaggaccatg gcttctgttc ttggtattac   64860
tcccattggt tttctttttt aaaatatatt gattaaatta atccaggtct tggaataaca   64920
tattctgcac agaaatcaaa gagacagaaa aagtgataaa taattgatgc agcctctgat   64980
atgttaaaca tgcaatgttg aaagaaaatt tttctccttt gacatacggt aagtctgagc   65040
atgtgtcata ataaaaagag cttgccacat tcttaaggtt tggaagaaaa ctaaaaatga   65100
aaaagaacaa ctttttatgt tgatatcatg atcttcagca tactctctgc caaaattact   65160
tcctatccag tgatttcata agatgtagca acattaaatt tttatctttt ttctgcaatt   65220
caggtacgag ttaagtaaaa atctaaacaa gacattcttg ggcctaagat gctccccaaa   65280
agagcatttc aaaagaagtt tgttgccact tgattttata agtatatgac aaacttgaat   65340
gaaacgaagt tagagcaaag aactggtcca aggcctggct tagtcacttt ttaacagtta   65400
gcatttattg agagattacc atgtgccaaa cattacataa aatgctttat attgattaac   65460
aaatataatc tttaccccat ctgatgagct acatactatt attatcctca ttttgattaa   65520
aaaaaaaaaa ctagtccaca gaggattata gaattcaccc aagattgtat tactaccaga   65580
aaccaaacac aggtagtgtt cctttaggaa ttcttgcttt taatcaatgt cctataaacg   65640
gataacctta agccctttcc ttcctaagcc tcagataact tgtctcaaac atgaggataa   65700
taaaaccgat tctacctatt tcccttggtt attttgagga acaagtgaga tcattacatg   65760
taaagatctc aataggctgg gcacaatggc tcatgccagt aatcccagca ctttgggaag   65820
ccgaggcagg aggatcagtt gatgccagga gttcaagacc agcctgggca aaatggtgag   65880
accccatctc tacaaaactt aaaattaaaa aattagctgg gcatggtgtc acatgcctat   65940
agtcccagat actcgggagg ctgaggcagg aggattgctt gggcacagga gttcaaggct   66000
atagtgagct atgatcatgc cctgggcaac agagtgagac tgtgtttctt ttttaaaaaa   66060
```

-continued

```
aaggtctcag taagttataa atcattacaa tctttagctt atttcctagt tttcagaaat   66120
gagcaagctg aaccctaagt agaattctta agtagatgtc cctttttcaac agaagggttt   66180 ctatgcttag gcaaatcaca taatattgac cttacaacat tattatactt tgaaattggt   66240
tatgatatcc tttttataga aaatataaga gcgctatgtg gaaagcagag ttgaactaga   66300
gtcaagaggg cccaacactc agctcagctt ttaccaactc atattcactt actcttcaaa   66360
tgtcccatct gtaaaacatg attccctatc tcacaggtta ttaaagttac ataccctgcat   66420 gtgctttgta aactactgaa caagaagctg tcctttgtat tactgccatg tcaaagaaga   66480
ataatgtgca acttacccag gagaaggaga aggaaaggat gtcattggca gggagctagc   66540
cccaggagcc acagtgtccc aaagactgtg gagagtctga atttgctgac tttgggtggg   66600
ttattttggg ggaaagcatt gttgtttttag tcacagttgg ctgggggtat ttccttgact   66660 tcggcccccca ccttccacat ggaaattatg ttttcattca tcctttcatt catgtaccaa   66720
aatattggtg tgcatctatc atgtgcctgg cattgtgtta attatgttaa acactgggga   66780
cacaacggta atgaaaatag agtccctatc ctcatagaac ttacattcta gagagggaga   66840
catgtaacag acaaaacatg aaactaagtt ataacagcat gggataagtg ctagaaggaa   66900
attaacattg acaggcgaga tgctggtgtg ggaaagaccc acttcaggtg ggcagtagca   66960
agaatgggaa tgctgaaggt ggaaaaggac agacagattt gaggcatctt ttaaaggaag   67020
aatggacata cttcttgatg gatctgatgt agaagacgag gaaagagagg attaggagat   67080
gactactagg tttctgcaat aagcagttaa aggacaagga tcctgtcacc atttactcat   67140
atgtggacaa ttggaagagg agggtgtgga agtcaataat accatttggg gtatgtcact   67200
tttcaaatgc ctgtaagaaa ttcaaatgtc aaattgaatg catgagccca gaacccaaag   67260
gaaagttctg gattgagaaa aaggtgggat gtcacgagct tatagacaat atttaaaatc   67320
atgttaacat tctgtttagg ccaggcgcag cggctcatgc ctgtaatcca gcactttggg   67380
aggctgaggt gggtggatca cctgaggtcg gggagttcaa ggccagcctg accaacatgg   67440
agaagccctg tctctactaa aaatacaaaa ttagctgggc atggtggcgc atgcctctaa   67500
tcccagctac tcgggaggct gaggcaggag aatcgcttga acctgggagg cagaggttgc   67560
agtgagccga gattgcgcca ttgcactcca gcctgggcaa caagagcaaa cctccatctc   67620
agaaaaaaaa aaaaaaattc tgtttaataa gtctgaaaaa ccttcaagaa caggtttctt   67680
ttaatcccaa atagtgaaat ttcaggatgg caataacttt caaaaaatgt atttccaccc   67740
agaaattgag agggaattct taggtcactg caaatcatcc cagtggagta acccaatgct   67800
ccagtgagaa aatggtgtaa cagaatgaga taggacttga actaagaagg atctgggctt   67860
gaattccagc tctgccattg ctaatgatgt ggccttatga aagtttcttt acccgtttga   67920
tcctcttttt aattatctat acaatggaaa tttaaaaata cctcgaaggt tgttgtgaac   67980
aatgtaaata acatctgcaa aaatgtctag cacagggtag aatcagtaag tagtagcaat   68040
attaaatttc tctctttttt tgcacagtaa aatgtcttga aagacacaac ctctacttgc   68100
aggcctcctt ctttcctgga ttcactccag tcatgtttcc catctctcat tccaccggat   68160
ctgctcttgt gaaagtcacc aatggtgttg attctgcctt caattttgta ctccttctca   68220
acagcattta acccaattga tcacttcttc cttggttagc ttttttctca gcttcagtga   68280
caccacacca tcctgatttt ccacatacgc cacagaaaga tccttctcag tctcctgtgc   68340
ttaactgttt tcccaagcag aaatgctaaa tgttggagaa cttaggctca gtcctagagc   68400 ctcattttttt ccatcctccc tccctccata ggtaacatta tccagtccta cagtttaaca   68460
```

-continued

```
tctgtcaaat cccaaattca catcttcccc tgaactctaa attcatacat ttaattgtct   68520
ctttggcatc atcatgtgac aagcacctcc agtttaacaa gtaaaaatag aactcttgac   68580
caccaacagc ccttcctcaa gtcttccacc atccagcaaa tggcatcatt atccatccaa   68640
tggtgctctg tcaaaatcct acctataagt acatactatt agctccatcc ctaaaataca   68700
gccacagtct gtctcaactc tgcttccaaa ccccaagatc agggcaccat cgtttctcat   68760
ggtttcaggc ttccacttca atccattctc ccatacgaga cattgtgacc tttttgaaaac  68820 ataaatcatg ccatgtaact ttcccatcta aaatctttcc acggctttct gttgcactta   68880
gaatgaaatc caagttgttt accacggttc gttaaggctt acatggttgg gcctcagctt   68940
cctctccaag ccgtctcctt ttaccacccc ctccagcaca ctaccctccc ccttcaccag   69000
tcttccttct ttctgctaag cttctttctg cttcaggatc ttaccctaat tgtttcctct   69060
gcctggaact ttctgctcca gatctttcca tcagctggcc ccttctcata attctcagag   69120
aagccttccc tccatccagt ctcaaatagc ttccactctc tcagcgatgc cctattcatg   69180
taaccctgtg ttattttctt tttattatgt gtatttactt gaaatcactt tgttgatcta   69240
tgtgtttaca tctgtgttat ctctctctcc tccactagac tatatgctcc aggagaacag   69300
gaacggattt ctcactcatc tatgtatagc gcctagacag aactgacaca taatagacat   69360
tcaaaaatat ttgtcaaatg agtgaatgaa cgaattcaca gtagttgtca ttgccctgct   69420
atgtacaaat ctgtggcacg ggtggtacgg aataccaccc tctacttggt tccatttttg   69480
ccacctggcc agctccttct gctttaacca actgtgtttt cttctcttta tctgcttaca   69540
cccacatttt atttatttat ttatttattt atttatttat ttattttaac ttctatttta   69600
ggttcagtgg catatgtgca ggtttgttac ataggtaagc tacatgtcac aaaggtttag   69660
catacagatt attttatcac ccaggtaata agcatagtac ctgataggta ttttttctga   69720 tcccttttcct ccttccacccc tttaccttcc agtaggcccc aatatctgtt gttcccctct  69780
ttacgtccat gtgttctcat cacttagctc ttacttataa gtgagaacat gcagtatttg   69840
gtattctgtt cctgtgttag tttgctaagg acaatggcct ccagctccat ccatgttcct   69900
gcaaaggata tgatcttgtt ctttttatag ctgtgtagca tttcatggtg tatatgtacc   69960
acattttctt tatccagcct accatcgatg tgcatttagg ttgatttcat gtctttgcta   70020
ctatgaatag tgctgtgatg aacatatgtg tgcatgtgtc tttatggtag aatgatttat   70080
actccttggg gtatatgccc aataatggga ttgctacatc aaatggtaat tctgtttcaa   70140
gttctttgag gaatcgacaa actgctttcc acaatggctg aactaattta cactcctacc   70200
agcagtgtat aatcattccc ttttcttcac aacctcgcca gcatctgtta tttcttgact   70260
ttttaataac agccattctg actggtgtga gatggtatat cattgtggtt ttgatttgca   70320
ttcctctaat aattaataat gttgagcatt ttcatattct tgttggcctc atgtatgtct   70380 tctttttgaaa agtgattgtt catgtctttt gcccactttt taatggagtt gtttgttttt   70440
tgcttgtaaa tttgcttaag tttcttacag tttctcgata ttagaccttt gttggatgca   70500
tagtttgcaa atattttctc ccattctgta ggttgtctgt ttactctgtt gacagtttgt   70560
tttggtgtgc agaagctctt tagtttaatt agattccatt ttccaatttt tatttcggtt   70620
gcaattgctt ttgtcatctt catcatgaaa tctttgccaa gtcctatgta cagcatggta   70680
tttcctaggt tatcttctag gggtttttta attaattaat taattttta ttatacttta   70740 agttctggga tacaagtgca gaacgtgcag gtttgttaca taggtataca tgtgccatgg   70800
```

-continued

```
ttgctgcacc catcaacctg tcatctacat taggtatttc ttctaatgct atccctcccc    70860 ttgccccca ccctaaacga caggccccag tgtgtgatgt accctccct gtgcccatat        70920 gttctcattg ttcgactctc acttatgagt gaaaacatgc agtgtttggt tttctgctcc      70980
tatgttagct tgctgagaat tatggtttcc agttttatcc atgtccttgc aaaggtaatg     71040
aactcattct tttttatggc tgcgtagtat tccatggtgt atatgtgcca cattttcttt     71100
acccaatcta tcattggtgg acatttgggt tggttcagag tatttgctgt tgtgaatagt     71160
gctgcaataa acatacatgt gcatgtgtct ttatagtaga atgatttatc atcctttggg     71220
tatacaccct gtaacgggat tgctgggtca gaagtatttc tagttctaga tccttaagga     71280
attggcacac tgtcttccac aatggttgaa ctaatttaca ctcccaccca cagtgtaaaa     71340
gcattcccta tttctccaca tcctctccag catctgttgt tccctgattt tttgatgctc     71400
accattctaa ctggtatgag atggtacctc attgtggttt tgatttgcat ttctctaatg     71460
accagtgatg atgagctgtt tttcatgttt gttggcagca taaatgtctt cttttgagaa     71520
gtgtctgttc atatccttca cccactttt gatgtgattt tttatatttt cttgcaaatt      71580
tgtttaagtc ccttgtagat tctggattgc tgacaaaggg cttctagggt ttttatagtt      71640
ttaggtttta catttaagtt ttcaatccat cttgagttga tttttggatg tggtgtaagg     71700
taaacattgg cctactggct agccatatac agaaggtttt gtatgtggtg taaggtagag      71760
gttggctcag tcctagagcc ccgtttttcc atcttccttc ccccataggt tggcctctac     71820
cttttactac gcaccattta ctgaatgggg aatcctttcc cattgcttgt tgcttgtttt     71880
ttgtcagttt tgtcaaagat tagatggttg taggtgtgtg ccattatttc tgggctctct     71940
attttgttcc attggtctat gtctctgttt ttgtaacagt aacatgctgt tttggttact     72000
gtagccctgt agtatgattt gaagtcagat aatatgatgc ctccagcttt gttccttttg     72060
cttgggattg ccttggttat ttgcacccct tttttggttc catatgaatt ttaaaatagt     72120
ttttttaatt ctgtgaggaa tgccattggt agttttatag gaatagcatt gaatctgtaa     72180
atcacttagg gtagtaccac cattttaatt gtattgattc ttcctatcca tgagcatgga    72240
atgtttttta atttgtcatc tctgatttct ttggacagtg ttttgtaatt ctcattgtac    72300
agatatttca cctccctggt tagctgtatt cctaggtatt ttattctctt tgtgggaatg   72360
ctactgattt ttgtacattg attttgtatt cttaaaattt gttgaaattg tttctcagat    72420
caaggagctt tggggcagaa gctatggagt tttctaaata cagaatcatg tcatttgcaa    72480
acagggatac ttggacttcc tctctcccta tttagatgtc ttttatttat ttctcttgcc   72540
tgattgctct ggccagaaat tccaatacta tgttgaacag gattggtgag aggggggcatc   72600 cttgtcttgt gctggttttc aaagagaatg cttccagctt ttgcccattc agtatgatgt   72660
gggctgtggg tttgccatag atggctctta ttgtttttgaa gcatgttccg tctatgccta  72720
gtttattgag aattttttaat gtgaatagat gttgaatttt atcaaaagcc ttttctgcac   72780
ctattgagat aatcatgtag tttttgtttt tagttctgtt tatgtggtga atcacattta    72840
ttgatttgcc tatgttgaac caattttgca tcccggagat aagcctactt gattacggtg    72900
gattggcttt ttgatgtcct gctggatcca gtttgctact attttgtgga ggattttttgc   72960 atctatgttc atcaaagata ttggcctgaa gttttctttt ttcgttgtct ctgccagggt   73020
tcggtatcac aatgatgctg gctggcctca tagaatgagt tgggaaggag tccctcctcc   73080 tcaatttct gaaagagtct cagctcttct ttatacatct agtagaattt ggctgtgaat    73140
ccatctgtcc tggacttctt ttggttggta ggcttttat tactgattca gtttcattat     73200
```

-continued

```
tggtctgttc aggattcaat ttcttcctgg ttcagtcttg ggaggttgta tgtgtccaga    73260
aacttatcct tttcttctag attttctagt ttgtgtgcat agaggtgtac atagtaatct    73320
ctgatgaatt tttgtatttc tgtagggtca gtggtaacat cccctttgtc atttctaatt    73380
gtgtttattt ggatcttctc tctttttttt attagtctag ctagcagtct atcttatttt    73440
ttttttccaa taaccaactc ctggatttat tgattttttg tatggttttt cacatctcaa    73500
tctccttcag ttcagctctg attttggtta tttctggtcg tctgctagct ttgtggttgg    73560
tacactcttg cttctctatt tcttctagtt gtgatgttag gttgttgatt tgagatcttc    73620
ctaacttttt gatgtgggtg tttagtgcta taaacttccc tcttaacact gctttagcta    73680
catcccagag attcttcatg ttgtatcttt gttctcatta gtttcaaaga actttctggt    73740
ttctccctta atttcattat ttactcaaaa gtcattcagg agcaggttgt ataatttcca    73800
tgtatggttt tgagtgattt ttagtcttga tttctatttt tattacactg tggtctgaga    73860
gtgtggttgg tatgatttgg ggcttttttt tgcatttgct gaggattgtt ttatgtccaa    73920
ttgagtggtt aactttagag tatgtgcaat gtgttgatga gaagaatgaa tattctggca    73980
ttttggggtg gagagttctg tagatgtaca ataggtccat ttggtcaagt gctgagttca    74040
tgttctgaat atctttgtta attttctgcc tcaatgatcc ctctaatact gtcagtgggg    74100
tgttgaagtc tcccagaatt attatgtggg aagttaagtc tcttcatagg tctctaagaa    74160
cttgctttat gaatctgctc ctatgttggg tccgtgtata tttaggatag ttaggtcttc    74220
ttgttgaata gagtccttta ccgttatgta atggccttct ttatcttttt tttttaatct    74280
tttttagttt aaaatctgtt ttgtctgaaa ttcagatagc aacccctgct ttttttctgtt    74340 tttcatttgc ttggtagatt tttctccaac cctttatttt gagccaatgg atgtcattgt    74400
atgtgagatg gttctctcaa agacagcata ccattgggtc ttgcttcttc atccagcttg    74460
ccactctgtg cctttttaatt gaagcattta gcccacttac attcaaggtt agtattgata    74520
tgtgtggatt tgatcctatc atcatgttgt tagctgattt tttatggaga cttgtttgta    74580
tagttgttta tagtgtcact ggtctgtgta cttaagtgtg ttcttgtagt ggtggtaaca    74640
gtctttcctt tccatattta gtgctccttt caggaccttt tgtaaggcag gtctgctgtt    74700
agcctgatga aatttccttt gtaggtaatc tgccccttct tgttagctgt ctttaatatt    74760
ttttctttca ttttgacctt ggagaatctg ataattatgt gtcttaggaa tggtcttctt    74820
gtgtaatatc ttgcaggagt tctctgcatt tcctgagttt gaatgttggc ctctctagtg    74880
aagttgggga agttttcatg gataatacac taaaatatat tttccaaatt gcttgcttta    74940
tccccatccc tttcagggat gccaatgagt gtagattta cataatccca tatttcttag    75000 aggtttatt cattattttt tattctttt tcttgtccga ctatttcaga gggttctgag    75060
attctttcct cagtttgatc tattttgctg ctaatacttg tgattacagt atgcaattct    75120
tgtagactat ttttcagctc tattagatct gttaggttct tttttatagtg gctattttgc    75180 ttataagctc ctgtatcatt ttattgtaat tcttagcttc cttggattga attttgacgt    75240
tctcctggat ctcaatggac ttaatttcta tccatattct gaattctatt tctgtcattt    75300
cagccatttc agtccagtta agaactctta ctgggaaaca agtttagtca tttgaggaa    75360 agaagacact gtggcttttt gaattgccag agttcttgct ctggttgttt ctcatctgtg    75420
tgagctggtg gcctttaact gtggtataaa tcgaatacag tcagtagact tatttcctgg    75480
atgttttcag aggatcgaaa atttgtgtag agtctttatt tgaagctgaa ttattgtcct    75540
```

-continued

```
tggtttcaca gaggggtata ttagcaaagc attttttggtg ttgaagtttg gggctgtgat   75600
tcagtaggtg gcacttaaac ataatggaag taggtaggct tttgctcagt cacgtggctc   75660
ctctgtattt tctcctaatt gcagccatct acctttcagt gctctgaaag tgtaggttcc   75720
tctcccactt gattgctggc tacagatctc agcttggcac ccacaggttg cacattgcag   75780
ctcccgggcg atcttgggct ttatgttccc tccccagctt gaaggcaaca ggggaaggaa   75840
ctttagcagt ggttgtggca gaggggcttt cacttgtctc ttggggtttc accccagaaa   75900
gatgcagacc agctatcagt cactatgatc agcccagaat gggctggctg tgctgtggac   75960
ccaagccggt aagaccctgc ctggtaataa gcagcagggt ggatgacacc tgggggagac   76020
aaactggcct ctccttaggg caactgcagc ttgctggagg tgtggctaaa gcactcaggg   76080
tttttgctcc ttccctggtc agcaggcagc aagggcagta ccactgcagt gacagcaccc   76140
acactttaaa tgttagtgtt tcccaaggct caagtagtta ttaaaattct atatctttt   76200 tgtgtgtgtg tgatgggtct cactttatca tccaggctgg cgtgtagtgg aacaatcatg   76260
gctcactgca gcctcaacct cccagtctca agccatcctt ccacctcagc ctcctgaata   76320
gctgggacca cagatgcaca tcaccacatc tggctaaatt tattattatt tttttgtttg   76380
tagagacagg ctctccctgt gtttcccagg ctggtcttaa attcctgggc tcaagtgatc   76440
ttcccacctc accctcccaa agcactgaga ttctaagtat gagccaccag gccctgccta   76500
aaattctatc acttaaacat ctcttatgtc tttgtcttct tttgtttttc tactgcctta   76560
cctcaggctc ttgttatctt ttaccttaac ctcttaaatg gtctcctaat tggcctttct   76620
ctctccagtt tcaccatttc taaattcaat ttccaatttt tctaatacac acattttcag   76680
ttaacctcca aagtttccac cttttataca cggtcctaag taaagtttga aaaggacctc   76740
agtgattagg ccgctgcctc catgagcacc acagttcaca gctcttcgat actcacctat   76800
gctccagcca ctccaaaaga cttttacatg tcctccattt tcctgtcttt gctctcatac   76860
agactgttcc ttcatctgta aatgcctttc catcagcccc cacccctccc atctgtctgg   76920
gagatgttaa actcatactc ttcctttaat acccaactca aggatctcct cttctgcaaa   76980
atcttcccca atctaccaaa ttccacattg gccctgattt ttctgtgctg ccactttccc   77040
taatacatac gtttgtaatt ttacttttca agttatatta caattattta ttaacttgtt   77100
gccacattgt gagcttatgt tttatttttg catctctatc agtcttcctg ggatataata   77160
atatgttact aataaacact tgttgatgga gaaaataaag acattaaaga taaatacata   77220
cagccactca ttaaacgtgc attataaaga agttgcggtt ccaaattatc attttagaag   77280
tagccacaga agataagtca tacatagtta cttttttagta tttccaattc aaaaagtgat   77340
gaagaataga aatcatatat tctggaaccc ctacttaata atttatgtta aatctcaaac   77400
actttgaaat ctggtgttta agaactgata gtcatcacct cctctcttct ctgtttgcca   77460
cttagaaaat gaccagttaa caacattctt tatttcacat gtatcttata attagttggt   77520
ttaaaaaaaa aaaaaaagcc agtaatctgt tttttttgttt tctttcttga gacagattct   77580
cactctacca ctctattgcc caggctggag tacagtggca tgatctcagc cctgcaacct   77640
ctgcctcccg ggtttaagca attctcctgc ctcagcctcg caagcagcta ggtgtgggcta   77700 caggtatgcg ccaccatgcc cagcttattt ctggtttttt ttttttttttt ttaagtagag   77760 ttggggtttc tccatggtga ccaggctggt ctcaaactcc tgaccttagg tgatctgccc   77820
acctagactt cccaaagtcc tgggattaca ggcgtaagcc accacaccca gctcagaaat   77880
ctgtttatta tgacagttcc aggttatttt ggaattcctg gaccaaatac acaaatccat   77940
```

-continued

```
tcttttaata gtccttggaa atacggagca tctgattaga tgccaaaagg aagggagatg   78000
cttggtatcc ttttggtggg tcttgaaaac actgggaaca ctaataactg ctagaactgt   78060
taaataacag agtcaccact aatggtgaaa atgcactatt aatataagcc tctttttttgc   78120 agggagtgga gagtctttta ttccctaaaa atatctgaaa gacgaaagca ggatatgcat   78180
ctcaactgta gcataaggcc tcttctggcc caaacaatct tccctacctc ttaagatctg   78240
ttcttcctac cattaaaatt agcatattgt ctttataaaa tccctgctaa aaagtaccta   78300
ggaaagtttc tcccatgcaa aaaataatta tcattactgt gttggccgct ccgtttgtca   78360
gattttcaaa gtgagagcaa aacccaaaga gataggagtg gtaagaaaca agaagctaga   78420
gctagaaaag gaagtctgaa aagagaagga taagacttga ggcaaaattc tgtctgcttt   78480
tgactgatga ttctcggttc tccaaagaaa tgcaaccttt gttttgtgct tacttacttc   78540
agtgacaaag tgaggactcc tgagttaatg gtctgcaaaa gcattgaaga ttaagagcaa   78600
tagacagaat tcctagcttg gggtgggctt cacttacaga gccttccatg agacctggct   78660
aaatgaaacc actctacatt ttcattctta atgaaagtgt gagaaagtct gagaaaacca   78720
agaactcttc ctaaaatgtc agaactagga ggaaaatcca cagtaccttt tacaaaatga   78780
aagtttaagt aaatgattgt acttgataac aatattagaa tccatcctgc ttctggcaaa   78840
gagaactttg cctactgtaa caagtttggc tggtctgctt tttaatttct ccatttcctg   78900
cttcctacac tgccacttgt ttctacctca aaggtgatca gtcttcagtg gcctgttcta   78960
tgtacctacc attttgaact tgtaatatct cccattgatt tcatgctgtt ctttctggaa   79020
tctgttggct gtgggggtct gttctgctat ggtatagtat gtacaggcag ttctgtgttt   79080
gtcttgtttc ttgctttgtc acaagacaag tatttcatta ctgtggtgtt ttttgttttt   79140
ttgctttgag acggagtttt gctcttgtcg cccaggctgg agtgcaatgg cacaccctcg   79200
gctcactgca acctccgcct cactgcaagc tttgcctcat gggttcaaac aattctcctg   79260
cctcagcctc ccaagtagct gggattacag gacccagcta attttttgtat ttttttagta   79320 gagatggggt ttcatcacgt tggccaggtc ggtctcgaat tcctgacctc aggttatttg   79380
ccacctccgc ctcccaaagt gctgggatta caagcgtgag ccaccacgcc cagcctactg   79440 tggatttta taggtcatta actcatgcat ttgagactgg ggcaggaaat aaataagata   79500
gtccttttgg aaatacacag taattgggca aatccctaca gaaagaaaga tgcttgatgt   79560
tattttggta agtcctgaaa atacccacca aacaagatga tcctggagca ttttccagtg   79620
ctagaaaagt aagaaaatcc taaaataaag atacatgtat atacattgtg taaagataca   79680
caatgatggg gacataaaac ctaactgaaa gagtgcccag tagccaaagc tggtacaatt   79740
tgagcaacaa tataaagaaa tatcataggc cgggcgcggt gtgtcagcac tttgggaggc   79800
caaggcgggt ggatcacgag gtcaggagtt caagaccagc ctgtccaaga tggtgaaacc   79860
ccatctctac taaaaacaca aaaattagcc aagcgtggtg gcaggcacct gtgatcccag   79920
ctacttggga ggctgaggaa ggagaatcgc ttgaacccgg agggcagagg ttgcagtgag   79980
ccgagatcac accactgcac cccaacctgg gcaatagagt gagactctgt cacaaaaaaa   80040
ataaataaat aaaaataaat aaaaataaaa ggaaatatca tattataacc taaagtataa   80100
aataaatatt cataaatcag tagtaatata aatgattgaa taaataaatg gaggagaagg   80160
gaaaagtctc ccatgcagaa ttccagataa tttacatagc ctctcctccc tcaaaaagtc   80220
aagcataatc ccccattccc taagtaggat ctgagcatag tgacttcctt ccaaagagta   80280
```

-continued

```
cagttatgga aaggggggaga gaatgagaac tttacggtag agaaacctgg cagacactac   80340
ctcagccagg tgatcaaagt cagcatcaac aatgctaagt catgttggtc gtaggcaacc   80400
ttaatatgat atggtgaaaa cagcacttga cctctgtggt cttcctgctg aaaacacaca   80460
accccagtct aatcatgggg aaaatgtcag ataaatcccg aatgagggac agtctacaaa   80520
atatctaacc agtgctcccc aaaactatca aggtcatcaa gagcaatgaa agtctgaaag   80580
actgttacag ccaaggggac ctaaggagac atgaggacta actataatgc agtgtcctag   80640
atgagatctt agaacagaaa aagaacgtga tggcatggca tggtggctcc cacctgtact   80700
cctagcattg agacttgggg taatcagata agagaaattt tatataaatg aaactatgcc   80760
aacatgttac tttctccagt ttacatttat tttccaataa atatttctca aatgaccctg   80820
agtgatataa tggtcaggac aggtcagcag gggaaaaata taggtagata cattttgttt   80880
ttaaaaataa gctttttactt ttagaacagt tttagatata cagaaaaatg tggccagttg   80940
tgatgactca cgcttataat cccagcactt tgggaggcca aggaaggcag atcacttaag   81000
cccaggagtt cgagaccagc ctgagcaaca tagcaagatc cccatctcta caaataattt   81060
taaaaatcag ccagcatggt ggcgtgtacc tgtggtccca gctgctcagg tggctaaggt   81120
aggaggatca cctgagccta ggaaatcacg gctgcagtga gccatgattg tgctaccaca   81180
ctctagcctg agtgatggag tgagaccctg tttcaaaaat aaaaaaaaga aaaaaaaaa   81240 gaacattacc taaaaactga ggaaatctga ataaactaga ggcttcagtt aataatagta   81300
tatcaatttt ggtttaacaa ttgtggcaaa tgtagcatac taatgtcata tgttaataat   81360
atgggaaact aggtggcata tggggggaaca ctgcgtacta tcttcacatt cttctgtaca   81420
tcaatttttt ttttttttga gacagagtgt cgctctgttg cccaggctgg agtgcagtgg   81480
cgcgatctca gctcactgca acctctgcct cccaggttca agcaattctc ctgcctccgc   81540
ctcttgagta gctggaatta caggtgacct caccatgccc agctaatttt taaaattatt   81600
tgtagagatg gggaccttgc tatgatgctc aggctggtct caaacccctg ggctcaagtg   81660
atctgccctc cttggcttcc caaagtgctg ggattatagg catgagccat tgcacctggc   81720
cacatttttt tgtatatcta aaactgttct aaaagtaaaa gcttattttt aaaaactaaa   81780
tgtatctacc tgtatttttc ccctgctgac ctgtcctgac cattgtatca ctcagggtca   81840
tttgtgaaat atttattgga aaataaatgt aaactggaga aagtaacatg ttggcatagt   81900
ttcatttata taaaatttct cttatctgat taccccaagt atcgatttgt catctgtaga   81960
tgcttcagaa ggccctaagt aatggtaagg gatccccagt ttatatgcct atgtttctca   82020
cccaggtgta tataacccttt gagtcagtgg caacacacca gcaaatgagt gaagtcacat   82080
gacaatttta ctggaagatt ggttcagcac acgaggagaa ggagttagtg gttaggttta   82140
aaaatacatc atagaataca aatttcaaag taaagtacac tttcaggctc ctggttacac   82200
ttcttttgcc attgaaaata ctccagcata agagtttgag aagcactgcc atgaacaacc   82260
caagtattgt tcatagattg aacacctgat acatggtaca taatgtgaat acagatatac   82320
attcatatat attactgttt ttcaagggaa catggatgct gctgtgatta atgaaacaca   82380
cttacatata tcgaagagg aaggctcagt ggaggctcag ctactgtctc agccaaagtc   82440
cttgccctgc atccctcac tccaccctca gcatcttgcc tggggtctcc tggttctgac   82500
ctccagcttc tctggcacct gagttcccct ctagctgggt gcgaattagc cctttttctac   82560 ctgtcagctc ctgttgccca gcatctacct gatggccaca cttcctgctc ctgcaactca   82620
gaatcaaaga tttcagcggc acctgtccct taacactcct ctcagcctag ctctggtgtc   82680
```

```
agaatgcttc tgtttttagt gtctgctgcc tttcttattt ttttccccag aaactgaaaa   82740
gctgaatcag tactcaattt tcccaacttt aacaaggatt tactttgaaa agttgtccag   82800 cattttaga ctacttcctt tgatagaagc tcagacttat caaaacatgt ataccctgta    82860
tgactgcttt cctctcacaa ttgggccata gaacatacag acagaaggga ggcagagaag   82920
agtacattaa tttcctggga ctgccataac aaagtaccac aaacagccca ggcagggtgg   82980
ctcatgcctg taatcccagg aatttgggag gccaaggtgg gtggatcacc tgaggtcagg   83040
agttcgagac cagcctgacc aacatggtga aaccccatct ctactaaaat acaaaaatga   83100
tccggatgtg gtggcaggca cctgtaatcc cagctactca ggaggctgag gcaggagaat   83160
cgcttgaact caggaggtgg gggttgcagt gagccaagat cacaacattg cactccagcc   83220
tgggcaacag agggagactc catctcaaag aaaaaaaaaa aaaagtacca caaaccagct   83280
ggcttgctta cacgacagaa atggattctc ccatagttct agaggccaga agtctgagat   83340
caaagagtca acaggattag ttcctgtgga gggctgtgag aaggaatctg taattatgaa   83400
aaaaaaaaat gagaataaac agtaacggag catcctttgt gcgcgcttcc atgctaagct   83460
caaaaacata atattgaagg aaaggactga aatatatatg catatatata tacacacata   83520
tatataatgt gtgtgtatat tatatatata tatatatata tatataca catatcatta    83580 ttttgctttt ctttatatta ttaccccaaa taaacactta cctcttggga taaatatttt   83640
gggacatttg tcctattatt taggataata atataaagaa aaacaaaaca atgattaaca   83700
caaaactcag gatagtagtt acctggggtg aaggtgcagg caggaagggg atgcaatggg   83760
gaaaggggga catagtggct tcaaagcact ggcaagataa gtcattagct ggatggatgg   83820
agggtgcatg aatgtttatt cttctttaaa caacgtaaat gctttataca cctatcagaa   83880
gttgggatta taggaaacag cctctgagat ggagattatt atataagaga tttatctggg   83940
tgtgttcttg gaatcaacaa ccgtgggagg aaattgaagg aagcagaatc cagtagggga   84000
agaatttgat cggcaaagca gtctcagtgg aggtcttggt caaccacata gagagttttg   84060
aacctcggat ggcccttcgg agttttcctg atttggtggt gggagacagc tctttataca   84120
ccatgttagt cagtcactgc atgcagccca cctgggagac gatcttgaac tttggcaaag   84180
acgctctcat cagctgaggc catccacaca gggtgctgac aactaaaggc tttttgctgg   84240
caatgttccc agcagccgag acaaagtcct tcattcctga aaggaactga gcagcacctc   84300
acagtgtcca ccacaacacg ggtttatata tttatatatt tttcacaata aaagttgtta   84360
tttaaaaaaa gaaaatggtt aaggcaagaa ggccaagcta taaaagggta tcctttaggg   84420
atggtacaaa atctcagaca aaacgaagtc aagagcatag ctagaggaat actgacgtgg   84480
aagaaagctg agcacagggt tgggagtgtc tgcccatgga gttgtacaca gattttctgc   84540
tggtggaggt gaaaccagtg aatcagatgt gattcggtaa tataacccag actatgacta   84600
acagacatcg tggagtcagc ttcactgggg tgagttagtt tgacaactcc cagaaaacta   84660
atgttgctaa ctggcctctg cttggtcccc acccaactgt aaggagcata agtagataga   84720 gacttttgt ttgtttgttt aagatgaagt tttactcttg tctcccaggc tggagcacaa    84780
tggcgtgatc ttggttcact gcaacctcca tctcctgggt tcaagcgatt ctcctggctc   84840
agcctcccga gtagttggaa ttacaggtgc gtgccaccat gcctggctaa ttttttttgta  84900 cttttagtag agacggagct tcaccatgtt gtccagactg gtctcaaatt cctagcctca   84960
ggtgatccac ctgccttggt ctcccaaagt gctggaatta caggcatgag ccacactgca   85020
```

```
cctggcctgt ggatggagac ttttatcctc aggctgagag atgtgtgttt ctttgattat    85080
acaatggaag agggtccact cgggtgctga aagatacctt gagaattcta gtgttaaaat    85140
atactcaaat catcatagga ggccacttcg acttctttcc cattgccaac catctcatag    85200
gaataaaagc tactgtgtat taattcttcg ctatgaatca ggcactgtcc taagtgcttt    85260
acctgtatta tctcaatcat tctttacaac agctaaatga cacagatact atcaatattt    85320
tctattgtgt tgataagaaa cgggaggtac aattgcatgt gcttcaattg cttactcaat    85380
gtctccaagc tagtaagtaa taagaccagc actgtttgta ggctggctgc ccagaagcta    85440
tcttttgtct gaacacttaa ctgcctgcca gagataggag agcatcaagc ttggttttga    85500
caagagctct gtgtgttgca cagttctctg ggcatggata cagcttgact tactggtcaa    85560
gtaggaaggg ctcagtgctg agatgcagac gtagtgtcca ggcatggagg gcatgcctgt    85620
tgggagaatg ctggtgggga cagacagcaa gggctctgag gtctggagac aatcttaacc    85680
tggctccagc tctgactcca aagcagcccc caggatctcc actctaagcc ccaagacagt    85740
tccacatgga aattcactcc tcatgagcac aaatatgggg atcaactaga atcatgacct    85800
gaagttcttg tctggagatg dattttgaga gtgaggcgag caataccact agacaaggaa    85860
ggatgctctg aagatttctt aattccttgg aaggcaacag aagctaagtg aaaaatcaag    85920
aggaaaaaat gtcttctctg aagcagaaaa tgtcaacact aggatgggaa cttttagggt    85980
tattcccact gaagatgggt taacagccag accctggagg caaactggct aggtcaatga    86040
cctaactcca aaattgggta atgagtgacc ctagaaaagt tactgaaact ctctgtacct    86100
tcgttagcat ggacacccac ctcctagcac tgccgccaag tatatacagc aacacctgtc    86160
aagtgtttag aacagggcct tacctgtttt aagtacctct gtgttattat tattagcaat    86220
ccctacttct ttctaggtag aaggacatca ttgttcacct tgacaattcc atcccagcct    86280
ttcttttttt cctccaggaa gtcagggtgt ggttcgggga tcaaaatcat tcagagtagc    86340
agagtagtga gtcatcattc tgtctagaag gaaggcaagt atctacacta ataagcaagt    86400
atacctggaa acacatcaaa ctttatgatt taaaaaatag aagaagtcgg acttagtggt    86460
acacacctgc tactcgggag gctgaggtgt gaggatcact tgagcccagg aattcaaagt    86520
taccatgagc tatgatcgtg ctattgcact ccagcccggg caacaaagca agactttgac    86580
tctaaaaagt caaaataaat aaataaataa ataaagtaat aaagtaataa aaattaaaaa    86640
tagaagacac aatcacactc tctggccctc tgattcctta tgtataaagt gtggtagggg    86700
ttgtggattc cactgggggc tcacaaattg ggttctgcag agccctggta ttccccaaag    86760
gtgtactggc ctcccaggac gtatggagca gaagccatgc aggcaggacc ccagcccccca    86820 cttcagccag agcagttcca cttgcatctg ttttctacat tgtaactgta agaataaaat    86880
atctgtagat ggaaatggag caggcccctg acgaaaaatg taatcaagct cttcctggag    86940
aagagtctca aagctcctct ttttgtaatt aagaatgcag ccattaaaat attacaccct    87000 tttctttat tcatgacaaa tccgaatgag cacaatttgg aaagcagcag ggaggggaat     87060
gaacaaattg aattaatttc tatgctgaat attaatatcg tgccacagaa agggagatgc    87120
tttgcaaatt taaggcagtt aagaaaacat ttttatgctt cttagtaatt tagacagcac    87180
tgcttctgaa aagtgctttt ctcctggcag ttgtgtatgt ttggtccagc aggcagactc    87240
actatagttg acttctctgt taggcacagt gcctagggcc catgacactt ttaggggccc    87300
acaaaaatgt tgtaactttc atttctatta aaatccaaat acatgtatat atatatacaa    87360
ttacatataa taatgaattc agcctggatt acactcctct ttgggccagt gtagtcataa    87420
```

-continued

```
aatacaattt ttaatatttt tacgaggaca gggtttatga aagcaaagtg cccacagccc   87480
cccaaagtca taaatctgtc ctgatgactg caactcactg cagtgaaagg gtcacaacg   87540 ggacctgctg tgcagacccc aagcccagct tagactccac cttaagtgtc aagtccatgc   87600
aatgtgttgt ggacttagct gtgtccacag cctcccgttt ttcctaatga tcccttgcct   87660
atgaatgtga tcccttcta ttcaaactgt ggtggcacat caacaggatg ggcatcacct   87720
ggggacttgg tagaaatgca tcatctctag ccccacctaa gacctactga atcaaaatct   87780
gcattatacc acattctctt cccctatcta accccagatt gaggagatca catcccaacc   87840
agggcctgcg cacagggctt caaggaaatg accagcagca aagtgaccga ggtgcacagc   87900
gaagccagaa tcaatgcaga agattgggag acatctactt tcagcttcca agtaaccacc   87960 ttactgggt gaaagacaga aacatctgct ttctccctat gtcctagata aaggggagac   88020
gggtgctagt tcataggtta cattaagttt tcttcttaaa gaggtgtttg cattgttttg   88080
aaatgtttga aaactctcta aattgaatga attcataagt tccttcctgc tataagtggc   88140
ctatttcagc cctaatcctc ctggccttgg gaagtttagc agcaccaatc acttcttctc   88200
tccagcttct aaccggttgg agaaacgtgc acaaggagcc tgaagatgat aaaaggacag   88260
tgccagcttt actaccagta aagctgaatg gggaagaaaa taaattccca cccccttgga   88320
aaggcctggt tgccctatag ccatatcaat aagtggcact cagaaccagt ttggaacctg   88380
gtcaagccag caacaacaat ttgctttggt gaagagcttt tacaagttgt ttacaatcag   88440
cattagctgc ttacttctga aagccagcca atcacagact cacctcaata aatacactat   88500
agtgacaacc aattaccaat agcctcatct gtgtacccac acctctgcgg atgatgttga   88560
agctcttaag cctctgcaac ttcgccagtc actgaacttc acacttccgt gagactctat   88620
ataaattagc ggtctgctcc aagagactgt acttcctttg ctatgcttaa caatccattc   88680
gattttgtct ttttatttt tagtatggga tgatagtctc atcatacttt gatacctga   88740 acctcagaat ctgcatgaat ataacctctc caaccaaatc caggtagaga agtttaattg   88800
gctaactaaa cttcatattt taactacata gaagaggcca agagggccct ggcatcctct   88860
tagtgatatg aacagctggt aggggaagag agagaataag aggaatcctg gttttcactg   88920
tccaaggagt gggaggtcca ctggactctc tctctccatc ttaccagcat gttagttact   88980
tctcagggag ggaggatgag gaagaggaaa gatgagggga tggagagagg aggtggaaat   89040
aatatttcaa aatggtttac tatggtgtga atgtttgcat ttccccaaaa ttcatatgtt   89100
aaaatcctaa ccccaaaggt atgatattta agaggtgggg cctgtgggag gaaagtacat   89160
tatgagggtg gagccttcgt gattgggatt aatgtcctta tagaagagac cccagaaagc   89220
tatatagccc cttccacagc gtgaagacac agcaagaaga catcatctat gaagcagaaa   89280
gcccttgcca aaacccaaat ctgcaagtgt cttgatcctg gacttcttag cctctagttg   89340
tgtgagaaac aaacttctgt tgtttataag ctacccagtt catggtactt tgttatagca   89400
gtccatatgg acaaagataa tattccttcc agagattgga gccaaatctc ctcatagaaa   89460
caggagaaag agacaataag ggcttcccgt aaacattctt tatcctaaca gttttgcaaa   89520
ttgattgggg agagaaggtg taaatactta aagcaattga tatggtttgg ctctgtctcc   89580
ccacccaaat cttatctcaa actgtaattc ccacgtgttg aaggtggggc ctggtgggaa   89640
gtgattagat catgggggtg gtttctaatt gtttagtacc atctccctag tgatggctca   89700
tgagtgagtt ctcacgagat ctgatggttt aaaagtgtgt ggcacctccc actttgcact   89760
```

-continued

```
ctctctcctg tgccatgtaa ggcatgtatt gcttcccctt tgacttccgc catgattgta   89820
agtttcctga ggcctcccca gccaggtgga actgtgagtc aattagacct cttttcttta   89880
taagttaccc agtctcaggt agttctgtat agtagtgtga aaatggacta ataacagcaa   89940
ttaagaaaca cttatagggc aaaatattct gagaataaga ctattggtaa taatgtgaag   90000
gattcttaga aaacatggaa tttgagatga tcttggagag atgaattaaa ttcatcaaaa   90060
atcacccggt gattatgaag caccacggtg tccagcattg agtcctgagc tgtataaaca   90120
agcagtcaca atttctaccc tcaagaagct cacagtctga gtcttctggt tctcaaatct   90180
agttatactt tagaatcacc tgagaagctt tttttaaaaa tgcccataat cctgatttaa   90240
ttggtctgag tgagtcctgg ccatcagtat cttttaaagc ctcaggtgta ggaaaagagt   90300
tcttgaagag acaaacaaa agataatcat aaaagaaaaa aatgtttaac ttaattaaaa   90360
taagactatt aaaagacatc accaggaaag tgaaaagaca agccacagac tgattgaaga   90420
gattgacaat gcatatatcc aacaactgga aacaacacaa atgtccctca ataggagaat   90480
ggataaataa attgtagtgc attgatacaa gggatactag acaacaataa aaattatgaa   90540
ctactgacac atggaacaag gtagatgaat ctcataggca ctttattgag agaaagaaga   90600
caaaagagta catactgagt aattcaattg ttaaattttt aagaacatag gtaaaactaa   90660
tttacggcag tcgacagtca tcttttagtg acttaactgg gaagggacac agcagaatgt   90720
tatgaaaaac tgtggatgtt tgtttttttga atctcaacct agggggcatg atacagaagg   90780
tatatacaag gataatcctt agagaagatg gctggagcca tcagcaaccg acacacccag   90840
ccactggggg aaatgagcat cttagtcctg ggagggatat ctgggcagag tctcagcatc   90900
cactacaccc tacactgcgt gatctaatgt ggaacttggg gctgagacgt actggtctaa   90960
atcagtgatt ctcaaagggc agtccctgac aagcagcatc agcaccatct gagaacttgt   91020
tagaaatgca aattattgac cctctaatga attggaaact ctgggttgag cctagcaatc   91080
ggctttcgca agccctccag gtgatttcaa tacgaactaa tatttgagaa caactggtcc   91140
aaaggggttt cacttgagat cgagagggga ttttattttt cttttctttt tttttttttt   91200
tttttgagaa atggaaggaa tcctggcaat gtcacaaagc atgtcaaata taacatggac   91260
agagaatgca gtttggagaa aagtgaacga gaaaactgtt tagcaaatgg gactaattac   91320
tagatcttat ttaaaatttt tttctcttaa tccaatagac catatggaaa tcatgtggat   91380
tcttaaacag cctggcagag gagcaaggta aaacacaggg aagagaatct ctatacagtg   91440
aaaattctaa taggagacat ttgaaatcat ctttgtgaaa agtaaggagg ataaaaagta   91500
tgagtgttaa cagtaaaaat gggaaggaaa aaatgactct gagagactcc acaatgattt   91560
gcatcagaat ttgaatctcc agtggggtga ggaagcaaag gttactataa agtatttttg   91620
tttttacatt aaaaatagag gcagggtttt gctatgttgc ccaggatggt ctcaaattcc   91680
taggctcaag tgatcctccc acttctgcgt cccaaagtgc tggattactg gcatgagcta   91740
ccatgcctgg cccactacaaa gttttgagat tttcatcact aggacaatag gagtcaccaa   91800
cacaaatggg gaagtcagga agagaatcca tactgaaagg aacatgaatt ttgtcttctg   91860
ttttggaaag taagcctatt acatccaggt ggagctgttt tataaacagc tagaaatgta   91920
ggacaggcag agtgcagtgg tttatgcctg taatcccaac accttgggag gctgaggcag   91980
gaggatggtt tgagcccagg agttcaagac caggcagggc agcatatgaa aaaatgtctt   92040
acatgttgac agaaatgtgt ttggtagaag tcaagcaaaa tgaggcataa gaaagcatca   92100
ttgaatgatg ataaaaatga ggtccgaagt gatcttattg catgtttggg tccatgtaaa   92160
```

-continued

```
ctgaatccta cccatttctc caacatgtaa cactcctata actagtcacc tttccactta   92220
tacagtaagc tattcaggaa agtgacttgg atctgttaga gtggaatcca gaatgtgacc   92280
catttcttcc ctttgcattt cttttccctct ttctgcctcc tatccccatc atttgtctgg   92340
ctcatttcat ccatcaggcc tcagctcaac tggcactcct caaaaagact ttctgtggct   92400
actctcaggg tcccctctag ttacctgttt atttctccta cagtacttttt agagcaaacc   92460 cttcttaaaa ataaactcta aaatataact gagggctctt tttttcagat gcttgactag   92520
caattcatgt tactcatcat cttgcttcca atgttccacc acatctgttc ctgcctcttg   92580
gatttgggta cagacacctt tcccagggct tggaagtggc tttctaagat ttacattgat   92640
caacctaggg ttaaaaccct ttcaggctgc tggcacttct gcttgcgcta gtgtgagggc   92700
ttatctcacc actgaaatgc tggttctcct gcagttgcac ttggtgggtc cagtttccct   92760
tttctgtaag ccacagaggg tggggaaaag agctctgcct tttcctgttt ctattcactc   92820
ttctttcccc tctactccgt cagtgtgcca caccccaggc tcctagccctt ctccaaccca   92880 gccaaaggaa gcctcagaag accgttctca tctcccagta ggctctggac actcacaaat   92940
acaattctga attagcagtc aaaaatacgc atataagttt tgtttacata gaatctcagc   93000
tctctcaaaa tcccctgttt acctcacaac tggattttac atgtatcaac aagcacagca   93060
aaatgcaaga taatttttat gaaatgtaaa cctctctgtg acttctaagg ggagaaacgt   93120
agtcttttgt tcccatctca gatccgccag agttgcctac ttagtttgaa tacaaatttg   93180
agttacaata aattatcctg agccattcca ggctaaccac tatttcggtt tccagatcag   93240
tccccattaa acatcaaaat tgcaagatac gtcacctcag tggagccact gccttgattt   93300
gcaatgtttg atctggcacc aatacaggtt tcttgacttc ttaatatact ctttcttatt   93360
ttttcactaa aattaacaaa aatgaattta gtattttgct taagtaggaa attgaaacat   93420
tccaagcgtt acacatctta aattatgtaa gtatgcaagt attttttttc tgctttcttt   93480
catacgcatt accacctctg caggagaagt aaaagtgaaa cccagccagg cgaggtggct   93540
cactcctgta atcccagcac tttgggaggc tgaggtgggc acatcatgag gtcaggagat   93600
cgagaccatc ctggctaaca ctttgaaacc cggctctact aaaattacaa aaaaattaac   93660
cgggcatggt ggcgggcgcc tgtagtccca gctactcgcg aggctgtggc aggagaatgg   93720
cgagaaccca ggaggcggag cttgcagtga gccgagatcg tgccaccgca ctccagcctg   93780
ggtgacagag acagactcca tctttaaaaa aaaaaaaaaa aaaaagtgaa acccaagaat   93840
cctctagctg taggaaagga atggctagag ccaagagaaa attaaacttg actaaaatgt   93900
gtcatataat ttcttatatt tcattgggct atcatccttc cctcccatga gcactggatt   93960
tatttaggag gcttatcatc ttacaagtta ctttaataca attgttccag aaaacagaag   94020
aattattaga cttgtatttt gaaaaataag cctcaaactc agcaataaga acccaaatac   94080
cgcaacaatt aaaaaacgag ccaaaggcca gatgcagtag ctcatgcctg tgatcccagc   94140
ctttaagagg gaggactgct tgagacctgg agtttgaggt cagcctggga aacatagcga   94200 gacccatct ctacaaaaaa taaaaaatta gtctaatgtg gtagcacatg cctgtagtcc   94260
tagctactca ggaggcttag gcaggaggat catttgagcc caggagttta aggctccagt   94320
gaactatgat tgtgccactt gcactctagc ctgggcgaca gagtgagacc tcacctctta   94380
aaaaataaag aaccaaagac cttaaaagac acatcaccaa agaagacata cagatgacaa   94440
ataagcatat gaaaaggtgc tccatatcat atgagaaatg caagttaaaa caacgagaat   94500
```

-continued

```
ccagaacact gacaacatca aatactggtg aggatgtaga gctacaggaa ctcttactca    94560
ttgctggtag gaatgcgaat tggtacagcc actttggaag acagtttgcc agtttcttat    94620
aaaattaaac atattgttac catgtgatcc agtaaccaca ctccttgata tttactcaaa    94680
gaagctgaaa acatgcctac acaaaaatct gcacacagat gcttatagca gctttactca    94740
taattgccaa aacttggagg caaccaagat acccccagta ggtgaatgga taaataaact    94800
gtggtacatc cagacaatgg aatatgattc agtgctaaga gaatgagata tcaagccatg    94860
aaaagacata gaggaaactt acataaatat tactaagtaa aataaggcag tttgaaaagg    94920
ctacacactg tataatttca actatatgcc attctagtga aggtaaaact taaagacaga    94980
aaaaaaaaaa taatcagtgc ttgccagaga taagtgggag gaagggatag ataggtaggg    95040
cacagaggat ttttagggtt cctgttgctc tactctgtat gatactatag tgatagacat    95100
atatcattat acatttgtcc atttgtataa tgggtgaacc atcatgtaaa ctgtggattc    95160
tagtgataat gatgtgtaaa tgtaggttca tcatttgtga caaatgtacc actctagtgg    95220
ggatgttgat aatggaagag tctatgtatg tgtgggggcg gaagatatat ggaaaatata    95280
tcatctattc aatttttcta tgaacctaaa actactctaa aatataaagt ctatttttaa    95340
aaatatgctt ctgtgtttta aaaacaagga ctgtagaatt attaatgttt tccaagatga    95400
aaatcactgt aatcacttat caatgaaagg aaaatgttac atattatcaa ttggattcta    95460
ataaacagaa tataatttat ttgaagaagc acagaattga tttatctcca gagatgagtt    95520
tagctttcaa atcatcagag atacagatta ccaacaatta aatactatgc tatagcatgg    95580
tagtttccag gcttctaaag tataaaaaca tattttcaat atcaaaaata ttttcagaat    95640
gtcacttcat aagtaccatg tattaatcat ttaataagaa aaatgacacc taagagtaga    95700
ctatgaggcc atatggaatg agatctttgc ccagcagaga tgacaggtac taactctacc    95760
aatcagattc tccttattgc aagtttgaaa tggagacaca caaagtcatg aaccagcagg    95820
gagcctgagg gagcaaaacc cttgagtaac caagaagcct ctcgaatgaa caggagacca    95880
gttgagtggt acttacctcc ctccaaccac atttcatctg gttcatcttt tttatttatt    95940
tttgcttttc cagacaaata agaaggggct gggcagaggg aagtagaagt aagttaatta    96000
atttatagcc ttggaagggc agcagcaggg ccaggaagga gttgagtcac gttaatggct    96060
cagcagagta gggactgccg ggtgaacaga taacctaaag ctgccttgag cctgtctgga    96120
atgatcttgc cagtccagaa ggagtctgtt ctccaggaag ctcaggcaca attaggttct    96180
tattttcctg ctcagagatg gaggagttcc tgttcttgat acctcatcac ctgactgaga    96240
cccacccatc ttccttaatt cccccatttc cttgtaataa atacttcaga attgaggtaa    96300
cttgagttta tcattgttct ttataactaa aaattatagc tagcacagaa attaaattta    96360
ttttgtcata atgaatattt gtcaaccatg aagacaaaca aaaatatact tagcattgta    96420
cattattttt cttgctcctc ctactttttta tcttttttaaa aggaaagcag aaggcagtct    96480
tttaggtgat aagcaattgt aaaataaaga aaacctacct tctgtttttaa tcactggtac    96540 agtaaatgta ttctttctca atgggatata gttacctata aatgaggctc ttttaggagt    96600
ttagaatact ttcccttaaa gtttcaaatg tttgtagtgt aaataaccaa tttcactgat    96660
gtttagaagg gaaggtagag gccgggcgcg gtggctcaca cctgtaatcc cagcactttg    96720
ggaggccgag gcaggcagat cacgaggtca ggagatcgag accatcctgg ctaacatggt    96780
gaaaccttgt ctctactaaa aatacaaaaa attagccaga cgtggtggcg ggcacctgta    96840
gtcccagcta cttgggaggc tgaggtagga gtatggtgtg aacctgggag gtggaggttg    96900
```

-continued

```
cagtgagcca aggtcgtgcc actgtactcc agcctgggcg ataaagcgag actctgtctc   96960
aaaaaaaaaa aaaaaaggga aggtagagag gaatgttatg attcacattc acaagcatca   97020
tgaatggttc tcttcaaaag ttcatttgga taaaaatttg gcctaatttg gaagtactgg   97080
ttccagttac tgattacaga gcctattttt atataacatg tttcaaattt gttacttttg   97140
ctaataagtg tgtgataatc atgtctgtgt gtgtgaattg tttcaaggtt tatcattcta   97200
ttaaagttag ggttatgcaa tgtggcagaa ttataatatt gatagtgtaa tgtgatttaa   97260
tctagaattc aatgactatc ttgttgaggg tgcctactag aattagaatt tttttataca   97320
agacaaatga atgttcactt tcatgttcaa caattgagta aatgatctgt aattttagga   97380
tatctaatcc atcaaggaca ttgcagcatg gttatcttaa atatttatca ctgaagagaa   97440
tccaattaat catcccaaat catatttcca cttatatagg cctccaacat ttctaccttc   97500 cattttatt cttcagacta tccaggtgta ctgggtttaa gaatcaaagt gtttaaaggg   97560
tatatcttca cattctgata ttactgtttt actatatcac tttttttggag cgtttgtttg   97620 cttatcgttg ctgtaccccc aacaaaaacc tggatgccta ataaagaacc aggcaaatca   97680
ttgcaaaaca ttgggttgtt ttttattttg tttgtattct aaggttagtt ttttgctttc   97740
atttgcaaaa ctcaaataat gaaaatattt tattgctacc taaaaagcat caaatagttc   97800
aacttgactt tatatcatcc agtgatcaag gggcttacaa agaaacaaaa gaagtccagt   97860
gatagagctg agaaaacgag ggaatgtagt aaaggatgag ctggtgacac caaaacctgc   97920
aaggcagagg tgaatgattt gagtacctaa atgcctgggg aggtaatgtg taaaatgacc   97980
atgtattcaa caagatggag ctgcaaaacc aacggtcaaa tggagagtac aatccttgcc   98040
tatagacact caaattcaat ttgactttga aacaaagaac actgtgctgc aaaaatatat   98100
gtctattatg tctatttcac cataaatttg tgcccccata tggtttttgga actcatgctt   98160 aggaatttga tctttatcta aaagcattag aaaagaagct gctgaaatag aagtagggtg   98220
gaaagagtga cactatcaga tttgtatttt gaaaaacagt attttagaaa aaaaacacaa   98280
aaccccaaaa acttctcagt aatattctta ctgtgataga tagtatatcc atgcatccat   98340
gaaaccaaaa caggatgttc tttccagctg cagtatagta actgaatagg aggtcatagg   98400
tagagttggt gaacagaaca cgtgtctgat ttttttccct cactaaaccc tctagaaata   98460
atttttttgg ccaggtgcgg tggctcacgc ctgtaatccc agcactttga ggccaaagtg   98520
ggcagatcac ctgaggtcag gagttcgaga ccagcctggc caacatggca aaacaccatc   98580
tcaactaaaa atacaaagct tagcaggcat gatggcacac acctataatc ccagttactc   98640
gggaggctga ggcaggagaa tcacttgaac ccgggaggcg gaggttgctg tgagctgaga   98700
ttgcgccact gcactccagc ctgggagact ccatctcaaa aaaaaaattt ttttaagtt   98760 aacaagcaca caaaaaacgt ggaaaaaagg gaaagagaca agagcactcg aaatgttgag   98820
gccagaaagc agatggaggg ttgtagccaa cttggagacc tcaaaaagcc aaatcctaat   98880
ctggtgatgg tgaaagccaa gaaccagcct gatttgtaac cacagaatcc caaaggtcca   98940
tgacatgata gcacaagcac ctctggaaat ggtggtgaag tggggcccca aatcaggagg   99000
tccagatgaa ggctgtttga gaagccagta gcttcccagg tctcccccat ctcctctgtg   99060
ctgctgagca acttgtccct tctgcacctg gactggagtg tggaagcaac ttgtcccttc   99120
ccacctgggc tgaggtgaag tgtattcttt ggagagggca aaataaatgg attctggact   99180
ggtggatacc gaacatagtt gaggattaaa atcttatacc aaaaacagga cttaagggaa   99240
```

-continued

```
catgtggata ctggatgctg agacagcttt ccctctttct ctacttggct tctaaaatat   99300
tcctagccag gactttcaga tcaggagagt cttctatgct atacaatttc tgaccaaagc   99360
aaggtgagaa tcataaaatg gcccattcat accatcttaa ggtaaaattc aactatttaa   99420
tcaagcactc ataagcatga gtcaataaca aataacagga aaaactcagt agtagggtta   99480
gtcaggacca ttactcaaaa gtaggaccaa aaaaaataca ttaaacataa gaatgaaaaa   99540
cattttttta aattagagca ccaatccagg agaaagaata ttcaaacaac tggagttgca   99600
gggtagaaaa aaaaaaacgg gaaagaggaa gaatgcaagt tatcaatgaa ataattgaag   99660
aaataattta agaaattttt tcaaaacaga aaaacatgat tttccagaat ggaaggaccc   99720
ataggtctct gatattgtga tgtgtggtaa taagaaatgt atattctgtc ttcacccct    99780 agttcctggc acagagcttc taaaaccctt ggaatttcct cagtgatagg ggtgaaagat   99840
ttttttcata atttcatttg taataagttc ctttcaacca cacctgagtt taagttaagt   99900
cggtacctct gggaggatgg ggctggtggt caaaggaacc aacaaccacg tggctagagg   99960
gtcagaactt tcagcccact tccagggagg gaaaaggggc tggagattga gtcaatcagc  100020
aatggccaac gaacacatgg aggtgctgga agggtgatat gcccacagag ggcatgaaag  100080
ccctacaccc ctttgcacat atcttcccta tacgtctctc ccatttggct tttcccgaca  100140
ggaacttacc aaaaaaattc tggagacaat gaagcagcct tcaaaattct gaacgaaagt  100200
taattccaat ctaggattct atgccatcca aactatcagc gaaaataag ggtcaaataa  100260 agacgttttc agatacgtac agttacaaaa attgacctcc tggatatttt ttctcaggaa  100320 actttttgggc aacatattct ataaacatga gtagaccaag agagtagaag tcactggatg  100380
ctgaaaataa ataggaaatc tcaagcggat ttaacacagg atactaaagg aatttccaag  100440
agaacgagag agggagacac cagatgacac ctatgcacct agcaaagaag ggaacacatc  100500
cagaaaaaat acttgtccag gtgtgtggct cacacctgta ttccagcact ttgtgagtct  100560
gaagtgggag gatggtttga ggttaggagt tcaagaccag gctgggcaac acagtgagac  100620
cccatctcta taaaaaattt taaaaaatta gccagacatg gtggtgcaca cctgtagtcc  100680
taggtatttg ggcgtctgag cagggaggat cacttgagcc caggagttca aggacgtaat  100740
gagctataat cacgccactg tactctagcc tgggcaacag agcaagacca tgtatccaaa  100800
ggaaaaaata tgaattggag gaggctaaag cagaggccgc ttcctaaaat tgttcccctt  100860
ttataatagg tctatgattc tgttctactt tcaagctagt aagttagctt gctttagttt  100920
catggatgct agcagaaaac ataagaccca gattcaaaga caaaggattt tattactcgt  100980
ggcacatcaa gcatcaagag catcagcatt atttgcatta gtttctctca ttcccgtgcc  101040
tcatggggca acacagatgg ctccagatgg aagcctgcac acacaataag gtggattaca  101100
gaagagaatc cttgagctta gggagccccg gtttctcata tgggcagtaa gcatccttgt  101160
gctttgctct caagggtgat gctatcttcc aatgctgttt gctatgcaaa cttcctttaa  101220
aaaggtagtc cagagcaaag ggtgatcagt cttcttgaaa gttgtgcagg aatgtgaaag  101280
acctattgag aattctctcc ccaacctacg tactcaaatg accttgtaca tttctttcac  101340
cgtacttatc acaattgcaa ttgcatagtt atttgagtga ttgttactat tttgtttctc  101400
ctctaaatca taagctctat aaaggtaggg accatgtctg ttttgttcat tgctacatct  101460
ccaatgactg gcagagtgca gatatatagt agaagcacaa taaatgtttt ttgaagaact  101520
actcatggat caccaaactt gagtacacta gatatacaaa cgaaagatga gtaacaggct  101580
acagatgtca cgaggcataa tgtactttaa tggtattcct ttttttttt tttttttttt  101640
```

-continued

```
tttttttttga gacagagtct cgctctgtcg ccaggctgga gtgcagtgga gcgatctctg 101700
ctcactgcaa gctccgcctc ccggattcac tccattctcc tgcctcagcc tctccgagta 101760
gctggaacta caggcgcccg caaccactcc ttgatatttc tttacattta tctggcactt 101820
attttacaaa gcacctttca tgcattattt catggaagct tcacaataaa actctgaatt 101880
agatgaagag gttaagagac ttgtccaaga tcactggact ttttacgtgt gaaacaaaca 101940
aacaaacaaa caaacaaaaa acaggcctga aatctgggca ttttaagcca atactttgtc 102000
ctctattttt tagtgatagt gtctctgtca cccaggctgg agtgcagtgg cacaatcata 102060
gctcactgta atgtcaaact cctggctcaa gcaattcttt caaataacta ggactacaag 102120
cacatgccac catgtgtggc taattatttt taattttttt agagacaaag tctcactgtg 102180
ttgcccaggc tggtctcaaa ttcctgtcct caagcaatcc tccaacctca gtctcccaaa 102240
gcactgggat aaagacacaa gtctctgtac ttggcctttg ttcttctatt tcataagaca 102300
ttattaccta tgacaattac gaagtagaat aatgtcaaaa gcaaaactag gggaaatatt 102360
ttcaatgctt actttaaatg aaagtttaaa cacctgtgaa aatatttcat ttatttatta 102420
cagttatcac agtgaagatg aaagagtaga attcagtttt catcattcta tgaattaaaa 102480
atagcaatgc tttttgtatt tataaagcat aaaatataca tcactttatt ctcgcaaaat 102540
gcaatgagct aggtattaca cgtctttcac ttaacagatg atgaaattga ggctcagaat 102600
gctttagcta gtagacagaa atcacacagc taattctccc atgagttaaa atatagatat 102660
gttaggctga aaatatgatg ccttctcata aaaggaaatt actttcccaa gaggcagatg 102720
ttcctttctt caatatctct caaaacccaa acataataga atacactcag tgtattctaa 102780
tatgttctac tattcattaa tctcttactt tgtcttacta tgataaatat tgtgaaatta 102840
agaaaccgtt tctaaaataa gccactcatc taagaagtga ttgaaagccg ttacatgtac 102900
acttatcttt agaattagat tttctctgga agtattaaga atttgattaa aaataaaat 102960 tactagttta acattgtaat gtgcctccaa ctcatacttc agtcatcaga tagtcactgt 103020
agcaaattaa gaaataccta atacaagtat aattttaaag tttccatttc ttccttctat 103080
tccttgtttc aatatgtttc acttctaatt tcatatatat aaatgaaaca tttctcattt 103140
gtgccattta tttttgcactt ataaattgct ttgtagggtt atctttttac acattgattt 103200
ctagcctttc acaaccagaa tgtaagctac tttaggacat ggatcatgtc ctatagttta 103260
agactttctc tcctgtctgg gccagtagat cattgtaatc cagcaatttg ggaggccaag 103320
gtgggaggat cacttgaggc tggaagttca aggccagctt gggccacata gtgaggcctc 103380
atctctacaa aaatttaaaa attagctgga catgatggta ccttcctgta gtactagcta 103440
ctaaggagac tgaggtgaga ggaacacttg agcctaggaa cccagaagtt tgaggttgca 103500
gtgagctatg attatgccac tacactacag tctgggtgac agagcaaggc ctgtctctag 103560
aaaccacaat cacaacaaca aaaacaactt cctccactcc actctctgct ttgcaccttg 103620
tcaagctcaa ttcaggtgag ttcctggctt tgctctcttt attcctctcc ccgtttaaag 103680
tcacctgaaa aattagccat actctgttcc cagggttaac ctaactaaag caagagtaga 103740
ttaccaccct tcaaaatcag catttttggag cttatcctca aagacaggcc agccctgatg 103800
acctggcacc aaggttaaca actggcctcc cacctccagt ctggagccca acgtggcctc 103860
acgtgtatga catgccttct gttccattgc tgttccatat tgctaatctg ggaattttc 103920 atgatgtttta gtcattccca ggaaagagag aaaaggcaaa caaagttgag acttgctttc 103980
```

-continued

```
tccccaggaa gatctggaat gtaaattaca cctcagagtt ttcctgacct gaagcaaggg 104040
agctgggtct ttttactcca tcatctggca gtcattggtt aagagctgcg ccaggggacc 104100
taaaatccca gctctgtgct tactggcaaa gcagcccaga cgcacaagag cagtcctccg 104160
aagaataaat acaggtactg tgaagcgagg ggaaaaaagc actgaagcac agaaatagtg 104220
aaagtgatcc cagcagatct ggtcaaagca cttacggtgt ctgctgcagc tctatccatc 104280
agaagaagac cacaaaaacc tgggcccca caacacagcc tgggacaact gctgggatgg 104340
ccagagccta cctgcaatag aagcagctaa tcccacaagg agaagatgag gtgatatgag 104400
cacagagccc tgtgtcccag gagaggagca tcaggacaga ttttagagct gtaacaacgg 104460
gagaggtctg atgaaagaaa gctcagagat gataaaggcc aatgtcaaag gacagaaaag 104520
gacagcagtg tgagcaattt tgaatgcaaa tgaatcactg tggcatccca aacagccaaa 104580
aggaaggcat ttgtgtgggt gctcctgcaa ttccttgggc ttgacctgag ttagagaata 104640
taattgtatt ggaggttggt gtggcttggg gaaagataaa ccacaaactt cattttctgc 104700
tacactgcta tctgctatta ctgagtccaa ataaaagtta aaagtactgt cagacattaa 104760
aggtaaaaaa agtaaagata ctggatctgt cttttcactc cctaccagca aatctatgca 104820
ttgtgttgct tcatctttcc aggtcaagag tctgacttat ctttttcattt atgccccaca 104880 atttacactg ccatataggg agatttttaa aaagacagta attagtctaa agatctctat 104940
ccatgttgtt tacaaaaata tgcaaaaaaa ttcctttctt tctttctttc tttctttttt 105000 ctttcttttct ttctttcttt ccttcttttct tccttccttt ctttctttcc ttctttctttt 105060 ctttcttttct ttctctctct ctctttctttt ctttctttttt tgagacagag ttttgccctc 105120
gttgcccagg ctggagtgca atggcacgat ctcggctcat agcaacctct gcctcccggg 105180
ttcaggcaat tctcctgcct cagcctcctg agtagctggg attacggcat gtgccaccac 105240
acccagatga ttttgtactt ttaatagagg cgggtttct ccatgttggt caggctggtc 105300
tcgaactccc gacctcaggt gatccgaccg cctcagtatc ccaaagtgct gggattacaa 105360
gcgtgagcta ccatgcccag cctcataaat attttaaag ttaggtacca cattaggcag 105420
ataaaaagga gtgttcctgt gttgaaaaag aagcaacata cgtggaaatg ataaacatga 105480
gattcaggtt ggtggttacc tgaaggaaga aaaaagggaa tgggaactgg aagaattaaa 105540
ccatgctttt ttgtatgcct gaaatgttgt gtaacaataa ttcaaataag taaatgaaaa 105600
tagaggccag gcatggggtt cctgcctgta atcccagcac tttgggaggc tgaggcagga 105660
aagatcactt gagttcagga attcaagact agcctaggca acatagcaaa accccctgtc 105720
tacgaaaaat tttaaaactt gccaggtgtg gtgttgcacg cctgtagtcc caactagtca 105780
ggtggctgag gtgggaggat cacttgagcc caggagatgg aggctacagt gagctatgat 105840
cacgctgctg cactccagct tgggtgacag agcaagtctt gtctccaaaa aaaaaaaaaa 105900
aaaaagcaga agaaaataca agctttagta tttcttgctt caccctaaag gatcattttg 105960
aatactccct gtccctgta ctttgttggg acatggtatg aagatactaa aggcttgaac 106020
ttatagtgac aggagaatta aagagtaaga aatcaactag gagatattta agtggtgact 106080
gaatatggag tagtaaagac ttggagatat tggtatgatt ttgaggtttt tgggaaaaaa 106140
ttgttcactt tcccattctg gagtccccag tccacatttt agaacaatct ctaaatcccg 106200
tatgtgttgc taaatcaact ttcagctctc atttagggat gcgaaataaa agtgtcgttt 106260
aatcaatatg cattccaaca aagctttttt aagcatttat ttgccagaca ttgtatgtgc 106320
cagacatgtc cttaaagacc aaattggtat tataatatga tgataatagc taatatttat 106380
```

-continued

```
tgagactttt actaaggcct gcactgtgtg ctaagcactt tgcctgcatt gtcttgttaa 106440
atcctcacag cagccctaca aaggtggtac tattgttatc cctaatgtat agatgaagaa 106500
atgcaagcct gcagagtaag ttccttaagg ttaactagag ctagaacgaa gatcagaatc 106560
caggatttag tgatgataaa tctgtatacc tcatcactgg tatatacaac aaaaatcaat 106620
ggaaaagttt ctatggtaat ctagaagaaa ttattagctt agctagagga ttcaatgaga 106680
gtttcaaaga aaaccgataa cagaatttta aaggataggt agcaaacaac attccagaaa 106740
gctttgacag aagcctgaga gcatatgata tatatgcagc tttgtgtgtt tcaatgacat 106800
atgcattcag gggcagtggc agaggtgggt ctggtgaggt tggtaggaag gaaattagga 106860
aggatagcac gttcgggacg gaggaggggt tgaaaaagaa gtgttggctg ggcgtggtgg 106920
ctcacgcctg taatcccagc actttgggag gctgaggctg gtgaatcatg aggtcaggag 106980
atcgagacca tcctggccaa catggtgaaa cccgtctcta ctaaaaatac aaaaattagc 107040
cgggtgtggt ggcacacacc tataatccca gctactcggg aggctgaggc agaagaatca 107100
cttgaacctg ggaggcagag attgtagtga gcagagatgg cagcccggca ctccagcctg 107160
gcaagagagc aaggcaagac tccatctcaa aaacaaaaaa aaagaaaaaa gaaaaagaaa 107220
aagaagaaga aggtcttcaa taattcctga gtaactctag aatgatctac gtcaggcttc 107280
tccaggggca ctacttgtgt gtaccttttc aaaactagct gaggaaatgg accgcaggta 107340
tacactcaac tataaataac ttaagcaatt atttgtttag aaagataatt acttttaaaa 107400
tatatgagtt tttacacttt tccacagcca taaaggactt tacttgagac cagttgtgtt 107460
aattgaccat gacattaaca aacaaccaaa tgttagttgt ctaacactga tagttttttct 107520 cagaagcgag gtaagtcaaa tttttaagctg cagatgttag ttttctggtg cagagatggt 107580
actatagaag tctatatctg tacaatcact taatgatcac acagtaatac tattattcat 107640 cttatttttac attatttggt atggatatgt acataaaaga acatgagtct gaccatcagg 107700
atacttggat cctaaaataa tattagctag atgtgcaatt tttattatgt catttatttta 107760 tctaaggctc aactcatctg taaagagaga ggtttgtagt agatgcaccc taagattgtt 107820
tttctgtgaa attgggtaac cactggtctt gacaagttta aaacgtagtt gaataattcg 107880
agtatatcca taggaaaatc gatgtaaaag tatacaagta acttaaaaac aaacactata 107940
aaaggaagaa aaattctggt gatgttaatt ggaaagacca agatcagacc atgaataagc 108000
agaagaaagg taagtttggc aggcgtggtg gctcacacct gtaatcccag cactttggga 108060
ggccaaggtg ggtggaccac aaggtcagga gttcgagacc agcctggcca acatagtgaa 108120
actccatctc tactaaaaat acaaaaatta gctgggcatg atggcaggtg cctgtagtcc 108180
cagctactcg ggaggctgag gcaggagaat agcttgaacc tggaggcaga ggttgcagtg 108240
agccgagatc atgacacaga actccagcct ggcaacagag cgagactgtg tctcaaaaaa 108300
aaacaaaaca aaaacagcc aaaacaaaaa gaagagaagt aagtttggaa attaattaag 108360
aaaagggtag aaattcttag taggtaaaat catgtatagg ataaatattt tgtttatttt 108420
ctcctcctca taaaacaact gattatccaa gactaccagt acattttcc ttgcagtcat 108480 ataacaataa tttcatattt tacctatttg tgtgacagct taaaatcttt ctagaataca 108540
taggctacgc aaattttaga attccttta attgtaccaa gagggtggta ttggaagatt 108600
actgaaaaga ttatcagaat tatacataat tgtgggttgt gtcactatgg gaaaccacat 108660
gtattgtatc actaaggtta caattataaa cacactctga ctcaaattat tgcaaaacat 108720
```

-continued

```
taccatattt gggtgaggtt tctagaggaa gagagcagcc aattaatcaa gcaataatat 108780
ttgctgagta tccactgtat acaaaatact aatataggtg ttgctgagta aacaggaaaa 108840
aagacaggaa aaaaaacaaa accagaagta ctgctgatgc agcacagggt ggtgaattga 108900
atttacagga tgggatagta attgccttca ttaagtttta tttggtggac agtgccagac 108960
ttaagaggaa gaaagaaaaa tcttgcagtg gaaagaacat gaaatataaa ataagatgcc 109020
taggttccaa tcccagctcg gtcacttagg agctatgcaa tcttttttctt tctttctttc 109080 tttctttctt tctttctttc tttttttttt tttttttagat ggagttttgc tcttgttgcc 109140
caggcaacct ccgcctcctg ggttcaagtg attctcttgc ctcagcctcc caagtagctg 109200
ggattacagg tgtgagccac cacgcccagc taattttttgt attttttagta gagacagggt 109260 ttcctcatgt tggccaggct ggtctcaaac tcctgacctc aggtgatctg cccacctctg 109320
cctcccaaag tgctgggatc tatgcaatct aaaatcattt agcctcattt ttttctttct 109380
gtaaaatggg tataatggta ctgataagaa cctcacttga ggttgcagtg agaaatcaat 109440
gaagcaatga tttgtaatct ataagagtaa acatgttaat tttcatccag tgttacccttt 109500 ggttaaacta tgtggtttat tctctttatc ttcttcacaa cgtttatcct cgaaaggaca 109560 cctgctttt tctgcatgtg tcagcatgct tctccttcct cttctctccc caaatgaacc 109620
atcagttttt caaatatcata gcttctgttt gccgtccatt cacaaaaaac aatgatttgc 109680
acattatgaa cacccaataa attacttaat aataaggtct tgcctctgaa catttatttg 109740
atactctcac atttcattta tgtgcagctg tcagattcat cttgctgcac atatttctga 109800
tcatgtcatg tcactgttca aaagttctca acagttcctc acggaatctg aacgcctatc 109860 ttaaaccctaa aggccttacc actcaaaatg tggtctccag atcaggagca ctggcatcag 109920
ctgggagcct gttattctac aggctgtatt ctggagaata cagattctcc agtctcatgc 109980
cacatctatt gaattaacaa cttcgtttttc acaagattcc caattgattc atatctacgc 110040
agctttgatt acatgtttaa tctctcataa acttcaagct tcaaaagcag ggttgctaga 110100
tttagcaaat aaaagtaaag gatgtccagt aaaatttgaa aacaatgagt aattttttggt 110160 ttaagtatgt ctccactgct tcatgggaca tactttttaa aagattgctt atctgcaatt 110220
cacatttgat taagtgtcct atatttaata tggcaaacct attcaggagg gtaggatcca 110280
tgtctaacat agctttgtat tcccctggaa tagtacagtg ccttccccaa ctgtttttgt 110340
ttttttttgt tttgctttttt gagacagagt cttgctctgt cacccaggct ggagtacagt 110400
ggcgcgacct cggctgactg caacctccgt ctcccgggtt gcagggacag ggacaacctc 110460
cgcctctcgg gttgcaatga cttctgcaac tctcctgcct cagcctccga gtagctggta 110520
ttacaggtat gcgccaccac gccccggata attttttgtat tttttagtaga gacggggtttt 110580 cttcatgttg gccaatctgg tcacgaactc ctgacctcag atgatctgcc cacggaggcc 110640
tcccaaattg ctgggattac aggcctgagc taccgcgccc ggccccaact gttcaatata 110700
tgtttgttta atgagtagaa atgagcttct tgagtatgga agtttctctt tttatttcaa 110760 cagtttttgga atacaggtgg attttttggta acatggataa gtcctttagc ggtaacttct 110820 gagatttttag tgcacccatc acctgagcag tgtaccctgt accaatacgt agtaatttat 110880
cccctcccca gtccccaaag tccatttttat cattcttatg cctttgaacc cacatagctt 110940
agctcccact tataagtgag aacataaaat atttggtttc ccattcctga gttacttcac 111000
ttagaataat ggcctccagc tccttccaag ttgctgcaaa aggcattatt tcgttcctttt 111060 ttatggctga gtagtattcc atggtgtata tacccacatt tgctctatcc actcattggt 111120
```

-continued

```
tgatggacac ttaggttggt tccatctctt tgcaattgcg aattgtgctg ctatgaacat 111180
gtatgtctag cttgctttt tccccctcaa cactgtatcc ccagagacta acacagtgcc 111240 ccgcacccg ttaaagaacc aaaaaatatt tgttggatga ataaaggagt atatcaagag 111300
caatctttca attatggaga gggtcgtgat gtgtattta atgaaagcca actatcttct 111360
ctaatatttg aaaaaacaat gtttaaaagg cttctatttg tacaccttt cacattttag 111420 ctggcagagt tcaggacttg atggaaacat aacgaagggc tcagaatgta ctcatcgcag 111480
actgagccca tatggtcaca gtggggagag cacgctgcac tcaagatgct agcaagcctg 111540
cagcaggcgg cccagcgaga cacggtcccc cgcccggcca ccaggcgccc gcgcacgcgc 111600
acagccgcgc tcagtccgcg agggccgggt cgagggaggc ggggctcccg gggtgcgcgt 111660
gcgcggcggc ctgagcggcg ggcccctccc ttagcggggg cgcgcggcgc tgaggaccgc 111720
acggaaacgg ggaagtcagg tggccgctgc cgccgccgcc gccgcggttt gtcgccagaa 111780
ggaagatggc ggatctggag gagcagttgt ctgatgaaga gaaggtaaga gtcgcggggg 111840
cgacggcgcg ggctgtcagg agccggctca gcccgggcgg gtgggccgga gtctggtcgc 111900
gggggaaggg cattggcccg cagctggcct tgccctcggc tgcccttcct cccccatcct 111960
tactgcgccc agtgcctgcc cctgtccgtc acccgaggcc ccgcgcgggg gcaggtctct 112020
gccaggcctg ctcgctccgc tccttgtagg tgtgtactcc gaaaatagga agcgggagcc 112080
gggcgacggc gggcggggcg cgggcgcggg ggagggcggc ggctgcccag gaccctctcc 112140
tgctgtcggg ccgcgggggcc tccgccgggg ccggggaccg gggaccaggg acgcaaaggg 112200
gtttgcgtcc gtgcctggga gcggcccaag ggcagtgccc agcgcggcgg cctggcctgt 112260
gagtgtagcg gcgggtgagg ggaagggaaa aatcgcttag gaagcagacc ttcacttctc 112320
ccttctactt cccctcctca aagcaaaatg cttccttttc tgatcctcta cggtttatcc 112380
ttttttttcc cttttcccat ggaggcatct ctccctcctt ctctctttcc tttcgtggct 112440
ctagcagtaa gcttgcagct cccatgttcc ccaggaggca gcggagttgc tcacaaaaag 112500 acgacccct ccccatagtt gttttctgcc cacgttggca gcagccccc ccggggggtcg 112560 atttggtggc acctcacttt cctgctagga cttcttccga agaggggaaa atgtgcaact 112620
ccttttactg tatattagat gctgtgacag caatggaacc agatgaacga cttaagttct 112680
cagatattta aaacgagtaa tggaataatt cattgaactg ctgctctctt aattcgcccc 112740
tttcgtttgg cttttgggaa cgtcccattc cgagggtggt ggggtagggg agaaccctgc 112800
taattttgac tgtttctcgg aaaggaccct tagaagtaac tgacagaaca taggaatgag 112860
ttagttgcag ggttggaaat gtccactctt cgttaaagag tgcttcattt ttaaatttca 112920
aagccagtga aggaaaatac aggtacattt aggtatgttg tggtgtttaa gaaatcttca 112980
tgtaagtctg aggatatttt catttaggac cctctgctct agatgttttt atatgctgtg 113040
ttcttgcacc gaaatagaag gttctgtccc attcccaatg tgaatggtca gaagtcagcc 113100
tcatctttat tttcggaaat cttttttct cttgtgttct tcggtgaaag tgataataca 113160 acaacaaat ggggggcgagc aacgtctcca tagcccacag acccagtagg cagatccccg 113220
tatccacaaa agttgctgta cagtattcaa tgtataatct tgataaataa tcctatttta 113280
tttaggtgac tgaaagtgta caggagtgca caaacatatt taaaattgag gcgtgctaaa 113340
aagcttaaaa agagattgtc gtgtttttat tctaccattc ttaagtgatg attagtagct 113400
caagtggcta gaaatctagc tgaagagaga ctactcggtg tgggagttaa tatagacctg 113460
```

-continued

```
ccatgtgttg taaaggccta aaataaaaaa gtttttaaa aatgagataa caagatgcct 113520
tattatctgg cactctcagg gcactaagct tcataaagag gaatgaggag gttgtgtgtc 113580
ttaaagcctg tgccgcctag tagcaaaaat gttttatggt taaatgaatg aaaattctaa 113640 tttgatttt gatgttttgt aagaatatta tgtagatatt ttacatataa attttatcac 113700
tatatttact aatttaaaaa ctgacaaaac ctttaggtta aattcaagta accagtaaag 113760
tgaaatttta acgttcttgt cacttgagat atctaaaggt tattttcatt ttggggagga 113820
ggatgtgtcc agtatgggat cagaaaacag agaggactta aaagtgatat tttaatatta 113880
ctcgttctac tgccttattg gtaattttca aaaataagct cttaagctgg gcacggtggt 113940
ttgcacctgt aatgccaact actctggatg ccaaggtgtg gaggatcgct tgagcccagg 114000
agttgtagac cagcctggta acatagcgag acctcatctc taaaaaaaaa tattaagttt 114060
tgaatacttt taagtttttg aaatttccat tctagattgc aaatttaagg aagagaagct 114120
gttaagatgt gtctagtacc atactttata tatgcttggc tcagttagat acattcatta 114180
cttaatttgt tgttgtaaga ggtagttcta ttaccatttc acagatgagt agagtgaggt 114240
tcaaaagctt taagtagttc acccaaggac ggtcaagatg aaggtagtat ttaaagtttg 114300
tcttagtcca acgttgatgt tcttgtgaca ttatgcgctc tcttctttt tttttttttt 114360 tttttttttt tttgatacag agtcccactc tgtcacgcag gctggagtgc agtggtgcaa 114420
tcttggctca ctgcaacctc tgcctccggg gctgaagcga ttcttctgcc tcagcctccc 114480
gagtagctgg ataacaggc acatgccacc atgcccagct aattttttgta tttttagtag 114540 agacggggtt tcgctatgtt gcccaggctg gtcttgaact cctgacctca ggtgatccac 114600
cccctcggcc tcccaaagtg ctgggattac aggcgtgagc caccatgccc agcagacatt 114660
atgctttctt aaacaaaatt gataagaacc tcttctggtt ttgtctcttc atttttaatt 114720
tgttgacagc ttattttgaa aaaggagaaa cgttgattct tccttagaca gggtctcact 114780
ctgtccaccc aggctggagt gcagtggtga tcatggctca ctgcagcctc aacttcctgg 114840
gctcaagcag tcctctcacc tcagtctccc caagtagctg ggagtacagg caggtgtgcc 114900
aggacaccca gcaaatttaa aaaaatttt tgtagagaca aggtctcacg atgttgtcca 114960
gggtggtctc acactcctgg ctcaaacgat cctcccactt gggcatccta aagtgctggg 115020
attacgggca tgagccatga ttcctagccc ttttttaaaa agtaatacca agcaaatagt 115080
gttaggttct aaatttttgt cttgatgatt ttagaataaa gcttattatt aacacattta 115140
aaggtgttat gttactgata ggaagcattt tagaaatcaa tctagaataa tagttttgtt 115200
ttttaaaatc atacacaatt gctttttgag gatactacta tgaagtttaa taaccttttc 115260
tcctttggcc actgggtgaa tgggaaataa atttagctga agaacacaat gaagttcttt 115320
aaagctctta acttgctata gtgtgtccca tagacttttt tttttttttt tttgagacgg 115380
agtctcgctc tttcacccag gcggtatctc ggctcactgc aagctccgcc tcctgggttc 115440
acgccattct cctgcctcag cctcccgagt agctgggact acaggcgctg ccaccgcgcc 115500
cggctaattt tttgtatttt tagtagagac gggtttcacc gtgttagcca ggatggtctc 115560
aatctcctga cctcgtgatc cacccgcctc ggcctcccaa agtgctggga ttacaggcgt 115620
gagccaccgt gcccggcctc ccatagactt ttttacatag ttacagaaac cctaggccaa 115680
aaacagttca ttttcattcc tgggtcagct gtattgtaca gtaaagcatt tttgtgaatt 115740
tgaaattgta tgaaattatg gtgtaaggct caattgaaaa gacccattcc gaaacctctc 115800
tctggataag agattcaagt tccagaagga atacacttag ttactgatgg gaaagatcgt 115860
```

-continued

```
ttttcttcct gtaacccttt acctcagtga ttacaataat ctgtcccata gcttcaactt 115920
ttaggtcttt gcagttgtct cccaggtaca tagctgtagc actaacttct ttcctgatta 115980
ctggtcagat ttttatctgc tattcatgtt cactggagat ggttaattag gtatgttcaa 116040
atggagcttg cctagaagta aatttataaa cgcccatctt ctttcctctc acacaaaggg 116100
ggtataatct actcttgata atttttctct ttatatcttt attcccatta ttccagtcat 116160
cctggttttt taatttcaga tttattctaa ctttttttgg ccctgtacct tacaatcaac 116220
tggtaaaagt tgtcacttcc atcgtcaaaa tatgtattat acaaataact tatttcttgc 116280
ttgaaaagtt aattcattta tattaatact tcgtttatta tctctgcatt gacctgattg 116340
ttaaataatg tttggtaaca aaatttcact gtacaaacag aatgcaactt gattatactt 116400
gttctgtgcc aacagttaag aagtaaagtc aagaaaaatg tctcatatct gttctttccc 116460
ttctgttata tttgccactg ttaggctttt actagaaaat ttctagacta atccctcctg 116520
tttcctgtat ctaagccatg ctttactttg tcatttctct actctcaaaa ttttagtgcc 116580
tggatcctcc attgccttta caaggaagcc aagttcttaa aatggtattc atggccttgt 116640
attccatttt aacctaaata gttctgacat tttcaatacg tattgttact taatcgtgct 116700
gtgaatttag agagacttca gagagctgca tactagtcca tttctctctc tttttttttt 116760 tttttgaga cagattctca ctctgtcacc caggctgcag tgcagtggca cgatctcggc 116820
tcactgcaac ctctgtctcc caggcccaag caattctcct gtcttagcct cctgagtagc 116880
tgggactaca ggcacacacc tgcgtcccta gctaattttt gtgtttttag tggagacagg 116940
gtttcgctat gttgcccagg ctggtctgga actcctgagc tcaggtgatc tgccagcttt 117000
ggcctcctaa agtgctggga ttacaggcgt gagcgaccac tcccagccac tggtccattt 117060
ctagcacctc agataaatta tttaatctct cagcctcagt ttgctctgaa atgtttagaa 117120
tgttgtagta agtaccttct tcattaagtt gttgtaagtc taaatgggct tggcatgtag 117180
taagcgcaca ataaatggta gttatttttc tctgctcatg acttttcatc tactttgagt 117240
gttggtactg ctcccaggtc tgtcccettt tttgaaacat gaaaatctca gtcatctctc 117300
aagatttagc ttagattaca cagctagttt agcctctcat ctgaactctt caagagatcg 117360
ttagtattaa atacaatttt gcgtaatagt tatttgctta ccgttttttc ccttttccat 117420
tggaattcct aagtggagac ataatgtcat ctttagcatc tgttgttact ctaccatgtg 117480
atgaatagga tggctgtacc tgcagtttat atacttctcc ctcagtgact ggcttcagaa 117540
attttgtgtg tgtaaaaaca atataagctg ccattgtatt tcataatatt aatgtaaaat 117600
tagaaatgtt tttattggct gggcgcggtg actcacacct gtaaccccag cactttggga 117660
ggctgaggca ggtggatcac ctgaggtccg gagtttgaga ccagcctggc caacatggtg 117720
aaaccctgtc tgtactaaaa gtacaaaaaa ttagctgggc gtggtgtcgt gcacctgtag 117780
tcccagctac tcgggaggcc gaggcaggag aatcgcttgg acccgggagg tggatgttgc 117840
agtgagcggt gatcgcacca ctgcattcca gcctgggcaa tagagcaaga ctccatctca 117900
aaaagtttaa aaaaaaattc ttattattga gaaggtaaac tcaagcaaaa agctattaat 117960
gtggacaata ttcattccta attctattct atagataaat tatgttattt caccaataaa 118020
gtgtaaaaac ttctgttgca gacaggaact tgatagcagc tgtagcatta gtggagtttt 118080
tcagactttg tacattaaag taaatttgta gtaaattttc agtgcatttg ggagccattt 118140
ttgcatgagt agttgaatag atagaataat tgcatgttag tgtgagaata cagatatgaa 118200
```

-continued

```
aacacttaga gcagagaatc taaaataatt tttaaggttg aaaagcagga tggcaaaact 118260
tggatctgtg gttccaagct atgacctaaa gcctaatcag tcacctgaag caaaaatttg 118320
ttaaagttat tatagcaata atttgttaaa taggagattc atgcatatca aagaaaatgg 118380
ggtctttgtc ttctgaaaac cactctctga caggttccat gaaaataccc atggctgttt 118440
caaaaaagaa tttcataaat tttattttga ggattaagta tagttttttgc attcttgctc 118500 ttatgacata tttacatgtt tcactatgca tctaatgact gagaactttt cttatacatt 118560
ctaattcgca gtgtttctac tggaaatgac ttttgaaatc catttacctc catcttcatt 118620
catttactaa atataccaca tttcactgat ttcagtactg atactttttt atattttaag 118680
atctctgaaa tcaggctgca ttgtacaatc aatgggttgt aatatttcat tggtagcgtt 118740
tttccttgtt tagtggtaca taaagttatg catcttatat tgattgtgaa tcaggatagg 118800
caaggatata gttcagtaac aaaactccta aaatctcagc acaagggtgt tgaatgtgga 118860
ggctttgtac tgcatctcat tcattccatg tatgtctagc gtgagttagc agagagccct 118920
gctcagggaa gtaatttagc gttccagttg gttagagagc ttccatctaa aactttcttc 118980
tcagtcactg cagtggtggg aaggaaatgg aatgaattgc acacttgttt ttttgtttttg 119040 ttttttttga gacggagtgt tactctgtca cctaggcttg agtgcagtgg cacaatctcg 119100
gctcactgca acctctgcct ccgggttcag gcaattctcc tgcctcagcc ttccgagtag 119160
ctggaaggag ctcacgtcac ttctgctcag atttcaatta gctaaagcaa gttacatgta 119220
taaacctaat ttcagaaagg tcagggcaga agaggagaat tggaatattt gtgaatagca 119280
gtaatgacag catagattaa gttttaaatt cactaaagtg tagcgatcac ctggaaggta 119340
gatacaatgc aaaactagat tcgaagagga attggacata tgtaatatac atactaaatt 119400
gggtctaaaa tttagaagat agaaaagcta cttctgccta ggggtatggt aaacatcagt 119460
tggggtcaag ctcataccag agagcacaac atagggaaaa ataacaggaa agtgggaaca 119520
agcaggcagt gagtttttgtg taaaaagaat tcagttaaat agttgagtgt ctactctata 119580
tttggtactt ttacaataag agatgcaaag gtgaattgtg ctgtttaaca gctgactgtc 119640 agggttttttc catctcatca atgttgacag tttgggccag atattgttgg gcaggtggac 119700
atgctgtgcg ttgtaggtgt ttagcaacat ccttagccca catgatatgc cactaccata 119760
acccaggctt accaatccag aatgtctcct ggtggacaga ttcacccctt gttgagaccc 119820
atgagtctag atagattaga gctggtaaga acagttgaga acctggctta agtggacttt 119880
aggacctggt ttaagttcgt cccacaagaa atggaggaaa aaaagatcgc caatagattt 119940
tagagttgga atcaagaaga cttgataaat gaatataggg gaaaggcgtg agtcagagaa 120000
aactgtgaac attaaagtct ggatgactgg gaattggtac cactagtaac aactggagaa 120060
cacaggaaag aggatacaca gctgggagga ataatggtga atttagtttt ggttgtacgg 120120
agtttgagat gctagtcatt gtctatgtga aaatgcctag cagatacgga gatagagaaa 120180
cagcttggaa aagaggtcag ctccagagat tatatagaga tttgagaatc ctctttttgt 120240
gggttaaagc gagatgggat aagcccttta ggacaaaaag cttagacatg ggaaagagga 120300
gagggcagga agcgtatact ttatactttg atttgaggaa taagaagtgg agagagacct 120360
aaaggtgagg agaaacccct gaggtcgaag tgttacctac tgatagctag cacagagtag 120420
gtgctgaggt cacagaatgt gacgagaatt tcaagaagga gcggtgctca gtgttgcaga 120480
gattaaggag tatgagattg aaaaaagcct ttggatttaa gagaaaggaa tgagaaacaa 120540
attataccta ctctatgcca gggactttaa catgtattct ctctattaat tgtcagaata 120600
```

-continued

```
accttgttat tatcttcatt gtacagacag gaaactggtg cagttaaggc tgtttaagtg 120660
gtggactagg gattagtggc cttcaagaga ataattttac tagtgtttgg agcaaggagt 120720
ggagagacat aagccagata actggagtct ataataaaaa gtatgtgtgt attttccctt 120780
ttccagaaac ggcatttcag tcttgtttgc cttgtaaact actcatcttt ggataaccag 120840
actcaaggac tttcttctct tcttttgtat cctgacatac ctctgctccc taagcaattt 120900
gtacttatct ttgttataac atttaccagt tttaataaat ttacctgttg tccttatttc 120960
ctgtgttctt cagggccagg ccttatgtct tcaccatctt tgtaattcca gtagagcgcc 121020
tagcctgtat taaatcagtg attttcaact ctggctgcac attagaatca actggagagt 121080
ttataaacaa aatgaacgca caggctcctc ttgtgggtga ggcctggagt gtctgtaatt 121140 ccttttgtt gttgttgttg ttgttgtttt aaagcttccc aggtgatctg aatgtgcaac 121200
taggattgag tctcactgta tcactgtatt aggggctcaa taaatgttga ctaaaggatg 121260
aggagtggag acagtaagta caaattattc ttgaaaaaaa ttggtagtga aacaaaagag 121320
aaaaatatgt attactactt tgtttttttcc tgctatttca ttttaagaat actttttttt 121380
tgtaagagaa cattctaggg tgtataaggg aaatgattca gaagggaaaa ggaaattgaa 121440
aacgtaagat aaagaatagt ttacataact tactttcttt tagttgatga taatgcctac 121500
tttggattca tgggtttctt catattttaa ataaatggta aaaacatatt taaagaagaa 121560
tcaatgttga gttctttaga tgacccagtt tcaggttaag tgctgtgggc cctgttttta 121620
attaccaatc aaaatgataa ttataaagga aaaaaattta gaggaaaact tattaaaaca 121680
aattaccact cttaagttta cccatattaa gataaattca cctgacacac agacatgtga 121740
tagtgatcac ttggtcataa actatttaaa tgtcataaag ttcaaaaaag tggtttttcc 121800
tccggtttta cctctaattc tcaaaagaca tagccatttt ttagagagct gtggaagaca 121860
acttcaaata attctttag ttgaagtgga aaagtgcata gtggctcctt taattttact 121920
accagtgtct aaagcagtga ccctttttgg tgttacattt tcttgagaat caagtaaaac 121980
ctataagtca tttctcaaga agactagaca cttcaaattt tacatctgaa gtcccttagg 122040
gcatgggtgc aatatctggt cacctttcag aatcacgtgg agagattttc taaaacatag 122100
atttctaggt ccccattctc tggagataga ttcactgggt ctggaataga gggtgggaat 122160 ctgtatttt tccaagcttt ccaggtgagt ctgactgccg ttcatatctg aaaaattcct 122220
accctaatgt ctccttcctt gatcatggcg gcccatacca tgtggaaatt atagggggctc 122280 taggtaggat tctcagataa aatactgatg cctcagtaaa tttgaattta agctaaacgg 122340
tgagtcattt ttagtatagc tatttcccat agtagtgtac ctttggactg ctggagagtg 122400
cagggtcctt tgcttctaaa tttaatggct ctagatggct gtttgggggt tttgtttttt 122460
gttgttgttt tttggtggtg tgtatgtgtg tacatgtatg tctgtgtgct accatgcaca 122520
tacattgtct gcttttttata ctttcatctc ctttaaacct tgcttaaggt ttaaaaaaat 122580 ttttttttaat ttttgttagt ttaccatttt tatagctgct ttggtgagga ctctatttcc 122640
tgttaaggaa ttgtttttctt cagacagttt taaaatctcc tggaactcaa gttttacctt 122700
agtgtttgaa aacatgttgc caaatgttca gcaaaggcac tagaacaatc tggagaattc 122760
atggacataa gcaggtgaag taacattaat tttgccatct attctgtaa attgtggtaa 122820 tgattgacaa cccacagtaa actctcacgt tgtaccctca tgttctagat ggtaattata 122880
aaactgaagt agcactacca attgcttctg acttccagta ataaacacat cttgaagagg 122940
```

-continued

```
tgacataggc tgagggaacc cagtcacttc cacctgtggt acttcaccat ggagcttgtc 123000
tttgcttgag aaaggtacat tctgtaccat taatgcaaag agtgcacacag tcaaggattg 123060 caaggcagaa agatacatgt gaagcttatg ttcatccagc cctccttccc tttgttctct 123120
ttccctgata agttttttcag tcttattcag caatgtaggt gtaagattgt acatttccaa 123180
attccatatt ccaagtatca taggccatta aaagtactag atgttttgca ctcactactt 123240
tttctgagat atcactcaag gccaaaggca acaattcaaa aacctgctga tacttgcctg 123300
gttcatcagg gtatcccata atgataccaa ggcttttgat cacagcttct catatcaaat 123360
atgctttacc ttccatttaa ggaggaccag ggagttagga acttcttgag gaaagtaagg 123420
caccactact ccacaggatt tagctacaag tagtgtcctt tttgggtctt tgtgactcac 123480
ctcttccatc actgtggtaa atgttcggct tctgcatgtg ttggtccgac atgatgtgtg 123540
aatgccgtaa caccagttag tatcacttgc cttggctctt tatctggcct cttgatcata 123600
ctagaaagaa tgtggagaag ctgattttc tttttagatt caagatgtag gcacgttgta 123660
tacaatctga gggcatcagt gtctctgtct ttgccagcag cacgtcaagt gcaatgtata 123720
gcaagcaata tccaagcatc agcagaaggt gtttttcact gcagtcagag acacttctga 123780
tcctaagcag catctcctga cacttgacaa aaagaaagta gtgcatagtg gaaagcagaa 123840
gacagtttcc tgtggggttt atcaaagtga actgtgcttt tacttgatgg agaaaacagc 123900
attctttcct ttctctccta agggaaggga ctggggaatt ctctctaaga ataatggaat 123960
taggctgggc acggtggctc atgcctgtaa tcccagcact ttgggaggcc aaggtgggtg 124020
gatcacttga ggtcagcagt tcgagatcat tctggccaac atggagaaac cccgtctcta 124080
ctaaaaatac aaaaattagc caggtatggt ggtgctcacc tgtaatccca gctacttggg 124140
aggctgaggt gggagaatca ctcaagccca ggaagtggag gttgcagtga gcggggatgg 124200
taccagtata ctccaagtct gggcaacaga gtgagacccc atccctcccc ccacaaaaaa 124260
agtggaatca acattatctg gttttgaaag atgaatatcc tttttttttt ttctttcctt 124320
gcctgaactg tttatgactg aaatctgttc attttcttca gagtcttgta gggattccaa 124380
agaaggttga atggaatcac aaactaccaa atggcaaagt gttcattttt gaggatggcc 124440
attttaggtc ttctaatttg ctccatcaaa gaacatttct cactatttaa taaattaatt 124500
ttatcttccc aatttgtgta ctaacaagga gttctctaca ggttgaggag tagaaacaag 124560
tgaaagaaga ttgcctaaaa ttgatataag agcttctaat tcattttctt tcactccact 124620
agcaatatcc ataaaatctt tcccagttac ttgatcactt ccaaagtctc agtagatttg 124680
caataaattg gagggttttt tttttttattt tttgtttttg agacagggtc ttgctctgtc 124740
agccaagctg gagtgtagtt tcacagtcat ggttcactgt atccttgacc tcccaggttc 124800
aagtgctcct cccatctcag cctcccaagt tgctgggacc acaggtgctc accatcatgc 124860
ctggctaatt tttttttttt taaatttttt gtagatacag gatctcacca tgttgaccag 124920
gctggactca agtgatcctc ccatcccagc ctcccaaagt gttgggattt tacaggtgta 124980
agccatggca cctggccaaa ttggacattt taaaatgttt atgttatccc gtaactcaaa 125040
gttctgatca ttattttcat ctgaggtatt tattgatgta aacttggatt cttcaataaa 125100
aattcagtta catagaagtt tagaggccgg gcgcggtggc tgatgcctgt aatcccagca 125160
ctttgggagg ccgaggcggg cggatcacga gatcaggaga tcgagaccat cctggctaac 125220
acagtgaaac cccgtctcta ctaaaaatac aaaaattagc ctggtgtggt ggcagcacct 125280
gtagtcccag ctactcagga ggctgagaca ggagaatggt gtgaacccag gaggcggagc 125340
```

```
ttgcagtgag cggagttcgc gccgctgcac tccagcctgg gtgacagaga gagactccat 125400
ctcaaaaaaa aaaaaaaaaa agtttagagc actcaagagg tttgactggc tcctgaattt 125460
cagggctcag tttctaatgt tttcgttcct atgaaggaac ttcattttct gcagcctttg 125520
tcaggttgct cagatcttcc ttagttaaaa cgttgttgta tgtcaaccac ttctctcctc 125580
ccttcacatc cattggctga taggaaacta gataatcaca cttgtaaatt tatgtctgag 125640
ataaaaataa tatgatctgt gtatcaccca tgacatgaac ccaaggaaag ttaaatagca 125700
acaattaaaa gtttgctgca aaaccaaaaa ttgaattata gaactcctat taccttttaa 125760
aatatctgtt tccattcatt tccaaaaatc tgaaattatc tgtaaacatt ttcccaatca 125820
aatctgtcta ggtagtgtgt aaaaattact tgaccttcac acacccagat acttttagtt 125880
atgctattgt tagttatgtt atttcataaa atgttatctc cttatttaca gttgataaat 125940
gaaatgatga ttttcaatac agtttcaaaa ctggattgaa attttgttag ttattagaaa 126000
ctagaaagtt tcagtgctga aaatacacaa cgggttgttt gtatttatca tctattttat 126060
tttccagttt gcattggctt ttctgggtct ttctacaact ttaattgtaa attttttcttt 126120 tatattttta tcatggcact caaactcaga aaacctgtta aggcaactac ataatgtgat 126180
ctaaaaatcc agttaacata ttgctatgga aaccaggaaa tagaaacagc actctaatca 126240
ttcctttaga caactatggc tctgtgtgtg tgtgtgtgtg tgtgtgtgtg tgtgtaaaac 126300
tttttaaatt cattaattta ttcatctttt attgaaagct gttactgaac ccaaaatctg 126360
taattgatct gtccataaat aggcccagtg ccttattacc agtaaattag tgtttttttaa 126420 tgagctatag tcattgataa attatgccat gccgtatcag gaaatctcca gtcaggccgc 126480
gttgtttatt tagcctgctg aggcctcttg gtatggtgtg aaggacacct gactgggctg 126540
aaagctaagt tctaactttg cccctcttac taaccagcta tgtgactctc ctgggaactt 126600
ttagggactc agtttctttta cctgcaaaat ggttcaatgc aagactttag taacgtaatg 126660
ggaactttcc ttttccataa aactgggaat caagaggtaa tctctttttga ggactgaaat 126720 cactcttatg taacctctgg ttacattatc atttccaagt gcctggcact tgggaaatga 126780
taactattct tactacattt ttctatgttt cattctgtag taaataagaa ctgaacctgc 126840
atagtaactg ttattttaac ccatgacttt caataacgaa gatatctatg tctcattatc 126900
tattgccatg attgaacaag ttggtatgag agccggaacg aactcaagtt ctaaccggca 126960
atgcccgttc cttagatcct attacctttg agtgttcatt tactcttgta ggtgccaatt 127020
tttatagcga aatacaaagt tatccaacac aattactcct aatagagttc accgaggccc 127080
caaaagctct ttttttaaaa tcatcataag atttcaacat tcaagaatta aacttttgtt 127140
ctgttgtgct tattcatcgc tatttgccca gttatttaat cagcctgctt ccggctatgg 127200
aaaaaaaaaa aagaaaaaaa gaaatggaag tctcctcagg gttaaactcc tctgttgttc 127260
ttccttgcag aaatttgagt tattatagta gaggataatc gttgcataat gaaatcattg 127320
ggacaattcg tccatccact tctacctccg cctctaacaa tgaactcctt gtttctgcgg 127380
tgcccaaatc tctctaaacc cggtgggcgc ggggcggtta gcggagacgt gggagaggcc 127440
gagagcaaag ctcgcgccct tcccggggtc agcgagcggg tgccaggagg gtgcgcgccc 127500
tgcctctgag cccggggtga cactcgcctc ccaagcgcca ggaggggggag actcggtccc 127560 gcttatctcc ggctgtgcta acttcagact gcctgagctg ggggaggaga gcgcgcagcc 127620
agggcgagaa aacttctcca cctagaaagt ttcaccttgt cgtgggcggg gcagaggcgg 127680
```

-continued

```
gaggaaacgc gaccccgcgg ggccaggcgc ggcgcggacg gcaggaaggg cgggggccga 127740
tttcctctgg gtggtgccag tccccacctc agcggtcctc ggaacccgcg gactagggga 127800
cggacagcac gcgaggcaga cagacacgtg ctggggcggg caggcgagcg cctcagtctg 127860
gtcgcctggc ggtgcctccg gccccaacgc gcccgggccg ccgcgggccg cgcgcgccga 127920
tgcccggctg agtcactggc agggcagcgc gcgtgtggga aggggcggag ggagtgcggc 127980
cggcgggcgg gcggggcgct gggctcagcc gggccgcagg tgacccggag gccctcgccg 128040
cccgcggcgc cccgagcgct ttgtgagcag atgcggagcc gagtggaggg cgcgagccag 128100
atgcggggcg acagctgact tgctgagagg aggcgggggag gcgcggagcg cgcgtgtggt 128160
ccttgcgccg ctgacttctc cactggttcc tgggcaccga aaggtaaaat tgcagcccct 128220
ttcagatcca gtacccaatc cctcgcctca ggggttctgc tttctttgtt ccctaagag 128280 acctgactgc tgttccaggg ggcaaaacca cgtaggtggg ctagagttta gggcttcgga 128340
aactgaagag acgtggccac ggcgaggacg aaactagaat ggggcttgtc tttttagggg 128400
gttgcttctg atggccacct gtatgactta ggagggagag gggcgctggg acagtgggtg 128460
atgtgtgact gttacggccc agcaagtttt aaagctggga tctgactcag cccttacaaa 128520
agggatccgg tcatcctcgt cccaccgtga tgcagccggc aaggtttgag ccgagctgtt 128580
tccttgttcc cagccttgct ttatctgtgt tatgttgggg tccttccaag gggcaggtgt 128640
ttctgtgaaa gtctgaattc atttctggca atcacgcggg gcttgtgatc catcaatttc 128700
catcgtacct tatctctttc tggggcttgt ggtggacatc tatcttatta ggtgaaatag 128760
attataacca gaggctgagc gatgtggcca gtcgtagtgc tgacccgata attaaagcac 128820
cagtgaaagt actttccctg actattgtca atgcagaatt tactccgaag tacggtttcc 128880
cattcatatc tttcatgttt taaaagagcc atttgctaat ttggcagttg gagagggctc 128940
caatggctca cgcatgaata gttgcccagt gtattttacc ttatcacagt tttatgttca 129000
aaggagccct cgggcagaat gaaatattgt caactctctt aggcaaaata atcaagatac 129060
tttaattgct atgttaagat ggtccatgaa tgtgagagga ttgtaagaac tgacgttgga 129120
ggcaatatag actatctgga ccctctcttg aatttttaaga agactgttca cattctgtag 129180
ctttgggtgg gggtttattc tgtcgctttc atcagccaga cacatgcaca ttgccatgca 129240
aatggattca gaaaaacatt atattccctt acagctaaac tattatagct gactaatgaa 129300
ttttttctgc atgaagatga tctgaaaatg atgtacatca tgtttctctg tgctacaggg 129360
acataaattg catttttatg taaacagtgt aagtggtgct tggattattt acaggtacat 129420
agctttcctt ccttgatcta agctaattga gctttgtttt gaacgtgtaa acttccataa 129480
tggaacataa gtgaggtact ttggttccta tcatttgcaa gtctgtggtg tattcaatgt 129540
tcattctttt tgaactgctg aataacagag ggaaaattta catcattcat aagaaatttt 129600
ggtagtacaa aaatgtgtct gatagcctat aaaatgtact gctgttttaa aaattctatt 129660
ccgttttcaa acttaatggt gtataagcta tagttattaa cttaaatata ttttgctttt 129720
aacatgatgg aatttgtggc atatagaaga cagtctgccg actactgctt tttcaaaatt 129780
gctttgttct tgatacatgg cagtaggggt ttacattaga tgtatactac atgctttcaa 129840
aattagttga tggagtttat cttcatgata aaaaatgtac cagattaatc atagcccgtc 129900
aatacgaaag ctcataacta atattttcac tacttttaaa cctataatag agaaaaatga 129960 cccctttgcta agcaagagaa atacccatat tttataaatt cctttttaaga ctatgtaagt 130020 atatgccttg cattaatctt gaaatcttta aaaaaaaatt gtcttaatga gggctagact 130080
```

-continued

```
aagaaataca tttcaaaaat caatttcctt agctgttttt aaaatagtgt ttgaagtagc 130140
attagtcata ttatccttct gcagatctac ataatagtct caaattaact tttttctcaaa 130200 tgtggtcatc tcaaaacaac gtgaataact cagaggagct aacatcctct aactggctta 130260
ttttctccaa gtggctgcac caaagacatg gcaacacccc catggtgagc acagttcctc 130320
acacattcag attacctccc atttctctgt cctcttcctc ctcaacccctt tcccttggtt 130380 tggtcagagc tgctttcaag gccttccgtg cccccatttc tccagcccag tttgctcgtt 130440
tcttctttag gcattaggct tagtgattct cgccagagcc atctacgctt tcttttccgt 130500
ggtctaaatc cctaagattt ccttggtctg ctgtgtttat tcataggata ctcaatttcc 130560
tcattgtgcc ctcttaaggg gagaaaatgt atgtagaaac tcaagtgtcc ggaagtgagc 130620
cttcttttcc tggctggtgt atgctgaaac tagtgttttt gacaccaagc ccttagggca 130680
gagtttcttc atgggttttg ctcagtgcaa aataaatagt cacttctcag taataaatga 130740
tagatacact gactaatgtt agttcagaat cactttgatg atgtgttctc aactgacact 130800
gagttgctgc tagatccaca tttgcctgac caaaaatagc taggacctat aggtagagta 130860
tcatatgtgc taggtactac agcattttct ttaaaagaaa gaaatggaat ctgcccttga 130920
gaagtttatg atctagatac acagacaaat atcacatatt aaatgaacac aaattcataa 130980
ttattaagag gacatcacat gagaaacgct ttcaaaatca tcctatttgc tatgaaataa 131040
tagaattttt ttttaaaaat caaagtttgg aacttaaaaa ccttaacatt ttcaagctgt 131100
ttctgcatac atcacctttc tgataccaaa acgaccttac aagataggca agtctgataa 131160
catcttaaca ttcttatgtt atagacaagg aaactgagct tgagactagc tccatgctat 131220
ttcaatagca ccataccacc tttcctcagc catcaactat tggaaacatt ttccatggag 131280
gcatcattag ggatgcttaa gatagtggta aatgatgaat ataacatatc tagtccctgg 131340 agttttgtc accttctctt tctccagttc tctctctctt tttttttta atttctttc 131400 ttttctttt ttctttctt tgtagtgaga cataccgaga aaaggtttca ttcatatgtg 131460
tggggcattc tgctcctgtt atcagattaa gagccgtgaa taattttgta atctatcctt 131520
ctatcagaaa gcccattctc agatatcttt tcagctgtgt taaacaggtt agtatattcc 131580
gcttgggatt tgtttcaata aaaacatcca gtaaaatctg actactttgc ttttcatggg 131640
acaaaatgaa aaaagtgctt ttataagctg taaaacttaa ttgagagaaa aaatcacgtg 131700
tggcatttgt agcaggaggt atgagctcag tgaaataaaa aagttaactt tgtaatcaca 131760
tacccaggta cacatatttc tctctgtgat tgcataaatg tgtgcaagta tgtttatgta 131820
ggttactccc attgatttta atttctataa taaattatgt agctataggg cccacaggcg 131880
attatataat gggcaataga atttgaaaat gtatctctcc taatataatt aaggatagca 131940
attatgaaat gtgcttagag aatcacaagt tatcgtgaaa gccaggttcc tgtactccaa 132000
gaatgtgaat gaggatttag tcattcattc aggacaattt tttgacaacc tacgaggcat 132060
agttctaaaa tctggcattt ccacagagta taaaacagat gaaaacctct aacctcatga 132120
cactctgttc tattgagttg gcaaacaata aagaaataca taactgaaat gtgttgtatg 132180
tcaggtgatg ataatagctt caaggtagaa taaaatggaa aagagaatag tgactgtcaa 132240
ggataagaga gagtggatgg tgattgaaaa actcaatagt gaggtcaggg aaggcttgtc 132300
ttcaaaggtg ggctttgggc tagaatctga aggagataag gaagtgagcc aggcgcatat 132360
gaggagcact tctcaggagt gctattctca tcttgttttt cctgaaattg tgcagttcac 132420
```

```
agcttgcaca actgtccata gactccctga ttttggaggg agatacctga atagtgcccc 132480 tgttttttgta gggaaatacc tggacagtgc ctgccatcat tagctaccat gttaaagatg 132540
aagatacagg agtggcccac atctcttggt ttatgagaca tggaagaaga agacccagag 132600
tgttgttttg ttttttttttt ttgttttttgt tttgttttgt tttgttttgc atccgcctgg 132660
tcccatccca tactccatcc tctatcagag atattgctcc attcagacaa ttttccttct 132720
tattttccac actgtgagcc tgtcacagtg ggatttgttg agaaggatac catggctttt 132780
ttcactgatc ccttccatag tataaatcta aagacagcaa gaggcagttg ctgatggtgt 132840
gcagcttctg tctgctatgc acttctttct ttcccctcgc tctccttcct tttccttttcc 132900 agtattaagt cactgcattg gattttcttc ctctttttctt cctttttccct tattcccta 132960 tttatatcct gtatcaagat ttgcaaacag gtaacttaaa tgaggaaact aaccatttca 133020
ctagggattg acaaactgct taggaaaagc agaggggcag tcactgcttg gcgtgattag 133080
agctgttgtg aggctcagtg tatggcatgg gcccatgtgg tagtatcttt cagattttca 133140
agagaagcta ggactctccc aattttaaaa tgttgactca gtgtctttaa aacaccatac 133200
agcttacagt ggcagaaagt ctgcaagcca gattgggctc ctgatggtcc aattgcagca 133260
gcatgcatgg cccgagagcc ccaggactgc ttctacaaaa tattttattt tctaaaattc 133320
tcagaaaatt aactaaacaa attttttaaa accaatattt tatgtcagtt cctattggca 133380
cgtggttatt tttctaaact catcagccca catactttac atcaaactat gtacatttct 133440
aaactaaagg gtaatctagt tatttcattc ttaaactgaa gtagtagttt tctgaaacct 133500
gaatccatca tggctttatg catcaatttc atttccaagt tctctgattc aggataaact 133560
ccccctttgg aatattgtct ttctctctct ctctctctct gtctctgtct ctggaaatga 133620
ctgaacttca cccgttgtta ttacctgcca ttgaaattca aaacatgcac tgccctcctg 133680
gtttccagtg ccctttaaaa gcaatcagat cagtgttaaa atctattttt ccaaaggaat 133740
aaaagctcac aggttgtgca ctaatttgtt tcctttaatc ctaaaatctc agtgaaatgc 133800
ccaagctagc agccctccag aaggccactg tgttagaaag ggagattatg tactgtattt 133860
cttcctacta tttttaaatgc aaatataata atatatcatg aaacagtgca catacagtat 133920
acatattaag atcagtggtc tattcctgtt ttgaaatggt ctcctactcc ttaatagttg 133980
gaattctgag gcagcaccta gactctcagg tccaatttga aaatgtatgt ttttttttaaa 134040 aaagaatgac ttggggaata actgtttgat aagaccgtgg aagatttcta attttttaata 134100 ttttattaaa aatgtaaaga aagacattca aagctgagac ctttgaaata atatggtctt 134160
tgcaagtcag agaaaaagag aagtggtaaa tttattagag ataggttgcc tcctttgagg 134220
cctaatcatg tgggaaagga aaacccagcc aaggtttggg tccataagac aattcaacct 134280
agctttaaaa ataggttttg gctttgcttg ggaccagagt gtatctagac cagcatttta 134340
gctattaaat tttaaaccta ggggtctttt aagggaaatt taatccatgt gtctttgatt 134400
cactaaatct taaatcatta ctcacaaact gtatgtccct ctaagctctt tgatgtccaa 134460
gagatctcta aaattgtgta aggccttttt gttccagaaa aaaataggaa gttggttttt 134520
gctaagcgtc agtaaacagc atcctcaaaa atctgattag gtctaaaatc ttgcaaccat 134580
gacagtatgg atgtttgaat gatgcaatgt gaaaatttta agcacttttt aaagtccttg 134640
tttaccagta atactcagtt gtaatcctta ctaaccccaa ggaaattatt ttgacacatt 134700
tcctctctgt tttgtaatat aaatacaaag cccaaatatt tattattttta ttctggcaca 134760 tagtaggtac tcagtaagta ttttgtagag tgttgaatga ctctttcttc tgcccagaaa 134820
```

-continued

```
cttctagcta atgtcagttc ttctattcaa tattgatatc catctgtcat accttggaat 134880
aagatctatt ctaagtcagt gaccttgttc gacaaatttt taaaataagc catctaacta 134940
aatatatgac atttattgaa attcattttg caccatgaag caactgcctt gcaaagagtg 135000
ctgaaaatag gaaggaattt ctagactaat ttgattaaat attcagttgt tgccatatgc 135060
tttctgaaaa ttgattttcc ccctttact attcctgtca tccttcctcc caccttgaca 135120
tgcttactga ttgaaagcta tgcacagaaa aagggcaggt cgcttgtatg tataagcaag 135180
agcagcaagt ccaaacaggc ttagaaaacg taatgctata atcacgagtt gtcataatat 135240
aggagagggg agagaggaat actcagcaat aagagtggtg ttgggtattg ctccaaatta 135300
catggatgac acatctttga actctattgt gtcgggggaa aacaccttct tgctgtagtt 135360
agatttcctg tttgtgaatg tgtattttct ggtaaccaga cttcctatat gaatttgaca 135420
tagctttaag tgcatttcaa atgacatgat taaagaatgg ctgctttgga gacagcagct 135480
ccttctctct taaagaaata aactatcatg ctaaaatata ggcattgaga tctttcttga 135540
taccatattg tgaatttcta atggctcatc acatttttat cctcagaaaa cctttcctgg 135600
tgaaaagcat gctgttttag tatcacattt ggggtgatgg aattggcaat ttcttatatc 135660
ttgagggggc ggggggggtaa aaggaaaatt gtgttaatag ggtcttaaaa tagagattct 135720
cttaggttaa cctgaagatt tactaaatac attatcatta cagcttgttt tgacatttaa 135780
ttgtagatgg cactgtatca gcactgactt atttatacag ctttgtttag acatgcctaa 135840
tttttatttc attggtggaa ccaaaccatc agtaataaat catatatcag tgtttttgta 135900
cacattcgta tttacatgac ttttaaaatt ccaatgtaaa ggtctcacaa cttgaaaaat 135960
gaatgaatgc ctgagtattt gaacagttgg gaaaatgtag ttcaatttaa gaaagatttt 136020
ttatgacaat tcttatgcca tatatagaaa atagataata aaggagaagg cctggaggtt 136080
tagatgggat attggatcaa tgagcaaagg aaggggaaag gtgggcggga tatgctgaag 136140
ggtcatgggc ttgagtgcac cctaagtcat aaagagggtg tcccattaag aatcaggctg 136200
cctgaattct aagtaggaaa gaggcaggtc aaaatggtgt ataggccagg cacagtggct 136260
cacgcttgta atccagcact ttaggaggcc aaggtggggtg gatggcttga gctcaggagt 136320
ttgagaccag cctgggcaac atagcaaaac cccctctta aaaaaattac aaaaagtagc 136380
tggacatggt ggcgcacact tgcagtccca gctactcagg aggctgaggt gggaggatca 136440
cctgagcctg ggaggccaag gctgtagtga gccgagatca taccactgca ctccagcatg 136500
ggtgacaaag agagaccctg tctcagaaaa agtgggggag ggagggtatg gaataaagta 136560
aagctcatgg gaaaatggta cctttaccat tttcccacct tgggaaatgg tgggaaaatt 136620
tagacattgc tttacaaagt ctaaatttct gccaacttgt gttacatgtg gtttgattct 136680
ggagaaagat agactatcat ctatccagtc ctaaattggg cctcttagtc tgtcctcccc 136740
tcagttacca ggaagaatag caggaatatg tcacagaagc agagaaagct tttattctga 136800
gtgtcagagg catgttctaa gcactctgtt atctactccc aggcactcta aatgaaattc 136860
cattttctct gaggaaatca aaatataaaa agaaaactca ggcaaattta taaaggtttt 136920
acaccatttt catgactgaa atattctagc atatctagct cattataatc tataaattcc 136980
tgttgggacc aaaagttatg gccctaaaac ctgttatctg taatccttt ccactgggat 137040 attgtctctg gggatatata ttagctttcc ttgaggatac taccttgaaa ccatttcttt 137100
ggtccttgac tatacaaagt tcatactagc atggatgtag gaattgtatt tttctattct 137160
```

-continued

```
aaatacgaat ttagacagtg atataaagat tcaaggaaag cttctatcaa ggcctgcctt 137220
cactacttgt cttttggctc ctctgagggt cttaggtgag ccactttcat ctgattctgc 137280
cctcacttca ggcagaattc atatggctcc agccaatggc tacactgtcc aaagtgagac 137340
tgtggtctca caaccatctg gttaatacaa gacagcaagc caatatgatc acttaggacc 137400
taggcaaacc tttgggctta aaatattacc ttagctattg ttgttttttaa tgagtatcaa 137460 atagtatgat atttgtaatt tgtattatgt aaagaagtaa ccaaagcaga gattgttgac 137520
aaaaaaaaaa acttcctcct aacataaatg aatatgcatt ttggactttt caaaaattcc 137580
ctttctgtct tgtcaaaatt aagatatttc taaattttat ttcggtctca ctaacacata 137640
cttggattat tgttcattga aatctgtacg tcaaggccca gtgattttaa acattctttt 137700
ggtcttcaaa gaacttacca aaaaaaattg ttctttaaat caccagaaaa gtgcagataa 137760
aatccagaca gtttcattaa tgacaatgaa aggtgacagc ccttgaatct atgtcataag 137820
ttgattaatt actttccaaa cattattaaa gatattagac gaataactta gactggtatc 137880
caggatcaag gttccttcat aatccctaaa tgggttttaa ttttcagagt tagatgatca 137940
ttatatgtga tttatttctt taacatcttt agactgttgg ctttattgaa aagagaggag 138000
agtatctgtt tcaatgtgtt ttcttttccc tgaagttatt ccttgcagaa ttcaataaaa 138060
ccggttttga aataaaaata attaaatgct ggcattttct gttaataagg gcccatagac 138120
ctgatgaatt atataaacat tacaaggaat ttaccactga gttcataatt atgtaaccat 138180
ttaatgccca aacctgccta ctgacagtga agacgttcaa tgagaatgga cattgtgcat 138240
taggataagg atgacctgga gtgaactttc attcttgttt tggttctttc ccattttgcc 138300
caattcatag cacctgattc tcttaaccag caagtctgtt tgcatgtctc cagtccaatt 138360
tttcgccatg cccactgcag tgattccaaa ctctcaccat ttcttaagct cttgcatctt 138420
ttgggctctc cttattctca gtataagatc tttccttata gtttagagag taaacacaag 138480
cccagttgtt tccatgtcac ccattattac ctctttctgt ctcaaaggat gaaacagtct 138540
tttctaccta agtcttgacc ctgttgttcc ccacacctgt gagcacctcc tccctctatc 138600
ctacccacct tacaactctt cccgtgttta aaatctccct caccattttt cttttttaaa 138660
aaaattatat tttaggctca gtggtacatg cgcagatttg ttacataggt aaactcgtgc 138720
cacagggttt atttcatcac ccaggtatta agcctagtac ccaatagtta tctttttctgc 138780 tcctctccct cctctgcccc ctcaagtaga ccccaatgtc tgttgttcct ttctttgtgt 138840
tcataggttc tcatcgttta gctcccactt ataagtgaga acatgcagta tttggttttc 138900
tgttcctttg ttagtttgct aaggataaca gcctccaatt ccatccatgt ttctgcaaaa 138960
gacagaatct cattcttttt tatgtctgca tagtattcca tggcttctct atttttcatt 139020
cacctcttac tcaacttact gattcttcta gaaagaaata aaacacacac atcaggcatc 139080
ctgataggat cttgaataca caatttcctt aagtagtcac tcctgttttc attttagcct 139140
ttaaataatg aattcttgaa aataaatgtc taactcagtt tctctacttt cttcattccc 139200
attcattctt aagtcattca actcaagcag tctgtaccac atgcccaaga aagtgtcctc 139260
attctaatca ccagtgccct cctcatggcc agatctgatg gacactggtt tttatccctt 139320
ttgacccgtc tgtagaattt gacaccatac attttatttc tcccttctcg aaagttctcc 139380
ttagcttatc tctccacatt ttctttgcct acaattgttc tttttaccct ttaaaacata 139440
aaggttagat tctagtcttc tgtaaggctc catctgaatt cctcctttct acttacaaaa 139500
cacattcaca agtgatctca cttcagtgac ttccaataca ccgatggacg agtggttcac 139560
```

```
aaaccgctct ctctcacttc ctcttttctc tagaccacca ctttcatgtt gtcagctacc 139620
ttacagactc caccacttag atgaccagaa gctacatcag ggttattaac tcaactaatt 139680
acttttaccc tcaaagtctc ctctccctat tttccttacc ttggtttatg atacccagat 139740
agacaatttt ttagccattc ttggctttc agtctcctct acaatcaaaa tccatattga 139800
ataattccca cataattttt ctcactttaa tatgtgtata atctagtcct tcctttcttt 139860
ccataatgct agaaactttg ttcaggaaca ttcttttgta tattgattga ttctgttgtc 139920
cattcattca ataaatgctt actaagtgcc atgtaatgac actatgctaa gggctaaaag 139980
tggagcttac actctgatgg gagacacaga taaataagtt actatatagt gtggtaaagg 140040
ctagataagg ggaagatagg tttgatgttt gagcacatag gagagttcct aattccttac 140100
tagaaggtaa gagatgcatc agagaaggct tcccagaact gttccctaag atgaggcttg 140160
aagagagagg acaacttatc catgtgaagt tgagggcaag aatatccata aagagggatc 140220
cacatgtgct gaaacccaga gtggctgagc acatggcttg cttcaagaac tggaagaggg 140280
cagagtggcc agagcctaga tttctaatgg tgtgatggca agaggcaaga ctggagagtg 140340
gggcagaaaa aaatggtatg tggtttgtaa gctctgccaa ggggttgaca ttttttttca 140400
gcaaagaagt gacatagtca aattgtcagt ttagaaagat atctctggta tgctaggggc 140460
agatgatcag ggtgagaatg gagaggaaga ccagcgagga agctgttgta gtaatccagg 140520
tatgaagtga cactgccctg accatgggca tggaagccaa taaggagatg gacatgttta 140580
aaatatttgt aggtgggtgt caaagatgat gtcctagaaa tatgggacat gttcagcact 140640
gaggtaggat acagagaggg agaccaggtt ttgtgggagt agatggagat aacagaagga 140700
tatccaactg ctccttcttg gtctcttgtc ccatctgtct ttgtctcctg acctattagc 140760
tttggtggcg ccatcactca gtcctcctct cttcattctc tacagtccct ctcctcggag 140820
atcccatcca ctctcatggc ttttcatgac gtctacatgc tgacaacttc ttaatttaaa 140880
tctctagccc agacctttct ccttaacccc gggactcaaa catccaactg catgcccggc 140940
atctccactt agatgcctaa aaaatgtatg tcaggctgag tgcagtggct catgcctgta 141000
atcccagcac tttgggaggc tgaggcgggt ggatagtgag gcgggtggtg gtcaggagtt 141060
caagaccagc ctggccaaca tggtgaaacc ccgtctctac taaaaataca aaatttagcc 141120
aggtgtggtg atgtgtgcct gtaatcccaa ctactcagga ggctgaggca ggagaatcgc 141180
ttgaacttgg gaggcggagg ttgcagttag ccaacaccac atcactgcac tccagcctgg 141240
gcaacagagc aagactccat gtcaaaaaaa taaaaataaa aaaacctcca ttgtgggcaa 141300
aactacattc ctggtctcct catatcctac aaacatgctt caccaaccag agtctgcatg 141360
tcggtaactg gcaaagccat tctctctgtt aaaaaagtca aaatccttgg catattctcc 141420 ttttttctc acatgcctca gatctgactc catcagtaaa tccggatgga gttcgatctg 141480
aggcatgtga caaaatagct ctgtcttcaa aatagaacca gaattcggcc acatctcccc 141540
actctcccct tccttcctgg cccaggccac cagggtcccc ctcctggaac accactggag 141600
cctcccagct ggcctcacca ctccaccttt gccctgaact gcccccccagc cactagcagt 141660 cttctctccc atatgatcga ggtgaataca ttccaacata atcccccctt gttcaacacc 141720
ctgcaatgac tccccatttc actccaataa aaacctgaat ctcccagggg cctacaaggc 141780
cttacatgct ctgcttcttt gtccttttga tctcagctcc cggtcaacaa agtccaggct 141840
tactggcccc cttgctgtgc ttcagacaca ccaggcacat ttagttcttc cttcttgcct 141900
```

-continued

```
ctgcccagaa atctctttc ccatctcaga catctgggtc cacaaaagcc accttcccaa 141960
tttccgagct acaaacctat ccccatacct ctcctccagg cagttctgat gccccagccc 142020 tacttttgt ttttccctgt aacacacatc aacttctgaa acactacatc atcagcttgt 142080
tatgggtatt aattgttgtc cccagctaaa aagtaagttc cacaagagca ggggtgttgg 142140
gttttgttta ctgatgtatc ccaagcatct gatgcatagt aggaccccag taaatacttg 142200
tcaaatttgg tcttaaatag ctgttgcata gacaaaagtg atattggaga gatggatttc 142260
gggattctct ggagatcctt caacaaaaca tatcagactt tctttaatgt ggccacagcc 142320
taatcttata cctttttcca ctgtcaaccc agcccacctg gcctctatgc caattgcagc 142380
ttcctggaca accctgcatc ttctccccag gtgcccgtgt gtgagtccac tccacccaaa 142440
gtgtctgtcc cctacctcag ctgcacctga gcagctccaa cttatcctgc aagacacagc 142500
tcaagtagta tcccctctga aatactcctt ggccccgctt tctgtctgca tagttagctc 142560
ttctcccccg tgctgctcca ctgacatgcg cacacctta cagcacagcc tgggcgtgtt 142620
gcaggtggaa ggtggagatt cccagtcaag gggcaacacc tgtatggttg gaaaagttgt 142680
ttgttttaat ttcttgccct ctcttctctc ttctatttct ttcctctccc ataaatacac 142740
ataccgccta tatacacaca acctgccctg aattgttttc cttgaattga tgagttacgt 142800
aaatgcaatc ctaagcacag ttgtttcag gttgtcctaa ccttttgctt tattgatttt 142860
tcaaggatcc agagtgttta ctgagtttca gaaattggat tctgtactta tttttctgta 142920
ctatcctagt tttatgagaa tctatttgct caggattctc tattcttta aaagtgttta 142980 agattttgt aaacagtttt gtttggttct ttattttctg gtgacatatt gatctcaaca 143040
taatgctatt catatacttt taattcttct tccaacactg ttaggattgc attatgttca 143100
cccaaggaat ccacatctgt acaaaatgtg gccaggtttg gctattcctt cacattcaca 143160
gtattctcat gatttctaac aattcttgtc tactttgcct aaataagaaa atgtcatata 143220
ctgacaattt tgatcgtgaa aaagagacct tagttcatac cagtgtcaga gtctacttgc 143280
aaacattgat ttccaagaaa atttctcagg tgtgagcaaa taagcaaaat aaattcagac 143340
ctaagagaaa atagcactac aaggaacgcc cagctcattc aaacgctctg cattttgaga 143400
ctagaggggg cttggccttt ggcaccctca cacctctccc tttgtctctc tgtccctggg 143460
tgctgatttc tcttcttttg tgtgacagcc actgtgaaaa gaatggggtt cactcaccac 143520
ctgcattcct ccacagccat ttgatatctg ctttcgataa cagcagagga aactgatcag 143580
tcatataaat ccaatcctga gcatagttcc tcgtttggaa ttgtaccatg ctttatgccg 143640
aggacatttt caaacacgga gggaggggat gtctgattca ttcgtgagta atgtaccagc 143700
ttcctctcca acttgtctcc cttcagtggt tcacattctg actattcagt cggtttatcc 143760
tttccaaacc cagtatttga atgcaactgg caaaggttga ttgcctcttt ttttttttaa 143820
tatatagact tggaaagatg tttctcaaat gtgatttgcg gatttatgtt attcagtctt 143880
cctggattaa ttgaacaaaa actggtaaca ctgctacaca gtctgaatca caaaattatg 143940
tccatccatt tggctgaaaa atacgaaaac aaatacttgt ataagttttc atgcatttta 144000
gcactttctt tacattgggg aagttcaacc ttcacacttt caagggcaat gaaacatttt 144060
tgtctgacct acaatttatt aatgggacaa aagcccatct gtcaatcagg gctctgagag 144120
ttcaatgtat tttctgaaca atatttttta cattatgtac aatggtaaaa acaaatgtcc 144180
atttattctt ctttccaaga agttgagtac tttcaaccat tcttaaaagg acaaagatgt 144240
ttgctgacag aatatgaatt tataaaggat aatcttgagg atataatggc attctattct 144300
```

-continued

```
ttttatcttt actcttgcca tatcagagtt ggataatagt ctcaatcata tgttacaact 144360
agaaaatgca caattggctt tttcttatgc taacaggcag ccattttcaa cttttttaaat 144420 gattatagga ctaagagggg atgcaaaaac agataagaat ctgaataaaa gcactatctg 144480
tcaaagaaac aacatttgtg taataatcaa gaaaccgttt agagcacccc ctggaaacat 144540
taattataac acatgcaaat cattcctgta caaagcttaa cttgtttatc tcctatagcc 144600
acctgtattt gaattttta ataagctcat ttattataaa taaagcatgt aaatcaatct 144660
gggaatacct tttctgtttc agaaatttca tgtaaatgac aggctgccac atacagtaca 144720
actatagagg ggaaaaagtt tctttactcc ctttcatata gttatacctt catatgcacac 144780 ttaaaaccac ctgccaggaa cttttaaaac atgtttaga tgcacagaag caaacccaaa 144840
tgaaaaaaat gctatgcagt tttgcaatac atatatacca cagaaagctt taaaaacatt 144900
ctaccccaac agataaatag atttggccca aatctttta atgtgagttt tgtgggtaaa 144960
aaagattatt gttcccttat ttttccccat ttgctgacga ctaggattgt catataaaat 145020
acattcctgg acatgcttat actaaacaaa ttatccactg tttatctgaa attcaaattt 145080
aactcagcat cctatatctt tacttgctaa atctcagttg ggatatgggc ttactctttt 145140
tttttttttt tttttttttt ttgagacaga gtctggctct gtcatccagg ctggagtgca 145200
atggtgtgat cacggttcac tgcagcctca acctccctag ctcaagtgat tctcccacct 145260
cagcttccac agtagctggg actataggca catgccacca tgcctggcta attttttatt 145320
ttttgtagag atggggtttg cccaggctgg tctcaaactc ctgaactcaa gcaatcgtct 145380
ggcctcagcc tcctgaagtg ctgggattgc tgcgtgagtc acagtgcctg gcctgagcta 145440
actctttttt aaagagttaa aatactggtt cctatttgtt ttacttctct agtatgggag 145500
gctgttactg tggcttctgt cttgggggca attttcgaag ggcttcaaga acttgaaccg 145560
aggttagagg aaaaccacaa gatggctaaa gggtgggaaa agaagaaata acactattta 145620
aactttagat gagaggacta aagtgatgaa acagtcacca ggtatttgga gtggtctcac 145680
ccaagggact gtgccaactt cctcattttt tatgagggca ggcaaaaact ggccaaaaca 145740
caagttagga taataagcat agtagctatt attaaatgct agggtgtgct gcataactga 145800
aggacagtgt ttctcacagt ttatctccaa ctctcatggc caacccatga gatgtatatc 145860
attatcccca cgttttgaat ataagaaact gacactcaaa tcagaaggca tgtcagtgaa 145920
aaaggccata ttcacatccc atctaagtct gtctgacact aaagcccaca ctctctccac 145980
tacactccac cttgtctcca gaatgttttg ggctgtttaa atgtgattat accaaagagc 146040
agttgaatgc actgaaaaat tctgaagatt cctcctgtcc cttcgattca ctgttggaaa 146100
ccattgtcaa ggtagtgtct ggctacgata gaagggattt ttgacatggc ctattgtttt 146160
atctttttaa agtaaatgta ggtgcttttg atgatcataa cactaactgt taagtcttta 146220
ggcataagaa tcaagcattc aactaagcat gtttacaaat ttgctttcag cccagtggat 146280
ctatccactt ttccatttag gttgcacatt tagatttcgg agtttatcct gttatcttca 146340
aatccacgga ctgtacactc tttgagggaa gaaactctta gtatctagtc aagtacgtgg 146400
catgcaatgg gtgctcccaa atacttgatt aatatcatat gatataatgt aatatgattc 146460
ttcataaaca gtgagtgttt ataaatacag tattttaaat gtcattagga atcttctatt 146520
ggaatcttaa ctttattta atagacctac ttttaaagtt aataaacata atataaatgt 146580
ggacagggct aagatttttc cctaagattt cactctggca agtcttcctg gagatttagc 146640
```

-continued

```
catggctatt tttatgactg taatttcctt aatatggggc ctcagccata ttccatcatc 146700
ataaatccct ttcttgcact taaaagcaat gttgaaatat tttccagttt ctatatctta 146760
actctttact tagatccatt atttccattt tgagattatc ttatgtaaat attgtagaag 146820
attttagaat tatataataa gaaaatacta gtataccacc tcagaaatct taactaatag 146880
atatgttttc aaatgcaaag tgaaatattt aaagtaatta ttcaagtaaa taaagagacc 146940
atctttgtcc caattacttg aatatttttac gtaaagttgg ttttatgcac ttgactttgt 147000
gtttaaactc aagtttgtag tattgtctac tggacattgt tagctcagga cctttttcagg 147060 agcaaggaat gaaagaatca ttttttaaact tatttaaaaa aagaaataag gaagaaaaga 147120
agaaatttta ctggctcgcc ttagcttaag acatggctgg atacagatgc tcagacaatc 147180
acatcaggag cctgcctccc tccgtgtctg ggctctctgg cctcttgggt cagtttcatg 147240
ctcaggctgg ctttctccac atagtggcaa agatgggcat cagacatccc aagttaacat 147300
catctttagt gctcatgctg tcagaatgaa agaggccctc tcccagcatc catattaaat 147360
ctccaaagag attctgtttg gccttgcttt ggccacatac tcaaccctga ccaagctccg 147420
tgtcaagaga acagagttcg ttgaaaggcc agcctggttt gcacactcat tctgtgttga 147480
aagatgtaga ccatgtgatt gacagtccca ggagatagga gagggagaat tttcaaaaga 147540
gttgccggta taagagacag tggattctgg gaaggtaaaa agaggtattt attaaaatac 147600
tgtgcctttg gaataaaaat cttttccagg aaatgcaaat aatttaaaac aattcaaata 147660
aggatcatac attttaaaac aattagaaat acactcagaa gaactgaatt gctcatttag 147720
tagatttcag ataatatttt ctcctctttg aacctcagtt ttgtcatctg gaaacacagg 147780
ataatgctta ccttataagg taatcatgat tagaagagat gatggagctg accatatcta 147840
tttactataa agtgctatct acatagttat aaattatgac agctaagaaa attaatccct 147900
aaagaaagca aaattaccta tgtcacggtt tagaaagtct ctctcttaag aagaaactta 147960
ttctattgcc tctgttgggt tttttcctga ggaatcggtg tttgaatgca atatacattt 148020
ttgtaggctc tgcaatgttt ttatgatgag gacagtgata gtgttgacaa ttactcaatg 148080
aatacttaga gatttgaatg tatcgctaga tttctgggaa atgaaaagac caatgtaagc 148140
tagttgaatg agaaaaccag aggtgggcag atggtggaca gattaagtcg ctggtttttaa 148200 aggtaggctg aactggtatt tgtaactatt aataacagcc atcttctttta aaggaagtac 148260 tcctaaatat caatagttta gtggccaagg tgccattgag atgatcactc ccaggaaatg 148320
ttttgccagt gatattacct taactttcat ctgaaaagaa ataaagaaat gttttatgga 148380
tgattcactt tcacctgata tgtgcacaac attttaagag aatgaattag tcagtctgtt 148440
tgaatcatct ttacgtgttc cttttagcag ggaactcaaa gttggttaaa tggctagctc 148500
tatttcagaa agcaaaaata acagaaacag tgaaaagaca gtctatattg aaagcctgat 148560
ccagacacat catgggggaa taaatatatc aggacaaaaa tatatgaaaa gtgaaagtat 148620
ttctggagta tttcactacc aatataaata ttaaaatgct cacacagcca gatctggcaa 148680
gttacataga tgaggaagtg aaagcaataa tatgccaagt caatggcatt ggtgtaaaat 148740
gtaatcatag aggaacaatc tcagagttga aaattattag aattggaaaa cactttgaag 148800
ttctttagtt ccacccagga gtatgccatt aaatatttaa taaccatccc tctgcgggct 148860
ttaataacaa gccctgattt gtagtgtttg ccaatttcta tggtgtcaat acagccacca 148920
tggctgattt taggctacca agatgaggtc actgaaacac aagttgggaa gagatgcaca 148980
tagtaggctg tcatgagcca gcacacagct ggttcagcat tataattttc aaataagaaa 149040
```

-continued

```
gcagttgacc tcagaggagt tgggtgactt gcctgggtca tacaaataat tagctgcact 149100
gccacaacta aacctaggcc ctctccagtg tttgacctca gaattgtgaa tgcattatga 149160
ggaaagcacc atgattgatt gattggtaag cccacgtgac tttctgtcct agttaagttc 149220
ccctttgagg gcctccatag acatttctac attgagttta aactatagtc tgcctatctc 149280
cactactggc ctgagatctc actgacattt ggaaagcgtt ttatttatct ttgtatcttc 149340
agcactctgt acagtatctg acacttagat gcttataagt gtttgttggg ggccatgtac 149400
gaacaataga gaacatgcat tgacctgcta tgtgccaggc agtgttctta gtgatttaca 149460
tgcattaact tattgaatcc ttagaataac tctcacaagt gaggtaggta ctataatcct 149520
gcccatattt tagatgagaa aatacaggct tagacttact tgcctaaggt aacatggaca 149580
gtgattggat ttaaacccta aaatctggcc agtgcctgtg cacttggcct ctcagttgtc 149640
actcatttaa ctagcagtta tcatcatagt gcccagctca gcgccaaata cttctaaaag 149700
gtctccctcc tttccttagg aaggacacaa aacgtttccc agaaaagatc tgatctgacc 149760
aacacacacc tttgttaatg gggaagggcc tttattaatg ggaatgatca aggaaatggg 149820
gcgtttttgg tgattacatt ttctcattat ctgaggttta aacagaaacc tctagtttaa 149880
ttaaaatttc tgttgctgac aataggccct agtcccattt ttttctttaa ttaaaaaagt 149940
taaccttttt ttgatgtatt cacttgaaaa atggcatcac catatggtaa cagataaatgt 150000 aaagaaggtg taggagatta aggtactaac tccaactgtg ttctgtgagg gttttctttt 150060
aaatagaaaa tatattcttc ttccccactg attttccatt tcatcaaatg aagtaacaaa 150120
aagcctattt ctacatgtgt acattttctt ggattcttgt ccactgagat ttagtacagt 150180
gtgtgactta tgtgcgaacc ttaagatatg aatcttattt taaaaacata atttaatata 150240
atatctctaa tttttttgtt tttgttttta tttttttttag atggagtctc gctctgtcat 150300
caggctggag tgcagtggcg caatctcaac tcactgcaac ctccaattcc ctggttcaag 150360
agattctcct gcctcagcct cccaagtagc tgggattaca ggcatgcgcc accacaccca 150420
gctaattttt gtacttttag tagagacggg gtttcaccat attggccagg atggttgtga 150480
tctcctgacc acgtgatcca cccacctctg cctcccaaag tgctaggatt acagattatt 150540
ttgaaggctc cttcaaaaag cctagaagaa aaaatgtcat tcacacttca cactgcatta 150600
atggacatca actaacatgc aaattggtta caatattttt ctcccttttg gcaataataa 150660
ttcgtttcct ttctttcatt ataatttcta cagaaaatac agcaataaat tatatattaa 150720
gctcaatttt gttagataca ctgataccat attgataagt gcagttaact tttcacataa 150780
tatttatttt tcccattgtg ctctagatgg tttagataca tatttgcagt ttggtttaca 150840
gtttgtattt gccctctagt acaacaaatt gtccctaatc cttttcttct atcccttgtt 150900
attccctcta ccagcaccaa aaatttgcta gtacattgca aaacaatgag aattacagat 150960
aaaatagcaa gcatttatat atactctata ttgatcaaag tgctttcaga gatgagatct 151020 cttttttgatc cttaaaatgg tcacgtgaga atatctgacc ctgggactca gaggtgggtg 151080
attgcctgga gtcacacagc tagagaggga aagggctaga atcagagggc tgattgtctg 151140
acttctgttc tagtgcatgc tcccacctcg ctttggaagc tgcttcggca tagtgaagca 151200
cttaagagca tggatgggtt cttgttagcc agacgtggaa ttgaatcttg gttctaactg 151260
tgtgatttta gcaagtttgc ttatctagaa gagaaggata ataatacttc cttcttcaca 151320
gggtggtgat gaagagtaaa tcaaagagtt tagcagaatg cttcccatat ggtaagcact 151380
```

-continued

```
caatacatgt tcttgttatt tttattatta catggctttg ccttactgag gcttcatctt 151440
gtcctctggt ccaactacag ttctctagct tggcttatcc cttcataacc tgtacccccca 151500 gtggcacgat cttggctcac tacaacctcc gcttcccaag ttcaagcaat tctcctgcct 151560
cagcctccca agtagctagg attacaggca cctgtcacca cacccagcta attttttttgt 151620 agtagagatg ggggttcaca gtgttggtca gcctgggttc aaactcctga cctcaagtga 151680
tctgcccacc tcagcctccc aaagtgctag gattacaggc atgaaccacc gcgctcagcc 151740
aggaattttc attctttatc ctcctttgag actcggctct agcatcattt ccagtcgagt 151800
tggtctccct tcctctgcat tctgataact gttaaccatc aagtgacttg agcttcccag 151860
ggaagggcat catgtctttg tagacatcca ataaatgtta gtagaagaaa gggggggtcct 151920 gccaataatc atatgtcttt cccacaattt aaactccttt tcaccctgtt actacttttt 151980
gcttgtcttc cctttgataa acattctact tcttcatcac ccattccctc aatttaacat 152040
ctgatactac tatagaaact actgccttga agatcaacaa acgggttcca tgtggaccaa 152100
cgtcctcctt gagaccctca cttggctttt gtgacacagt gcaatatttg ctctcttgat 152160
gcctcactga ccttaacctt ccttgactcc tgcatagatt tctcaactgt gggtatcccc 152220
taagatttag gccatttgcc ttctcttctt tcatctagtc cattcatgaa cacacccatt 152280
cctggtttta accatcacct ctgtgcagat aatgtgcaaa gtttatttct agtcggagtg 152340
gagtctctgt tactctgcca atcaagttct aaatttttat tccttctagt gcagcagtgg 152400
caaatacctg acactcatgt gtctcactca agacagatac tgtttcaccc aagactgatc 152460
atgctgcttt cccagtcaag gcaggcttct cagaatcctt ctcatttccg cctctgttct 152520
ttggcactaa tgctctgtct gcccagagtt ttcattcttc acttgttcca ggcacctgct 152580
tcctggtgaa taatgtaaaa cctgctagtc atccttatag gagaatatgc actcatttcc 152640
cagcagcaca cccgactcaa cgtggttaaa accaatctac cattcccata tattcagcct 152700
aacttcccag tgcagtctac cctagtttta taacttgttc tacttttcca gataactgct 152760
aatcatcttt gtttgtcttt gctttctttt ttgcactgtg tttgatatat tagggtatca 152820
aatcctactt attcaaatat gtcccttatt cattccttct atccttggtg ctaccatatt 152880
tgttctggct cttgttacct cattatggga tataaaaata gcctgtcaac tggtctttcc 152940
attgccagga tctctctgtt ctaagccacc ctgcctccag atcaatcttc ctagagtaaa 153000
accttcattg tatgacggtc tagctcaaaa ttccttaatg attattaatc acctcttaaa 153060
gtccccaatt cttagactat tagtagggta aaattatttt tgatttggag tcaaaaaatt 153120
ttggacgcaa attttggcta ctacacttaa ccattatgta acttcaaatt tcggcttaat 153180
ttttattcat catttattca gtatctattt gtttaacacc ttctgcatct caggctctgt 153240
actaggtact tgggatacaa tgatgagcca agcagacctt gtccttgctc tcctggacct 153300
cacaacatgg tgaacttgtc tctattgctc atgatcataa taatcctaag tacaggctgt 153360
gcttttttcc cttgatactt gtagcttttg gtttgtgcta tgcagggtat tgtaatacca 153420
tttgcagtgc cacaataatc agcatatatg tgttatcact cagccacatt gcagcttcac 153480
tgaagggcag gggctatgtc ccatttctca tagcgcaagc acagtgccct gcacatacca 153540
gctgctcagt gatttctgat gtggtttttg tagatccagg gttagtcttt ggcagtcatg 153600
atgcctagta tgtttttaga ggctcccttt gtcctatcag aattatgcta tttaaaaaaa 153660
agtcatacct atttagttta tattcattct aaggcctctc ctttccaacc tactaccctg 153720
cctataacta ttataaggag aactcacaat gtttataact tgtgcacctt aagtttttaaa 153780
```

-continued

```
tactgaataa caggcccatt catgtttcct catagaaata ctgtctatat gcatacaatg 153840
aaatgttaaa ataatgttct ttttactaaa tagctttttg acttggtaat gaacaatatg 153900
ttgtttttcc ctgagaagta gttctaggac tttagttctg aagattatgt tgtattttat 153960
acattttcag cctcctgttt ttcagttccc agtgatctta cattaaacat ttgtctgtct 154020
aaaacaatag gttaactata gccaaattat aaccatacca ttcctctcca cacaaaatcc 154080
tataaacagc atgtgatcat attgcttcta gaatttatga ttgtttttctt ccaaaaggaa 154140 gctaaattta gcctagtaat tctacatgcg ctcaagaaaa caatgcctgc tgtgatttct 154200
agaataaatg aatgtgaacc acagttcctt tacttgacta acagagaaag tttaaatatc 154260
aacctagtca ttaaccacag ttattaaacc acgttaaaca accagcaagg gttaagaaag 154320
aaagttgcta tgtttttttct ttcattgctg aatgagtcta acttagttac tgtatcaacc 154380
ttaatacaga acattgtttg catctcaatg gttctctaaa attattcgtt catggcttga 154440
gttctaaaat taaactatgt ggagtcatgt ccaaccgcac aatgcatctt tatgtgaaac 154500
ttgctagagt ttttgttttc cttctatgta aaagtccagt tgggaagctt tatttctgat 154560
agattaaatg gtataggtct ttcagttttc tcttcatttc tgacaactga actgctctcg 154620
ccttgaacct gttttggcag ataaacctct cataatgaag gcccccgctg tgcttgcacc 154680
tggcatcctc gtgctcctgt ttaccttggt gcagaggagc aatgggagtg taaagaggca 154740
ctagcaaagt ccgagatgaa tgtgaatatg aagtatcagc ttcccaactt caccgcggaa 154800
acacccatcc agaatgtcat tctacatgag catcacattt tccttggtgc cactaactac 154860
atttatgttt taaatgagga agaccttcag aaggttgctg agtacaagac tgggcctgtg 154920
ctggaacacc cagattgttt cccatgtcag gactgcagca gcaaagccaa tttatcagga 154980
ggtgtttgga aagataacat caacatggct ctagttgtcg acacctacta tgatgatcaa 155040
ctcattagct gtggcagcgt caacagaggg acctgccagc gacatgtctt tccccacaat 155100
catactgctg acatacagtc ggaggttcac tgcatattct ccccacagat agaagagccc 155160
agccagtgtc ctgactgtgt ggtgagcgcc ctgggagcca aagtcctttc atctgtaaag 155220
gaccggttca tcaacttctt tgtaggcaat accataaatt cttcttattt cccagatcat 155280
ccattgcatt cgatatcagt gagaaggcta aaggaaacga aagatggttt tatgtttttg 155340
acggaccagt cctacattga tgttttacct gagttcagag attcttaccc cattaagtat 155400
gtccatgcct ttgaaagcaa caattttatt tacttcttga cggtccaaag ggaaactcta 155460
gatgctcaga cttttcacac aagaataatc aggttctgtt ccataaactc tggattgcat 155520
tcctacatgg aaatgcctct ggagtgtatt ctcacagaaa agagaaaaaa gagatccaca 155580
aagaaggaag tgtttaatat acttcaggct gcgtatgtca gcaagcctgg ggcccagctt 155640
gctagacaaa taggagccag cctgaatgat gacattcttt tcgggggtgtt cgcacaaagc 155700 aagccagatt ctgccgaacc aatggatcga tctgccatgt gtgcattccc tatcaaatat 155760
gtcaacgact tcttcaacaa gatcgtcaac aaaaacaatg tgagatgtct ccagcatttt 155820
tacggaccca atcatgagca ctgctttaat agggtaagtc acatcagttc cccacttata 155880
aactgtgagg tataaattag aaataagtat cagtctcaaa aagaatatcc agggcttctt 155940
ttgtgctttg taaatggtgt ttatccaaaa tagttgcaga ttttttccaa gaaaattgag 156000
gaattgaatc ttcatttaca cctaaaatta tatctttaaa atgtaaatgg taactaaaag 156060
aaaaatgttt ttacaattca gatttgcatg ttcgtgacat ttcagattat attaaagtta 156120
```

-continued

```
tttcccatat aagctttttt atatttacac agattttatc agatttacac agattttatc 156180
agatttacac agattttat cacagcagca attcccataa aacataatta ttgacatttc 156240
tatataatct ctgcaacatt tacaagatgt tcaagctaat ttgtatgcct taaagaattg 156300
ttccttatga gattatattc tctcactgat acacaactga ttaatctata ttcttgacat 156360
tacttaaagg aacttaactt taaaaaacct cttctgaaat gctggtaaat aaaacatttt 156420
taaatgagct cgtatacttc tctaaataac ctgtaagagt agagaggaaa tgtttgttcc 156480
caagtccttc ctttagagct tgactttaat catggacttc cttctggaaa agacttgtgt 156540
ctaccaagtt ctagcttggc actttacctg gttggtattt gttatttata agcataaata 156600
ttttggttga tgattattta tacttatatg aaatggtatt ttcttaggag ctgttagaga 156660
tattcttggt gctgtgattt aaatatagta acagctacca gctatacctg gagatttatc 156720
ctgctagtca gttgatcacc tggtctgagt gtttattgtg gctttgagtt tcttgatctg 156780
ggccagattt ggaatacgga cctgactatg accatcattg aatgaacaaa tagtatagct 156840
tttctaaaga cagtttgact ttggcatggt atgtttcact tactttaaca ggtttcaatc 156900
taagatataa aggttataat tgcaatcagg tagaacatta aacatgtcct cagtagcata 156960
aagtatataa tttgctgagg ggtaaaggca tatgaattca gagacatttg gttgactttt 157020
gctgaaatgt ctgggacact tctctagatg gaaactatag ttaacttta tgatgctagg 157080 aaaatacttc caagaaagtc agttcatctt ttggtgaact aaaaacaaaa cttccttcct 157140
ctctcttcca aagtctatga atatacataa cataaatgca catacattcc aactaagact 157200
tatttcccct acatacattt aatatatgtt gcaaagaagc aatagaattc cttatgaagc 157260 tcccccttt ctttactaga aactacaaaa gaatgaaagg aaacaaaatg attttcagaa 157320
acctgggatt aggaaataaa aatataatat taatagcatt acagagaaga tatttttctg 157380
catccagtaa gttgattctg agacacaagt tttaaaagag tctattagga attcctccag 157440
ggctcctaga gcacatggat ttgctatttta aatctttctt tgttaaaaat taaaagaag 157500 ggtagggcaa gaaaaaaatt aaaaagagaa ttcataaagg tatattgata tctcattttt 157560
taaattttgt acatttcaat ccttagatgt aaaaatactt atcaattcta gaaattctca 157620
aaacacatct gaatttttatc ctaccctttt gactttttta gtgttccaag ggagacaaac 157680
agacaggatt agccaatgaa attcaggtca gttttatcgc ccaggaaaaa ttcccaaaat 157740
gcactagcca cacctgaaac cattatcact cccatcacaa aaattcttgc gggaaacaag 157800
atggaacttg ccaacatagt cttcttacaa aggaagccaa cttttacact ggccaaattc 157860
catagacaaa taccttcaaa cctcctctat ttatttgcct gtttatcttc tctggttaca 157920
aagatcaaaa ttcttctgag actgagacta cacatattct ctctctccat ataccccatc 157980
cagacctcag attgttccaa taatgagcat ataatcattt cctagcttaa tgccaaaatg 158040
aaggcaccta gagccattca tcacacacaa aaaaaacaaa atgattacaa gatcaaagct 158100
gtttagcagg actctcaagc aataagatga ctccattttg tcttggcaga tttacttggc 158160
cagaaatcaa gtgacccttt taataatttc ttggaactga gtttttactt tggcatcaag 158220
tttggtgaaa agacacacat attgtagttt tgttattaac atctctaata catttataaa 158280
gggactcttg tggacaaggt taagaaagct gagctgcagc agtaactttc tacttatgct 158340
tctgcccagt cctcagtgtt gacacattgc tgaaagaggg atttcctggc actccaagag 158400
ctctccacca tgtgcaaaaa gtgtttctat cacaagatca gataatggga gtgccaggga 158460
cgggcctttt acattttagg ggtccagcag gtgtaccagg cctgacttgc ttgtttagga 158520
```

-continued

```
tcacatattt tgttgctttt cccagtctca catttcatga agtatgtcta tgcaaactct 158580
tcacatgcat cttctcatat tgatgacatc acaaaagccc tcttttgagt catttgataa 158640
ttcccagtac tcgtcatctt cacccataag ctatttgtgc ttcagaactc tttgtctcca 158700
catatgatgc tgtttctgga aacttatccc aagccacaaa tgcccactta tagaatacca 158760
gtgttgttga ctatgtcagt tgttctataa gaatatattc ttgatcctca caatgtgtcc 158820 atttttttatg ttgcttttga aagtgattct caagaatttg tttacagtga cttccaatat 158880
tgagtactat gagattatac acccacaaat aattactaaa tctgtttaat atctttacct 158940
cctcctttac ccattcatca atcaacctct ataagcatcc taaattagta ttgattgaag 159000 ttgtttttagg ctaatgcata ttctctaaat agcatattat tattcaaaat aaaataattg 159060
agaaaattgt cccataatat ggatggaacc tttgtaaagg cccatatgta gggagaaaaa 159120
accctcatct ctatttgagg ataagcagta gcaaaaattt cattaacttg tttaaaatta 159180
agtggaattt aattttaaga ctgtggaatc tctaacagtc ttttacatat aagggattga 159240
ttaatgtgac aatttcagga aaaaaggag aatcagtaca cattggccca atctcctaca 159300
aatgagaatc aatacagaat aagagaattt tttaaatccc caaatcagca aagatcctgt 159360
tccctaagtt atagaatatt tattaaaaca agtgaaatcg tacattttag aaaaaatttt 159420
aatcaaagtt gaaattagaa aagcattctt gaaatagctc tcgcctctca gaaaatacaa 159480
ttagcacaca acactgtttt tcttgaagtt ctattatcaa agttttgctc tatagataag 159540
catttgaaag acctgtagca agtattttcg ccaacatctt gatgacctta atgaccaaag 159600
ttggatcaag tgaaggggaa aagcatttgg tgccagacac acctgggtgg aagtcctggt 159660
ttactgcata ccaaccatgt gacttctgcc acattacctg acttcttgga ggctgagtct 159720
cattggtatc atgcagataa caatacctac ttcacaggtt tttgtgaaaa tttgggataa 159780
tatatatgag gtacctggca caagatgact ataaatttag cccgttggga gacagcatgg 159840
actaatggaa agagactaaa atcagagatg ttggttcaaa tctgaacccc accgtcttct 159900
acctggatgg ccatgaaagc attatttaaa ctctgaaccc atcgtcctgc gtgcaggact 159960
atagtgtgga caagtatatt aataacatct gtaaaaggtc ccaacttggt ccttggcaca 160020
aaataaatag cagctattat tgtaaggaat acttgcgtaa agaaagacaa attcaaatga 160080
ttggattatt ctctggaaga ggcacattct ggttctattg tttacaagtc tttcacttcc 160140
ctctctaact gttatgagtg acctacctcc ataatggtta atttgtgtta tgttgttctt 160200
aagattataa tagttccaaa aaagagatgg ggtgaggagt ggtggtagtt tgaggggggca 160260 gaggatgggg agaaagacaa ttgaatcaaa actgtactat agtcaagtta gaaggtataa 160320
attgttctcc ttcctctcac tttcaatcct aactatccat gacctaagat attactctta 160380
tgtactttgt catatcttgc attcaagaat ttgcagataa tgcagtttta gaaaaagtca 160440
acctcatagt ttgtttgtat tgggcttcct tgttttttaaa tatcatttat actcaaattc 160500
aaagagtagc caactgcttc ccaaaataaa ggaaacttaa ggtagtaatt ttccatctcc 160560
gtttcacaga atgccaaagt taaagagtca ctactcagag ccatcaaagg aagaaagcaa 160620
agtgattaga acaattttaa aggaggacaa aaatcaaaac aagatgcaaa caaggaataa 160680
taggaatagg cagaaaaata aacatacagt gatgtttctt tattatgatt ataaagatga 160740
tagatgagta aaatcgagtt acatttaagt tgtaatggaa gaaaataatt gcagccttcc 160800
atcaggaaac cacaaggacc gttattgatc tgtcatcctc agggcatgtc tcgtaatatt 160860
```

-continued

```
taataaaata aacaaagatt tataactttt ataggccata tatctataat ctcccacacc 160920
acttgaactg tgaatgtgga gtcaatgtta caaataacat ccatgtgatt atactggttt 160980
ggcatgcctt attccaacaa tctagcactc tcaagagaat gtattttgta ttagggatga 161040
aaaatgtgaa gccagattat agagtttttt acttattgtg ctcaaaaatg agaaaatgtt 161100
atccaatatg aaaaatgttg ttaaggattc ttcattctta atattagaca gcctttcaaa 161160
cctaaatatt aaatatcttg gccatatgcc aaatgtaata gctaccaaag caaaatcttg 161220
caagaaagaa aatccttgag gtataaagat tcaatgtact tttaaaaaa tgtaagtaaa 161280 aggttattaa ttttacattt catttctttt tctttcctag acactacttc atcctctcat 161340
aggctcaggg agtcactgct tcctaacttc tttattttaa ttatccatgc tactcattcc 161400
acgaaaagtg gcatattgca ttattttatt aaaagaaatt taaaattagt ttctttccag 161460
aattttgtaa cgccccctga gatcactggg cacaccttg gggtgttaga aaacatgtta 161520
caaaatgaac ctttaattcc ttttgctttt tcccttcctc ttgctgactg ctctttaaac 161580
cattacatgg ctcattcaca agtctctcta ccccaggaaa gatgaaaaag caaaggcatg 161640
atgtttttat aacctaatag caagagaaca cagtgctgaa gctgtcacca aaactgtggg 161700
taggttttac ccgtgggtta tattaattca tgatatgatt gataatatct ctcacttgtg 161760
tggggaatga agcgttaact atgccgcatg cattttaaat taatttgaca ttattcttaa 161820
tgtcctttca agcaggtggc attataacct gtgtcttatt taggtagttg atttctacac 161880
ggagattcat ctgataaaac tgatatcgca aacgggaagg agtttgtaca aaatgaaata 161940
aatcttaaag ttgatttttg taaagcccaa atgttaatta aaatctttga atccacaact 162000
ctgatacatg atattttcat tgacataaac atgattagcg atttctggaa gcatgtggga 162060
tgctgcattg ataaggatat gaacctcctt gagtaataat gtatatttt actccgaata 162120 ctgtttcaca ttttgggtgt tacatcctta cttcagactt ctgccttatc agtggccatc 162180
ccaccctatg ttcttatctc ctcagtctaa aaagaaaaat ggggacccat cagaatttgg 162240
atagaagacc ctccaggaat ttctgccact gcttattcat gggttggcac agacactgat 162300
tcagtgggca cacagagttc agaatgattc agagcccaga tatgtgccct aagtcacatc 162360
tccagcgtcc agggaggact gtaaagtgct cgttatcagg aaaatgaaac caagggctca 162420
gctactcctg aagtcattaa aactccttcc cttgattttt ttttttttt ttttaaatag 162480 tatatgtggt aaccgaatct aggatcctgg atacattcca gtctgctaat tacatatttt 162540
tttctaacta aaatgttcca ggcaggttca tttgcatgtg aattacttgc tgagccatgt 162600
tgacttccta ttctaaaagc ctcactctgc cttgggaagc agtttactgc acttcaccct 162660
agacctagtc taatgttgga gcagacaaag tgtagctacc catatatact tcaaaaatat 162720
tttccagtct ccccacaaga ggaaagaaaa atgtctagca attgcatgct aatttagacc 162780
aaagctttgt tttaaccatt cttggtgatc acaaatgggg aaaaatgatt tatgaacagt 162840
ataactataa aacaaacaaa aaaaaaccat tgtgaattca gagtgaagtc tgacttcatt 162900
tgtcttattt gggtaaatca gcaaaatgtt catcagtcag aggacattaa aatggtagat 162960
gatacttcaa atcgtgccct agataaaagg agagaattaa ggttagtttt gatttgtaaa 163020
ccattctctt cgaaggctga ttttataaaa attaagtttg ctgagtcatc atctcaaata 163080
tatagttatt catgattagt taaaatttgt gtctgtgtat caaagaagta aatttgtatg 163140
atattaaatt ttctaacaat gttttaaatt ttaaaatgtc cgattaacac ttgcatctag 163200
caaccagtct actaactaaa ctataggtga agtcatgctc aggaaatggg gaaaatgcac 163260
```

-continued

```
agattaaatt ggtctgttag ctctgagtga atcaatagta tttagtgcta atgcactaag 163320
gagattacaa gcactaatgc agtagcagtc aatagcgaaa actaatatct ctaaaaaata 163380
tcttgacaat aaaatgtgca atattttcca tttatcttaa gctaattaca ttacctgctt 163440
gttctttcat cttattagtt taagccaagt gctagaagcc taaccatttt atttagtgca 163500
taaaagggcc aaaaccttgt aatcattgtt ttcagcagga gacagaggaa aggattaatt 163560
catgtaacca agattcaacc agaaattcaa cagatattta tttagtctct aaacctgata 163620
gtattacaat ggagaatgag ctagactgta cctgtcttca acaagcagat agactagtga 163680
agatgacagt aaacattcag tcacaccagt gaacaaatac atcatgataa tttatgaaat 163740
gtgctgtgag ggaaataaac atctgtgaat gcaaatgaga gggaatatct aaatttggta 163800
gttgagtcac aaaaggctgt cctgaggagg tgaaagctaa cctttatata aagcttaaaa 163860
ctttaaaaaa gcaatacgtc tttagtacac aggcaaatat ataaactaaa tatataaact 163920
aatagtcatt acttatttca caagctttac atcttaacta caagctgcta cattaaatca 163980
gctttcttaa gtggtttgtg gtcattagtg catactatct tacacttaga aaaacattgc 164040
aagaagtagt acaatgctgg agaatttaac tttttaaaac atttcctgcc ttaaaataaa 164100
cagcagtaaa tgtgtttaaa cattcttttg atttctaaat gaattaagtt acttttatt 164160 atgtggttct tcttcatatg aagaaaataa tatgtagatt actagaagct aagaacatac 164220
tttagatcct gctcacactc actgcctttc ctggcctgtc accttaatca gcttctttga 164280
aaatcactgt ttcttacata ggccaggttg tttcttcctt gtttccctct tcttccttct 164340
atggccaacc cttgggaccc cgtttgtcag aagaacatgt tcctctttgg ggaggagggg 164400
attgtccttt taccaataag ttttatgacc aagagaaaca taagaatctg agaacacaca 164460
aaataagctc ttttgaaact atcaaaatta taaacattaa tagaattcaa gggaatgtga 164520
tgctgaagtg atcccaagtc acattgtctt tctgcctctg tgcactgtac tctgcacaat 164580
tgcatccatt tttagaccat ttccttctca tgagaatcat gtgcatggag gccaaaggag 164640
agacaagtgc tcacaaggat atcatgagca cttatgaatg tacaaatgag tgctctccag 164700
tcagtgccat ctttatattg ttccggttta taggcaatgc cttcatcttt acctacgac 164760 acatgttgcc tttctgtttc attttaatcc tgttcatcta tacatattta atcacacaaa 164820
tatctaaata agtttatgtc ttgtagggaa ggcactttgt catgcttctt tgtacctaag 164880
catatgcttt gcaaatcata aacaatagtg ttgattttat ttgatataaa aacttggatt 164940
ctcaaaagaa atctatgtgt tcacacgata aacagagacc atctgaattg ccaaagtatg 165000
actgaatcat aagcagtatt gttttagtca tctttacaga ccaggaagat ttgaaataca 165060
ggtgtaaaaa gatgtgtgag gcatcaaaag aaatattcac ctttctttgt gttcattttt 165120
tttatttttg cttggccgag aaagaagggg tgttttccaa gggaatagga ggcttcaggg 165180
cttattcctg tgcctacaag tcagagaggt cactggcttg ccccttcctg aaggctgtaa 165240
ttacaggcag aggactattt attttcccgt aaggcgacca gaatcttgag tgtaaaaact 165300
gtttacaaga gtacactgtg tataggggtt acacacaacc tcaggaaaat aataggaaag 165360
tgagactatt tttcttcatg tattcaataa tatgagaagg tccaagactc tggaaatgtt 165420
ctaaagtaca ataatagaga tgaatatgag gtcaaattag gtgatcctgg ggcttaagga 165480
actgaattaa atgaataaag aagaggaatt tctaataggg cataatctaa ctgataattt 165540
gttaaatgta aacttatttg tggctccaac atcatggtaa acaagaatga ataaatgtat 165600
```

-continued

```
tagtaagagt aattgagaag tatttctaat gtgaaaaaca ccaattacat tgggtttatc 165660
tggcgccaat gtggaaataa atgagcaata tttcttactc tcaactaaac ttactctcac 165720
tttcagaact gttataggaa aggtattgat tcaagtagag ttgggcatgc aaagcacaag 165780
atcaattctg ttactggcct gatattaagg atattagtca gtgtttgaaa aaatgatttg 165840
taatatataa gtagtagttt aacaaagtag gtaaaacttg taattaattt caaaaggtca 165900
aagcagagat tattgacatg tacaaagagg acccgcttta tatgtgcctg ctttgaaaag 165960
taataccgta gtatggtaaa ttgtgactaa ttctgagatt ttctgtctag attctttta 166020 aaaccaaatg cttaagaaaa aaacatgaga catgagtagc aattacattt tttaggctga 166080
gtaggtagca taattgcctc atgcctgcct cctgtctcca tttgttttta gtagattttg 166140
cacagaaaaa catgttgacc tcggtactga aattttggag ttcactattt gcggcacagt 166200
tacagatcac agaaaaaatg tacaacagga cttcaccaca cctaacaaaa gaaagttttc 166260
ttattaaaaa aaaaaccctc caaattattg tgagatctag ggtaaccatg gtgttaacta 166320
tatgctattt gatatcttat aaccctggtg ataagataac aatccaattg aatgcagatg 166380
aactcatgaa aaaagaagga ttatgaaata tttggaaagt aaacacctaa attttcataa 166440
gtaaatatta attatttgtg tgatctttag atatgaaagc ttcccctgca tgcacttggc 166500
tcttggaacc agctgttaaa actccagcac cttagttaat accctgtatg ctggtggttc 166560
aagaactagt taagaaacag tcacatttttc tattttcact gccaatgtat aataaaatct 166620
ctgttccagt gaatggctgg ccaattattt taataacgat gttggcatgg cttcatttta 166680
cctttcttgc tattagcaaa gctttccttt tgtactctga agtacgggta aatcacaaat 166740
taaactgagc tgttgtttgt ttaatgctgt gtttcctgct aaccttattc ttgtctatca 166800
acctgaacgt agttccccag tggctcagaa aaccctcaat tgggattaag taatagttta 166860
cacaaccttg ctcagtcatt aacctgtgtt gactttctca ttcttgtgtt ccagcctcat 166920
ttaagagttt cttaagcact ctatccagtt gctggtttgg tgacaactaa caatacctat 166980
ttaatcaaga aatttaatat ttccaaggaa tcatttatcg tatctcagac ttcttcatta 167040
acataatcta attcagtctt gtattccttc ttcaaaataa agcctggttt cattcatagt 167100
aaatatgaag cttaaaaatt tttacttctt ttcttctcta tacacacaaa gcagaaagag 167160
aaaattgtat attatcattc cagacaggtt ttttttttttg tttagtgtat tgacattgat 167220
gccaataaga taaaactaga cctcagtggc tcctcctcaa ctccacccaa tctatttgtc 167280
tccaaagtgc tgttggagta agtaatcttt gttaagagca aacctatttg tatatctgat 167340
gataatctga gggataataa tatgatattt aaggagtttc tgtccttggc cctgactatt 167400
tcctggtcct ccttcacgcc cagtgatgtg ctggtaaatg ttaaactctg gggggagggg 167460
cagcagaagc ccctaatttg tagcatttgc caatttctat ggtgtaaata tcccactgag 167520
ccagtttcaa ggtaccactg aaacagcgtt agtcactgaa caacaatgag gaagagatgt 167580
acacacttgg ctctgtgaac tgttatgaga tggttcaagc acagcactgc caccctgtcc 167640
tacacgcaac ctgtcattct tgtagttccc agaatccatc agcctccctc acaaccctgc 167700
cttaacacgt gtagcttggt ccacttcaga ttccctttaa cactcatttt gtcaagtgaa 167760
cactttttcc ctattcttta aaacttccat gctggcattt tccttcccag gacatttttc 167820
cctagccttc aactcatccc tgcccccat attctggatt tgttgcgttt cctgagcaca 167880
ccagtagcac tctgcttatt tctaccatgt ctcttatcac actccgtggt aatgtgtcca 167940
acagttccat cgttagcccc ctgaggggat gaactatgcc atttatctcc acagtccagc 168000
```

-continued

```
acctaataca atagcttgaa caatatatac atttatcgga tgagcaaaga agtatgacag 168060
agccctgtat gtaaaatata ttactataaa tagaatgctg attcataaaa ataattattt 168120
agataaaaca gttttttccgt ctctcccta aatccctaaa aactaattta tagaattggg 168180 gagtttttcaa gagctaaatt agcactggag aaaaactggg gagtttttact cactattacc 168240 tatgcccctc ccgtccccccc acacacaccc tccttcattc accagtctgc aatgaagatt 168300
gatcaaagaa caaagaagaa gaaaaatgaa agaaaaagga aagattaaga tagggaggggt 168360 gaatagatag gaattccaga gttttgtaat cgaaatttgg aactcagaat taaagtcatt 168420
aaaaggagaa agagggaata ctttctctgc tcccgtaagg ttttctcaag cctttcaaca 168480
gcactcaccc tttgagcggg tgataccatc tgtaagaggg actttacgca atgctttagt 168540
gggcgtggct tgagcagtga caccagtaga gatacccccct tgaaactttc atttgaagtc 168600
cacagatttt cactattggt caccaatcca tgatttcaag ttgaaaatga tatatgggtt 168660
aaggaaaaga ggccgggcgc ggtggctcac gcctgtaatc ccagcacttt gggaggccga 168720
ggtgggcgga tcacgaggtc aggagatcga gaccatcccg gctaaaacgg tgaaaccccg 168780
tctctactaa aaatacaaaa aattagccgg gggtaatggc gggcgcctgt agtcccagct 168840
acttgggagg ctgaggcagg agaatggcgt gaacccggga ggcggagctt gcagtgagcc 168900
gagatcccgc cactgcactc cagcctgggc gacagagcga gactccgtct caaaaaaaaa 168960
aaaaaaagga aagaagtta agggcaaagg tctttatcaa caccatcctt cctgtggcca 169020
caggatcgta atcccagtgg caacattcaa aggcaccaag tacgtgcttg gtacagagag 169080
aagctttcct gagcttggcc ttggtgtaga tgcagtgaga actgagtaag ggcctctggc 169140
agggaccttg gctgctgaga aggggagccc acagatggag gtttctgatc aacaggtcct 169200
atcagaaaca agggagcaga taagtaaaga gtctcactcc acggtggcaa gatggaaagg 169260
agggataaga ggtcatgaca gttggattaa tggcaggcta gaatatagtc atgggcttga 169320
acgatatatt gggacacaat tgaaggactc ttgtttcatc catcgttcat ctctcctggc 169380
cctctgtgaa gacatttatc acctgtttct attgaatgtg acactgttag gcacataaac 169440
agaccatggc tcttaccacc tccaagaaga actacttctg ttttatttgt tagtgcaggg 169500
taattggtgt tgtgtcttct gaaaatctct tatacttcta tgagtaagtg cattgaaatt 169560
gtttctgtta actaagtaga ggaaagcaga aaacctcttt gcactaagca ttaaaaccttt 169620 cctaacttgg aacaattttc tttatgaatc actctgtcac tcctggctat gattgaagtg 169680
cagtatgaag gctgctaacc aaaaacacat ggacacagtc tgtttcagat ctgattcacc 169740
ttaggaaatg atgataaaga agcaaaagtt ttaacactta gaattccaag gtccatatca 169800
ttgtagaatt gattctttttg aattgtggtg gtacctcaag agaaaggatt tatttatttc 169860
atttatattt aaatgcgttt gtatacatat gtatataaac ccatatacac atatacataa 169920
aatatattct gctccaagta tttatctctc ttttctcttt actaatccag cttccattaa 169980
gaactggctc aacttcgacc tctgccatga gccttctcca gctgttaaag cccacacaga 170040
tcttattttt ttcctagtct tagaggattt actgccagta cagtgttttc agaatgtaac 170100
tatcaactga gttcttatac tttgcatcag ttagctattg tacgtgtcaa tcttttgtct 170160
ccctatgtag aggctagacc caaggtagaa gcatttgcca ggattgacaa acgatagcct 170220 gttttttatat tctcaacaag tgaaaactta ttttgtttat attttttttcc ctttttatac 170280 agttaaacac tcacatgcac gcacacacac acacacacac acacacacac acacaggcca 170340
```

-continued

```
cagggaccct atggccctca aagactagca tatattctat ctagcccttt cccaaaaaac 170400
atgtgccaac ccctgcatta gagaatagtg taaaataata gtggacagat aacaggtcca 170460
caaattttgg agagccatgg atgaccttac ttatgaactt aagtaattct cttcaatagg 170520
tgtgagtgtt tccattttac agatgatgaa attgaggctc attgatctaa acaattggat 170580
tttgtcttca taggcattat gagggcttac tagaccaaca atagtgataa taataactgt 170640
ttagttgcac aaggcaggga tttatgtctt ttttatttgc tgccatatcc ttcagcacct 170700
agaacagtct gtcacatggt atggtattat attcattttc cagagctccc ataacaaatt 170760
accacaaact gggtggctga aaacaacaga aatttatcct cacatggttc tggaggccag 170820
atgtctgaaa tcaaggcatc agccagggcc atgctccctc tggaggctct agggaggact 170880
ccttccttgc ctcttgcaat tctggtgtcc caggcatctt aggttgtggc agctttactc 170940
ccctctctgc ctccatcttt atgtggcagt ccaccatgtc tctctgtgtc ccctcttctt 171000
ataaggacaa cagtcattga attcagggca ctcactaaat ccaggatgat ttcatctcaa 171060
gatccttaac taatcacata tcaaagagcc tatttccaaa taaggtcacg atctgacttt 171120
ccaggtggac atgaattttg ggaagacatt attcggccta ctgtaggtct tctaaatgaa 171180
gtgaccattt aatatgtttc tggcactgga ttcatttcat ttaagcctca aaacaaatct 171240
gttatgtaga tatgtgtttt cccactttac aagtgaagaa ctgaggttta gagatctagg 171300
aatcctaaag ctgcacagcc aggaagggca gggccacccc tgacccaagt tctctgctag 171360
gttagcatgg ttgtcacagg acaagctgag aaggtattta gggagcatta cactaaaaag 171420
ttgtagaagt cggcttaagg aagaagattc taaaatcaaa ggaatcagat tgtaggaggc 171480
catgtaggca atttcctttta attcaataga agagagtata agaatcagcc aggcatggtg 171540
gctcatgcct gtaatcctaa cactttggga ggtcgaggtc gaaggattgc tagagcctgt 171600
gaattcaaga ccagcctggg caacatggca aaatcccatc tctacaaaga aatacaaaaa 171660
ttagccaggt attgtggcac atgcctgtag tcccagctac tctggatgct gaggagggag 171720
gatctcttga gcccagaagg gaagaggttg cagtgagcca agattgtgcc actgcactgc 171780
cgcctgggtg acagagccag agcctttcaa gcaagcaagc aagagggaag gagggagagg 171840
ggagagagag agagagagag agagagagag agagagagag agagagagag agaaaagaaa 171900
cggagagaga gggagggagg gaaggaagga gggaaaaaga gagaaagaaa gagaaatatg 171960
aaagaaagaa agagtaagga aggaaagaaa gaaggaaaga aagaaaaaga aagaaagaa 172020 agagaaagaa agaaagaaag aaagaaagaa agaaagaaag aaagaaagaa agaaagaaag 172080
aaagaaagaa gatatgaaca ataaaggaaa gactcaaaga tggttcagat ctcaaactta 172140
cggagagggt agctattgat gcattgagaa ataggaagct ggaagaggaa atcagtttgg 172200
agagaaaagt gatggctttg aacatcatca atggcgtatt caaacatagc ttgaaggcat 172260
ttgcagagac agggctggtc ctcggaagag atggcaacgg ggtgtgtaga gttaggtcat 172320
caccacgagg ctgtgagggc agagccacag tagcttccat caccttgtga atcaccagtg 172380
ctcagcccgt ggctggctgg ccggatgcct gcttatgctg tgctcccggc tgtctggctg 172440
cacacacaac cgcagagcat gccctctctg gctagggcag aaagaaattg aagcctctta 172500 aatttttgccc cccccagctt tgctcccttg ctaggacttc caggccatga ctattgaagc 172560 cataggggcag gattacttcc tcaagaggcg ttagtggaaa cagatgtgtt gaggaagcct 172620 ctttctttttc aactgtgccc tgagcacatc agatggagtc ctcttcatag cacaaaacaa 172680
cttggtcaga ttcttagggt ttgaccatag caccctaaca gcctggccgt gcattaagga 172740
```

-continued

```
ccccaaagag aaggatctgc tttgccagag agctgactct tctgtatttt acagacaatt 172800
ctgaattcaa tgtcaacatc ttagacatct cagtacagac agtaaagagt taaaatatgt 172860
ctataagaaa cagcgccaga ccctgaaatt gaaagctctg tgcctccctg cgtgcagtca 172920
gttccacact gtcctctctc ccagttctat ttaataaaaa aaaacatgag tgaaatttag 172980
ggaaataaga attcctgaaa ttaaagcaat taagttttca gtcaactgta tgaaaagctc 173040
tagacaaaga ggtactttct atttcaaaat atgtatttcc cagaaaacca ttaccatatc 173100
tagctagaat ttctacaaag aatgattatg aataaagtat atattcaaat gcttctggta 173160
atttagtcat ggtcaaagag gagagaaagg tgatacaagt gaactggcaa agattttaca 173220
agatagtaca ttttttaaaaa ttttatttgc aagactgatt taaattatct atagatgagc 173280
taaatctgtc ctatagatca attaaatgaa tcactatttt aaatatatca cattcttaat 173340
tacactgaat taaatataat tacatattca ctgcatacat cataatgtta attagggaaa 173400
cattttgaat caaatatatt gagatatata gcacttcaat tttctttta taaaaaaagc 173460 tatatgacta agtcaggtaa aaagaatctg gcaagtactc atagaaagct aaaggaagac 173520
tagattaatt gatgtatcgc atcaaggctt acaaattgta gaggaattcc tattctttaa 173580
ctctatgaca gtatataaga ctttgggcta aggaagcaag tttgcaacaa gttttttaaaa 173640 aataataaaa caggaggcag ggcacgtggc tcacacctgt aatcccagca ctttgggaag 173700
ccgagacagg tggatcacaa ggtcaggggt tcaagaccaa cctggccaaa atggtgaaac 173760
ccagtctcta ataaaaatac aaaaaagtta gccagatatg gtggcgggca cctgtagtct 173820
cagctattca ggaggctgaa gcagggaatt gcttgaaccc aggaggcgga ggttgtagtg 173880
agccgagatc acgccactgc actccagcct cggcgacaga gctagactcc atctcaaaat 173940
aaataaataa ataaaaattt taaaaaataa ataaaataaa aaataaaaca cattgtttac 174000
cattgtttct cagagacata cgattatttt agaagtggat aagcctttt ttttatact 174060 ttaagtttta gggtacatgt gcacattgtg caggttagtt acatatgtat acatgtgcca 174120
tgctggtgtg ctgcacccac taactcgtca tctagcatta ggtatatctc ccaatgctat 174180 ccctcccct ccccaccccc acacagtccc cagagtgtga tattcccctt cctgtgtcca 174240
tgtgatctca ttgttcaatt cccacctatg agtgagaata tgcggtgttt ggttttttgt 174300
tcttgcgata gtttactgag aatgatgatt tccaatttca tccatgtccc tacaaaggac 174360
atgaactcat catttttat ggctgcatag tattccatgg tgtatatgtg ccacattttc 174420
ttaatccagt ctatcattgt tggacatttg ggttggttcc aagtctttgc tattgtgaat 174480
atgccgcaat aaacatacgt gtgcatgtgt ctttatagca gcatgattta tagtcctttg 174540
ggtatatacc cagtaatggg atggctgggt caaatggtat ttctagttct agatccctga 174600
ggaatcgcca cactgacttc cacaatggtt gaactagttt acagtcccac caacagtgta 174660
aaagtgttcc tatttctcca catcctctcc agcacctgtt gtttcctgac tttttaatga 174720
ttgccattct aactggtgtg agatggtatc tcattgtggt tttgatttgc atttctctga 174780
tggccagtga tgatgagcat ttttcatgt gttttttggc tgcataaatg tcttctttg 174840 agaagtgtct gttcatatcc ttcgcccact ttttgatggg gttgtttttt tcttgtaaat 174900
ttgtttgagt tcattgtaga ttctggatat tagccctttg tcagatgagt aggttgcaaa 174960
attttctccc atttgtaggt tgcctgttca ctctgatggt agtttcttt gctgtgcaga 175020 agctctttag tttaattaga tcccatttgt caattttggc ttttgttgcc attgcttttg 175080
```

-continued

```
gtgttttgac atgaagtcct tgcccatgcc tatgtcctga atggtatgcc taggttttct 175140
tctagggttt ttatggtttt aggtctaacg tttaagtctt taatccatct tgaattaatt 175200
tttgtataag gtgtaaggaa gggatccagt ttcagctttc tacatatggc tagccagttt 175260
tcccagcacc atttattaaa tagggaatcc tttccccatt gcttgttttt ctcaggtttg 175320
tcaaagatca gatagttgta gatatgcggt tatttctgag ggctctgttc tgttccattg 175380
atctatatct ctgtttttggt accagtacca tgctgttttg gttactgtag ccttgtagta 175440
tagtttgaag tcaggtagcg tgatgcctcc agctttgttc ttttggctta ggattgactt 175500
ggcgatgcgg gctctttttt ggttccatat gaactttaaa gtagtttttt ccaattctgt 175560
gaagaaagtc attggtagct tgatgggggat ggcattgaat ctataaatta ccttgggcag 175620
tatggccatt ttcacgatat tgattcttcc tacccatgag catggaatgt tcttccattt 175680
gtttgtatcc tcttttattt ccttgagcag tggtttgtag ttctccttga agaggtcctt 175740
cacatccctt gtaagttgga ttcctaggta ttttattctc tttgaagcaa ttgtgaatgg 175800
gagttcactc atgatttggc tctctgtttg tctgttattg gtgtataaga atgcttgtga 175860
tttttgtaca ttgattttgt atcctgagac tttgctgaag ttgcttatca gcttaaggag 175920
attttgggct gagacatggg gttttctaga tatacaatca tgtcatctgc aaacagggac 175980
aatttgactt cctcttttcc taattgaata ccctttattt ccttctcctg cctgattgcc 176040
ctggccagaa cttccaacac tatgttgaat aggagtggtg agagagggca tccctgtctt 176100
gtgccagttt tcaaagggaa tgcttccagt ttttgcccat tcagtatgat attggctgtg 176160
ggtttgtcat agatagctct tattattttg aatacgtccc atcaataccct aatttattga 176220 gagtttttag catgaagggt tgttgaattt tgtcaaaggc ttttctgcat ctattgagat 176280
aatcatgtgg tttttgtctt tggttctgtt tatatgctgg attacattta ttgatttgcg 176340
tatattgaac cagccttgca tcccagggat gaagcccact tgatcatggt ggataagctt 176400
tttgatgtgc tgctggattc ggtttgccag tattttattg aggattttg catcaatgtt 176460 catcaaggat attggtctaa aattctcttt tttggttgtg tctctgccgg ctttggtatc 176520
aggatgatgc tggcctcata aaatgagtta gggaggattc cctcttttttc tattgattgg 176580 aatagtttca gaaggaatgg taccagttcc tccttgtacc tctggtagaa ttcggctgtg 176640
aatccatctg gtcctggact cttttttggtt ggtaagctat tgattattgc cacaatttca 176700
gcctgttatt ggtctattca gagattcaac ttcttcctgg tttagtcttg ggagtgtatg 176760
tgtcgaggaa tttatccatt tcttctagat ttttctagttt atttgcgtag aggtgtttgt 176820
agtattctct gatggtagtt tgtatttctg tgggatcggt ggtgatatcc cctttatcat 176880
tttttattgt gtctatttga ttcttctctc tttttttcttt attagtcttg ctagcggtct 176940
atcaattttg ttgatctttc aaaaaaccag ctcctggatt cattattttt tgaagggttt 177000
tttgtgtctc tatttccttc agttctgctc tgatttagtt atttcttgcc ttctgctagc 177060
ttttgaatgt gtttgctctt gcttttctag ttctttttaat tgtgatgtta gggtgtcaat 177120
tttggatctt tcctgctttc tcttgtgggc atttagtgct ataaatttcc ctctacacac 177180
tgctttgaat gtgtcccaga gattctggta tgttgtgtct ttgttctcgt tggtttcaaa 177240
gaacatcttt atttctgcct tcatttcgtt atgtacccag tagtcattca ggagcaggtt 177300
gttcagtttc catgtagttg agcggttttg agtgagattc ttaatcctga gttctagttt 177360
gattgcactg tggtctgaga gatagtttgt tataatttct gttctttttac atttgctgag 177420 gagagcttta cttccaacta tgtggtcaat tttggaatag gtgtggtgtg gtgctgaaaa 177480
```

-continued

```
aaatgtatat tctgttgatt tggggtggag agttctgtag atgtctatta ggtctgcttg 177540
gtgcagagct gagttcaatt cctgggtatc cttgttgact ttctgtctcg ttgatctgtc 177600
taatgttgac agtggggtgt taaagtctcc cattattaat gtgtgggagt ctaagtctct 177660
ttgtaggtca ctcaggactt gctttatgaa tctgggtgct cctgtattgg gtgcatatat 177720
atttaggata gttagctctt cttgttgaat tgatcccttt accattatgt aatggccttc 177780
tttgtctctt ttgatctttg ttggtttaaa gtctgtttta tcagagacta ggattgcaac 177840
ccctgccttt ttttgttttc catttgcttg gtagatcttc ctccatcctt ttattttgag 177900
cctatgtgtg tctctgcacg tgagatgggt ttcctgaata cagcacactg atgggtcttg 177960
actctttatc caatttgcca gtctgtgtct tttaattgga gcatttagtc catttacatt 178020
taaagttaat attgttatgt gtgaatttga tcctgtcatt atgatgttag ctggttattt 178080
tgctcgttag ttgatgcagt ttcttcctag tctcgatggt ctttacattt tggcatgatt 178140
ttgcagcggc tggtaccggt tgttcctttc catgtttagt gcttccttca ggagctcttt 178200
tagggcaggc ctggtggtga caaaatctct cagcatttgc ttgtctgtaa agtattttat 178260
ttctccttca cttatgaagc ttagtttggc tggatatgaa attctgggtt gaaaattctt 178320
ttctttaaga atgttgaata ttggccccca ctctcttctg gcttgtaggt ttctgccgag 178380
agatccgctg ttagtctgat gggcttccct ttgagggtaa cccgaccttt ctctctggct 178440
gcccttaaca tttttttcctt catttcaact ttggtgaatc tgacaattat gtgtcttgga 178500
gttgctcttc tcgaggagta tctttgtggc gttctctgta tttcctgaat ctgaacgttg 178560
gcctgccttg ctagattggg gaagttctcc tggataatat cctgcagagt gttttccaac 178620
ttggttccat tctccccatc actttcaggt acaccaatca gacgtagatt tggtcttttc 178680
acatagtccc atatttcttg gaggctttgc tcatttcttt ttattctttt ttctctaaac 178740
ttcccttctc gcttcatttc attcatttca tcttccattg ctgataccct ttcttccagt 178800
tgatcgcatc ggctcctgag gcttctgcat tcttcacgta gttctcgagc cttggttttc 178860
agctccatca gctcctttaa gcacttctct gtattggtta ttctagttat acattcttct 178920
aaattttttt caaagttttc aacttctttg cctttggttt gaatgtcctc cgtagctcag 178980
agtaatttga tcgtctgaag ccttcttctc tcagctcgtc aaagtcattc tccatccagc 179040
tttgttccgt tgctggtgag gaactgcgtt cctttggagg aggagaggcg ctctgctttt 179100
tagagtttcc agtttttctg ttctgttttt tccccatctt tgtggtttta tctacttttg 179160
gtctttgatg atggtgatgt acagatgggt ttttggtgtg gatgtccttt ctgtttgtta 179220
gttttccttc taacagacag gaccctcagc tgcaggtctg ttggaatacc ctgccgtgtg 179280
aggtgtcagt gtgccctgc tggggtgcc tcccagttag gctgctcggg ggtcaggggt 179340
cagggaccca cttgaggagg cagtctgccc gttctcagat ctccagctgc gtgctggaga 179400
accactgctc tcttcaaagc tgtcagacag ggacatttaa gtctgcagag gttactgctg 179460 tcttttttgtt tgtctgtgcc ctgcccccag aggtggagcc tacagaggca ggcaggcctc 179520
cttgagctgt ggtgggctcc acccagttcg agcttcccgg ctgctttgtt tacctaagca 179580
agcctgggca atggcgggcg cccctcccca gcctcgctgc cgcttgcagt ttgatctcag 179640
actgctgtgc tagcaatcag cgagactccg tgggcgtagg accctccgag ccaggtgggg 179700
atataatctc gtggtcgcc gttttttaag ccggtcgaaa agcgcaatat tcgggtggga 179760
gtgacccgat tttccaggtg cgtctgtcac cctttcttttg atccctgacc ccttggcttc 179820
```

-continued

```
ccaagtgagg caatgcctcg ccctgcttcg gctcgcgcac ggtgcacgca cccactgacc 179880
tgcgcccact gtctggcact ccctagtgag atgaacccgt acctcagatg gaaatgcaga 179940
aatcacccgt cttctgcgtc gctcacgctg ggagctgtag accggagctg ttcctattcg 180000
gcatcttggt ccgtggataa gccttaaaag gctcaatact tttttaaaaat ttcctataaa 180060 atccagaatc tatctagatt tttgagcagc ctgtagtggt tggaggacca tgattttttac 180120 tacatttggt cagcctaaac atcccaagca atgatttgtt ctgacagcag actgataaag 180180
ttttttttac tccttggaat cggaaaaaaa aatcacaagg gaagctttgg aagccacccc 180240
ggtagagctg gaagagaatt tcgaaatcaa ttcgctcaac ctctcctttta cggcaagaaa 180300 atgtgctaga ttggaggtga agacctggag ccagagagcc taggcttatc ctagccctgc 180360
actgaaggta atgtgaacac tcagtgcctc agtttccttc taggcttctg ttctgagatt 180420
catgaattaa tatttgtaaa tgcttagaac tgtgtctaac acattgtaaa cactaggaac 180480
aaatgctaag gtcatgcaac ttcatcaatg cctccctggg gtagaacgca gccttggccc 180540
atgggcattg ctcattcttc tttagacaag gctcttaggc atccctagag tgtgggttgg 180600
cttcctatgc ctgtacgtaa gaagtatgat gtaaatgtaa ggatatagga ttcaaaatca 180660
acaattagga ttcaaatgct aaatattatt gactcaactc tctgaatctt agtttcttca 180720
tctgtaaaat tataatgatc atacaaacca agtcacagac tgttcagagg agcaaatgag 180780
ataatgtact ttgaaaacca ataatctact ctgcaaatgt tatgtaacaa ttattgtgag 180840
ttcagcaaag ccatgagaat gtttcaaact gcttaggaca tcaagaattg gggtggggaa 180900
aattcttaat aggtttctcc atatcctcat tttccatttt tcattgtttt aaaattattt 180960
ttctatgata tacatatata tatatatata tatatatata cacaccacac aaaagaatta 181020
tgttacggtc ctgcattgct tgcattctga gaaatgcatg aataggccaa tttgtcattg 181080
tacaaaacat atagagtgta cttatactaa cctaggtgat atagcctact acacacctag 181140
gctgtatggt atgaccttttt gctcctaggc acaaacctgt aaggcaatgt tactctgctg 181200
aatactgtag gcaattgtaa cacaatggta agtatttgtg tatctaaata tatctaaaga 181260
tataaatatg tctttataag tataacaata tatctttaat atactagtat atattttata 181320
gatacaaatg tataaatata tctatagatg tactagtcta tatatttata gactagaaaa 181380
ggcacagtac aaatatgata ttattagggg gtgtggtaat tcatgcctgt aatcccagca 181440
ctttgggagg ctaaggtggg agaattgctt gagccctgga gtttgaggtt acagtgagct 181500
acgaacacat cactgcactc cagcatgggt gacaggggga taccctgtct ctcaaaaaag 181560
aaactaaaac aataagatag aatcttatgg gaccaccata atatattcag tctatcactg 181620
attgaaatgt cattatgcag cacatgacta tatatatgta tatatatata atatatatat 181680
atacacacac acactacata tatacaacac acatgcatat acatatgtgt tgtgtgtgtg 181740
tgttttgtgt gtgtgtatat atatatatat atattatata taatatatct atatatatat 181800
gggatataaa aaaatatcat atctctccac caggctcaaa aagggaacat tacctttgaa 181860
gtccctgaat atcccatcct agcaatattc tccctcctgg aaaagtggta aacacacatt 181920
gtaagtcatg tgtttgtctt tccttttgcct gtagttgcgc tacacaggtg tgtgcccaga 181980
aaatattctt tattgatgca tgggttcctt cttgactcag agatctcaag ctatacggta 182040
tcttcctgca gccttatagt gtccacctta ttctttgtca ctcatttccc tttccagcca 182100
ataagcacat tacctctgtc attcaatgaa ctcgtaaaga gagatttaga aaagagctgt 182160
tcacctcagg ttcacctgag caaggtgggt gtcagtgact gtggaaagtg gagcacagct 182220
```

-continued

```
gccagagcag cgcaaggacc caagaaatgg gagggtcttg actcgggata accatcactc 182280
tgagattcat tggatgtcct agattgtcac cttgccttac accttaaggg agaaaggata 182340
aaaagataag cagcaatgtg aagctactaa ggagcttaga cttttcctgc aggcctttgg 182400
gaagcaactg aagctttgaa gaagggaatg acagcttgag actgcttcaa ggcagaagag 182460
atagagacca gaagccagtg aggaagcact taggctggcc aggggtacag gtgtggctgg 182520
aagggctgcc cagaagcacc actgtggacc aggctgagca ggactgagtg actggttaga 182580
tataggaaat gccagagaaa gagaaggtgg tgatgatgaa atttcagagt tacctaaatg 182640
caagcatggt atgttcataa ccaaataggt agcaaggaga gctaggtttg agagccaaag 182700
ctgattagta cagaatgcga gtgttatctc tgctgtttca gaaaataaag attaatttca 182760
gccttaaagt cgggacttaa atgagatgat ctccgaaagc cctttccatt tttgtaattg 182820
tgcaatcctc agaacgttgc ccagaatcag taagcagaag caaagaaatt cggagtttga 182880
acattcagga gagctgtttc tctgatgcct gctccaatgg aactgggcac tgtggactga 182940
gcctcggctc actgagtctc ctcctgagga gtgtgataag aaacctcaca gggctgctgt 183000
gggtcttatt atcgcatgaa aatacccacc tcagtgcctg gcacattctg tgcagaaaaa 183060
gtttgatttc ctccctccct tccttccttc cttccttttt cctcccttg ttaccagtag 183120 gagagagtca gggctggttc cctgcggggt gctggtgtga aacctgctct ttagactctt 183180
ctgcagttcc ccaaagcgct actgtcccag agaactgctt tctgccagca atgctcagtt 183240
ttaccctaag acacgataac tcctggcttt gagggaagca caggtagcaa ggggacccct 183300
gacagcaaat gtgtagttgt tcttccagct aggccccacc ccaccttaaa tgccacagtc 183360
caggcactgt gtctacagtg ctgagataaa gcaaccccgt cttttccaca caaatgagca 183420
gcaaacatat tgctgattat ctttgaggga cataa                             183455
```

```
<210> SEQ ID NO 9
<211> LENGTH: 125840
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
aggtgacccg gaggccctcg ccgcccgcgg cgccccgagc gctttgtgag cagatgcgga     60
gccgagtgga gggcgcgagc cagatgcggg gcgacagctg acttgctgag aggaggcggg    120
gaggcgcgga gcgcgcgtgt ggtccttgcg ccgctgactt ctccactggt tcctgggcac    180
cgaaaggtaa aattgcagcc cctttcagat ccagtaccca atccctcgcc tcaggggttc    240
tgctttcttt gttcccctaa gagacctgac tgctgttcca gggggcaaaa ccacgtaggt    300
gggctagagt ttaggggctt cggaaactga agagacgtgg ccacggcgag gacgaaacta    360
gaatgggcct tgtctttta ggggttgct tctgatggcc acctgtatga cttaggaggg    420
agaggggcgc tgggacagtg ggtgatgtgt gactgttacg gcccagcaag ttttaaagct    480
gggatctgac tcagccctta caaaagggat ccggtcatcc tcgtcccacc gtgatgcagc    540
tggcaaggtt tgagccgagc tgtttccttg ttcccagcct tgctttatct gtgttatgtt    600
ggggtccttc caaggggcag gtgtttctgt gaaagtctga attcatttct ggcaatcacg    660
cggggcttgt gatccatcaa ttttccatcg taccttatct ctttctgggg cttgtggtgg    720
```

-continued

```
acatctatct tattaggtga aatagattat aaccagaggc tgagcgatgt ggccagtcgt       780
agtgctgacc cgataattaa agcaccagtg aaagtacttt ccctgactat tgtcaatgca       840
gaatttactc cgaagtacgg tttcccattc atatctttca tgtttttaaaa gagccatttg      900 ctaatttggc agttggagag ggctccaatg gctcacgcat gaatagttgc ccagtgtatt       960
ttaccttatc acagttttat gttcaaagga gccctcgggc agaatgaaat attgtcaact      1020
ctcttaggca aaataatcaa gatactttaa ttgctatgtt aagatggtcc atgaatgtga      1080
gaggattgta agaactgacg ttggaggcaa tatagactat ctggaccctc tcttgaattt      1140
taagaagact gttcacattc tgtagctttg ggtggggggtt tattctgtcg ctttcatcag     1200
ccagacacat gcacattgcc atgcaaatgg attcagaaaa acattatatt cccttacagc      1260
taaactatta tagctgacta atgaattttt tctgcatgaa gatgatctga aaatgatgta      1320
catcatgttt ctctgtgcta cagggacata aattgcattt ttatgtaaac agtgtaagtg      1380
gtgcttggat tatttacagg tacatagctt tccttccttg atctaagcta attgagcttt      1440
gttttgaacg tgtaaacttc cataatggaa cataagtgag gtactttggt tcctatcatt      1500
tgcaagtctg tggtgtattc aatgttcatt ctttttgaac tgctgaataa cagagggaaa      1560
atttacatca ttcataagaa attttggtag tacaaaaatg tgtctgatag cctataaaat      1620
gtactgctgt tttaaaaatt ctattccgtt ttcaaactta atggtgtata agctatagtt      1680
attaacttaa atatattttg cttttaacat gatggaattt gtggcatata gaagacagtc      1740
tgccgactac tgcttttttca aaattgcttt gttcttgata catggcagta ggggtttaca     1800
ttagatgtat actacatgct ttcaaaatta gttgatggag tttatcttca tgataaaaaa      1860
tgtaccagat taatcatagc cagtcaatac gaaagctcat aactaatatt ttcactactt      1920
ttaaacctat aatagagaaa aatgacccTt tgctaagcag gagaaatacc catattttat      1980
aaattccttt taagactatg taagtatatg ccttgcatta atcttgaaat ctttaaaaaa      2040
aaattgtctt aatgagggct agactaagaa atacatttca aaaatcaatt tccttagctg      2100
tttttaaaat agtgtttgaa gtagcattag tcatattatc cttctgcaga tctacataat      2160
agtctcaaat taacttttttc tcaaatgtgg tcatctcaaa acaacgtgaa taactcagag      2220
gagctaacat cctctaactg gcttatttttc tccaagtggc tgcaccaaag acatggcaac      2280
acccccatgg tgagcacagt tcctcacaca ttcagattac ctcccatttc tctgtcctct      2340
tcctcctcaa cccttttccct tggtttggtc agagctgctt tcaaggcctt ccgtgccccc      2400
atttctccag cccagtttgc tcgtttcttc tttaggcatt aggcttagtg attctcgcca      2460
gagccatcta cgctttcttt tccgtggtct aaatccctaa gatttccttg gtctgctgtg      2520
tttattcata ggatactcaa tttcctcatt gtgccctctt aagggggagaa aatgtatgta     2580 gaaactcaag tgtccggaag tgagccttct tttcctggct ggtgtatgct gaaactagtg      2640
tttttgacac caagccctta gggcagagtt tcttcatggg ttttgctcag tgcaaaataa     2700
atagtcactt ctcagtaata aatgatagat acactgacta atgttagttc agaatcactt      2760
tgatgatgtg ttctcaactg acactgagtt gctgctagat ccacatttgc ctgaccaaaa      2820
atagctagga cctataggta gagtatcata tgtgctaggt actacagcat tttctttaaa      2880
agaaagaaat ggaatctgcc cttgagaagt ttatgatcta gatacacaga caaatatcac      2940
atattaaatg aacacaaatt cataattatt aagaggacat cacatgagaa acgctttcaa      3000
aatcatccta tttgctatga aataatagaa ttttttttta aaaatcaaag tttggaactt      3060
aaaaacctta acattttcaa gctgtttctg catacatcac ctttctgata ccaaaacgac      3120
```

-continued

```
cttacaagat aggcaagtct gataacatct taacattctt atgttataga caaggaaact    3180
gagcttgaga ctagctccat gctatttcaa tagcaccata ccaccttcc tcagccatca    3240 actattggaa acattttcca tggaggcatc attagggatg cttaagatag tggtaaatga    3300
tgaatataac atatctagtc cctggagttt ttgtcacctt ctctttctcc agttctctct    3360 ctctttttt ttttaattt ctttttttt ctttttttct tttctttgta gtgagacata    3420
ccgagaaaag gtttcattca tatgtgtggg gcattctgct cctgttatca gattaagagc    3480
cgtgaataat tttgtaatct atccttctat cagaaagccc attctcagat atcttttcag    3540
ctgtgttaaa caggttagta tattccgctt gggatttgtt tcaataaaaa catccagtaa    3600
aatctgacta ctttgctttt catgggacaa aatgaaaaaa gtgcttttat aagctgtaaa    3660
acttaattga gagaaaaaat cacgtgtggc atttgtagca ggaggtatga gctcagtgaa    3720
ataaaaaagt taactttgta atcacatacc caggtacaca tatttctctc tgtgattgca    3780
taaatgtgtg caagtatgtt tatgtaggtt actcccattg attttaattt ctataataaa    3840
ttatgtagct atagggccca caggcgatta tataatgggc aatagaattt gaaaatgtat    3900
ctctcctaat ataattaagg atagcaatta tgaaatgtgc ttagagaatc acaagttatc    3960
gtgaaagcca ggttcctgta ctccaagaat gtgaatgagg atttagtcat tcattcagga    4020
caattttttg acaacctacg aggcatagtt ctaaaatctg gcattccac agagtataaa    4080 acagatgaaa acctctaacc tcatgacact ctgttctatt gagttggcaa acaataaaga    4140
aatacataac tgaaatgtgt tgtatgtcag gtgatgataa tagcttcaag gtagaataaa    4200
atggaaaaga gaatagtgac tgtcaaggat aagagagagt gggatggtga ttgaaaaact    4260
caatagtgag gtcagggaag gcttgtcttc aaaggtgggc tttgggctag aatctgaagg    4320
agataaggaa gtgagccagg cgcatatgag gagcacttct caggagtgct attctcatct    4380
tgtttttcct gaaattgtgc agttcacagc ttgcacaact gtccatagac tccctgattt    4440
tggagggaga tacctgaata gtgcccctgt ttttgtaggg aaatacctgg acagtgcctg    4500
ccatcattag ctaccatgtt aaagatgaag atacaggagt ggcccacatc tcttggttta    4560
tgagacatgg aagaagaaga cccagagtgt tgttttgttt ttttttttgt tttttgttt    4620 tgttttgttt tgttttgttt tgcatccgcc tggtcccatc ccatactcca tcctctatca    4680
gagatattgc tccattcaga caattttcct tcttattttc cacactgtga gcctgtcaca    4740
gtgggatttg ttgagaagga tacccatggc tttttcact gatcccttcc atagtataaa    4800
tctaaagaca gcaagaggca gttgctgatg gtgtgcagct tctgtctgct atgcacttct    4860
ttctttcccc ctcgctctcc ttccttttcc tttccagtat taagtcactg cattggattt    4920
tcttcctctt ttcttccttt tcccttattc ccctatttat atcctgtatc aagatttgca    4980
aacaggtaac ttaaatgagg aaaactaacc atttcactag ggattgacaa actgcttagg    5040
aaaagcagag gggcagtcac tgcttggcgt gattagagct gttgtgaggc tcagtgtatg    5100
gcatgggccc atgtggtagt atctttcaga ttttcaagag aagctaggac tctcccaatt    5160
ttaaaatgtt gactcagtgt ctttaaaaca ccatacagct tacagtggca gaaagtctgc    5220
aagccagatt gggctcctga tggtcccaat tgcagcagca tgcatggccc gagagcccca    5280
ggactgcttc tacaaaatat tttattttct aaaattctca gaaaattaac taaacaaatt    5340
ttttaaaacc aatattttat gtcagttcct attggcacgt ggttattttt ctaaactcat    5400
cagcccacat actttacatc aaactatgta cgtttctaaa ctaaagggta atctagttat    5460
```

-continued

```
ttcattctta aactgaagta gtagtttttct gaaacctgaa tccatcatgg ctttatgcat   5520
caatttcatt tccaagttct ctgattcagg ataaactccc cctttggaat attgtctttc   5580
tctctctctc tctctgtctc tctctctctc tgtctctgtc tctggaaatg actgaacttc   5640
acccgttgtt attaccctgc cattgaaatt caaaacatgc actgccctcc tggtttccag   5700
tgccctttaa aagcaatcag atcagtgtta aaatctattt ttccaaagga ataaaagctc   5760
acaggttgtg cactaatttg tttcctttaa tcctaaaatc tcagtgaaat gcccaagcta   5820
gcagccctcc agaaggccac tgtgttagaa agggagatta tgtactgtat ttcttcctac   5880
tattttaaat gcaaatataa taatatatca tgaaacagtg cacatacagt atacatatta   5940
agatcagtgg tctattcctg ttttgaaatg gtctcctact ccttaatagt tggaattctg   6000
aggcagcacc tagactctca ggtccaattt gaaaatgtat gttttttttt aaaaaagaat   6060
gacttgggga ataactgttt gataagaccg tggaagattt ctaatttta atatttattt    6120 aaaaatgtaa agaaagacat tcaaagctga gacctttgaa ataatatggt ctttgcaagt   6180
cagagaaaaa gagaagtggt aaatttatta gagataggtt gcctcctttg aggcctaatc   6240
atgtgggaaa ggaaaaccca gccaaggttt gggtccataa gacaattcaa cctagcttta   6300
aaaataggtt ttggctttgc ttgggaccag cattgggacc agagtgtatc tagaccagca   6360
ttttagctat taaattttaa acctaggggt ctttttaaggg aaatttaatc catgtgtctt   6420
tgattcacta aatcttaaat cattactcac aaactgtatg tccctctaag ctctttgatg   6480
tccaagagat ctctaaaatt gtgtaaggcc tttttgttcc agaaaaaaat aggaagttgg   6540
tttttgctaa gcgtcaataa acagcatcct caaaaatctg attaggtcta aaatcttgca   6600
accatgacag tatggatgtt tgaatgatgc aatgtgaaaa ttttaagcac tttttaaagt   6660
ccttgtttac cagtaatact cagttgtaat ccttactaac cccaaggaaa ttattttgac   6720
acatttcctc tctgtttgt aatataaata caaagcccaa atattcatca ttttattctg    6780
gcacatagta ggtactcagt aagtattttg tagagtgttg aatgactctt cttctgccc    6840 agaaacttct agctaatgtc agttcttcta ttcaatattg atatccatct gtcatacctt   6900
ggaataagat ctattctaag tcagtgacct tgttcgacaa attttttaaaa taagccatct  6960 aactaaatat atgacatta ttgaaattca ttttgcacca tgaagcaact gccttgcaaa    7020
gagtgctgaa aataggaagg aatttctaga ctaatttgat taaatattca gttgttgcca   7080
tatgctttct gaaaattgat tttcccccttt ttactattcc tgtcatcctt cctcccacct  7140
tgacatgctt actgattgaa agctatgcac agaaaaaggg caggtcgctt gtatgtataa   7200
gcaagagcag caagtccaaa caggcttaga aaacgtaatg ctataatcac gagttgtcat   7260
aatataggag aggggagaga ggaatactca gcaataagag tggtgttggg tattgctcca   7320
aattacatgg atgacacatc tttgaactct attgtgtcgg gggaaaacac cttcttgctg   7380
tagttagatt tcctgtttgt gaatgtgtat tttctggtaa ccagacttcc tatatgaatt   7440
tgacatagct ttaagtgcat ttcaaatgac atgattaaag aatggctgct ttggagacag   7500
cagctccttc tctcttaaag aaataaaacta tcatgctaaa atataggcat tgagatcttt   7560
cttgatacca tattgtgaat ttctaatggc tcatcacatt tttatcctca gaaaacctttt 7620 cctggtgaaa agcatgctgt tttagtatca catttggggt gatggaattg gcaatttctt   7680
atatcttgag ggggcggggg ggtaaaagga aaattgtgtt aatagggtct taaaatagag   7740
attctcttag gttaacctga agatttacta aatacattat cattacagct tgttttgaca   7800
tttaattgta gatggcactg tatcagcact gacttatta tacagctttg tttagacatg    7860
```

-continued

```
cctaattttt atttcattgg tggaaccaaa ccatcagtaa taaatcatat atcagtgttt     7920
ttgtacacat tcgtatttac atgactttta aaattccaat gtaaaggtct cacaacttga     7980
aaaatgaatg aatgcctgag tatttgaaca gttgggaaaa tgtagttcaa tttaagaaag     8040 atttttatg acaattctta tgccatatat agaaaataga taataaagga gaaggcctgg     8100
aggtttagat gggatattgg atcaatgagc aaaggaaggg gaaaggtggg cgggatatgc     8160
tgaagggtca tgggcttgag tgcaccctaa gtcataaaga gggtgtccca ttaagaatca     8220
ggctgcctga attctaagta ggaaagaggc aggtcaaaat ggtgtatagg ccaggcacag     8280
tggctcacgc ttgtaatccc agcactttag gaggccaagg tgggtggatg gcttgagctc     8340
aggagtttga gaccagcctg ggcaacatag caaaacccc ctcttaaaaa aattacaaaa      8400
agtagctgga catggtggcg cacacttgca gtcccagcta ctcaggaggc tgaggtggga     8460
ggatcacctg agcctgggag gccaaggctg tagtgagccg agatcatacc actgcactcc     8520
agcatgggtg acaaagagag accctgtctc agaaaaagtg ggggagggag ggtatggaat     8580
aaagtaaagc tcatgggaaa atggtacctt taccatttc ccaccttggg aaatggtggg      8640
aaaatttaga cattgcttta caaagtctaa atttctgcca acttgtgtta catgtggttt     8700
gattctggag aaagatagac tatcatctat ccagtcctaa attgggcctc ttagtctgtc     8760
ctcccctcag ttaccaggaa gaatagcagg aatatgtcac agaagcagag aaagctttta     8820
ttctgagtgt cagaggcatg ttctaagcac tctgttatct actcccaggc actctaaatg     8880
aaattccatt ttctctgagg aaatcaaaat ataaaaagaa aactcaggca aatttataaa     8940
ggttttacac cattttcatg actgaaatat tctagcatat ctagctcatt ataatctata     9000
aattcctgtt gggaccaaaa gttatggccc taaaacctgt tatctgtaat ccttttccac     9060
tgggatattg tctctgggga tatatattag ctttccttga ggatactacc ttgaaaccat     9120
ttctttggtc cttgactata caaagttcat actagcatgg atgtaggaat tgtattttc      9180 tattctaaat acgaatttag acagtgatat aaagattcaa ggaaagcttc tatcaaggcc     9240
tgccttcact acttgtcttt tggctcctct gagggtctta ggtgagccac tttcatctga     9300
ttctgccctc acttcaggca gaattcatat ggctccagcc aatggctaca ctgtccaaag     9360
tgagactgtg gtctcacaac catctggtta atacaaagac agcaagccaa tatgatcact     9420
taggacctag gcaaaccttt gggcttaaaa tattaccttta gctattgttg ttttttaatga    9480 gtatcaaata gtatgatatt tgtaatttgt attatgtaaa gaagtaacca aagcagagat     9540
tgttgacaaa aaaaaaaact tcctcctaac ataaatgaat atgcattttg gactttttcaa     9600 aaattcccctt tctgtcttgt caaaattaag atatttctaa attttatttc ggtctcacta     9660
acacatactt ggattattgt tcattgaaat ctgtacgtca aggcccagtg attttaaaca     9720
ttcttttggt cttcaaagaa cttaccaaaa aaaaattgtt ctttaaatca ccagaaaagt     9780
gcagataaaa tcccagacag tttcattaat gacaatgaaa ggtgacagcc cttgaatcta     9840
tgtcataagt tgattaatta ctttccaaac attattaaag atattagacg aataacttag     9900
actggtatcc aggatcaagg ttccttcata atccctaaat gggtttttaat tttcagagtt     9960 agatgatcat tatatgtgat ttatttcttt aacatcttta gactgttggc tttattgaaa    10020
agagaggaga gtatctgttt caatgtgttt tcttttccct gaagttattc cttgcagaat    10080
tcaataaaac cggttttgaa ataaaaataa ttaaatgctg gcattttctg ttaataaggg    10140
cccatagacc tgatgaatta tataaacatt acaaggaatt taccactgag ttcataatta    10200
```

-continued

```
tgtaaccatt taatgcccaa acctgcctac tgacagtgaa gacgttcaat gagaatggac   10260
attgtgcatt aggataagga tgacctggag tgaactttca ttcttgtttt ggttctttcc   10320
cattttgccc aattcatagc acctgattct cttaaccagc aagtctgttt gcatgtctcc   10380
agtccaattt ttcgccatgc ccactgcagt gattccaaac tctcaccatt tcttaagctc   10440
ttgcatcttt tgggctctcc ttattctcag tataagatct ttccttatag tttagagagt   10500
aaacacaagc ccagttgttt ccatgtcacc cattattacc tctttctgtc tcaaaggatg   10560
aaacagtctt ttctacctaa gtcttgaccc tgttgttccc cacacctgtg agcacctcct   10620
ccctctatcc tacccacctt acaactcttc ccgtgtttaa aatctccctc accatttttc   10680
ttttttaaaa aaattatatt ttaggctcag tggtacatgc gcagatttgt tacataggta   10740
aactcgtgcc acagggttta tttcatcacc caggtattaa gcctagtacc caatagttat   10800
cttttctgct cctctccctc ctctgccccc tcaagtagac cccaatgtct gttgttcctt   10860
tctttgtgtt cataggttct catcgtttag ctcccactta taagtgagaa catgcagtat   10920
ttggttttct gttcctttgt tagtttgcta aggataacag cctccaattc catccatgtt   10980
tctgcaaaag acagaatctc attctttttt atgtctgcat agtattccat ggcttctcta   11040
tttttcattc acctcttact caacttactg attcttctag aaagaaataa aacacacaca   11100
tcaggcatcc tgataggatc ttgaatacac aatttcctta agtagtcact cctgttttca   11160
ttttagcctt taaataatga attcttgaaa ataaatgtct aactcagttt ctctactttc   11220
ttcattccca ttcattctta agtcattcaa ctcaagcagt ctgtaccaca tgcccaagaa   11280
agtgtcctca ttctaatcac cagtgccctc ctcatggcca gatctgatgg acactggttt   11340
ttatcccttt tgacccgtct gtagaatttg acaccataca ttttatttct cccttctcga   11400
aagttctcct tagcttatct ctccacattt tctttgccta caattgttct ttttaccctt   11460
taaaacataa aggttagatt ctagtcttct gtaaggctcc atctgaattc ctcctttcta   11520
cttacaaaac acattcacaa gtgatctcac ttcagtgact tccaatacac cgatggacga   11580
gtggttcaca aaccgctctc tctcacttcc tcttttctct agaccaccac tttcatgttg   11640
tcagctacct tacagactcc accacttaga tgaccagaag ctacatcagg gttattaact   11700
caactaatta cttttaccct caaagtctcc tctccctatt ttccttacct tggtttatga   11760
tacccagata gacaattttt tagccattct tggcttttca gtctcctcta caatcaaaat   11820
ccatattgaa taattcccac ataatttttc tcactttaat atgtgtataa tctagtcctt   11880
cctttctttc cataatgcta gaaactttgt tcaggaacat tcttttgtat attgattgat   11940
tctgttgtcc attcattcaa taaatgctta ctaagtgcca tgtaatgaca ctatgctaag   12000
ggctaaaagt ggagcttaca ctctgatggg agacacagat aaataagtta ctatatagtg   12060
tggtaaaggc tagataaggg gaagacaggt ttgatgtttg agcacatagg agagttccta   12120
attccttact agaaggtaag agatgcatca gagaaggctt cccagaactg ttccctaaga   12180
tgaggcttga agagagagga caacttatcc atgtgaagtt gagggcaaga atatccataa   12240
agagggatcc acatgtgctg aaacccagag tggctgagca catggcttgc ttcaagaact   12300
ggaagagggc agagtggcca gagcctagat ttctaatggt gtgatggcaa gaggcaagac   12360
tggagagtgg ggcagaaaaa aatggtatgt ggtttgtaag ctctgccaag gggttgacat   12420 ttttttttcag caaagaagtg acatagtcaa attgtcagtt tagaaagata tctctggtat   12480
gctagggggc agatgatcag ggtgagaatg gagagggaag accagcgagg aagctgttgt   12540
agtaatccag gtatgaagtg acactgccct gaccatgggc atggaagcca ataaggagat   12600
```

-continued

```
ggacatgttt aaaatatttg taggtgggtg tcaaagatga tgtcctagaa atatgggaca   12660
tgttcagcac tgaggtagga tacagagagg gagaccaggt tttgtgggag tagatggaga   12720
taacagaagg atatccaact gctccttctt ggtctcttgt cccatctgtc tttgtctcct   12780
gacctattag ctttggtggc gccatcactc agtcctcctc tcttcattct ctacagtccc   12840
tctcctcgga gatcccatcc actctcatgg cttttcatga tgtctacatg ctgacaactt   12900
cttaatttaa atctctagcc cagacctttc tccttaaccc cgggactcaa acatccaact   12960
gcatgcccgg catctccact tagatgccta aaaaatgtat gtcaggctga gtgcagtggc   13020
tcatgcctgt aatcccagca ctttgggagg ctgaggcggg tggatagtga ggcgggtggt   13080
ggtcaggagt tcaagaccag cctggccaac atggtgaaac cccgtctcta ctaaaaatac   13140
aaaatttagc caggtgtggt gatgtgtgcc tgtaatccca actactcagg aggctgaggc   13200
aggagaatcg cttgaacttg ggaggcggag gttgcagtta gccaacacca catcactgca   13260
ctccagcctg ggcaacagag caagactcca tgtcaaaaaa ataaaaataa aaaaacctcc   13320
attgtgggca aaactacatt cctggtctcc tcatatccta caaacatgct tcaccaacca   13380
gagtctgcat gtcggtaact ggcaaagcca ttctctctgt taaaaaagtc aaaatccttg   13440
gcatattctc ctttttttct cacatgcctc agatctgact ccatcagtaa atccggatgg   13500
agttcgatct gaggcatgtg acaaaatagc tctgtcttca aaatagaacc agaattcggc   13560
cacatctccc cactctcccc ttccttcctg gcccaggcca ccagggtccc cctcctggaa   13620
caccactgga gcctcccagc tggcctcacc actccacctt tgccctgaac tgcccccag   13680 ccactagcag tcttctctcc catatgatcg aggtgaatac attccaacat aatccccct   13740 tgttcaacac cctgcaatga ctccccattt cactccaata aaaacctgaa tctcccaggg   13800
gcctacaagg ccttacatgc tctgcttctt tgtccttttg atctcagctc ccggtcaaca   13860
aagtccaggc ttactggccc ccttgctgtg cttcagacac accaggcaca tttagttctt   13920
ccttcttgcc tctgcccaga aatctctttt cccatctcag acatctgggt ccacaaaagc   13980
caccttccca atttccgagc tacaaaccta tccccatacc tctcctccag gcagttctga   14040
tgccccagcc ctactttttg tttttccctg taacacacat caacttctga aacactacat   14100
catcagcttg ttatgggtat taattgttgt ccccagctaa aaagtaagtt ccacaagagc   14160
aggggtgttg ggttttgttt actgatgtat cccaagcatc tgatgcatag taggacccca   14220
gtaaatactt gtcaaatttg gtcttaaata gctgttgcat agacaaaagt gatattggag   14280
agatggattt cgggattctc tggagatcct tcaacaaaac atatcagact ttctttaatg   14340
tggccacagc ctaatcttat accttttttcc actgtcaacc cagcccacct ggcctctatg   14400
ccaattgcag cttcctggac aaccctgcat cttctcccca ggtgcccgtg tgtgagtcca   14460
ctccacccaa agtgtctgtc ccctacctca gctgcacctg agcagctcca acttatcctg   14520
caagacacag ctcaagtagt atccctctg aaatactcct tggccccgct ttctgtctgc   14580
atagttagct cttctccccc gtgctgctcc actgacatgc gcacacctttt acagcacagc   14640 ctgggcgtgt tgcaggtgga aggtggagat tcccagtcaa ggggcaacac ctgtatggtt   14700
ggaaaagttg tttgttttaa tttcttgccc tctcttctct cttctatttc tttcctctcc   14760
cataaataca cataccgcct atatacacac aacctgccct gaattgtttt ccttgaattg   14820
atgagttacg taaatgcaat cctaagcaca gttgttttca ggttgtccta acctttttgct   14880 ttattgattt ttcaaggatc cagagtgttt actgagtttc agaaattgga ttctgtactt   14940
```

-continued

```
attttttctgt actatcctag ttttatgaga atctatttgc tcagcattct ctattctttt   15000
aaaagtgttt aagatttttg taaacagttt tgtttggttc tttattttct ggtgacatat   15060
tgatctcaac ataatgctat tcatatactt ttaattcttc ttccaacact gttaggattg   15120
cattatgttc acccaaggaa tccacatctg tacaaaatgt ggccaggttt ggctattcct   15180
tcacattcac agtattctca tgatttctaa caattcttgt ctactttgcc taaataagaa   15240
aatgtcatat actgacaatt ttgatcgtga aaaagagacc ttagttcata ccagtgtcag   15300
agtctacttg caaacattga tttccaagaa aatttctcag gtgtgagcaa ataagcaaaa   15360
taaattcaga cctaagagaa aatagcacta caaggaacgc ccagctcatt caaacgctct   15420
gcattttgag actagagggg gcttggcctt tggcaccctc acacctctcc cctttgtctc   15480
tctgtccctg ggtgctgatt tctctttctt tgtgtgacag ccactgtgaa aagaatgggg   15540
ttcactcacc acctgcattc ctccacagcc atttgatatc tgctttcgat aacagcagag   15600
gaaactgatc agtcatataa atccaatcct gagcatagtt cctcgtttgg aattgtacca   15660
tgctttatgc cgaggacatt ttcaaacacg gagggagggg atgtctgatt cattcgtgag   15720
taatgtacca gcttcctctc caacttgtct cccttcagtg gttcacattc tgactattca   15780
gtcggtttat cctttccaaa cccagtattt gaatgcaact ggcaaaggtt gattgcctct   15840
tttttttttt aatatataga cttggaaaga tgtttctcaa atgtgatttg cggatttatg   15900
ttattcagtc ttcctggatt aattgaacaa aaactggtaa cactgctaca cagtctgaat   15960
cacaaaatta tgtccatcca tttggctgaa aaatacgaaa acaaatactt gtataagttt   16020
tcatgcattt tagcactttc tttacattgg ggaagttcaa ccttcacact ttcaagggca   16080
atgaaacatt tttgtctgac ctacaattta ttaatgggac aaaagcccat ctgtcaatca   16140
gggctctgag agttcaatgt attttctgaa caatattttt tacattatgt acaatggtaa   16200
aaacaaatgt ccatttattc ttctttccaa gaagttgagt actttcaacc attcttaaaa   16260
ggacaaagat gtttgctgac agaatatgaa tttataaagg ataatcttga ggatataatg   16320
gcattctatt cttttttatct ttactcttgc catatcagag ttggataata gtctcaatca   16380
tatgttacaa ctagaaaatg cacaattggc tttttcttat gctaacaggc agccatttc   16440 aactttttaa atgattatag gactaagagg ggatgcaaaa acagataaga atctgaataa   16500
aagcactatc tgtcaaagaa acaacatttg tgtaataatc aagaaaccgt ttagagcacc   16560
ccctggaaac attaattata acacatgcaa atcattcctg tacaaagctt aacttgttta   16620
tctcctatag ccacctgtat ttgaattttt taataagctc atttattata aataaagcat   16680
gtaaatcaat ctgggaatac cttttctgtt tcagaaattt catgtaaatg acaggctgcc   16740
acatacagta caactataga ggggaaaaag tttctttact ccctttcata tagttatacc   16800
ttcatatgac acttaaaacc acctgccagg aacttttaaa acatgtttta gatgcacaga   16860
agcaaaccca aatgaaaaaa tgctatgcag ttttgcaata catatatacc acagaaagct   16920
ttaaaaacat tctaccccaa cagataaata gatttggccc aaatcttttt aatgtgagtt   16980
ttgtgggtaa aaaagattat tgttcccttta ttttttcccca tttgctgacg actaggattg   17040
tcatataaaa tacattcctg ggacatgctt atactaaaca aattatccac tgtttatctg   17100
aaattcaaat ttaactcagc atcctatatc tttacttgct aaatctcagt tgggatatgg   17160
gcttactctt ttttttttttt ttttttttttt tttttgagac agagtctggc tctgtcatcc   17220
aggctggagt gcaatggtgt gatcacggtt cactgcagcc tcaacctccc tagctcaagt   17280
gattctccca cctcagcttc cacagtagct gggactatag gcacatgcca ccatgcctgg   17340
```

-continued

```
ctaatttttt tatttttttgt agagatgggg tttgcccagg ctggtctcaa actcctgaac   17400
tcaagcaatc gtctggcctc agcctcctga agtgctggga ttgctggcgt gagtcacagt   17460
gcctggcctg agctaactct tttttaaaga gttaaaatac tggttcctat ttgtttttac   17520
ttctctagta tgggaggctg ttactgtggc ttctgtcttg gggggcaatt ttcgaagggc   17580
ttcaagaact tgaaccgagg ttagaggaaa accacaagat ggctaaaggg tgggaaaaga   17640
agaaataaca ctatttaaac tttagatgag aggactaaag tgatgaaaca gtcaccaggt   17700
atttggagtg gtctcaccca agggactgtg ccaacttcct cattttttat gagggcaggc   17760
aaaaactggc caaaacacaa gttaggataa taagcatagt agctattatt aaatgctagg   17820
gtgtgctgca taactgaagg acagtgtttc tcacagttta tctccaactc tcatggccaa   17880
cccatgagat gtatatcatt atccccacgt tttgaatata agaaactgac actcaaatca   17940
gaaggcatgt cagtgaaaaa ggccatattc acatcccatc taagtctgtc tgacactaaa   18000
gcccacactc tctccactac actccacctt gtctccagaa tgttttgggc tgtttaaatg   18060
tgattatacc aaagagcagt tgaatgcact gaaaaattct gaagattcct cctgtccctt   18120
cgattcactg ttggaaacca ttgtcaaggt agtgtctggc tacgatagaa gggatttttg   18180
acatggccta ttgtttttatc ttttttaaagt aaatgtaggt gcttttgatg atcataacac   18240
taactgttaa gtctttaggc ataagaatca agcattcaac taagcatgtt tacaaatttg   18300
ctttcagccc agtggatcta tccactttttc catttaggtt gcacatttag atttcggagt   18360
ttatcctgtt atcttcaaat ccacggactg tacactcttt gagggaagaa actcttagta   18420
tctagtcaag tacgtggcat gcaatgggtg ctcccaaata cttgattaat atcatatgat   18480
ataatgtaat atgattcttc ataaacagtg agtgtttata aatacagtat tttaaatgtc   18540
attaggaatc ttctattgga atcttaactt tattttaata gacctacttt taaagttaat   18600
aaacataata taaatgtgga cagggctaag atttttccct aagatttcac tctggcaagt   18660
cttcctggag atttagccat ggctattttt atgactgtaa tttccttaat atggggcctc   18720
agccatattc catcatcata aatcccttttc ttgcacttaa aagcaatgtt gaaatatttt   18780
ccagtttcta tatcttaact ctttacttag atccattatt tccattttga gattatctta   18840
tgtaaatatt gtagaagatt ttagaattat ataataagaa aatactagta taccacctca   18900
gaaatcttaa ctaatagata tgttctcaaa tgcaaagtga aatatttaaa gtaattattc   18960
aagtaaataa agagaccatc tttgtcccaa ttacttgaat attttacgta aagttggttt   19020
tatgcacttg actttgtgtt taaactcaag tttgtagtat tgtctactgg acattgttag   19080
ctcaggacct tttcaggagc aaggaatgaa agaatcattt ttaaacttat ttaaaaaaag   19140
aaataaggaa gaaaagaaga aattttactg gctcgcctta gcttaagaca tggctggata   19200
cagatgctca gacaatcaca tcaggagcct gcctccctcc gtgtctgggc tctctggcct   19260
cttgggtcag tttcatgctc aggctggctt tctccacata gtggcaaaga tgggcatcag   19320
acatcccaag ttaacatcat ctttagtgct catgctgtca gaatgaaaga ggccctctcc   19380
cagcatccat attaaatctc caaagagatt ctgtttggcc ttgctttggc cacatactca   19440
accctgacca agctccgtgt caagagaaca gagttcgttg aaaggccagc ctggtttgca   19500
cactcattct gtgttgaaag atgtagacca tgtgattgac agtcccagga gataggagag   19560
ggagaatttt caaagagtt gccggtataa gagacagtgg attctgggaa ggtaaaaaga   19620
ggtatttatt aaaatactgt gcctttggaa taaaaatctt ttccaggaaa tgcaaataat   19680
```

-continued

```
ttaaaacaat tcaaataagg atcatacatt ttaaaacaat tagaaataca ctcagaagaa   19740
ctgaattgct catttagtag atttcagata atattttctc ctctttgaac ctcagttttg   19800
tcatctggaa acacaggata atgcttacct tataaggtaa tcatgattag aagagatgat   19860
ggagctgacc atatctattt actataaagt gctatctaca tagttataaa ttatgacagc   19920
taagaaaatt aatccctaaa gaaagcaaaa ttacctatgt cacggtttag aaagtctctc   19980
tcttaagaag aaacttattc tattgcctct gttgggtttt ttcctgagga atcggtgttt   20040
gaatgcaata tacatttttg taggctctgc aatgttttta tgatgaggac agtcatagtg   20100
ttgacaatta ctcaatgaat acttagagat ttgaatgtat cgctagattt ctgggaaatg   20160
aaaagaccaa tgtaagctag ttgaatgaga aaaccagagg tgggcagatg gtggacagat   20220
taagtcgctg gttttaaagg taggctgaac tggtatttgt aactattaat aacagccatc   20280
ttctttaaag gaagtactcc taaatatcaa tagtttagtg gccaaggtgc cattgagatg   20340
atcactccca ggaaatgttt tgccagtgat attaccttaa ctttcatctg aaaagaaata   20400
aagaaatgtt ttatggatga ttcactttca cctgatatgt gcacaacatt ttaagagaat   20460
gaattagtca gtctgtttga atcatcttta cgtgttcctt ttagcaggga actcaaagtt   20520
ggttaaatgg ctagctctat ttcagaaagc aaaaataaca gaaacagtga aaagacagtc   20580
tatattgaaa gcctgatcca gacacatcat gggggaataa atatatcagg acaaaaatat   20640
atgaaaagtg aaagtatttc tggagtattt cactaccaat ataaatatta aaatgctcac   20700
acagccagat ctggcaagtt acatagatga ggaagtgaaa gcaataatat gccaagtcaa   20760
tggcattggt gtaaaatgta atcatagagg aacaatctca gagttgaaaa ttattagaat   20820
tggaaaacac tttgaagttc tttagttcca cccaggagta tgccattaaa tatttaataa   20880
ccatccctct gcgggcttta ataacaagcc ctgatttgta gtgtttgcca atttctatgg   20940
tgtcaataca gccaccatgg ctgatttttag gctaccaaga tgaggtcact gaaacacaag   21000
ttgggaagag atgcacatag taggctgtca tgagccagca cacagctggt tcagcattat   21060
aattttcaaa taagaaagca gttgacctca gaggagttgg gtgacttgcc tgggtcatac   21120
aaataattag ctgcactgcc acaactaaac ctaggccctc tccagtgttt gacctcagaa   21180
ttgtgaatgc attatgagga aagcaccatg attgattgat tggtaagccc acgtgacttt   21240
ctgtcctagt taagttcccc tttaagggcc tccatagaca tttctacatt gagtttaaac   21300
tatagtctgc ctatctccac tactggcctg agatctcact gacatttgga aagcgtttta   21360
tttatctttg tatcttcagc actctgtaca gtatctgaca cttagatgct tataagtgtt   21420
tgttgggggc catgtacgaa caatagagaa catgcattga cctgctatgt gccaggcagt   21480
gttcttagtg atttacatgc attaacttat tgaatcctta gaataactct cacaagtgag   21540
gtaggtacta taatcctgcc catattttag atgagaaaat acaggcttag acttacttgc   21600
ctaaggtaac atggacagtg attggattta aaccctaaaa tctggccagt gcctgtgcac   21660
ttggcctctc agttgtcact catttaacta gcagttatca tcatagtgcc cagctcagcg   21720
ccaaatactt ctaaaaggtc tccctccttt ccttaggaag gacacaaaac gtttcccaga   21780
aaagatctga tctgaccaac acacaccttt gttaatgggg aagggccttt attaatggga   21840
atgatcaagg aaatggggcg ttttttggtga ttacattttc tcattatctg aggtttaaac   21900
agaaacctct agtttaatta aaatttctgt tgctgacaat aggccctagt cccatttttt   21960
tctttaatta aaaaagttaa ccttttttttg atgtattcac ttgaaaaatg gcatcaccat   22020
atggtaacag ataatgtaaa gaaggtgtag gagattaagg tactaactcc aactgtgttc   22080
```

-continued

```
tgtgagggtt tttctttaaa tagaaaatat attcttcttc cccactgatt ttccatttca  22140
tcaaatgaag taacaaaaag cctatttcta catgtgtaca ttttcttgga ttcttgtcca  22200
ctgagattta gtacagtgtg tgacttatgt gcgaacctta agatatgaat cttattttaa  22260
aaacataatt taatataata tctctaattt ttttgttttt gtttttattt tttttagatg  22320
gagtctcgct ctgtcatcag gctggagtgc agtggcgcaa tctcaactca ctgcaacctc  22380
caattccctg gttcaagaga ttctcctgcc tcagcctccc aagtagctgg gattacaggc  22440
atgcgccacc acacccagct aattttttgta ctttttagtag agacgggggtt tcaccatatt  22500 ggccaggatg gttgtgatct cctgaccacg tgatccaccc acctctgcct cccaaagtgc  22560
taggattaca gattattttg aaggctcctt caaaaagcct agaagaaaaa atgtcattca  22620
cacttcacac tgcattaatg gacatcaact aacatgcaaa ttggttacaa tattttttctc  22680 ccttttggca ataataattc gtttcctttc tttcattata atttctacag aaaatacagc  22740
aataaattat atattaagct caattttgtt agatacactg ataccatatt gataagtgca  22800 gttaacttttt cacataatat ttattttttcc cattgtgctc tagatggttt agatacatat  22860
ttgcagtttg gtttacagtt tgtatttgcc ctctagtaca acaaattgtc cctaatcctt  22920
ttcttctatc ccttgttatt ccctctacca gcaccaaaaa tttgctagta cattgcaaaa  22980
caatgagaat tacagataaa atagcaagca tttatatata ctctatattg atcaaagtgc  23040
tttcagagat gagatctctt tttgatcctt aaaatggtca cgtgagaata tctgaccctg  23100
ggactcagag gtgggtgatt gcctggagtc acacagctag agagggaaag ggctagaatc  23160
agagggctga ttgtctgact tctgttctag tgcatgctcc cacctcgctt tggaagctgc  23220
ttcggcatag tgaagcactt aagagcatgg atgggttctt gttagccaga cgtggaattg  23280
aatcttggtt ctaactgtgt gattttagca agtttgctta tctagaagag aaggataata  23340
atacttcctt cttcacaggg tggtgatgaa gagtaaatca aagagtttag cagaatgctt  23400
cccatatggt aagcactcaa tacatgttct tgttatttttt attattacat ggctttgcct  23460
tactgaggct tcatcttgtc ctctggtcca actacagttc tctagcttgg cttatcccctt  23520 cataacctgt accccagtg gcacgatctt ggctcactac aacctccgct tcccaagttc  23580
aagcaattct cctgcctcag cctcccaagt agctaggatt acaggcacct gtcaccacac  23640
ccagctaatt ttttttgtagt agagatgggg gttcacagtg ttggtcagcc tgggttcaaa  23700
ctcctgacct caagtgatct gcccacctca gcctcccaaa gtgctaggat tacaggcatg  23760
aaccaccgcg ctcagccagg aattttcatt ctttatcctc ctttgagact cggctctagc  23820
atcatttcca gtcgagttgg tctcccttcc tctgcattct gataactgtt aaccatcaag  23880
tgacttgagc ttcccaggga agggcatcat gtctttgtag acatccaata aatgttagta  23940
gaagaaaggg gggtcctgcc aataatcata tgtctttccc acaatttaaa ctccttttca  24000
ccctgttact acttttttgct tgtcttccct ttgataaaca ttctacttct tcatcaccca  24060
ttccctcaat ttaacatctg atactactat agaaactact gccttgaaga tcaacaaacg  24120
ggttccatgt ggaccaacgt cctccttgag accctcactt ggcttttgtg acacagtgca  24180
atatttgctc tcttgatgcc tcactgacct taaccttcct tgactcctgc atagatttct  24240
caactgtggg tatcccctaa gatttaggcc atttgccttc tcttctttca tctagtccat  24300
tcatgaacac acccattcct ggttttaacc atcacctctg tgcagataat gtgcaaagtt  24360
tatttctagt cggagtggag tctctgttac tctgccaatc aagttctaaa tttttattcc  24420
```

-continued

```
ttctagtgca gcagtggcaa atacctgaca ctcatgtgtc tcactcaaga cagatactgt   24480
ttcacccaag actgatcatg ccgctttccc agtcaaggca ggcttctcag aatccttctc   24540
atttccgcct ctgttctttg gcactaatgc tctgtctgcc cagagttttc attcttcact   24600
tgttccaggc acctgcttcc tggtgaataa tgtaaaacct gctagtcatc cttataggag   24660
aatatgcact catttcccag cagcacaccc gactcaacgt ggttaaaacc aatctaccat   24720
tcccatatat tcagcctaac ttcccagtgc agtctaccct agttttataa cttgttctac   24780
tttttccaga taactgctaa tcatctttgt ttgtctttgc tttctttttt gcactgtgtt   24840
tgatatatta gggtatcaaa tcctacttat tcaaatatgt cccttattca ttccttctat   24900
ccttggtgct accatatttg ttctggctct tgttacctca ttatgggata taaaaatagc   24960
ctgtcaactg gtctttccat tgccaggatc tctctgttct aagccaccct gcctccagat   25020
caatcttcct agagtaaaac cttcattgta tgacggtcta gctcaaaatt ccttaatgat   25080
tattaatcac ctcttaaagt ccccaattct tagactatta gtagggtaaa attattttg    25140 atttggagtc aaaaaatttt ggacgcaaat tttggctact acacttaacc attatgtaac   25200
ttcgaatttc ggcttaattt ttattcatca tttattcagt atctatttgt ttaacacctt   25260
ctgcatctca ggctctgtac taggtacttg ggatacaatg atgagccaag cagaccttgt   25320
ccttgctctc ctggacctca caacatggtg aacttgtctc tattgctcat gatcataata   25380
atcctaagta caggctgtgc tttttttccct tgatacttgt agcttttggt ttgtgctatg   25440
cagggtattg taataccatt tgcagtgcca caataatcag catatatgtg ttatcactca   25500
gccacattgc agcttcactg aagggcaggg gctatgtccc atttctcata gcgcaagcac   25560
agtgccctgc acataccagc tgctcagtga tttctgatgt ggttttttgta gatccagggt   25620 tagtctttgg cagtcatgat gcctagtatg tttttagagg ctccctttgt cctatcagaa   25680
ttatgctatt taaaaaaaag tcatacctat ttagtttata ttcattctaa ggcctctcct   25740
ttccaaccta ctaccctgcc tataactatt ataaggagaa ctcacaatgt ttataacttg   25800
tgcaccttaa gttttaaata ctgaataaca ggcccattca tgtttcctca tagaaatact   25860
gtctatatgc atacaatgaa atgttaaaat aatgttcttt ttactaaata gcttttttgac   25920 ttggtaatga acaatatgtt gtttttccct gagaagtagt tctaggactt tagttctgaa   25980
gattatgttg tattttatac attttcagcc tcctgttttt cagttcccag tgatcttaca   26040
ttaaacattt gtctgtctaa aacaataggt taactatagc caaattataa ccataccatt   26100
cctctccaca caaaatccta taaacagcat gtgatcatat tgcttctaga atttatgatt   26160
gttttcttcc aaaaggaagc taaatttagc ctagtaattc tacatgcgct caagaaaaca   26220
atgcctgctg tgatttctag aataaatgaa tgtgaaccac agttcctta cttgactaac    26280 agagaaagtt taaatatcaa cctagtcatt aaccacagtt attaaaccac gttaaacaac   26340
cagcaagggg ttaagaaaga aagttgctat gttttttctt tcattgctga atgagtctaa   26400
cttagttact gtatcaacct taatacagaa cattgtttgc atctcaatgg ttctctaaaa   26460
ttattcgttc atggcttgag ttctaaaatt aaactatgtg gagtcatgtc caaccgcaca   26520
atgcatcttt atgtgaaact tgctagagtt tttgtttttcc ttctatgtaa aagtccagtt   26580
gggaagcttt atttctgata gattaaatgg tataggtctt tcagtttct cttcatttct    26640 gacaactgaa ctgctctcgc cttgaacctg ttttggcaga taaacctctc ataatgaagg   26700
cccccgctgt gcttgcacct ggcatcctcg tgctcctgtt taccttggtg cagaggagca   26760
atggggagtg taaagaggca ctagcaaagt ccgagatgaa tgtgaatatg aagtatcagc   26820
```

-continued

```
ttcccaactt caccgcggaa acacccatcc agaatgtcat tctacatgag catcacattt   26880
tccttggtgc cactaactac atttatgttt taaatgagga agaccttcag aaggttgctg   26940
agtacaagac tgggcctgtg ctggaacacc cagattgttt cccatgtcag gactgcagca   27000
gcaaagccaa tttatcagga ggtgtttgga aagataacat caacatggct ctagttgtcg   27060
acacctacta tgatgatcaa ctcattagct gtggcagcgt caacagaggg acctgccagc   27120
gacatgtctt tccccacaat catactgctg acatacagtc ggaggttcac tgcatattct   27180
ccccacagat agaagagccc agccagtgtc ctgactgtgt ggtgagcgcc ctgggagcca   27240
aagtcctttc atctgtaaag gaccggttca tcaacttctt tgtaggcaat accataaatt   27300
cttcttattt cccagatcat ccattgcatt cgatatcagt gagaaggcta aaggaaacga   27360
aagatggttt tatgtttttg acggaccagt cctacattga tgttttacct gagttcagag   27420
attcttaccc cattaagtat gtccatgcct ttgaaagcaa caattttatt tacttcttga   27480
cggtccaaag ggaaactcta gatgctcaga cttttcacac aagaataatc aggttctgtt   27540
ccataaactc tggattgcat tcctacatgg aaatgcctct ggagtgtatt ctcacagaaa   27600
agagaaaaaa gagatccaca aagaaggaag tgtttaatat acttcaggct gcgtatgtca   27660
gcaagcctgg ggcccagctt gctagacaaa taggagccag cctgaatgat gacattcttt   27720
tcggggtgtt cgcacaaagc aagccagatt ctgccgaacc aatggatcga tctgccatgt   27780
gtgcattccc tatcaaatat gtcaacgact tcttcaacaa gatcgtcaac aaaaacaatg   27840
tgagatgtct ccagcatttt tacggaccca atcatgagca ctgctttaat agggtaagtc   27900
acatcagttc cccacttata aactgtgagg tataaattag aaataagtat cagtctcaaa   27960
aagaatatcc agggcttctt ttgtgctttg taaatggtgt ttatccaaaa tagttgcaga   28020
ttttttccaa gaaaattgag gaattgaatc ttcatttaca cctaaaatta tatctttaaa   28080
atgtaaatgg taactaaaag aaaaatgttt ttacaattca gatttgcatg ttcgtgacat   28140
ttcagattat attaaagtta tttcccatat aagctttttt atatttacac agattttatc   28200
agatttacac agattttatc agatttacac agatttttat cacagcagca attcccataa   28260
aacataatta ttgacatttc tatataatct ctgcaacatt tacaagatgt tcaagctaat   28320
ttgtatgcct taaagaattg ttccttatga gattatattc tctcactgat acacaactga   28380
ttaatctata ttcttgacat tacttaaagg aacttaactt taaaaaacct cttctgaaat   28440
gctggtaaat aaaacatttt taaatgagct cgtatacttc tctaaataac ctgtaagagt   28500
agagaggaaa tgtttgttcc caagtccttc ctttagagct tgactttaat catggacttc   28560
cttctggaaa agacttgtgt ctaccaagtt ctagcttggc actttacctg gttggtattt   28620
gttatttata agcataaata ttttggttga tgattattta tacttatatg aaatggtatt   28680
ttcttaggag ctgttagaga tattcttggt gctgtgattt aaatatagta acagctacca   28740
gctatacctg gagatttatc ctgctagtca gttgatcacc tggtctgagt gtttattgtg   28800
gctttgagtt tcttgatctg ggccagattt ggaatacgga cctgactatg accatcattg   28860
aatgaacaaa tagtatagct tttctaaaga cagtttgact ttggcatggt atgtttcact   28920
tactttaaca ggtttcaatc taagatataa aggttataat tgcaatcagg tagaacatta   28980
aacatgtcct cagtagcata aagtatataa tttgctgagg ggtaaaggca tatgaattca   29040
gagacatttg gttgactttt gctgaaatgt ctgggcacct tctctagatg gaaactatag   29100 ttaactttt atgatgctag gaaaatactt ccaagaaagt cagttcatct tttggtgaac   29160
```

-continued

```
taaaaacaaa acttccttcc tctctcttcc aaagtctatg aatatacata acataaatgc    29220
acatacattc caactaagac ttatttcccc ctacatacat ttaatatatg ttgcaaagaa    29280
gcaatagaat tccttatgaa gctccccctt ttctttacta gaaactacaa aagaatgaaa    29340
ggaaacaaaa tgattttcag aaacctggga ttaggaaata aaaatataat attaatagca    29400
ttacagagaa gatattttc tgcatccagt aagttgattc tgagacacaa gtttaaaag     29460 agtctattag gaattcctcc agggctccta gagcacatgg atttgctatt taaatctttc    29520
tttgttaaaa attaaaaaga agggtagggc aagaaaaaaa ttaaaagag aattcataaa     29580 ggtatattga tatctcattt tttaaatttt gtacatttca atccttagat gtaaaaatac    29640
ttatcaattc tagaaattct caaaacacat ctgaattta tcctaccctt ttgactttt     29700 tagtgttcca agggagacaa acagacagga ttagccaatg aaattcaggt cagtttatc     29760 gcccaggaaa aattcccaaa atgcactagc cacacctgaa accattatca ctcccatcac    29820
aaaaattctt gcgggaaaca agatggaact tgccaacata gtcttcttac aaaggaagcc    29880 aactttaca ctggccaaat tccatagaca aataccttca aacctcctct atttatttgc     29940
ctgtttatct tctctggtta caaagatcaa aattcttctg agactgagac tacacatatt    30000
ctctctctcc atatacccca tccagacctc agattgttcc aataatgagc atataatcat    30060
ttcctagctt aatgccaaaa tgaaggcacc tagagccatt catcacacac aaaaaaaaca    30120
aaatgattac aagatcaaag ctgtttagca ggactctcaa gcaataagat gactccattt    30180
tgtcttggca gatttacttg gccagaaatc aagtgaccct tttaataatt tcttggaact    30240 gagttttac tttggcatca agtttggtga aaagacacac atattgtagt tttgttatta     30300
acatctctaa tacatttata aagggactct tgtggacaag gttaagaaag ctgagctgca    30360
gcagtaactt tctacttatg cttctgccca gtcctcagtg ttgacacatt gctgaaagag    30420
ggatttcctg gcactccaag agctctccac catgtgcaaa aagtgtttct atcacaagat    30480
cagataatgg gagtgccagg gacgggcctt ttacatttta ggggtccagc aggtgtacca    30540
ggcctgactt gcttgtttag gatcacatat tttgttgctt ttcccagtct cacatttcat    30600
gaaatatgtc tatgcaaact cttcacatgc atcttctcat attgatgaca tcacaaaagc    30660
cctcttttga gtcatttgat aattcccagt actcgtcatc ttcacccata agctatttgt    30720
gcttcagaac tctttgtctc cacatatgat gctgtttctg gaaacttatc ccaagccaca    30780
aatgcccact tatagaatac cagtgttgtt gactatgtca gttgttctat aagaatatat    30840
tcttgatcct cacaatgtgt ccatttttta tgttgctttt gaaagtgatt ctaaagaatt    30900
tgtttacagt gacttccaat attgagtact atgagattat acacccacaa ataattacta    30960
aatctgttta atatctttac ctcctccttt acccattcat caatcaacct ctataagcat    31020
cctaaattag tattgattga agttgtttta ggctaatgca tattctctaa atagcatatt    31080
attattcaaa ataaaataat tgagaaaatt gtcccataat atggatggaa cctttgtaaa    31140
ggcccatatg tagggagaaa aaaccctcat ctctatttga ggataagcag tagcaaaaat    31200
ttcattaact tgtttaaaat taagtggaat ttaattttaa gactgtggaa tctctaacag    31260
tcttttacat ataagggatt gattaatgtg acaatttcag gaaaaaaagg agaatcagta    31320
cacattggcc caatctccta caaatgagaa tcaatacaga ataagagaat tttttaaatc    31380
cccaaatcag caaagatcct gttccctaag ttatagaata tttattaaaa caagtgaaat    31440
cgtacatttt agaaaaaatt ttaatcaaag ttgaaattag aaaagcattc ttgaaatagc    31500
tctcgcctct cagaaaatac aattagcaca caacactgtt tttcttgaag ttctattatc    31560
```

```
aaagttttgc tctatagata agcatttgaa agacctgtag caagtatttt cgccaacatc   31620
ttgatgacct taatgaccaa agttggatca agtgaagggg aaaagcattt ggtgccagac   31680
acacctgggt ggaagtcctg gtttactgca taccaaccat gtgacttctg ccacattacc   31740
tgacttcttg gaggctgagt ctcattggta tcatgcagat aacaatacct acttcacagg   31800
tttttgtgaa aatttgggat aatatatatg aggtacctgg cacaagatga ctataaattt   31860
agcccgttgg gagacagcat ggactaatgg aaagagacta aaatcagaga tgttggttca   31920
aatctgaacc ccaccgtctt ctacctggat ggccatgaaa gcattattta aactctgaac   31980
ccatcgtcct gcgtgcagga ctatagtgtg gacaagtata ttaataacat ctgtaaaagg   32040
tcccaacttg gtccttggca caaaataaat agcagctatt attgtaagga atacttgcgt   32100
aaagaaagac aaattcaaat gattggatta ttctctggaa gaggcacatt ctggttctat   32160
tgtttacaag tctttcactt ccctctctaa ctgttatgag tgacctacct ccataatggt   32220
taatttgtgt tatgttgttc ttaagattat aatagttcca aaaaagagat ggggtgagga   32280
gtggtggtag tttgagggggg cagaggatgg ggagaaagac aattgaatca aaactgtact   32340
atagtcaagt tagaaggtat aaattgttct ccttcctctc actttcaatc ctaactatcc   32400
atgacctaag atattactct tatgtacttt gtcatatctt gcattcaaga atttgcagat   32460
aatgcagttt tagaaaaagt caacctcata ggttgtttgt attgggcttc cttgttttta   32520
aatatcattt atactcaaat tcaaagagta gccaactgct tcccaaaata aaggaaactt   32580
aaggtagtaa ttttccatct ccgtttcaca gaatgccaaa gttaaagagt cactactcag   32640
agccatcaaa ggaagaaagc aaagtgatta gaacaatttt aaaggaggac aaaaatcaaa   32700
acaagatgca aacaaggaat aataggaata ggcagaaaaa taaacataca gtgatgtttc   32760
tttattatga ttataaagat gatagatgag taaaatcgag ttacatttaa gttgtaatgg   32820
aagaaaataa ttgcagcctt ccatcaggaa accacaagga ccgttattga tctgtcatcc   32880
tcagggcatg tctcgtaata tttaataaaa taaacaaaga tttataactt ttataggcca   32940
tatatctata atctcccaca ccacttgaac tgtgaatgtg gagtcaatgt tacaaataac   33000
atccatgtga ttatactggt ttggcatgcc ttattccaac aatctagcac tctcaagaga   33060
atgtattttg tattagggat gaaaaatgtg aagccagatt atagagtttt ttacttattg   33120
tgctcaaaaa tgagaaaatg ttatccaata tgaaaaatgt tgttaaggat tcttcattct   33180
taatattaga cagcctttca aacctaaata ttaaatatct tggccatatg ccaaatgtaa   33240
tagctaccaa agcaaaatct tgcaagaaag aaaatccttg aggtataaag attcaatgta   33300
ctttttaaaa aatgtaagta aaaggttatt aattttacat ttcatttctt tttctttcct   33360
agacactact tcatcctctc ataggctcag ggagtcactg cttcctaact tctttatttt   33420
aattatccat gctactcatt ccacgaaaag tggcatattg cattatttta ttaaaagaaa   33480
tttaaaatta gtttctttcc agaattttgt aacgccccct gagatcactg ggcacaccct   33540
tggggtgtta gaaaacatgt tacaaaatga acctttaatt ccttttgctt tttcccttcc   33600
tcttgctgac tgctctttaa accattacat ggctcattca caagtctctc tacccccagga  33660 aagatgaaaa agcaaaggca tgatgttttt ataacctaat agcaagagaa cacagtgctg   33720
aagctgtcac caaaactgtg ggtaggtttt acccgtgggt tatattaatt catgatatga   33780 ttgataaatat ctctcacttg tgtggggaat gaagcgttaa ctatgccgca tgcattttaa  33840
attaatttga cattattctt aatgtccttt caagcaggtg gcattataac ctgtgtctta   33900
```

-continued

```
tttaggtagt tgatttctac acggagattc atctgataaa actgatatcg caaacgggaa   33960
ggagtttgta caaaatgaaa taaatcttaa agttgatttt tgtaaagccc aaatgttaat   34020
taaaatcttt gaatccacaa ctctgataca tgatattttc attgacataa acatgattag   34080
cgatttctgg aagcatgtgg gatgctgcat tgataaggat atgaacctcc ttgagtaata   34140
atgtatattt ttactccgaa tactgtttca cattttgggt gttacatcct tacttcagac   34200
ttctgcctta tcagtggcca tcccacccta tgttcttatc tcctcagtct aaaaagaaaa   34260
atggggaccc atcagaattt ggatagaaga ccctccagga atttctgcca ctgcttattc   34320
atgggttggc acagacactg attcagtggg cacacagagt tcagaatgat tcagagccca   34380
gatatgtgcc ctaagtcaca tctccagcgt ccagggagga ctgtaaagtg ctcgttatca   34440
ggaaaatgaa accaagggct cagctactcc tgaagtcatt aaaactcctt cccttgattt   34500
tttttttttt tttttttaaat agtatatgtg gtaaccgaat ctaggatcct ggatacattc   34560
cagtctgcta attacatatt tttttctaac taaaatgttc caggcaggtt catttgcatg   34620
tgaattactt gctgagccat gttgacttcc tattctaaaa gcctcactct gccttgggaa   34680
gcagtttact gcacttcacc ctagacctag tctaatgttg gagcagacaa agtgtagcta   34740
cccatatata cttcaaaaat attttccagt ctccccacaa gaggaaagaa aaatgtctag   34800
caattgcatg ctaatttaga ccaaagcttt gttttaacca ttcttggtga tcacaaatgg   34860
ggaaaaatga tttatgaaca gtataactat aaaacaaaca aaaaaaaacc attgtgaatt   34920
cagagtgaag tctgacttca tttgtcttat ttgggtaaat cagcaaaatg ttcatcagtc   34980
agaggacatt aaaatggtag atgatacttc aaatcgtgcc ctagataaaa ggagagaatt   35040
aaggttagtt ttgatttgta aaccattctc ttcgaaggct gattttataa aaattaagtt   35100
tgctgagtca tcatctcaaa atatatagtt attcatgatt agttaaaatt tgtgtctgtg   35160
tatcaaagaa gtaaatttgt atgatattaa attttctaac aatgttttaa attttaaaat   35220
gtccgattaa cacttgcatc tagcaaccag tctactaact aaactatagg tgaagtcatg   35280
ctcaggaaat ggggaaaatg cacagattaa attggtctgt tagctctgag tgaatcaata   35340
gtatttagtg ctaatgcact aaggagatta caagcactaa tgcagtagca gtcaatagcg   35400
aaaactaata tctctaaaaa atatcttgac aataaaatgt gcaatatttt ccatttatct   35460
taagctaatt acattacctg cttgttcttt catcttatta gtttaagcca agtgctagaa   35520
gcctaaccat tttatttagt gcataaaagg gccaaaacct tgtaatcatt gttttcagca   35580
ggagacagag gaaaggatta attcatgtaa ccaagattca accagaaatt caacagatat   35640
ttatttagtc tctaaacctg atagtattac aatggagaat gagctagact gtacctgtct   35700
tcaacaagca gatagactag tgaagatgac agtaaacatt cagtcacacc agtgaacaaa   35760
tacatcatga taatttatga aatgtgctgt gagggaaata aacatctgtg aatgcaaatg   35820
agagggaata tctaaatttg gtagttgagt cacaaaaggc tgtcctgagg aggtgaaagc   35880
taacctttat ataaagctta aaactttaaa aaagcaatac gtctttagta cacaggcaaa   35940
tatataaact aaatatataa actaatagtc attacttatt tcacaagctt tacatcttaa   36000
ctacaagctg ctacattaaa tcagctttct taagtggttt gtggtcatta gtgcatacta   36060
tcttacactt agaaaaacat tgcaagaagt agtacaatgc tggagaattt aacttttttaa   36120 aacatttcct gccttaaaat aaacagcagt aaatgtgttt aaacattctt ttgatttcta   36180
aatgaattaa gttactttttt attatgtggt tcttcttcat atgaagaaaa taatatgtag   36240
attactagaa gctaagaaca tactttttagat cctgctcaca ctcactgcct ttcctggcct   36300
```

-continued

```
gtcaccttaa tcagcttctt tgaaaatcac tgtttcttac ataggccagg ttgtttcttc    36360
cttgtttccc tcttcttcct tctatggcca acccttggga ccccgtttgt cagaagaaca    36420
tgttcctctt tggggaggag gggattgtcc ttttaccaat aagtttatg accaagagaa     36480 acataagaat ctgagaacac acaaaataag ctcttttgaa actatcaaaa ttataaacat    36540
taatagaatt caagggaatg tgatgctgaa gtgatcccaa gtcacattgt ctttctgcct    36600
ctgtgcactg tactctgcac aattgcatcc atttttagac catttccttc tcatgagaat    36660
catgtgcatg gagggccaaa ggagagacaa gtgctcacaa ggatatcatg agcacttatg    36720
aatgtacaaa tgagtgctct ccagtcagtg ccatctttat attgttccgg tttataggca    36780
atgccttcat ctttacctac agacacatgt tgcctttctg tttcatttta atcctgttca    36840
tctatacata tttaatcaca caaatatcta aataagttta tgtcttgtag ggaaggcact    36900
ttgtcatgct tctttgtacc taagcatatg ctttgcaaat cataaacaat agtgttgatt    36960
ttatttgata taaaaacttg gattctcaaa agaaatctat gtgttcacac gataaacaga    37020
gaccatctga attgccaaag tatgactgaa tcataagcag tattgtttta gtcatcttta    37080
cagaccagga agatttgaaa tacaggtgta aaaagatgtg tgaggcatca aaagaaatat    37140
tcacctttct ttgtgttcat ttttttttatt tttgcttggc cgagaaagaa ggggtgtttt    37200
ccaagggaat aggaggcttc agggcttatt cctgtgccta caagtcagag aggtcactgg    37260
cttgcccctt cctgaaggct gtaattacag gcagaggact atttatttct ccgtaaggcg    37320
accagaatct tgagtgtaaa aaactgttta caagagtaca ctgtgtatag gggttacaca    37380
caacctcagg aaaaataata ggaaagtgag actattttttc ttcatgtatt caataatatg    37440
agaaggtcca agactctgga aatgttctaa agtacaataa tagagatgaa tatgaggtca    37500
aattaggtga tcctggggct taaggaactg aattaaatga ataaagaaga ggaatttcta    37560
atagggcata atctaactga taatttgtta aatgtaaact tatttgtggc tccaacatca    37620
tggtaaacaa gaatgaataa atgtattagt aagagtaatt gagaagtatt tctaatgtga    37680
aaaacaccaa ttacattggg tttatctggc gccaatgtgg aaataaatga gcaatatttc    37740
ttactctcaa ctaaacttac tctcactttc agaactgtta taggaaaggt attgattcaa    37800
gtagagttgg gcatgcaaag cacaagatca attctgttac tggcctgata ttaaggatat    37860
tagtcagtgt ttgaaaaaat gatttgtaat atataagtag tagtttaaca aagtaggtaa    37920
aacttgtaat taatttcaaa aggtcaaagc agagattatt gacatgtaca aagaggaccc    37980
gctttatatg tgcctgcttt gaaaagtaat accgtagtat ggtaaattgt gactaattct    38040
gagattttct gtctagattc tttttaaaac caaatgctta agaaaaaaac atgagacatg    38100
agtagcaatt acattttta ggctgagtag gtagcataat tgcctcatgc ctgcctcctg     38160
tctccatttg tttttagtag attttgcaca gaaaaacatg ttgacctcgg tactgaaatt    38220
ttggagttca ctatttgcgg cacagttaca gatcacagaa aaaatgtac aacaggactt     38280 caccacacct aacaaagaa agtttttctta ttaaaaaaaa aaccctccaa attattgtga    38340
gatctagggt aaccatggtg ttaactatat gctatttgat atcttataac cctggtgata    38400
agataacaat ccaattgaat gcagatgaac tcatgaaaaa agaaggatta tgaaatattt    38460
ggaaagtaaa cacctaaatt ttcataagta aatattaatt atttgtgtga tctttagata    38520
tgaaagcttc ccctgcatgc acttggctct tggaaccagc tgttaaaact cccagcacct    38580
tagttaatac cctgtatgct ggtggttcaa gaactagtta agaaacagtc acattttcta    38640
```

-continued

```
ttttcactgc caatgtataa taaaatctct gttccagtga atggctggcc aattatttta   38700
ataacgatgt tggcatggct tcattttacc tttcttgcta ttagcaaagc tttccttttg   38760
tactctgaag tacgggtaaa tcacaaatta aactgagctg ttgtttgttt aatgctgtgt   38820
ttcctgctaa ccttattctt gtctatcaac ctgaacgtag ttccccagtg gctcagaaaa   38880
ccctcaattg ggattaagta atagtttaca caaccttgct cagtcattaa cctgtgttga   38940
ctttctcatt cttgtgttcc agcctcattt aagagtttct taagcactct atccagttgc   39000
tggtttggtg acaactaaca atacctattt aatcaagaaa tttaatattt ccaaggaatc   39060
atttatcgta tctcagactt cttcattaac ataatctaat tcagtcttgt attccttctt   39120
caaaataaag cctggtttca ttcatagtaa atatgaagct taaaaatttt tacttctttt   39180
cttctctata cacacaaagc agaaagagaa aattgtatat tatcattcca gacaggtttt   39240 ttttttttgtt tagtgtattg acattgatgc caataagata aaactagacc tcagtggctc   39300
ctcctcaact ccacccaatc tatttgtctc caaagtgctg ttggagtaag taatctttgt   39360
taagagcaaa cctatttgta tatctgatga taatctgagg gataataata tgatatttaa   39420
ggagtttctg tccttggccc tgactatttc ctggtcctcc ttcacgccca gtgatgtgct   39480
ggtaaatgtt aaactctggg gggaggggca gcagaagccc ctaatttgta gcatttgcca   39540
atttctatgg tgtaaatatc ccactgagcc agtttcaagg taccactgaa acagcgttag   39600
tcactgaaca acaatgagga agagatgtac acacttggct ctgtgaactg ttatgagatg   39660
gttcaagcac agcactgcca ccctgtccta cacgcaacct gtcattcttg tagttcccag   39720
aatccatcag cctccctcac aaccctgcct taacacgtgt agcttggtcc acttcagatt   39780
ccctttaaca ctcattttgt caagtgaaca cttttttccct attctttaaa acttccatgc   39840
tggcattttc cttccccagg acatttttcc ctagccttca actcatcccc tgcccccat    39900 attctggatt tgttgcgttt cctgagcaca ccagtagcac tctgcttatt tctaccatgt   39960
ctcttatcac actccgtggt aatgtgtcca acagttccat cgttagcccc ctgaggggat   40020
gaactatgcc atttatctcc acagtcccag cacctaatac aatagcttga acaatatata   40080
catttatcgg atgagcaaag aagtatgaca gagccctgta tgtaaaatat attactataa   40140
atagaatgct gattcataaa aataattatt tagataaaac agtttttccg tctctcccct   40200
aaatccctaa aaactaattt atagaattgg ggagttttca agagctaaat tagcactgga   40260
gaaaaactgg ggagttttac tcactattac ctatgccct cccgtccccc ccacacacac   40320
cctccttcat tcaccagtct gcaatgaaga ttgatcaaag aacaaagaag aagaaaaatg   40380
aaagaaaaag gaaagattaa gatagggagg gtgaatagat aggaattcca gagttttgta   40440
atcgaaattt ggaactcaga attaaagtca ttaaaaggag aaagagggaa tactttctct   40500
gctcccgtaa ggttttctca agcctttcaa cagcactcac cctttgagcg ggtgatacca   40560
tctgtaagag ggactttacg caatgcttta gtgggcgtgg cttgagcagt gacaccagta   40620 gagataccc cttgaaactt tcatttgaag tccacagatt ttcactattg gtcaccaatc    40680
catgatttca agttgaaaat gatatatggg ttaaggaaaa gaggccgggc gcggtggctc   40740
acgcctgtaa tcccagcact ttgggaggcc gaggtgggcg gatcacgagg tcaggagatc   40800
gagaccatcc cggctaaaac ggtgaaaccc cgtctctact aaaaatacaa aaaattagcc   40860
gggggtaatg gcgggcgcct gtagtcccag ctacttggga ggctgaggca ggagaatggc   40920
gtgaacccgg gaggcggagc ttgcagtgag ccgagatccc gccactgcac tccagcctgg   40980
gcgacagagc gagactccgt ctcaaaaaaa aaaaaaaaag gaaagaagt taagggcaaa    41040
```

-continued

```
ggtctttatc aacaccatcc ttcctgtggc cacaggatcg taatcccagt ggcaacattc   41100
aaaggcacca agtacgtgct tggtacagag agaagctttc ctgagcttgg ccttggtgta   41160
gatgcagtga gaactgagta agggcctctg gcagggacct tggctgctga gaaggggagc   41220
ccacagatgg aggtttctga tcaacaggtc ctatcagaaa caaggggagc agataagtaa   41280
agagtctcac tccacggtgg caagatggaa aggagggata agaggtcatg acagttggat   41340
taatggcagg ctagaatata gtcatgggct tgaacgatat attgggacac aattgaagga   41400
ctcttgtttc atccatcgtt catctctcct ggccctctgt gaagacattt atcacctgtt   41460
tctattgaat gtgacactgt taggcacata aacagaccat ggctcttacc acctccaaga   41520
agaactactt ctgttttatt tgttagtgca gggtaattgg tgttgtgtct tctgaaaatc   41580
tcttatactt ctatgagtaa gtgcattgaa attgtttctg ttaactaagt agaggaaagc   41640
agaaaacctc tttgcactaa gcattaaaac cttcctaact tggaacaatt ttctttatga   41700
atcactctgt cactcctggc tatgattgaa gtgcagtatg aaggctgcta accaaaaaca   41760
catggacaca gtctgtttca gatctgattc accttaggaa atgatgataa agaagcaaaa   41820
gttttaacac ttagaattcc aaggtccata tcattgtaga attgattctt ttgaattgtg   41880
gtggtacctc aagagaaagg atttatttat ttcatttata tttaaatgcg tttgtataca   41940
tatgtatata aacccatata cacatataca taaaatatat tctgctccaa gtatttatct   42000 ctctttttctc tttactaatc cagcttccat taagaactgg ctcaacttcg acctctgcca   42060
tgagccttct ccagctgttt aagcccacac agatcttatt tttttcctag tcttagagga   42120
tttactgcca gtacagtgtt ttcagaatgt aactatcaac tgagttctta tactttgcat   42180
cagttagcta ttgtacgtgt caatcttttg tctccctatg tagaggctag acccaaggta   42240
gaagcatttg ccaggattga caaacgatag cctgttttta tattctcaac aagtgaaaac   42300
ttattttgtt tatatttttt tcccttttta tacagttaaa cactcacatg cacgcacaca   42360
cacacacaca cacacacaca cacacaggcc acagggaccc tatggccctc aaagactagc   42420
atatattcta tctagccctt tcccaaaaaa catgtgccaa cccctgcatt agagaatagt   42480
gtaaaataat agtggacaga taacaggtcc acaaattttg gagagccatg gatgacctta   42540
cttatgaact taagtaattc tcttcaatag gtgtgagtgt ttccatttta cagatgatga   42600
aattgaggct cattgatcta aacaattgga ttttgtcttc ataggcatta tgagggctta   42660
ctagaccaac aatagtgata ataataactg tttagttgca caaggcaggg atttatgtct   42720
tttttatttg ctgccatatc cttcagcacc tagaacagtc tgtcacatgg tatggtatta   42780
tattcatttt ccagagctcc cataacaaat taccacaaac tgggtggctg aaaacaacag   42840
aaatttatcc tcacatggtt ctggaggcca gatgtctgaa atcaaggcat cagccagggc   42900
catgctccct ctggaggctc tagggaggac tccttccttg cctcttgcaa ttctggtgtc   42960
ccaggcatct taggttgtgg cagctttact cccctctctg cctccatctt tatgtggcag   43020
tccaccatgt ctctctgtgt cccctcttct tataaggaca acagtcattg aattcagggc   43080
actcactaaa tccaggatga tttcatctca agatccttaa ctaatcacat atcaaagagc   43140
ctatttccaa ataaggtcac gatctgactt tccaggtgga catgaatttt gggaagacat   43200
tattcggcct actgtaggtc ttctaaatga agtgaccatt taatatgttt ctggcactgg   43260
attcatttca tttaagcctc aaaacaaatc tgttatgtag atatgtgttt tcccacttta   43320
caagtgaaga actgaggttt agagatctag gaatcctaaa gctgcacagc caggaagggc   43380
```

-continued

```
agggccaccc ctgacccaag ttctctgcta ggttagcatg gttgtcacag gacaagctga    43440
gaaggtattt agggagcatt acactaaaaa gttgtagaag tcggcttaag gaagaagatt    43500
ctaaaatcaa aggaatcaga ttgtaggagg ccatgtaggc aatttccttt aattcaatag    43560
aagagagtat aagaatcagc caggcatggt ggctcatgcc tgtaatccta acactttggg    43620
aggtcgaggt ggaaggattg ctagagcctg tgaattcaag accagcctgg gcaacatggc    43680
aaaatcccat ctctacaaag aaatacaaaa attagccagg tattgtggca catgcctgta    43740
gtcccagcta ctctggatgc tgaggaggga ggatctcttg agcccagaag ggaagaggtt    43800
gcagtgagcc aagattgtgc cactgcactg ccgcctgggt gacagagcca gagcctttca    43860
agcaagcaag caagagggaa ggagggagag agggagagag agagagagag agagagagag    43920
agagagagag agagagagag agagagaaaa gaaacggaga gagagggagg gagggaagga    43980
aggagggaaa aagagagaaa gaaagagaaa tatgaaagaa agaaagagta aggaaggaaa    44040
gaaagaagga aagaaagaaa aagaaagaaa agaaagagaa agaaagaaag aaagaaagaa    44100
agaaagaaag aaagaaagaa agaaagaaag aaagaaagaa agaaagaaga tatgaacaat    44160
aaaggaaaga ctcaaagatg gttcagatct caaacttacg gagagggtag ctattgatgc    44220
attgagaaat aggaagctgg aagaggaaat cagtttggag agaaaagtga tggctttgaa    44280
catcatcaat ggcgtattca aacatagctt gaaggcattt gcagagacag ggctggtcct    44340
cggaagagat ggcaacgggg tgtgtagagt taggtcatca ccacgaggct gtgagggcag    44400
agccacagta gcttccatca ccttgtgaat caccagtgct cagcccgtgg ctggctggcc    44460
ggatgcctgc ttatgctgtg ctcccggctg tctggctgca cacacaaccg cagagcatgc    44520
cctctctggc tagggcagaa agaaattgaa gcctcttaaa ttttgccccc cccagctttg    44580
ctcccttgct aggacttcca ggccatgact attgaagcca tagggcagga ttacttcctc    44640
aagaggcgtt agtggaaaca gatgtgttga ggaagcctct ttcttttcaa ctgtgccctg    44700
agcacatcag atggagtcct cttcatagca caaaacaact tggtcagatt cttagggttt    44760
gaccacagca ccctaacagc ctggccgtgc attaaggacc ccaaagagaa ggatctgctt    44820
tgccagagag ctgactcttc tgtattttac agacaattct gaattcaatg tcaacatctt    44880
agacatctca gtacagacag taaagagtta aaatatgtct ataagaaaca gcgccagacc    44940
ctgaaattga aagctctgtg cctccctgcg tgcagtcagt tccacactgt cctctctccc    45000
agttctattt aataaaaaaa acacatgagt gaaatttagg gaaataagaa ttcctgaaat    45060
taaagcaatt aagttttcag tcaactgtat gaaaagctct agacaaagag gtactttcta    45120
tttcaaaata tgtatttccc agaaaaccat taccatatct agctagaatt tctacaaaga    45180
atgattatga ataaagtata tattcaaatg cttctggtaa tttagtcatg gtcaaagagg    45240
agagaaaggt gatacaagtg aactggcaaa gattttacaa gatagtacat ttttaaaaat    45300
tttatttgca agactgattt aaattatcta tagatgagct aaatctgtcc tatagatcaa    45360
ttaaatgaat cactatttta aatatatcac attcttaatt acactgaatt aaatataatt    45420
acatattcac tgcatacatc ataatgttaa ttaggggaaa cattttgaat caaatatatt    45480
gagatatata gcacttcaat tttcttttta taaaaaaagc tatatgacta agtcaggtaa    45540
aaagaatctg gcaagtactc atagaaagct aaaggaagac tagattaatt gatgtatcac    45600
atcaaggctt acaaattgta gaggaattcc tattctttaa ctctatgaca gtatataaga    45660
ctttgggcta aggaagcaag tttgcaacaa gtttttaaaa aataataaaa caggaggcag    45720
ggcacggtgg ctcacacctg taatcccagc actttgggaa gccgagacag gtggatcaca    45780
```

-continued

```
aggtcagggg ttcaagacca acctggccaa aatggtgaaa cccagtctct aataaaaata   45840
caaaaaagtt agccagatat ggtggcgggc acctgtagtc tcagctattc aggaggctga   45900
agcagggaat tgcttgaacc caggaggcgg aggttgtagt gagccgagat cacgccactg   45960
cactccagcc tcggcgacag agctagactc catctcaaaa taaataaata aataaaaatt   46020
ttaaaaaata aataaaataa ataataaaac acattgttta ccattgtttc tcagagacat   46080
acgattattt tagaagtgga taagcctttt tttttttatac tttaagtttt aggatacatg   46140
tgcacattgt gcaggttagt tacatatgta tacatgtgcc atgctggtgt gctgcaccca   46200
ctaactcatc atctagcatt aggtatatct cccaatgcta tccctcccccc ctcccccac   46260 cccaccacag tccccagagt gtgatattcc ccttcctgtg ttcatgtgat ctcattgttc   46320
aattcccacc tatgagtgag aatatgcggt gtttggtttt ttgttcttgc aatagtttac   46380
tgagaatgat gatttccaat ttcatccatg tccctacaaa ggacgtgaac tcatcatttt   46440
ttatggctgc atagtattcc atggtgtata tgtgccacat tttcttaatc cagtctatca   46500
ttgttggaca tttgggttgg ttccaagtct ttgctattgt gaataatgtc gcaataaaca   46560
tacgtgtgca tgtgtcttta tagcagcatg atttatagtc ctttgggtat atacccagta   46620
atgggatggc tgggtcaaat ggtatttcta gttctagatc cctgaggaat cgccacactg   46680
acttccacaa tggttgaact agtttacagt cccaccaaca gtgtaaaagt gttcctattt   46740
ctccacatcc tctccagcac ctgttgtttc ctgacttttt aatgattgcc attctaactg   46800
gtgtgagatg gtatctcatt gtggttttga tttgcatttc tctgatggcc agtgatgatg   46860
agcatttttt catgtgtttt ttggctgcat aaatgtcttc ttttgagaag tgtctgttca   46920
tatccttcgc ccactttttg atggggttgt tttttttcttg taaatttgtt tgagttcatt   46980
gtagattctg gatattagcc ctttgtcaga tgagtaggtt gcaaaaattt tctcccattt   47040
tgtaggttgc ctattcactc tgatgatagt ttcttttgct gtgcagaagc tctttagttt   47100
aattagatcc catttgtcaa ttttggcttt tgttgccatt gctttttggtg ttttggacat   47160 gaagtccttg cccatgccta tgtcctgaat ggtaatacct aggttttctt ctagggtttt   47220
tatggtttta ggtctaacgt ttaagtcttt aatccatctt gaataaattt ttgtataagg   47280
tgtaaggaag ggatccagtt tcagctttct ccatatggct agccagtttt cccagcacca   47340
tttattaaat agggaatcct ttccccattg cttgtttttc tcaggtttgt caaagatcag   47400
atagttgtag atatgcagcg ttatttctga gggctctgtt ctgttccatt gatctatatc   47460 tctgtttttgg taccagtacc atgctgtttt ggttactgta gccttgtagt atagtttgaa   47520
gtcaggtagc gtgatgcctc cagctttgtt cttttggctc aggattgact tggcgatgcg   47580
ggctcttttt tggttccata tgaactttaa agtagttttt tccaattctg tgaagaaagt   47640
cattggtagc tttatgggga tggcattgaa tctataaatt accttgggca gtatggccat   47700
tttcacgata tggattcttc ctacccatga gcatgttctt ccattgtttt gtatcctctt   47760
ttatttcctt gagcagtggt ttgtagttct ccttgaagag gtccttcaca tcccttgtaa   47820
gttggattcc taggtatttt attctctttg aagcaattgt gaatgggagt tcactcatga   47880
tttggctctc tgtttgtctg ttattggtgt ataagaatgc ttgtgatttt tgtacattga   47940
ttttgtatcc tgagactttg ctgaagttgc ttatcagctt aaggagattt tgggctgaga   48000 caatgggggtt ttctagatat acaatcatgt cgtctgcaaa cagggacaat ttgacttcca   48060 ctttttcctaa ttgaatacccc tttatttcct tctcctgcct gattgccctg gccagaactt   48120
```

-continued

```
ccaacactat gttgaatagg agtggtgaga gagggcatcc ctgtcttgtg ccagttttca   48180
aagggaatgc ttccagtttt tgcccattca gtatgatatt ggctgtgggt ttgtcataga   48240
tagctcttat tattttgaaa tacgtcccat caatacctaa tttattgaga gttttttaaca  48300 tgaagggttg ttgaattttg tcaaaggctt tttctgcatc tattgagata atcatgtggt   48360
ttttgtcttt ggctctgttt atatgctgga ttacatttat tgatttgcgt atattgaacc   48420
agccttgcat cccagggatg aagcccactt gatcatggtg gataagcttt ttgatgtgct   48480
gctggattcg ttttgccagt attttattga ggattttttgc atcaatgttc atcaaggata   48540
ttggtctaaa attctctttt ttggttgtgt ctctgcccag ctttggtatc agaatgatgc   48600
tggcctcata aaatgagtta gggaggattc tctcttttttc tattgattgg aatagtttca   48660
gaaggaatgg taccagttcc tccttgcacc tctgatagaa ttcggctgtg aatccatctg   48720
gtcctggact cttttttggtt ggtaaactat tgattattgc cacaatttca gctcctgtta   48780
ttggtctatt cacagattct acttcttcct ggtttagtct tgggagagtg tatgtgtcga   48840
ggaatttatc catttcttct agattttcta gtttatttgc gtagaagtgt ttgtagtatt   48900
ctctgatggt agtttgtatt tctgtgggat tggtggtgat atcccctttta tcatttttta   48960 ttgtgtctat ttgattcttc tctcttttct tctttattag tcttgctagc ggtctatcaa   49020
ttttgttgat cctttcaaaa aaccagctcc tggattcatt aatttttttga agggtttttt   49080 gtgtctctat ttcctcagtt ctgctctgat ttagttattt cttgccttct gctagctttt   49140
gaatgtgttt gctcttgctt ttctagttct tttaattgtg atgttagggt gtcaattttg   49200
gaactttcct gctttctctt gtgggcattt agtgctataa atttccctct ccacactgct   49260
ttgaatgcgt cccagagatt ctggtatgtt gtgtctttgt tctcgttggt ttcaaagaac   49320
atctttattt ctgccttcat ttcgttatgt atccagtagt cattcaggag caggttgttc   49380
agtttccatg tagttgagcg gtttttgagtg agattcttaa tcctgagttc tagtttgatt   49440
gtgctgtggg ctgagagata gtttgttata atctctgttc tcttacattt gctgaggaga   49500
gctttacttc caagtatgtg gtcaatttttg gaataggtgt ggtgtggtgc tgaaaaaaat   49560
gtatattctg ttgatttggg gtggagagtt ctgtagatgt ctattaggtc ctcttggtgc   49620
agagctgagt tcaattcctg ggtatccttg ttgactttct gtctcgttga tctgtctaat   49680
gttgacagtg gggtgttaaa gtctcccatt attaatgtgt gggagtctaa gtctctttgt   49740
aggtcactca ggacttgctt tatgaatctg ggtactcctg tattgggtgc atatatattt   49800
aggatagtta gctcttcttg ttgaattgat ccctttacca ttatgtaatg gccttgtctc   49860
ttttgatctt tgttggttta aagtctgttt tatcagagac taggattgca accctgcct    49920 ttttttgttt tccatttgct tggtagctct tcctccatcc ttttattttg agcctatgtg   49980
tgtctctgca cgtgagatgg gtttcctgaa tacagcacac tgatgggtct tgactcttta   50040
tccaatttgc cagtctgtgt gtttttaattg gagcatttag tccatttaca tttaaagtta   50100
atattgttat gtgtgaattt gatcctgtca ttatgatgtt agctggttat tttgctcgtt   50160
agttgatgca gtttcttcct agtctcaatg gtctttacat tttggcatga ttttgcagcg   50220
gctggtaccg gttgttcctt tccatgttta gcgcttcctt caggagctct tttagggcag   50280
gcctggtggt gacaaaatct ctcagcattt gcttgtctgt aaagtatttt atttctcctt   50340
cacttatgaa gcttagtttg gctggatatg aaattctggg ttgaaaattc ttttctttaa   50400
gaatatggaa tattggcccc cactctcttc tggcttgtag ggtttctgcc aagagatccg   50460
ctgttagtct gatgggcttc cctttgaggg taacccgacc tttctctctg gctgcccta   50520
```

-continued

```
acatttttc cttcatttca actttggtga atctgacaat tatgtgtctt ggagttgctc   50580
ttctcaagga gtatctttgt ggtgttctct gtatttcctg aatctgaacg ttggcctgcc   50640
ttgctagatt ggggaagttc tcctggataa tatcctgcag agtgtttccc aacttggttc   50700
cattctcccc atcactttca ggtacaccaa tcagacgtag atttggtctt ttcacatagt   50760
cccatatttc ttggaggctt tgctcatttc tttttattct ttttctcta aacttccctt   50820 ctctcttcat ttcattcatt tcatcttcca ttgctgatac cctttcttcc agttgatcgc   50880
atcggctcct gaggcttctg cattcttcac gtagttctcg agccttggtt ttcagctcca   50940
tcagctcctt taagcacttc tctgtattgg ttattctagt tatacattct tctaaatttt   51000
tttcaaagtt ttcaacttct tttcctttgg tttgaatgtc ctcccgtagc tcagagtaat   51060
ttgatcatct gaagccttct tctctcagct cgccaaagtc attctccatc cagctttgtt   51120
ccgttgctgg tgaggaactg cgttcctttg gaggaggaga ggcgctctgc gttttagagt   51180
ttccagtttt tctgttctgt ttttttcccc atctttgtgg ttttatctac ttttggtctt   51240
tgatgatggt gatgtacaga tgggtttttg gtgtggatgt cctttctgtt tgttagtttt   51300
ccttctaaca gacaggaccc tcagctgcaa gtctgttgga gtaccctgcc gtgtgaggtg   51360
tcagtgtgcc cctgctgggg ggtgcctccc agttaggctg ctcgggggtc aggggtcagg   51420
gacccacttg aggaggcagt ctgcccattc tcagatctcc agctgcatgc tgggagaacc   51480
actgctctct tcaaagctgt cagacaggga catttaagtc tgcagaggtt actgctgtct   51540
ttttgtttgt ctgtgccctg ccccgagagg tggagcctac agaggcaggc aggcctcctt   51600
gagctctggt gggctccacc cagttctagc ttccaggctg ctttgtttac ctaagcaagc   51660
ctgggcaatg gcgggtgccc ctcccccagc ctcgctgccg ccttgcggtt tgatctcaga   51720
ctgctgtgct agcaatcagc gggactccgt gggcgtagga ccctccgagc caggtgaggg   51780
atataatctc gtggtgcgcc gttttttaag ccggtccgaa aagcgcaata ttcgggtggg   51840
agtgacccga ttttccaggt gcgtctgtca cccctttctt tgatccctga cccccttgtgc   51900 ttcccaagtg aggcaatgcc tcgccctgct tcggctcgcg cacggtgcac gcacccactg   51960
acctgcgccc actgtctggc actccctagt gagatgaacc cagtacctca gatggaaatg   52020
cagaaatcac ccgtcttctg cgtcgctcac gctgggagct gtagaccgga gctgttccta   52080
ttcggccatc ttggctccgt ggataagcct taaaaggctc aatacttttt aaaaatttcc   52140
tataaaatcc agaatctatc tagatttttg agcagcctgt agtggttgga ggaccatgat   52200
tgtttactca tttggtcacc taaacatccc aagcaatgat ttgttctgac agcagactga   52260
taacagtttt ttttactcct tggaatcgga aaaaaaatca gcaagggaag cttttggaag   52320
ccacccggta gagctggaag agaatttcga aatcaattcg ctcaacctct ccctttacag   52380
gcagaaaatg tgctagattg gaggtgaaga ccctggagcc agagagccta ggcttagtcc   52440
tagccctgca ctgaaggtaa tgtgaacact cagtgcctca gtttccttct aggcttcttg   52500
ttctgagatt ccatgaatta atatttgtaa aatgcttaga actgtgtcta acacattgta   52560
aacactagga acaaatgcta aggtcatgca actcatcaat gcctccctgg ggtagaacca   52620
gccttggccc atgggcatgc tcattcttct tttagacaag gctcttaggc atccctagag   52680
tgtgggttgg ccttcctatg cctgtacgta agaagtatga tgtaatgtaa ggaatatagg   52740
attcaaaatc aacaattagg attcaaatgc taatatttat tgactcaact ctctgaatct   52800
tagtttcttc atctgtaaaa ttataatgat cataacaaac ccaagtcaca gacttgttca   52860
```

-continued

```
gaggagcaaa tgagataatg tactttgaaa accataatct actctgcaaa tgttatgtaa   52920
cattataatt gtgagttcag caaagccatg agaatgtttc aaaactgttt aggacatcaa   52980
gaagttgggg tggggaaaat tcttaatagg ttttctccat atcctcattt tccatttatt   53040
cattgtttta aaatttattt ttcttatgat atacatatat atatatatat atatacacac   53100
acacaaaaga attatgtacg gtcctgcatt gcttgcattc tgagaaatgc atgaataggc   53160
aattttgtca ttgtacaaac atcatagagt gtacttatac taacctaggt gatatagcct   53220
actacacacc taggctgtat ggtatgacct tttgctccta ggcaacaaac ctgtacagca   53280
tgttactctg ctgaatactg taggcaattg taacacaatg gtaagtattt gtgtatctaa   53340
atatatctaa agatataaat atgtctttat aagtatacaa atatatcttt aaatatacta   53400
gtatatattt atagatacaa atgtataaat atatctatag atgtactagt atatatattt   53460
atagactaga aaaggcacag tacaaatatg atattattag cggggtgtgg taattcatgc   53520
ctgtaatccc agcactttgg gaggctaagg tgggagaatt gcttgagccc tggagtttga   53580
ggttacagtg agctacgaac acatcactgc actccagcat gggtgacagg gggatacccct   53640 gtctctcaaa aaagaaacta aaacaataag atagaatctt atgggaccac cataatatat   53700
tcagtctatc actgattgaa atgtcattat gcagcacatg actatatata tgtatatata   53760
tatatatata tatatatata tatatatggg atataaaaca aatactcata tctctaccac   53820
caggctcaaa aagggaatat tacctttgaa gtcccctgaa tatcccatcc tagcaatatt   53880 cctcccctc ctggaaaagt gggtaaacaa caattgtaag tcatgtgttt gtctttcctt   53940
tgcctgtagt tgcgctacac aggtgtgtgc ccagaaaata ttctttattg gatgcatggg   54000
gtttccttct tgactcagag atctcaagct atacggtatc ttcctgcagc cttatagtgt   54060
ccaccttatt ctttgtcact atttcccttt cccagccaat aaagcacatt acctctgtca   54120
ttcaaatgaa ctcgtaaaga gagattttag aaaagagctg gttcacctca ggttcacctg   54180
agcaaggaat gggtgtcagt gactgtggaa agtggagcac agctgccaga gcagtgcaag   54240
gacccaagaa atgggagggt cttgactcgg gataaccact ctgagattca ttggatgtcc   54300
tagattgtca ccttgcctta caccttaagg gagaaaagga taaaaagata aggcagatgt   54360
gaaagctata ctaaggagct tagacttttc ctgcaggcct ttgggaagca actgaagctt   54420
tgaagaaggg aatgacagct tgagactgct tcaaggcaga agagatagga gaccagaagg   54480
ccagtgagga agcacttagg ctgggccagg ggtacaggtg tggctggaag ggctgcccag   54540
aagcaccact gtggaccagg ctgagcagga ctgagtgact ggttagatat aggaaatgcc   54600
agagaaagag aaggtggtga tgactgaaat ttcagagtta cctaaatgca agcatggtat   54660
gttcataacc aaaataggta gcaaggagag ctaggtttga gagccaagct gattagtaca   54720
gaatgcgagt ggttatctct gctgtttcca gaaaataaag attaatttca gccttaaagt   54780
cagggactta aatgagatga tctcgaaagc cctttccatt tttgtaattg tgcaatcctc   54840
agaacgttgc ccagaatagt aagcagaagc aaaagaaatt caggagtttg aacataagag   54900
agagctgttc tctgatgcct gctccaatgg gaactgggca ctgtgactga gccctcggct   54960
cactgagtct cctcctgagg agtgtgataa aacctcacag ggctgctgtg ggtcttatta   55020
tacatgaaaa tacccacctc agtgcctggc acattctggg tgcaggaaaa agtttgattt   55080
cctccctccc ttccttcctt ccttcctttt tcctcccttt gttaccatag gagagagtca   55140
ggctggttcc ctgcgggtgc tggtgtgaaa cctgctcttt agactcttct gcagttcccc   55200
aaagcagcta ctgtcccaga gaactgcttt ctgccagcaa tgctcagttt taccctaaga   55260
```

-continued

```
cacgataact cctggctttg agggaagcac aggtagcaag gggacccctg acagcaaatg   55320
tgtagttgtt cttccagcta ggccccagcc ccaccttaaa tgccacatcc aggcactgtg   55380
tctacagtgc tgagataaag caaccccgtc ttttccacac aaatgagcag caaacatatt   55440
tgctgattat ctttgaggga cataacgttg cccagaatag taagcagaag caaaagaaat   55500
tcaggagttt gaacataaga gagagctgtt ctctgatgcc tgctccaatg ggaactgggc   55560
actgtgactg agccctcggc tcactgagtc tcctcctgag gagtgtgata aaacctcaca   55620
gggctgctgt gggtcttatt atacatgaaa atacccacct cagtgcctgg cacattctgg   55680
gtgcaggaaa aagtttgatt tcctccctcc cttccttcct tccttccttt ttcctccctt   55740
tgttaccata ggagagagtc aggctggttc cctgcgggtg ctggtgtgaa acctgctctt   55800
tagactcttc tgcagttccc caaagcagct actgtcccag agaactgctt tctgccagca   55860
atgctcagtt ttaccctaag acacgataac tcctggcttt gagggaagca caggtagcaa   55920
ggggacccct gacagcaaat gtgtagttgt tcttccagct aggccccagc cccaccttaa   55980
atgccacatc caggcactgt gtctacagtg ctgagataaa gcaaccccgt cttttccaca   56040
caaatgagca gcaaacatat ttgctgatta tctttgaggg acataatgaa tcagactgag   56100
atttagtcat atttgcacaa tgctttacat ctgagatact gaaagcttaa tccaaggttt   56160
ccctgttagt tgaagtccta ctgttagggc tcaaagacag ggtgcagctc tgtaagccag   56220
tccctgatgc cttgatccca atcattgagt ttatcaggat tctccatagg aagacacaag   56280
gagcacctct gctgcagcaa atgctggagt gttagttttt cctagaggct agtgcctcaa   56340
cacctcttct gcagatctca gctatggaga aaatgaaaaa gaaaaaggtt agagtctcct   56400
ggcttatgaa atttgaatgc cacttgaacc tgacatattt attttttagc tctaaatcac   56460
acaagatcaa gaagttctgc agatcctatt ccaacattgt gcaatgtctc tatatttaca   56520
aattttattt gatggggggg gcaatagaga cataatttaa tcctattagt tcttgaggag   56580
atactattta gagatctcac taattcctgt cctgaaggag aagacttgaa gtgtgcaata   56640
taaatattgc attaactcta atacagagtt ctacatttac gccttacatg tgtgcaaaca   56700
ggtgcacaga ggctaaagtt ctggttgtat tgctctccct ccatttacaa aagatcagtg   56760
agttcctgct tgcagattct ctgaggagac ccttagtttc atctcctctt cattcttctg   56820
ctggcctgat tcagcaagac caaccacaaa gcaaactgag taggcaaatg ggctttatct   56880
ctggtgactt tgcagatgca ctaatttttc agcaggctgt cattaaatgc ctactgggtg   56940
ctaggcataa tacagggtcc tggggataaa agatgataag acaattcctg tcctcttgtt   57000
gatagaaggc aggtagtttg tggtcaaaga ctctcattca cacccaccag attgttttta   57060
tatcccagtg aatccattat gtctctggca gcaccacaca ccaggtcaag tttgaggctt   57120
taaagttccc aggatgtcac ctagacttag agatgaagaa acactaacaa aagaagaaac   57180
aagacaacca caaaaacctg agcctgaaga gctgccacct ctataatgga atatttcaaa   57240
tggccttaga tttaaaattg gtctttgctc ctttaagcag attcccttag ctctggctat   57300
ctctgcaaaa tggatgattg atcaccaata gaaacttaat tatcaattaa tcggttgcta   57360
tcgaattgct ggtacatctc agttatctgc tactcctcag agtaatccat agtactttag   57420
tgaagaaata cttctaatta aacagggaaa tagcacttgc taatatatca aagtaaatga   57480
ctagacctaa aacattagta ttaattacaa gagtcagtgg gtttagcatc tctaagtttc   57540
tatttgctaa tttattgcca ctgaaaatga agaaatcgtt gttgatatat aaaatagagc   57600
```

-continued

```
attttaggtg gtttttaatc ataaaagtca gtagatgtaa aaactctgga ttgcatgtgg    57660
cagacatttg accttaagga ataaggtcgc tatacagaag gataactaaa cttttatttg    57720
tttgttctta aacaataaaa tgatttgaaa tatactttga tcattttgtg attattatca    57780
tatgggatga taatagagaa tttcttactt cctaatcatt ttcctacact tatagttaca    57840
tacaaagatg taatgaaatt tgctctcctt ttcttccaag gtatacatca ttttccttaa    57900
tactttctcc cgtccccatc gtctaccca gatttaccaa ttcccagcta tctccttagg    57960
acagtcaaga accaaatact cccatttgtc ccttataaac tcttttaact tccccaattt    58020
ctggaaaaac aaaaagcttt aataatatag ttttatatct ccatactcat cccccatcta    58080
cttataattg attcacttgt tcattcattc aattaatatt tactaaacat ctactatgca    58140
tgatagttaa tcaactactg gcaataccat ggtgaacgag tagggtccct gatcgcagcg    58200
agctgcttgg gagaagtttc acattatctt ataaatcacg caagcaaatg ttatgttgca    58260
gcttgtaact atgttacagc tatgctatgg gtacacaggt aaatgatatt atgagaatct    58320
acactagaag catttgactt agatagtggg gtcaggcag gcctcctgaa gaaatggtga    58380
taagctaaga tctgaaggag atgtaggagt taacaaggtg aatgaaggtg gaaggagcat    58440
ttcaagccgg gaaatagcat ctgcagaggc ccttaatggg agaacacgtg acatatttgg    58500
agcgctgaaa gaaggcctgc tcgctggagc actaagaaca cagatctgga gaagttgggc    58560
aggggccgga tgatgggaag ggagccatac agtccatgtt aaaaaaatgt tgttctttat    58620
cctaacagca atggggaagc attgagtgtt ttaaatagag agggatatgg tcagatttgt    58680
gtttgaaaaa gaaaatcctg ctgcagtgtg aagaacagat cacctggcaa gggtaacagt    58740
ggatgtggtg ggtctagtta agaagccgcc gcagtagtcc aggaaggaat gaggtggcta    58800
ggatgaaaat tgggaggaag ggcatgaagg agaagactgg atgggtctag gaggcattta    58860
gaaatgaaat tgttgggaat tggtgatgga ctgtatatgg gggcggaggg agagggagga    58920
attggagatg acacttagat ttctgacttg tgcacctgga ggaatggtag agccattcac    58980
tgaggtgtgt agtgtcctaa ggtcaggcag gaggaagatt gtggtttcta ggatgggcat    59040
gttgttgaat ctgaggtctc tgagacatgt gaatggagat acttgagtga tgttatctac    59100
aagtgctggg ctctttgttt gtttgtttg tttttattgc gtgggaggtc ttccagaaaa    59160
cctgctagac aaattctaaa agaaatataa cactcatgct gggttctatt gtgagagatt    59220
tatataaact agcttgttta atagttacac aagctctata aggtaagtac tattttttta    59280
gttctctcta ctttacagat taggggggaat aaaacacaga aattacatga ttttctgaat    59340
acagaaagat tattacataa agcaagtaag cattaggggc caggatttga tgccagcact    59400
tgggtcagtg ctctgtggcc tcccagtgag ttatccgtta accaccactc cctaccatct    59460
ctctgcacaa gaatgcacaa aggcacacat ttaaaaatat aatgtcagaa catgcctcta    59520
acatttatta ttattccagt tgaaattcat ctcatcagac ttgcctgcta gaagcattac    59580
ctttgtgtca agggctgaga catttaaaag ttttgttttt cttataatag cagcagctaa    59640
gttccatttt taggcgtgca catattgaac catggtgtga attgcgatag taaggtttta    59700
gagtctataa ataatgccta gtgaaattgg agccattcag tccctagaaa tatttatgcc    59760
tatctgtggc tatttgtcta tttgcatgat tatccttgcc attatcctcc aggctctgaa    59820
aatacacact gaaaggtttc ttaccagctt gttcatgtct ggattacat taactctatg    59880 accatatttt attccagaca cttctgagaa attcatcagg ctgtgaagcg cgccgtgatg    59940
aatatcgaac agagtttacc acagctttgc agcgcgttga cttattcatg ggtcaattca    60000
```

-continued

```
gcgaagtcct cttaacatct atatccacct tcattaaagg agacctcacc atagctaatc   60060
ttgggacatc agagggtcgc ttcatgcagg taagtgcttt ctgagagtag ctgtgtctgt   60120
tctatctggt attgtgcaat taatttgttt tcgttttttgc agtaaggtat ttgcaaatac   60180
tgtaaagtcc aaatcatagt agaaactgga acacagactg aaagccaaac aatgaagcct   60240
ggtctacttt ctgttaaatg tgtggtctct ttttattaag ttcttgaagc tttcagtttg   60300
aatctgtttg ctttaatttt ctcgtccaga atggtgtggc attttttttc catttataat   60360
ttctgtcacg tgattggaaa ataaaatgaa acaaagcact tctaggcaat tttttttttat   60420 ttcaagggaa gctacagatc aaaggagagc tattgtgtga accatgcatc ttcatgagaa   60480
gaaacattca catcattgag aaatattggc aggagttagg aagggacaac attatcatca   60540
aaatcccatt gtaactcaag ctctcctgat tctgtaaaat ggtagggttg gatgcaaata   60600
agttcagata caaaaaaaat ccagatttta ttaagaaatg gttttaatgg atagcaacag   60660
tatttctgta caacaaaagt ttccatttca acttactgtg tttcctagat acaagaacca   60720
tagcactttg cagaaattaa aagactctct tgttgggttg gttttttgctg ttttgtagtt   60780 attggtgcct ttaacatgag ttgttagtag attcttgatg aggaaagaat gacaatagca   60840
tctatggaaa tcttgaactt ctgtgaatac tagaaatttc ttttaaaggg agatttcgta   60900
attgtctgat gtagttagta ccctcatcag acaataacct ctagtaaacc aactgagaat   60960
gataagcttt tcctataact tgcctgtcta tacatcctat atgtgtattc ttctacaaaa   61020 catttttttta attaccactc tctttatagc agcctggata ttgatcattg ccatatttta   61080
aaacctgtaa gttatgtttt tcttgtacta aagggcatgg tggaattttt tcaaggtcaa   61140
aaaccatgta aataaaacct tcctagctca aaactaatca tacaggtcct gttatctaat   61200 tattcccta gtaatctccc ttctattgct tcacattgaa ctacgccttt tctccccctt   61260
tcctctgtcc attccactgt gcttgtttat ccaactcatc catcttgacc atttaattct   61320
atccttaact tctcaaacct gaaggaggga agccccgccc ctcccacaga gacatgcact   61380
ctaatggatt tgaaatatgc tcatatctat tatgtgtaaa atgtgtagta ttgttctgtg   61440
tttatacatg ttttttaattt acatcaatgg cattctatac aattgcaaaa atacaaagaa   61500
ggactagaaa agctggcatc tattgatttc ctaatgtgtt cattatgttg atttgccccc   61560
ttttatcttt atttctgctt tttttttttt caaaatcgtc cattacctca ccaatccagt   61620
tttgtatgaa taagcttttt atgattactt tagctccgac tttttttaac atcaaaagtt   61680
ccctggccta tttccacatt ctaaagttgt aatacaattc cttatttaaa tatgttgctt   61740
tattaactga gtaaattctg ctgtgtgaca gagtcaatcg cctgagggat atgtcacgca   61800
tcagtctcat tatagaaacg ctgtagcaaa tgtttttattc ttgtctccta gcctttgtgt   61860
aaaagaaact atattttgcc tattaactat gcatccaaaa caaaaggtaa aaaaaatgct   61920
tattttatga aaagtactgg tatcactgat ttttttttaaa agtggctttt aatttatcaa   61980
ataagtatca agaactacct aactttgctt tactatacaa acgaatgaag caaaggaaac   62040
agtgacacag aacttacctt taagaaatta aattttagta ggaaagatac ctgataataa   62100
tagtacctac agacaaaggg ctattcgaaa ccacagagaa tctatttctc tgacgcttgc   62160
ctaagagaat ttcattccat taaattttat aaagaaacct aaagcatttg aaggatcaaa   62220
caatcaacat cactgaagtc catatatttta cagtaaataa tagtgcggga ggagtcagga   62280
gtggagcaca gatatggcaa cctcccactt taatctgtca gagcagtgac ttcctacaaa   62340
```

-continued

```
gttctgtaaa tgttttgact gcaccacagt gttaaatgta tggctaggcc tgagtttcta   62400
caactcgtgt tttagtaaat acgatgaagt ttctgttaca aaatagaatg gacatttttt   62460 ttcccccaa agacagctgc cctacacaaa agggaacaga aagatgattt tacttccttc   62520
ctaccctgaa gcctaatggc aaagttgctt tgcaaatttt tttctcccaa gagtttgcag   62580
ctgtttctgt ctttcctatt gtgcttatgt tcagctctgg ctgggaacac aagctacagc   62640
cccagctgtt gggtgcaaag tgaatcaggt atttcacagt ggtcatttga ttagaaagaa   62700
ttatattgtt tagctaacaa cattttgtgt atggcaggga agacattttt gacatgttcc   62760
taacatttaa tgatgtgtaa cttatcttgt acaggtgcag ctatatctga aaatactgat   62820
gcatacatat atttaagtct caatatctgc agagccatgt caatgtagat gaagatttaa   62880
aaataatttt tatttgcatg atcactctct tgggatactt cgaagtaaaa tagtaggata   62940
agcaatgttt gagatagtgt aagtgaacaa tgagaacgtg ccttcttaca gactggggaa   63000
ggagatgtag aacagagtca gacttgggaa cattaacaca gtgtacacag ctacgtggga   63060
gagggaagag ggattctcat gaagatcaca ggactaatca cagggattgt ccacgtctcc   63120
cttctgagcg cctcgtctaa tctacatcca gaacaatgct tccttgattt tttttaacag   63180
cacttgtata aggcttttaa tctctaaatg caaagcattg ctattaaaat atttgtgcat   63240
gactgtcagg ccagggagag tgagtggatc agggatgcga gaggggggtgg ggaggccctt   63300 tcaagaattg tttcaagttc agctccacaa atactcactg ggcaactact atgtgcacta   63360
cactgtgcct gctcccaatg gccacagcct gggcactgtc actgctgcta ctgggctccg   63420
tggttccatc ctagctcttc ccgcatgccc ctttcgcctc tccaagttcc taaatgttgt   63480
taccacccac tcatcactcc tgttctcttc tgcctcttaa ctggactagt tggatcttaa   63540
gtaagaaacc caaggaggta gagatcacct aaaaagatgt cccatgttca agatcattac   63600
ttatgaccac tacttaaagg actgtgttag taatcagtga acctaagaat aattactcac   63660
ttccaataag aaaaatttgt ttatctgttg acctcctgtc ttcaaattcc ttcagttccc   63720
gtgcccccat cgtggcatgt cagtgctttc tgtgagaagc ctgtagtatg catcatgttt   63780
ggaattactg ccatttttaga gtatgtagat gcagatcccc aattcgtcaa tgttgtgaac   63840
atctggcaga gacacagctg aaggaagctt caacttgaac aatgattctc tttagggatt   63900
tctaacttac ccatctcttt tataaaataa tcagataaaa atattatctg ccttttttgtg   63960 tgtgtacatc attaacttag ttttaaccct aaagaatgtt agctttggct tttttttttt   64020
ttttttcaca gtgtctcgct ctgttgccca ggctggagtg cagtggtgca atcttggctc   64080
actgtaaccc ccacctccag tattcaagca attcttgtgc cttagcctcc tgagtagctg   64140
ggattacagg cacgtaccac catgcccagc taattttttgt acttttagta gagacgggtt   64200
tttcgccatg ttggccaggc tggtctagaa atcctggcct caagtgatct gcccgccttg   64260
gcctcccaaa gtgctgggat tacaggtatg agtcaccgtg cccacaagat ttggtatatt   64320
tctttagagg aaaatacact caagggttct gaaatttctt ttgtgtaaga aagaactttt   64380
tataaataat aatttcagtt atgtccataa ctaaaaatca aggattccat ttatatgaaa   64440
tatctagaat aggaaaacct atagagatag aaagtagatt agtggtagtc aagggctaag   64500
aggatatggg gagactggga atgacagcta agggatgtgg ggcttctttt tgagataatg   64560
aaagcattct acaaccctgt ctcaaaaaaa aaaaaaatta aaaccgttca attgtccact   64620
ttaaaaacaa tggggggaggt atacagaaac tgcatacaaa catcttatct taaattgtat   64680
tcatcattct taaaatttaa ttctattaat aaaacggttt aattaaagat aaaactgtat   64740
```

-continued

```
atgggaggta aggagatatg gcctttacat atttgtggat atctcacaca aagttacttt  64800
gttcaggttt acagatttgg gggcctagcc acaacagttt tatttgtaca tgtatttctt  64860
ccccatgtcc tatctacaag gggctatgtg agatcaaaac cacaaccatt tggtaaattc  64920
agattctgcc ctgccccaaa tgtattagtc ctgtattttc aaggccatta aagaaaaaat  64980
atcctgtgac ctaattacta aagattagtt gttgaatagt aggaactcaa agataattgt  65040
tggtcttcta ttttatgcga attcttctaa gattcccagg ttatttatca taagaattac  65100
atttacatgg caaatttagt tctgttccta gaaatatctc catgacaacc aaaaggaact  65160
cctaatttct ggcacacatt acttcagggg tattttgaga gttaaagtgg ttaatcgatt  65220
atttagaatc ctagcaataa gagaaagaaa agaattaagg gtagaaaaac atttatagca  65280
gtaggtatcc ctgcagagaa cgggctaatg atcaactaaa aaggcatttg catctgtggt  65340
acagcctctg cgcaaaattc caaatggcat tctcacttcc aagtcacctc acttctccat  65400
gtgccttcct gtcttctcat cttcatccca ttttctatag caagcaacac tcatgctaac  65460
tcgtgatcaa aagtagagct tggcggagtg tgctagtaac attttctcta tgccctcaaa  65520
aactagttag atgcagagac tttctcctta ggcacactta acttgtgcag caaaaattac  65580
tgaaacacgg agtaactggc gaggcaaata tattgtgaaa tttgttttag tacttttact  65640
cacgagtggc tcttgggagc tcagagttga agctttttca atggtattta ctctggtgct  65700
ccaagagcct agcagttgag tgtttaagag gtcaagcaca tggattctgg cctcagataa  65760
agctctgtgg aaatctgact catgtacttt ctagctgaaa ttctatgttg tatttttttt  65820
aaggaaaata atagtaccta ccttatagga gtattgtgag gagtaaataa aatctccatt  65880
taaagcactt ggcacaatat gtgactcagt ttcctgttat gaaagtacaa acatttggtg  65940
cttttcagac aaagcttttt aacagaggat acacatatca atcaatccaa gtccagaggt  66000
gcaaagagct tccgaaaaga aagagaaagg ttaattcttt ctgggaaagg actatttgga  66060
tgggcttcag atatttcata aagtcaaaga tgatgaccta gtaattaaga agggattgct  66120
tattatagat ttgggaaatg gtattaaaaa gagcaagaag gtaggagaaa aaaagggctc  66180
taggaggtga ttgttatgta gccggtctaa gtagaacgga ggaaaccagg gagacagaca  66240
caaaatgcag gtgtccattg caaggttcat agtgatgaat aatcttcagt gaagtgcaaa  66300
gcatagaatg agctggaaaa caaagtcagg gtattaagac agactggtgt tctgtgttgc  66360
ttttgacctg tgtgtgagaa aaggagtttt tttgcttttg tgttttttgtt tttgttttgt  66420 tttttgtttt acctttgcag tttgaagtga ttggcaacag ccaaagaaat atgggggggta  66480 ttgggcagga gtataggaaa aatgagatgt gatgagccca gaagggagtt aagattgcaa  66540
aattgggtaa ccaaaatctg gagaatttgt aatagaagct ttagaagtct aacatctgat  66600
attctgcttg taaccagtac ccaaagggag gtgggactgg taattgaatt tctgttcact  66660
ttgcctgcaa aggtcaccaa tacctattgg gccctaactt taggaaataa caatagtttc  66720
caacctttcc catcctgacc aagtgaccct tcatccatca cttaacttct gtgcaaatat  66780
aaccaccctt tttaatggag atgttttgaa agcgttgagt gtttagagta gaacaaacat  66840
tagagcacaa atgtcatgat gtttaacttt tacagctgta tgtgagcttg gttagtttct  66900
ctatcaacaa tccactctct gagaacaaat taggtacttt gagaatcttc ccaaattgct  66960
tcaggatact tggctccttt gttatgctga agaaaaaaatt tacaattgtt ccccagaaca  67020
tttatatgtt gtatgtgttt gttagagtac aaagcagtta attattgctg taattttcat  67080
```

-continued

```
tcccattata cgaatgagaa agctgaggta gagggagtga ctatgtaatc gtaatctcac    67140
agatgtccat gtttgtcctg tgatttcata cccatcgcga gtaaatgcat gttcaatgca    67200
atgtaaaagg ctattagaga tgttgggcaa tttcacaaag tagatttcaa gtctagggct    67260
gtgctgagcc tcctccacct tcatgtatat gcaacccagt ggcctactta agagtgaaag    67320
tttctctgag aactccaaca ccctcctaaa aatctaagtg ttcatgtaag ataatcattt    67380
ggattttatc ccaattgttg tcaattatgc tctgaacttt attattactg ggttctagga    67440
acaggacaga tggaaattag atagctggga aacatcccaa attttaaaaa cctgaaagca    67500
aaaatgacat caatcatcaa acctcatttc ccgggcattg ttaaaaccat caggccttat    67560
tttaaagcca gaccaagaag cagagtttta taatccaagt aataatatat tgtgggacag    67620
tggtttataa aaaaatacaa cacatcattt caaagtagct gggggcctgt tttgacctga    67680
aaagatctat aaatgtggct taagagtagc acagctggaa ctagctccag tattccagac    67740
tccgcgtcca ctactcttaa ccattacatc aagggaaact gcctggcagg gaggattaag    67800
aggatatatt taaaaaataa tccagattca ttgtagcatg tgtggtgtct tctttctgga    67860
gagagttttg gttcctccat tttccaatac aattgcaggg atttgtctgt atgtgctgcc    67920
aattgattga aagatctctt tcccttgaaa ccattaaaag atcataggca aagtctgtct    67980 tggggggttca gataatttgg cttcaaggca agagattaga agatgacata ttgatttaca    68040
atgaggggaa ctgttgggtc ttcagttcaa acacccacaa gccctgctaa tctgttatta    68100
ccattatcat ctacattttc cacttatatt taaactgagc ttgttggaat aaggatgtta    68160
taactttttt gctgtttagg ttgtggtttc tcgatcagga ccatcaaccc ctcatgtgaa    68220
ttttctcctg gactcccatc cagtgtctcc agaagtgatt gtggagcata cattaaacca    68280
aaatggctac acactggtta tcactgggaa gaaggtaagc tgttcccaca gggaatttcc    68340
atagacgtgg ttttttcccaa atgcatattt acaaccagtg tcacttggcc ctttataatg    68400
tctctcttca tcttaaattt acccctcctc cattaagttc tttagtgagt attccagaga    68460
tcttctgaaa tctagttaat ttgttctcca agaaagacta gacctaaggg aggtctttt    68520 caaaacttct cctttttgtcc tatatttctc aacaagaaaa ataaacacac agaatgagaa    68580
ttacagtcct aatgacagag ctctagtgca ggcagataaa tcctggaaat gtacattgga    68640
atccgactcc aaccaataat ccctttttctc ctagagaaga aagtgcatct tgatgccaga    68700
atgacatgca actttactta gaattttcca gagattcaag tgtgttttcc caccacttaa    68760
attatactct cttgttatttt taaaatcatc tcagacaggg cacaatgtcc ctactatgta    68820
gaacctctaa cattgtgtgg caatgctatg ctcactggac aataatgtta cttttttcaca    68880 tacctgctaa caataaagga aaggaaggaa tcagattttt aaaattttaa tcaccgttat    68940
gacaggattt gcacacatag ttgctaagtc tagaaaattc catcaaatga tatttacatg    69000
taccttttgt gtacttactt tataattaat taacaaacta gatacccctc tggaagctct    69060
ttccacccct tctcttcaca gatcacgaag atcccattga atggcttggg ctgcagacat    69120
ttccagtcct gcagtcaatg cctctctgcc ccaccctttg ttcagtgtgg ctggtgccac    69180
gacaaatgtg tgcgatcgga ggaatgcctg agcgggacat ggactcaaca gatctgtctg    69240
cctgcaatct acaaggtagg aatctctaac agctggcata catgttttttg tttggtgttt    69300 tttttttttt tttggtttgg tttgtttgt tttttgtttt tttagataca aatcccacta    69360
atgaaaaaaa tttaaaaatc aatttactca tttagctgtg agtcatcagc taaagcacca    69420
tctctctctt ggctttatcc ctcgggcagg gaggggtgg tgtttgggca tcccccccaag    69480
```

-continued

```
tcctgcacct gaagtgcttg cttcacattg tctaggttct atcgctgggc agctgctcac   69540
ctttagtgcc gtgtgaataa aagagtggtg gtgaataagc aacagtgctc cccattttct   69600
cacactgggg cctgttccct cctgactcac ccactctctg attcctcgcc acttcctata   69660
taggccaagt gcccagacat gagcctccat cacagaaaca gatctgttca tggcatatcc   69720
tggaaccctg agctgaatcc tgcaaactgg tgatccctgc catgctgggg cacacaggac   69780
agttttcttc ctgtccgatg catagatggt ggccttgtct gttcacagat gagactgaag   69840
attatttccc ggggtgaggt gggcaaggca agtggagggt caacacccat gggtggctgt   69900
gagtcttcct tcagtgttcc cagaaaaaaa agcaaaggct caacggatga ctatactaac   69960
atctatactt ctgtaagcca tgccactctt taattcattc caaaaatatt tattgagtgc   70020
ataccattta gcaggctgcc ctctagtccc tgaggagata tagtccagaa caagatgagc   70080
acatctcttg ctgatagaga actcagtttc tggcaatgga cattggctct aacatcgcag   70140
ccatgctaac tgtgttgcct tatttgctta agcatatatt cggcactatg aaaatctcca   70200
cgcaattttt aaaaatttct tagtccaaaa catcttgctt aaaaacactt ccctggtgag   70260
aacccagtgt gtatttttct ctgtgtgcat gtagaaaagt tggactttag taaatagttc   70320
ttatgaaaga ttcaagttaa aggtctcggt cacctggttc atgcccaagt aaacaaaatg   70380
tgcgagtcag aacaagaacc accccaagt gcatggctgt tttcatttag ttacggtttg    70440
gagcaagatt tgtagtgggt gactgggttt taaaccaagt tattttctgt taggtgtgac   70500
acagttatta agacttagct tgattgacca gagaataaac taaagacagt gacaaaacaa   70560
atttaaatct atactgtagt atttgtgtac ttttttgttg ttcagtatac ttttggaacc   70620
gtatgcaatt ttatactttt ataaacaaac aacttcagca atttgagaca ctaggaatct   70680
gaactctgct attccatgaa atagatatgg aaaatatatg tgtgtgtgcc catgcaatta   70740
aatcacaaca atttcatttc aaaaataacc aagctggtat tttaagtaaa gaaaatggtt   70800
tgataacctg tacaaatgaa acatttaatt tttactaatg tgcttccttt tactaagcat   70860
aaaagctata ctaaaatgct taaaaataaa gtaaatattt cagaattttc tggaaccaga   70920
gaatctcttg caatatttaa atgtccctcc tctctcaccc ttcttaactc tagcattcta   70980
tagttgatga ttctcaaagg ttgcgtgcta ccatgcacaa gtcagtgagg cttaagctgc   71040
agttaggaag gcagggcagc tgagtccata aatccctcta ggttcatagt tgttaggaag   71100
atttcatgct gcaccagact gtgacagtta gcattcttcc tgcaaaacat aagacagact   71160
cgaggtgggt gttaagatgg ccgagtagga acagctccgg tctgcagctc gcagcaagat   71220
cagtgcagaa ggcaggtgat ttctgcatgt ccaacagagg tacacggctc atctcattgg   71280
gactggttag acagtgggtg cagcccacag aggttgagct gaagcaaggt gggatgttgc   71340
ctcacctggg aagggcaagg gattggggaa ctccctcccc tagcaaaagg aatccttgag   71400
ggactgtgtt gtgaggaaca atgcattccg gcccagatac tacacttccc tatggttttg   71460
gcaactaaca gaccaggaga ttccctcatt tgcctacacc accaggaccc tgggtttgaa   71520
gcacaaaact gggcggccat ttgggcagac accgagcagg agttttttt cataccccag    71580 tggtgcctgg aatgccagca agacagaacc attcactccc ctggaaaggg ggctgaagcc   71640
agggagccaa gtggtctagc tcagtggatc ccacccctac agaacccagc aagctaagat   71700
gcactggctt caaattctca ctgccagcac agcagtctga agttgacctg ggatgctgga   71760
gcttggtgca gggaggggtg tccaccatta ctgaggcttg aataggctat tttcccctca   71820
```

-continued

```
cactgtaaag ggtacagctt cagcagactt aaacattcct gcctgctggc tctgaagaga   71880
gcagcaaatc ccccagcaca gtgctctagc tctgctaagg gacagattgc ctcttcaagt   71940
gggcccctga cccctgtgcc tcctgactgg gagacacctc ccagcagggg tcgacagaca   72000
cctcacacag gagagctctg gctggcatct ggtgggtgcc cctctaggat gaagcttcca   72060
gaggaaggaa taggcagcaa tctttgctgt tctacagcct ctgctagtga taccctggca   72120
aacagggtct ggagtggacc tccagcaaac tccagaagac ctgcagcagt gaggcctgac   72180
tgttagaaga aaaactaaca aacagaaagc aatagcatta acataaacaa aaagaacgtc   72240
cacacaaaaa ccctattcaa aggtcaccaa catcaaagac caaaggttga taaatccatg   72300
aagatgagga aaaaccagcg cagaaaggct gaaaattcca aaaaccagaa cacctcttct   72360
cctccaaagg atcacaactc cttgccagca aggaaacaga attggacaga gaatgagttt   72420
aacaaattga cagcagcagg cctcagaatt tgggtaataa caaactcctc caagctaaag   72480
gagcatgttc taacccaatg caaggaagct aagaaccttg aaaaaaaagc tagaggaatt   72540
gctaactaga ataaccgttt agagaaaaac ataaatgacc tgatggagct gaaaaacaca   72600
gcatgagaac ttcatgaagc atacacaagt atcaatagcc aaatcaatca agtggaagaa   72660
agaatgtcag agattgaata tcaacttaat gaaataaagt gtggacaa gattagagaa   72720 aaaagaatga aaaggaatga acaaaacctc caagaaatat gcgactatgt gaaaagacca   72780
aacctacatt tgattggtgt acctgaaagt tacaggggaga atggaaccaa gttggaaaac   72840
actcttcaga atattatcca ggagaacttc cccaacctag caagacagcc caacattcaa   72900
attcaggaaa tacagagaac accacaaaga tactcctcta gaagagcaac accaagacac   72960
ataatagtca gattcaccaa ggttgcaatg aaggaaaaaa tgttaagggc agccggagag   73020
aaaagtcggg ttacccacaa agggaagccc atcagactaa cagtggatct ctctgcagaa   73080
accctacaag acagacacaa gacagggatg ccctctctca ccactcctat tcaacatagt   73140
gttggaattt ctggccagga caaacaggca ggagaaagaa ataaagggta ttcaattagg   73200
aaaagaggaa gtcaaattgt ccctgtttgc agatgacatg attgtatatt tagaaaactc   73260
catcgtctca gcccaaagtc tccttaagct gataagcaac tttagcaaag tctcaggata   73320
caaattcaat gtgcaaaaat cacaagcatt tttatacacc aataacagac aaacagagag   73380
ccaaatcatg agtgaactcc cattcacaat tgcttcaaag agaataaaat acctaggaat   73440
ccaacttaca agggatgtga aggacctctt caaggagaac tacaaaccac tgctcaagga   73500
aataaaagag gatacaaaca aatggaagaa tattccatgc tcatggatag gaagaatcaa   73560
tatcatgaaa atggccatac tgcccaaggt aatttataga ttcaatgcca tccccatcaa   73620
gctaccaatg actttcttca cagaattgga aaaaactact ttaacgttca tatggaccca   73680
aaaaagagcc tgcattgtca agtcaatact aagccaaaag aacaaagctg gaggcatcat   73740
gctacctgac ttcaaactat actacaaggc tacagtaacc aaaacagcat ggtactggca   73800
ccaaaacaga gatatagatc aatggaacag aacagagccc tcagaaataa taccacacat   73860
ctacaactat ctgatctttg acaaacctga caaaaacaag gtatgggaa aggattctct   73920 atttaacaaa tggtgctggg aaaactggct agccatatgg agaaagctga aactggatcc   73980
cttccttaca ccttatacaa aaatttattc aagatggatt aaagatgtaa atgttagacc   74040
taaaactata aaaaccttag aagaaaacct aggcaatacc attcaggaca taggcgtggg   74100
caaggacttc atgtctaaaa caccaaaagc aatggcaaca aaagccaaaa ttgacaaatg   74160
ggatctaatt aaactaaaga gcttctgcac agcaaaagaa actaccatca gagtgaacag   74220
```

-continued

```
gcaacctaca gaatgggaga aaatttttgc aatctactca tctgacaaag ggctaatatc   74280
cagaatctac aaagaactca aaccaattta caagaaaaat ctaacaaccc catcaacaag   74340
taggcaaagg atatgaacag acacttctca aaagaagaca tttatgcagt caaaagacac   74400
atgaaaaaat gctcattatc actggccatc agagaaatgc aaatcaaaac cgcaatgaga   74460
taccatctca caccagttag aatggcaatc attaaaaagt caggaaacaa tatgtgctgg   74520
agaggatgtg gagaaatagg aacactttta cactgttgat gggactgtaa actagttcaa   74580
ccattgtgga agacagtgtg gtgattcctt agggatctag aactagaaat accatttgac   74640
ccagctgtcc cattactggg tatatacca aaggattata aagcatgctg ctgtaaagac   74700
acatgcacat gtatgtttat tgcagcacta ttcagaatag caaagacttg gaaccaaccc   74760
aaatgtccaa caatgataga ctggattaag aaaatgtggc acatatatgc catggaatac   74820
tatgcagcca taaaaaagga tgagttcatg tcctttgtag ggacatggat gaagctggaa   74880
accatcattc tgagcaaact atcgcaagaa caaaaaacca aacaccgcat gttctcactc   74940
ataggtggga attgaacaat gagaacacgt ggacacagga aggggaatat cacacaccgg   75000
ggcctgttgt ggggtcgggg gaggggggag agttagcatt aggagatata cctaagtaaa   75060
tgacaagtta atgggtgcag cacaccaaca tgcacatgta tacatatgta acaaacccgc   75120
acattgtgca catgtaccct agaacttaaa gtataataaa aaatatatat aaaaaaagaa   75180
accctacaag ccagaagaca gtgggggcca atattcaaca ttcttaaaga aaataatttc   75240
cttcccagaa tttcatatcc agccaaacta agcttcataa gtgaaggaga aataaaatcc   75300
tttacagtca agcaaatgct gagagatttt gtcaccatca ggcctgtctt acaagagctc   75360
ctgaaggaag cacaaaatat agaaaggaaa aaccggtacc acctactgca gaaacatacc   75420
aaattgtaaa gaccattgac actgtgaaga aactacatca accaatgggc aaaataacca   75480
gctaggatca aattcacaca taacactatt aaccttaaat gtaaataggc taaatgcccc   75540
aattaaaaga cacagactgg caaattggat aaagagtcaa gacccattgg tgtgctgtat   75600
tcaggagacc catctcacgt gcaaagacac acataggctc aaaataaagg ggcggaggaa   75660
gatttaccaa gcaaatggaa agcaaaaaaa gcaggggttg caatcctagt ctctgataaa   75720
acagacttca aaccaacaaa gatcaaaaaa gacaagaag ggcattacat aatggtaaag   75780
ggatcaacac aaccagaaga gctaactatc ctaaatatat atgctcccaa tacaggaaca   75840
cccagattcg taaagcaagt ccttagagac ctacaaggag acttagactc ccacacaata   75900
ataataggag actttaacac cccactatca acatcagaca gatcaaggag acagaaagtt   75960
aacaagggta tccaggactt gaactcggct ctggaccaag cagacctaat agacatctac   76020
agaactctcc attccaaatc agtagaatat acattcttct cagcaccaca tagcacttat   76080
tctaaaattg gccacataat tggcagtaaa acactcctca gcaaatgcaa acaaacagtc   76140
tctcagatga cactacaatc aaattagaac tcgagtttaa gaaactcact taaggccggg   76200
tgcagtggct tacgcctgta atcccagcac tttgggaggc tgaggcgggc ggatcacaag   76260
gtcaggagat ccagacatcc tgactaacat ggtgaaaccc catctccact aaaaatacta   76320
aaaattagct gggcatggtg gcgggcgcct gtagtcccag ctactcggga ggctgaggca   76380
ggagaatggt gtgaacccag gaggcggagc ttgtagtgag ccgcgaaggc gccactgcac   76440
tccagcctgg gcaacagagc aagactccat gtcaaaaaca aaaacaacaa caacaaaaaa   76500
gaagctcact caaaaccaca caactacctg gaaactgaat aacctgctcc tgaatgacta   76560
```

-continued

```
ctgactactc ggtaaacaac tggtacattt gttatttttc aagttaaata atgaaattaa   76620
ggcagaaata aataagttct ttgaaaccaa taagaacaaa gacaaagaca caacatatca   76680
gaatctctgg gacacagcta aagcagtgtt tagagggaaa tttgtagcac taaatgccca   76740
caggagaaag tgggaaagac ctaaaatcaa cccctaacat cacaattgaa agaactagag   76800
aagcaagagc aaacaaattc aaaagctaac agaagacaag aaataactaa gatcagagca   76860
gaactgaagg acatagagac acgaaaaacc ccaggagctg gtttttttgaa aagatcaaca   76920 aaattgatag actgctagcc agaatcatca agaagaaaag agagaagaat caaatagaca   76980
cagtacaaaa tgataaaggg gatatcacca ctgatcccac agaaatacaa actaccatca   77040
gagaatacta taaatatctc catgcaaata actagaaaat ctagaagaaa tggataaatt   77100 cctggcacaca tacagcctcc caagactaaa ctaggaagaa gttgaatccc tgaatagacc   77160
aataacaagt tctgcaattg agacagtaat taacagccta ccaaccaaaa aaagcccagg   77220
accagacgga ttcacagccg aattctacca gaggtacaaa gaggagctgg taccattcct   77280
tctgaaacta ttccaaacaa tagaaaaaca agggactcct ccctaactca ttttatgagg   77340
ccagcatcat cctgatacca aaaccagaca gagacacaac acaaaaaaag aaaatttcag   77400
gccaatatcc ctgatgaaca tcgatgtgaa catcctcaat acaatactgg caaaccaaat   77460
ccagcaacac atcaaaaagc ttatccacca caatcaagtt ggcttcatcc ctggaatgta   77520
aggctggttc aacacaggca aatcaataaa cataatccat cacataaaca gaaccaatga   77580
caaaaaccac acgattattg caatagatgc agaaaaggcc ttcgataaaa ttcaacaccc   77640
cttcgtgcta aaaactctca acaaactagg tgttgatgga acatatctca aaataataag   77700
agctatttat gataaaccca cagccaatat cattttgaat gggcaaaagc tggaagcatt   77760
ccctttgaaa accagcacaa gacaaggatg ccctctctca ccgctcctat tcaacataac   77820
attggaagtt ctggccaggg caatcaggca ggggaaacaa ataaagggta ttcagatagg   77880
aagagaggaa gtcaaattgt ctctgtttgc agatgacatg attgcatatt tagaaaaccc   77940
catcgtctca gcccaaaatc tccttaagct gataagcaac ttcggcaaat tctcaggata   78000
caaaatcaat gtgcaaaaat cacaggcatt cccatacacc aataatagac aaacagagag   78060
ccaaatcatg agtgaagtct cattcacaat tgctacaaag agaataaaat acctaggaat   78120
acaacttaca agggatgaaa aggacctctt caagaactac aaaaggaact aaacaaatt   78180 tacaaggaaa aaaaccatca aaaagtgggc caaggatata aacagacact tctcaaaaga   78240
agacatttag gtggccaaaa aacatatgaa aaaaagctca tcatcactgg ttattagaga   78300
aatgcaaatc aaaaccacaa tgagatccca tctcacacca gttagaatgg tgatcattaa   78360
aaagtcagga acaatatgt gctggagagg atgtggagaa atagggaatg cttttacact   78420
gttggtggga gtgtaaatta gttcaaccat tgtggaagac agtatggcga ttcctcaagg   78480
atctagaatc agaaatacca tttgacccag caatcccatt actgggtata tacccaaagg   78540
attataagtc attctaatat aaagatacat gcacacgtat gtttattgca gcactactca   78600
caatagcaaa gacttggaac caacccaaat gcccatcaaa gatagactgg ataaagaaaa   78660
tgtggcacat atatgccatg gaatactatg cagccataaa aaaggatgag ttcatgtcct   78720
ttgcagggac atggatgaag ctggaaaccg taattcccag caagctaaca caggaacaga   78780
aaaccagaca ctgcatgttc tcactcataa gtgggagttg aaccatgaga acacatggac   78840
acaaggaggg aaacatcaca cataggggcc tgtcgggtgg cggggtcta ggggagggat   78900 agcattagga gaaataccta atgtagatga cagataatct tatgtgtctt aaactttgca   78960
```

-continued

```
ggcacaaaat ccagctaatg tatggagttt cactttctaa tacatgcaag ttaacctgct   79020
tttcaaggta catgatgttc agtggctaaa attctttaca gttctagata tgagagattt   79080
caggactgta agcccattat tttgcttcaa acatggtatc tgatctcata cttaaagagc   79140
aatgagaaat gcttcagaaa agggagagca ctttttaata tattctgaat gtattaggat   79200
gcagttatca tatcttgtaa ggttgaaaat tcaggccggg cgtggtggct catgtctgta   79260
atcccagcac tttgggaggc cgaggtgggc agatcacgag gtcaggagat cgagaccatc   79320
ctggctaaca cggtgaaacc ctgtctccac taaaaatagg aaaaattagc taggcatggt   79380
ggcaggtgcc tgtagtacca gctactcggg aggctgaggc aggagaatgg cgtgaacctg   79440
ggtggcggag cttgcagtga gccaagattg ctccactgca ctccagcctg gatgacagaa   79500
cgagactctg tctcaataaa aaaaaagaaa gaaagaaaga aaattcaacc ccagtgagac   79560
aacagaacta ttcattgatc agaatactca gaaaagcagt attatatagg gataggaggg   79620
taggcaggca gtatactgcc accagtaaat atatttgtga gttctactaa agaggaaagg   79680
agaccccttt tggagttttt ttgttctgtt ttgtttttgt tttttagttt tctcatgttt   79740
tatcctaatg ggttttgaaa gcatgatcat ttaaaatact gttggaatgg gcccatcagt   79800
gatgtgatct ttcacctgtg aaaagacaag ggctactttt gtggctgtat ctcccctatc   79860
cagacaggta ggagacccag cctctgtggc tttatgccgg acgctcattt cctgcccaca   79920
gagtttctct gcccttcagg ataactcaga gtttgccagc cattgttggg tctatccaag   79980
ggtgtgtagt tcacaactgc ttccttcctt tttccctaga agggtaaagg ttaccccata   80040
agctaagggg aaaatgccca gcccagagag aaaagctaag cagagcgagc ctcttggatc   80100
ctgagggtct agcagagggc ttataatatc tcttcctatt gccagtgccc cagttgcgca   80160
gctctctgcg tcttttctca aatcatcacc caatccgttt gcctttata gaaagtgatg   80220 gtaatgatgt gtgtagagtg acagacttca gtttttacat agaaagacgg gatgtaggca   80280
gtgggatcag gccaacatca gccttgggca gcgtttcag tggggaagcc tcctcattag   80340
aagagccggc agcagctgtg tgactgcctc aggctgaaga gagtcctggg agggttggat   80400
gtcttgttct ctcctactgg atttctacca taataataat aaacagattt atttttctag   80460
tagttctcat ttgactagac atggatgagg taaatttttca ggaaaggcac aacagtgtaa   80520 tggatttta tgggtaaaat ggctatcata aaagctttaa gctaaaactt taaaggggtt   80580
tgataacgag ggtacattaa gactttggtt tgcaattatt tacttaggaa ggatggaaat   80640
gtttgcaagt ttgaatttgg ctaaaagccc ttcttaattg taaaagaatc acttttagat   80700
gttcacaagc tgagctttag caaatacctt tactggttct tgagttgcct ctatcttagt   80760
tttcccacca ttgtacttta cagcacaatt tacaatatgt ccccacccccc aaaagagcat   80820 ttcctttctc aattgtcaca aagctgctga gaagaagctt attttttaact tggaaatgtg   80880 ttttgtttta atagttttag cctgagagca attatcttac acactttata ggtgcctaat   80940
gcggtcttaa atcatgactg accaaggttt atcaataaat ccattgataa cataccagaa   81000
atgagtctgc aataacaaaa tgagtctgtt atttgcttaa catcaaccat caggggggaaa   81060 aatttaatcc taaaaatgag atataaaaca ataccaatga agataattag gaaaaattgt   81120
tacaatactg attttgggcc ctctctggtt ccgtttttat ctatttctaa aagaaacaac   81180
ataacacatg tattaaatat tacataattt ttaaaaggct gagtgtgtca actaaccagc   81240
ctggtataca tcaaatagtg accatatttta aagaacaagg aaaaatcttc agtcattaat   81300
```

-continued

```
aaatgtgaac taataggtaa aaagaagtag attcactttt catttgttag tgcctggtgc  81360
ataggaggtg ctttattaag aaataattaa tgaaacctgg gcagcataac aagaccccgt  81420
ctctacagaa atttaaaaat tagctgggtg aggtggcgca cacctgtagt cctgtctact  81480
agagaggctg aggcgggagg attgcttgag cccaggagtt tgaggctgca gtgagctagg  81540
actatgccac tgcactgcag actgggcaag agtgagaccc ccatctctaa aagtaaataa  81600
gtaaataatg aatgaatgaa tgaatgaatg aattattggc agatatgtgt tccaaaacca  81660
tctatatgtt tcatattatg ctagctgctg aatgcaactg ggcaaacact ggataccaaa  81720
tgaggtattt ttactgtgca acttttgtct ctgggtgggg aataccatag caaccagaat  81780
gtagtgcacg cagccagtgc acagagcaag gcgtataatg gctggacctt ggcttataga  81840
gcacatgaag gagtttgata agagctcagt ccgaaggctg atgaagagtt acaatcagag  81900
ttatgagcaa gtaaaagtct gggcccaacg tgtttctact cctaccctaa agagccctag  81960
aagatgaatt cacttcagaa tggcccaaaa agggccaggt ccaatggctc atgcttgtaa  82020
tcctagcact ttgggaggcc aaggcaggag gatcacttga gcccaggagt ttgagaccag  82080
ctgggcaacg tagtgagacc ctgtctctag aaaaaaaaaa aatagccaag catggtggcc  82140
cacgcctgtg atcccagcta ctcaggaggc taatgtggga ggattgcttg agctcaagag  82200
gttgaggctg cagtgagcca tgatcacgcc actgcactcc agcctgaaca acagagccag  82260
actctgtctg aaaagaaaa gaaaagaaag aaggaagaaa ggaagggagg gaaagaaaaa  82320
gaaagaaaga gagagagaga gaaagagaga aagaaagaaa gaaagaaaga aagaaagaaa  82380
gaaagaaaga aagaaagaaa gaaagagaaa gaaagagaag gaaggaagca gagaaaggaa  82440
agaaagaaag aaagaaagaa agaaagaaag aaagaaagaa agaaagaaag aaagaaaaga  82500
aagaaagaac ggaaggactc gaaaagcccc tttattccta ccaagctgca tctgctcttt  82560
gtcccatctt tggatctcct gaaaacaact tgtttcatta acatgtcatg tagttttaat  82620
gtttgttcca gatgctctga aatttgtgac ccttttccct ttagtgaaaa ttaaattttt  82680
actaaattgt gggaaaatga aagaatttca gactatttaa ggatatacat tttgtttgtt  82740
cgttttccat atatgtgaaa aattataata tattgggttt ttttaaaagt tctatgttgt  82800
ccttgtaggt tttcccaaat agtgcacccc ttgaaggagg gacaaggctg accatatgtg  82860
gctgggactt tggatttcgg aggaataata aatttgattt aaagaaaact agagttctcc  82920
ttggaaatga gagctgcacc ttgactttaa gtgagagcac gatgaatacg taaggatctt  82980
aaaatgcttt gctggggtgt gcttggaaaa taggttttgt ttttgaatga atatttcttt  83040
taaaattgct caagaagctc atctcttgaa ttaaaaaggg tcttggcctg tcacatgcct  83100
tgtgggtctg ttctgttttg ttcttgtaat cccatttact cattggattt gaagagagag  83160
aaaggtgaca tggcctaggt gaagagaaga ggccagaaat gggagtttct caaccattta  83220
tgcgacaagt cttcaggtgt tgtctgagta gatttgcaag agtagcacta gttgggatca  83280
cttcatcctt ggagtcttca aatgtagagt ctccaaaggc tttttctaca gaaatcagta  83340
aacagctcag catggatcct ctcttttaaa ttcactttct aaacctcaga aatgtagtga  83400
ggcagctgaa tcacgtgttt gagacttttt tagatgagtt aaaatttata ttcagcttat  83460
atttactggc actgcaatat atgggctgta tctcactgaa ccatccccac ggtcctggga  83520
gggagcagta tcattcctat aatataaaag aggtacctga agttcagaga gatgaagtgt  83580
ggcttcacag aggtaatcca gagagtaaga gctgaacaag ccttcagctc agctctgatc  83640
atcttctgat ccaagacccg tgctagttct actgtattct acatgtaccc ttctacaagc  83700
```

-continued

```
tttgaattcc ataatcatca gagaatccag aaattattca ttatcacata ataacaacac   83760
tcaaatattt aaagttttat ggttgaatct ttatgattga acccattcta tcaggtggtt   83820
attttatatc taatagaatt catttcaggg ttacacaaag gtccgaatct atccatttta   83880
ctgagaccaa aacactaatg aaggtaatat ttgttagctg aatggcaaaa caaatttttt   83940
ctagaaatct cccttgtaaa atctccaaaa ctcttaatca ttgcatataa atcaggacct   84000
gtaaaagtaa agcataattc attctctcct ttaaaaagtt atttaataaa tcaaattgta   84060
tttaaatttt ctcagaacta tatgattatt cattcagaaa taattctatg gaaagccatc   84120
acaatttcat tatcatttaa gtaatttaaa taagcatgta caagtataac cacagaaatg   84180
tacctgttga catactttaa tgaagagatt ggcctatttg tagttagccc attgtttcat   84240
atgcatctga agtggaccaa agattatccc caaatattaa tattatccaa acttagatta   84300
ttatgcacta ttcaactggt gaggtcttta tggataaggt ctgatatttc ctgtttgtct   84360
gtataagtgc tatagtacca ttaatgtaaa gtttagtata agcagggtgc agtggcttac   84420
gcctgtgatc ccagcacttt ggcagaccaa ggcaggagga tcacctgagc ccaggaattc   84480
aagaccagcc tggcaacgt agtgagactc catctctacc aaaaaaaaaa aaaaattttt   84540
ttttaattaa ccagatgccg tggcatgcac ctctagttcc aactcctgag tccagaggat   84600
cccttgagcc caggagttca aggctgcagt gagctatgac tatgccactg ccctccagcc   84660
tgggtgacag agcaagatcc tgtctctttt tacataaaaa taaaagttaa gtttatcata   84720
gtatagaaat aggattatat aattttttggc cttaatgctt atcttgaaac tctgcttgct   84780
attcaaagca gtcagctcac catttagagt taatgtcact tcctataaaa caacctaacc   84840
agaaaattcc ttggatttgt catgtattaa actttgggtt tttttttccag attgaaatgc   84900 acagttggtc ctgccatgaa taagcatttc aatatgtcca taattatttc aaatggccac   84960
gggacaacac aatacagtac attctcctat gtggtaagga agattctatc ctatcatgtt   85020
tgatttttac ttaatctatt taaattataa gatgaacaag ttactttgtt ttgtttttat   85080
ctcccctcca ggatcctgta ataacaagta tttcgccgaa atacggtcct atggctggtg   85140
gcactttact tactttaact ggaaaattacc taaacagtgg gaattctaga cacatttcaa   85200
ttggtggaaa aacatgtact ttaaaaaggt gttgtaaatt tatttttttgt tgcatctgtc   85260 aatttgaatt aatatctgta ccttaaaaat taagcagatt gttttgtgtg tgtgtgtgga   85320
gaagaaaaat caagatgttt atttgtttac tctcctactg acaaaacttc ctccttccaa   85380
aattcatcta ctccttttgc tgatttttct tcctttctct tgtttttttag caatcctact   85440 tttcagtttt gtcttcccat ccaccctctt tattgttata gcttaggatc ttagctatac   85500
tatgagctgt gagagtctgg tcattgataa taatttaaaa taaacatttt catcaagatt   85560
tgtaattaga ctaagtcact ctggggaagg aagaaatggg gaaaattggg tctggaagac   85620
agttatgttt ctgcttctta gagttggaag agctcagttt aatcaagtac caaaagtact   85680
ttaaaggttt ttttttcaaa tctcaaatgt tttccagtca aggatagctt gtccacaaca   85740
aaggtaagtt tgagatccag tcagattaaa cagcctacac tagaaaaggc ttccactcag   85800
gaaattccca cttaggaacc attgagttat atcctttttga tttgtggata taattctaaa   85860
atatgtgtat ctctaatagc taaaattcac ttccttaatt ttttttgttc agtgtgtcaa   85920
acagtattct tgaatgttat accccagccc aaaccatttc aactgagttt gctgttaaat   85980
tgaaaattga cttagccaac cgagagacaa gcatcttcag ttaccgtgaa gatcccattg   86040
```

-continued

```
tctatgaaat tcatccaacc aaatctttta ttaggtaagt agaagcttct gatgggtata   86100
agaaaacaat gaatacaagg atgattttgc tgtagaatag tcaagaggaa ttgcagtttt   86160
atctctggct ttgatgctgt tatgttgctt ttgaaggctt ctttccaatt caggagagaa   86220
aactatattc aggttctgag tgtagtttga cttatcaatg ctagttcatt ccaagaagta   86280
tcttatcctg ttctattaca tttaaacaga gtatagcaaa atagtttaat gtggcattgt   86340
agtatacatg cacttacatt atgtacatat caattctata ctaaccttag tgcccagaag   86400
tggaattacc tttttttcttc cattctctag atatgttttt gtcctgcctg ctttacacac   86460
agcttttctt tatgccagac tctctttgaa ttgatatctc attggaccca gttcaatctg   86520
ccttgtttcc gttaattcta tcagtctagc aacaatagtt aagttcggtt ttctttgtat   86580
ttttttcaga ggtgaaatat ttattttgtg taattcggtg aataaaatac aaatgcattt   86640
cttaagctta tgaaatatgc attttaaaaa tattttcaag ttaaataagt tgtttccaaa   86700
gaacagttac ccatgaactt ccatttgatg ttgactgtgc ctctgacctg taatcagtgc   86760
aggtgattaa attgaatccc tctcttacag tacttggtgg aaagaacctc tcaacattgt   86820
cagttttcta ttttgctttg ccagtggtgg gagcacaata acaggtgttg ggaaaaacct   86880
gaattcagtt agtgtcccga gaatggtcat aaatgtgcat gaagcaggaa ggaactttac   86940
agtggtaagt cctttgagca atggttctac tcagagctct gcatctttgc ctctaaccat   87000
gtggctttca tggtacctga gacatctcag tttcgccttt aaggtttgct agttaatttc   87060
cttgcagtgt agccaagtag tatttttttat ttaataactg aaattatcta gagtcttggg   87120
ctaaccatgt ggaaaaaata catacacata cacacatgca catataatgt ttagacaaga   87180
atgaagatta ccaatttgag acagtgtttt tttatgtttg ttggttggtt ggttttgagg   87240
gtttttttga gacagtatct caccctgtca tccaggctgg agtgcaaggg cacgatctca   87300
gctcactgca atttcccct cccaggttca agcgattctc cacctcagcc tcccaagtag   87360
ctgagactac aggcacgagc catcatgcct ggctaatttt tgtattttttt ggtagagacg   87420 aggtttcacc atgttggcca ggctggtctt gaactcttga cctcaaatga tctgcccacc   87480
tcggcctccc aaagtgctgg gattacaggc atgagctact gtgcctggcc tgaggcagtg   87540
tttttacaga cagtcagtac aaatggaaat cacagcattt ccctagtccc ttttttaatgt   87600 gtcatagaac atggaccctt ttgctctaat aaaatccttg gaaaaggttg ctgatcttgc   87660
agcagtattc ttgcatttct aagcagctga cgtatgcttt cttacagccc cctgttcttc   87720
ttatcattct tcttgtccct ttgttagctc tttcttgaaa gagctaacaa agaaagagca   87780
ttagaatatt tatgttatgt cctaaagtgt gaatgttatt tgctgtttct ccacctatcc   87840
ttattttata taggtcacat taaagtggta gttttagttt agaccttaga aagcttggag   87900
ttatttccaa agattccata cattttgttg atgtttttct ctaatataaa ataccataat   87960
ctagtaggac ttgagcactc aactcagaat gaaagttcta agtgctcttg ctcaagcaag   88020
gtcttgattg gtcaggtgat agattgaatt acagcacttc cttttagatt ctccatccaa   88080
tatttcttga agactaaagc cacaatgttc tttaattaca aaaaccaatt tggggctaaa   88140
aatgtcaagc caaatcacca aataataagg tcatttcaaa taagattttt cttggccttc   88200
tcaatcagcc acattgcatc acctctagag agtattatta gattttttatc atattcctga   88260 gagattgtac tctagggagt caccatatga agcaaagcat tttgaaacca atccccacac   88320
atggccacaa acaaagttag agtaccactg ctattaattt aaaggacatc agttctccac   88380
aactaagcat aacaatgttt cattaaccaa ataagaataa tagtgaccct ctttggtgtt   88440
```

-continued

```
ggtatgagac cttttaaagt agaaatctga gaaattatta gtttatctaa ttaatgctga   88500
gcctccatta ttaagataat gactgaattt cctttcttct ccctcattgg cattaaagtg   88560
acactcagaa tgccttagct tcagtcattc atttgtaatc aaatatttat taaaaacttt   88620
ttaggtgtca cacatgagag ttacatatcc caaggatgat tcaaacaatg gtagacgata   88680
aaaatcttat ttgtttatat atctggaaat ataaacttct gttgtttttag tgacaaacat   88740 gttagtacag tagaactgta cattagaatc ggacaagagt gaaaaattca gtggatctat   88800
tttactattt actatttatt ttactgtcgt ttgtgaaaag tactttataa ggagatatgt   88860
attcattcca tgttccttgc cacttataga atttaaagct gaccatgatg aattgaaccc   88920
atttattatt taacaaataa aaactcttgg tcaggtctga tttagatata taggtccagc   88980
cacaataact ttaagtccaa taaacttgaa tcctttcaaa acaagaacaa tcatcttcat   89040
aacaaaatgt atattaaatt gttaacatgt gcattatgcc ctaggagcct gcagtttatt   89100
gtgtagttct caaatttctt gttatgtaaa caattattgt gatgacagtt aaattgttca   89160
tgtccatcag gaataaataa cttttagcat tataatatta attttatata aaactaaata   89220
gtataatttt atccatatta tatctctatc agtttttatct gctgcctata tacatttta   89280 atgtaagatc attttttaaa tgattttta aagaaaatag caaataacaa attctgtttg   89340 tccttttttat gtatatcctg agtcctttttt ctattgtggg cataagtaat tgtttttatct   89400 ccaactatac ttgtcaaaga aaaggaaatc taagggatgt tgttgcttgt ttgtcttttc   89460
cttgggggaa aaatgcaacc gttaaccta gatgtaccac tatgtgttgc tggtttagtc   89520
taagtacaat caagaggaag ctacattttc caaaattcca taaatcagaa ttccaaagag   89580
gaagatttga aatgagacat gaaagggcat gaaataataa tagcagaggc tttgtaaaat   89640
agagagcata ggaaaaggtt tcagtataaa atatgtcata gacaaaaaga tagcatggga   89700
gtgaagacac tgaattttgg agttaatggc ctaggattta tattcgctat tctgccactc   89760
caagctgtgt gacctggcct aatgacataa gtttgcaaag ctcagtttct tcatttgtaa   89820
actgtgggta atcataatac ccacctatag gattatcagg agaattaaat gagaccaact   89880
ttgtaaagta ttttgcacag aacctggcat tcaataatta atagcttaaa agacactaat   89940
aagattacct aacaacatag ttaattatca tgttcaccat atggtgcttg gtgctttaca   90000 aagcactta ccatgtggta tccaacatgg taaatagcat tttcatctta attcctaaat   90060
gaggaaactg agttattcag tgtgggccct accttagttc ccatagcttg ggttaaagct   90120
aggagatgag ccaaggcctt ctaaccccac aaagctgagc tcccagtctg cctgactgcc   90180
tcacacaaca aggggcagtt cctccaggtg actgtcctgt cttcttaagg aaaataaaat   90240
gatgagatga aggccagctt cagatagatc agcacagttt atgctgggca ggtggagctc   90300
tgtgtttctt tgaagggtgg gttgtttgga taattttgca tgtatcgtgt ttccagaaat   90360
gtgtagtcta acattaggaa gttaaataca gattttttca aaaattatat attttcaatt   90420
gattggggtg gtaaattata aagttgctat ggatgttgcc aagctgtatt ctgtttacag   90480
tggataattg tgtctttctc taggcatgtc aacatcgctc taattcagag ataatctgtt   90540
gtaccactcc ttccctgcaa cagctgaatc tgcaactccc cctgaaaacc aaagcctttt   90600
tcatgttaga tgggatcctt tccaaatact ttgatctcat ttatgtacat aatcctgtgt   90660
ttaagccttt tgaaaagcca gtgatgatct caatgggcaa tgaaaatgta ctggaaatta   90720
aggtaagaaa tgctttaaac actgtcttaa atcatcagct caaacttaat tgacttcata   90780
```

-continued

```
gctatgtgaa tacaattgtt gtacttggcc attgtatctt atacaacacc agcaaatata   90840
taaactctga aaaacaaatc tttttggcat aaaactaaaa gataagaata accgtggact   90900
gcattttaat gaagcattaa aaaacccttt cttgtgtatg tattaaaacg tagcaaatgt   90960
gggacacaaa ttatccatta aagaggatcc gcgtcatgca ttatcttgct gatgttatac   91020
atttccccgg acatgttacc taaatgtgct cattataaga taaaacataa gagctgtgaa   91080
agtaaatgca tcaattgtat ctccgttctt ccttgtaata cttggaattt tgtatctggg   91140
tatggtcatc tctaagctaa tttgtaaatg gaactagata tctgccacct taggaacata   91200
ttagcttcta aatgtaattt aatagagaat aacagatcat cttttctaaa gcaagcctgt   91260
tgcaaacaaa gaacactaag acccagaaag gttaagtgat tgacaagtga caaaatagtg   91320
gcagaataat aaagactaga gtgcagcttt tttatgtccc ttcagtagtt tctacttcaa   91380
ataataacac aggcaaaatg ctcaagactt gaattattca tagctccagt cactagaaac   91440
agcaaaatat ttatccttca acatgttgtt aaaacattta gaattttttt tcctgaaaga   91500
tgatctgaat gcaaatatga acaaacataa agcaatagga tagtctttat ttggttgtaa   91560
tataggcttt catgggtcat ctccatctaa gtaataatat gtttccattg aaatttttct   91620
gactttttca acaaaaattt aactgcagcc caacttatgc atatgttcac gttcatacaa   91680
gtttactaac ctcattattg tgttttgtac aataattaag caagcccagc ataaaattga   91740
atggaagccc gcttcaatga acagtgtgtt tacaaaagca aagttctttc atctgcttct   91800
ttaattagtt ttagaaaggg agaaataagc ttttatcact tcttttttttt taataaaact   91860 aatctagtgt gacctttttgc tttcaacaat tactgtgttt gccatttgaa agattccatt   91920 tggttttttct tgatgataac aaaggtttat gtgcaaatag ttttacactc acagaaactc   91980
tatttttctg ttcctgtatc tatgatgaag ggattagaga taaacggttc tttatctacc   92040
cttccaagca cagtctttat ggaagagaaa acttctcttt ccataaatta aatacccatt   92100
attcaacatc ctacaaaatt gttggaccaa gaaaaacata atttggcatc atcctcggcc   92160
tgtcaatggt attcccaaca tggcgaaagg gtcttctaga gactggcaaa aaacacttta   92220
ttttcttgcc tatatatgga ataactcttt ctctaacaag tgtatagcac ctgccacgtg   92280
acagaatagt aatctagtgg gagcagtggc aattcaggga gattatttta gtatcatggt   92340
tcaatatttt ttcatacttc atttttctta tgtatgagag gaaagcaaag gcataagaga   92400
atatttgttg tgtcagcaat ctaactcttt atcaatacgt taagttgatc acattaaaac   92460
ttctacctct cagccaggca cggtagctca tacctgtaat cccagcactt gggaggcca   92520 aggcgggtga atcacttgag atcaggagtt caagaccagc ctggccaaaa tggtgaaacc   92580
ccatctccac taaaaataca aaaattagct gggcatggtg gtgggtgcct gtaatcccag   92640
ctactcagga ggctgaggga cggaggtgac ctgagtcctg aaggcggagg ttgcagtgag   92700
ccaagatggc accactgcac tccagcctgg gagacagagc aaaaaaaaaa aaaaaaaaa   92760 aaccacgtac ttcatcaatg aaagtgttct ggagagaatc atgtgtttag aatgagatat   92820
gctctttatt gccaggaaga tttcatgctc ctcatgcagc catgcatgca agagttccta   92880
gggtgaaaag agattgtgat cattccctgc cctagttgtg agagtccctc aattcatagt   92940
aagcccagtg actacaccat gggcaaaagg gcgagccagg tttggatgag ggaacacaat   93000
aggggtcaag cataagtcac ccctcagaat gaatcctaag ccccatggat ggagaaggaa   93060 gttttttggcc aaggcttcaa gtcccccaag agcagtcgta gacagtggtc atcaaaagta   93120
ggtacctctt tgtgggtata catgactccc caaatgcctc tatcaacaac agctcatgtt   93180
```

-continued

```
tgtatggaat tttacagttg acactgtact ttggcatatt ttatttcatt tgagtctcat    93240
gtggacccat gaggttggga ggtcagtgat gattatcccc atttatagat aggtaaacaa    93300
aggtttagga agattagctg atttgtcttg ggtcacccag gaagcaaaga gcagaactgg    93360
ggctcacact caggcttctt gattccaaat ttggtcttct gtcactgcat acactaaatt    93420
acagtatttc ttatattaac tctcatttaa tgtatactaa aataccatta tagagacact    93480
tttctatcat atgctattta tatatctatg cagttcttta gagggaatag ctcttaactt    93540
tttataaata tctaaaaatt tattctgttt aaagaaactc tgtatttctc cctgagtgtc    93600
ttatttctga cttttttatgc atgagcatat cttatgaaaa gtagaaaagt attctgtttc    93660
atgctggaac aaggactgcc tgacattgcc ttgggggttt atcttattct gcagcatata    93720
ggaacatatg agaataaaga tgcttcaaat gttcaatctg gagaagtcag gtcaaacagg    93780
aaaaagaagc acaggaagat gagccagggc agggagcggg gacttggtct atgacactgt    93840
catcacagga acaaatgctg agagctcagg aggaggtgaa gcatcagtgt gtgggcattg    93900
gaaggatcaa aaaggaagca tggttttgaa ccatcctaat ccacctgctg cccagagcca    93960
gccagatgtt gtccttctcc ctttgaataa tttatgtgca actctacccc tcaatctcag    94020
tcaaaaccac catgaactca gttctgagtc cagacaggat aaaagtgaag ggttcttttt    94080
tcagaggtta tttggcccag tgtcgaaacc tgttcttatt aatggtgctc aacgcttact    94140
ctcaaactag tatttctttg tgctgcccag gttaatgggc attctgcaaa atatatatat    94200
attctttttc cagggcagtt tcatagtatc taataataaa gatagtaaaa aatatattcc    94260
tgtggtttca tggtacctag tagtaaaggt ccccaactag ccagcaaagc caccagttta    94320
attttggttt gcccagcttt tcccaaatgg ccagggaagt tttccccaaa atgcctatta    94380
acatctggtg gaactcagtt ctgaagctgt ctgtgaggtt cgttgcttgg ttcctaagtt    94440
gagggacttg tgtcctctat gtgaagtgta aatctcaccc cctcaccacc acctcactaa    94500
tttcctactg ctgatctccc tggactttgg accctcagcc tggctgagtc ctgctgccaa    94560
actgtactga cttgcccaga cccagcctgt ggccacctgg gtgtatgaaa acttgaagga    94620
ccctcctctc atagtgttat ttttcagatc ctacccactt ccactcccat ctgctcggtt    94680
ctgtaaccat ctcagacatg agtccccggg tgtgaatact caatagaaac atgtcacacc    94740
tggccagggt tggagaggaa agagacatgg tacatcctga tatagcacat tgggagtaat    94800
tagttttcat ttttgaaatg gatccatttt gacattgcag tgagaggaag aaatccttac    94860
tcatctttat attctcagtg actagaactg tgtctaacac acagtagacg gtaagtagat    94920
tttgtgtcaa atggaatttg atttgcttca tgatctagcc cctttctgga taatagttct    94980
ccatatgtaa agcagaaatg acaataatac ctacttcagg gggagtatct ttgcaggata    95040
atatgagatg attataacta aattgctcta tgtctgttgg agattaaaga tcagaaagct    95100
ctctctcttt tgttgcttta tttttaaacc cacatattac cattttagtg actgaaatca    95160
ccctgaagca gttgaatgac ttttatttaa taatagttaa tattcaataa taaatattaa    95220
tataattaat agtaaaattt ctaaatataa gttttttagc atctcaataa agctatgttt    95280
actttctttt attttaaatg acaaaaatta gcctatacct tttaaaattt ttcctttttt    95340
gggccccatt gttatataga agtgagctac cagtatcact tttgtaatat ctgggacttt    95400
acgcttctaa tatgcatata tatatatatg tgtgtgtgtg tgtgtgtgtg tgtgtgtgtg    95460
tatacatatg tgtgtgtgtg tatatatata tatatataac tgatagtagt tgcttatata    95520
```

-continued

```
agtcactact taccatgtgt cctttggtat ctacatataa aatgagacac agtggatgtg    95580
tgatctgttt ttgtttttaga gaagccttta tgcaacaacc agggagatcc taagcctgaa    95640
accataagta ttggaaacac aaatgttgta cattcatccc ttcccccaac cttagttatt    95700
atctaagcaa gcaagacaca ttttagacct tttctcataa atcaaatcct acagctcttt    95760
aatctctttt ctttgtcatt ccctgaattc cctccaatat gtggataagg gttttatccc    95820
ccttcagacc tagccaacaa gttgtcgttt gaagccctaa agtcatctct tagattgctg    95880
agcttctgtg ttgtgttggc ctgtgtggct gacctggttc aatggactac acatactgct    95940
tctagaagta tcataaggat agggtttgtc tatatccatt ttatctgaaa ctccaacatc    96000
aggttataaa gaagtatttt cttcccactt cttttcctag aataataact gcctgaccaa    96060
tcaatctatt gagatccgta tgagaccatg tatgtgaatg gagtttgccg agtattaaag    96120
attatataaa acaaaggagc agcatttttag ctattatggg ctgctctttg ttagtaagaa    96180
gaatagtaat atgctttgat atatgtcacc tcaaaataat agcttgctca ataaataact    96240
gtactcatta agtcttgata tgagaaatta tacctaggtt tgcacttctt tcgcaaggct    96300
aattattggt ttctcaaaca aaacgttgat atttttaaaa tgcctgatgg taacttcagt    96360
taactaaata tgccacatta actaattttt aaaaaatttt tgtgtaacta tgtaattgtt    96420
caaaataatg gaattgtgct ctcaaattat aatagtcata cagcatctca cataaatttc    96480
ttttaaaatg aattcactta tgtataggac tcaagtgtgc aagaaggatg aaagtaaact    96540
acccaactca aacaaaaaaa gaatgtatta atattaacat aacataatac agtgttaata    96600
cattaacaac tatttaacat cagatctctg gagatgagac ccggacatca gtatttttta    96660 aagtttttcac ggtgattcca aaagcaaagt caaggctgag aatctctgca ttgggcagtg    96720
ttagatagtg caacaactga atctctacat tgcgtctttt ttgccaaaca ttgatacccc    96780
ctgaggacaa tggtgaggtg atgataggta agacatcatt ccacatttaa ggatgtgaag    96840
caagaacctc tttcctttc tttaaggtcc aatttgatgc aaaagctata tgctataatt    96900
cctaactaac acatgccctg aaatggtcat gctcccttt agccatccca attcccatga    96960
aaattagtat catagaatcg tgtgccttgg caaacaacat ggcctgtgtt tgcagtatat    97020
ttatattcct ttgccattgt tagcattcct gcagaactgt gaagtgttaa caacctttt    97080 tttttttttt cctttcaggg aaatgatatt gaccctgaag cagttaaagg tgaagtgtta    97140
aaagttggaa ataagagctg tgagaatata cacttacatt ctgaagccgt tttatgcacg    97200
gtccccaatg acctgctgaa attgaacagc gagctaaata tagaggtggg attcctgcat    97260
tcctctcatg atgtaaataa ggaagccagt gtaattatgt tattctcagg cttaaaataa    97320
atcattaaag ctcatttatg tgtgggtttt ggctcatcaa ctcagcctgc attcctagtt    97380
gttattttag aaatagtgag ctttttgcca cattgtctcc ttccccaagc ctgggaggta    97440
gatctcaaaa gttctttcta cccacactgc ttctccatca cgccacactc ttcccaaaat    97500
ttgctgtaat tctcagaaga aataaggatg catccaagag tgtccttcta ctgcctccca    97560
ccaccccagg aggccagagc cagtgttcca ctgccaacca ctgtgatcac taatgcatag    97620
agtcccataa ataaaggaag atgcatgcat caaacaaagt aaaataaaga ttaaactact    97680
ttacagtaac ttttttcgtg tagacaactg aatcaaacaa gctagaacca aagcgagtga    97740 tcttttcat tcttttttta gcagcttat tgtgatgtaa ttcacatacc atgcaattca    97800
cccattgaaa gtgcacagtt caatgggttt cagtatatta tattgtcaat ttctttgaat    97860
tgaggtaaaa tatacataat gtaatgtttg ccatttttgac catttttaaa tgtacaatta    97920
```

-continued

```
agttgcatta atttcattca cagtgttgta taaccatcag cattacctaa ttccagaact   97980
ttttcgtcac cccaaacaga tactctataa ccaataagca gcagctccac atacccttct   98040
ctcccccggc tcctgataac ttccaatcta ctctttctct ctagaatttg cctattctag   98100
atatttcatg tgagtggaat catacaatat ttgtcttttt atgtgtggcc tattttactt   98160
aacataatgt ttatccacgt ggatgaacat aagattcatc cacgttgtag cctgtgtcgg   98220
tacttcattc cttttgtgg atgaataata ttccattgta tatatcccac atttatccaa    98280
gagtaagtga ttttttaaagg gttcctgaag tcttctgaag ttataaaatg gaaaaacaca  98340
caaaaattag aaaatcaaag gctgaatcat gagatcagag ttggaatttc agaaggacca   98400
taaatcctaa aaatcataaa atgttagagc cagaagggac ttcaaagatt tctgctgtgt   98460
atcaaaactg aagtaaaaat attctgagac tttattgttc catcataaca gtacaattat   98520
ttacctctta tgggaagtct tctctgccct ccaccccacc gtccaggaca gaattaatgt   98580
cccattgtct ctgttgatta ctgtttagtc atacttctat ggtacatacc acactgtact   98640
ggaatcattt atttatatgt ctgtctcccc ttctatactt cagttcctgt tttttgtaca   98700 tcttttatc cctaatacct agttacaaat acaaacagct aagtaccaca taagtactta    98760
agggatcagt gtcccctaat tatttgaaca ctggagcata attgaggaat ctcttattat   98820
cctgaaggca gttatgccat ttgtagaatg gtaataacca gttggtattt gggacccaaa   98880
gtgctacaac ctgtgtagta caaatatcta tcatggctaa atgctgactt ttctttattt   98940 gtcatttta gtggaagcaa gcaatttctt caaccgtcct tggaaaagta atagttcaac    99000
cagatcagaa tttcacagga ttgattgctg gtgttgtctc aatatcaaca gcactgttat   99060
tactacttgg gttttttcctg tggctgaaaa agagaaagca aattaaaggt gcattttttgt  99120 tactgttcat ttttagaagt taccttaaga acacagtcat tacagtttaa gattgtcgtc   99180
gattcttgtg tgctgtctta tatgtagtcc ataaaaccca tgagttctgg gcactgggtc   99240
aaagtctcct ggggcccatg atagccgtct ttaacaagct ctttctttct ctctgtttta   99300
agatctgggc agtgaattag ttcgctacga tgcaagagta cacactcctc atttggatag   99360
gcttgtaagt gcccgaagtg taagcccaac tacagaaatg gtttcaaatg aatctgtaga   99420
ctaccgagct acttttccag aaggtatatt tcagtttatt gttctgagaa atacctatac   99480
atatacctca gtgggttgtg acattgttgt ttatttttgg ttttgcattt atattttat    99540 aaaaacctaa aggaagtatt tacctctgcc aagtaagtat ttgacacaaa attacatggc   99600
tcttaatttt aaaagaaccc atgtatatat tacattatga ttttagagtc cataagctct   99660
catttcacaa aaaggttaat ttgagcaaaa gtaatttgtt tatcatctaa gtgcaatagt   99720
aagaaattgc gaagctctct tttacaatcc aggaagagtt aagttacaaa atatacttat   99780
ttaaatgtaa gttggaactg ctacatttt tacctgttga agcccaaaca ttgaaattat    99840
actgttagta attcttcgaa gtgttttcaa tgaactgtta gtacacagcc tttttcccac   99900
catattctag gacttgaatg tattttgaga cttagccaag gaaaaccttc aattatgcca   99960
tgaaaaaaag gaggggtcaa tatcatcagc tttgtaaaac actatgccta gtaatgttca   100020
ggttaatcag agttttcatg ttgtttttatt taaatctcct ggtaaaagca aaaggtctgt  100080
attgtatcag ctccattatc tttagaagtt acaggatgtg agtcaagtac aagcatttcc   100140
ttggttgaat atttaccatt ggacaaataa aatgagtcac agatcattga ggatactgga   100200
aaagttagaa gttgctcatc caaacaagtt caagagcaat gaagcactta acattttaac   100260
```

-continued

```
attttcaaca cttactacct cttatgtttt gaagtttatg ttatttctat ggagatacac 100320
atagtaaaca ttgtctttgc cctgattcca ttcacctttta aaaatccatt cgtttaaccg 100380
tgtggaaaaa tcaaacctag tttattgttt tgaaatttag atctatttag tattttatgt 100440
gcacatttag tgcatctatt tagtatttta tatgcacatt tcatagttct aatctgagat 100500
cattaaaatt tacaaatttt ctttgaaaaa aaaacttacc taatcttctt tgaacctcct 100560
tactcaccaa agctctgtca tcattgctaa gaaggttgag tttcacactc ttttctccat 100620
tgagcctgct ccttggagac atgaaaagaa aacaggtaaa agagggtcat ttagagagaa 100680
tgagaaaata ggtgcacagc caaaacctaa tgaagaggca actgcagagc tttcctctct 100740
acatctggtg gggacagcat tctcatcaga cttttttcacg gagacctaga gtgctatgtg 100800
gtgtgacatc agggtggcac actgatggtt tcaattggtt tctgcacatg ttggaattta 100860
gctgaagagt cacgttttca tgccaaaggg cttttatcca tgtctcacca aggatttccc 100920
tcaatctgtg cacccttaag catttagagc cctgatctcc agatgcaaag gctttaggaa 100980
gtgagaatga aagacctgag tttagagagg ctgattggca ttcccaatcc cctgggaag 101040 gtttagagac cctgactcct tggaattaag ggagcaagta cccagctagg ctccttcctt 101100
cctcactcac ccaacatttc aggtacttca ctgatgttcc acatccttct ttaaaggttg 101160
ctcttgtctt ttttctggct agtgtctact ataactgtaa ttgatgccca acgctttct 101220 ggaaccactt ttggccaagt tcatttatta ttaatcaaac tgtccactgt agaaaatact 101280
aaaaatgctc aagtgggatt aggaatagtc aaggtactaa cagcattctt tttatgccct 101340
tctctcagat tctgattctc ctgcttattt gcaaacaaat gatacatttt ggtgctaatg 101400
aggaaccccc acataacctt ctccctgtgt tacatactaa tacatttcaa tactatgcct 101460
agtttatctt catgtcagtt gctgtggcta tgatgccccc tccttgatat gtgtgaattc 101520
ccagtggaaa gagaaaggga aagtggaaat gccctatttg gcattaagaa attgactatc 101580
agcaccattt cttcccctga aataaaaaaa aaaattctcc ttgcaaaagg gaactttgcc 101640
tgaggttctt acagagcttt ggttataaag atcaacttat aaagaatgct taccccttttc 101700 atagtgtcct taactaaaca acaaggatgg tccactaacc gagatctaac ctgccttctc 101760
taaacaacag taacactaaa tccagtgcca tcactgcaca gtggagaatt taccactaat 101820
gtgaaaagct ttcagttttg ggaatatagc cattatttat ttctaatcat atgtgtattt 101880
ttcccttggc caggaatcca taggttttgc acaatagtaa ttaattccat taacaaatag 101940
tagtgtctca aaaggcatct ttttcatttt cttatatttg agctggattt ttgtgagacg 102000
aggcaattgc tcaactacct ttgctgctac cactgcttcc attcttaagg acatagtata 102060
ttcaaaaata aaccataagc atggcttttt gctattgata aagagagaaa tgtctaagga 102120
aatgagggta aaaagctttc aaaattaata cttagtctac ttaaatgaaa atctgtaaac 102180
atctaatgaa atgcttgtat atataactta gtatcttttc ccaatttatt atcattttta 102240
tcaaactaat tccattataa aagctcttcc tgtttcagtc cccattaaat gaggttttac 102300
tgttgttctt taataatttt ccttcatctt acagatcagt ttcctaattc atctcagaac 102360
ggttcatgcc gacaagtgca gtatcctctg acagacatgt cccccatcct aactagtggg 102420
gactctgata tatccagtcc attactgcaa aatactgtcc acattgacct cagtgctcta 102480
aatccagagc tggtccaggc agtgcagcat gtagtgattg ggcccagtag cctgattgtg 102540
catttcaatg aagtcatagg aagaggtaag tatttccact cagcttttttg ttaaatacga 102600 ttttccagta agcattttat ctttggcctt tgcagattag gaacttagac aatggtgaaa 102660
```

-continued

```
gcaactgaca gagcagtgat aacaagtgta cttgatttct gttctataga aatgtagccc 102720
tgtaaatcat atccgtgggg atttgccctt gtgcatggaa gcaattggat aatcccccaa 102780
atatattaga actaaatcac aattcgtcct cgtcctgtgt gtactagcaa ttatagtttc 102840
ttcaaaggtg ccatttactt tcttctaaaa ctcagggcca ggcgcagtgg ctcacacgtg 102900
taatcccagc actttgggag gccgaggcag gtggatcacc tgaggtcagg agttcaaaac 102960
catcctggcc aacatggcaa aaccccgtct ctactaaaaa aatacaaaaa ttagccaggc 103020
gtggtggcgg gtgcctttaa tcccaactac tggggaggct gaagcaagga gaattgcttg 103080
aacccaggag gtggaagttg cagtgagcca aggttgtgcc acagcactcc agcctgggca 103140
gcagagcgag actccatgtc aaaaaaataa atacttataa ataaataaat atcactcctt 103200
taattttgag tattttttatt caatctctct ccagtctttc tttaccctga gaacagtgac 103260
aaactctatg aagcctggtt tatagcagtt tgtacactgc tggacagcat cagaagacag 103320
agaatttata gcattctcct gatctaaagc aacatatatc atctctacaa tgcactccaa 103380
tttctttata caaagataaa tgaatatttg taataagcta gccaaagcag caataacagc 103440
tagcataaac agtatttgtg gaaatattta gcaggaaaag aaaccaatca aaaaccggga 103500
aatgaacttc attcttcttg ttgttttttt ttttctaaaa agcttttacc cttaatacta 103560
aatggcctct gatccctttt attctatatg tgctgcaaga ggttgtacag gcatctgcca 103620
gtgtgataca agagaagctg atggcgtgat ttcccttata tgaacacaag gccttctcac 103680
tttcctgtgg tagcatccac acattcttct gtcaaacacc ccagagcgta atcctttgtg 103740
tgctccttct tccccaagag tggcttcact gttaacaaac atctttccat ttctcttcag 103800
agtaatatat agttctgtca taggcctata aatcccagta attgcatcaa tttttagagtg 103860 tgtggactca ctaattgtgt tctaattcta cacatttgga aaactagaat tttttatcat 103920
gaaaggtact aaaatggcaa ttatttctct tttgaagtta taatcattaa cagctctata 103980
aatattagct actatgtatt tatatgtttt tctgcaggag aataggagca ctcaaaagca 104040
taagttttat tttattcttc tttgcattag tagagggcag cctaatgcct gacactcaca 104100
tactaggcac tcatggtgtc ttggccagct ggatgaatta attagtgaat gacttacaca 104160
gctatcagac atttggcacc tctgggggaa attactgcca ctggataaaa ggctaccatt 104220
gggaaaatga tgtggttaaa gccagagaga actggatgaa gtgagtcagg gtgaatttgc 104280
ttcatctggg caactgcctt tcagtttctg ccaacctgga ttacgtatta accagtgact 104340 aatgggaaa tccttattct ataatactaa tcctattttt aatggtaaca ttttattttc 104400
atttcagctt attagaatat agagaactta ttttattata gttcttcatg tgggttaact 104460
ttattttcat attttaaaat actatgtcat cctttaaaaa aatttatttg atgaggccga 104520
tgttactcac cttttcagtg gttccactgt ggttgaatat tttattaggt taggctttaa 104580
tatgagtcat atcatctaca acttattcat gaattaaata atcacattgc ttatatcctt 104640
gggtgaaatg tgttgcatct acatatatat ttacaaacac acctacgtac ctatagtggt 104700
attgttaaaa gtatttttta aatgtactct tttgctgtat agaaagaaga aagaataaaa 104760
tgaagctcat aaagggtttg ataaataatt atttcataat taaatgttac gcagtgctaa 104820
ccaagttctt tcttttgcac agggcatttt ggttgtgtat atcatgggac tttgttggac 104880
aatgatggca agaaaattca ctgtgctgtg aaatccttga acagtaagtg gcattttatt 104940
taaccatgga gtatactttt gtggtttgca acctaataaa tagcttataa taaaacgttg 105000
```

-continued

```
atttacactt tccccttgtg gaaaaatcag ctaccactga aattatgggc ctaatcctga 105060
aaatttgttt tgttctagac ttttattgaa ctacttcccc tgaaatgatc cctcagagcc 105120
ctcattagta aggggtagg agaaatgagg ttcttggatg aactgagtat catttaacta 105180
taactatgtt tggtttataa tatttgtttt gcaagtgaca tttctggaaa ctattggaag 105240
catgttggca cctacagtag taatgactca ttttacccag aggcattact ataattattt 105300
tttaaccaca acttccatta aaaagataaa aaatgaaata agacaaacag gagaaaacta 105360
cgctggccaa aaattgaaaa atcataagta tggtaatacc tcatttatcc acattttgg 105420 agagtgaggc attccacata catgaacttc ctaaataaat gaaacctacc cctttttaat 105480
gctggaacat tacttaaaat tttagctgtt attgagaaaa tcttttttaag atgaaatgca 105540 tactctgttt aagggaatgc ttccaaatac aaactaagtc tttattggtg accccaagcc 105600
ataattacag ccataaatta ctatattaca caaacagtgt actccacata catagtgttc 105660
ctggctccgc ctgtgttgac aggtctcaca tgcttgcgtt ttctactccc atttctcatt 105720
ttctgcttgc aaattgcagc agcctgaaaa atgttaacca gctctactac aaactttata 105780
tgggacttaa taagctttaa gtgcacaaat gaaagatttt cctgcaagat actttactgt 105840
cacaattatt tcagtctttt taaaatataa atcaacatgc taagtagtgt tctacatggt 105900
taattttgtt ggaagtctga ccatgaggga aataaatgga cagtctttat gaaacctaag 105960
tataaccttt gcactaagtt tataggagac aaactggtgg ctggttggac tctatcttgc 106020
aaaagtgggc ataggtggtg actggaaggc acagtgcacg gtggcatcat tcactcagat 106080
gtgatgtaaa aagaacactc tgcagtcaaa ccctcaggac aagatgctaa ctgtgtggtt 106140
taccatttca ttgctcttcc tatctaaatt tgacaaaagt attcactgtt ccataatgaa 106200
gttaatgtct ccaccactgg atttctcagg aatcactgac ataggagaag tttcccaatt 106260
tctgaccgag ggaatcatca tgaaagattt tagtcatccc aatgtcctct cgctcctggg 106320
aatctgcctg cgaagtgaag ggtctccgct ggtggtccta ccatacatga aacatggaga 106380
tcttcgaaat ttcattcgaa atgagactca tgtaagttga ctgccaagct tactaactgg 106440
caaactagct gtaagccagc catcccttca aaataggcct gctctgagtc tttaaaaagc 106500
tagtagccaa agatgcacat ttaaaatgtt agcatcattc aaatgcacct caaagtcttc 106560
tatcctggtg ggaaatagtg acacctggaa gggtttcctg gagcaatgat tcttacttgc 106620
tctgcaagca accttgctct accttccctc tgataggac atttagtcat ctttgcatgt 106680
ctactatgtg ccagaaactg tgcacagcac aggagaagtg gaagcagagc aagcctcagc 106740
ccatatggaa tgttaactct acaaggcatt gaaaaattaa ctccagatgc gttccttgct 106800
gttccttgtc cttgccatcc actctcacac ctcaggaact ttgcacttgt gctccctcag 106860
cctggaacac tctccccgca aatagccacg tatctcactt cctcatcttc ttcagctttt 106920
ggccgtaatg ccatcttcaa cataagcctt ccctaatctg tttaaaattg caactgacca 106980
cccaccctca tggcttcaga ctcctcttcc ctgctctatt ttcccccatc acacttaact 107040
gtcatctgat acatgcatga agctgcctga agctgcccaa tactatggcc atgagccaca 107100
tgtaaaagga ggctagttcg aactgaaatg tgctgtacgg tgtagaatac atcccagatt 107160
ctgaatactt agtattaaaa aaaaagaag gtgaaatatc tcactagtag ttgtttatat 107220
tgattacatg ctgaaatatt ttggattttg ggggttgaaa aatacattgt gaaaattaat 107280
ttcacctgtt tcttttact tttgagtatg gctactagaa aattttatat tacatgtgtg 107340 tcttgctttta tatttctatt gaatagcact gtagtagata ataaacaaat aaacaatagc 107400
```

-continued

```
tatatagatg tatatgtatg catatatatg tacacacacc ctcatcccat tagaatggaa 107460
gctcatgagg gtaggatttt tgtgtatttt gttcactgct gtggctccaa cacctaaaac 107520
agtgtttagc acatagactc gcagtaaata attgttgaat gaatcagcta agggttacaa 107580
aaaaaggttc ttagcctctt gcaagtggta gatttttttc ttgacattta tgccaggacc 107640
taaaagtcac caggccagga ccagggaggg tgggaataag aatctcaaga actgaattca 107700
tagaaggcct caagctccgt ctcggttcct gctctccaag tctctgtggg aggtaatgaa 107760
gttgatcaaa agcaacttta taaatatggg gtcaaattat cagagaaaat aagctctagg 107820
agagtaatga gatattactc agccaaaaga ataaaacatt ccctggcagt gaactttttgc 107880 agataaggcg aattgacctt acaaagcaca cagctgccct gacagacccc actttcccac 107940
ttcaactttt gttattaccc tgatggatta atgtggctgg aggtgctacc ttctctaggg 108000
tactgttacc ccaggattaa agcatgatag agatttcctg ttatccagaa cggaatagtg 108060
ccatggcctt ttttaatcca aggagctgat actgagagca accacaaacc cagatgtgtc 108120
ttaaagagaa acctaaaacc aggaactggc cttttctctat gctgtgtgca ttgagtgggg 108180
ctacagccct tttgcagggt ccccactgac tacatcttgc actgacaaac tcctcagtga 108240
ctgttgaagg ggaatacccc attcctgatt gccagccagt gacatcacca gacttgacag 108300
ctgagtggtt tggggtgatt tctttctgag cctcctctat tcactgtgct tctgatgttc 108360
taacatcttg ggccttacta accctggagg aactgtccct cccaaggcta gctaattcct 108420
gcaaatagta aacagcttgc cttcaaagca tacctgtcat gtgcaaacca accaatccag 108480
agcccttatc taacctcctc ctttatcagg ctcttacact ttgggctact atccacctgc 108540
cctaatcacc ccagggccca gttccagaca actagaacta tcctcggagc ctgctgaaat 108600
actccagatt ggccagctcc aaacctgctt accctgcctt accagtttct tcccaggaa 108660 actgcaatga aggctcttgc tcatgttttt cccctctctc tctctgcctc tagagcccag 108720
ggcttccccc atgtgaccct gcatgacagg gtgtgcctcc tcctcttgca aactgtgaat 108780
agcaaactat cttttcaatg gcagttgtct cctgttctgt tggcctcatc atacctggaa 108840
aataataaaa ctacatttta aaacacctcc attttcccat ctggaaaatg gagcctgtaa 108900
cacctgcctg acagaagtgt agaagtagct gtaatttatg aaaacaatta gcctggtgtg 108960
ttgcatacaa taaatactta acaaatggtt gatctgtcaa tggggcacac tttttgttgt 109020
tgttgttttg ttttttgttt ttggagacaa ggtctctgtc acccaggctg gagtgcagtg 109080
gcacagtcat agtgcactgc agtatccaac tcctgggctc aagcaatcct ccttcctcag 109140
actcctaagc agctgggact ataggtgcac accaccacac caggctaatt tttttgtggg 109200
cggtggatgg gagtaaagac aggatctcac tgtgttgccc aggctgatct caaactcctg 109260
gcctcaagcc atcctctcgc cttggcctct caaagttctg ggattacagg cttgagccat 109320
taagaccaaa ctaattttttg agacaagata atttttttata aataaatatt tcagaattct 109380
aaggtcaaaa ttagaacagt agatgcttag tttatgcttt tctaactctc tttgactgca 109440
gaatccaact gtaaaagatc ttattggctt tggtcttcaa gtagccaaag gcatgaaata 109500
tcttgcaagc aaaaagtttg tccacagaga cttggctgca agaaactgta tgtaagtatc 109560
agaatctctg tgccacaatc caaattaagt gacaaggagg aatctgtttc ccactgttca 109620
atgctagtta agctgtttttc tcttcttatg caaaagtcct ttatttctgt tacaatctta 109680
aatcgatgtg taagccctgg ggatgtgggt gggactttca gactttatcc aacagagaat 109740
```

-continued

```
ttaaaaggat tctccatagg gggtcttaaa cagctgttgt gtacttttgc ttttctcagt 109800
ccttccctcc agtagctctc aatgttgtgg tttcacactg cattagtgtt ggggagggag 109860
aatttgatct tcagcatttg acagtgaaaa ggagagggct gggaacacaa ataccaacat 109920
attgcaactt cccaagagtg gatttgaagc cagcctgcag aagccctacc aaaaatggta 109980
tttggcaatg aatatacaaa gaactttatt tgtgtctggc tgcctggcta tgtaatacaa 110040
cagtcaacag tttgtaattg agttcatgtt ttcccttgca tagcactgat tcatgactta 110100
tggtatgtgt gaatgaaaaa gggtgtgcta ttaatttcct accttggttt tggtcactgt 110160
aacaacataa aagccagctt aaacagagga tgcatagccc cagatagcgg aaattgattt 110220
ttgttgaact tcgctgtttt tcttagatgc tttactgtgt atcctagttc tctattacct 110280
cagtggtggg atatatgagt tttgtgtgct aacctagctc atttaagaat gaaaaagtaa 110340
agtatcagtc ccctgtcatg ctctcccata aaactgagta tcgctaatca gttgacaagc 110400
gaagattggt gattgcttgg gtagttaatt agcatacttc atttagcaac caaagtaaac 110460 ccacaggga gacagcctta ctactgcaga tctacattaa agcaaaaagg actttcttat 110520
gccatacaat tcatgatctc tttcctcagc ctgttgaatt ggcaatgtca atgtcaagca 110580
tttttattca agaattctgt tgtaatttag tgttagtcaa tagaggccag atgaaatact 110640
tccttcagaa gttatggatt tcaaatactg aagccacttg tttaatctgt agatattcag 110700
catcattgta aattattcta tttcagccac gggtaataat ttttgtcctt tctgtaggct 110760
ggatgaaaaa ttcacagtca aggttgctga ttttggtctt gccagagaca tgtatgataa 110820
agaatactat agtgtacaca acaaaacagg tgcaaagctg ccagtgaagt ggatggcttt 110880
ggaaagtctg caaactcaaa agtttaccac caagtcagat gtggtaatgt attggttatc 110940
tctgagtttc tcctctttta ctttcatatc caactttttt tgaagtttta tcactactta 111000
attttttaaa aaaattcaac accaccaatt ccagttttct tcatatgtaa aaatggactt 111060
gtctgatacg tacacattgt atattttcat aaattcactc atttgttcaa aaatatttgt 111120
tgagtggggc aacataccag ctccttagga agcccagagc tgaaccaggc atgaaccctg 111180
tcggccaaga actttggctc agaagggaag agatgagatg gtcaacaatg actgtgacac 111240
aggtggcctg gaatgggccc tgattctcat agccccaggc gagcaagaat tccacatcaa 111300
gaaatctgga agctgtaact gaggcagtct agcagtgagg gcatgatccc tgggcctagc 111360
tagtaaagtg ccttcccttta tctgcaaagg ccatccttct tgcgcagaac aagctctcaa 111420
aaggcatgca cctgagtgct gaggctggga gaaatactca cctgggcagc cagattcacc 111480
acattcccct tccaccatat ggagaagtgg catttgaatt gggttaaagg acagcaggtt 111540
tggagttggg cagctgggca atggaaatac cgatccaggt gtggcagaag agcaggaaag 111600
tataagcacc tgtaaagtta taaggaaaca gtacttagtt atttggcaag aacagaacac 111660
agagagggaa gttatgagaa taaatggaga aaaatatact tatactaggt catagagttc 111720
cttgaaaact gaactagaga gtatggaatt tattctctgg taatgtggaa acaaaaaagt 111780
aatcagatta gactgcaatc tttcatcatt gtattagtcc gttctcacac tgctataaag 111840
aaatactgag cctgggtaac ttataaaaag agatttaatt ggctcacagt tctgcagact 111900
ctacaggaag catggctgga gaggcctcag ggagctttta cccatagcag aaggcaaaat 111960
aggagcaggc attttacatg gcaggagcag gaccaacggg gctgtgggaa gtgccatgca 112020 ctttttaaaca accagatctc ctgagaactc tatcacaaga acagcaccaa aggaagaaat 112080
ctgcccccat gatccaatca cctccaacca cgcccctccc tcagcattgg ggattacaat 112140
```

-continued

```
tttacatgag agttgggtgg gaacacagag tcaaaccata tcattccgcc ctagttcctc 112200
ccaaatctca cgtccttctc acatttcaaa acacaatcat gccttcccaa cagtccccca 112260
aaatcttaac tcattccaac atcagctaaa aagtccaagt ccaaagtctc atctgagata 112320
aggcaagtcc cttctgccta tgagcctgta aaataaaaaa acaagttagt tgcttacaag 112380
atacaacggg ggtacaggca ttgggtgaat gctcccattc caaacgggag aaattggcca 112440
aagcaaaggg gctccaggcc ctacacaagt ccgaggccct atgcaagtcc aaaacccagc 112500
aaggcagtta ttaaatctta aagctccaaa ataatttttt tgactccatg tctcatatcc 112560
agggcacgct gatgcaaggg atgggctccc aaggccttgg gcagctctgc tcctgtggct 112620
ctacagggct cagccccatg gctgctttca tcggctggca ttgagtgcct gcagcttttc 112680
caggcacacg gtgcaaactg tcagtggatc tacctttctg gggtctagag gatggtggcc 112740
ctcttctcac agccccacct ggcaaagccc cagcactaag gggaggtctc agggagcttt 112800
ttacccatgg cagaaggcaa agcaggagca ggcatcttgc atggcaggag caggaccaag 112860 tgggggggagg gggagcatct tatatggcag gagcaggacc aaggtggtga caagctttca 112920
ccaaggggag aggtgccaca cacttttaaa caaccagatc tccgtagaat tctatcacga 112980
gaacagcacc aaagggagaa atctacctcc atgatgcagt cacctcccac caggcctcag 113040
ctcccacact ggggattata attcaacatg agatttgaat ggggacacaa atccaaacca 113100
tatcaatcat tctccaagac aacttgaaag gagtagaagc aggaagatga agtgagaagt 113160
ggaacttgaa ataagacaca atgagaatgg aaaggaagag atgaaaggag gagcatctca 113220
gaggtagaat cagaagtatt taccaaggaa ttgataaaaa gtcaaagatt agcaaagata 113280
tatgctcatg caataacaca tatatgaagc acagaagcaa aagctggact cagaacaaaa 113340
atagcaagtt gagccttaaa cacactgagt ttgccttggg agtagaatgt ccaggcagag 113400
aagtccatca ggcaattgaa aatgtgaatc tgcaacttgt aaaaaatgta ttattcagcc 113460
tgggctgtca tacaatagac cacagactgg ttggcttaaa caacaaaaat gtatttctaa 113520
ccattctgaa ggctagaagt ccaagatcag gatgtcagca tggttgggct ctattgaggg 113580
ctctcttcct ggcctataga tggccacctt cttgctgtgt cctcacatgg ctaaaagaat 113640
aagagtcagt tctccagtat ctcttcttag aagggcacta atcccagcat gaatgcccac 113700
cctcatgacc ttgtctaaac tgaattacct ctaaatggcc ccatcattaa acattgtcac 113760
agtggggctt agagcttcaa catatgaatt tccggggaac acaattcagt ccatagcagg 113820
ggtcaaggct gggaatatgc ttttgagagt ccaaaagcaa ttattcagta gtccaaaagc 113880
aattattcaa ctacatatat aaagtgaaag agaaaagcag tgaggtaagg gacccagaag 113940
caaagaccac catgaaagtc agagtaagag aaagtttcaa ggagaaattg gatgctcaac 114000
agagtccact gctactcagt acaccagaag ggtcttggaa gctgagtaac ttgagtgatt 114060
tggaggtcta gagtgtgctt aggagcacag gtgttgaatg gaatggagag tacacttatt 114120
ctattcacat gttgtaagtc agaggactgt gatgtctgaa gatagagaaa catttgatgt 114180
ttcagtcctt aaggatgaca actaaaaaag gaaaatgtgc aaacaaagta gtcagaaaat 114240
aatgttcatg ggggacatgc acttgaagag aaagggttgg tagctttga gagatgatgg 114300 gtcagagatc tgagtgtggc atgggaagca agaagtcatc tcatccacct ctctgtgaat 114360
cagcaagagg gagaggtgtg acccctattg gcaagagttg caaagaaatt gtgacttcaa 114420
ctgaaagctg agtttcagtt cctgtgagga ggtaggggaa ctattagaga ataagacgag 114480
```

-continued

```
gtgactggga gtttgttttc aatgagtaag taggtcatag gtcatggtgg aggaccagga 114540
cttcagcatg catgagattg gtaagagaaa gtgatagtgc catgtagagc ttaatgcctg 114600
ggattttgat cctgaaagat tctgaaagag gtgaaagaag tgggtgctag agagggagac 114660
tggggacatg ttagtgacag tggcaggtga aggcaaaaga tagggagaat taacccatcc 114720
tccaagaaca tactgttcat tcagacttga gggttagtct gccattaaga agccagagcc 114780
aacccttaca actcaataat aagactgtct tagtcgtttt gtgctgctat aacacaaatac 114840 cacaaattgg gggatttata atgaacagaa atgtatttgg cccacagttc tggaggccag 114900
gaagtccaag atcaaggggc cacatgtgct gaaggtcttc ttgctgtgtc ataacatggt 114960
ggaaggcatc acatgggtgt gagagagtgc aagagagagc aagaggtgaa cagattctct 115020
aacaaacccc cttccacaat aatgaactga ctcccaagat aatgacatta attcacccat 115080
gagagtagag cctcatgacc taattacctc ttaaagatcc ctcctctgaa cactgttgca 115140
ttgggagggg attaagtgtc caacacatga actttggggg acacattcaa accatagcaa 115200
aggcaatatt actcaatttt tttaagtaag cagaagattc gaatagacat tttaccaaag 115260
agacgtaaga atagctagct aatgagcaca tgaaatgaaa catatgccca catgaagatt 115320
tgtacatgaa tgatcacagt agttttcttc ataatagcca aaaaccagaa gcaatcttaa 115380
tgtccatcaa cgggtgaatg gataaaaaaa aaatgtggtg tgtccataca atggactaaa 115440
ccattcatca acataaagga attactgatg cctactacag catgataaac ctcagaaaca 115500
ttatgttaag tgaaaaaaag gcagataaaa aaattacatg ttgaatggtt ccatttatat 115560
gaaatttcta gaaagaggca gaactacaga gtcagaaaac aaatcagtgg ttgcctgggg 115620
ccaagagaag gagtgaagat aaaccacaaa tggacatgag ggaattttct ggaatgttga 115680
gatgatctaa aactggactg tgatgatatg atagctgcac gtctatataa atttactaaa 115740
catcatttaa tcactttaat ttactaaaca tcaccaatca cttaaaattg gtgagtttta 115800
tgatctataa attataccctc aacaaagctg atttataaaa aaagagcctg atgaaatttt 115860
ggatgtttag ggcaagtgtt gggattctaa gcttcttgac agccacatac atgcaacaat 115920 accccacct ccccaacaaa cacacacaga cagcacagag gccaaggctt ccaccatagc 115980
cacagtcact cagatacttg actggaaatg tacatagatt tctgcagata ggatggtgct 116040
atttctttct cactctcatc gaaagacact attttgtgct acataaaggc tgaacctgaa 116100
taatctgtac ataatgctgc tttgggaaat ggttactgat tgcatggata aatttgcaca 116160
gtgttttact tccaggacag cgcaatcttg aatgttgaca tggaacattt ccaaaagcat 116220
gcaatgagct atgtgtatgt tgaaacctgc gaccaaaaac ttgcctgctt gtagattggg 116280 ttttcttttct agaaaatgcc caaatggagt ttggctaaaa tctgaatact ctttaagtcc 116340
attcaaacaa aatcggagtg tcactacact ggaaatcact cacaccctcc tctgaaccct 116400
tttgcaatgg gtgttgtaat tgtattatac gttgtttcac acttaataca agttcttcca 116460
ttaaactgtg tattgacttc cttgttctca gcccttatct gcctcatctt tctgaagtgt 116520
ttaacattat tgtaaccctc attttttcttg aaatttcctc ttcctttggt ttctgggaca 116580
ctgaaacttc cagtttttcct cctgcttcta ggttgttttc tttatcctca atggcttctc 116640
ttccttctgt cttccttctc tcagatgtag ctgtctccca ggattttttgt ctttaggggt 116700 catcctccac caacagttgg aaccattccc atcaataacc acctttgatt ctctctacct 116760
ggatgtcatc atcagtgtca caaatttacc atgttcagaa tcaaactctt tcctgccaaa 116820
ccctcaattt ctcacctcct ggctttgatt aatggcatca ccattgtgta atttacccac 116880
```

-continued

```
tcctcattct tttcagtgtt cggtttttca ggttttgaca aatgcatgca gttgtgtaac 116940
caccacccca acaatcagga catagaacag ttctatcatc tcagaaaatt tccttatgct 117000
cctttgtagt caacctctac cctatcccca ggacctggaa atcagaaaac cagatttatt 117060
ttctgtctct agagttttac tttttctaaa atgtcatata aatggaatca tgcagtcagt 117120
agtcttatga gtctgtctcc ttttacttcg catattacat ttgagagcca tccatgttgt 117180
cgtatcagta gtagtaacgt atcagtaatt cattcctttc ttattgtggc aaaaaaatac 117240
ataaaattta ccatctgaac gattttttatt ttatttttaag ttccagggta catgtgcaag 117300
atgtgcagat ttgttacgta ggtaaacgtg tgccatggtg gtttgctgca cctatcaacc 117360
catcacctgg gtattaagct cggcatgcat tagctgcttt tcctgatgct cctcccctcc 117420
ctcgataggc cccagtgtgt gttgttccct tccctgtgtt catgtgctct cattgttcag 117480
ctcccactta gtgagaactt gcggtatttg gtttttctgtt cctgcgttag tttgctaagg 117540
ataacagctt ccagcttcat ccatgtccct gcaaaagaca tgatcttgtt ccttttttatg 117600 gctgcataca accatttttta aatacacagt acagtattgt taactatgtg aacattgttg 117660
tgcaatagat tcctagaact ttttcatctt agcaaaactg aaactctata tccattaaac 117720
aattctctct ctccccccagg ccctggcaac cacaattcta ctttgtctaa gagtttgact 117780
acttcagata cctcatataa gtggaatcat gcagtatttg tcttttttagg accgacttat 117840 ttcatttagc aaaatattct caagcttcat ccatgttcta gtatatgaca agatttcctt 117900
ctttttaaag gcagaataat attccattgt acatatatgc cacattttct ttatccattc 117960
atctgtcaat ggacatttag gtttcttata cctcttggct attatgaata gtgccgcagt 118020
ggccatggat gtaaaaattc tctttgagat cctttttttc aattcttttg tatatacaca 118080
cagagacagg attgctggat catatggtaa tttttattttc aaattttttgg ggacctctct 118140 actgttttcc acagcagagt agttcatctc tttttatttt tgagtagtat tccatcgtac 118200
agatgtacca cattttattt atccattcac cagttaaaga acatttgggg ccaggagagg 118260
tggctcacgc ctgtaatccc agcactttgg gaggccgagg agggcagatc acttgatgtt 118320
aggagttcga gaccagccta gccaacatgg taaaaccceca tctccactaa aaatacaaaa 118380
aattagccgg gagtggtggc acatgcctgt aatcccaact attcaggagg ctgcggcggg 118440
acagttgctt gaaccctgga tgcagaggtt gcagtgagct gagatcatgc cactgtactc 118500
cagcctggat gacagagtga gacccgtctc aaaaataata ataataaaga acatttgagt 118560
tctttccatt ttcaggcaat tacttataca taattgtaat ggctatgaca tttgcttgaa 118620 ggttttttctg tgaacgtaat ttttattttct cttgggtgaa tatctaggtg taagagtaac 118680 taactgggt gtaagataag tgtacattca actttatgag aaactgccaa ctatttttca 118740
aagtggctgt atcatttttat gtccccacca gcgatccata agagttccag ttgttcagca 118800
tcctctcccg cacttgacat tgtcagcttt ctgattgtta gtcattctaa ttggttgtag 118860
tgctgtctca ttttctttttt aatctttatt tcccaatggc tagtgatgtc gagcctcttt 118920
tcatgagctt atttgccatc cttatatcac ctttagtaaa gtgtctactc aaatcttttg 118980 cctatttta agtatttatt aataatatta atttagttag ggtttatttt attggcttgt 119040
ttttgtttct tattgaattg ttcgagttct ctgtatattg tggatacaag catatcttat 119100
gcgatacact tttgccaatg cattttttttt tcttttggga cgaagtctca ctctgtcacc 119160
cagcctgaag tgcagtggtg caatcttggc tcactgctac ctctgcttct tgggttcaag 119220
```

-continued

```
tgattctttt acctcagcct cgccagtagc tgggattgca ggcatgagcc accatgccca 119280
gctaattttt gtatttttag tagagacagg gtttcaccat gttggccagg ctcctgactt 119340
caagtgatcc gcctgccttg gcctcccaaa gtgctgggat cacaggcatg agccaccggt 119400
gacacttggc ccacaaatgc atttttctag tctgtggatt acctttcat ttatttaatg 119460 gtatccttca aaaagcaaaa gtttttgatt ttgttgaaaa ttttatcagt ttaccaattg 119520
ataaaacttt atcaatttat tttttttctt ttatcaatcc tggtgttgat gttgtatctc 119580
catgcatcta ctcttgaatg ctcagatttg cctatcatcc ttccttgctc acttacctca 119640
gtagcaaccc tgtctatcac ttttcatagc ttacaaccat ctttcacatt taatcatttc 119700
tttgatcatc accttcagta aagttaggcc agatattctc cagatgagct tattgctggt 119760
gctcaaatgc tcaaaatggc ttgaccaatg ccatacagta agcacggatg atagcgctct 119820
catggcttga aactaaaact gacttgtttc ctaatgcaca tgaattgtac acctccctcc 119880
cctcaccccc gacccccct caaccgacag acacacacac acacacacac acacacacac 119940
acacacacac acaccagc ttctctcttc ttggtcatca tcctaatcag catcacctcc 120000
tctttcactg tccctcccct caccctgctg tcagccccac aatgctttca ggggagtgtg 120060
gagtgcagac aatacaatgc tcttcctgga aaccttcttc ctcttacctc cctgtcccgt 120120
gagtcctcca gctattttct gatacccagt tattgcccac gtcctttaat tccttggaaa 120180
attacccaac tccatccccc ttttatgtga ctttgtctcc agacaaatct acatgtagcg 120240
tagactgtca gatagggaga cctgatcaca gaactttggc ttcctcatcc taaaataaaa 120300
ccaattacat cacaggattg taaccaagta caatccatta taaggattaa ataagatgtt 120360
ttgtaaagga tataatgcct atgcatgaat cattatatga caaatacact ctttcactac 120420
cttaattcca gagaaaagcc tcataggctt ccgtattgta ggtatgcagg agtgtccctc 120480
acctattctt attcagaaac ctcctaactg gcctccatat tgtgaatcag cttctccttt 120540
ctgttctaag cttggcgctt acagatgcca tctccctgag cacaactcag aactcagcca 120600
tgtcccattg atttcagtct aacgcacttt cttttttttt tttttgaga cggagtctca 120660 ctctatcgcc caagctggag tgcaggggcg cgatctcagc tcactgcaac ttccacctcc 120720
caggttcaag cgattgtcct gcttcagcct cccaagtagc tgggattaca ggtgcacacc 120780
accatgcctg gctaattttt gtattttag tagagacagg gtttcaccat gttggccagg 120840
ctggtcccga actcttgacc tcaagtgatc tgcccacccc cgcctcccaa agtgctggga 120900
ttacagatgt gaaccacctt gtcccgtcct gtctaaccca ctttcaacat ttaaaaacct 120960
ccacagcaca gtcccatttc aatcttatgg gtccctaatc ccttcccta ctccaacatg 121020 tcaagcaacg tgaactatta tactttatgg tttaataaga acacatatgc agccaggcgc 121080
cgtggctcat gcctgtaatc ccagcacttt gggaggccaa ggagggtgga tcacctgagg 121140
tcaggagtta gagaccagcc tggccaacat ggagaaaccc cgtctctact aaaaatacaa 121200
aaattagcct ggcatggtgg caggcgccta taatcccagc tactcaggag gctgaggcag 121260
gagaatcgct tgaacccggg aggaagaggt tgcagtacac caagattgca ccacttcact 121320
ccagcctggg caaaagagcg aaactccatc tcaaaaaata aaaaggaaa gaaagaacac 121380 atgtgtactg ttactcctgg ccccaccccc tccacccaaa actctccctc tgccctcata 121440
ttacctgcac ctataaaaca aagtctccct gttcctcaag acccacctta ctgtcactct 121500
cttcctgcag cctttctcag taccctacta ttatctcttt gacttttggc aacctttgta 121560
cctctttgat attactgctc tatattacag ctattatctt attgtcctgt gtggcagtta 121620
```

-continued

```
tctgctcaat tctcttaacc ctgttcattc agccctggga cctatctagt aacttgaaca 121680
gtaacctact cgtatgtgat caagggtcaa ttgatacttg ttaaattgat tttaaatgtt 121740
aatgcatatt ctgggacttg aaagttaaca cgatgatgtt gtcagaagtg attgttgatt 121800
gttaagattt tcagactttg aaaacttcta cttttgcaaag ctgaattaga cagcaaagtt 121860
ctgtagctcc ctcctggcaa ggggtttgag ttttctgttg ggatcaaggc agtcagcagc 121920
catcaagggt tcttgcactt gggcaaagaa gtcattaatg gtaatttgta tcagcaatta 121980
cagcatctac ctcatttctt tctttcagtc gcagcgttca aaggcaggct ttattctcct 122040
tcttgctggg tactgcaagc tacacttgcc tctcagtttt atgtcttcct actccagctg 122100
tctggtgtgg attttccttc tgctccaagc ttccttcatt tcttcctcct tatgcttcct 122160
actcttagag tggcctggaa gtgttgctgg gccagaactg cccccctggg tcctgtccac 122220
aggggcggcc tctgcccatg ctgactctcc tcgtgtcatt cttgcatggg cacatgtcca 122280
gggggagata atatgtatga cctggtctat cctgagcaca gtgttttaaa tcaagaaatt 122340
gcatgtttat tgaagttcag tagaccaaac aagacctaag ggtcaggaac tcttaaatgt 122400
ttatcccagt gtggactcag atgtattggg gaattttagc aagtcactta acctctccgt 122460
gtccctgtga tcttcctata tagtactgat acggctattt tatatgaatc tagtactttc 122520
acatcttcat gtgacagttt tattgaaatt aattttcaat agagaaactt gttgccttgc 122580
agtttttttt atttctgatt tttaatatgt attttttactt atgttgattt agaccttccc 122640
atttaatagt aacctttcaa tgtggttaca tttcttaaag agtatttatg ttcagtttga 122700
aaccacacaa atttaaattt tgggaggctt tcttcttctt ttacaagtaa tgtaaaattg 122760
tagtgaagct attggaaaag aaaaggatag aaacatgtta gtgctttgac acagcgggag 122820
agaattttgg aagagatatt ctaccaacta cagatggaat cttcatcatc atgtagactt 122880
cagatattct tttagaaaac tttacattta cttataatct aaaccttact tgtttaaaca 122940
agtcatgaaa tgtatagctt aataattgcc tttaagaaaa ttgttgccca aaacagaaac 123000
cgtattgagt atgtaaagcc aagtttagtt accaagacct actgatttcc tttcatatat 123060
gtatggtcac atctctcacc tcatctgtcc tgtttcttgt tttactagtg gtcctttggc 123120
gtgctcctct gggagctgat gacaagagga gccccacctt atcctgacgt aaacaccttt 123180
gatataactg tttacttgtt gcaagggaga agactcctac aacccgaata ctgcccagac 123240
cccttgtaag tagtctttct gtacctctta cgttctttac ttttacagaa atgcctgcct 123300
tcaaagggtc tcttacagca tgtctttctt tttggaacag atatgaagta atgctaaaat 123360
gctggcaccc taaagccgaa atgcgcccat ccttttctga actggtgtcc cggatatcag 123420
cgatcttctc tactttcatt ggggagcact atgtccatgt gaacgctact tatgtgaacg 123480
taaaatgtgt cgctccgtat ccttctctgt tgtcatcaga agataacgct gatgatgagg 123540
tggacacacg accagcctcc ttctgggaga catcatagtg ctagtactat gtcaaagcaa 123600
cagtccacac tttgtccaat ggtttttttca ctgcctgacc tttaaaaggc catcgatatt 123660
ctttgctctt gccaaaattg cactattata ggacttgtat tgttatttaa attactggat 123720
tctaaggaat ttcttatctg acagagcatc agaaccagag gctggtccc acaggccacg 123780 gaccaatggc ctgcagccgt gacaacactc ctgtcatatt ggagtccaaa acttgaattc 123840
tgggttgaat ttttttaaaaa tcaggtacca cttgatttca tatgggaaat tgaagcagga 123900
aatattgagg gcttcttgat cacagaaaac tcagaagaga tagtaatgct caggacagga 123960
```

-continued

```
gcggcagccc cagaacaggc cactcattta gaattctagt gtttcaaaac acttttgtgt 124020
gttgtatggt caataacatt tttcattact gatggtgtca ttcacccatt aggtaaacat 124080
tcccttttaa atgtttgttt gttttttgag acaggatctc actctgttgc cagggctgta 124140
gtgcagtggt gtgatcatag ctcactgcaa cctccacctc ccaggctcaa gcctcccgaa 124200
tagctgggac tacaggcgca caccaccatc cccggctaat ttttgtattt tttgtagaga 124260
cggggttttg ccatgttgcc aaggctggtt tcaaactcct ggactcaaga aatccaccca 124320
cctcagcctc ccaaagtgct aggattacag gcatgagcca ctgcgcccag cccttataaa 124380
tttttgtata gacattcctt tggttggaag aatatttata ggcaatacag tcaaagtttc 124440
aaaatagcat cacacaaaac atgtttataa atgaacagga tgtaatgtac atagatgaca 124500
ttaagaaaat ttgtatgaaa taatttagtc atcatgaaat atttagttgt catataaaaa 124560
cccactgttt gagaatgatg ctactctgat ctaatgaatg tgaacatgta gatgttttgt 124620
gtgtattttt ttaaatgaaa actcaaaata agacaagtaa tttgttgata aatattttta 124680
aagataactc agcatgtttg taaagcagga tacattttac taaaaggttc attggttcca 124740
atcacagctc ataggtagag caaagaaagg gtggatggat tgaaaagatt agcctctgtc 124800
tcggtggcag gttcccacct cgcaagcaat tggaaacaaa acttttgggg agttttattt 124860
tgcattaggg tgtgttttat gttaagcaaa acatacttta gaaacaaatg aaaaaggcaa 124920
ttgaaaatcc cagctatttc acctagatgg aatagccacc ctgagcagaa ctttgtgatg 124980
cttcattctg tggaattttg tgcttgctac tgtatagtgc atgtggtgta ggttactcta 125040
actggttttg tcgacgtaaa catttaaagt gttatatttt ttataaaaat gtttattttt 125100
aatgatatga gaaaatttt gttaggccac aaaaacactg cactgtgaac attttagaaa 125160
aggtatgtca gactgggatt aatgacagca tgattttcaa tgactgtaaa ttgcgataag 125220
gaaatgtact gattgccaat acaccccacc ctcattacat catcaggact tgaagccaag 125280
ggttaaccca gcaagctaca aagagggtgt gtcacactga aactcaatag ttgagtttgg 125340
ctgttgttgc aggaaaatga ttataactaa aagctctctg atagtgcaga gacttaccag 125400
aagacacaag gaattgtact gaagagctat tacaatccaa atattgccgt ttcataaatg 125460
taataagtaa tactaattca cagagtattg taaatggtgg atgacaaaag aaaatctgct 125520
ctgtggaaag aaagaactgt ctctaccagg gtcaagagca tgaacgcatc aatagaaaga 125580
actcggggaa acatcccatc aacaggacta cacacttgta tatacattct tgagaacact 125640
gcaatgtgaa aatcacgttt gctatttata aacttgtcct tagattaatg tgtctggaca 125700
gattgtggga gtaagtgatt cttctaagaa ttagatactt gtcactgcct atacctgcag 125760
ctgaactgaa tggtacttcg tatgttaata gttgttctga taaatcatgc aattaaagta 125820
aagtgatgca acatcttgta                                              125840
```

METHOD OF TARGETING PATIENT-SPECIFIC ONCOGENES IN EXTRACHROMOSOMAL DNA TO TREAT GLIOBLASTOMA

RELATED APPLICATIONS

The present application claims priority under 35 U.S.C. § 371 to International Application No. PCT/US2018/014588 filed Jan. 19, 2018, which claims benefit under 35 U.S.C. § 119(e) to U.S. Provisional application No. 62/448,625 filed on Jan. 20, 2017 and U.S. Provisional application No. 62/576,681 filed on Oct. 25, 2017, the contents of each of which is incorporated by reference herein in its entirety.

FIELD OF THE INVENTION

The present invention generally relates to methods of identifying oncogenes present in extrachromosomal DNA (ecDNA) in an individual suffering glioma, and targeting such oncogenes present in a brain tumor, so as to treat glioma, preferably glioblastoma. The methods include identifying a drug to target specific oncogenes present in ecDNA in a patient. The methods herein use patient specific information to develop precision medicine and provide a patient-specific treatment regimen to treat glioma.

BACKGROUND OF THE INVENTION

Cancer genomes are subject to continuous mutagenic processes in combination with an insufficient DNA damage repair. (Roos, W. P., Thomas, A. D. & Kaina, B. DNA damage and the balance between survival and death in cancer biology. *Nat Rev Cancer* 16, 20-33 (2016)). Somatic genomic variants that are acquired prior to and throughout tumorigenesis may provide cancer cells with a competitive advantage over their neighboring cells in the context of a nutrition- and oxygen-poor microenvironment, resulting in increased survival and/or proliferation rates. (Yap, T. A., Gerlinger, M., Futreal, P. A., Pusztai, L. & Swanton, C. Intratumor heterogeneity: seeing the wood for the trees. *Sci Transl Med* 4, 127ps1.0 (2012)). The Darwinian evolutionary process results in intratumoral heterogeneity in which single cancer-cell-derived tumor subclones are characterized by unique somatic alterations. (Aparicio, S. & Caldas, C. The implications of clonal genome evolution for cancer medicine. *N Engl J Med* 368, 842-51 (2013)). Chemotherapy and ionizing radiation may enhance intratumoral evolution by eliminating cells lacking the ability to deal with increased levels of genotoxic stress, while targeted therapy may favor subclones in which the targeted vulnerability is absent. (Kim, H, et al. Whole-genome and multisector exome sequencing of primary and post-treatment glioblastoma reveals patterns of tumor evolution, *Genome Res* 25, 316-27 (2015); Sequist, L. V. et al. Genotypic and histological evolution of lung cancers acquiring resistance to EGFR inhibitors. *Sci Transl Med* 3, 75ra26 (2011)). Increased clonal heterogeneity has been associated with tumor growth and mortality. (Andor, N. et al. Pan-cancer analysis of the extent and consequences of intratumor heterogeneity. *Nat Med* 22, 105-13 (2016)). Computational methods that analyze the allelic fraction of somatic variants identified from high throughput sequencing data sets, are able to infer clonal population structures and provide insights into the level of intratumoral clonal variance. (Roth, A. et al. PyClone: statistical inference of clonal population structure in cancer. *Nat Methods* 11, 396-8 (2014)).

Glioblastoma (GBM), a WHO grade IV astrocytoma, is the most prevalent and aggressive primary central nervous system tumor. GBM is characterized by poor response to standard post-resection radiation and cytotoxic therapy, resulting in dismal prognosis with a two-year survival rate of around 15%, (Dolecek, T. A., Propp, J. M., Stroup, N. E. & Kruchko, C. CBTRUS statistical report: primary brain and central nervous system tumors diagnosed in the United States in 2005-2009, *Neuro Oncol* 14 Suppl 5, v1-49 (2012)).

The genomic and transcriptomic landscape of GBM has been described, (See Ceccarelli, M. et al. Molecular Profiling Reveals Biologically Discrete Subsets and Pathways of Progression in Diffuse Glioma. *Cell* 164, 550-63 (2016); Verhaak, R. G. et al. Integrated genomic analysis identifies clinically relevant subtypes of glioblastoma characterized by abnormalities in PDGFRA, IDH1, EGFR, and NF1, *Cancer Cell* 17, 98-110 (2010); and Brennan, C. W. et al. The somatic genomic landscape of glioblastoma. *Cell* 155, 462-77 (2013)). Intratumoral heterogeneity in GBM has been characterized, in particular, with respect to somatic alterations affecting receptor tyrosine kinases. (See Snuderl, M. et al. Mosaic amplification of multiple receptor tyrosine kinase genes in glioblastoma. *Cancer Cell* 20, 810-7 (2011); Sottoriva, A. et al. Intratumor heterogeneity in human glioblastoma reflects cancer evolutionary dynamics. *Proc Natl Acad Sci USA* 110, 4009-14 (2013); and Szerlip, N. J. et al. Intratumoral heterogeneity of receptor tyrosine kinases EGFR and PDGFRA amplification in glioblastoma defines subpopulations with distinct growth factor response. *Proc Natl Acad Sci USA* 109, 3041-6 (2012)).

Thus far, no effective treatment has been developed to treat gliomas, in particular, GBM, which is not only extremely aggressive, but also changing and differ cut in each patient.

SUMMARY OF THE INVENTION

The present inventors have found that extrachromosomal DNA (ecDNA) harbors oncogenes that are patient specific. The present inventors discovered using the patient-specific oncogenes present in ecDNA as a therapeutic target as an effective treatment of gliomas, such as glioblastoma. The present invention relates to methods of identifying drugs that target specific oncogenes present in ecDNA to treat gliomas.

According to non-limiting example embodiments, the invention provides a method of identifying a drug that targets against an oncogene present in an extrachromosomal DNA (ecDNA) in a human suffering from glioma. The method includes providing a brain tumor specimen from a human suffering from glioma; performing whole genome sequencing on the brain tumor specimen; determining the presence of an ecDNA in the brain tumor specimen (e.g., by gene alignment based on the whole genome sequencing); identifying the presence of an oncogene present in the ecDNA, wherein the oncogene is an oncogene selected from the group consisting of MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; and identifying a drug targeted against the oncogene, wherein the drug inhibits the function of the oncogene present in said ecDNA, so as to inhibit tumor growth of the glioma in the human. Examples of the present methods further include administering the drug targeted against the oncogene in ecDNA to the human, in an amount sufficient to treat glioma in the human.

US 12,559,789 B2

3

According to non-limiting examples, the oncogene is an oncogene selected from the group consisting of MET MET/CAPZA2, MDM2, CDK4, SOX2, PIK3CA, MECOM, PDGFRA, EGFR, MYCN, and MYC. According to further embodiments the oncogene is selected from MET and MET/CAPZA2.

Examples of the present method include administering the identified drug targeted against the oncogene present in the ecDNA to the human, in an amount sufficient to treat glioma in the human.

According to preferred embodiments, the glioma is a glioblastoma. According to further preferred embodiments, the glioblastoma is an adult glioblastoma. The glioma may be a primary or recurrent glioma.

According to example embodiments, the whole genome sequencing is performed using Illumina sequencing or PacBio sequencing.

According to preferred embodiments, the determination of the presence of ecDNA is performed by sequence alignment followed by identifying misalignment against a reference gene, wherein said misalignment against a reference gene is indicative of the presence of ecDNA.

According to further example embodiments, when more than one oncogene is present in the ecDNA, then more than one drug is identified as targeting against the more than one oncogene.

According to preferred embodiments, if the MET ecDNA oncogene is present, the drug is a drug selected from the group consisting of Capmatinib, Crizotinib, Cabozantinib, Cabozantinib, ABBV-399, ABT-700, ABT-700, AMG-208, MK-246, Tepotinib, JNJ-3887760, BMS-817378, Foretinib, and SGX-523. Preferably, if MET oncogene is present in ecDNA, the drug is a drug selected from the group consisting of capmatinib and crizotinib.

Embodiments of the present method further include verifying the presence of ecDNA and of an ecDNA oncogene using in situ hybridization (FISH).

According to another non-limiting example embodiment, the present methods include implanting the brain tumor specimen into a patient-derived xenograft (PDX) mouse and administering the identified drug to the PDX mouse to determine if the identified drug kills the tumor glioma and/or inhibits tumor glioma growth in the PDX mouse. The use of PDX mouse model allows determination if the drug is a suitable drug for targeting glioma in the human.

In particular, provided herein is a method of identifying a drug that targets against an oncogene present in an ecDNA in a human suffering from glioma, which includes providing a brain tumor specimen from a human suffering from glioma; performing whole genome sequencing on the brain tumor specimen determining the presence of an ecDNA in the brain tumor specimen by gene alignment based on said whole genome sequencing; identifying the presence of an oncogene present in the ecDNA, wherein the oncogene is an oncogene selected from the group consisting of MET MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; identifying a drug targeted against the oncogene, wherein the drug inhibits the function of the oncogene so as to inhibit the tumor growth of said glioma in said human; implanting the brain tumor specimen into a patient-derived xenograft (PDX) mouse, and allowing the brain tumor cells to grow in the PDX mouse for a predetermined time period; administering the identified drug into the PDX mouse containing the implanted brain tumor specimen; and determining if the identified drug inhibits tumor glioma growth in the PDX mouse. Inhibition of tumor glioma growth in the PDX mouse is indicative of the identified drug being suitable for treating the glioma in the human.

As with other methods herein, examples of this method further include administering the identified drug targeted against the oncogene present in the ecDNA to the human, in an amount sufficient to treat glioma in the human. According to non-limiting examples, the oncogene is an oncogene selected from the group consisting of MET, MET/CAPZA2, MDM2, CDK4, SOX2, PIK3CA, MECOM, PDGFRA, EGFR, MYCN, and MYC. According to further embodiments the oncogene is selected from MET and MET/CAPZA2.

The glioma may preferably be a glioblastoma. According to further preferred embodiments, the glioblastoma is an adult glioblastoma. The glioma may be a primary or recurrent glioma. According to example embodiments, the whole genome sequencing is performed using Illumina sequencing or PacBio sequencing. According to preferred embodiments, the determination of the presence of ecDNA is performed by sequence alignment followed by identifying misalignment against a reference gene, wherein said misalignment against a reference gene is indicative of the presence of ecDNA.

According to further example embodiments, when more than one oncogene is present in the ecDNA, then more than one drug is identified as targeting against the more than one oncogene. According to preferred embodiments, if the MET ecDNA oncogene is present, the drug is a drug selected from the group consisting of Capmatinib, Crizotinib, Cabozantinib, Cabozantinib, ABBV-399, ABT-700, ABT-700, AMG-208, MK 246, Tepotinib, JNJ-3887760, BMS-817378, Foretinib, and SGX-523. Preferably, if MET oncogene is present in ecDNA, said drug is at a drug selected from the group consisting of capmatinib and crizotinib. As with other methods herein, this method includes verifying the presence of ecDNA and of an ecDNA oncogene using in situ hybridization (FISH).

The invention also relates to screening one or more drug candidates to target an identified oncogene in a human suffering from glioma, and if the drug candidate(s) is determined to be effective for targeting the ecDNA oncogene (or the most effective drug for targeting the ecDNA oncogene), administering the drug candidate to a human in need thereof. In particular, the present invention includes a method of screening a drug candidate for treatment of glioma in a human suffering from glioma, that includes providing a brain tumor specimen from a human suffering from glioma; performing whole genome sequencing on the brain tumor specimen; determining the presence of an ecDNA in the brain tumor specimen based on the whole genome sequencing; identifying the presence of an oncogene present in the ecDNA, wherein the oncogene is an oncogene selected from the group consisting of MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; implanting the brain tumor specimen into a patient-derived xenograft (PDX) mouse, and allowing brain tumor cells to grow in the mouse for a predetermined time period; administering a drug candidate into the PDX mouse, the PDX mouse containing the implanted brain tumor specimen; and determining the tumor glioma growth in the PDX mouse, wherein inhibition of the tumor glioma growth in the PDX mouse receiving the drug candidate is indicative of the drug candidate in treating glioma in the patient.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

BRIEF DESCRIPTION OF DRAWINGS

The patent or application file contains at least one drawing executed in color. Copies of this patent or patent application publication with color drawing(s) will be provided by the Office upon request and payment of the necessary fee.

Non-limiting example embodiments are described herein, with reference to the following accompanying Figures:

FIG. 1A depicts a schematic study overview.

FIG. 2B depicts in the top: DNA copy number and genomic rearrangements at ecDNA loci that were predicted with the copy number based approach. The bottom depicts: representative FISH images showing amplification of MYC, CDK4, PDGFRA in tumor, neurospheres and PDXs (red) and control chromosomal probes (green). EGFR amplification in neurospheres and PDX (green) and Chr7 control are shown. The bottom: depicts representative interphase FISH (Tumor and PDX) and metaphase FISH (neurospheres). Arrows in metaphase FISH images mark extrachromosomally DNA elements.

FIG. 8 depicts predicted ecDNA elements in primary tumors, neurospheres, and xenografts using whole genome sequencing. Segmented copy numbers, structural variation (SV) breakpoints, and fusion junctions have been visualized over patient tumor and its derived model systems for each predicted extrachromosomal region (whose boundaries have been indicated with vertical dots). In cases where one end of a fusion gene junction or SV breakpoint pair does not fall within the predicted ecDNA region, those points have been plotted outside the region.

FIG. 11D depicts validation of predicted ecDNA elements in primary and recurrent gliomas using whole genome sequencing, FISH and DNA copy number profiling. Days-to-secondary surgery vs. IDH1 status.

FIG. 14 depicts table 3A which sets forth Sample Information in interphase FISH experiments.

FIG. 15 depicts Table 3B, which sets forth terminology used in example interphase FISH experiments.

Figure 16:
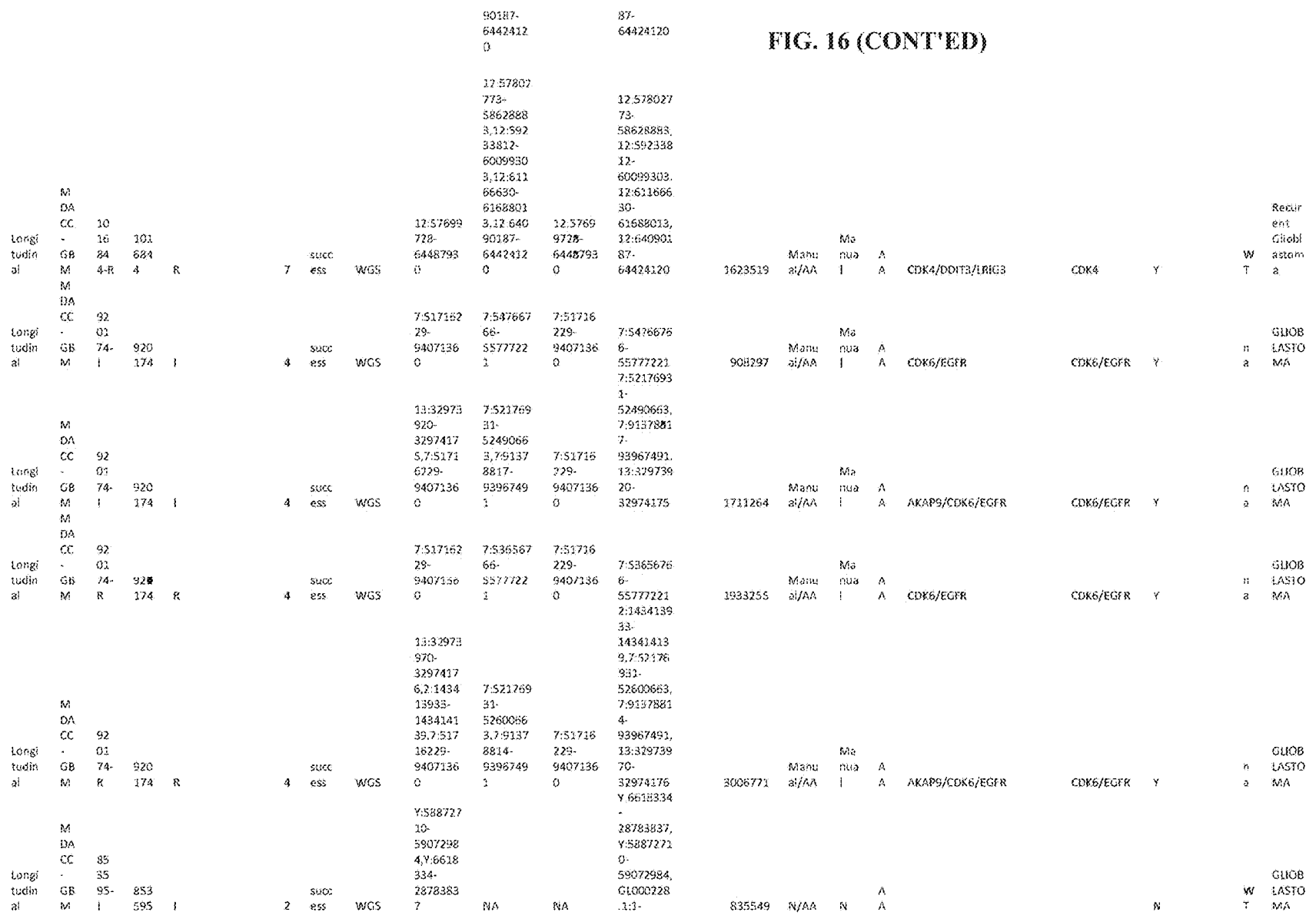
Figure 16:
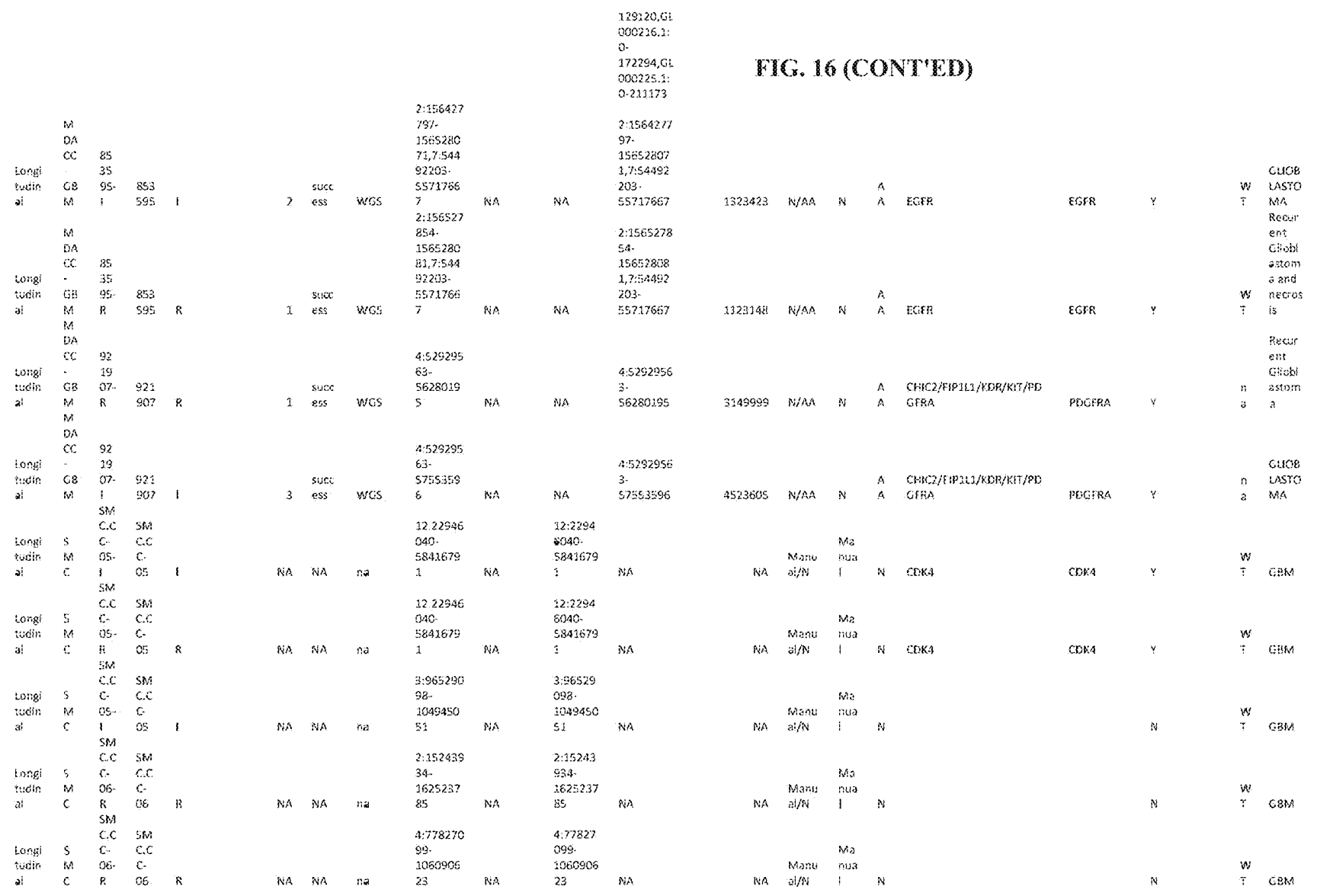
Figure 16:
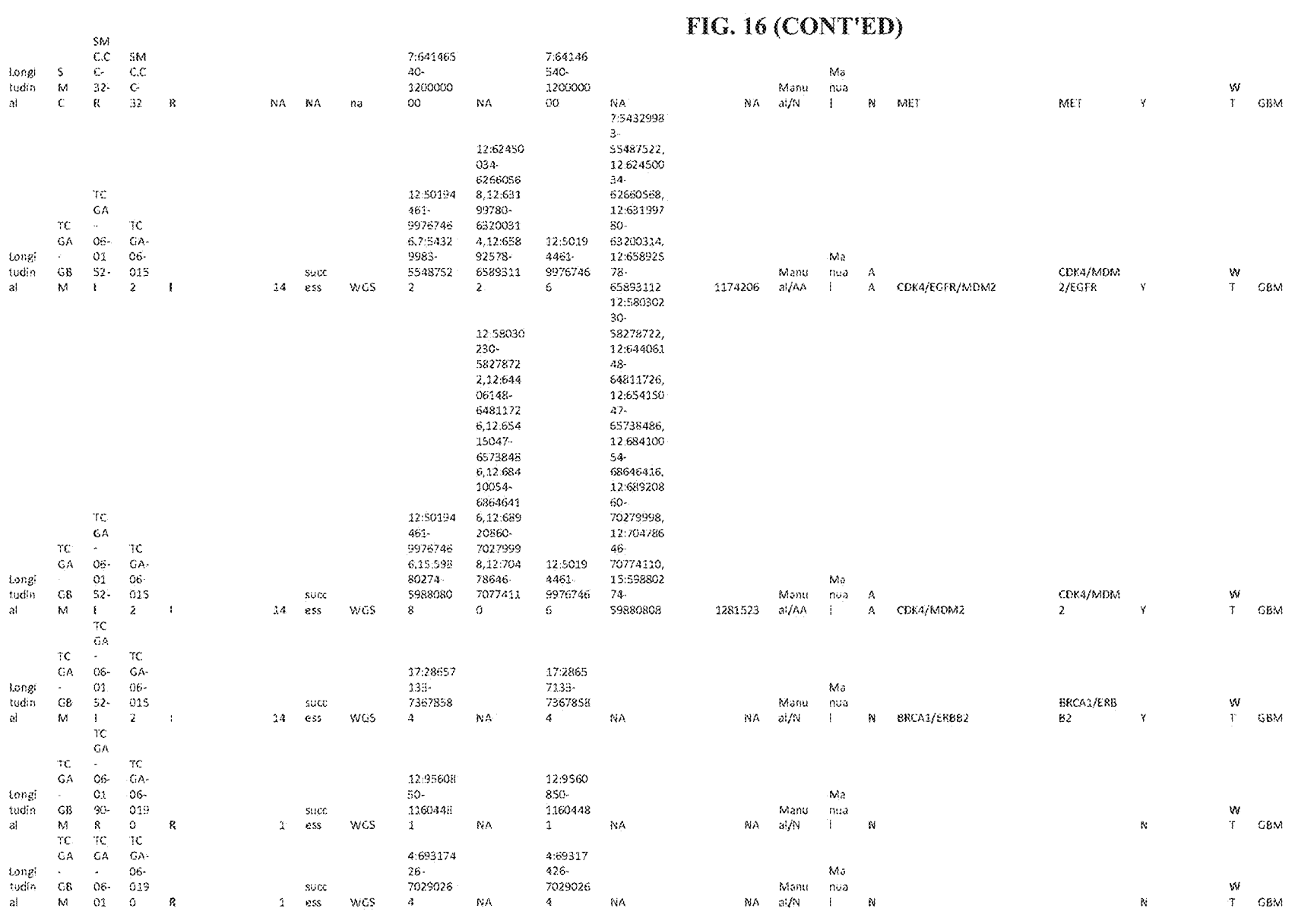
Figure 16:
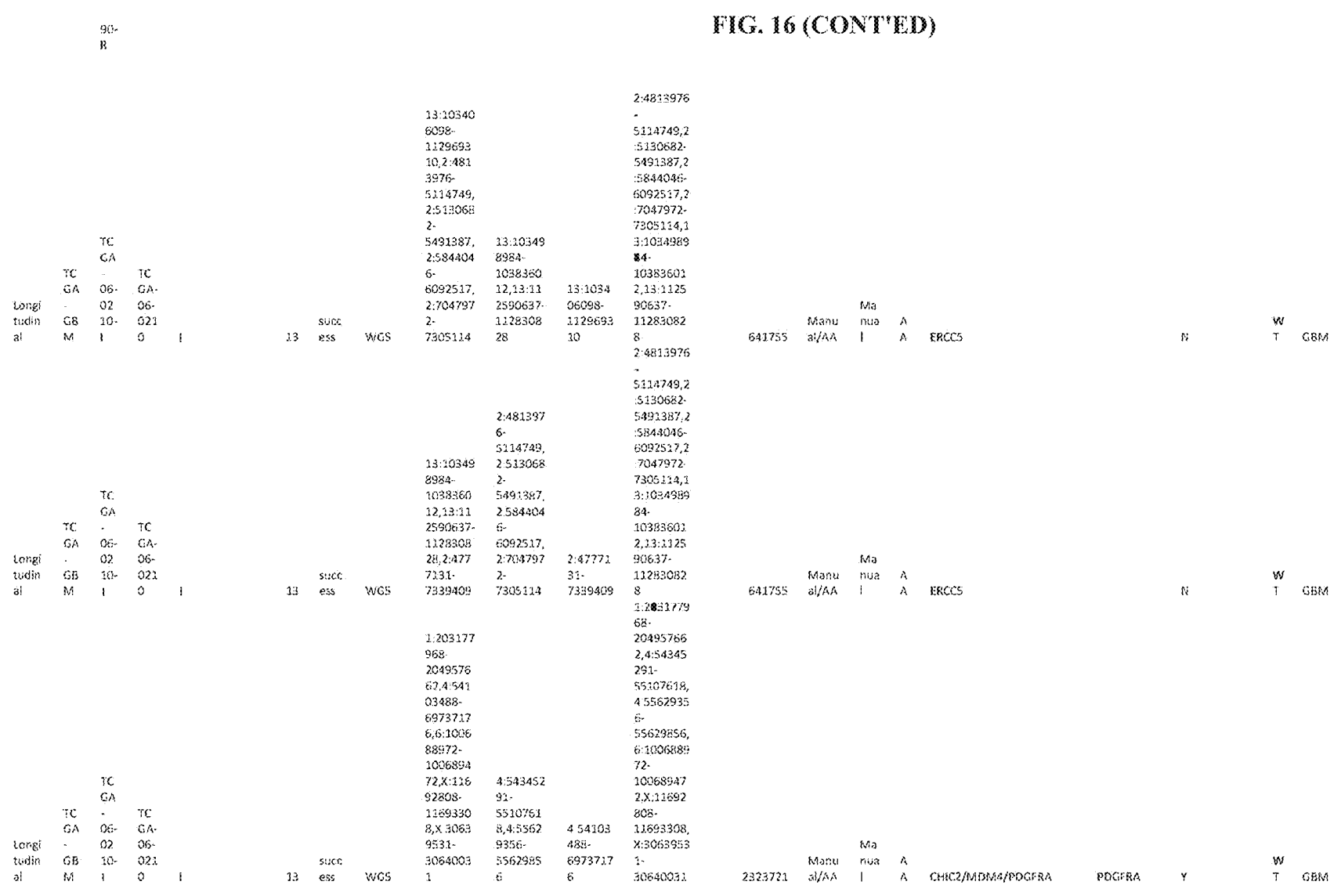
Figure 16:
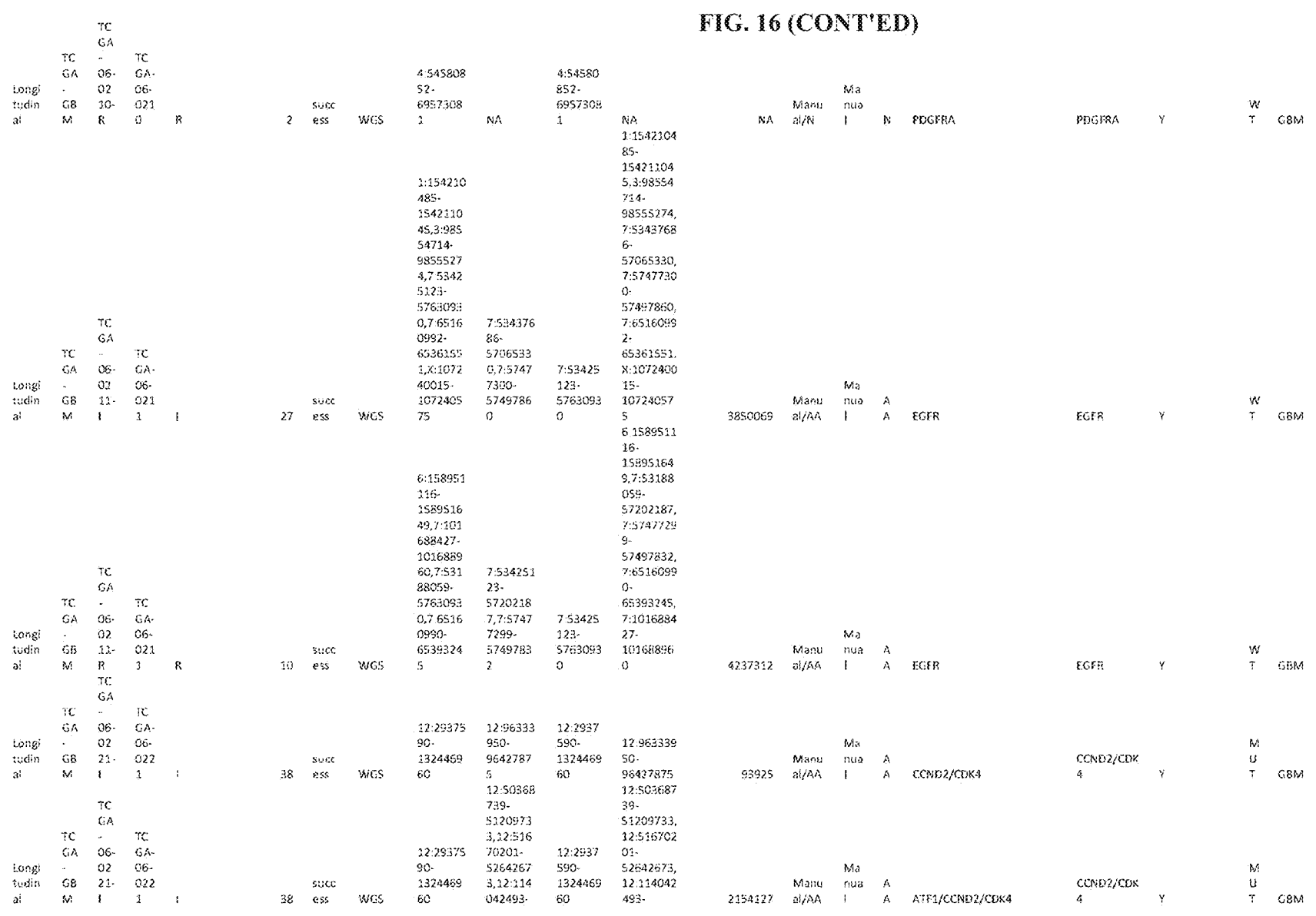
Figure 16:
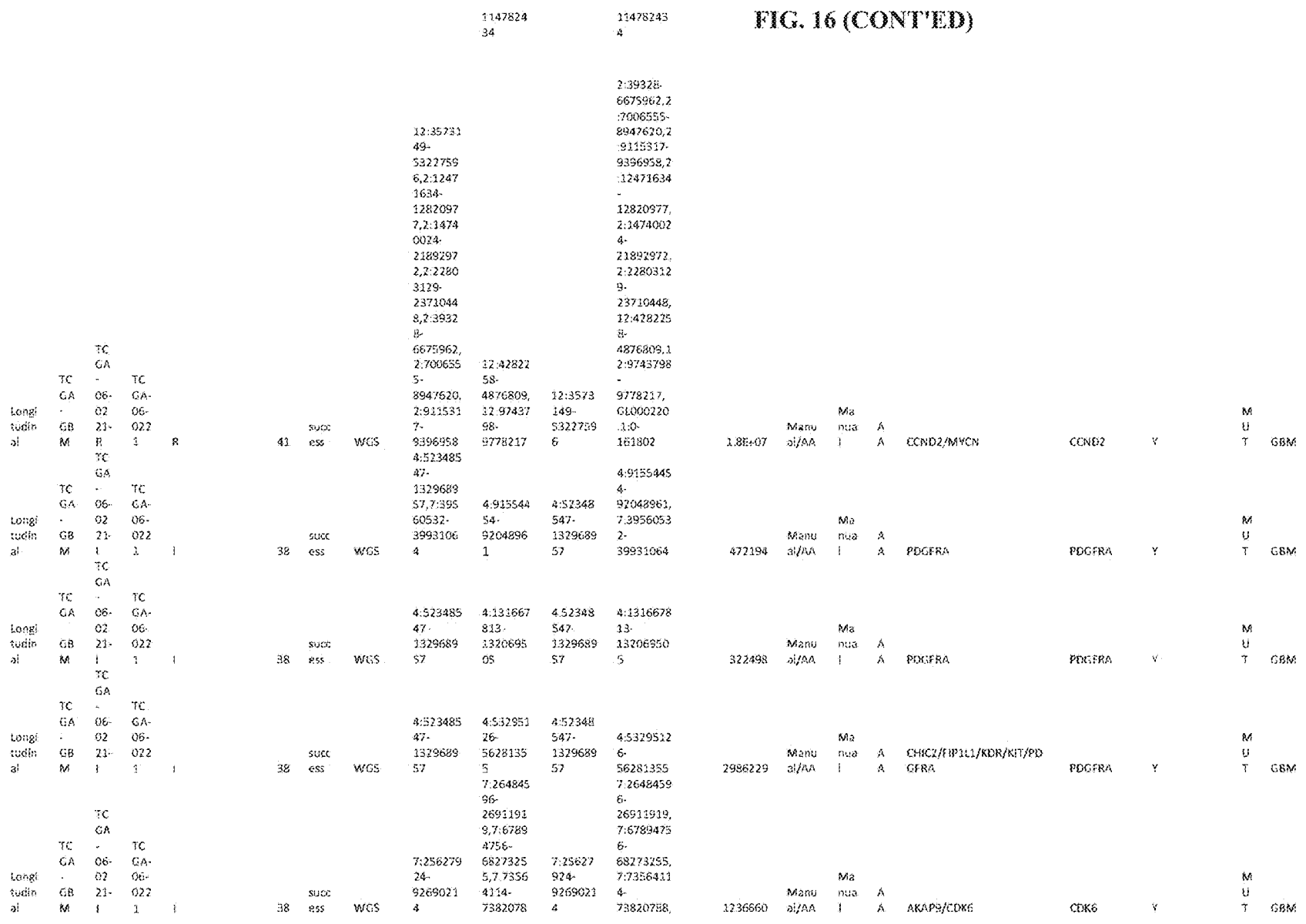
Figure 16:
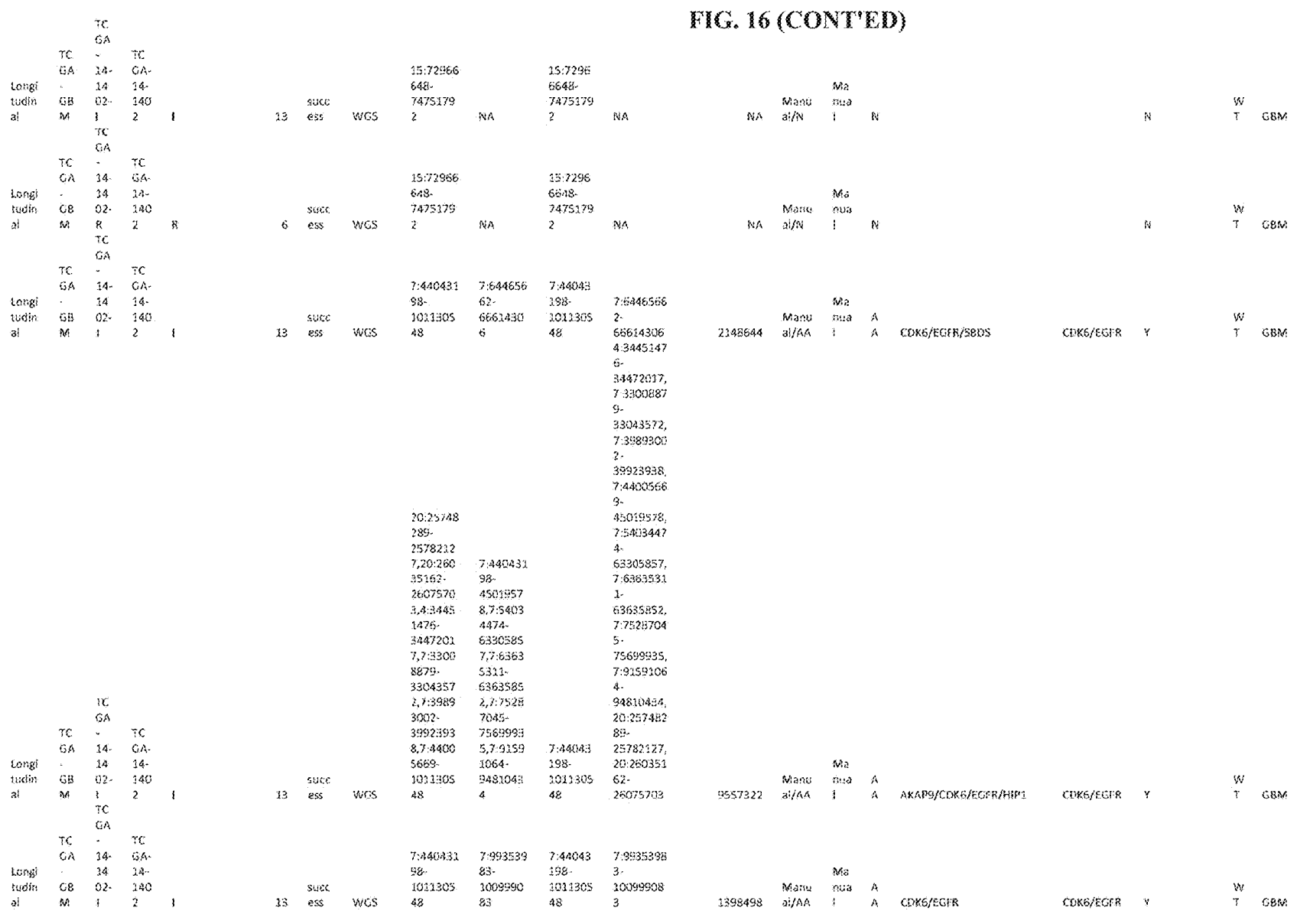
Figure 16:
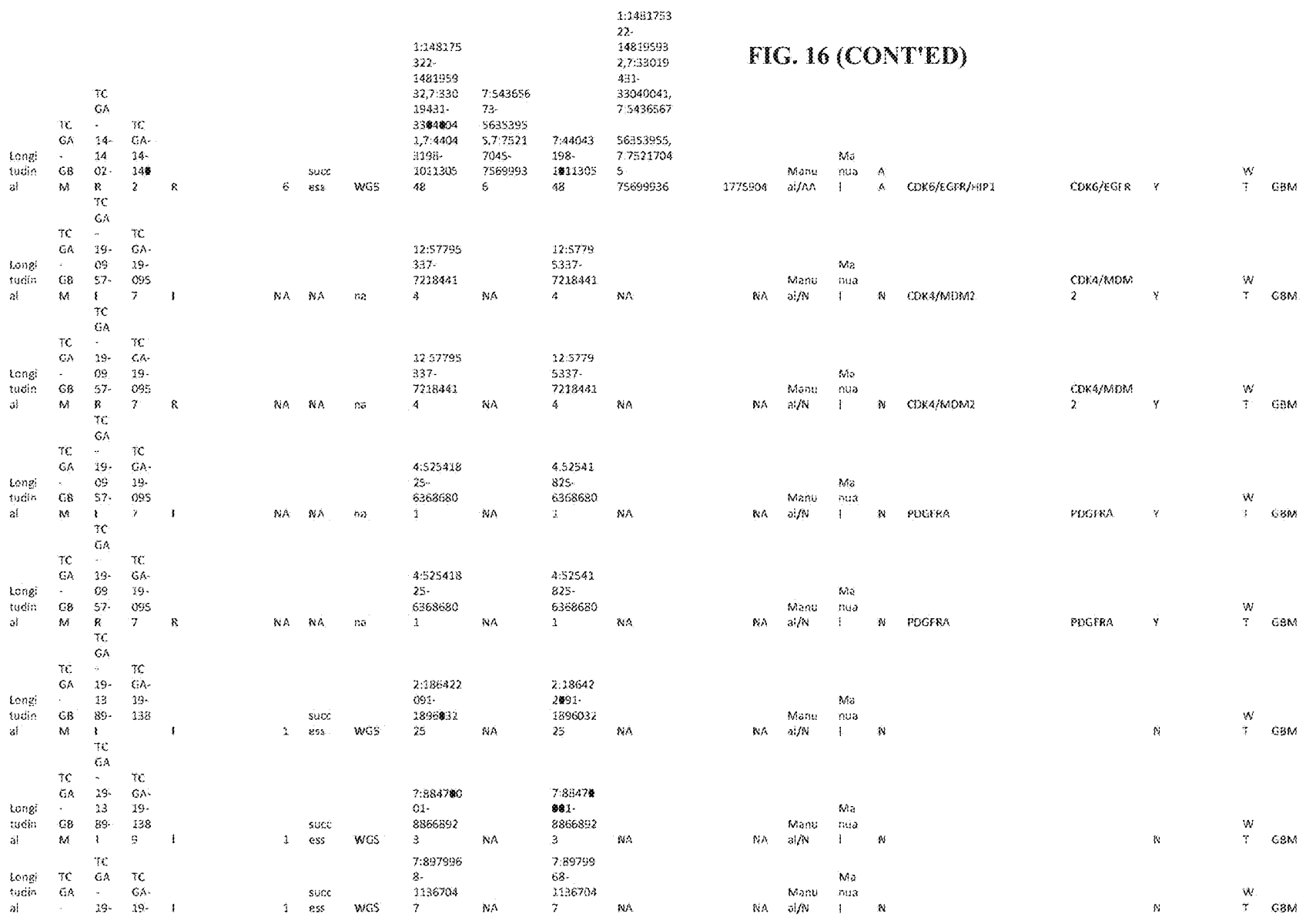
Figure 16:
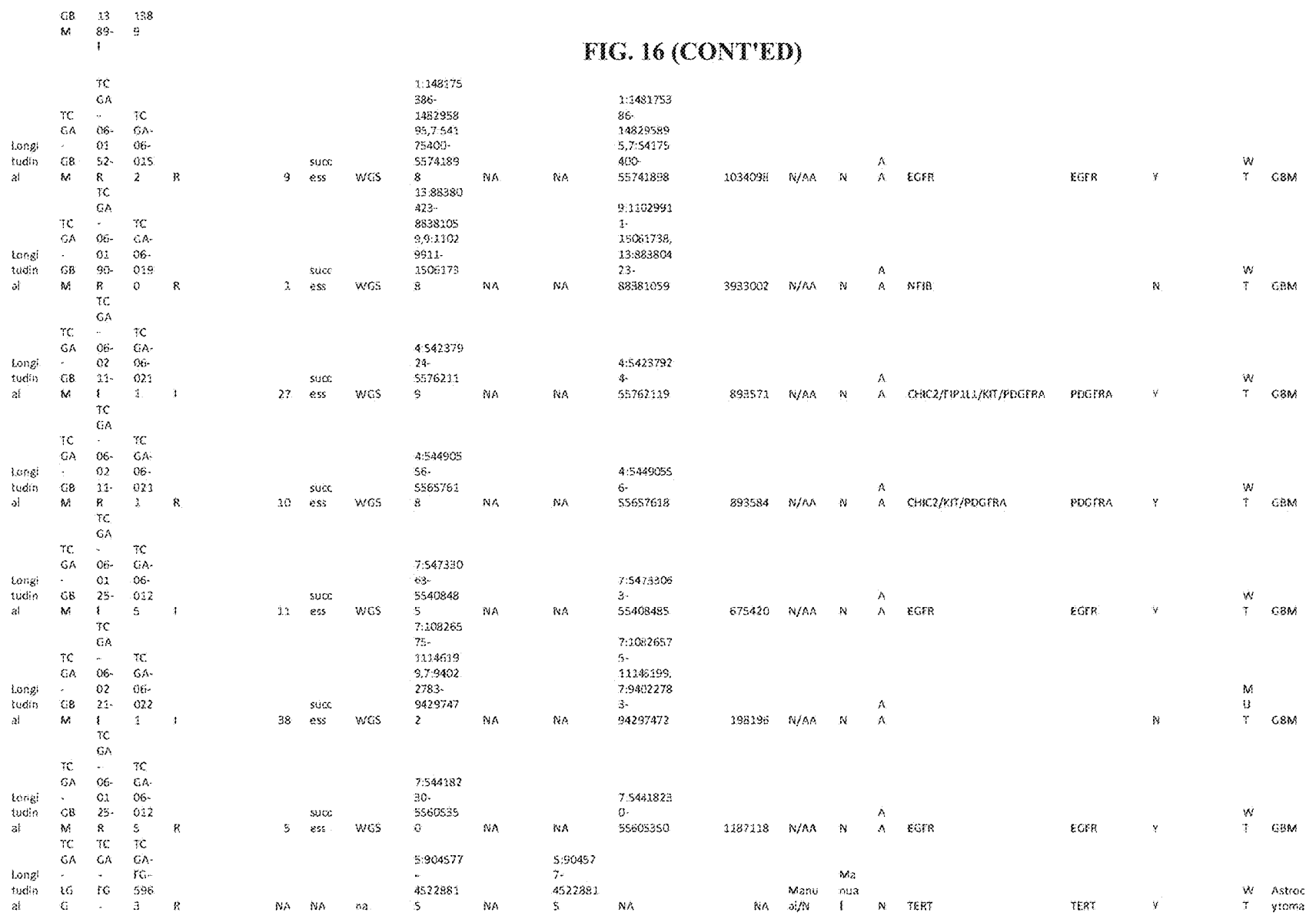
Figure 16:
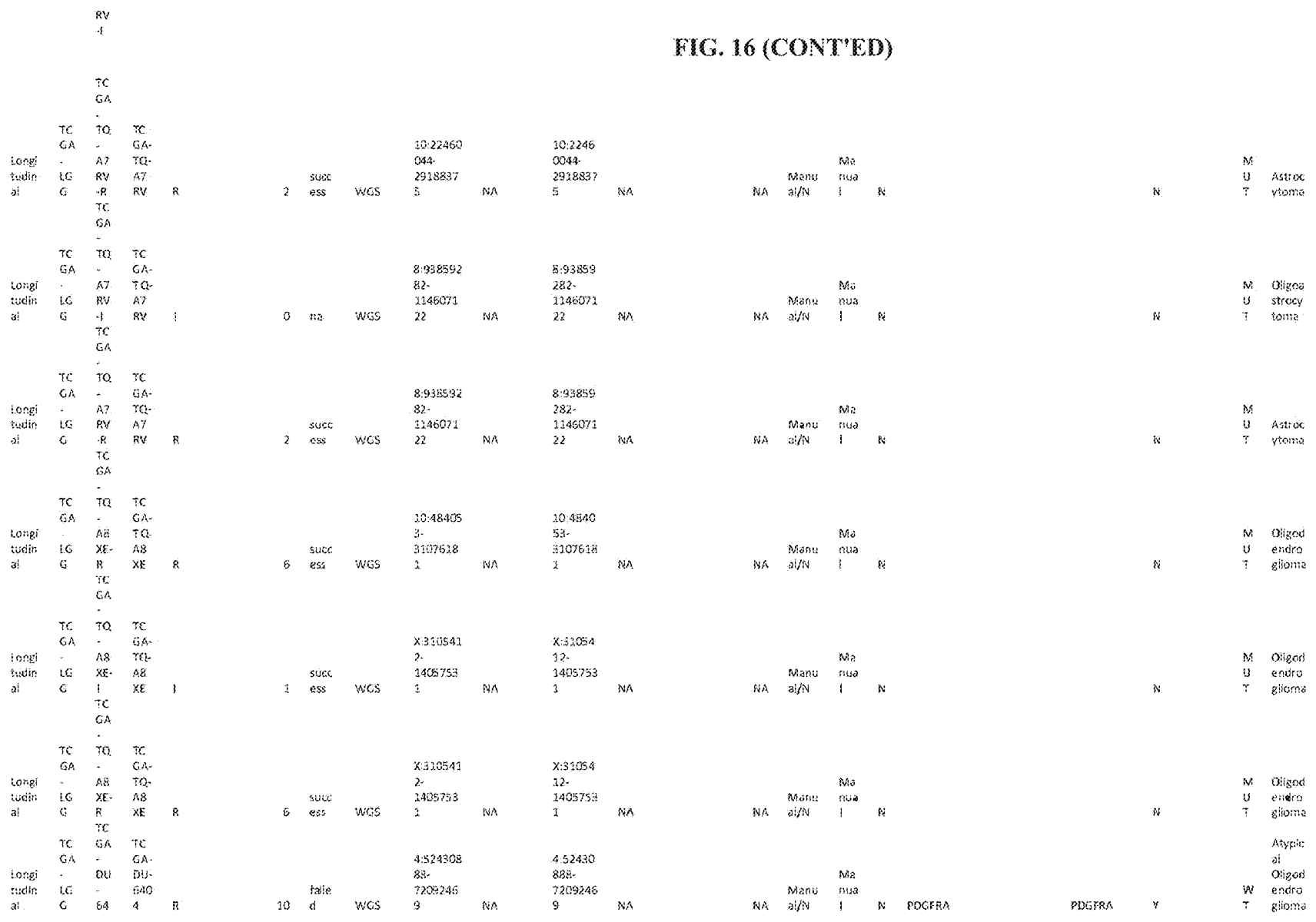
Figure 16:
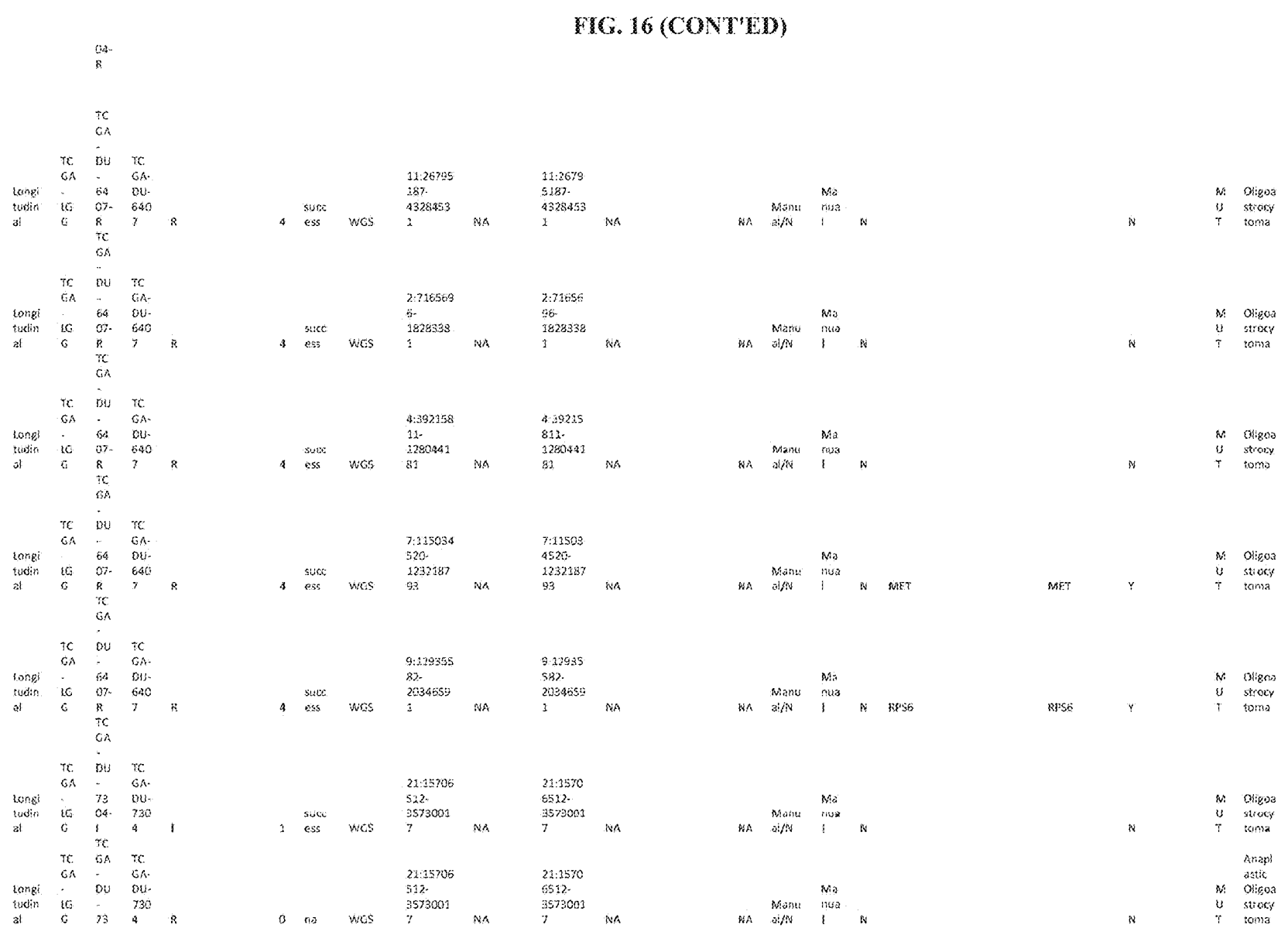
Figure 16:
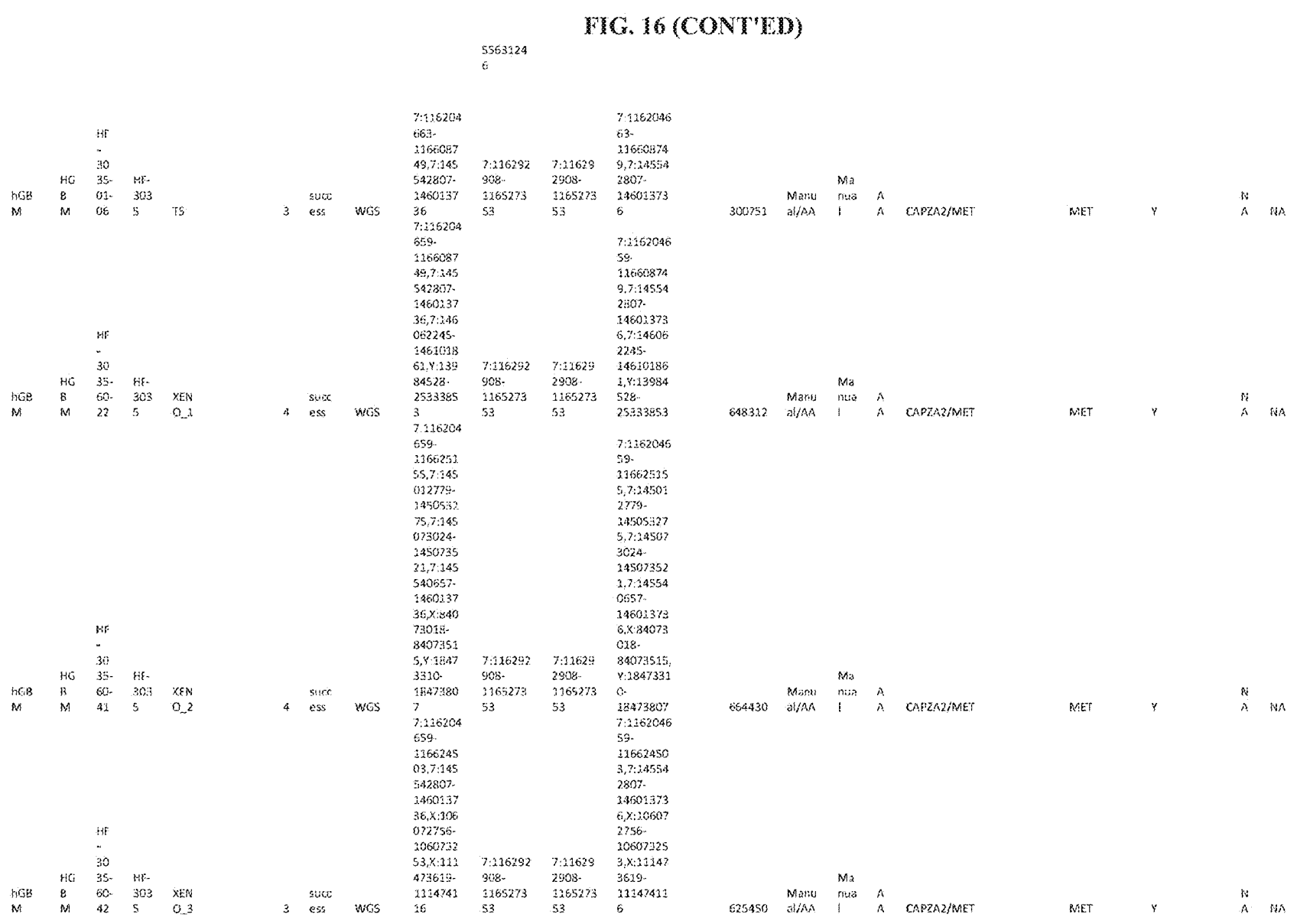
Figure 16:
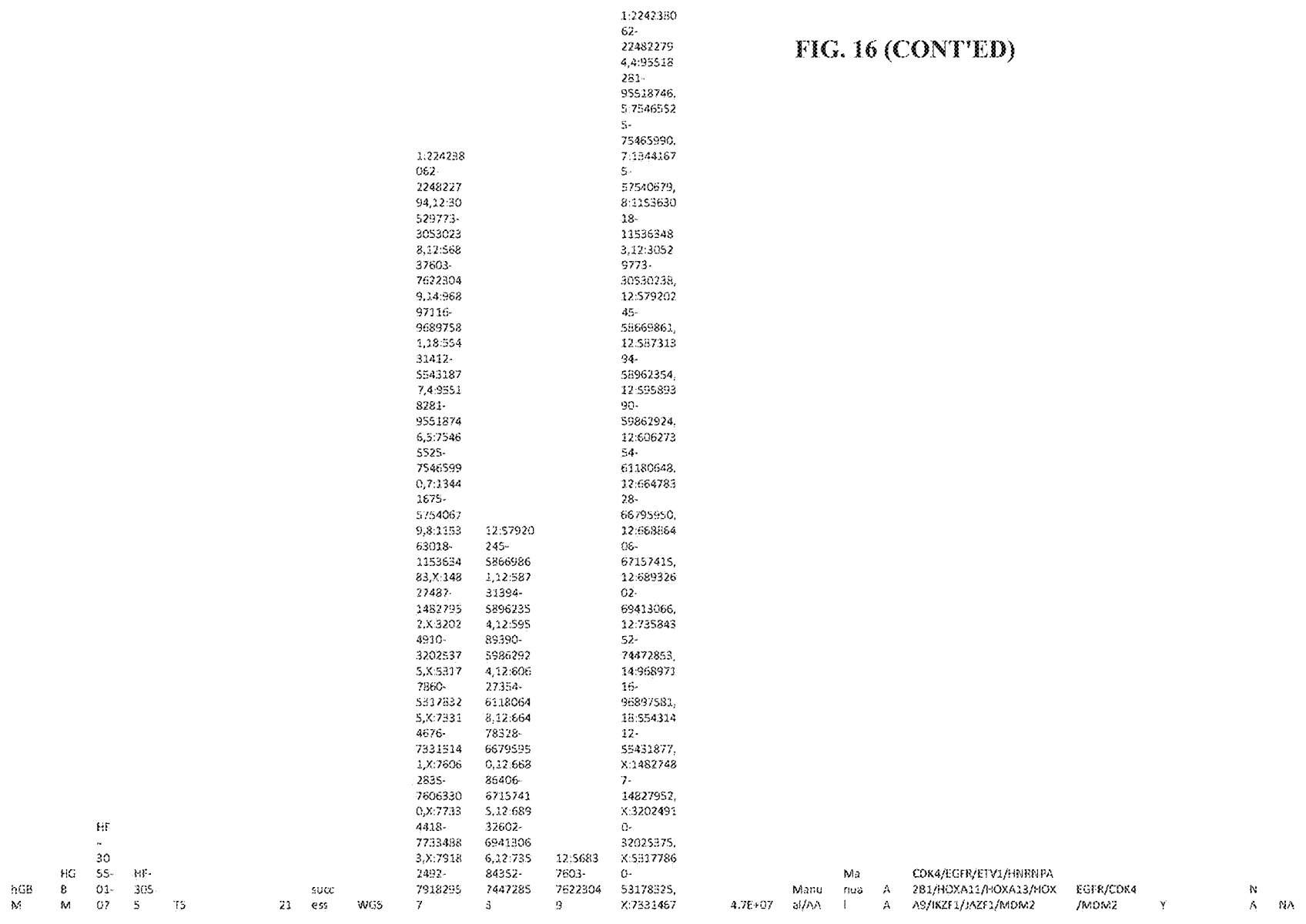
Figure 16:
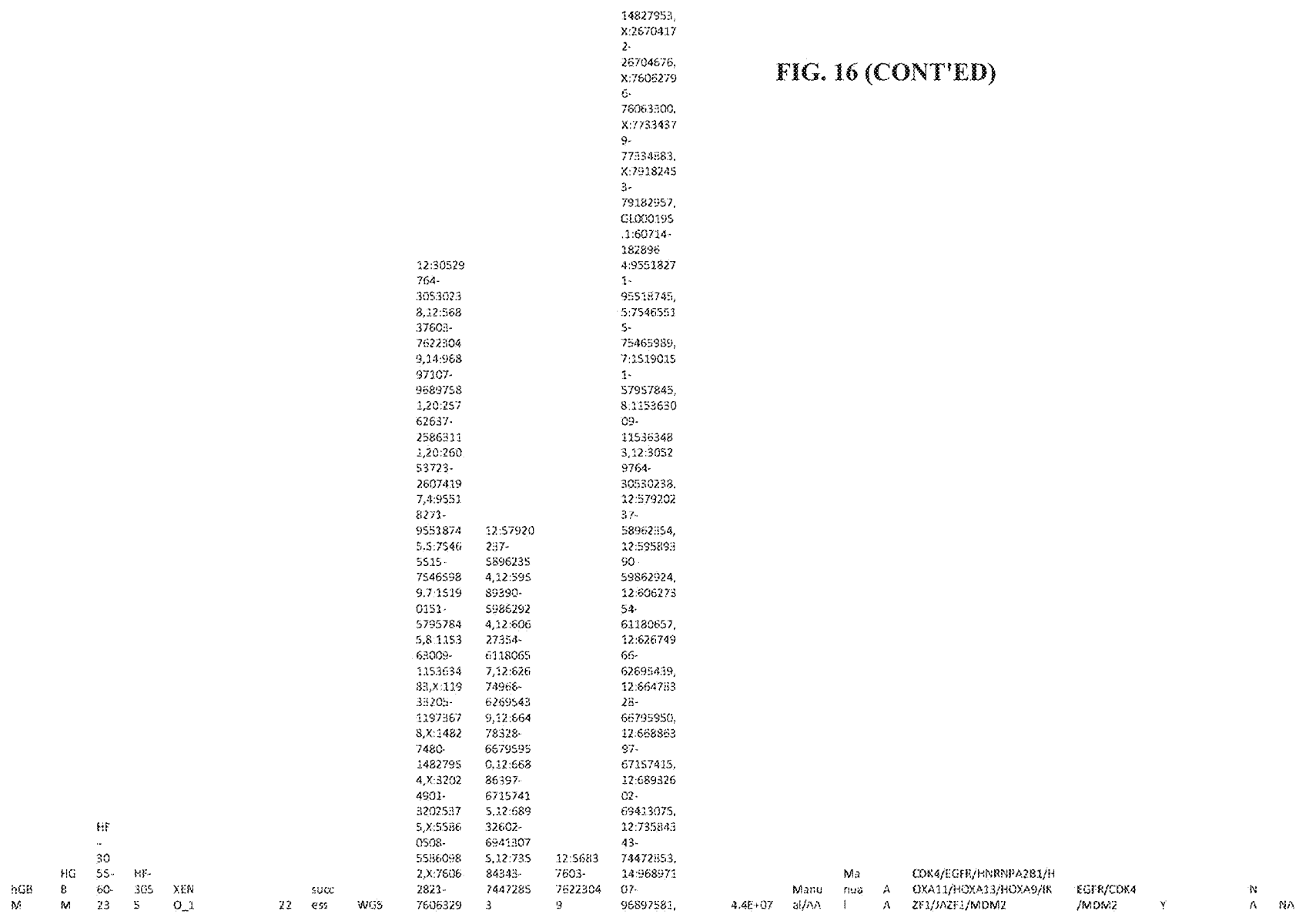
Figure 16:
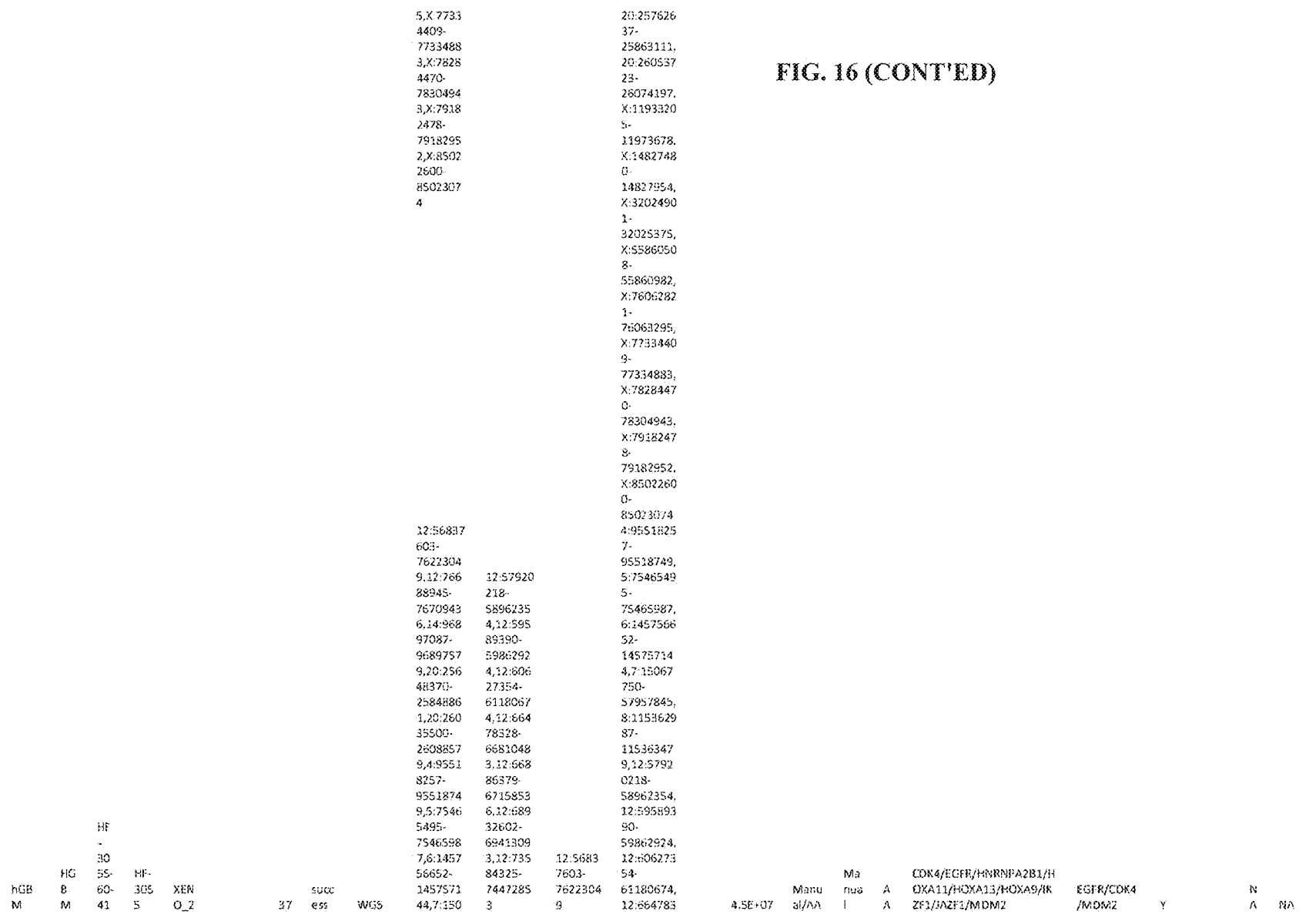
Figure 16:
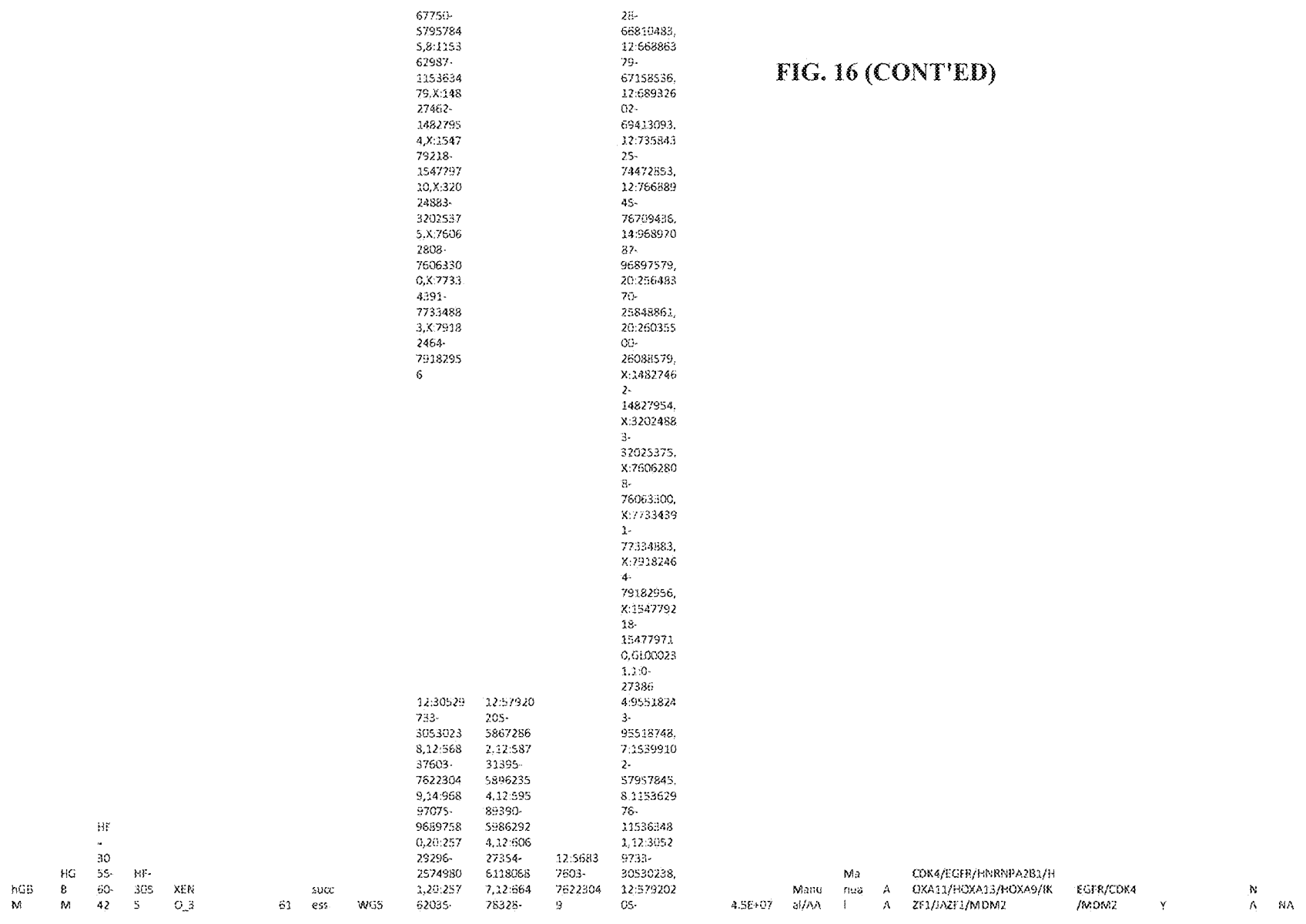
Figure 16:
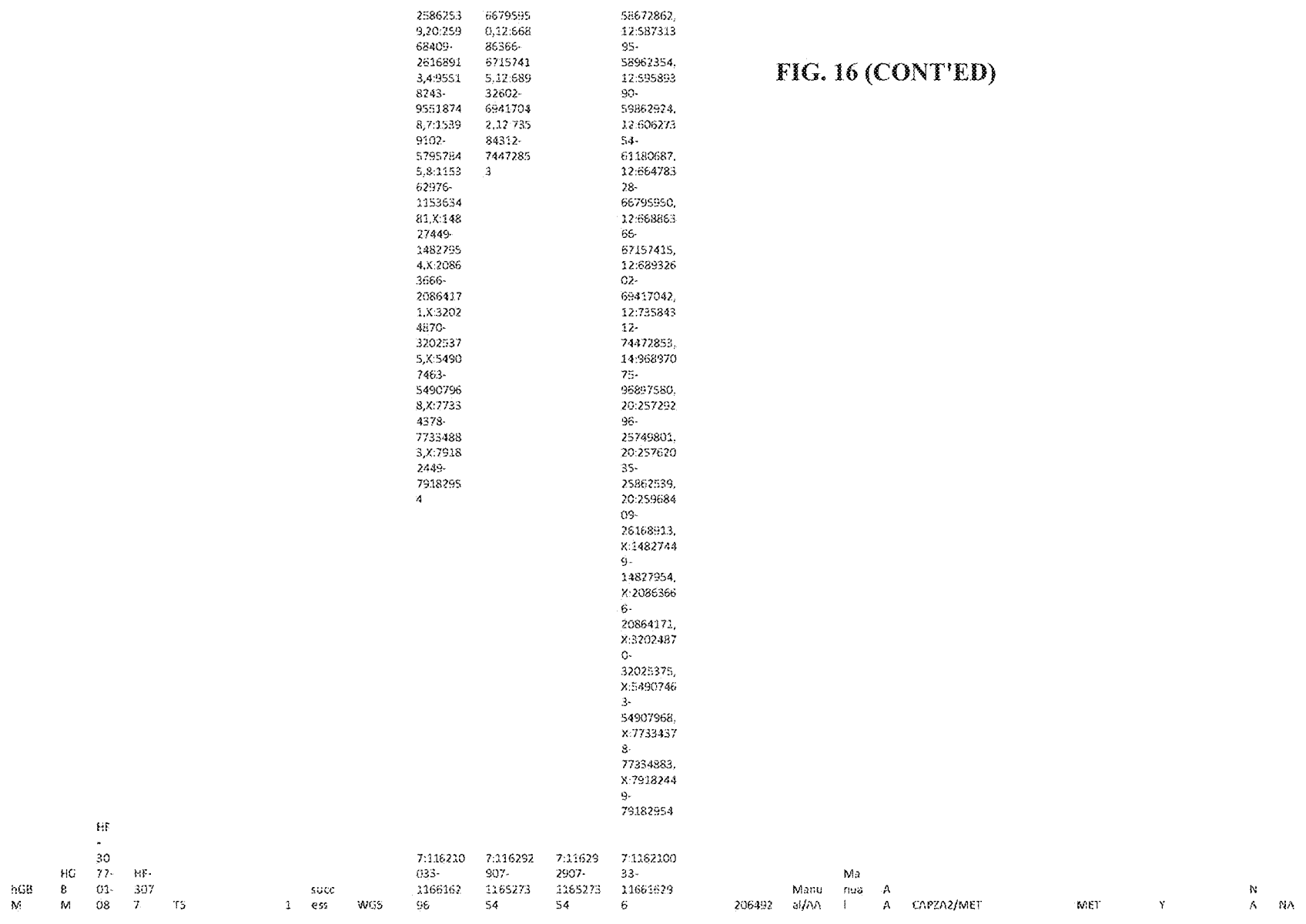
Figure 16:
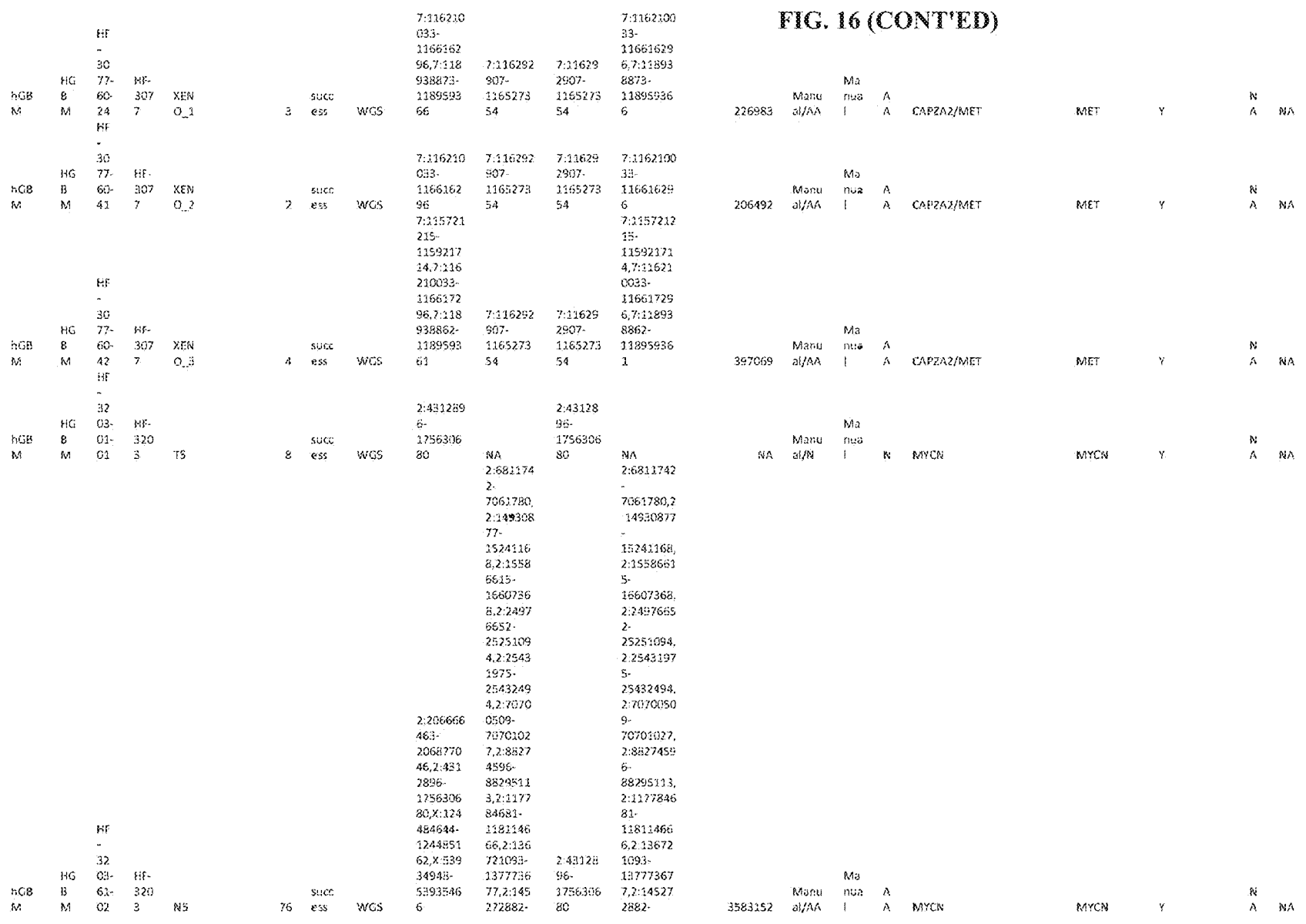
Figure 16:
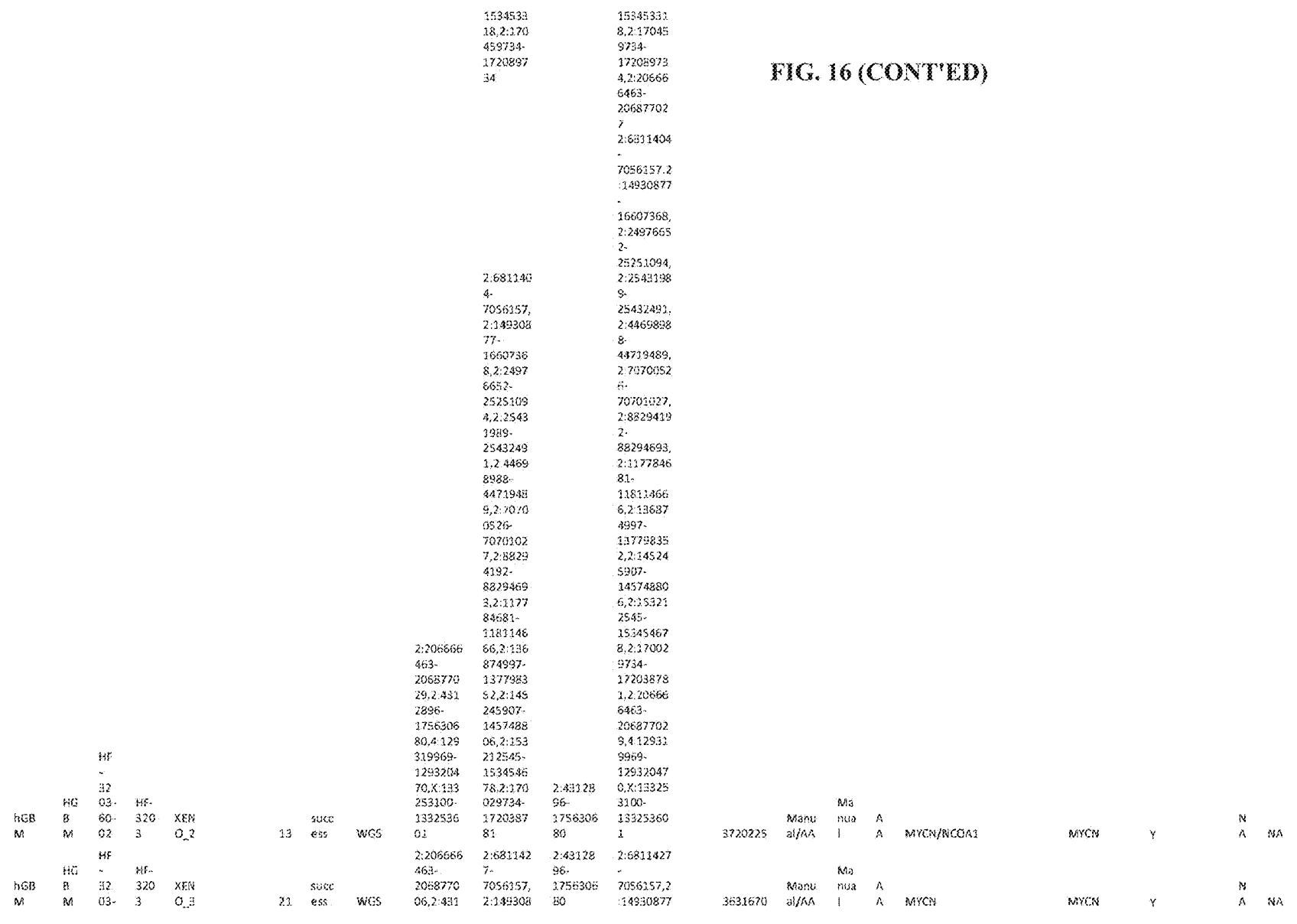
Figure 16:
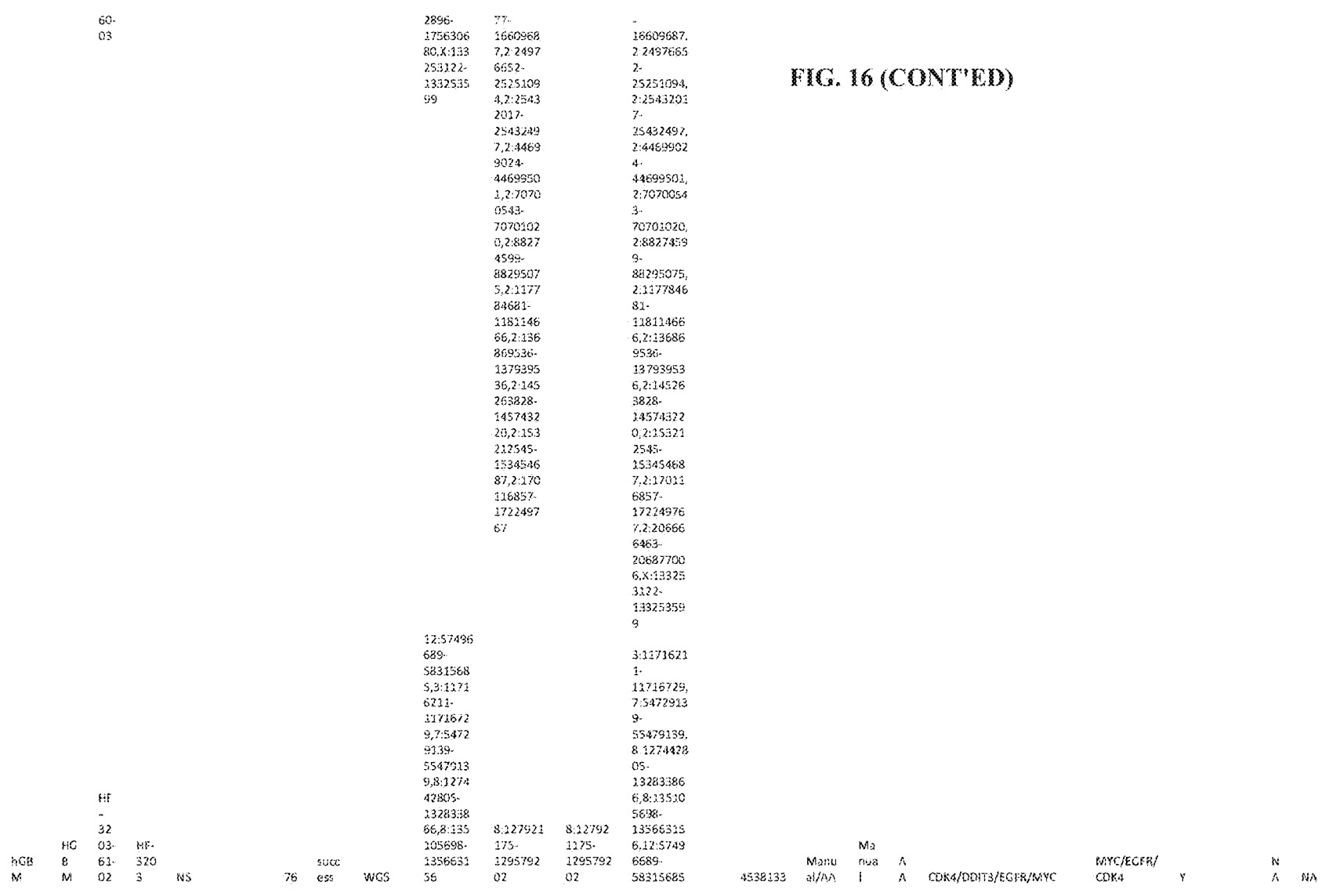
Figure 16:
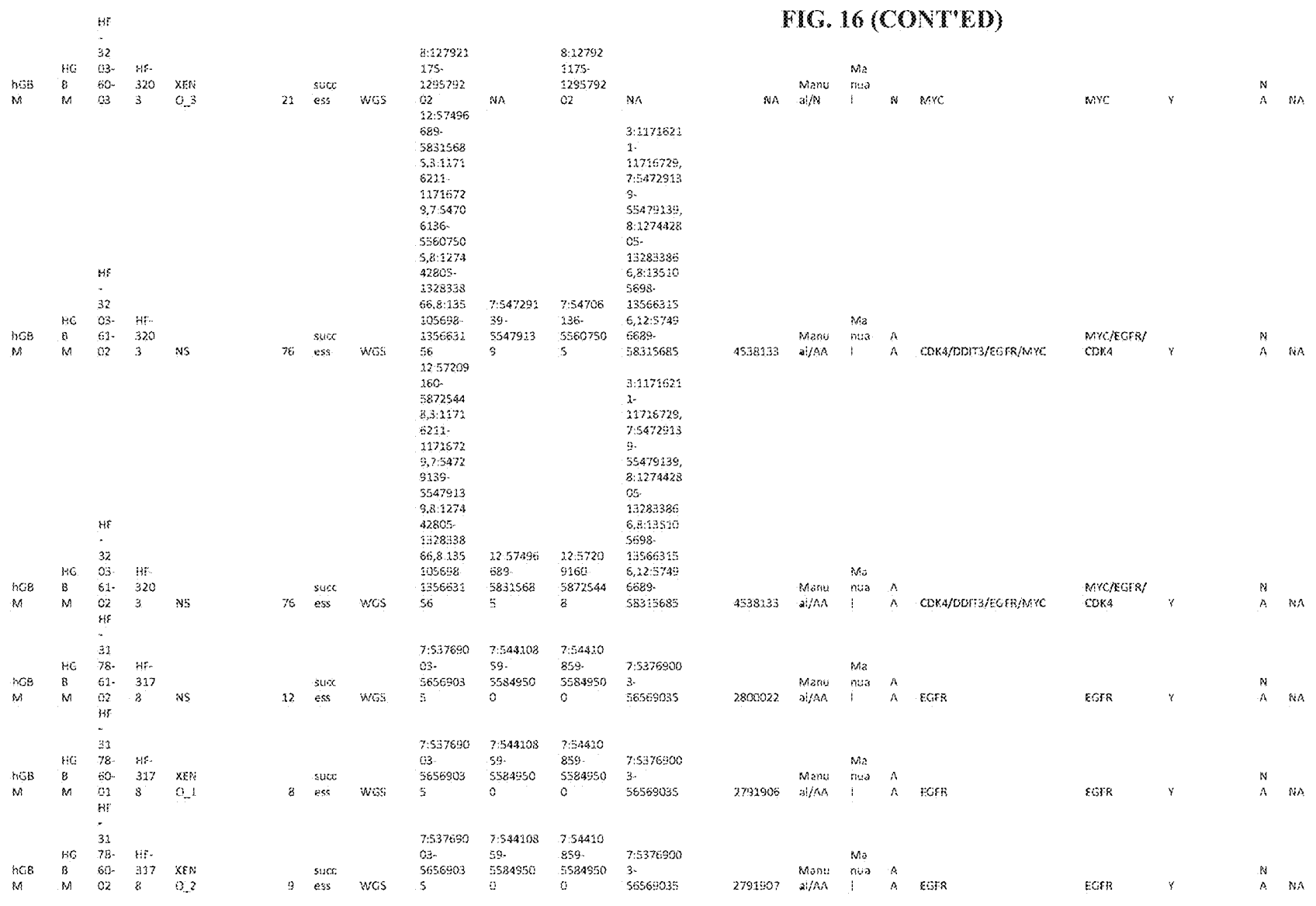
Figure 16:
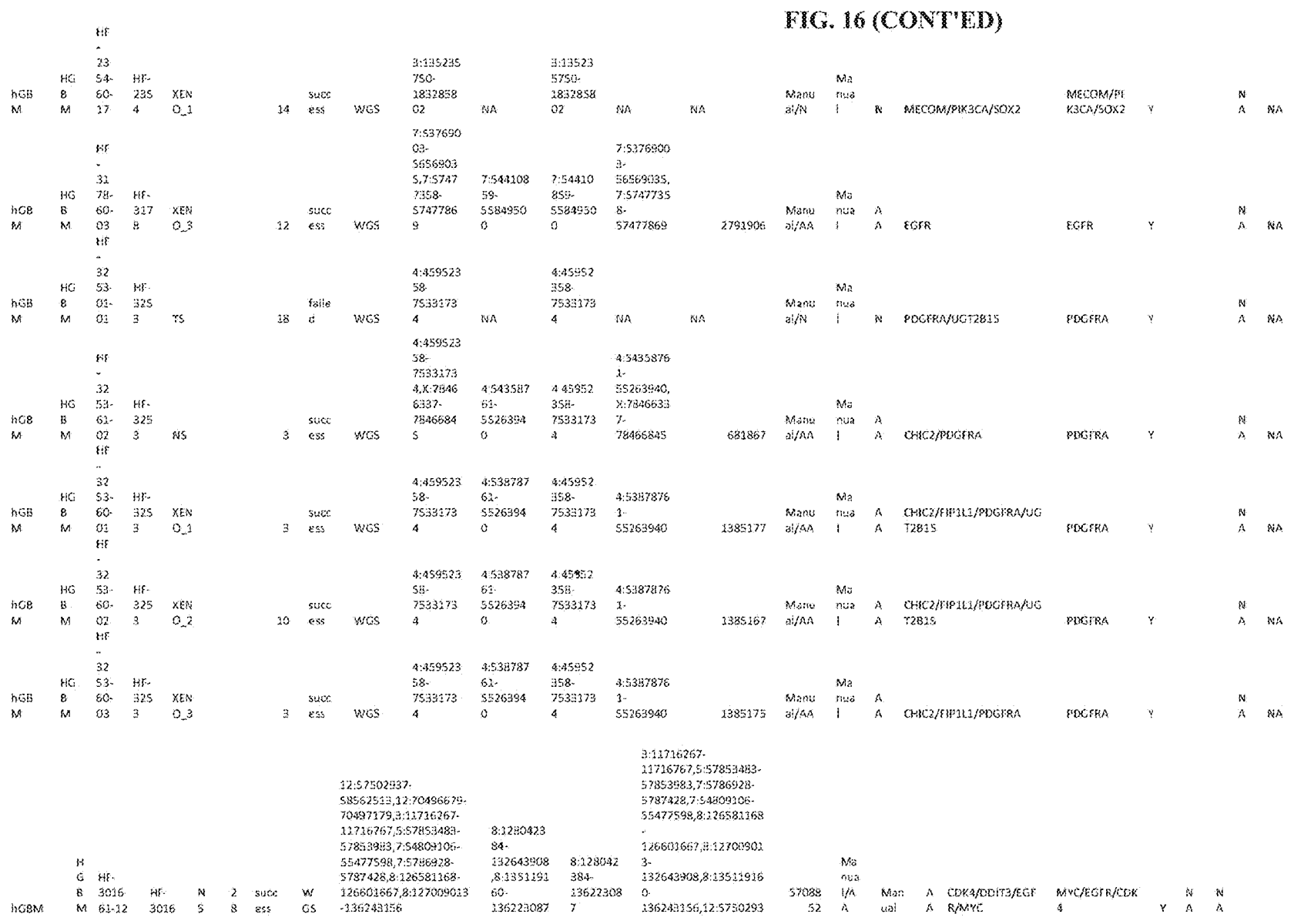
Figure 16:
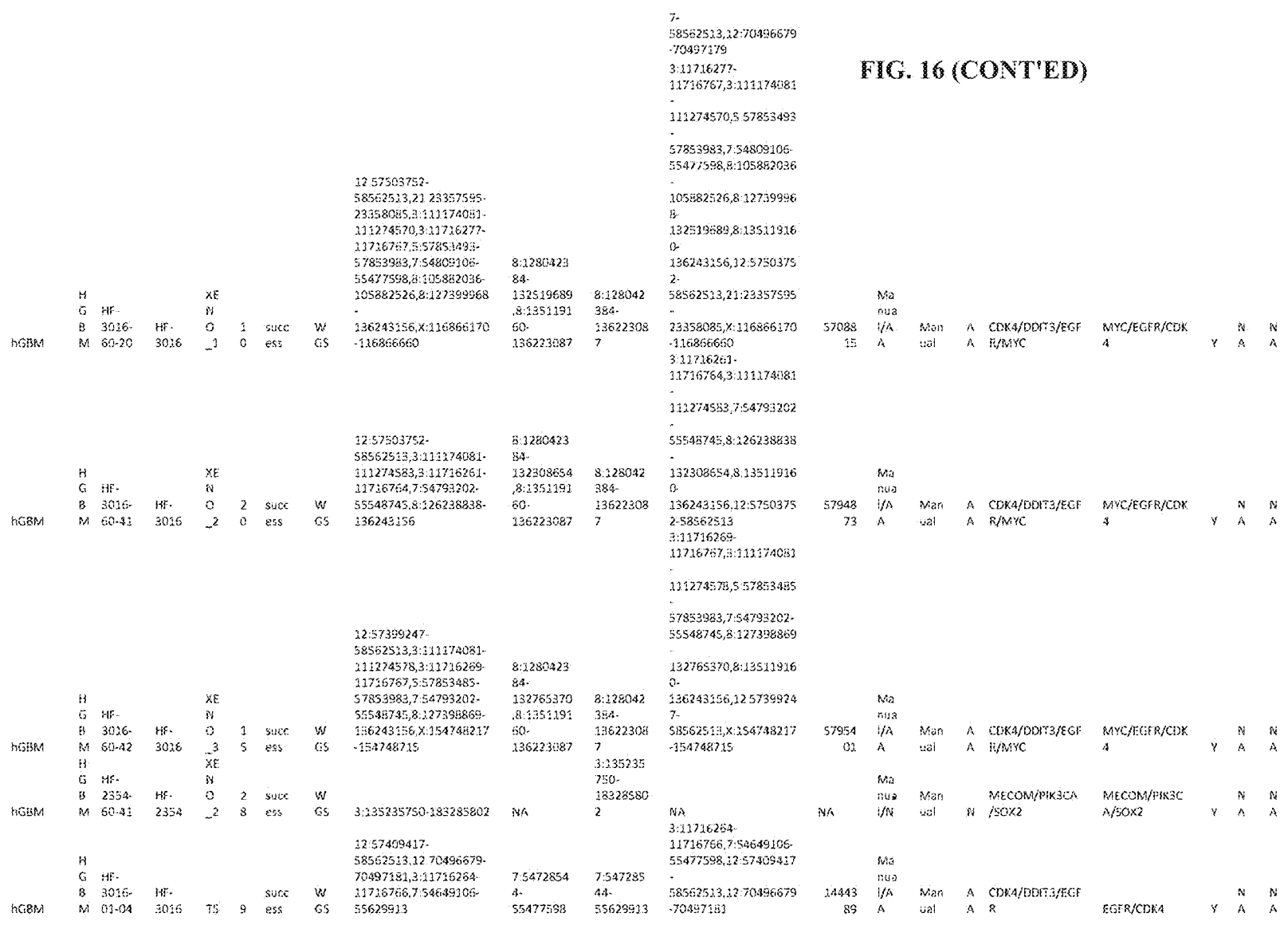
Figure 16:
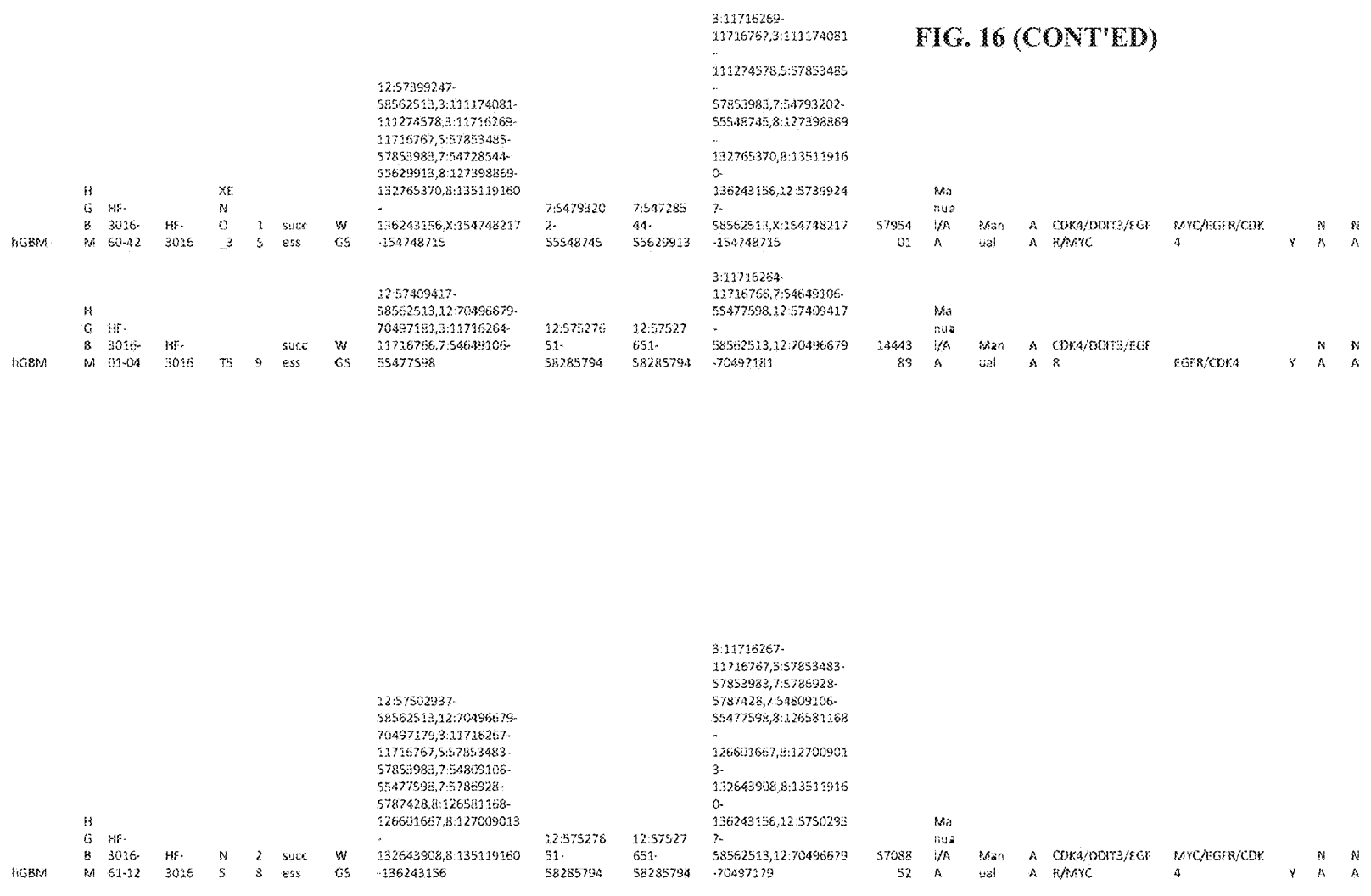
Figure 16:
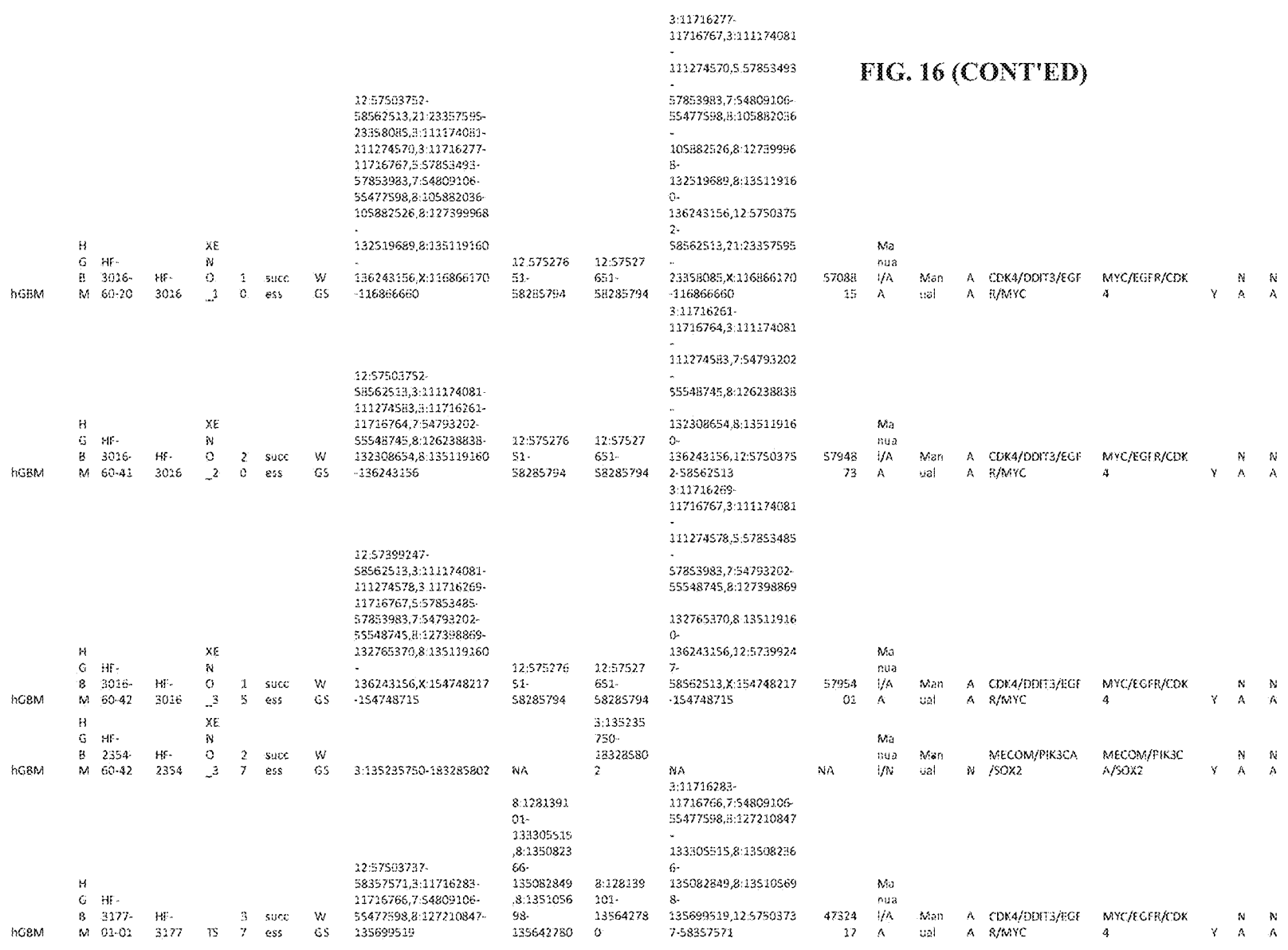
Figure 16:
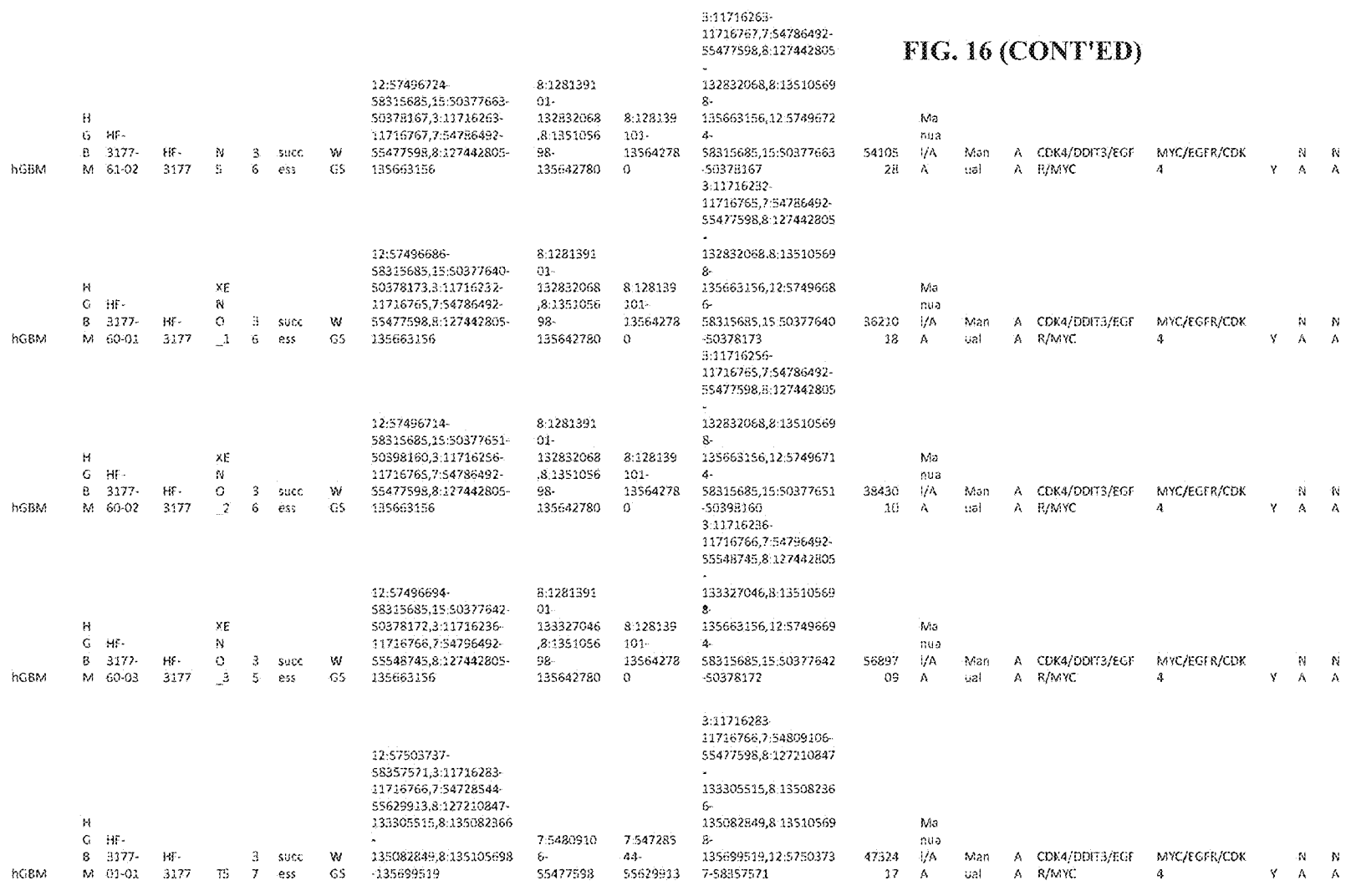
Figure 16:
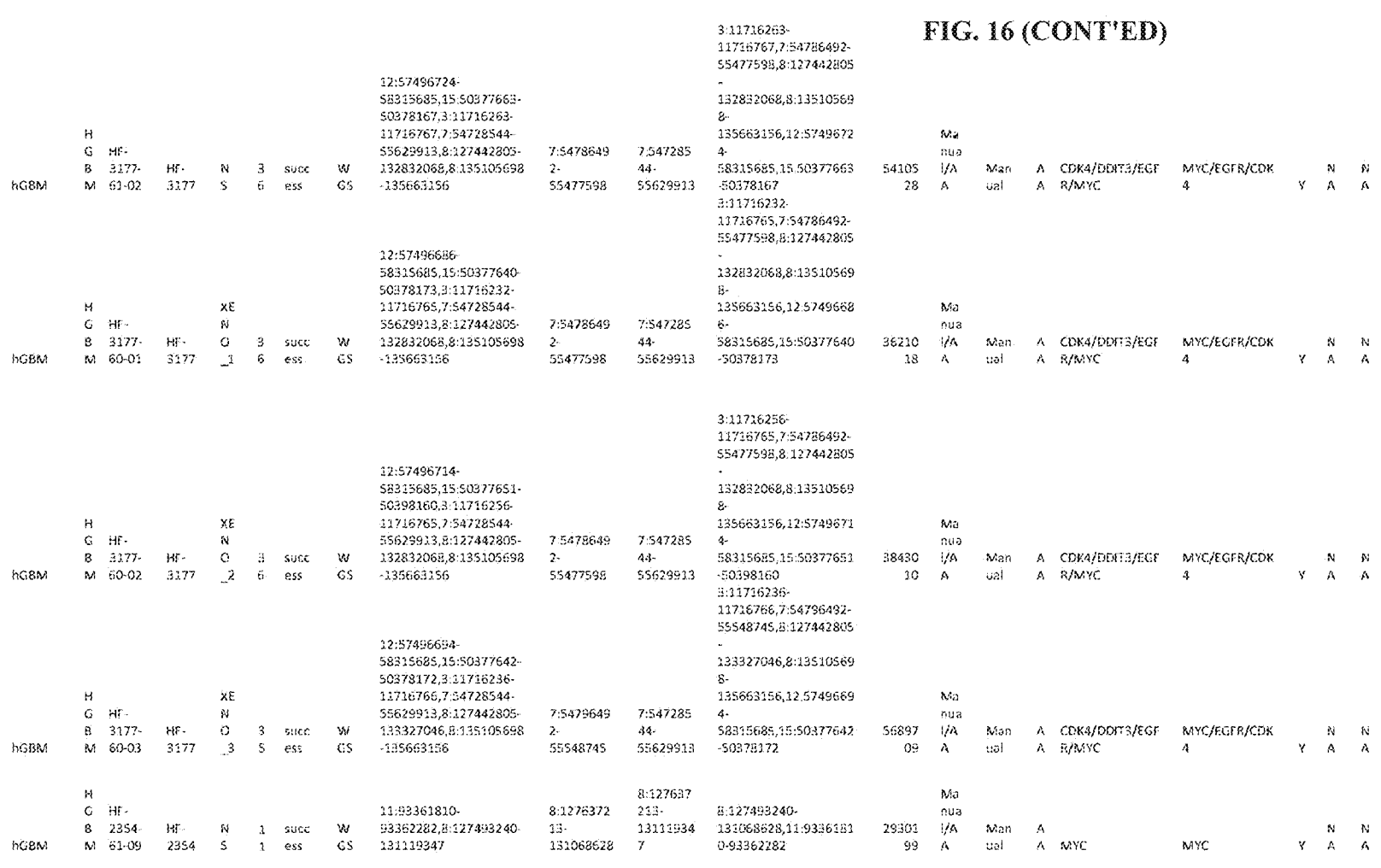
Figure 16:
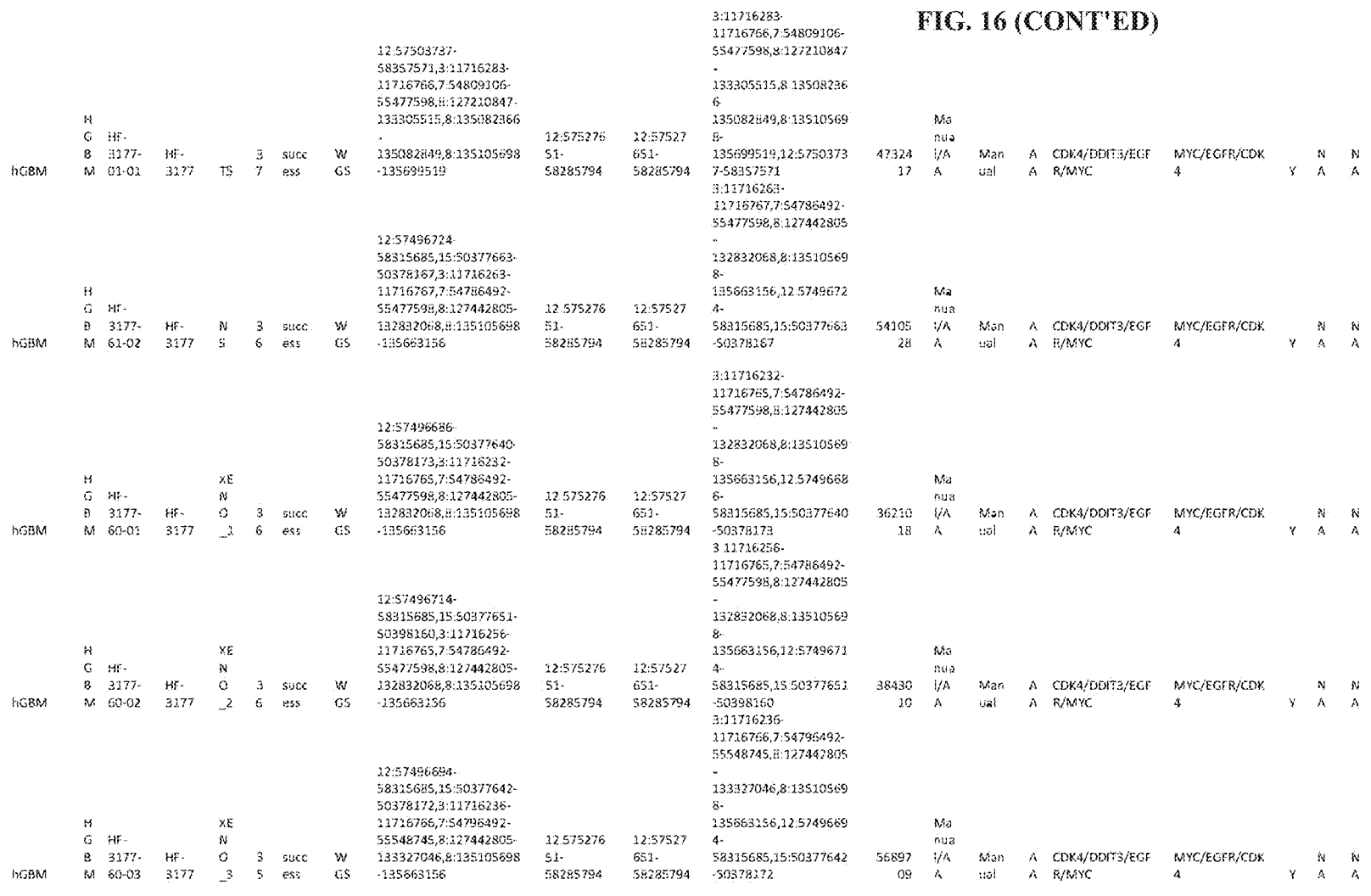
Figure 16:
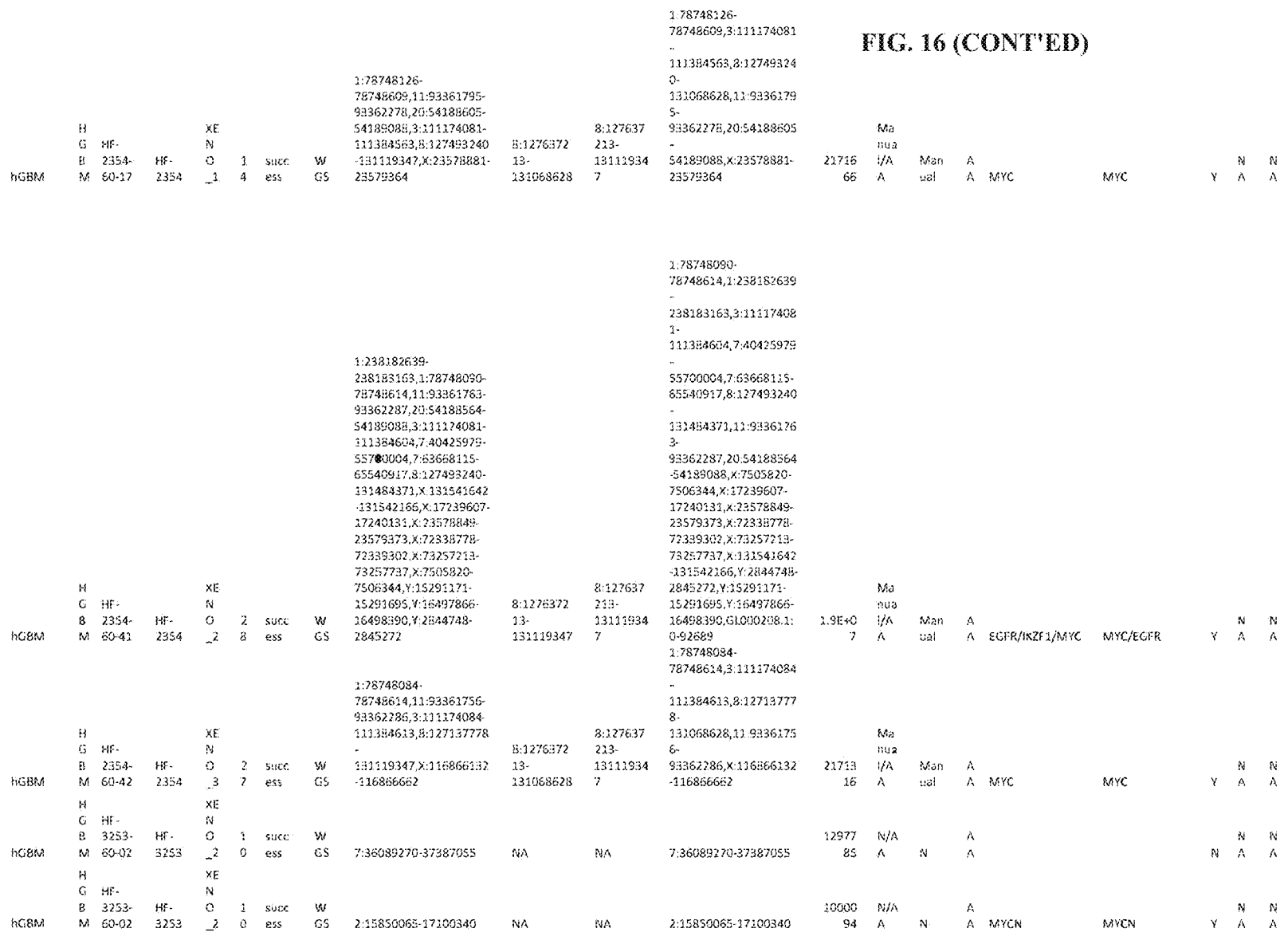
Figure 16:
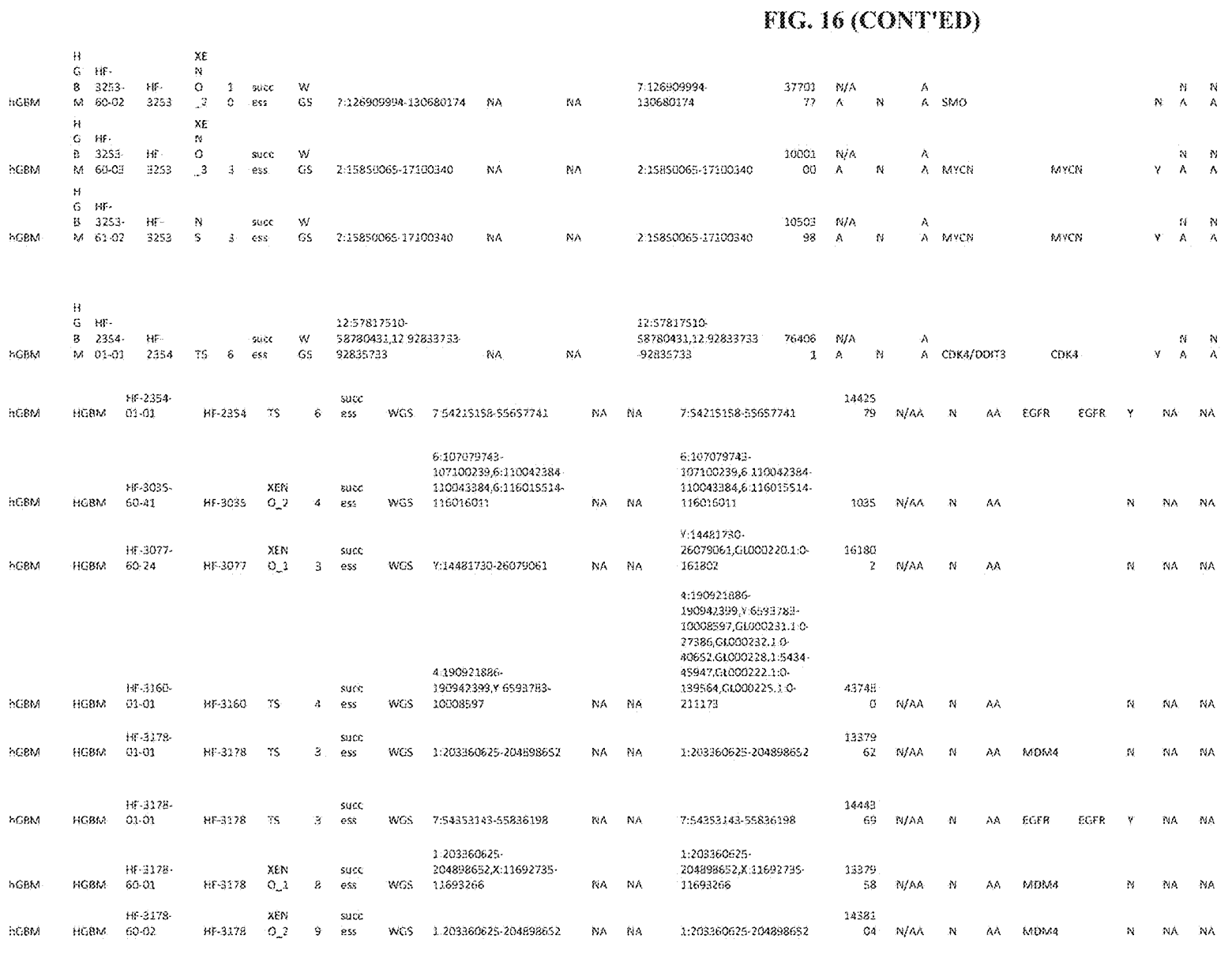

FIG. 16 sets forth Table 3C, which sets forth information relating to interphase FISH experiments.

FIG. 17 sets forth Table 3D, which shows a sample map relating to interphase FISH experiments, FIG. 18 sets forth Table 4A, which details FISH signal per nucleus for sample HF 3035.

FIG. 19 sets forth Table 4B, which details FISH signal per nucleus for sample HF 3055.

FIG. 20 sets forth Table 4C, which details FISH signal per nucleus for sample HF 3077.

FIG. 21 sets forth Table 4D, which details FISH signal per nucleus for sample HF 2354.

FIG. 22 sets forth Table 4E, which details FISH signal per nucleus for sample HF3016/HF3016-R (HF3177).

FIG. 23 sets forth Table 4F, which details FISH signal per nucleus for sample HF2927.

FIG. 24 sets forth Table 4G, which details FISH signal per nucleus for sample HF3178.

9

Figure 1A:
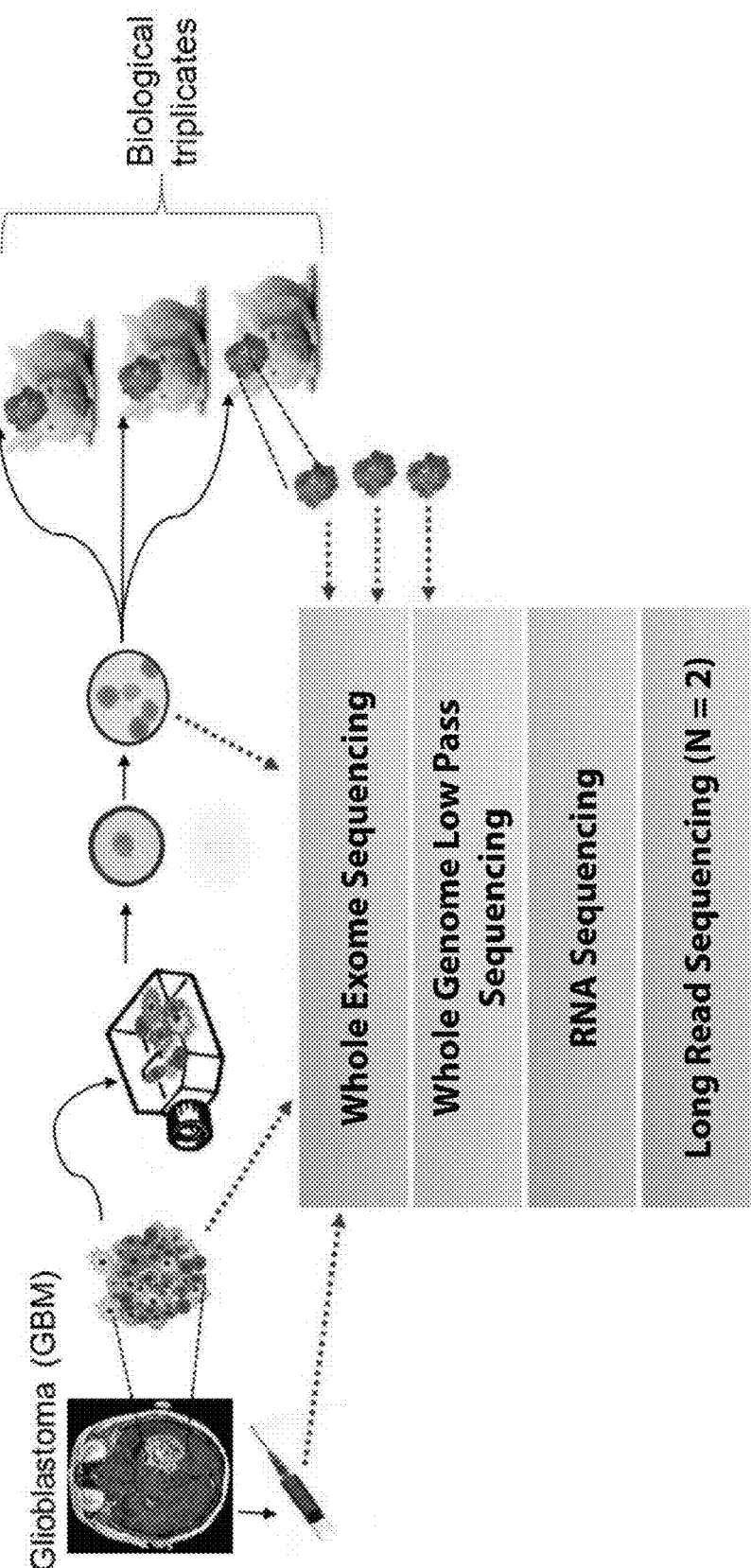
FIG. 1A depicts a comprehensive comparison of GBM, derived neurospheres, and PDX models. Genomic and transcriptomic characterization were performed on thirteen (13) patient tumors, their derivative neurospheres and xenograft models. Long read PacBio sequencing was performed on two xenograft tumors.

FIG. 25 sets forth Table 5, which sets forth FISH results for predicted DM and non-amplified control genes in primary-recurrent GBM pairs (genes in primary-recurrent GBM pairs (50 cells counted)).

FIG. 26 sets forth Table 6, which details alignment of the selected contigs on the hg19 chromosome 7.

FIG. 27 sets forth Table 7, which sets forth mutation counts and tumor purity estimates for individual samples.

Figure 28:
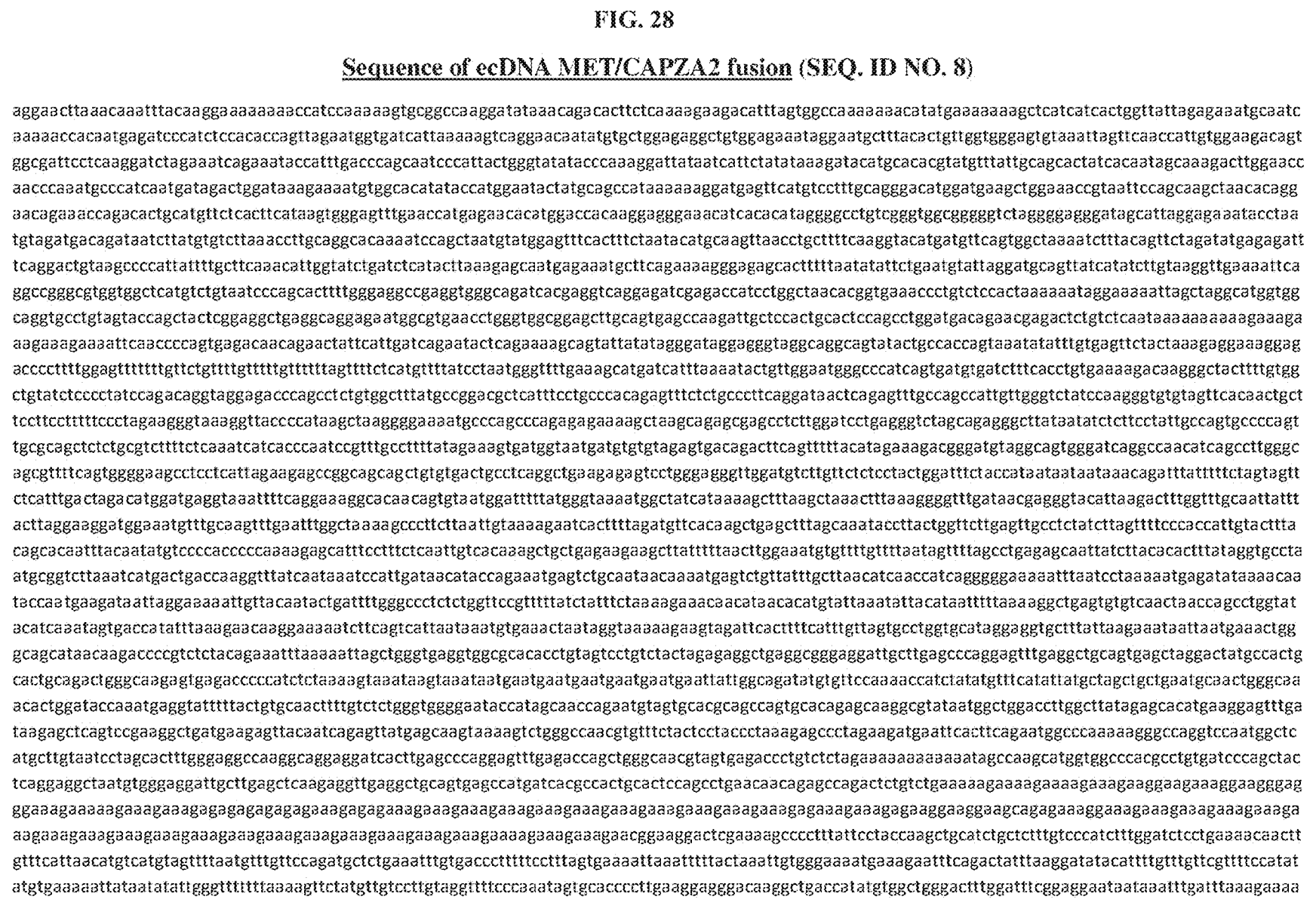
Figure 28:
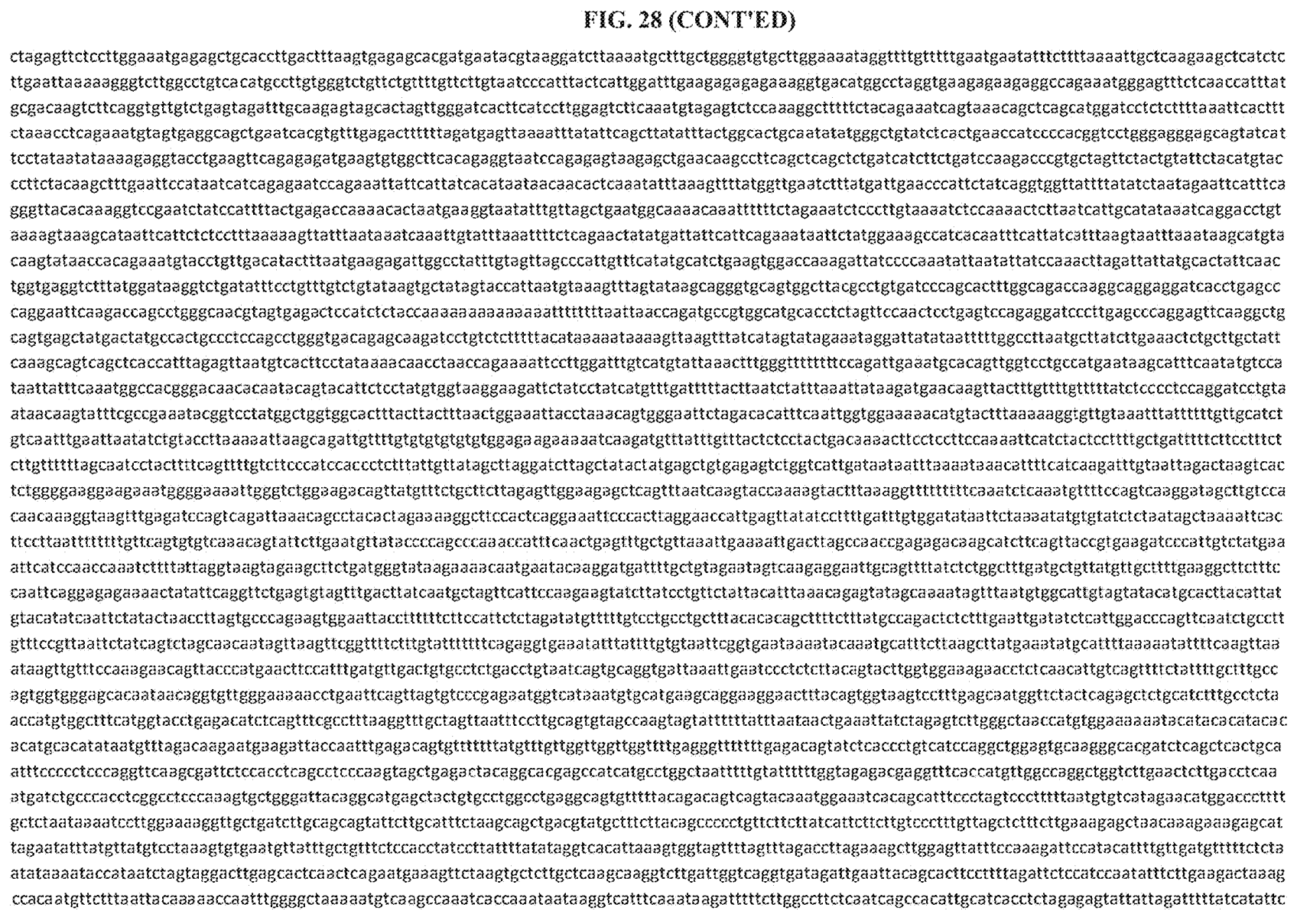
Figure 28:
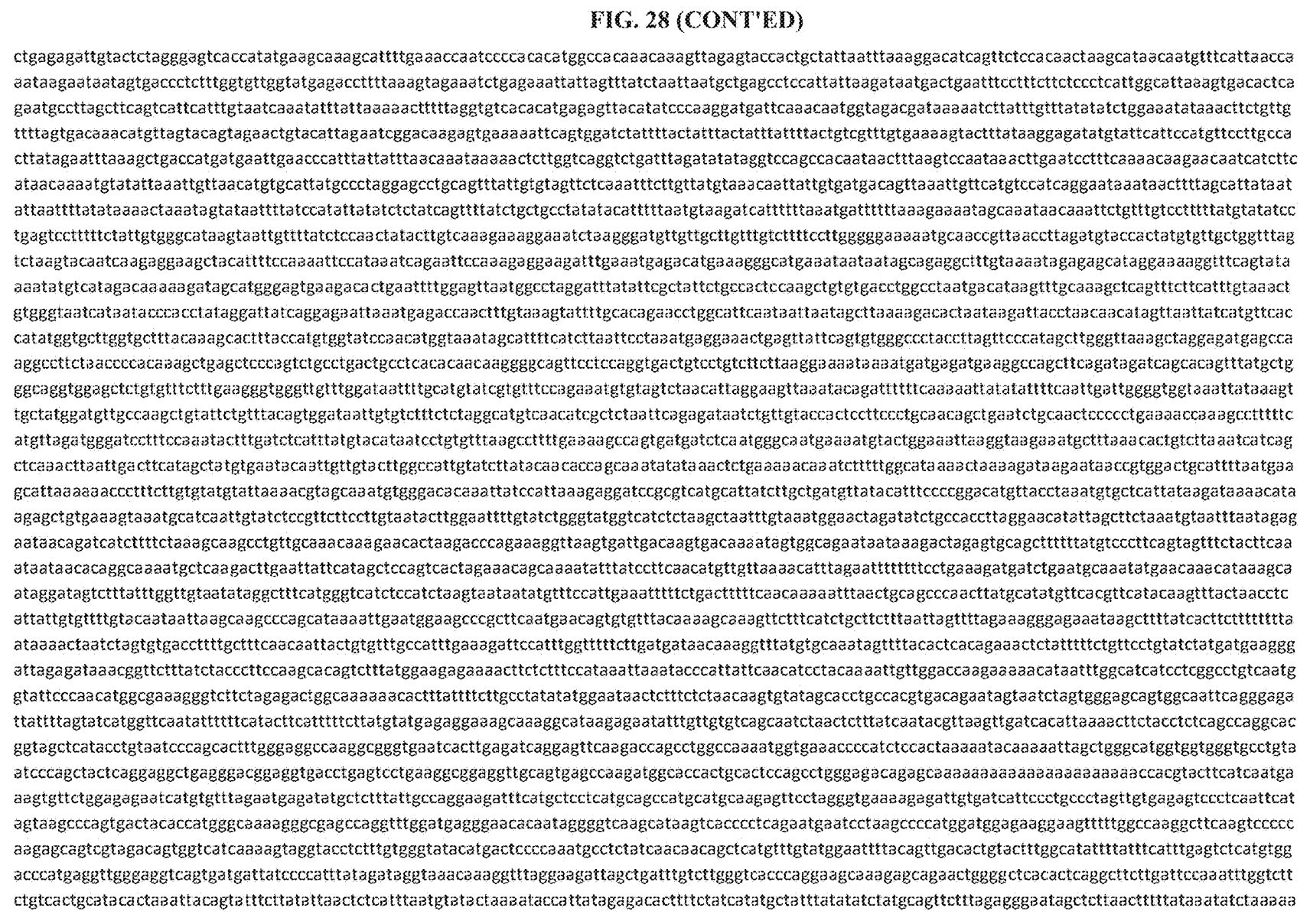
Figure 28:
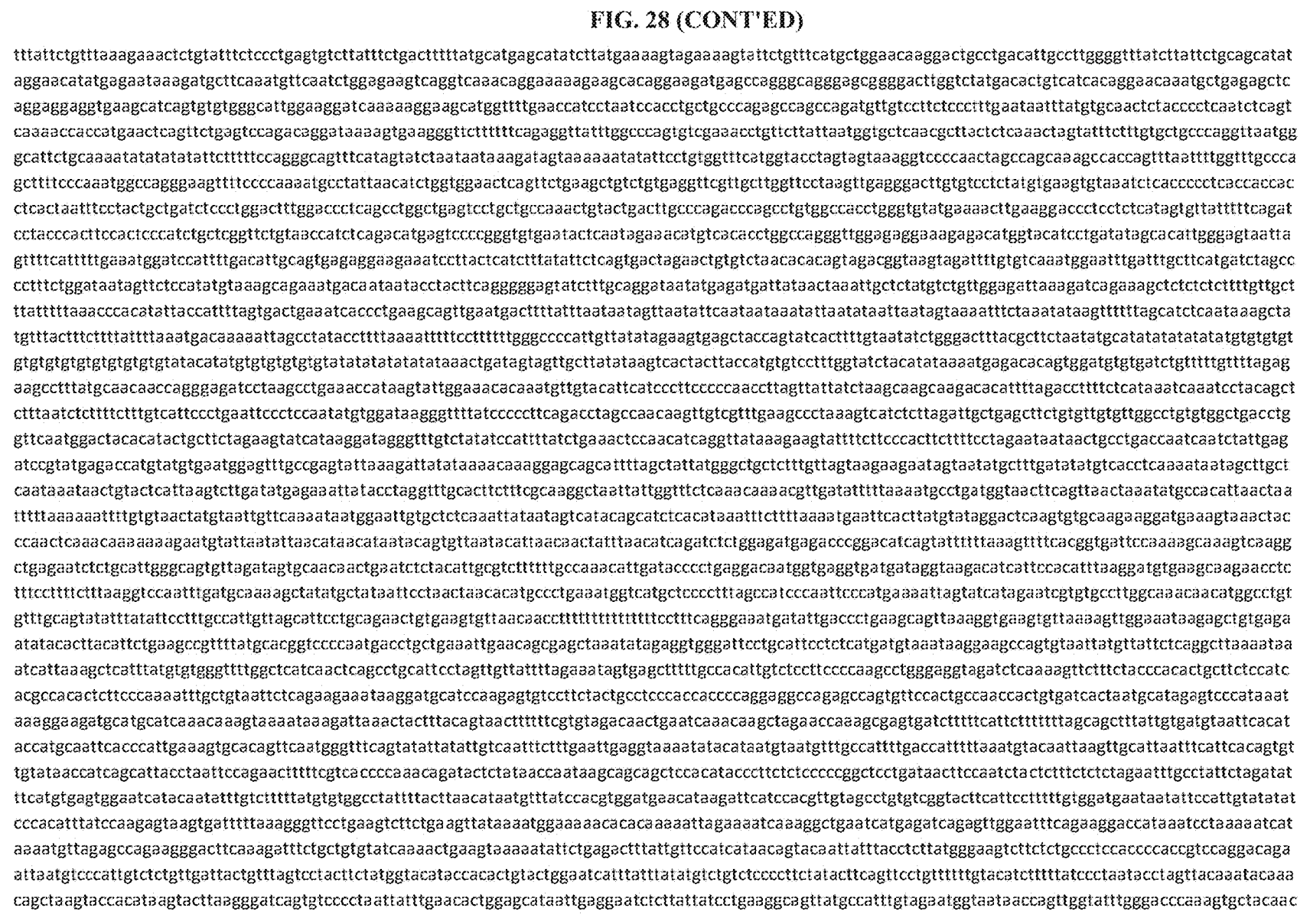
Figure 28:
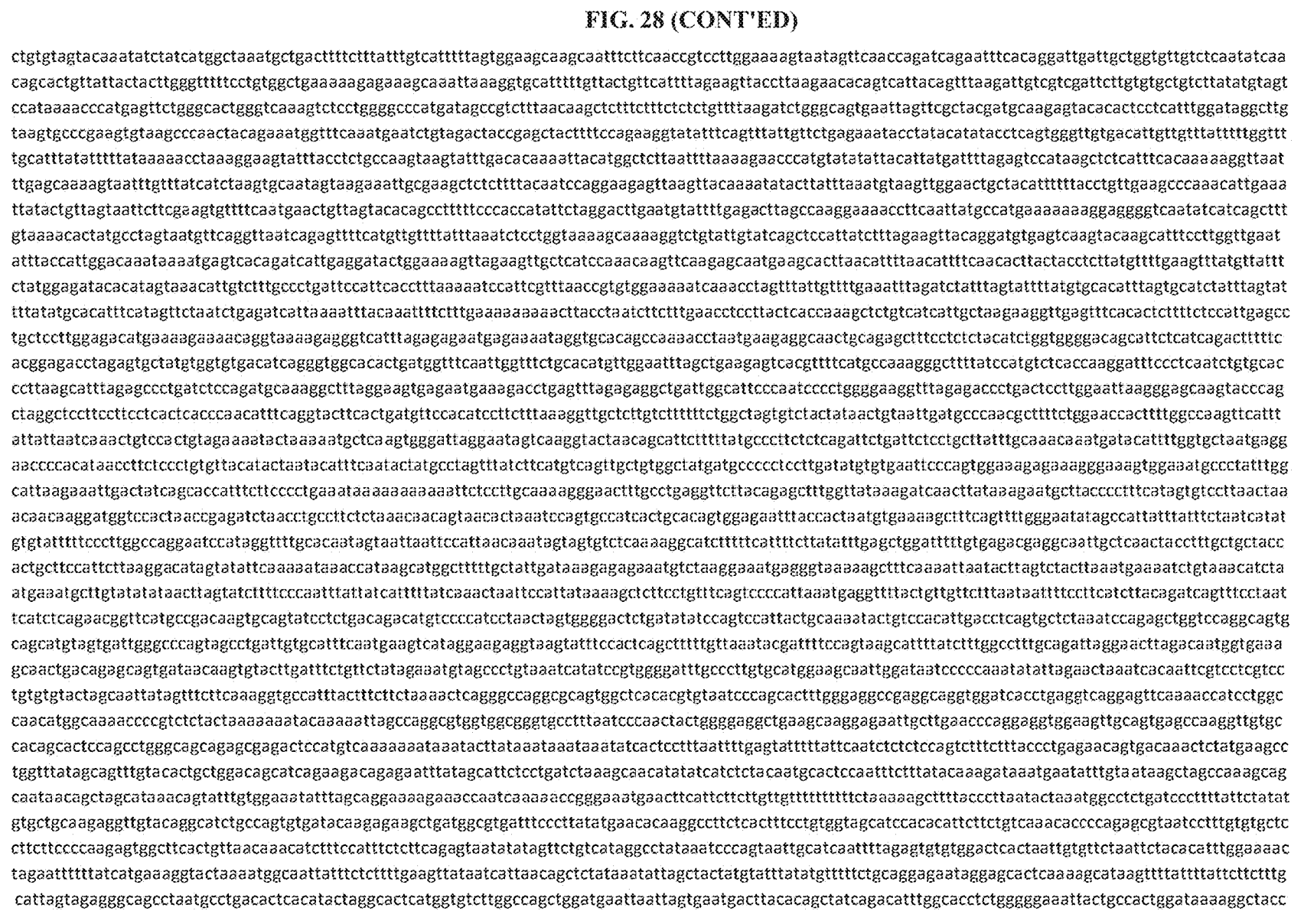
Figure 28:
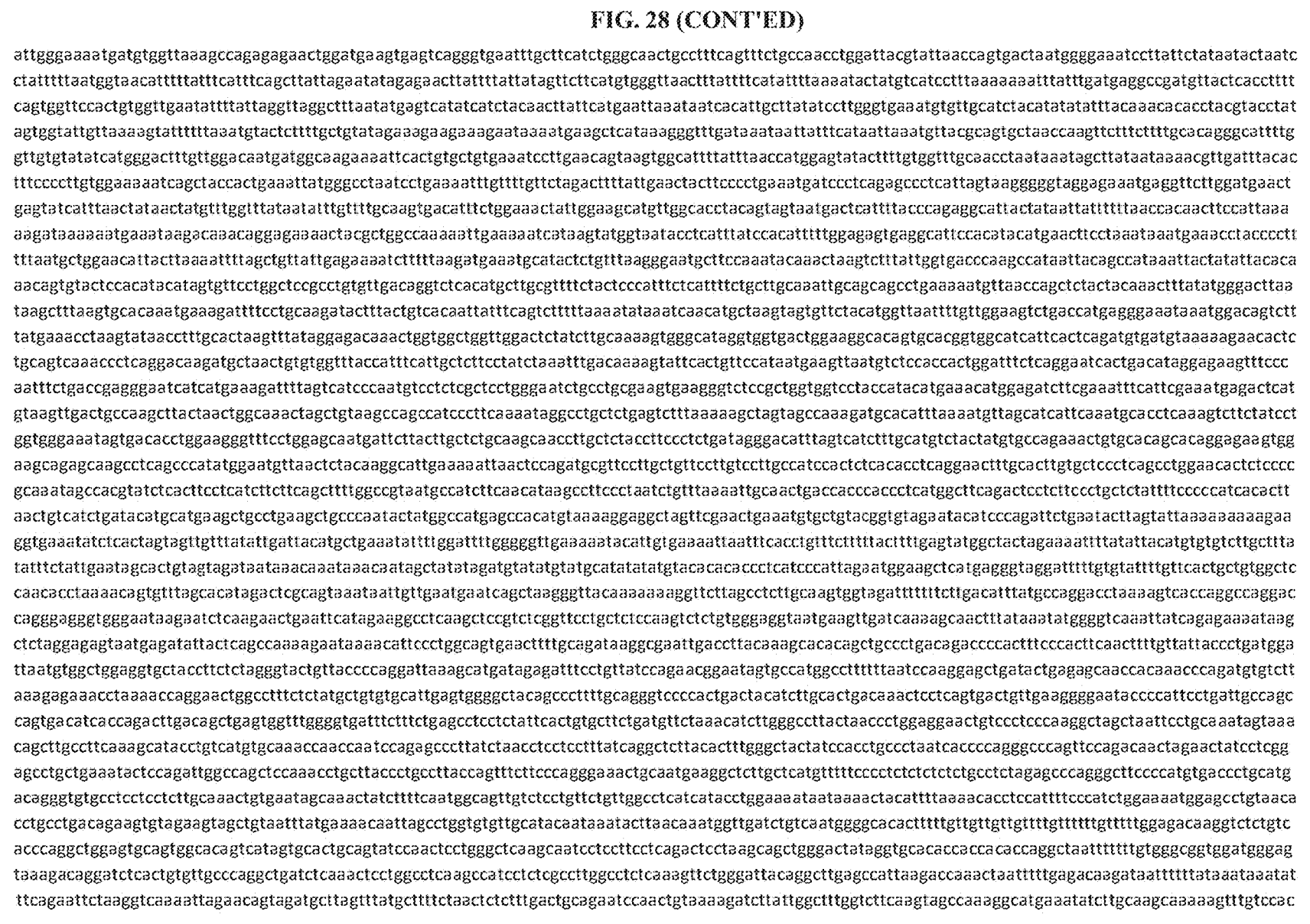
Figure 28:
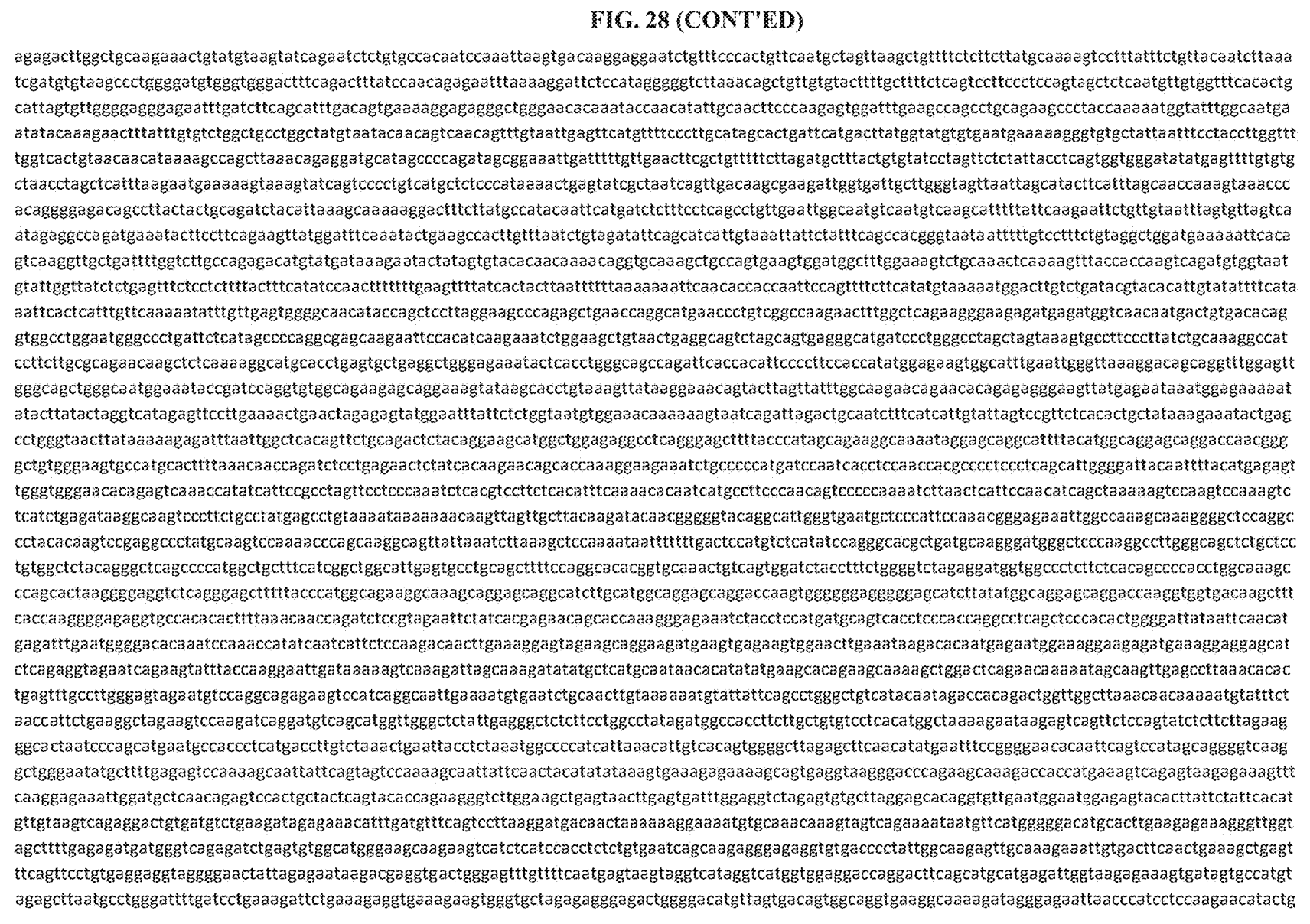
Figure 28:
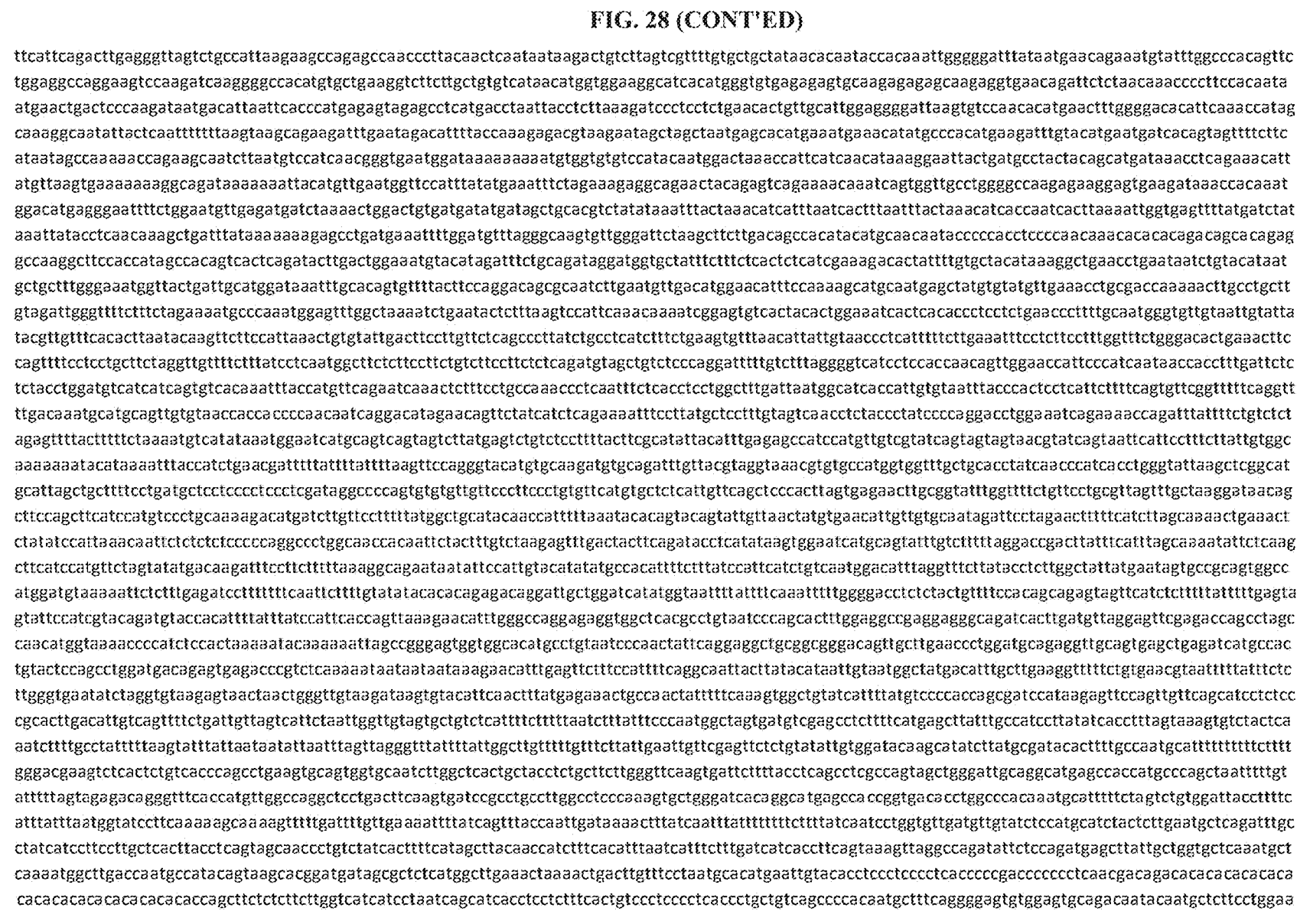
Figure 28:
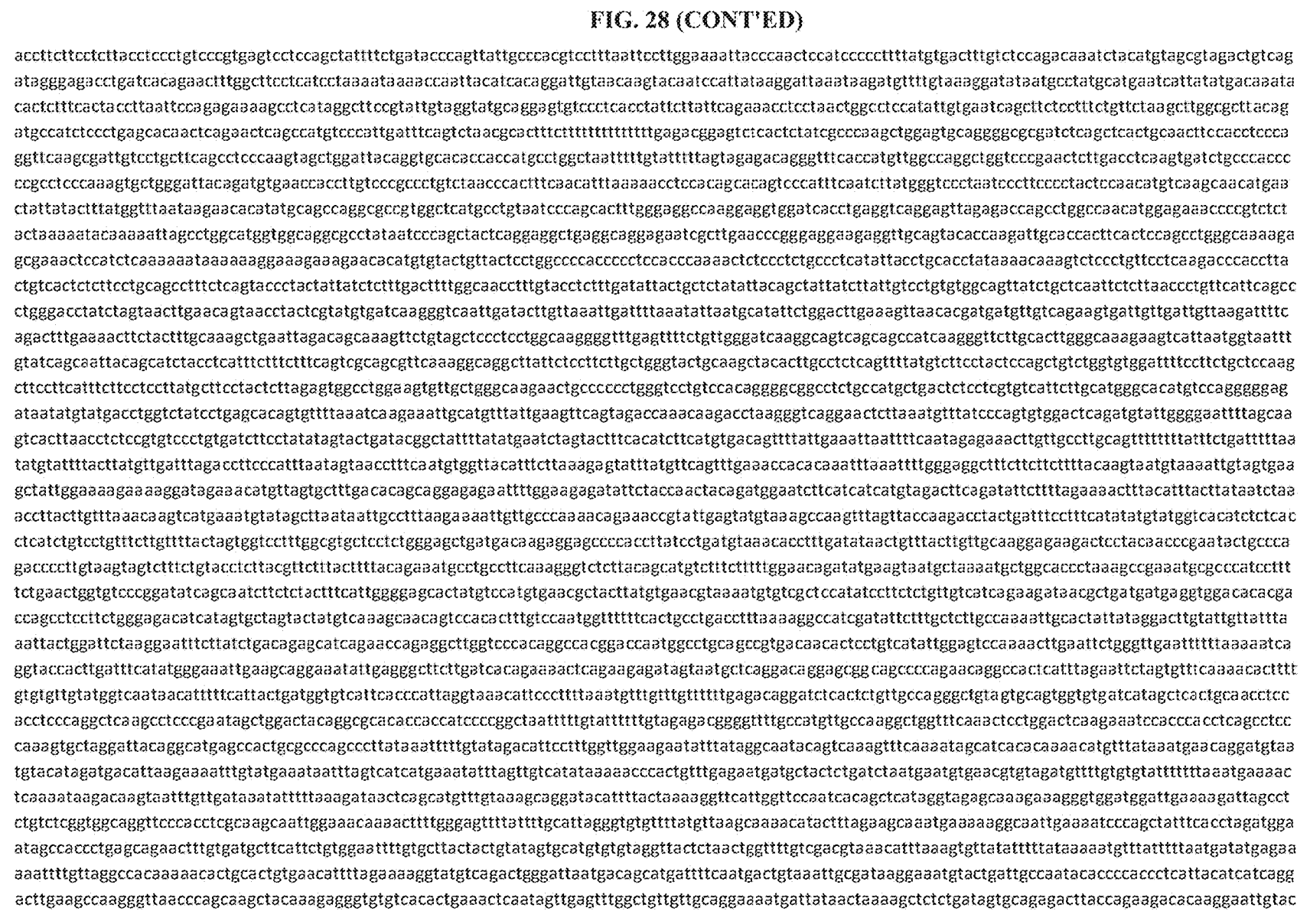
Figure 28:
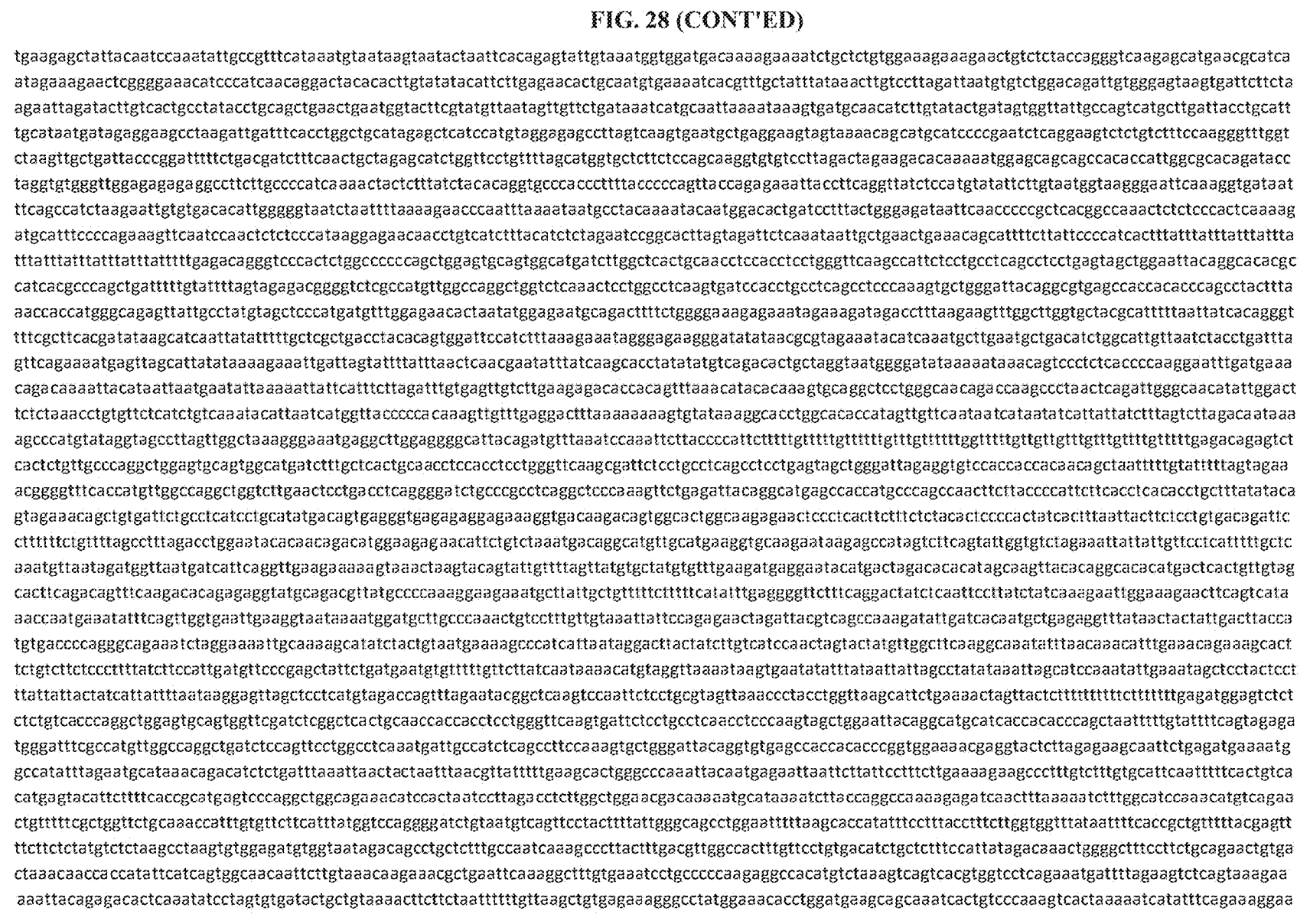
Figure 28:
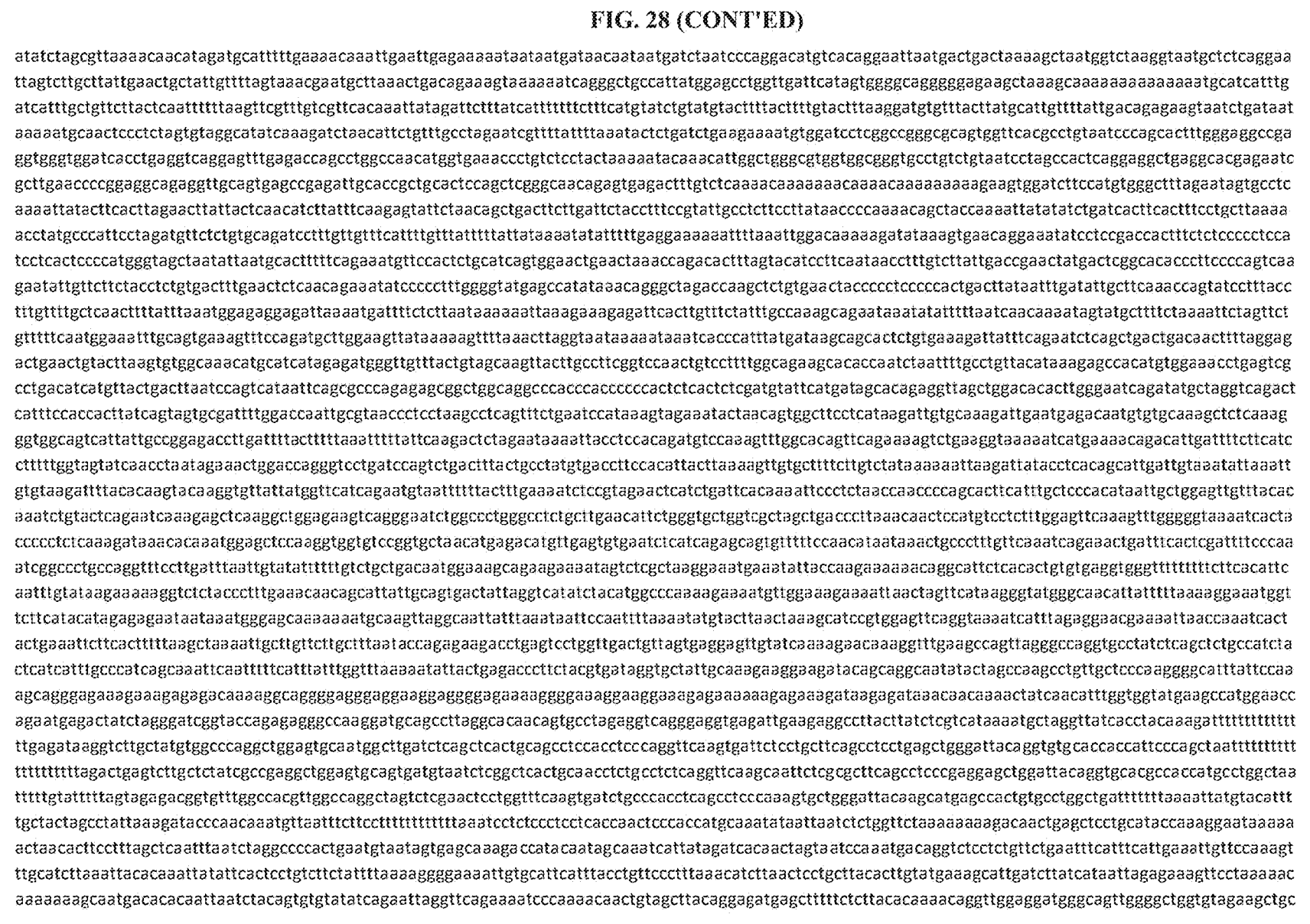
Figure 28:
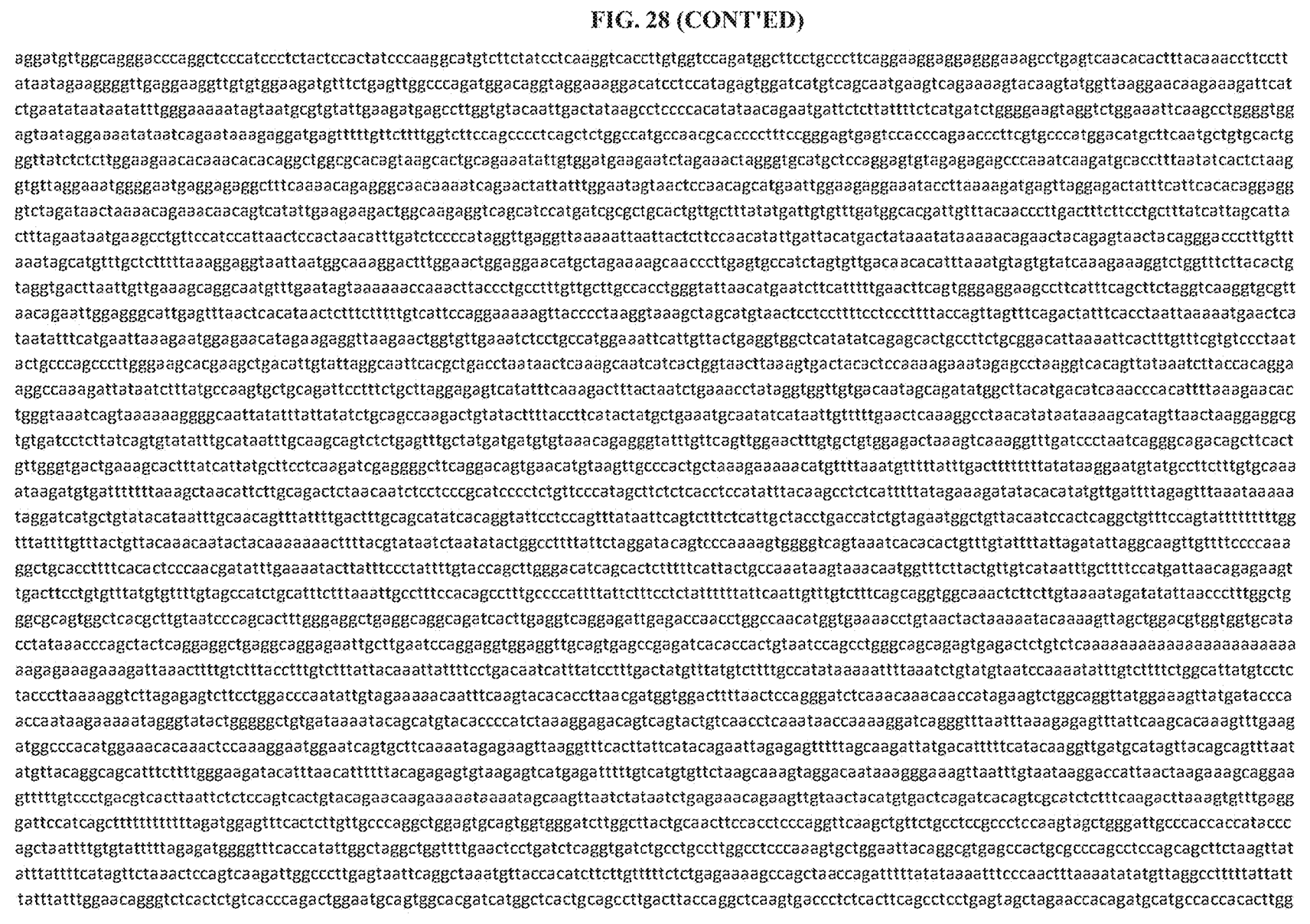
Figure 28:
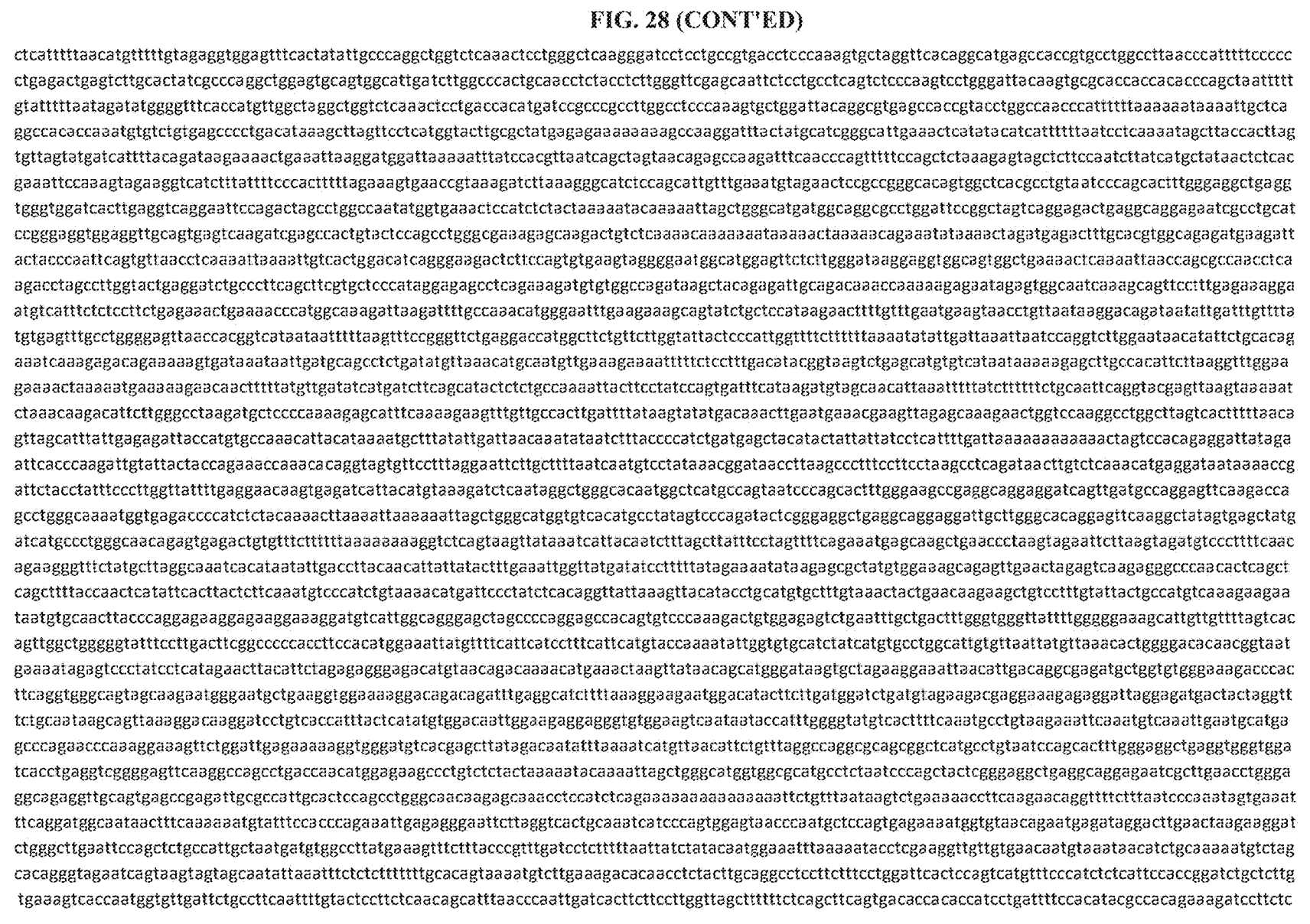
Figure 28:
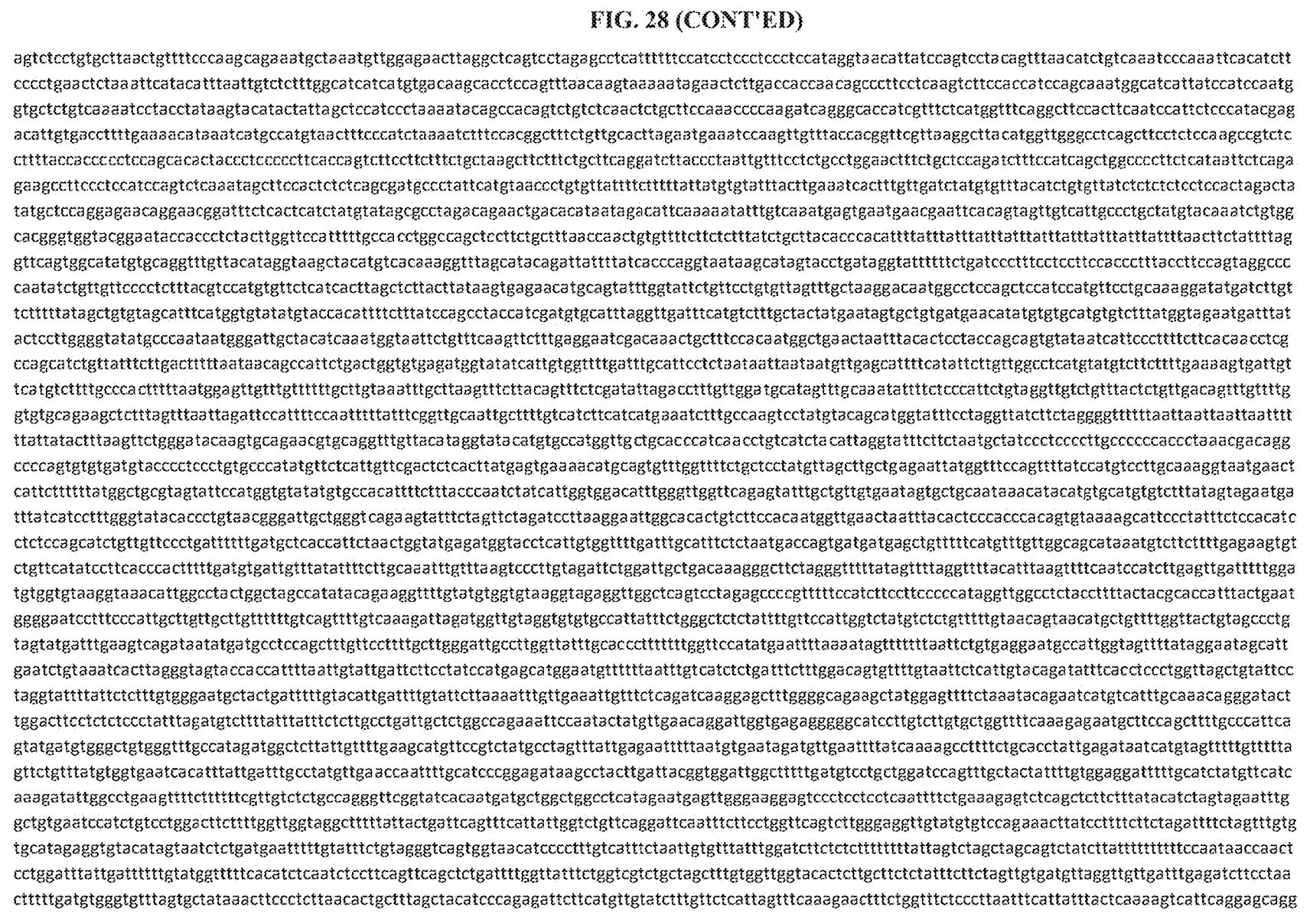
Figure 28:
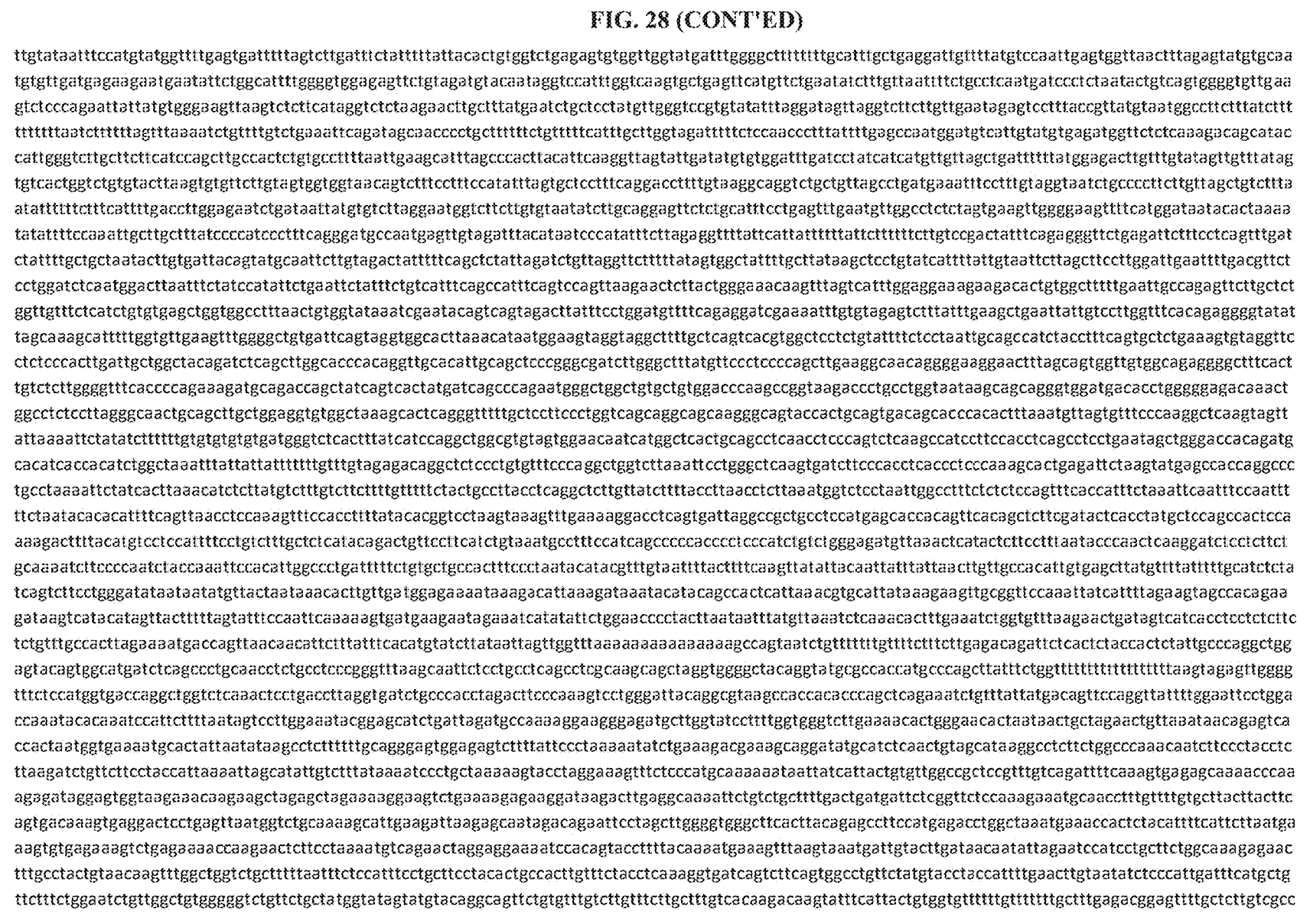
Figure 28:
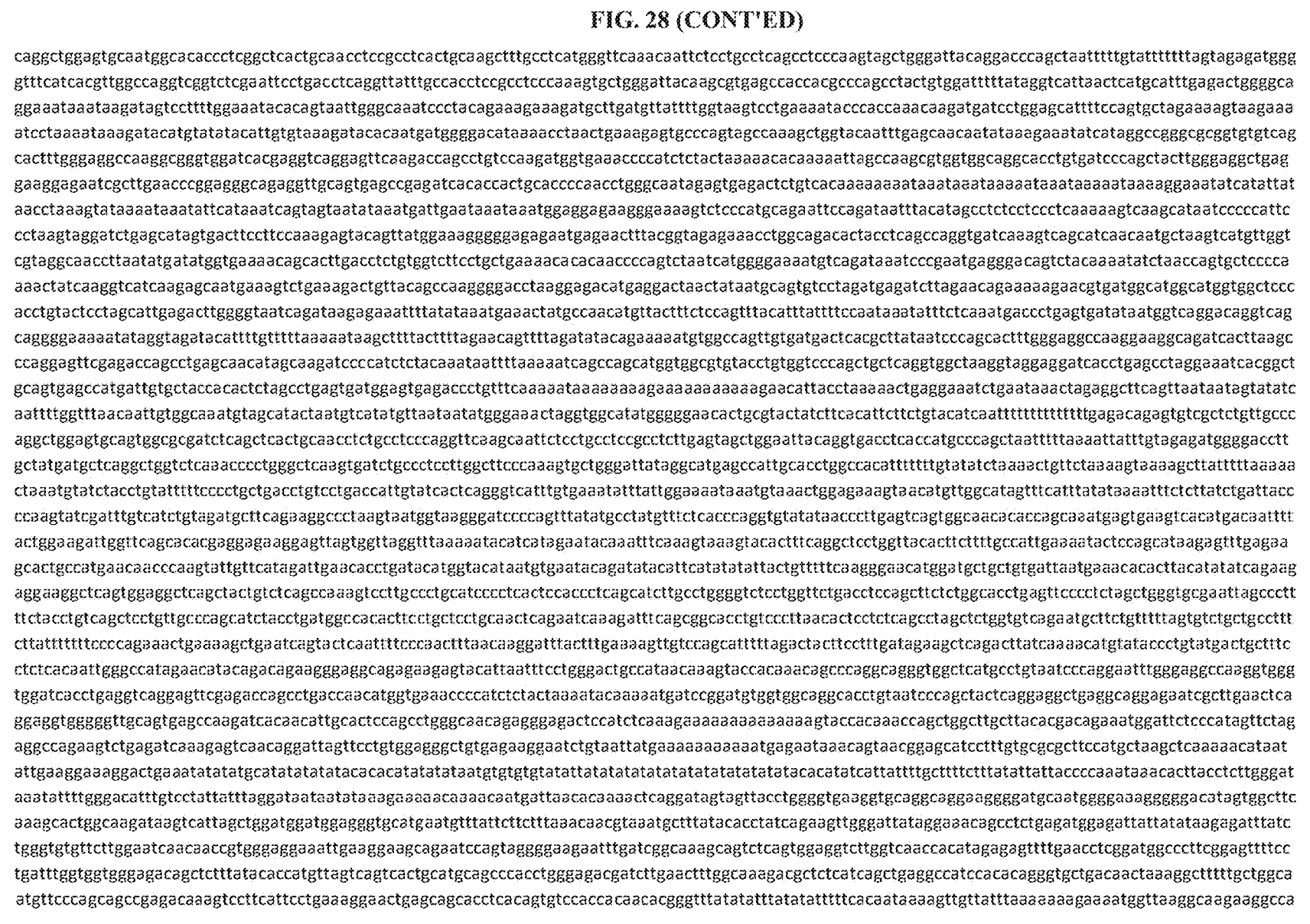
Figure 28:
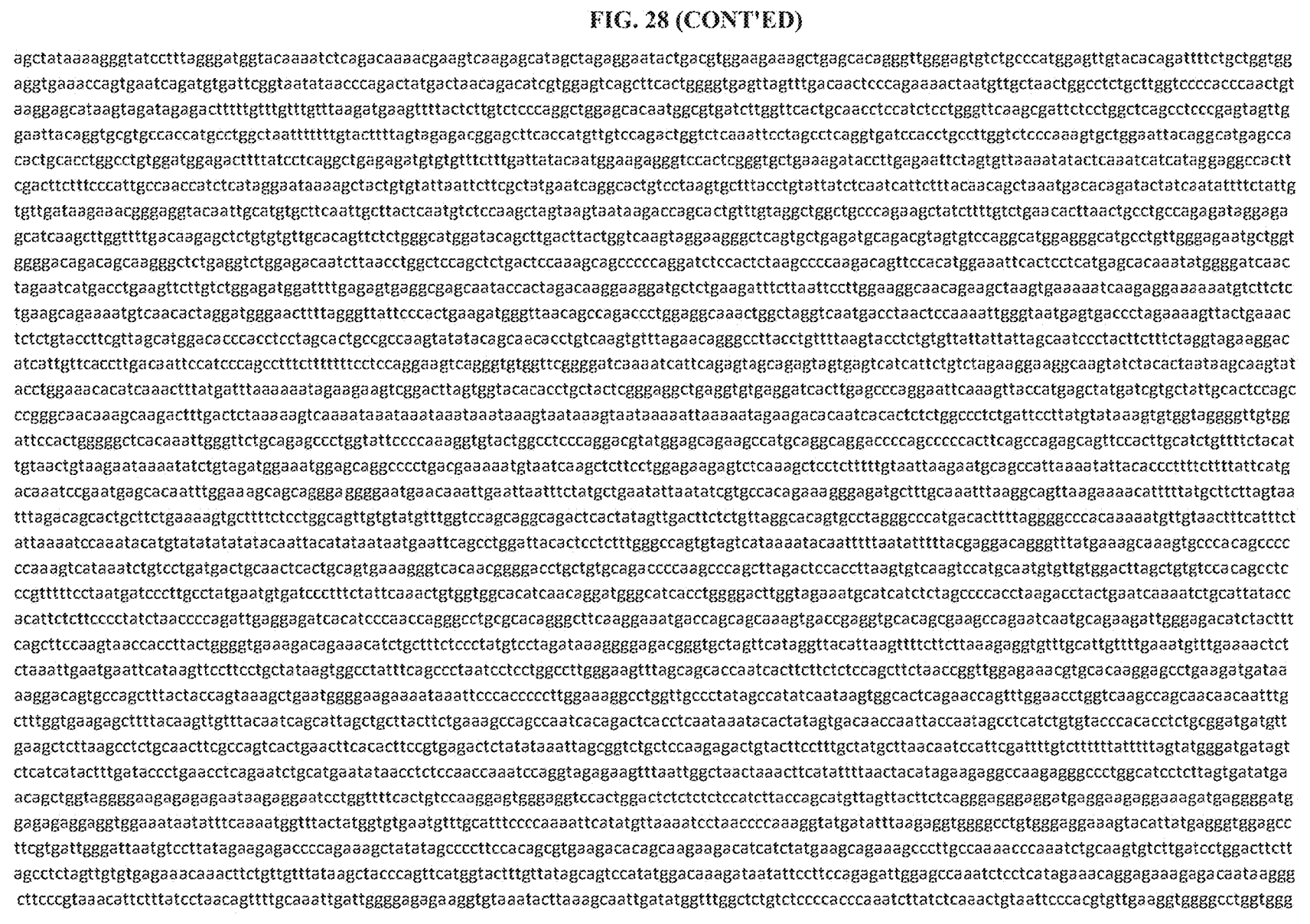
Figure 28:
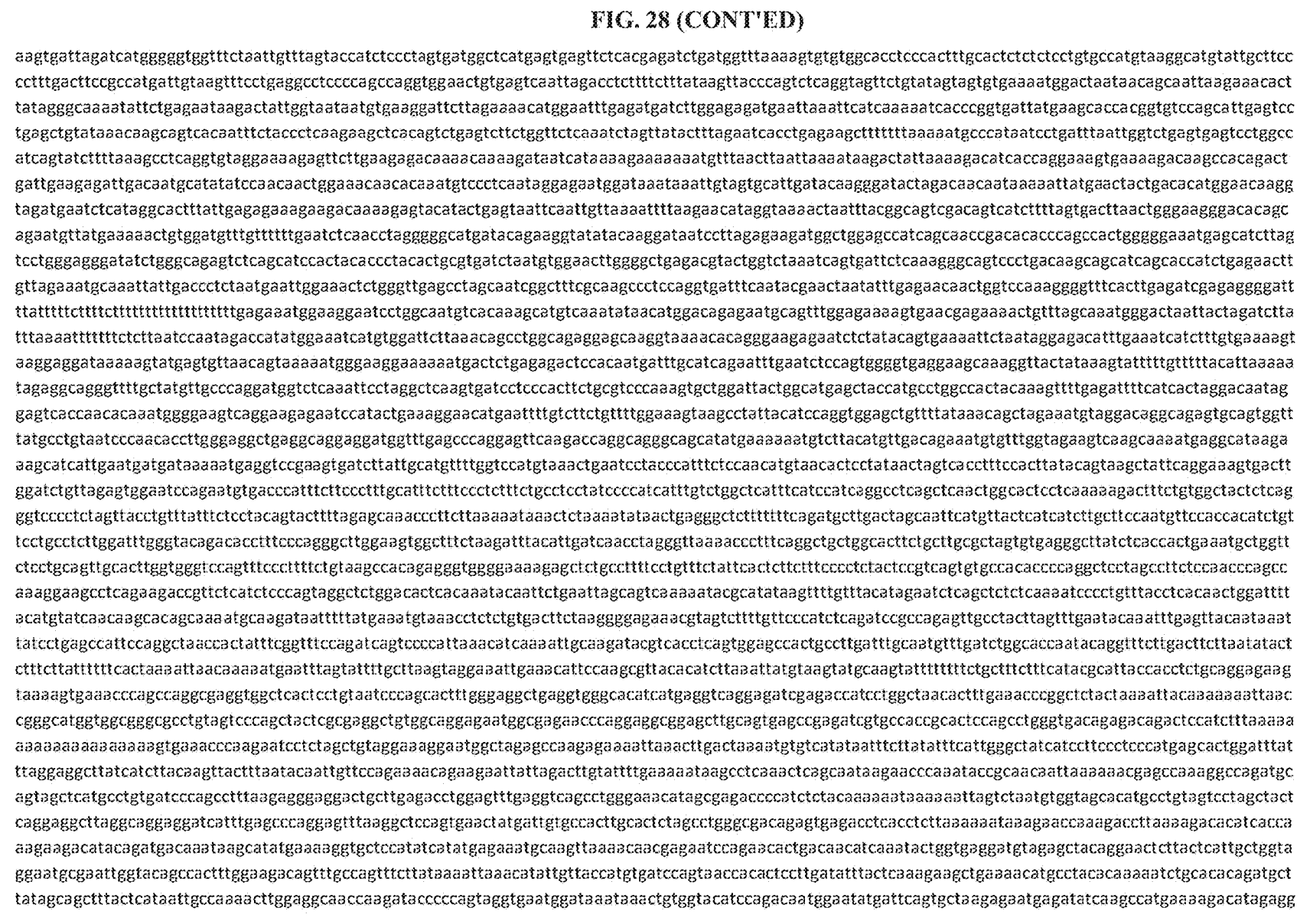
Figure 28:
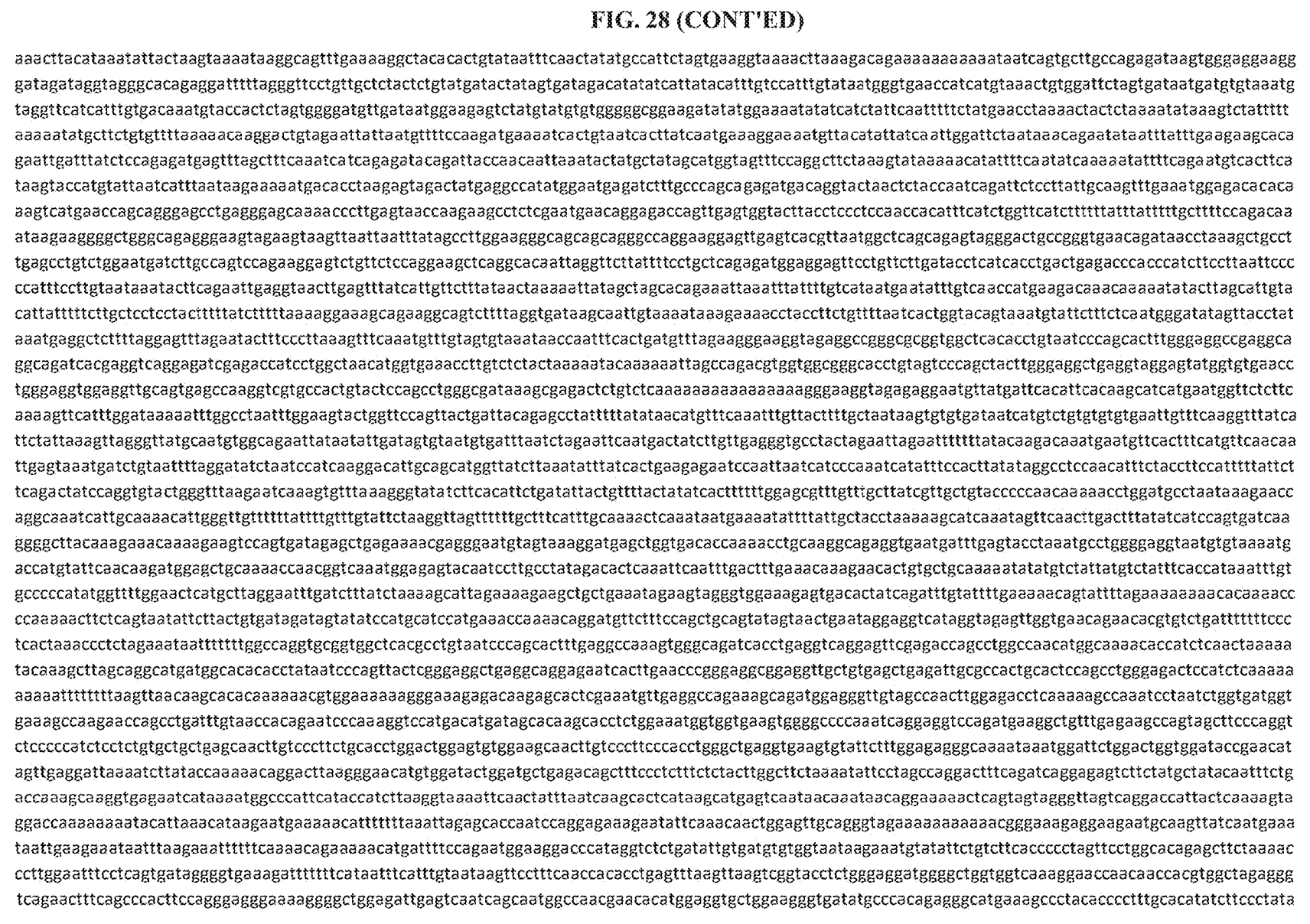
Figure 28:
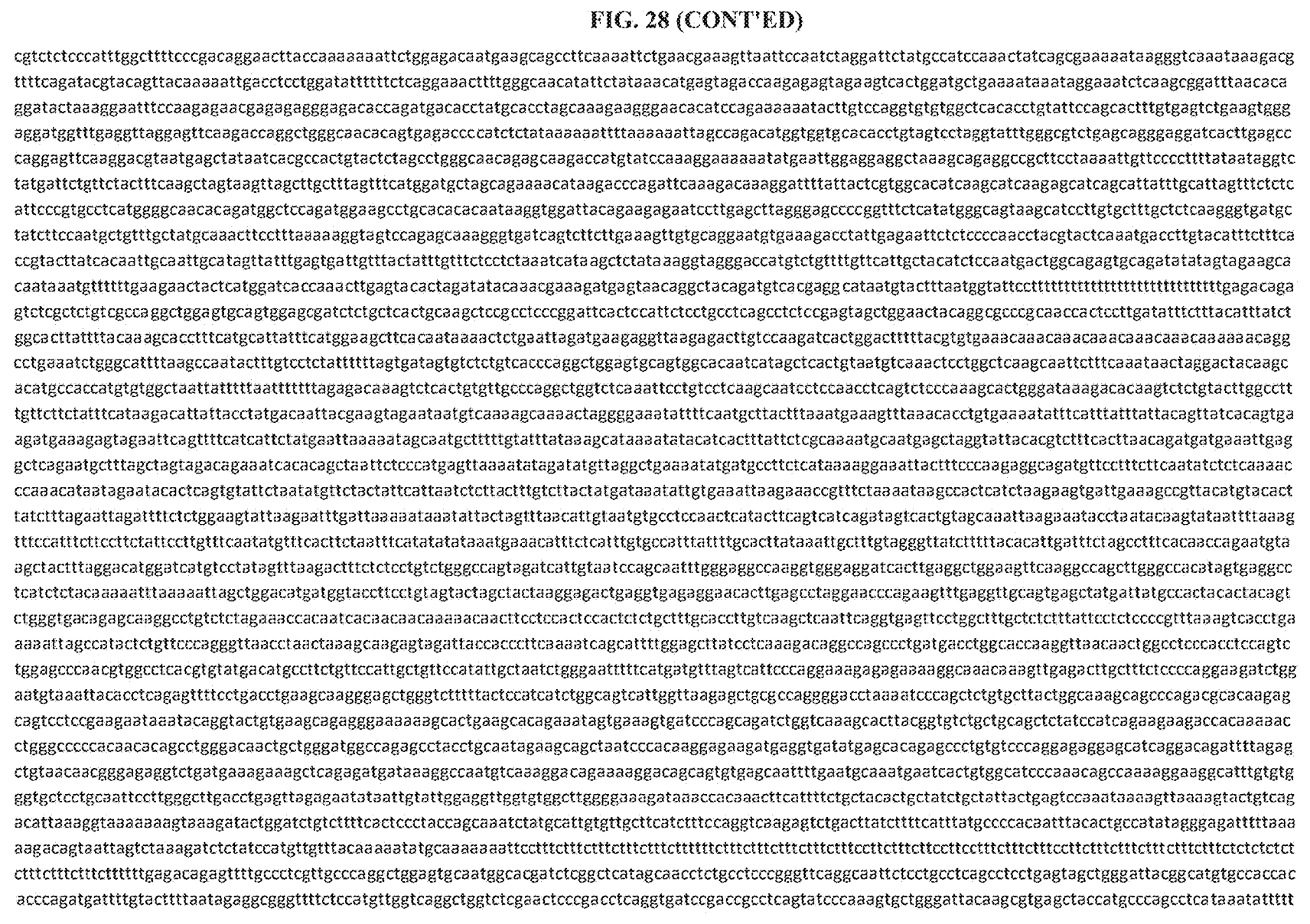
Figure 28:
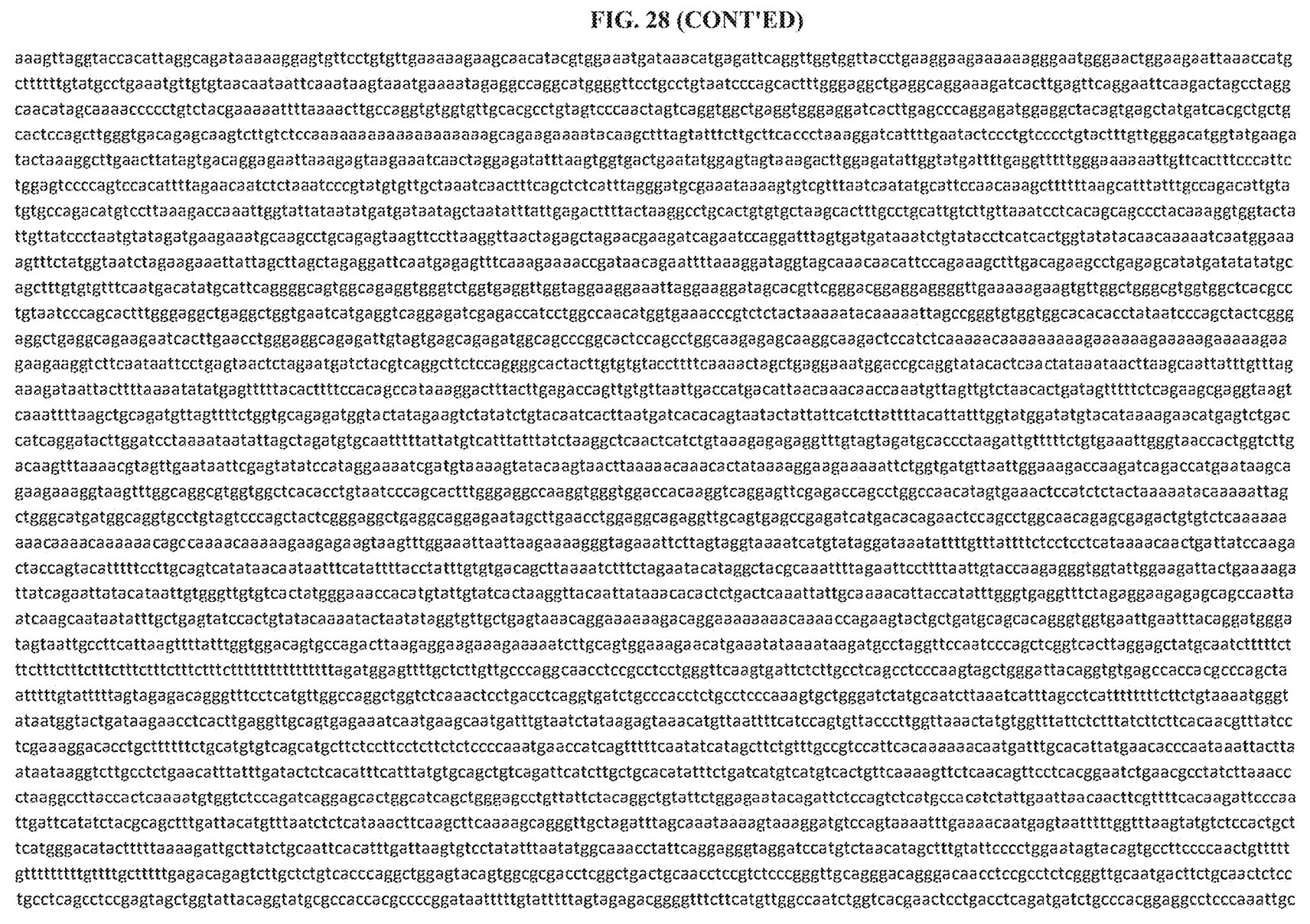
Figure 28:
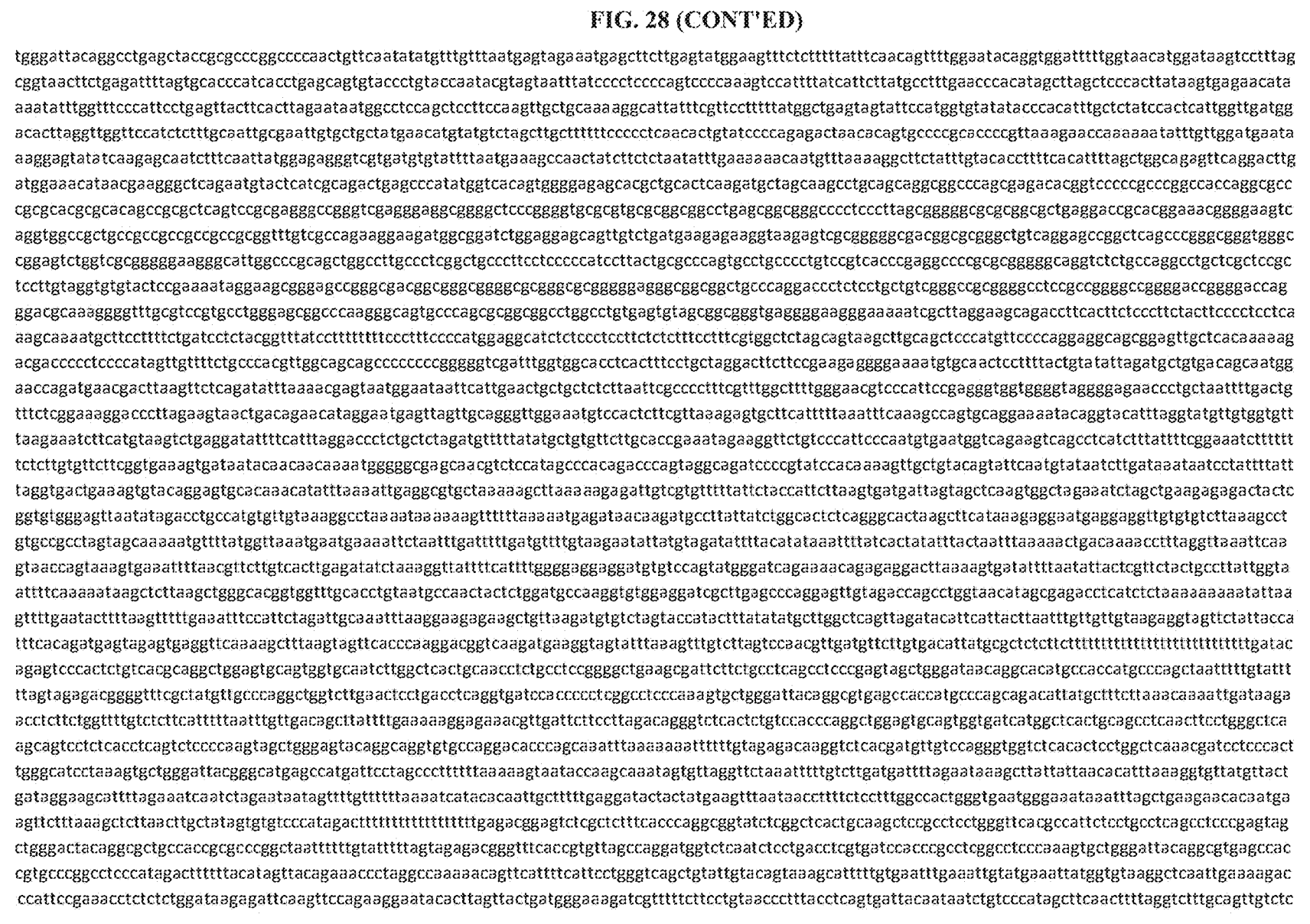
Figure 28:
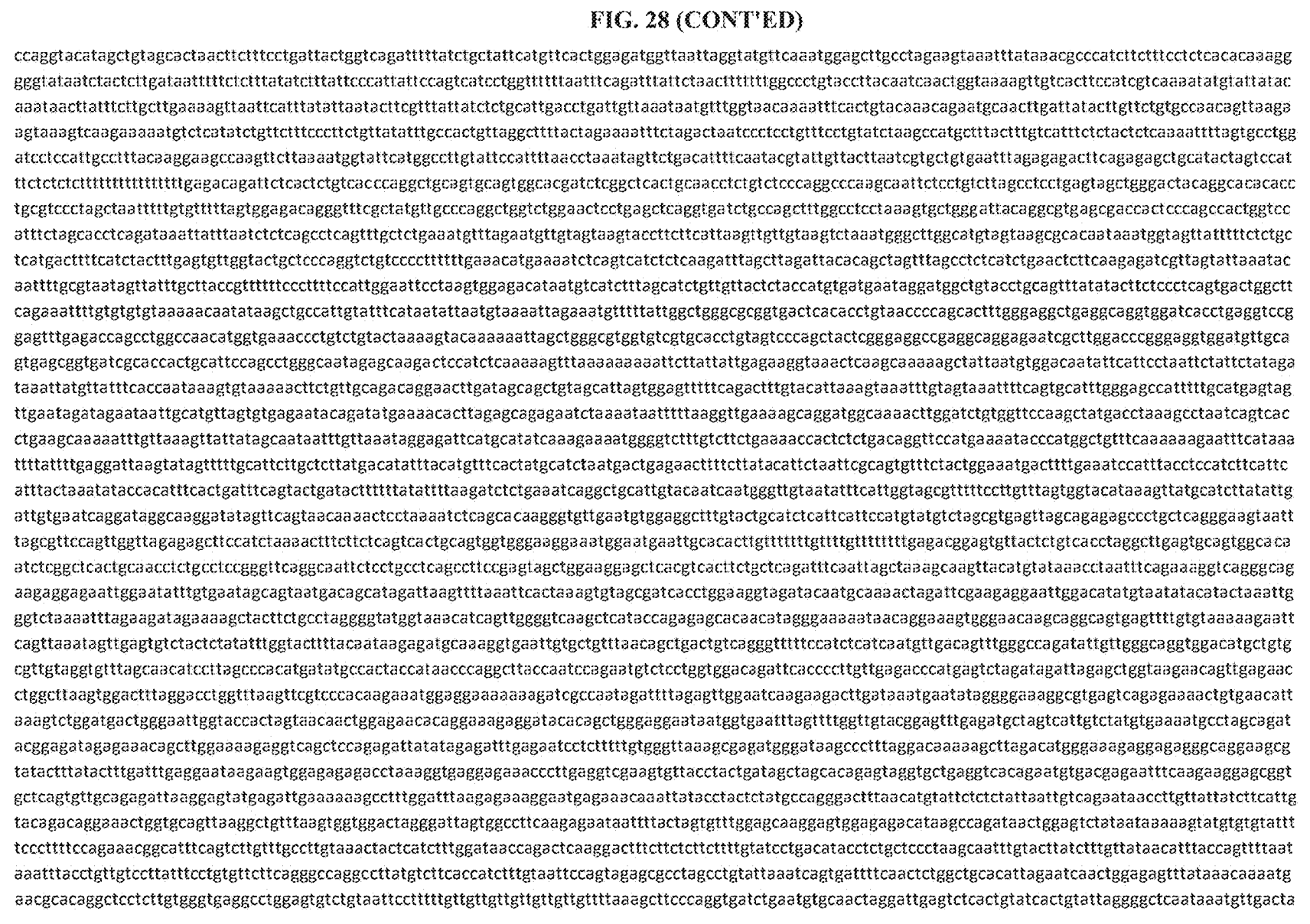
Figure 28:
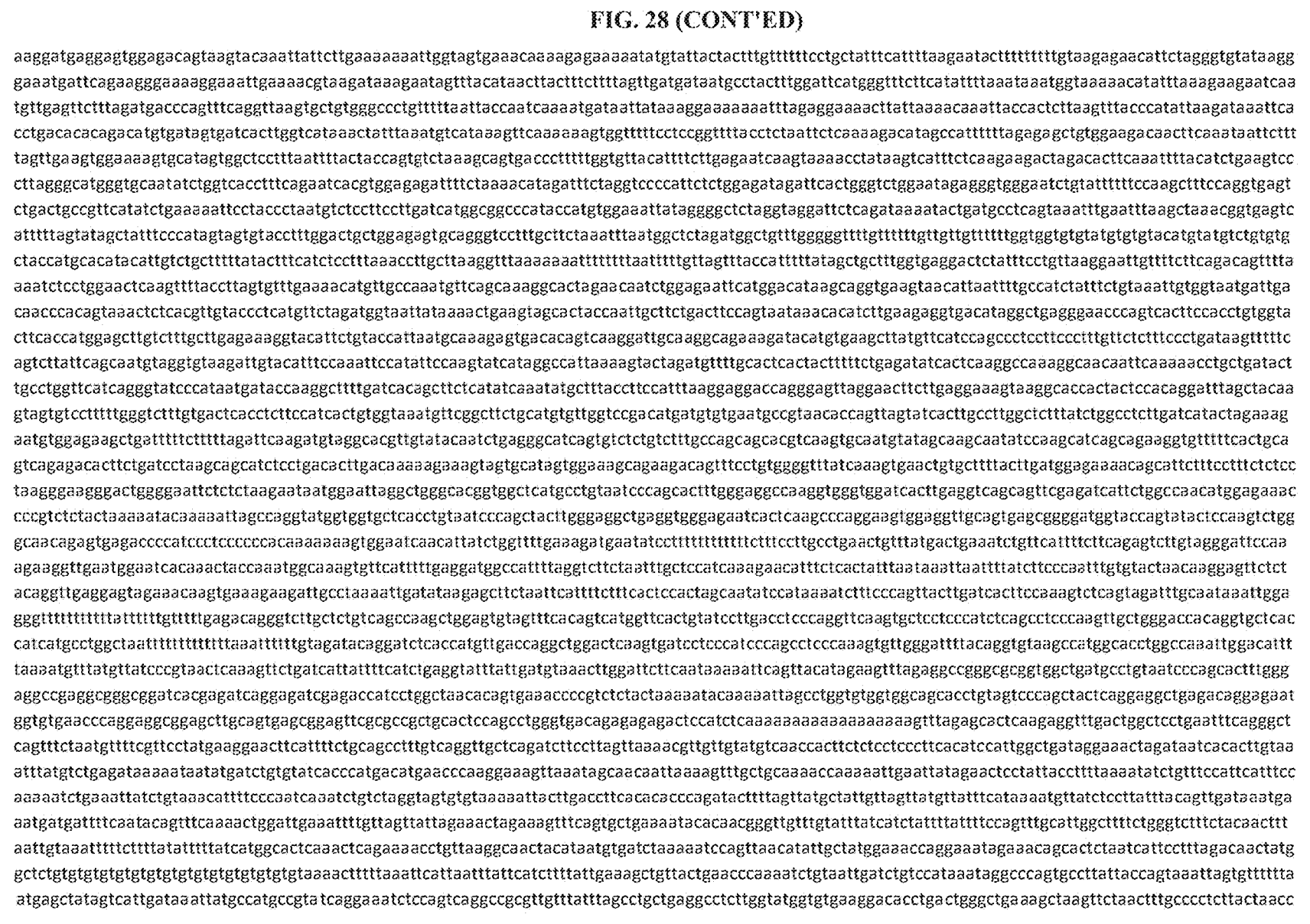
Figure 28:
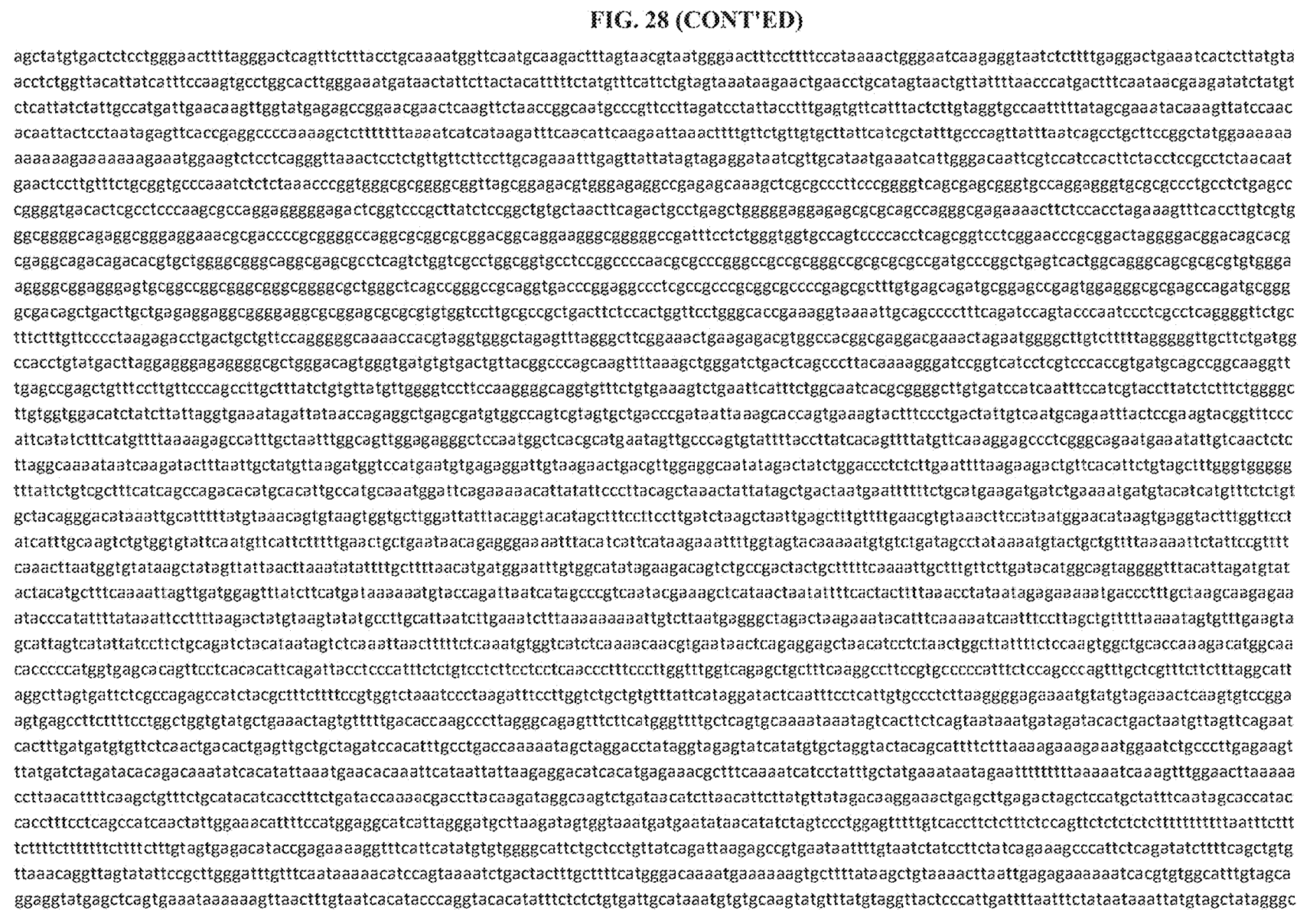
Figure 28:
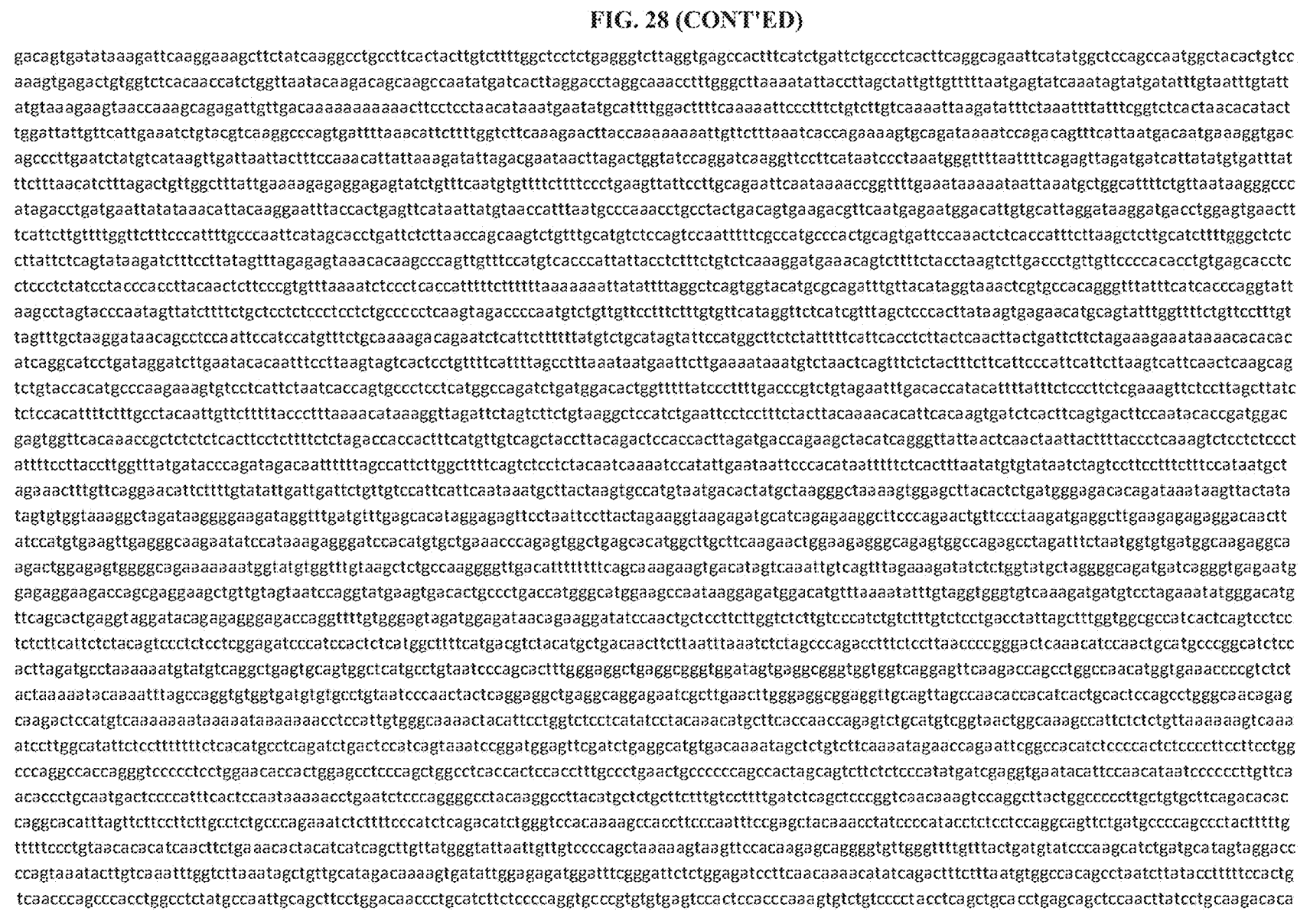
Figure 28:
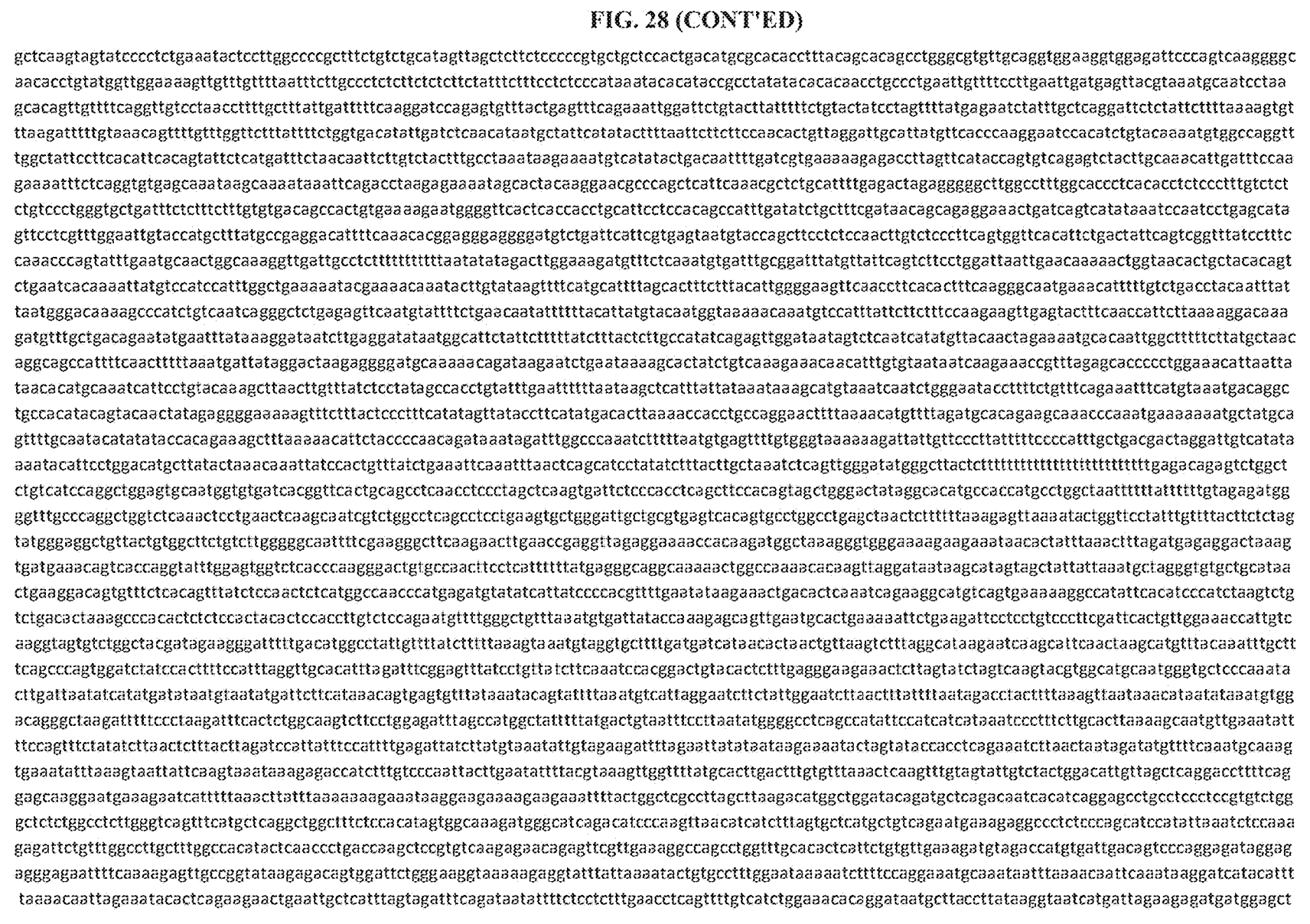
Figure 28:
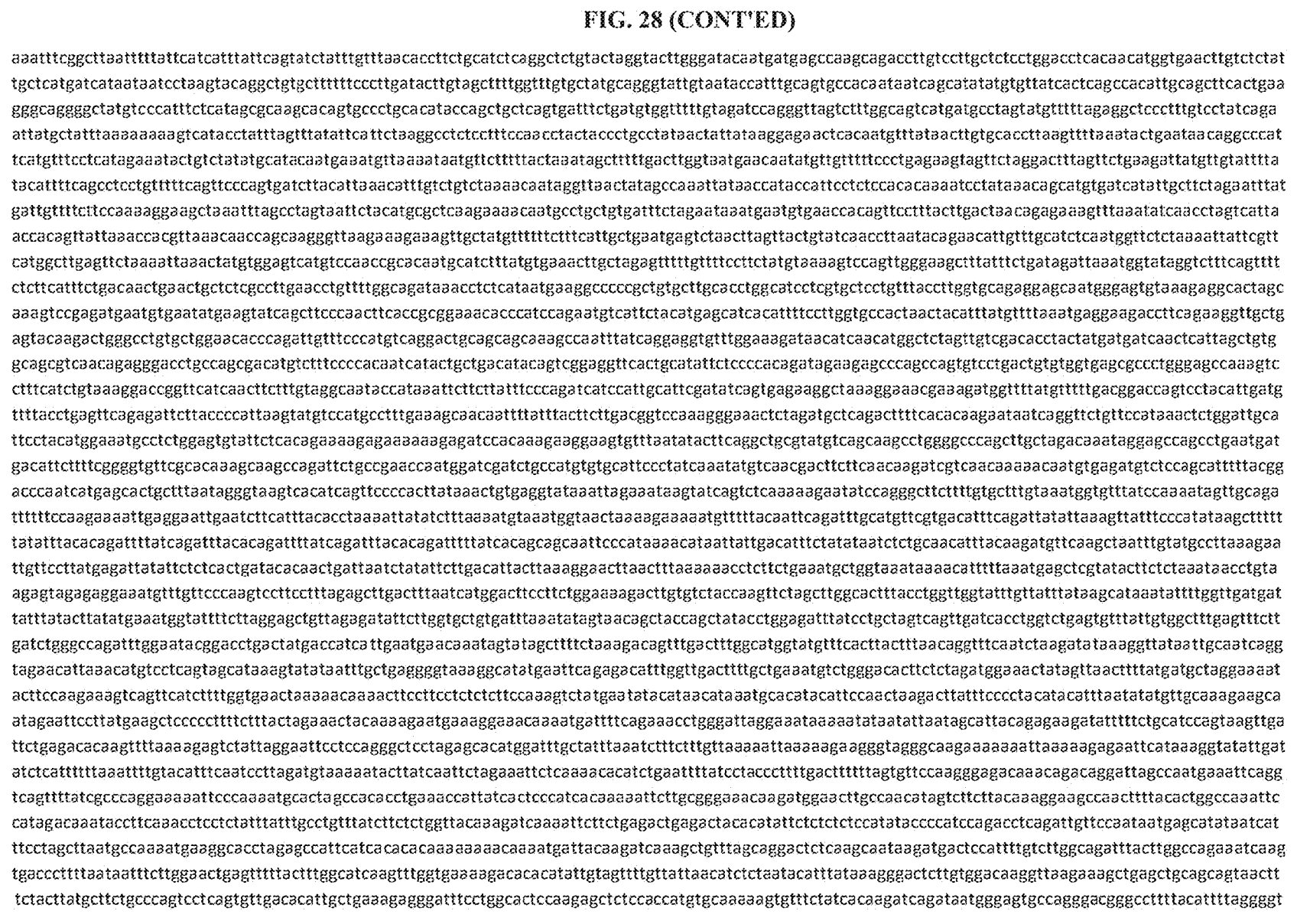
Figure 28:
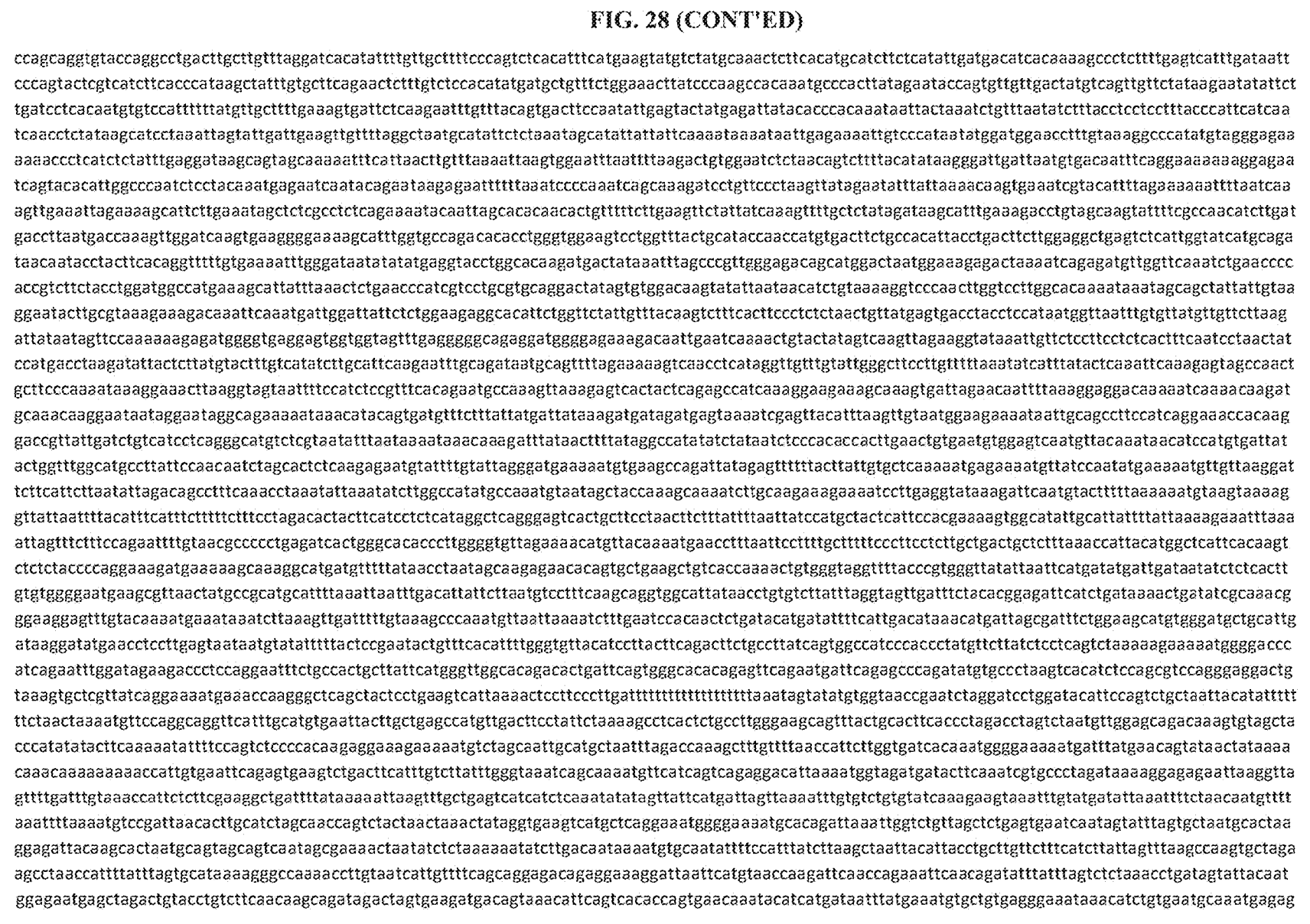
Figure 28:
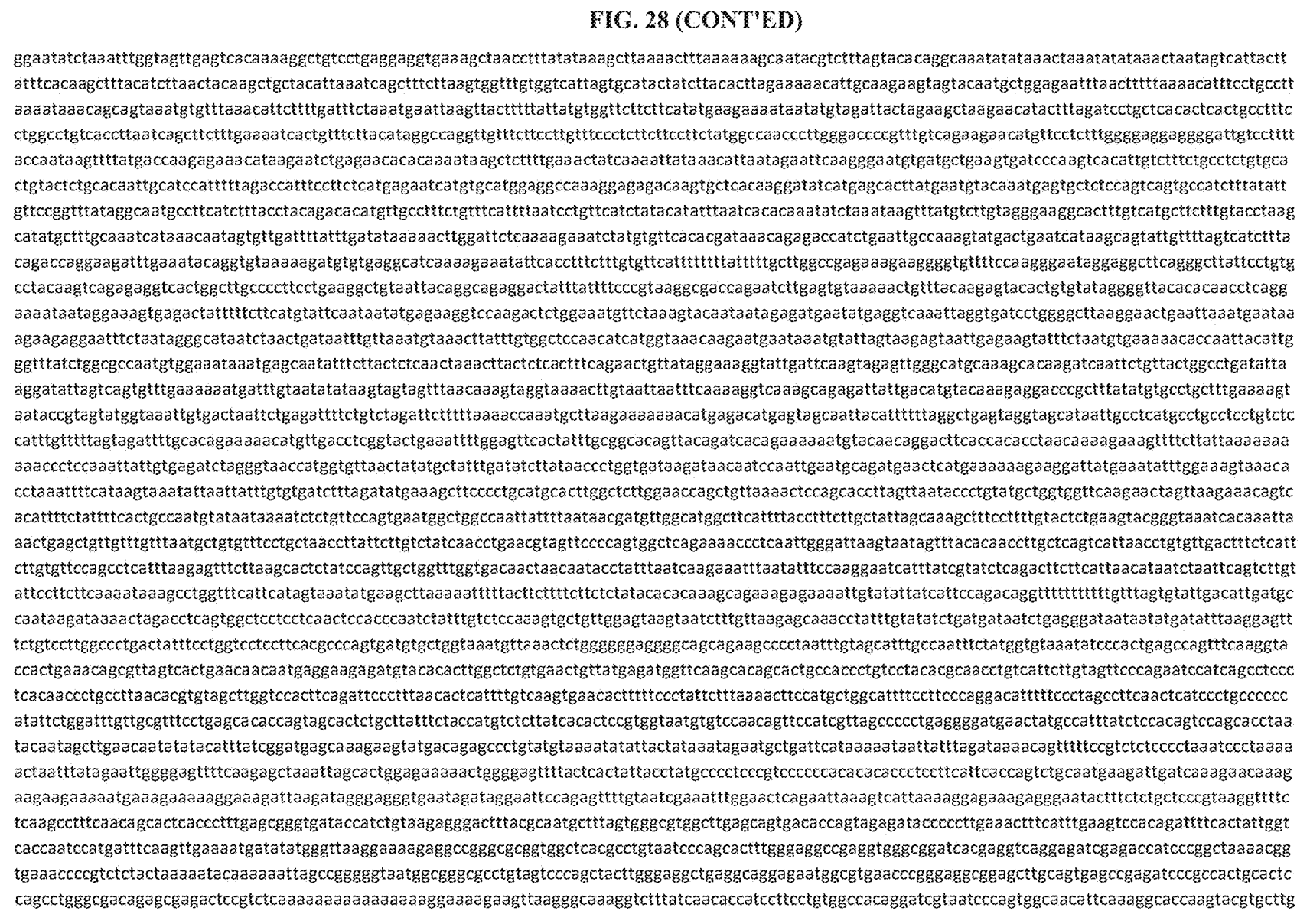
Figure 28:
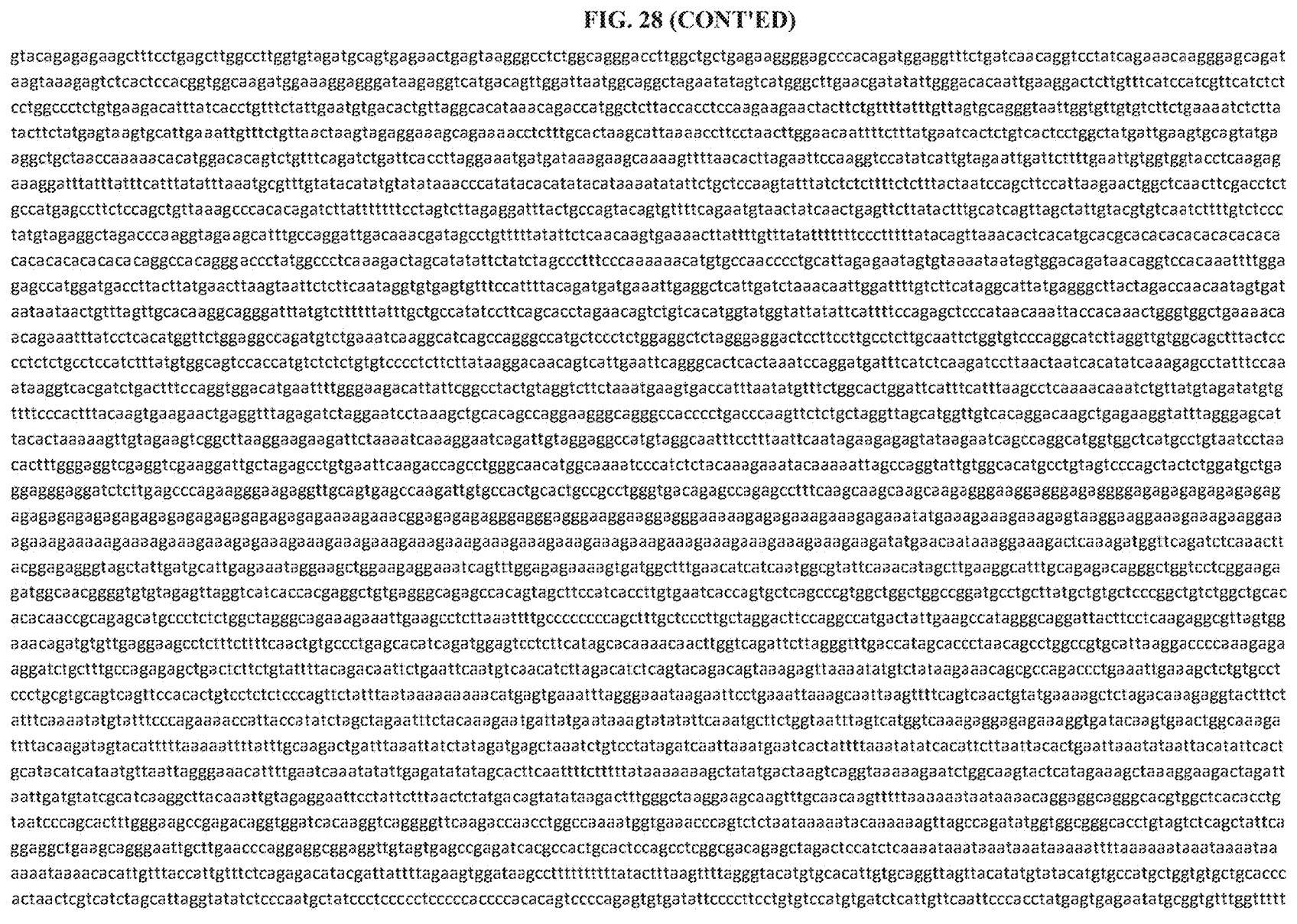
Figure 28:
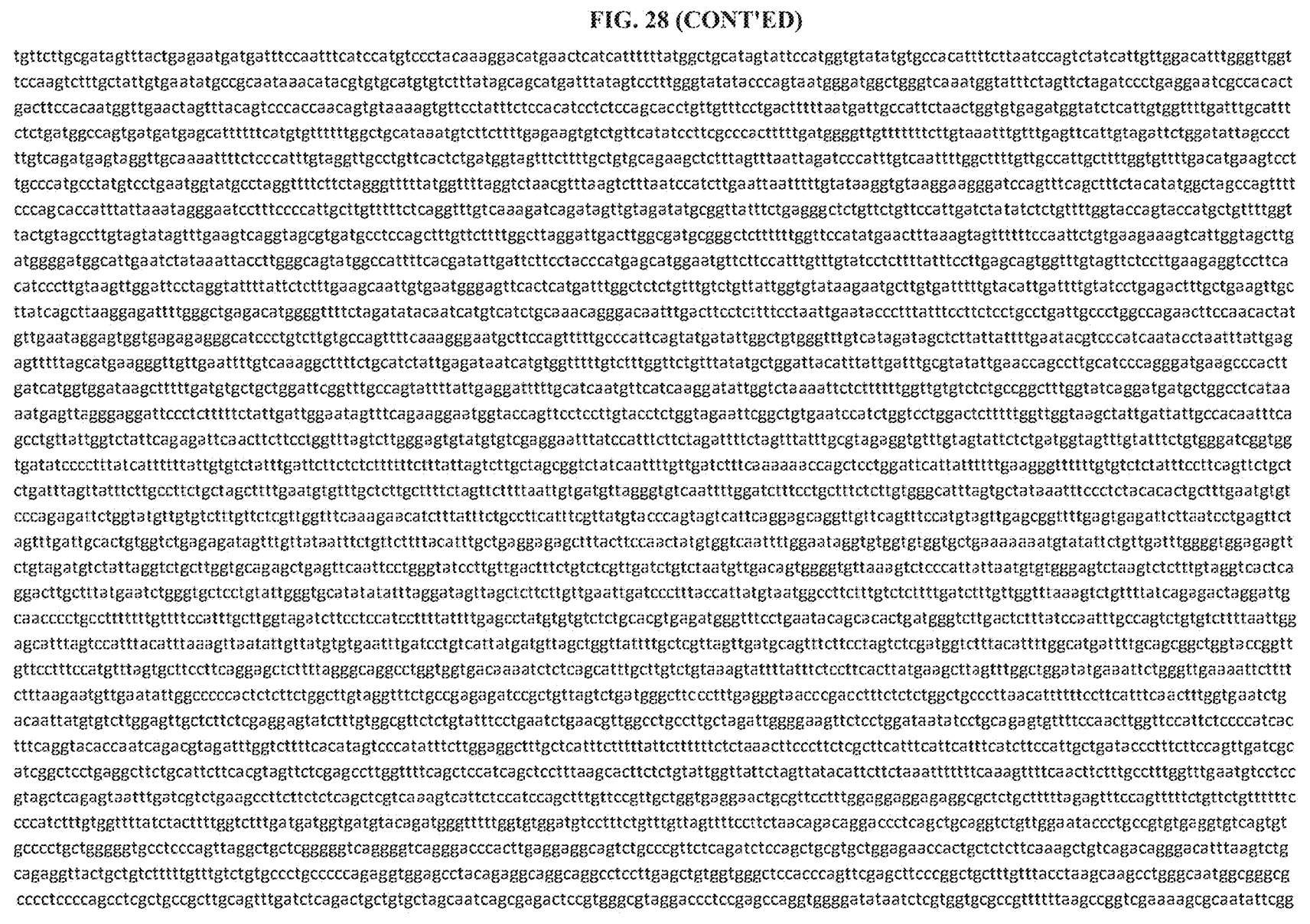

FIG. 28 depicts an example sequence (SEQ. ID. NO. 8) of an ecDNA MET/CAPZA1 fusion gene in accordance with one non-limiting example embodiment of the present invention.

Figure 29:
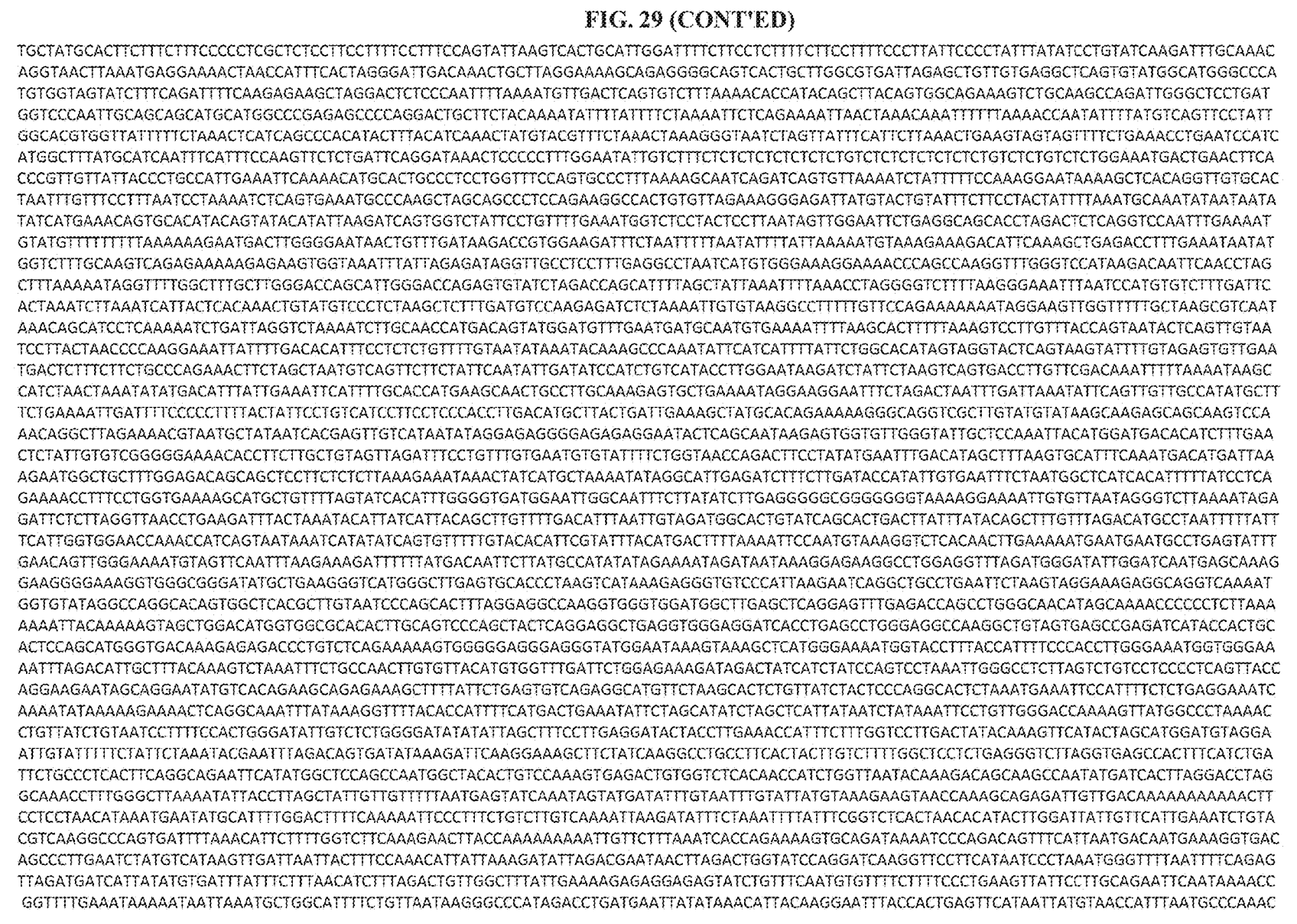
Figure 29:
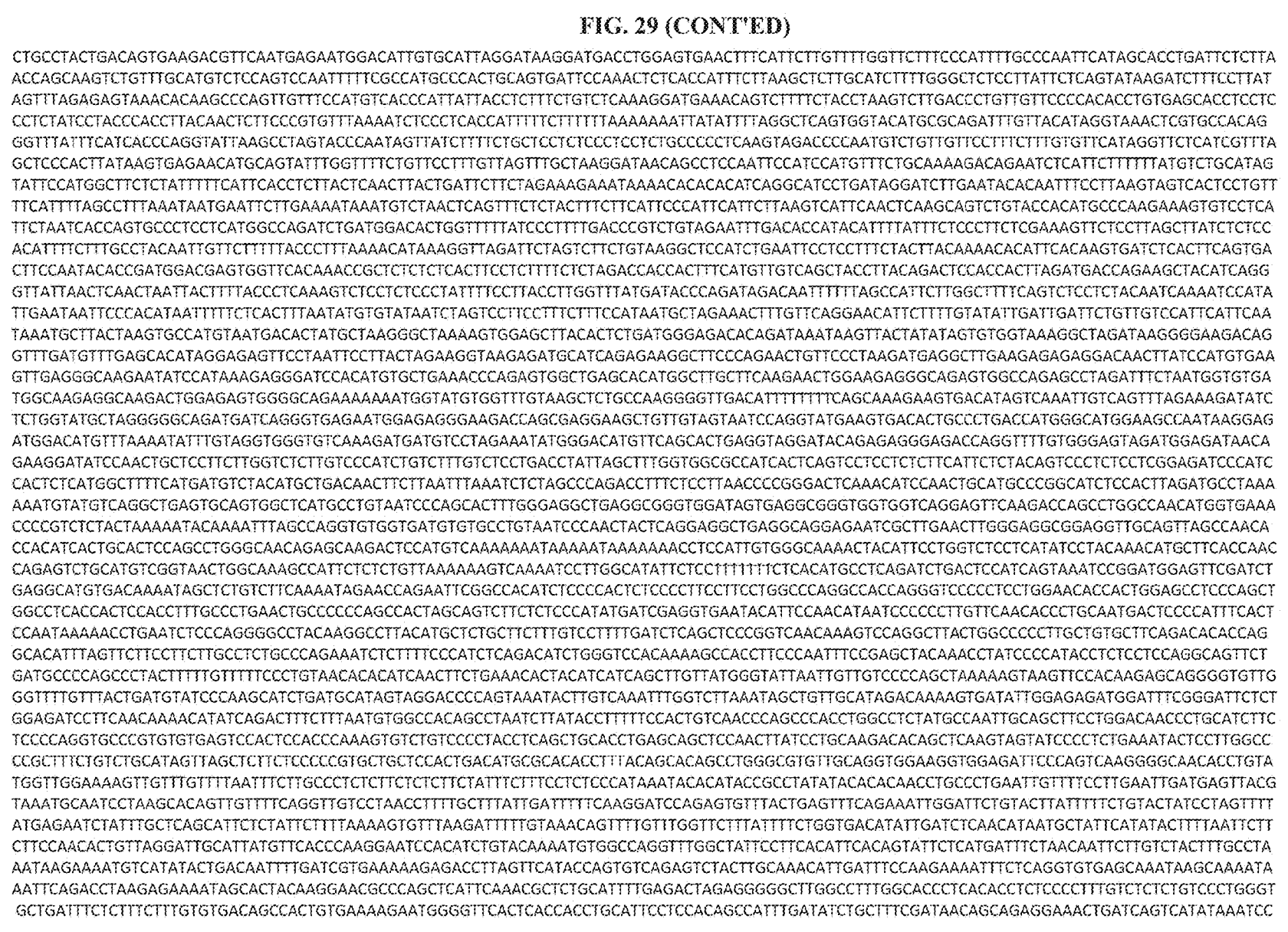
Figure 29:
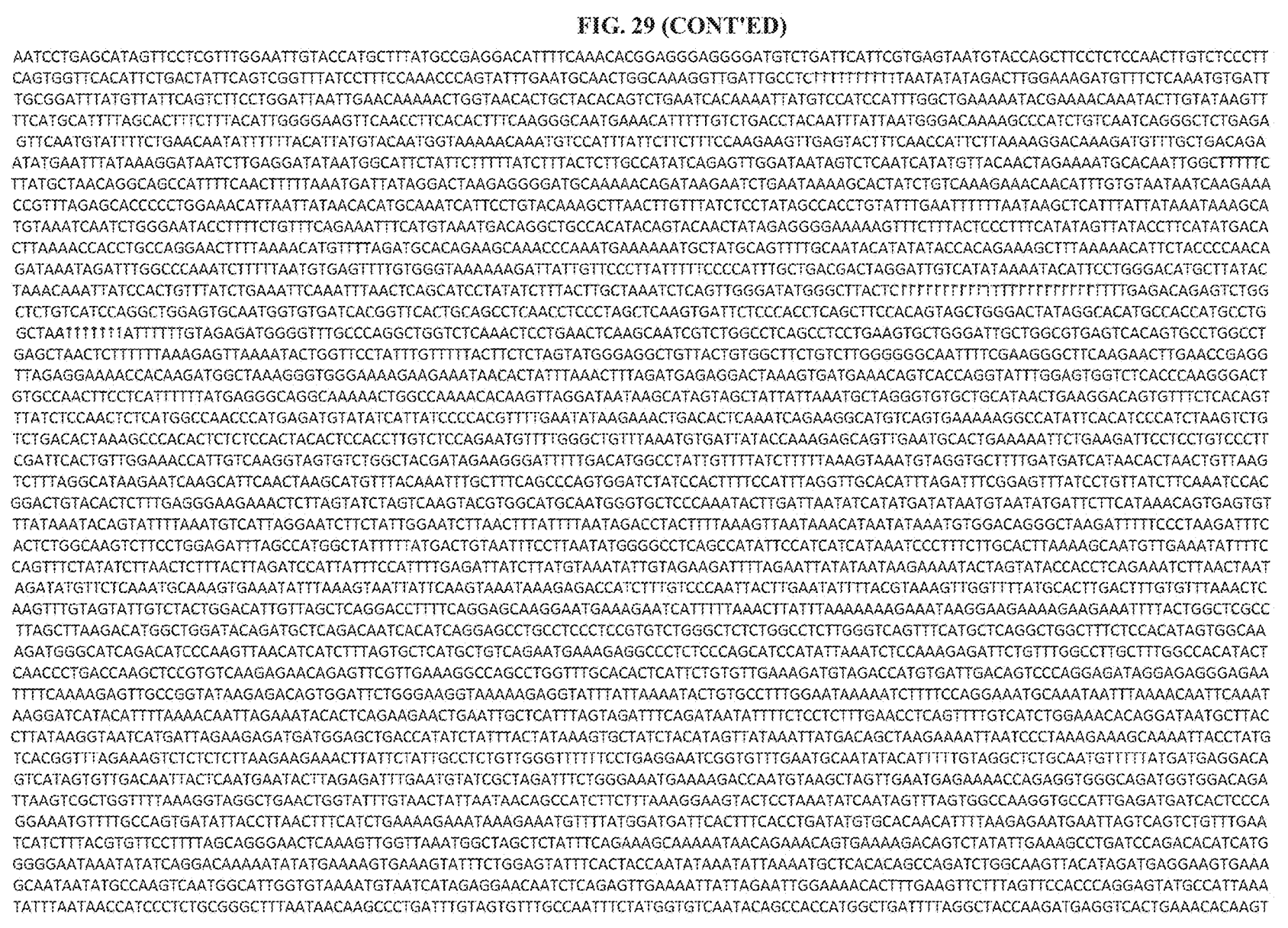
Figure 29:
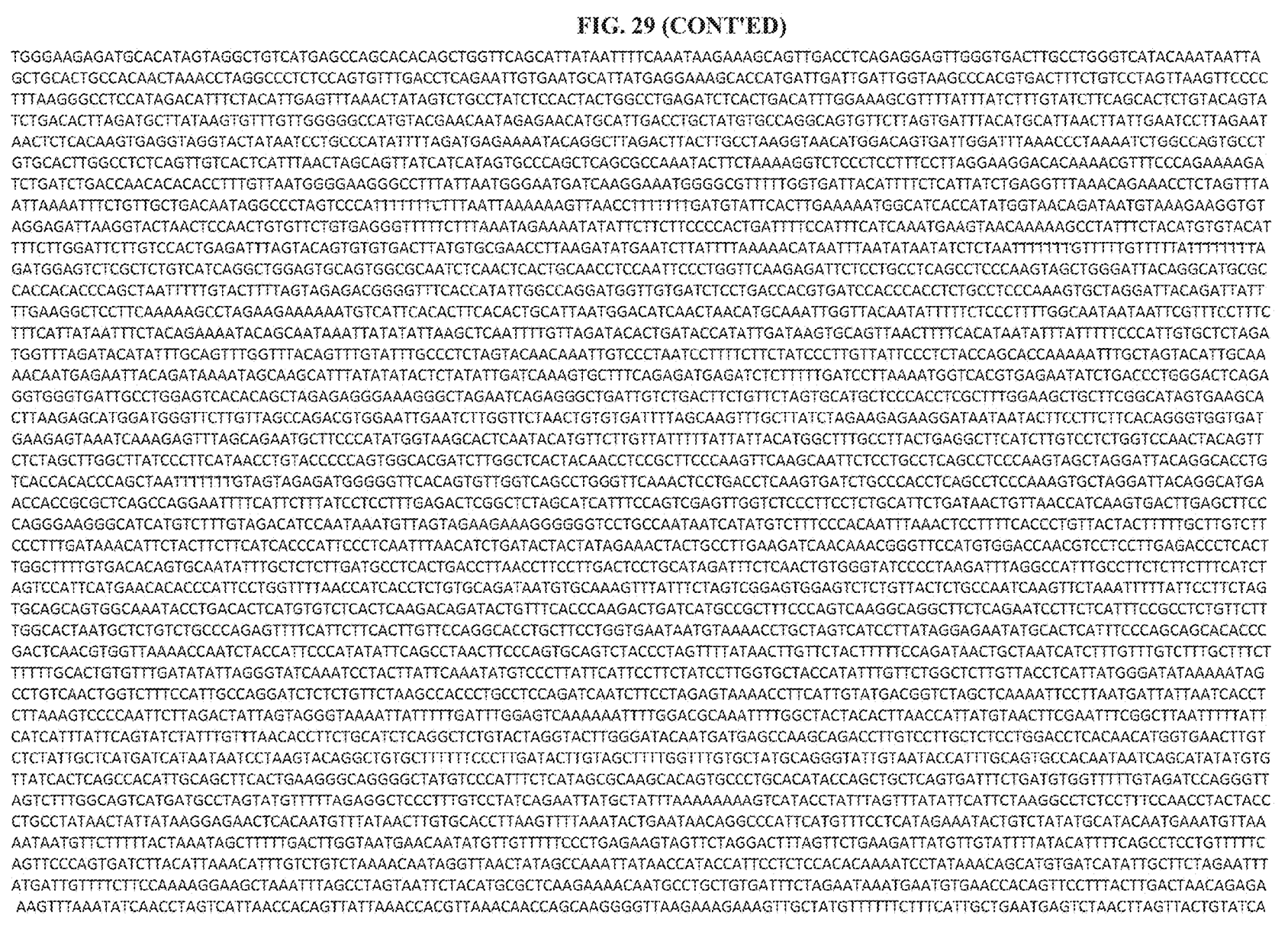
Figure 29:
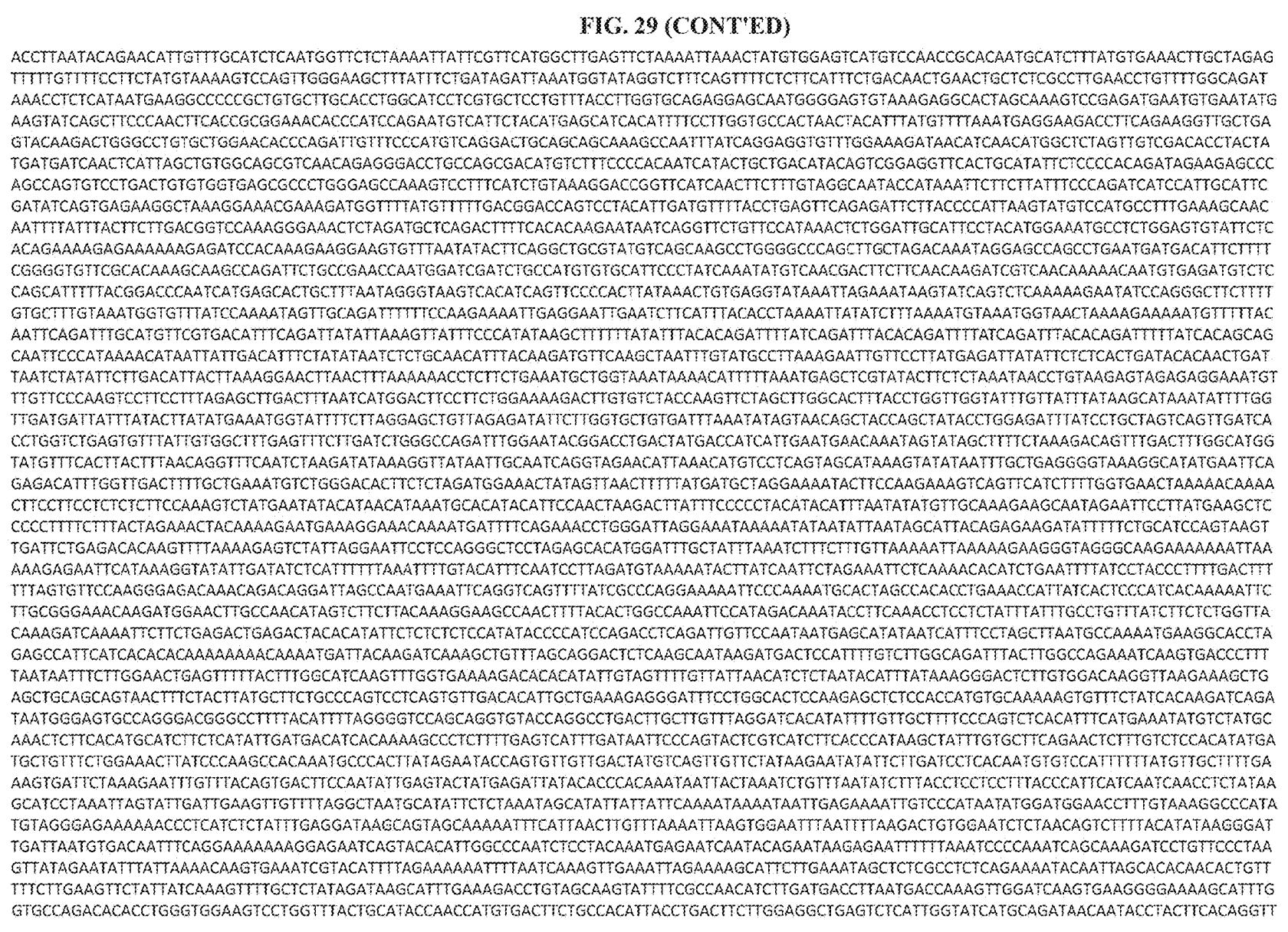
Figure 29:
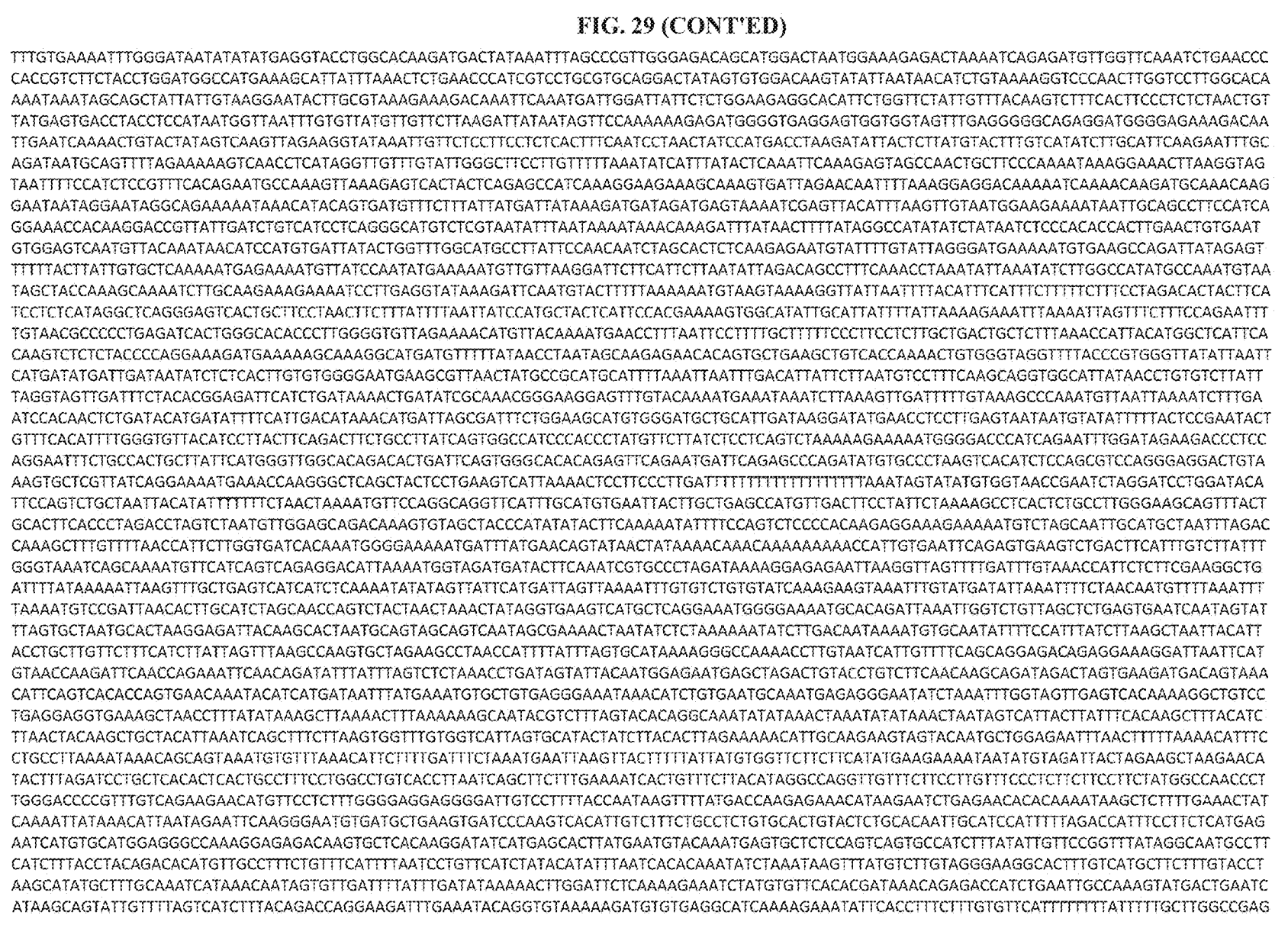
Figure 29:
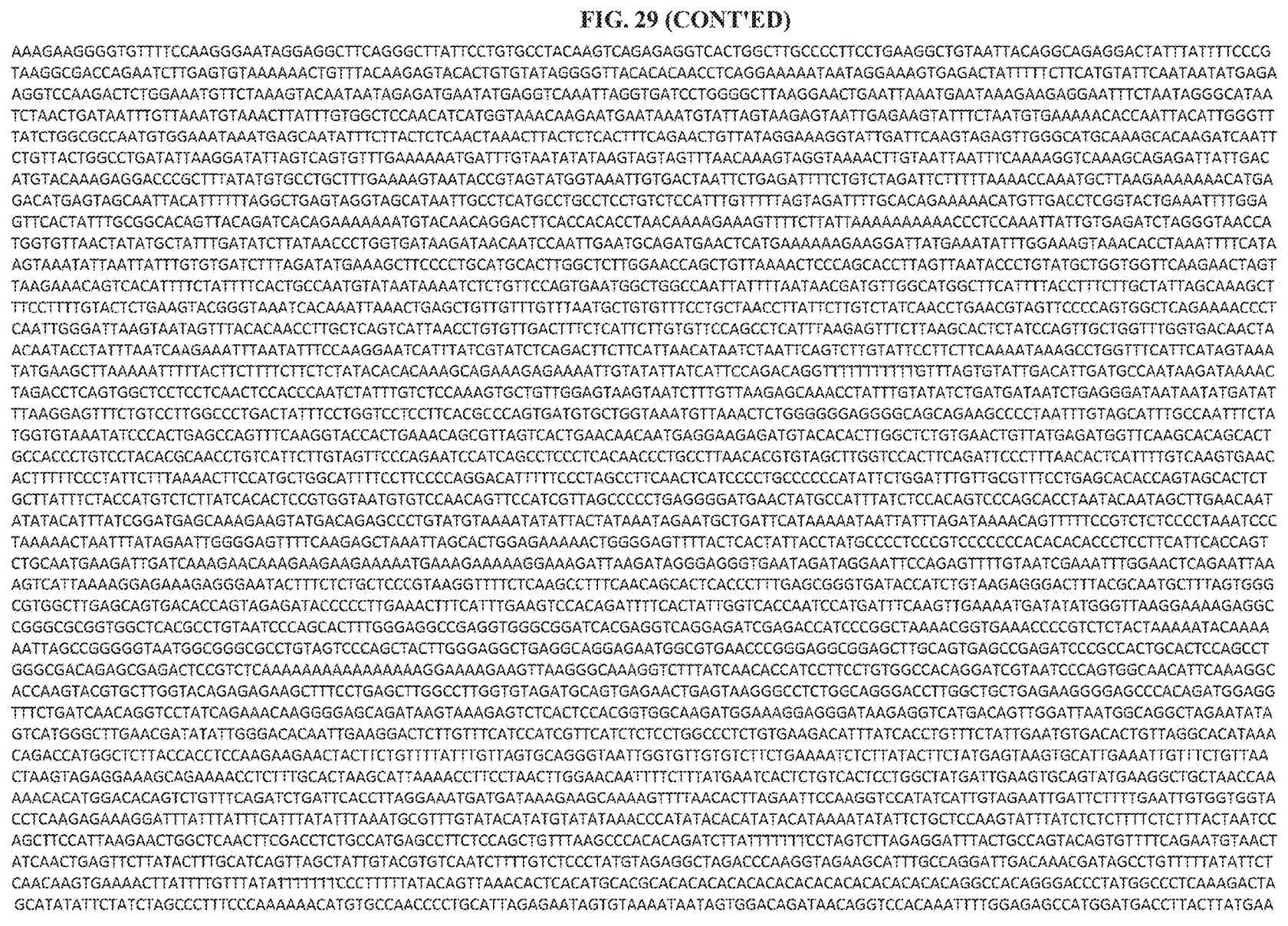
Figure 29:
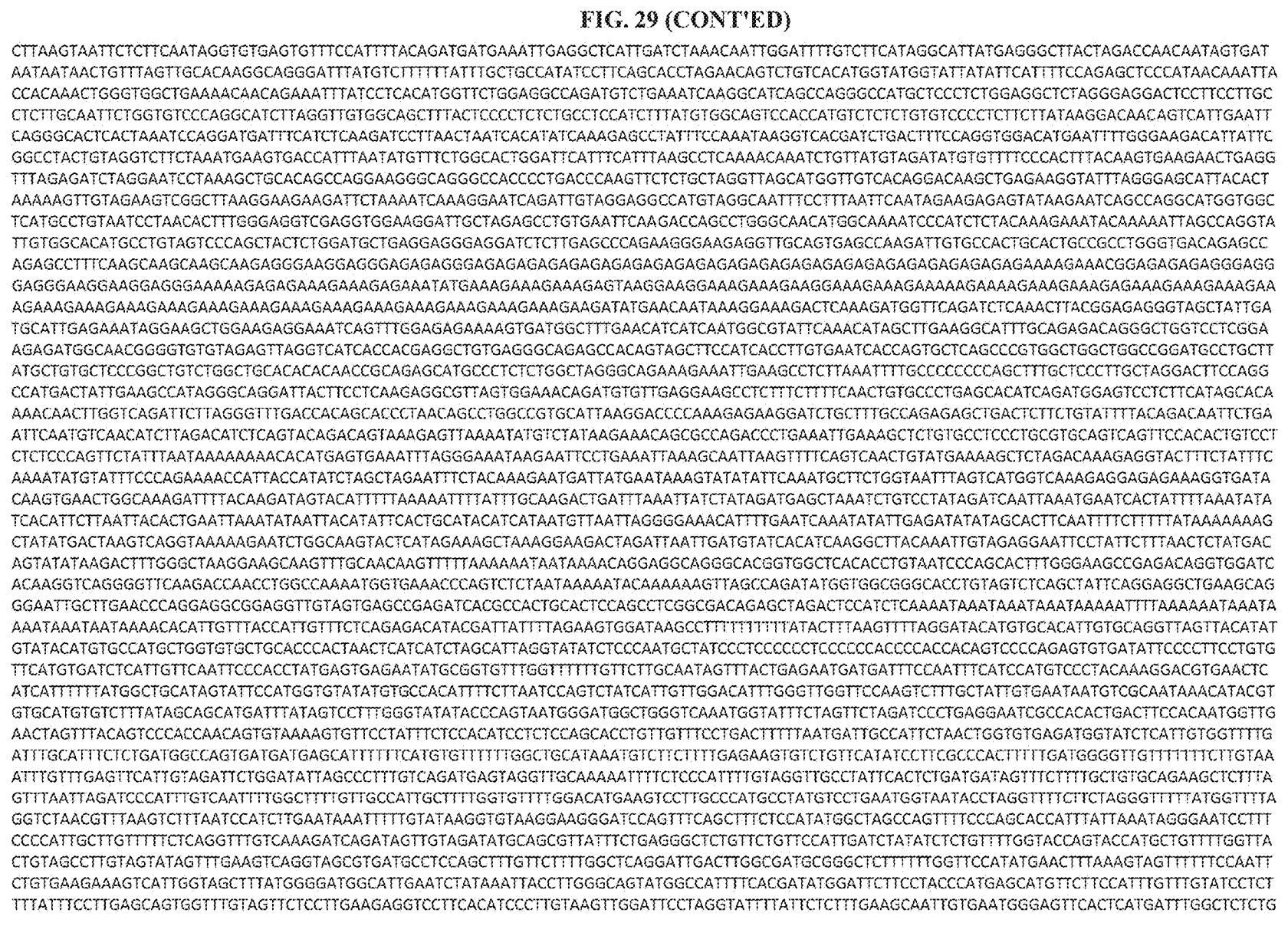
Figure 29:
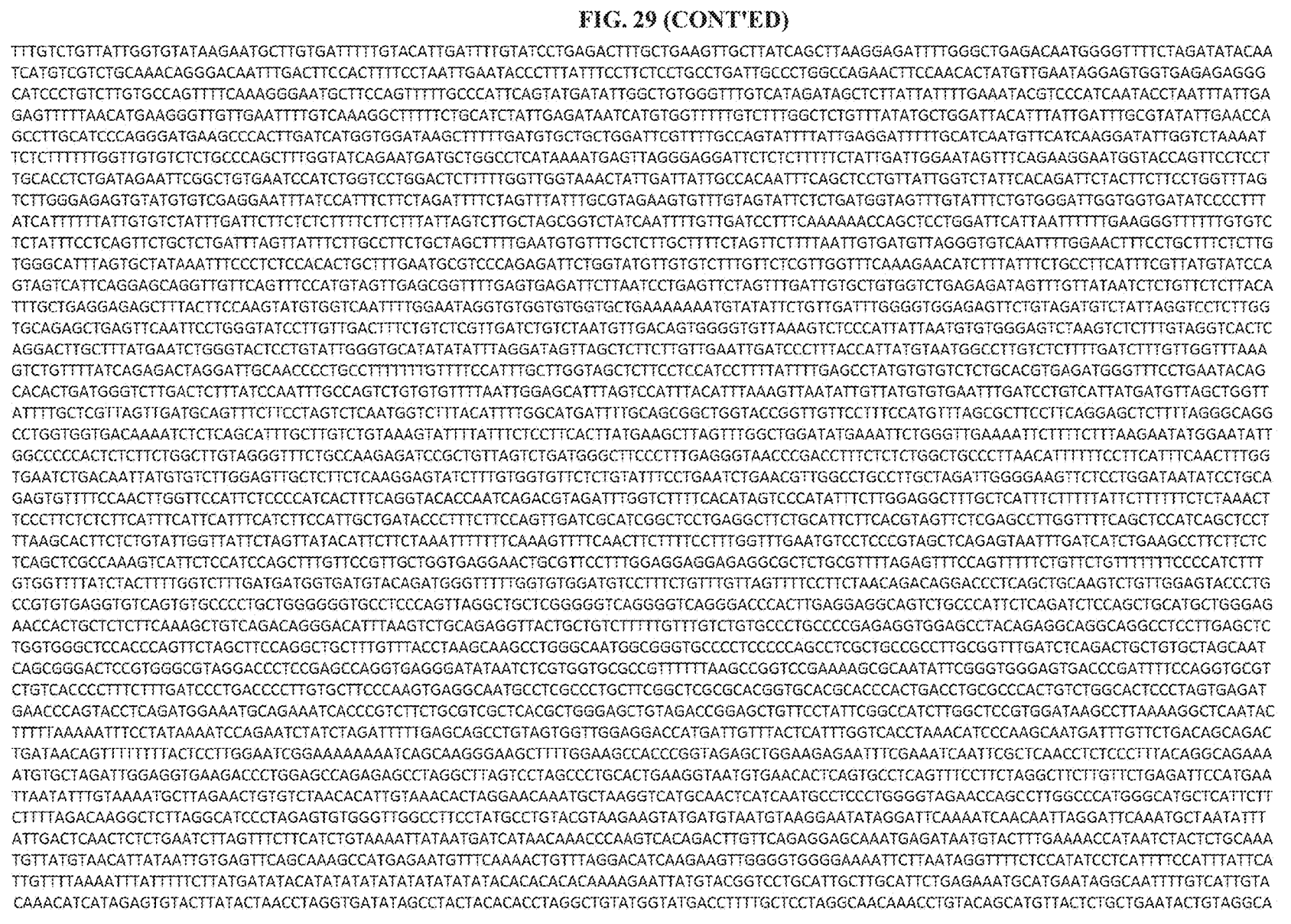
Figure 29:
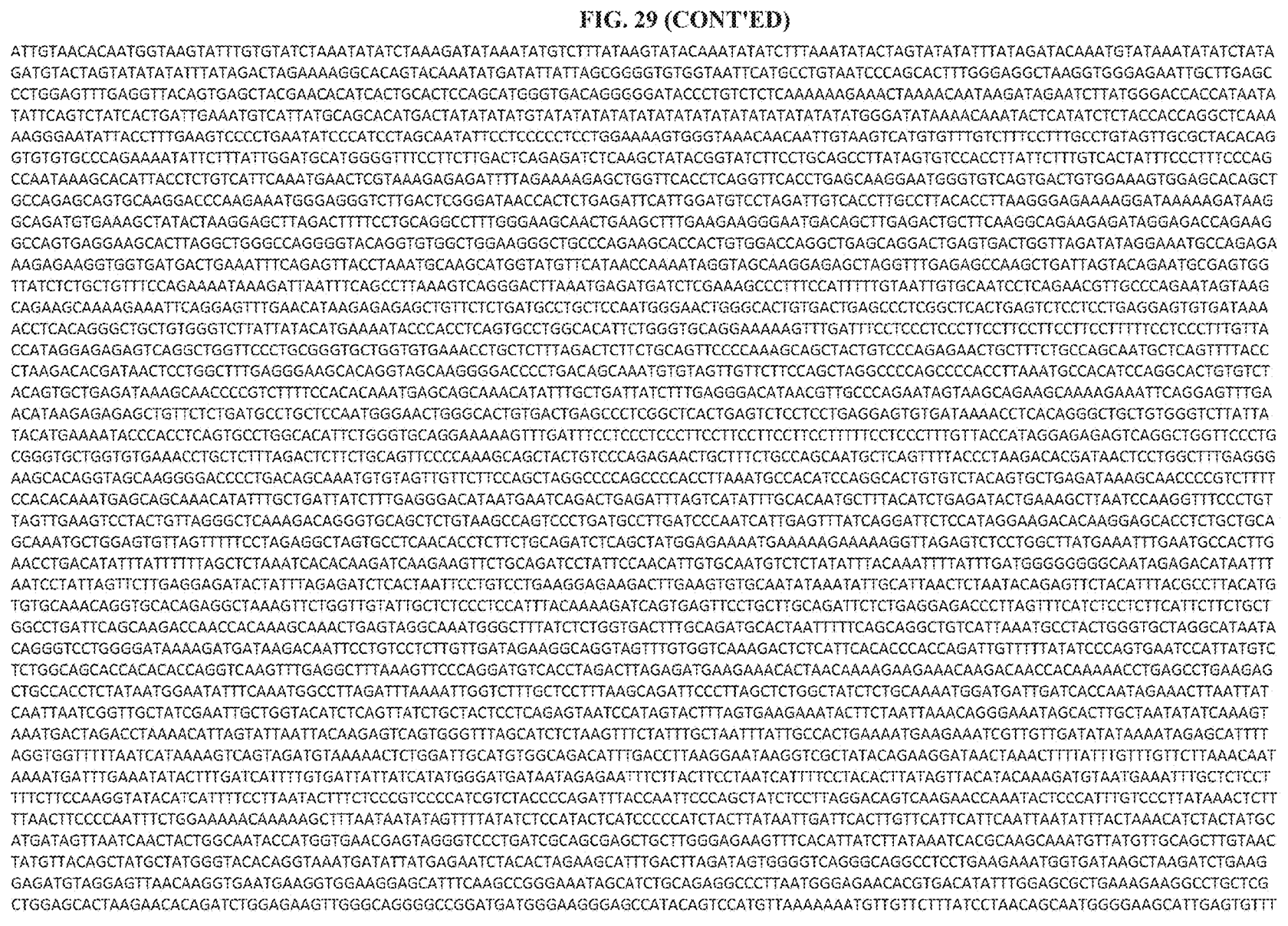
Figure 29:
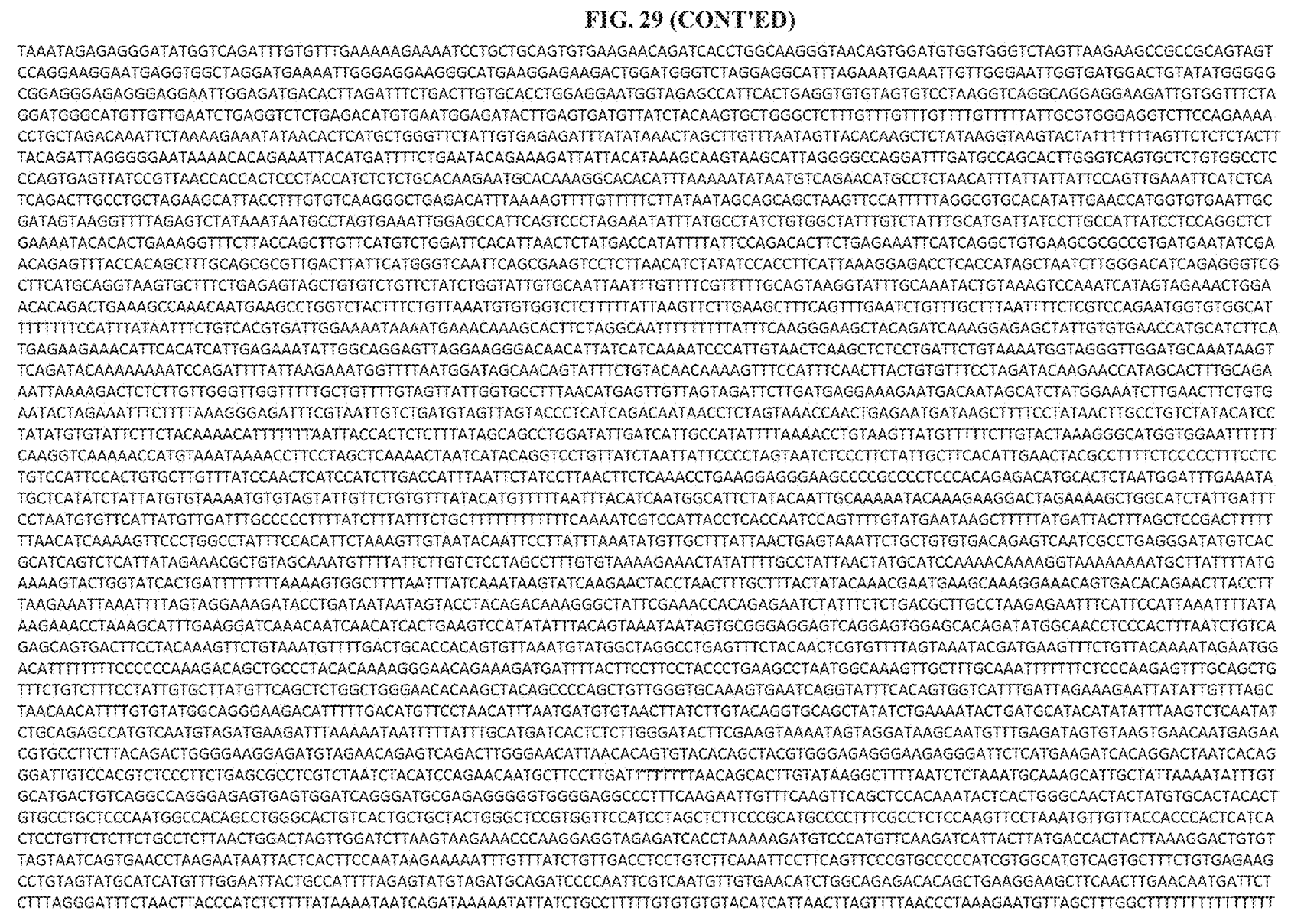
Figure 29:
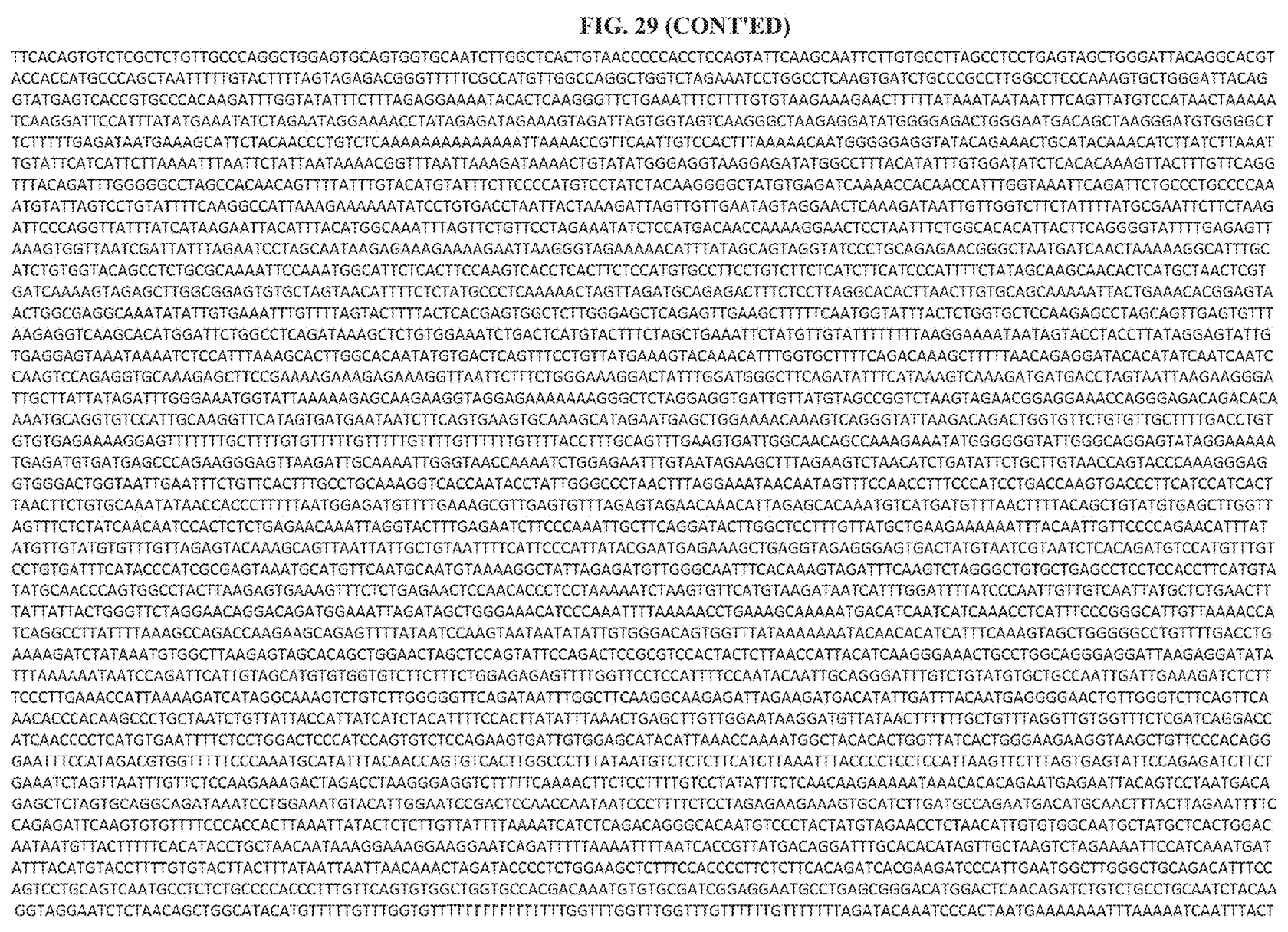
Figure 29:
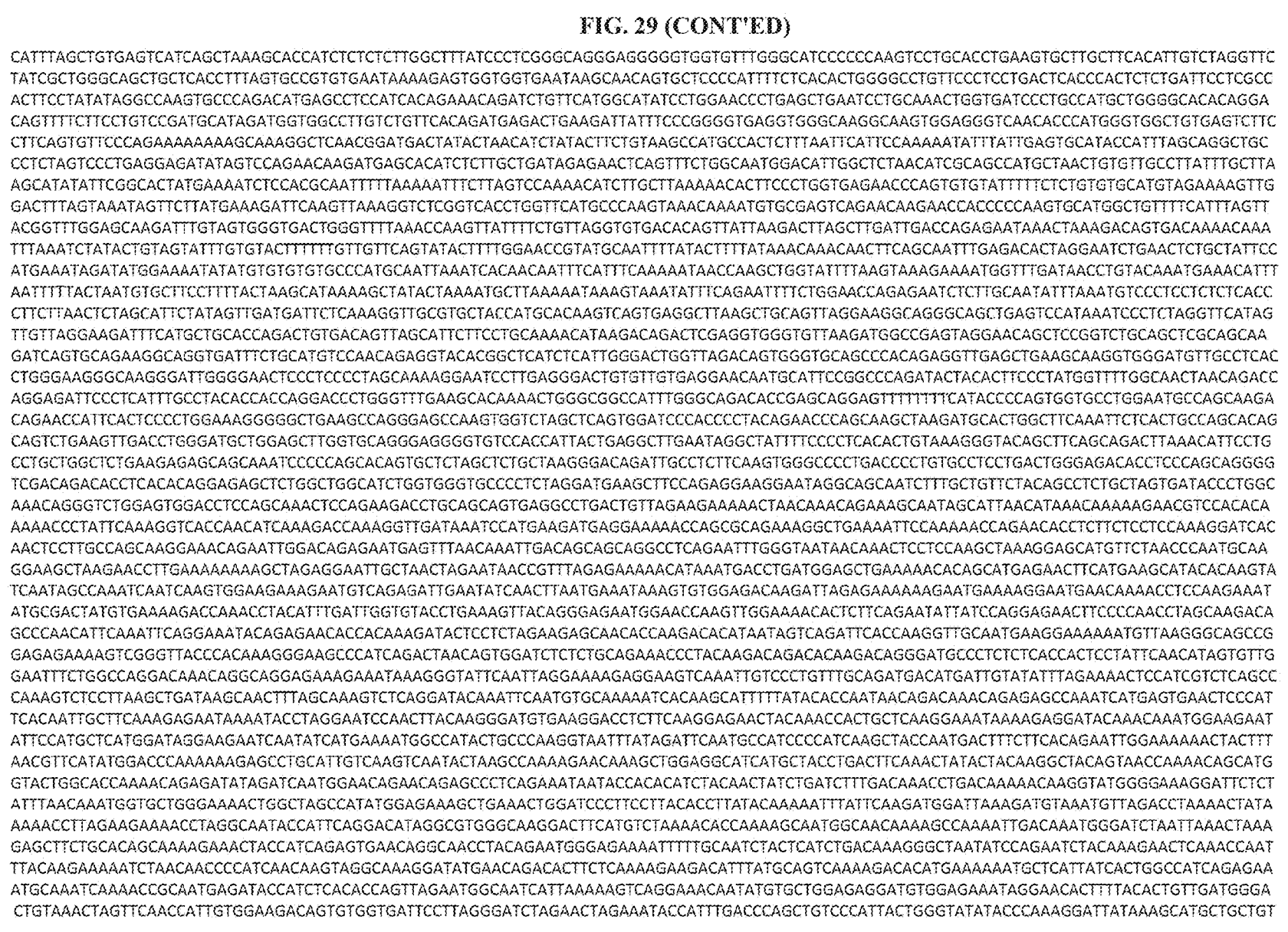
Figure 29:
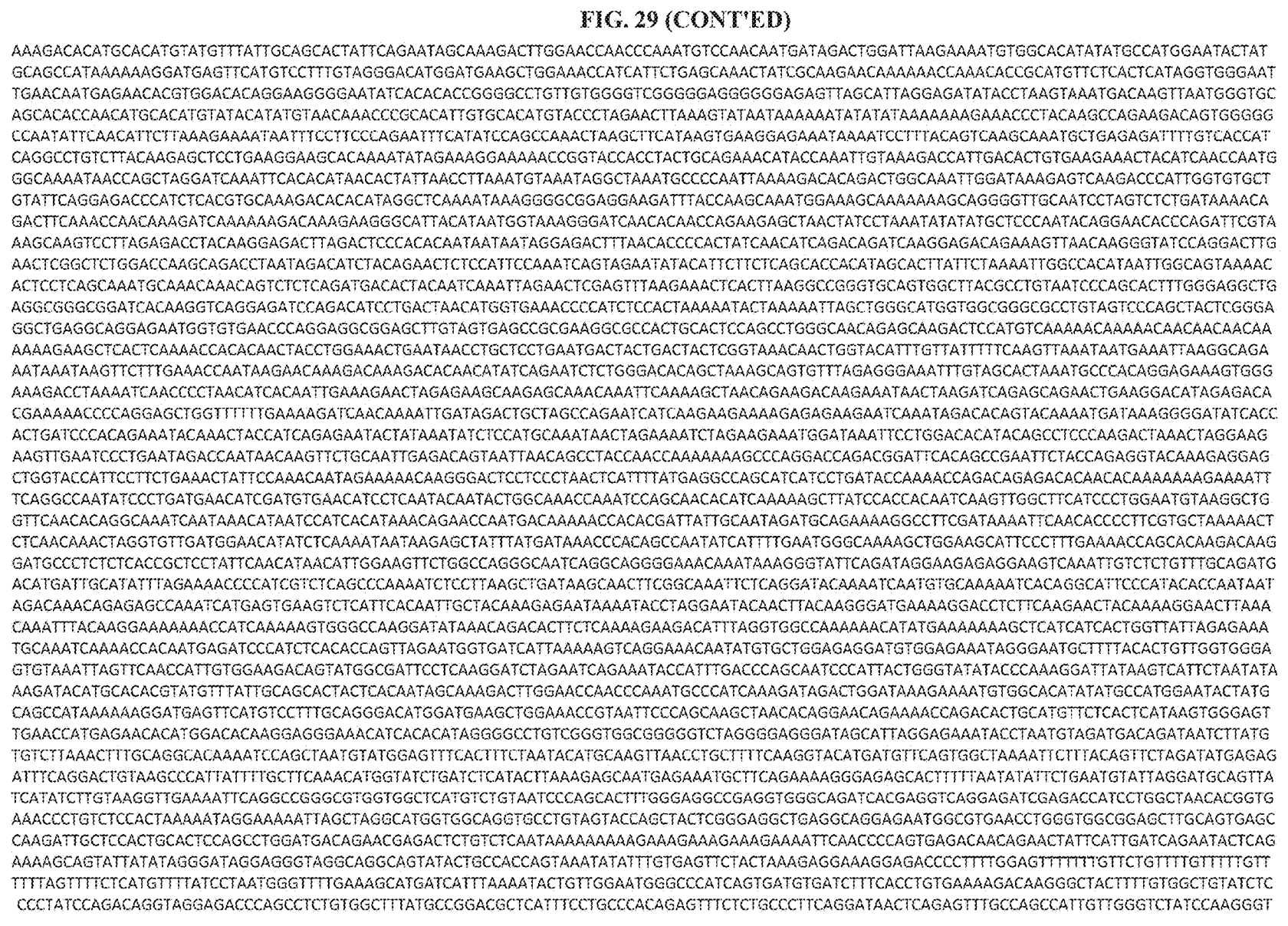
Figure 29:
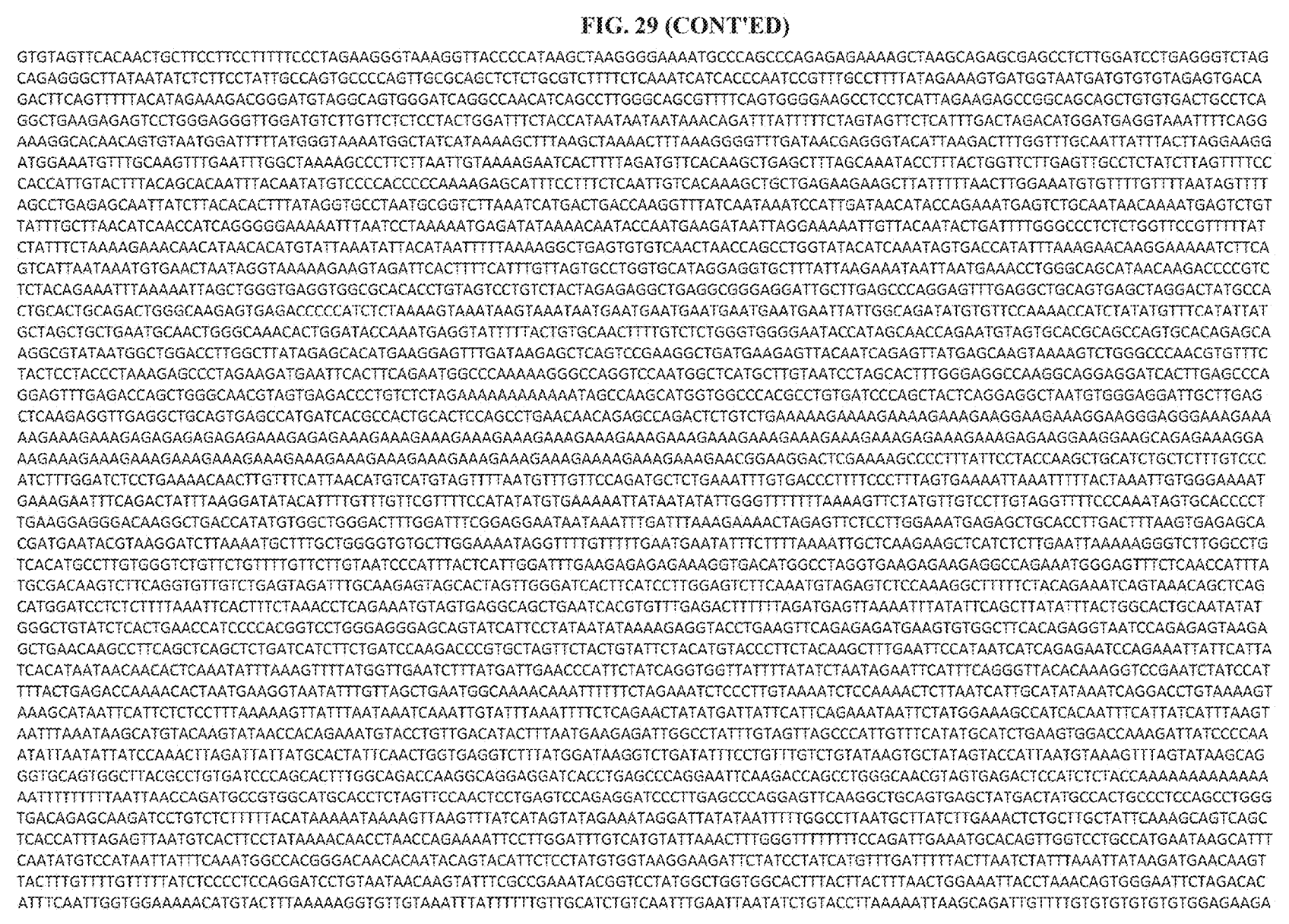
Figure 29:
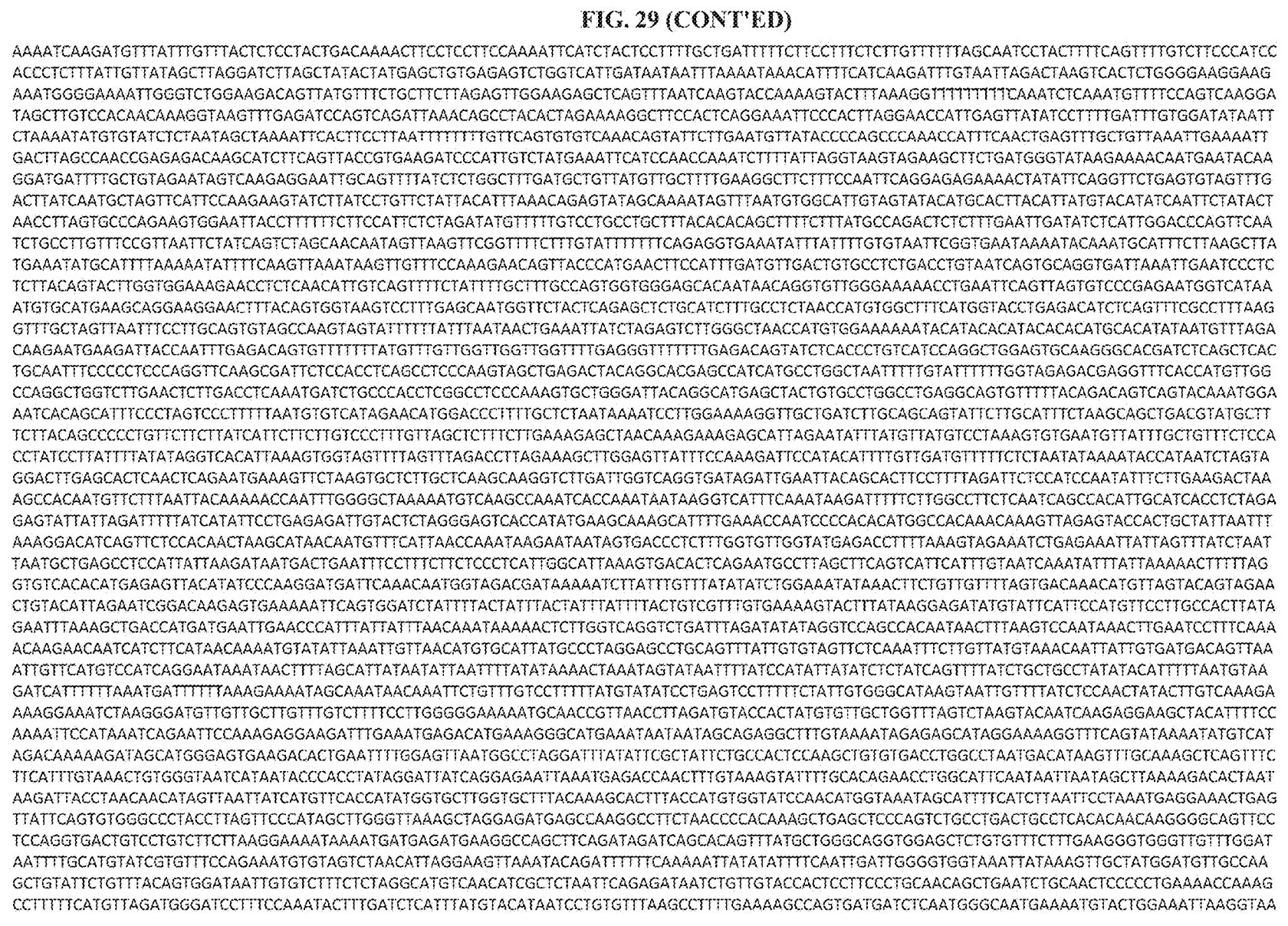
Figure 29:
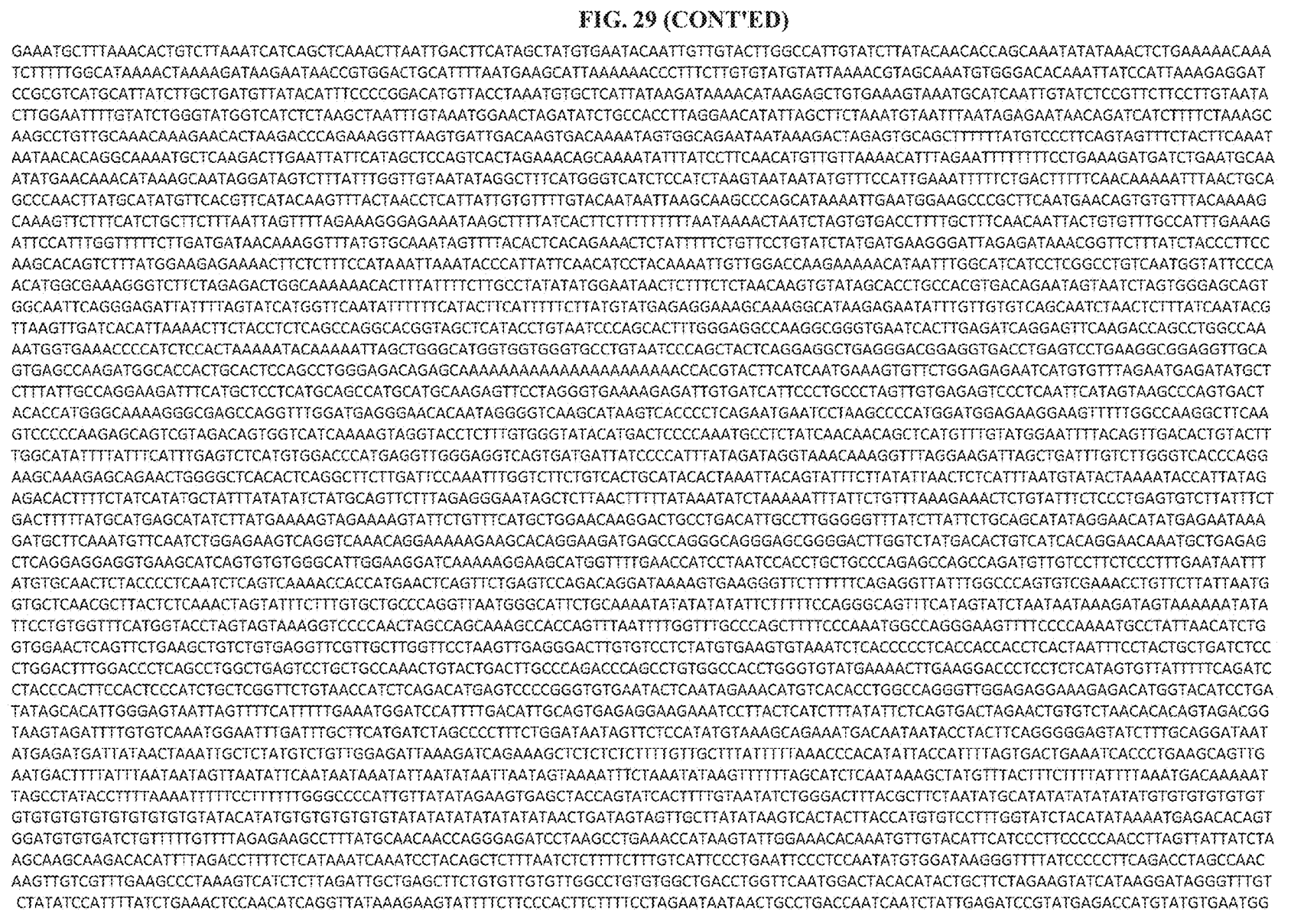
Figure 29:
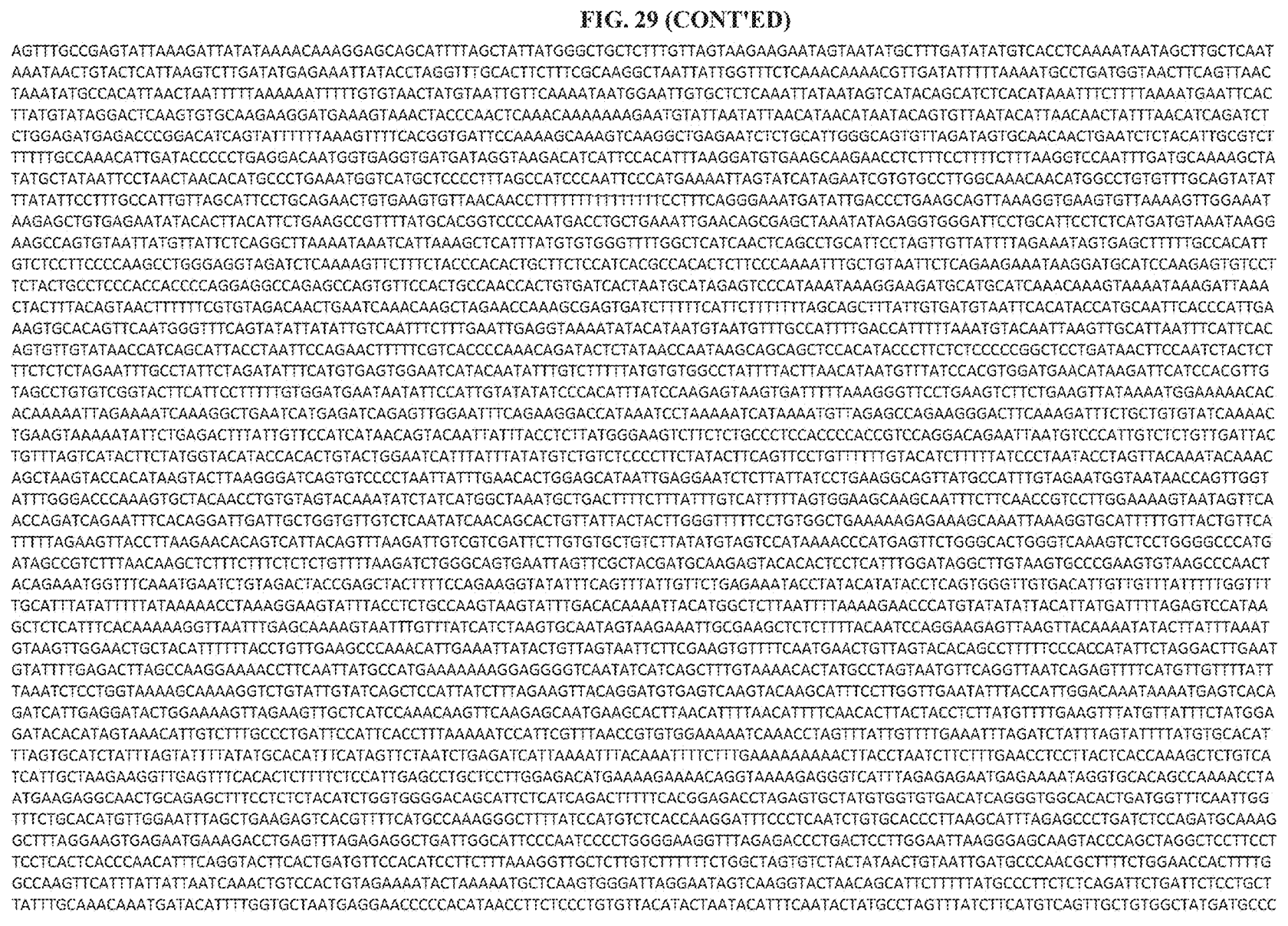
Figure 29:
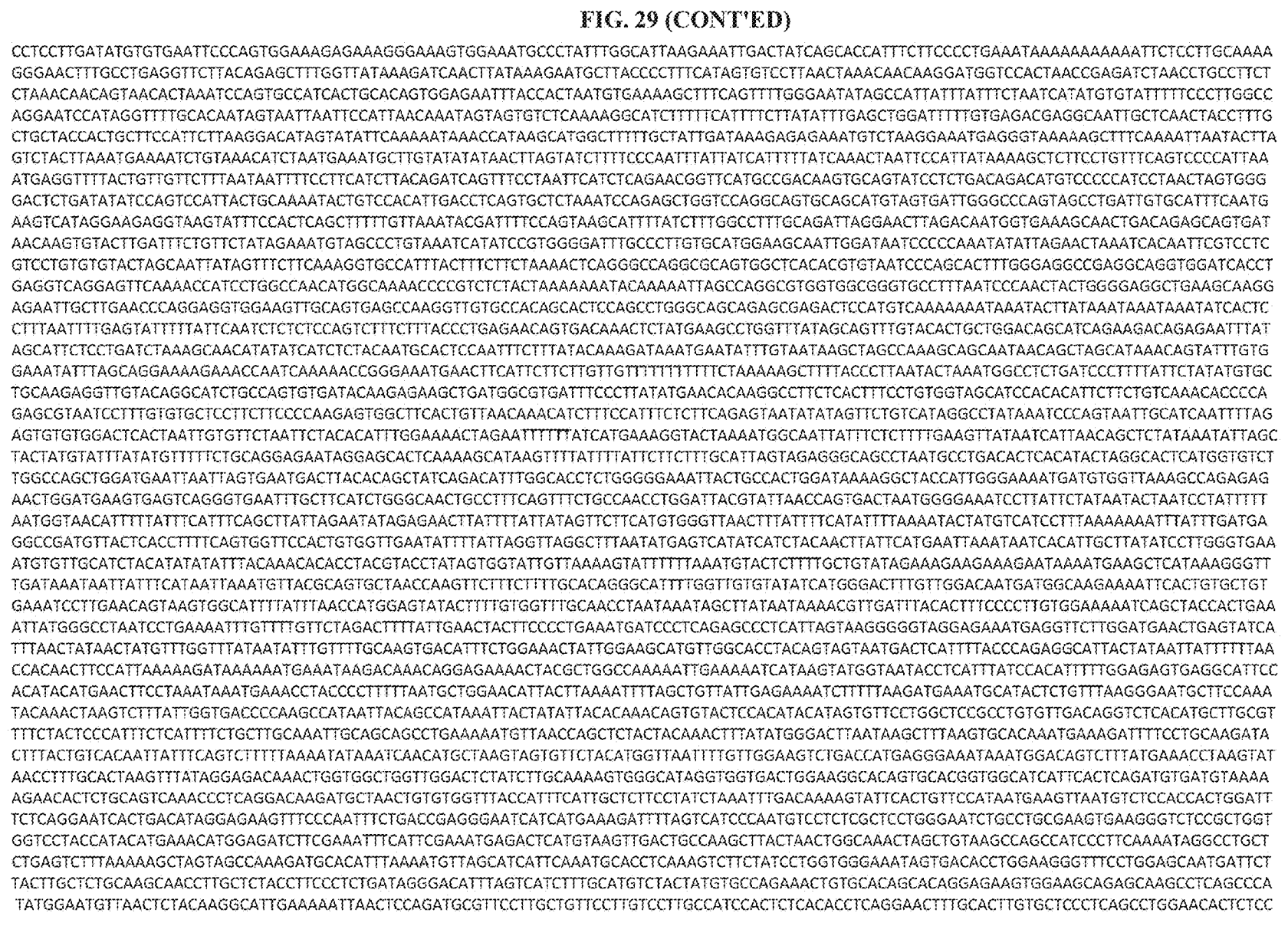
Figure 29:
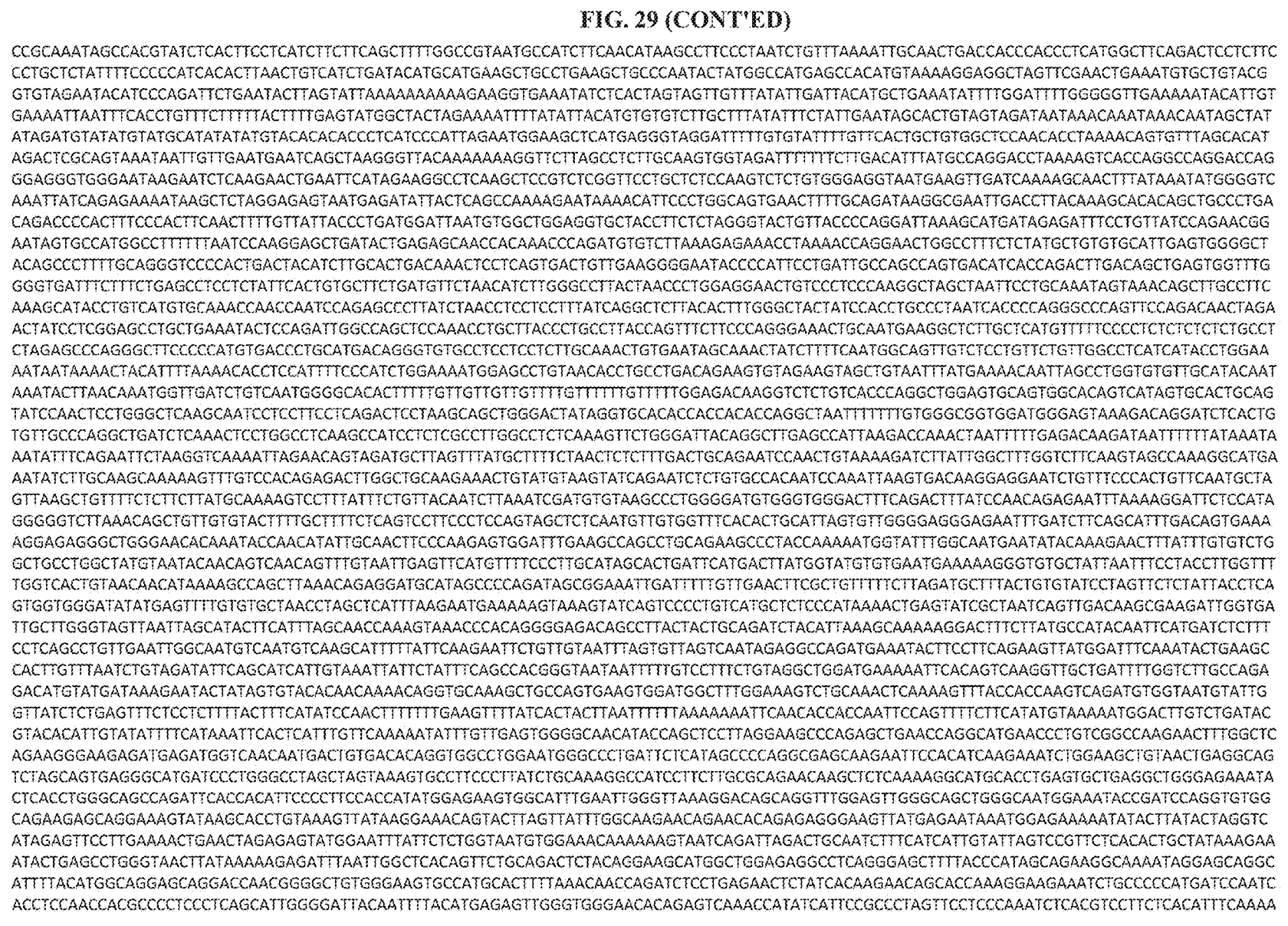
Figure 29:
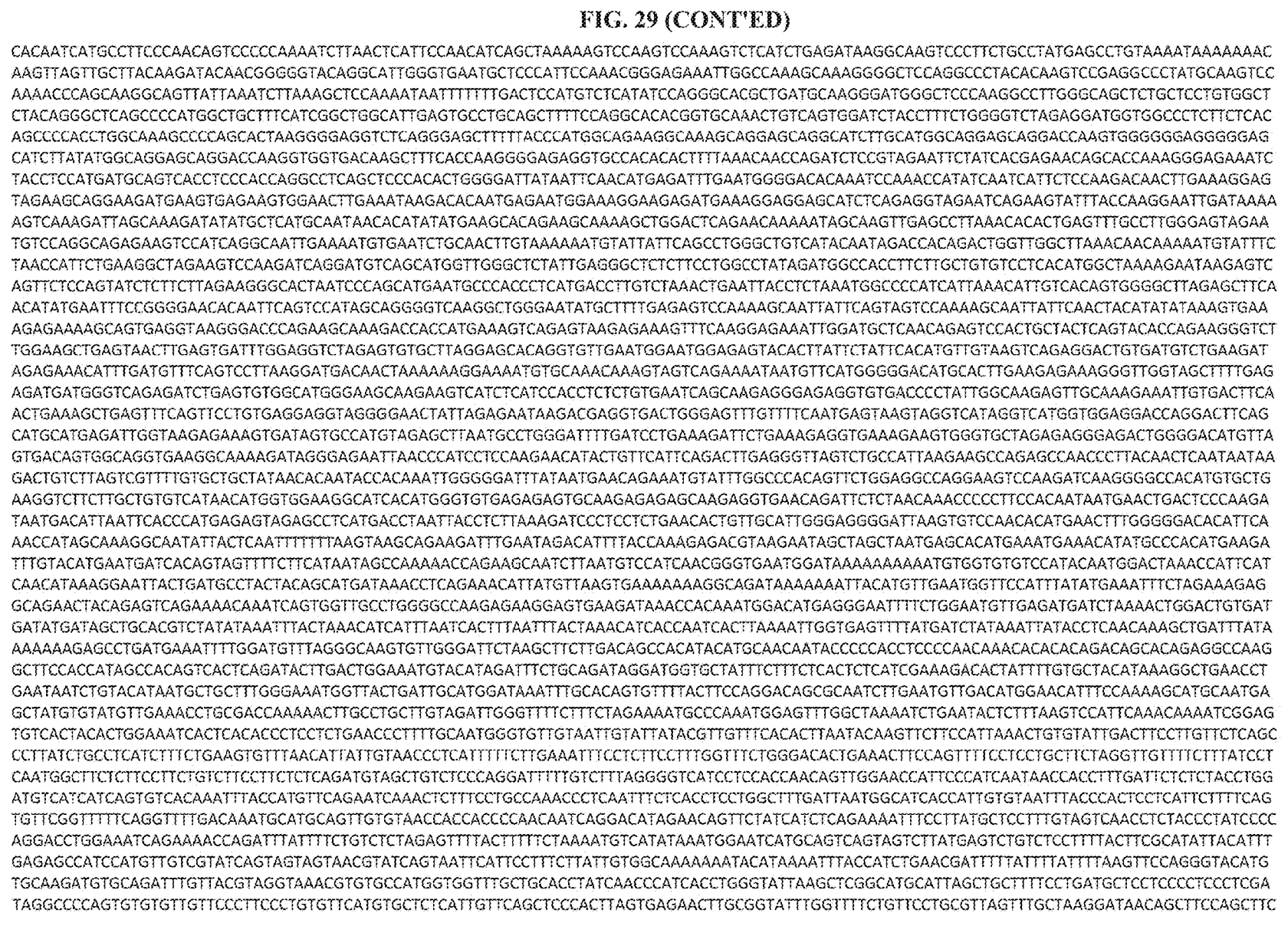

FIG. 29 depicts an example sequence (SEQ. ID. NO. 9) of an MET gene on the ecDNA of HF3077, in accordance with one non-limiting example embodiment of the present invention.

DETAILED DESCRIPTION OF THE INVENTION

Glioma, and glioblastoma (GBM) in particular, is a heterogeneous tumor that is highly resistant to chemo- and radiotherapy. New modalities for treatment are urgently needed. Modeling of tumors through cell culture and orthotopic xenotransplantation are essential approaches for preclinical therapeutic target screening and validation, but in gliomas and GBM have yet to result in novel treatments. It is not clear to what extent these models truthfully recapitulate the parental tumor.

The present invention provides a method of targeting ecDNA for treatment of glioma. It is normally understood that oncogenes are present in chromosomes. The present inventors also discovered that oncogenes are present in ecDNA, i.e. ecDNA oncogenes. The inventors speculate that ecDNA oncogenes derive from chromosomal oncogenes. The present inventors discovered that ecDNA oncogenes comprise sequences that are a large portion of the full length of chromosomal oncogenes (90%, 94%, 95%, 98%, 99% or more of the full length of chromosomal oncogenes) and have the same function as full length chromosomal oncogenes in promoting tumor growth and progression in gliomas. The inventors have found that the ecDNA oncogenes are active in promoting tumor growth in gliomas. Accordingly, the present invention relates to a method of identifying ecDNA oncogenes and targeting such oncogenes to treat glioma.

Here, the present inventors have developed methods for identifying patient specific drugs that target against oncogenes present in ecDNA in a patient's brain tumor. This allows the patient's treatment to be personalized to the precise oncogenes in the patient's glioma tumor(s). The inventors also showed that neurosphere and/or orthotopic xenograft tumor models are genomically similar, capturing over 80% of all genomic alterations detected in the parental tumors.

The present inventors' work contributes to understanding how genomic heterogeneity of glioblastoma (GBM) contributes to the poor response to therapy, which is characteristic of this disease. To evaluate how genomically heterogeneous tumor cell populations are affected by selective pressures arising from the transitions from tumor to culture to xenograft, the inventors performed a comprehensive genomic and transcriptomic analysis of thirteen GBMs, the glioma-neurosphere forming cultures (GSC) derived from them, and orthotopic xenograft models (PDX models) established from early passage neurospheres.

The present inventors performed DNA and RNA sequencing on GBM tumor samples and the neurospheres and orthotopic xenograft models derived from them. The inventors used the resulting data set to show that somatic driver alterations including single nucleotide variants, focal DNA alterations, and oncogene amplification in extrachromosomal DNA (ecDNA) elements were in majority propagated from tumor to model systems. In several instances, ecDNAs and chromosomal alterations demonstrated divergent inheritance patterns and clonal selection dynamics during cell culture and xenografting. Longitudinal patient tumor profiling showed that oncogenic ecDNAs are frequently retained after disease recurrence. The inventors' analysis shows that extrachromosomal elements increase the genomic heterogeneity during tumor evolution of glioblastoma, independent of chromosomal DNA alterations. The inventors' results highlight the evolutionary process of GBM cells, placing emphasis on the diverging dynamics of chromosomal DNA alterations and extrachromosomally amplified DNA elements in tumor evolution. The present results show that patient-specific drugs may be identified that target specific ecDNA oncogenes present in a tumor of that particular patient. The results also show that the present PDX mouse model method has a predictive value for use in evaluations of drugs or drug candidates.

In view of the present studies and results, provided herein are inter alia, methods of identifying a drug that targets against an oncogene present in ecDNA, which may be used in treatment of glioma, such as glioblastoma, in a patient. The methods include targeting patient-specific oncogenes present in ecDNA. Also provided are methods that include a PDX mouse model to determine if the identified drug inhibits tumor glioma growth and would be suitable for treating the glioma in the patient.

Any publications or references mentioned in this specification are indicative of the level of those skilled in the art to which the invention pertains. All patents, publications and/or references herein are incorporated by reference to the same extent as if each individual publication was specifically and individually indicated as having been incorporated by reference, in its entirety.

Definitions

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

BRCA1 associated protein-1 (ubiquitin carboxy-terminal hydrolase) (BAP1) is a deubiquitinating enzyme that in humans is encoded by the BAP1 gene. BAP1 encodes an 80.4 kDa nuclear-localizing protein with a ubiquitin carboxy-terminal hydrolase (UCH) domain that gives BAP1 its deubiquitinase activity. The BAP1 gene is (RefSeq Gene ID (=NCBI Gene ID) 100505510)

BRCA1 and BRCA1 are a human gene and its protein product, respectively. BRCA1 is a human tumor suppressor gene (to be specific, a caretaker gene), found in all humans; its protein, also called by the synonym breast cancer type 1 susceptibility protein, is responsible for repairing DNA. The BRCA1 gene is (RefSeq Gene ID (=NCBI Gene ID) 672).

CAPZA2 (Capping Actin Protein Of Muscle Z-Line Alpha Subunit 2) is a protein coding gene. The CAPZA2 gene is (RefSeq Gene ID (=NCBI Gene ID 830).

G1/S-specific cyclin-D2 is a protein that in humans is encoded by the CCND2 gene. The CCND2 gene is (RefSeq Gene ID (=NCBI Gene ID) 894).

The term "CD" refers to the Cluster of Differentiation. CDK4 refers to Cyclin dependent kinase 4 also known as cell division protein kinase 4 is an enzyme that in humans is encoded by the CDK4 gene. The CDK4 gene is (RefSeq Gene ID (=NCBI Gene ID) 1019). Cell division protein kinase 6 (CDK6) is an enzyme encoded by the CDK6 gene. The CDK6 gene is (RefSeq Gene ID (=NCBI Gene ID) 1021).

A cancer "driver gene" is one whose mutations increase net cell growth under the specific microenvironmental conditions that exist in the cell in vivo.

The terms "drug" and "drug candidate" mean any drug or potential drug or composition, or combination of drugs, including one or more active agents such as antibodies (i.e., biologics), small molecules and/or other compounds that are identified as having, or potentially having a therapeutic effect of alleviating, treating, and/or curing a disease, tumor, illness, injury, ailment or condition. The active agents include the oncogene-inhibitors discussed herein. However, as is well known, drugs may further include various excipients to aid in formulation, release, coating, etc. of a drug. Thus, the term "drug" should not be limited to any particular formulation, but is intended to include any formulation that includes an active ingredient, such as an oncogene inhibitor, as discussed herein.

The EGFR gene provides instructions for making a receptor protein called the epidermal growth factor receptor. The "epidermal growth factor receptor" (EGFR; ErbB-1; HER1 in humans) is a transmembrane protein that is a receptor for members of the epidermal growth factor family (EGF family) of extracellular protein ligands. The EGFR gene is (RefSeq Gene ID (=NCBI Gene ID) 1956). The epidermal growth factor receptor is a member of the ErbB family of receptors, a subfamily of four closely related receptor tyrosine kinases: EGFR (ErbB-1), HER2/neu (ErbB-2), Her 3 (ErbB-3) and Her 4 (ErbB-4). The ERBB2 gene is (RefSeq Gene ID (=NCBI Gene ID 2064)). In many cancer types, mutations affecting EGFR expression or activity could result in cancer, Deficient signaling of the EGFR and other receptor tyrosine kinases in humans is associated with the diseases such as Alzheimer, while over expression of their signaling is associated with the development of a wide variety of types of the tumors. Interruption of EGFR signaling either by blocking EGFR binding sites on extracellular domain of the receptor or by inhibiting intracellular tyrosine kinase activity can prevent the growth of EGFR-expressing tumors and improve the patient conditions.

The term "exome sequencing" also known as whole exome sequencing (WES), is a transcriptomics technique for sequencing all of the protein-coding genes in a genome known as the exome). The sequencing includes two steps: the first step is to select only the subset of DNA that encodes proteins. These regions are known as exons—humans have about 180,000 exons, constituting about 1% of the human genome, or approximately 30 million base pairs. The second step is to sequence the exonic DNA using any high-throughput DNA sequencing technology The term "Extrachromosomal DNA" or "ecDNA" is any DNA that is found outside the nucleus of a cell. It is also referred to as extranuclear DNA or cytoplasmic DNA. Most DNA in an individual genome is found in chromosomes, but there is also DNA found outside the nucleus, which is the ecDNA. In eukaryotes extrachromosomal DNA is primarily found in organelles. Mitochondrial DNA is a main source of this extrachromosomal DNA in eukaryotes.

F-box/WD repeat-containing protein 7 is a protein that in humans is encoded by the FBXW7 gene. This gene encodes a member of the F-box protein family which is characterized by an approximately 40 amino acid motif, the F-box. The FBXW7 gene is (RefSeq Gene ID (=NCBI Gene ID) 55294).

"Genomic" means a full set of chromosomes.

"Gliomas" are tumors arising from glial cells, and may occur in the spinal cord or the brain. Any tumor that arises from the glial (from the Greek word for "glue"), or supportive tissue, of the brain is called a "glioma." Gliomas are the most common type of brain tumor. There are four main types of glioma: (1) Ependymomas: ependymal cells, (2) Astrocytomas: astrocytes (of which glioblastoma multiforme (GBM) is a malignant astrocytoma, (3) Oligodendrogliomas (oligodendrocytes), and (4) mixed gliomas. Astrocytes get their name because they are "star-shaped". They are the most abundant glial cells in the brain that are closely associated with neuronal synapses. They regulate the transmission of electrical impulses within the brain.

Glioblastoma, also known as glioblastoma multiforme, GBM or grade IV astrocytoma, is a fast-growing, aggressive type of central nervous system tumor that forms on the supportive tissue of the brain. Glioblastoma is the most common grade IV brain cancer. Glioblastoma and malignant astrocytoma (grade III astrocytoma) are "high-grade" astrocytomas. Glioblastomas may appear in any lobe of the brain, but it develops more commonly in the frontal and temporal lobes. The terms "glioblastoma" and "GBM", are used interchangeably herein.

The term "gliomagenesis" means the formation and development of gliomas. "Gliomas" refer to a tumor that arises from glial cells in the brain or spinal cord.

"Glioma-neurosphere" cultures in the present invention are neurosphere cultures prepared from a glioma brain sample of a subject. In such cultures, resected brain tumor specimens are collected from a subject, under a protocol approved by the hospital Review Board of the hospital in which the subject is a patient, and graded pathologically according to WHO criteria. In forming neurosphere cultures, a portion of each tumor specimen is used for cell culture. Tumors are dissociated enzymatically and neurospheres enriched in cancer stem-like cells (CSC) are cultured. After dissociation of the fresh tumor sample, tumor cells are placed in growth medium in culture. The neurosphere medium (NM) may include for example, DMEM/F12 (Dulbecco's Modified Eagle Medium/Nutrient Mixture F-12) supplemented with N2 (Gibco), 0.5 mg/ml BSA (Sigma), 25 μg/ml gentamicin (Gibco), 0.5% antibiotic/antimycotic (Invitrogen), 20 ng/ml basic fibroblast growth factor (bFGF), and 20 ng/ml epidermal growth factor EGF (Peprotech). DMEM/F-12 is a widely used basal medium for supporting the growth of many different mammalian cells. However, other suitable culture medium for neurospheres and would be known to those skilled in the art. After neurospheres are formed they are dissociated and re-plated in the original media volume, this is considered "passage 1". From then on, roughly every ten days the neurospheres are dissociated and re-plated, being one passage older each time. For the work in the present application, neurosphere cultures were used that were between 7 and 18 passages. Neurosphere cultures were serially passaged in vitro. No mycoplasma contamination was identified in the subset of samples tested. Cells with passages between 7 and 18 were used for mouse implants and molecular analysis, except for those designed "high passage", where passage 40 was used.

The terms "humans", "subjects", and "patients" (and the singular forms of these terms), are used herein somewhat interchangeably. The use of one of these terms herein is intended to encompass each of these terms. In the present methods, the subjects and patients are human. However, it is contemplated that the methods may be applied to other mammals, perhaps with some modifications to the methods, which may be determined by those skilled in the art, using the information, methods and techniques described herein.

Generally, "Long Read Sequencing" enables one to obtain sequences longer than 10 kb. An example of a Long Read sequencing technique is set forth in the below examples. The PacBio Sequencing Systems, used in the present application, are built on Single Molecule, Real-Time (SMRT) Sequencing technology, and provide high consensus accuracy, uniform coverage, and long average reads. As a result, these unique platforms deliver a comprehensive view of genomes, transcriptomes, and epigenomes.

Mutations in isocitrate dehydrogenase, "IDH" 1 and 2, occur in gliomas. These mutations, which occur early in gliomagenesis, change the function of enzymes, causing them to not produce NADPH. IDH mutations are oncogenic. It is not clear whether the mechanism is through alterations in hydroxylases, redox potential, cellular metabolism, or gene expression.

"Intratumoral heterogeneity" including genetic and non-genetic mechanisms refers to biological differences amongst malignant cells originated within the same tumor.

"MDM2" is mouse double minute 2 homolog (MDM2) also known as E3 ubiquitin-protein ligase MDM2 is a protein that in humans is encoded by the MDM2 gene. MDM2 is an important negative regulator of the p53 tumor suppressor. The MDM2 gene is (RefSeq Gene ID (=NCBI Gene ID) 4193).

MET is a single pass tyrosine kinase receptor essential for embryonic development, organogenesis and wound healing. Abnormal MET activation in cancer correlates with poor prognosis, where aberrantly active MET triggers tumor growth, formation of new blood vessels (angiogenesis) that supply the tumor with nutrients, and cancer spread to other organs (metastasis). cancer stem cells are thought to hijack the ability of normal stem cells to express MET, and thus become the cause of cancer persistence and spread to other sites in the body. Both the overexpression of MET/HGFR, as well as its autocrine activation by co-expression of its hepatocyte growth factor ligand, have been implicated in oncogenesis. c-MET also called tyrosine-protein kinase MET or hepatocyte growth factor receptor (HGFR), is a protein that in humans is encoded by the MET gene. c-MET can cause a wide variety of different cancers, such as renal, gastric and small cell lung carcinomas, central nervous system tumors, as well as several sarcomas when its activity is dysregulated. Targeting the ATP binding site of c-MET by small molecules inhibitors is one strategy for inhibition of the tyrosine kinase. The MET gene structure in the present invention is from the Ensembl resource, ID is "ENST00000397752" which corresponds to two UCSC RefSeq genes NM_000245.3 and NM_001324402.1.

"c-MET inhibitors" (also referred to herein as "MET-inhibitors") are oncogene inhibitors, specific to inhibiting c-MET (or MEI). The inhibitors refer to a compound that inhibits the function of c-MET These inhibitors have therapeutic application in the treatment of various types of cancer. Many c-MET inhibitors are currently in clinical trials.

Non-limiting example embodiments of c-MET inhibitors (MET inhibitors) include Crizotinib and Cabozantinib. Crizotinib received accelerated FDA approval for the treatment of patients with locally advanced or metastatic non-small cell lung cancer (NSCLC) that is ALK-positive as detected by a test approved by the U.S. Food and Drug Administration (FDA). Capmatinib, also known as INCB28060 and INC280, is an orally bioavailable inhibitor of the proto-oncogene (hepatocyte growth factor receptor [HGFR]) with potential antineoplastic activity. Other MET inhibitors and oncogene inhibitors are known or may be developed and are included herein.

"MYC (c-MYC)" is a regulator gene that codes for a transcription factor. The protein encoded by this gene is a multifunctional, nuclear phosphoprotein that plays a role in cell cycle progression, apoptosis and cellular transformation. A mutated version of MYC is found in many cancers, which causes MYC to be constitutively (persistently) expressed. This leads to the unregulated expression of many genes, some of which are involved in cell proliferation, and results in the formation of cancer. The MYC gene is (RefSeq Gene ID (=NCBI Gene ID) 4609).

The MYCN gene is a member of the MYC family of transcription factors and encodes a protein with a basic helix-loop-helix (bHLH) domain. The MYCN gene provides instructions for making a protein that plays an important role in the formation of tissues and organs during embryonic development. The MYCN gene is (RefSeq Gene ID (=NCBI Gene ID) 4613).

"Oncogenes" are genes that have the potential to cause cancer. In tumor cells, they are often mutated or expressed at high levels. Most normal cells will undergo a programmed form of rapid cell division (apoptosis) when critical functions are altered. Activated oncogenes can cause those cells designated for apoptosis to survive and proliferate instead. Oncogenes discussed herein include, but are not limited to an oncogene selected from MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1. According to further non-limiting example embodiments, the oncogenes are oncogenes selected from MET MET/CAPZA2, MDM2, CDK4, SOX2, PIK3CA, MECOM, PDGFRA, EGFR, MYCN, and MYC. According to further embodiments the oncogenes is MET or MET/CAPZA2.

"ecDNA oncogenes" or "an oncogene present in ecDNA" are also genes that cause cancer, and are believed to perform the same function and result as their corresponding full length chromosomal oncogenes, as discussed herein. Structurally, ecDNA oncogenes are shortened versions of the corresponding full length chromosomal oncogenes (or substantially the same as shortened versions of the full length chromosomal oncogenes). The ecDNA oncogenes herein may be referred to by the same name as the corresponding full length chromosomal oncogenes, but are for example, 90%, 94%, 95%, 98%, or 99% or more of the length of the corresponding full length chromosomal oncogenes. As used herein, when the presence of an oncogene is identified in ecDNA, those ecDNA oncogenes are oncogenes selected from MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1. According to further non-limiting example embodiments, the oncogenes in ecDNA are oncogenes selected from MET, MET/CAPZA2, MDM2, CDK4, SOX2, PIK3CA, MECOM, PDGFRA, EGFR, MYCN, and MYC. According to further embodiments, the oncogene in ecDNA is MET or MET/CAPZA2. In some instances, ecDNA oncogenes may be fused one to another. By way of non-limiting example, fused oncogenes may include for example, MET/CAPZA2, CDK4/ MDM2, BRCA1/ ERBB2, BRCA1, ERBB2, CCND2/ CDK4. These, and other oncogene fusion genes are intended to be encompassed by the oncogenes provided herein.

MDS1 and EVI1 complex locus protein EVI1 (MECOM) also known as ecotropic virus integration site 1 protein homolog (EVI-1) or positive regulatory domain zinc finger protein 3 (PRDM3) is a protein that in humans is encoded by the MECOM gene. The MECOM gene is (RefSeq Gene ID (=NCBI Gene ID) 2122).

The MET gene structure in the present invention is from the Ensembl resource, ID is "ENST00000397752" which corresponds to two UCSC RefSeq genes NM_000245.3 and NM_001324402.1. Further oncogenes used herein include the following: MDM2 (RefSeq Gene ID (=NCBI Gene ID) 4193); CAPZA2 (RefSeq Gene ID (=NCBI Gene ID 830); CDK4 (RefSeq Gene ID (=NCBI Gene ID) 1019), SOX2 (RefSeq Gene ID) (=NCBI Gene ID) 6657), PIK3CA (RefSeq Gene ID (=NCBI Gene ID) 5290), MECOM (RefSeq Gene ID (=NCBI Gene ID) 2122), PDGFRA (RefSeq Gene ID (=NCBI Gene ID) 5156), EGFR, (RefSeq Gene ID (=NCBI Gene ID) 1956), MYCN (RefSeq Gene ID (=NCBI Gene ID) 4613), MYC (RefSeq Gene ID (=NCBI Gene ID) 4609), TERT (RefSeq Gene ID (=NCBI Gene ID) 7015), SMARCA4 (RefSeq Gene ID (=NCBI Gene ID) 6597), RP56 (RefSeq Gene ID (=NCBI Gene ID) 50939, HGNC Symbol=IMPG-2), FBXW7 (RefSeq Gene ID (=NCBI Gene ID) 55294). CDK6 (RefSeq Gene ID (=NCBI Gene ID) 1021), CCND2 (RefSeq Gene ID (=NCBI Gene ID) 894), ERBB2 (RefSeq Gene ID (=NCBI Gene ID 2064)), BRCA1 ((RefSeq Gene ID (=NCBI Gene ID) 672), and BAP1 (RefSeq Gene ID (=NCBI Gene ID) 100505510).

The term "oncogene inhibitor" refers to a compound (or drug that includes a compound) that inhibits the function of an oncogene present in ecDNA. The compound can be e.g. small molecule or antibody, but is not limited to such. Oncogene inhibitors include inhibitors of chromosomal oncogenes, which due to the present discoveries by the present inventors, are believed to act similarly against ecDNA oncogenes (which are shortened versions of the corresponding full length chromosomal oncogenes). The oncogene inhibitors herein, although they may have been originally developed to inhibit chromosomal oncogenes, may be used in the present invention to inhibit one or more oncogenes present in ecDNA to either slow or stop the proliferation or growth of the tumor.

The terms "orthotopic xenograft models" and "orthotopic xenografts" are patient derived xenograft (PDX) tumor models in which tumors or tumor cells are either implanted or injected into the equivalent organ from which the cancer originated. Orthotopic xenograft models have similar tumor microenvironment as the original tumor and are therefore deemed to more closely resemble the natural tumorigenesis in human. In the orthotopic PDX models described herein, following IACUC guidelines in an institutionally approved animal use protocol, GBM neurosphere cell suspensions are implanted into 8-week old female nude (immunodeficient) mice. The PDX experiments herein are performed in nude mice, also known as "athymic nude mice". The PDX studies may also be performed with severely compromised immunodeficient mice (SCID), as well as with genetically modified mice such as NSG (NOD.Cg-Prkdcscidl12rgtm1Wj1/ SzJ1) marketed by The Jackson Laboratory.

In the present PDX models, animals are anesthetized and dissociated neurosphere cells are injected using a syringe at a defined intracranial location. Alternatively, tumor cells from the tumor specimen, which have not been grown in a neurosphere culture, are injected into the animal. Animals are monitored by an observer blinded to the group allocation and sacrificed upon first signs of neurological deficit or weight loss greater than 20%. Brains are harvested, and placed in a coronal matrix for 2 mm sections, with the first cut across the implant site. Brain sections are alternately frozen in dry ice and embedded for storage. For subcutaneous xenografts, dissociated neurosphere cells (or tumor specimen cells) are injected in the flank of nude mice. Animals are sacrificed, and tumors excised when diameter reaches a certain size. Both of these models may be varied, as would be apparent to those skilled in the art.

PDGFRA, i.e. platelet-derived growth factor receptor A, also termed PDGFRα, i.e. platelet-derived growth factor receptor α, is a receptor located on the surface of a wide range of cell types. This receptor binds to certain isoforms of platelet-derived growth factors (PDGFs) and thereby becomes active in stimulating cell signaling pathways that elicit responses such as cellular growth and differentiation. The receptor is critical for the development of certain tissues and organs during embryogenesis and for the maintenance of these tissues and organs, particularly hematologic tissues, throughout life. Mutations in the gene which codes for PDGFRA, i.e. the PDGFRA gene, are associated with an array of clinically significant neoplasms. The PDGFRA gene is (RefSeq Gene ID (=NCBI Gene ID) 5156).

The PIK3CA gene is an oncogene involved in many complex and intricate intracellular signaling pathways, including the PI3K-AKT-mTOR network. This pathway plays an important role in the regulation of cell growth, proliferation, differentiation, motility, survival, metabolism, and protein synthesis. The PIK3CA gene is (RefSeq Gene ID (=NCBI Gene ID) 5290).

RP56 is also known as IMPG2 interphotoreceptor matrix proteoglycan 2. The protein encoded by this gene binds chondroitin sulfate and hyaluronan and is a proteoglycan. The encoded protein plays a role in the organization of the interphotoreceptor matrix and may promote the growth and maintenance of the light-sensitive photoreceptor outer segment. The RP56 gene is (RefSeq Gene ID (=NCBI Gene ID) 50939, HGNC Symbol=IMPG2).

Transcription activator BRG1 also known as ATP-dependent chromatin remodeler SMARCA4 is a protein that in humans is encoded by the SMARCA4 gene. The SMARCA4 gene is (RefSeq Gene ID (=NCBI Gene ID) 6597).

SRY (sex determining region Y)-box 2, also known as SOX2, is a transcription factor that is essential for maintaining self-renewal, or pluripotency, of undifferentiated embryonic stem cells. Sox2 has a critical role in maintenance of embryonic and neural stem cells. Sox2 is a member of the Sox family of transcription factors, which have been shown to play key roles in many stages of mammalian development. The SOX2 gene is (RefSeq Gene ID (=NCBI Gene ID) 6657).

"Telomerase reverse transcriptase" (abbreviated to TERT, or hTERT in humans) is a catalytic subunit of the enzyme telomerase, which, together with the telomerase RNA component (TERC), comprises the most important unit of the telomerase complex. Somatic mutations in the promoter of the gene for telomerase reverse transcriptase (TERT) are the most common noncoding mutations in cancer. The TERT gene is (RefSeq Gene ID (=NCBI Gene ID) 7015).

"Transcriptomic" means of or pertaining to a transcriptome. Transcriptome is the complete set of RNA molecules (transcripts) produced in a cell or a population of cells.

"Whole genome sequencing" (also known as WGS, full genome sequencing, complete genome sequencing, or entire genome sequencing) is a laboratory process that determines the complete DNA sequence of an organism's genome at a single time. Whole genome sequencing entails sequencing all of an organism's chromosomal DNA as well as DNA contained in the mitochondria. According to non-limiting examples, Illumina and Pac Bio equipment and/or methods may be used to perform whole genome sequencing.

A "xenograft" is a tissue graft or organ transplant from a donor of a different species from the recipient.

Recognizing that ecDNA may play an important role in tumorigenesis, and gliomagenesis, the present inventors have performed research and experiments, the results of which provide direct evidence that ecDNA enhance genomic diversity during tumor evolution, and show how ecDNA elements mark major clonal expansion in otherwise stable genomic background. The inventors' analysis provides a comprehensive study of the fate of chromosomal SNVs and ecDNA oncogene amplifications in GBM in a panel of tumors and derivative models. The inventors further demonstrate the widespread presence of ecDNA driven oncogene amplification through extensive FISH analysis on sets of paired primary and recurrent tumor samples. Focal gene amplifications have traditionally been recognized as homogeneously staining regions (HSR) and these may originate from chromosomal insertions of ecDNA. The inventors did not observe HSR-like staining patterns for the amplified genes in this study, which suggests that this is not a common mechanism for gene amplification in GBM.

Figure 6:
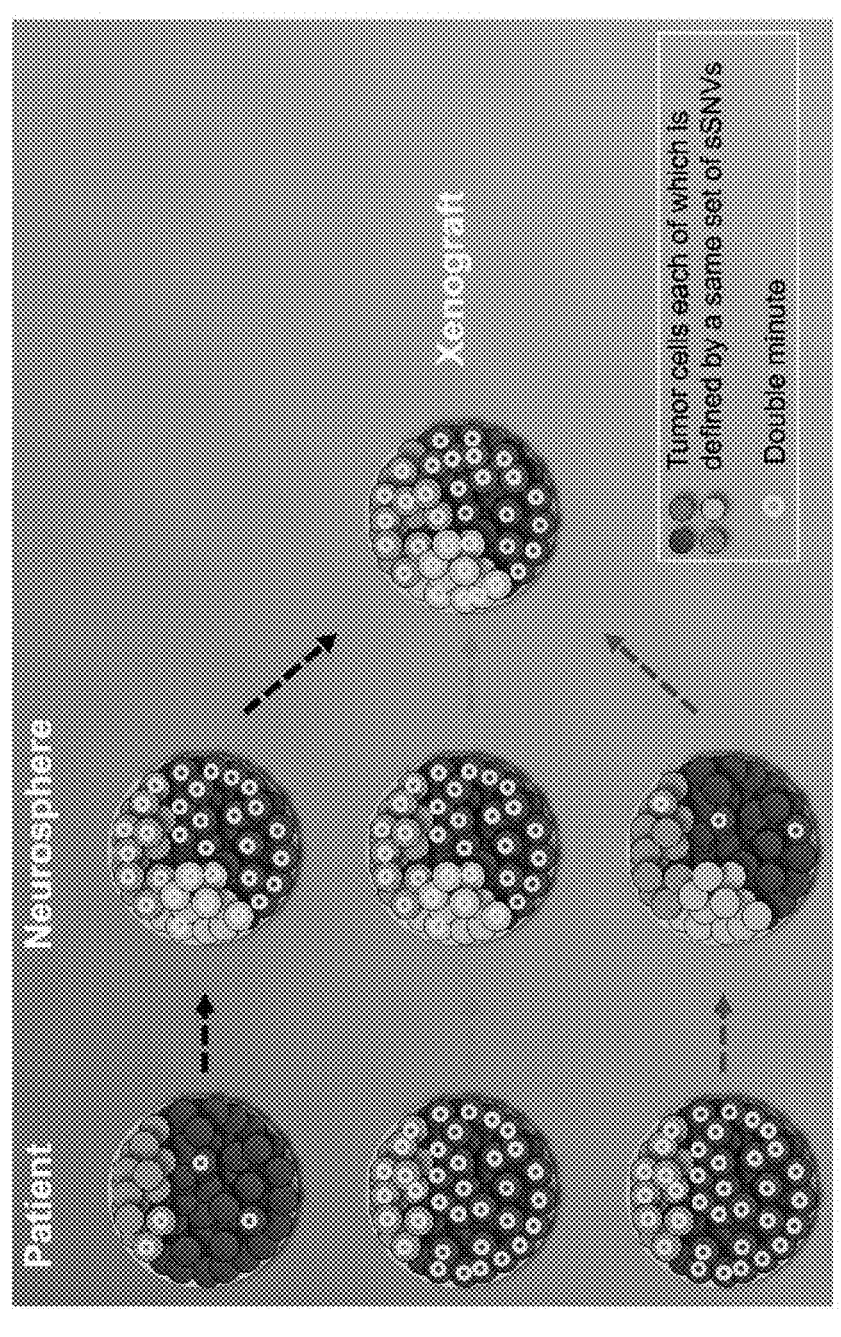
FIG. 6 depicts a schematic illustration of extrachromosomal DNA element contribution to clonal evolution in GBM patient derived models. The proliferation patterns in GBM tumors and models in which ecDNAs provide a dominant evolutionary force.

The inventors captured the early stages of Mir ecDNA expansion in the patient tumors (e.g., HF3016 and HF2354 tumors) with 0.5-2% of cells presenting amplification (<30 copies/nucleus), with no evidence of chromosomal based gene amplification, while in all derived models, as well as the HF3016 recurrence (HF3077), the frequency of MYC amplification increased to 100% of cells with up to 100 copies/nucleus. These results are consistent with an origin through excision of a MYC containing chromosomal DNA segment and end joining into a circular ecDNA, with subsequent amplification of the ecDNA, followed by selection of MYC-amplified cells in vitro and in the recurrent minor. Spindle assembly and chromosome segregation during mitosis lead to genetically identical daughter cells, containing similar sets of chromosomal sSNVs and DNA copy number alterations. Double minutes (represent small fragments of ecDNAs are replicated during S-phase, but lack the centromeres that dictate the organization of the mitotic spindle, and as a result are randomly distributed across the daughter cells during mitosis. EcDNA elements thus inherit in a radically different fashion than chromosomes. This divergence in inheritance mechanism may explain, for example, why the evolution of the MET event was not similarly captured by sSNVs (see FIG. 6), and shows that extrachromosomal elements play a key role in increasing genomic diversity during tumor evolution. FIG. 6 depicts a schematic illustration of extrachromosomal DNA element contribution to clonal evolution in GBM patient derived models. The proliferation patterns in GBM tumors and models in which ecDNAs provide a dominant evolutionary force.

The present inventors have found the extrachromosomal bodies containing oncogenes provide a therapeutic target in treating gliomas such as glioblastomas. The oncogene inhibition in the ecDNA eliminates the driver genes in glioblastoma, confirming the clinical application of using oncogene in ecDNA as a target; for example, a target against MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1, present in ecDNA. The present invention represents the first time showing that oncogene inhibition of the MET oncogene in ecDNA, for example, has good efficacy. In a preferred embodiment, the present invention provides MET inhibition target against the MET oncogene present in ecDNA as possessing, clinical efficacy and promise, in patients having MET ecDNA oncogenes.

The present study is consistent with the observation that double minutes are present in 10-40% of GBM. These lesions frequently involved genes on chromosome 12p, including CDK4 and MDM2, span up to several megabases in size, and can be recognized by an intermittent amplification-deletion DNA copy number pattern. The present inventors have identified the presence of ecDNA and specific oncogenes contained therein. The present data show that ecDNA may vary in size. This study confirms that it is the oncogene(s) present in ecDNA that affects the mechanism of tumorigenesis. The present invention emphasizes the importance of targeting oncogene inhibition present in ecDNA as a treatment for gliomagenesis.

The present inventor discovered that the oncogene present in ecDNA drives tumor growth and progression. The present invention provides identification of a drug that targets against the ecDNA oncogene. Such drug and drug candidates shall sufficiently inhibit the ecDNA oncogene activity to inhibit brain tumor growth and brain tumor progression.

According to non-limiting example embodiments, the invention provides a method of identifying a drug that targets against an oncogene present in an extrachromosomal DNA (ecDNA) in a human suffering from glioma. Such method includes providing a brain tumor specimen from a human suffering from glioma; performing whole genome sequencing on the brain tumor specimen; determining the presence of an ecDNA in the brain tumor specimen (e.g., by gene alignment) based on the whole genome sequencing; identifying the presence of an oncogene present in the ecDNA, wherein the oncogene is an oncogene selected from the group consisting of MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; and identifying a drug targeted against the oncogene, wherein the drug inhibits the function of the oncogene, so as to inhibit tumor growth of the glioma in the human. According to example embodiments, the identified oncogene present in the ecDNA is an ecDNA oncogene that matches a significant portion (e.g., 90%, 94%, 95%, 98%, or 99% or more in length) of a corresponding full length chromosomal oncogene of the same name.

Non-limiting example methods optionally include first identifying a human suitable for treatment, e.g by diagnosing glioma in the human.

According to example embodiments, the method also includes administering the identified drug targeted against the oncogene present in the ecDNA to the human, in an amount sufficient to treat glioma in the human. The oncogene inhibitor (also referred to herein as a drug, which includes the oncogene inhibitor) may be administered in the form of a pharmaceutical compound or a pharmaceutically acceptable salt or prodrug thereof. The oncogene inhibitor may be formulated for various methods of administration known to those skilled in the art. In some embodiments, the pharmaceutical composition is formulated for intravenous injection, subcutaneous injection, oral administration, or topical administration. In sonic embodiments, the pharmaceutical composition is a tablet, a pill, a capsule, a liquid, a suspension, a gel, a dispersion, a solution, an emulsion, an ointment, or a lotion.

Methods of administration may include any method known to those skilled in the art. By way of non-limiting example, drugs herein may be administered to a human in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In the present aspects, further embodiments include various doses and administrations of an effective amount of the drug. Example embodiments may be formulations for the drug to be administered once; multiple times over the span of one day; multiple times over multiple days, continuously, etc, depending on the patient and the identified oncogenes and drugs to be used. The present drugs may be administered over multiple days or weeks, as may be determined by those skilled in the art. Suitable doses and frequency of administration would be known, or may be determined by those skilled in the art.

Methods may also include administering the drug in a form effective for treatment, which form may include one or more excipients. Also included herein are combination therapies, which may include administration of one or more oncogene-inhibiting drugs or formulations, and alternatively one or more additional drugs or treatments. By way of non-limiting example, the additional drugs or treatments may include one or more of an anti-inflammatory agent, an immunomodulatory agent, chemotherapeutic agent, an apoptosis-enhancer, a neurotropic factor, an anti-viral agent, and the like.

In non-limiting examples of the present methods, the glioma may be glioblastoma. According to further embodiments, the glioma is adult glioblastoma. In example embodiments, the glioma is a primary glioma and in other embodiments it is a recurrent glioma.

In examples of the present invention, the whole genome sequencing is performed using Illumina sequencing or PacBio sequencing, although it should be understood that other whole genome sequencing methods may be used.

According to example embodiments, gene alignment is performed using sequence alignment software, such as Burrows-Wheeler Aligner (BWA), from sequences derived from a biospecimen that are aligned to the reference of the human genome, to identify the presence of ecDNA, wherein misalignment against a reference gene is indicative of the presence of ecDNA.

According to example embodiments, determination of the presence of ecDNA the determination of the presence of ecDNA is performed by sequence alignment followed by identifying misalignment against a reference gene, wherein said misalignment against a reference gene is indicative of the presence of ecDNA. According to non-limiting embodiments, the presence of ecDNA is confirmed by performing Amplicon *Architect method.

The oncogene(s) present in ecDNA, identified by whole gene sequencing, include a large portion of the length of known oncogenes, such as MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1. As discussed above, the ecDNA oncogenes comprise a significant portion of the length of their full length chromosomal counterparts. By way of non-limiting example embodiment, the oncogene(s) present in ecDNA are 90%, 94%, 95%, 98%, 99% or longer of the length of MET, MET/CAPZA2, MDM2, CDK4, SOX2, PIK3CA, MECOM, PDGFRA, EGFR, MYCN, MYC, TERT, SMARCA-1, RP56, FBXW7, CDK6, CCND2, ERBB2, BRCA1, and BAP1 chromosomal oncogenes. The ecDNA oncogenes identified in the present invention are identical to or substantially the same as the corresponding portion of the corresponding full length chromosomal oncogenes. However, the ecDNA oncogenes are shorter in length than the full length chromosomal DNA oncogenes. The ecDNA oncogenes may be shorter than full length chromosomal DNA oncogenes by either not including the first portion of the chromosomal DNA oncogene, the end of the chromosomal DNA oncogene, or by not including portions of chromosomal DNA oncogene at both ends.

The genebank numbers of the chromosomal DNA oncogenes are as set forth above. By way of non-limiting example, the sequence of MET on the ecDNA in a particular patient (HF3077, noting that the sequences vary from patient to patient) is provided herein as SEQ ID NO. 9 (FIG. 29). The sequence of MET/CAPZA2 ecDNA in a particular patient (noting that the sequences vary from patient to patient) is provided herein as SEQ ID NO. 8 (FIG. 28) by way of non-limiting, example.

According to non-limiting example embodiments, the oncogene(s) present in ecDNA, identified by whole gene sequencing include significant portions of known full length chromosomal oncogenes, including e.g., MET, MET/CAPZA2, MDM2, CDK4, PIK3CA, MECOM, PDGFRA, EGFR, and MYCN, and MYC. By way of non-limiting example embodiment, the oncogene(s) present in ecDNA include 90%, 94%, 95%, 98%, 99% or higher portion of the full length of chromosomal MET, MET/CAPZA2, MDM2, CDK4, SOX2, PIK3CA, MECOM, PDGFRA, EGFR, MYCN, and MYC. Genes can fuse with other gene partners. Therefore, further included herein are fusion genes of the ecDNA oncogenes herein. "Fused genes", "fusion genes", or "gene fusions" as those terms are used herein, are genes that are present together in ecDNA. In yet further examples of the present methods, the oncogene comprises MET or MET/CAPZA2. The oncogene(s) present in ecDNA have a 90%, 94%, 95%, 98%, 99% or higher portion of the length of chromosomal MET or MET/CAPZA2, and other oncogenes.

The sequence of the MET ecDNA oncogene is a lengthy portion (or substantially identical lengthy portion) of the full length chromosomal MET DNA, and because the length of the MET ecDNA is such a significant length of full length chromosomal MET, and acts functionally the same as chromosomal MET, it has enough similarity to determine that it is the ecDNA MET oncogene. The ecDNA MET oncogene has the same or similar function and result as the full length chromosomal MET oncogene. In the present invention, in example embodiments, the percentage overlap of the two MET ecDNAs with the wild type MET is 93.9% and 99.4%, respectively, but because each patient is different, and the ecDNA oncogene is different, these percent of length overlap should not be deemed limiting.

The function of the ecDNA oncogenes (which are shortened versions of the full length chromosomal DNA oncogenes) are the same as, or similar to the function of the chromosomal DNA oncogenes. They function similarly in promoting tumor growth. The ecDNA oncogenes are believed to be the driving force of tumor growth in glioma tumors. The result is the same for ecDNA oncogenes as for full length chromosomal oncogenes, tumor growth, and tumor progression.

According to example embodiments, more than one oncogene may be present and therefore, more than one drug may be identified as targeting against the more than one oncogene.

In example embodiments, where the identified ecDNA oncogene is MET or MET/CAPZA2, then in certain embodiments, the drug comprises at least one MET-inhibitor drug selected from capmatinib and crizotinib. Other MET-inhibitors are known in the art or may be further developed that may be used in the present invention. By way of non-limiting example. MET-inhibitors may include one or more of the following: Capmatinib (INC280, Novartis), Crizotinib (PF-02341066, Pfizer), Cabozantinib (XL184, Exelixis), Cabozantinib (XL184, Exelixis), ABBV-399 (AbbVie), ABT-700 (AbbVie), ABT-700 (AbbVie), AMG-208 (Amgen), MK-2461 (Merck Sharp & Dohme Corp), Tepotinib (EMD 1214063, EMD Serono/Merck KGaA), JNJ-38877605 (Johnson & Johnson), BMS-817378 (Bristol-Myers Squibb), Foretinib (GSK1363089, GlaxoSmithKline), SGX-523 (SGX Pharmaceuticals). It should be understood that some of the above-listed inhibitors are also inhibitors of MET/CAPZA2, ALK, and/or other oncogenes and fused genes and may be used to inhibit such oncogenes and fused genes. Inhibitors of each of the oncogenes listed herein are included herein as inhibitors of corresponding ecDNA oncogenes. By way of non-limiting example, oncogene-inhibitors that may be used in connection with inhibiting the present ecDNA oncogenes, may include presently known, or to be developed inhibitors of each of the following oncogenes: MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1. Non-limiting examples of oncogene inhibitors that may be used in accordance with the present invention include the following: EGFR—cetuximab, erlotinib, and gefitin; CDK4—alvociclib, abemaciclib, palbociclib, and ribociclib; PDGFRA—imatinib, sunitinib, and nilotinib; PIK3CA—alpelisib; TERT—Imetelstat; CDK6—alvociclib, abemaciclib, palbociclib, and ribociclib; ERBB2—Trastuzumab, and pertuzumab.

The present methods optionally further include verifying the presence of ecDNA using fluorescence in situ hybridization (FISH), such as interphase FISH. The present methods may also include verifying the presence of the ecDNA oncogene using FISH.

According to other non-limiting example embodiments, the present method further includes preparing a neurosphere cell culture by dissociating the brain tumor specimen and placing the dissociated brain tumor specimen in growth medium to culture into neurosphere cell cultures; implanting the neurosphere cell cultures into a patient-derived xenograft (PDX) mouse, and allowing tumor cells from the neurosphere cell cultures to grow in the PDX mouse for a predetermined time period; and administering the identified drug targeted against the oncogene into the PDX mouse, and determining if the identified drug inhibits tumor glioma growth in the PDX mouse. Inhibition of tumor glioma growth in the PDX mouse is indicative of a suitable drug for targeting glioma in the human.

According to further non-limiting example embodiments, the present method includes implanting tumor specimen cells into a patient-derived xenograft (PDX) mouse directly, and allowing tumor cells to grow in the PDX mouse for a predetermined time period; and administering the identified drug targeted against the oncogene into the PDX mouse, and determining if the identified drug inhibits tumor glioma growth in the PDX mouse. Inhibition of tumor glioma growth in the PDX mouse is indicative of a suitable drug for targeting glioma in the human.

According to further non-limiting embodiments, included herein are methods of identifying a drug that targets against an oncogene present in an extrachromosomal DNA (ecDNA) in a human suffering from glioma, that include providing a brain tumor specimen from a human suffering from glioma and performing whole genome sequencing on the brain tumor specimen. The method includes determining the presence of an ecDNA in the brain tumor specimen (e.g., by gene alignment) based on the whole genome sequencing; identifying the presence of an oncogene present in the ecDNA, wherein the oncogene is an oncogene selected from the group consisting of MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; and identifying a drug targeted against the oncogene, wherein the drug inhibits the function of the oncogene so as to inhibit the tumor growth of the glioma in the human. The brain tumor specimen is implanted into a patient-derived xenograft (PDX) mouse, and allowing the brain tumor cells to grow in the PDX mouse for a predetermined time period. The identified drug is administering into the PDX mouse containing the implanted brain tumor specimen; and then it is determined if the identified drug inhibits tumor glioma growth in the PDX mouse; wherein inhibition of tumor glioma growth in the PDX mouse is indicative of the identified drug being suitable for treating the glioma in the human.

The present methods may also include administering the drug targeted against the oncogene to the human, in an amount sufficient to treat glioma in the human.

As in other methods herein, the determination of the presence of ecDNA is performed by sequence alignment followed by identifying misalignment against a reference gene, wherein said misalignment against a reference gene is indicative of the presence of ecDNA.

The presence of ecDNA is confirmed by performing Amplicon Architect method.

As in other methods herein, when more than one oncogene is present in the ecDNA, then more than one drug is identified as targeting against the more than one oncogene.

According to example embodiments, the oncogene includes an oncogene selected from MET, MET/CAPZA2, MDM2, CDK4, SOX2, PIK3CA, MECOM, PDGFRA, EGFR, MYCN, and MYC, and fusion genes thereof. According to further examples, the oncogene is MET or MET/CAPZA2.

The present invention also includes verifying the presence of ecDNA and/or an oncogene using fluorescence in situ hybridization (FISH).

Also provided herein, is a method of screening a drug candidate for treatment of glioma in a human suffering from glioma. Such method includes providing a brain tumor specimen from a human suffering from glioma; performing whole genome sequencing on the brain tumor specimen;

determining the presence of an ecDNA in the brain tumor specimen based on the whole genome sequencing; identifying the presence of an oncogene present in the ecDNA, wherein the oncogene is an oncogene selected from MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; implanting the brain tumor specimen into a patient-derived xenograft (PDX) mouse, and allowing brain tumor cells to grow in the mouse for a predetermined time period; administering a drug candidate into the PDX mouse, the PDX mouse containing the implanted brain tumor specimen; and determining the tumor glioma growth in the PDX mouse, wherein inhibition of the tumor glioma growth in the PDX mouse receiving the drug candidate is indicative of the drug candidate in treating glioma in the patient. In examples of the present invention, tumor growth in the PDX mouse is compared to tumor growth in a control PDX mouse, to which a control drug was administered, or no drug administered. Examples of the present methods may further include measuring mortality (e.g. mean survival time) of the PDX mouse as compared to a control mouse that is not administered the drug.

The drug candidate may be administered to the PDX mouse at a suitable frequency and over a suitable period of time (such as, but not limited to, once a day for five days), which may be determined by one skilled in the art.

Further example methods are directed to identifying a drug that targets against an oncogene present in an extrachromosomal DNA (ecDNA) in a human suffering from glioma, including providing a brain tumor specimen from a human suffering from glioma; performing whole genome sequencing on the brain tumor specimen; determining the presence of an ecDNA in the brain tumor specimen by gene alignment based on the whole genome sequencing; identifying the presence of an oncogene present in the ecDNA, wherein the oncogene is an oncogene selected from the group consisting of MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; identifying a drug targeted against the oncogene, wherein the drug inhibits the function of the oncogene so as to inhibit the tumor growth of the glioma in the human; implanting the brain tumor specimen into a patient-derived xenograft (PDX) mouse, and allowing the brain tumor (glioma) cells to grow in the mouse for a predetermined time period; administering the identified drug into the PDX mouse containing the implanted brain tumor specimen, and determining if the selected drug inhibits tumor glioma growth in the PDX mouse; wherein inhibition of tumor glioma growth in the PDX mouse is indicative of a suitable drug for targeting glioma in the human.

The drug candidate may be administered to the PDX mouse at a suitable frequency and over a suitable period of time (such as, but not limited to, once a day for five days), which may be determined by one skilled in the art.

Tumor growth in the PDX mouse is compared to tumor growth in a control PDX mouse, to which a control drug was administered; and wherein inhibition of tumor glioma growth in the PDX mouse compared to the control mouse, is indicative of the drug being suitable for targeting glioma in the human.

Examples of the present methods include administering the drug targeted against the oncogene to the human, in an amount sufficient to treat glioma in the human.

As indicated above, further embodiments of these and other methods throughout this application include the following. Non-limiting example methods optionally include first identifying a human suitable for treatment, e.g. by diagnosing glioma in the human. According to example embodiments, the method also includes administering the drug targeted against the oncogene to the human, in an amount sufficient to treat glioma in the human. In non-limiting examples, the glioma is glioblastoma. According to further embodiments, the glioma is adult glioblastoma. In other embodiments, the glioma is a recurrent glioma. In examples of the present invention, the whole genome sequencing is performed using Illumina sequencing or PacBio sequencing. According to example embodiments, gene alignment is performed using sequence alignment software, such as Burrows-Wheeler Aligner (BWA), to identify the presence of ecDNA, wherein misalignment against a reference gene is indicative of the presence of ecDNA. The oncogene(s) present in ecDNA, identified by whole gene sequencing include 90%, 94%, 95%, 98%, 99% or higher of the length of chromosomal MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1.

According to example embodiments, more than one oncogene may be present and therefore, more than one drug may be identified as targeting against the more than one oncogene. In example embodiments, the identified oncogene is ecDNA is MET or MET/CAPZA2. If MET oncogene is present in ecDNA, then in certain embodiments, the drug comprises at least one MET-inhibitor drug selected from capmatinib and crizotinib. The present methods optionally further include verifying the presence of ecDNA using interphase fluorescence in situ hybridization (FISH).

Also provided herein are methods of screening drug candidates for treatment of glioma in a human subject suffering from glioma, comprising: providing a brain tumor specimen from a human suffering from glioma; performing whole genome sequencing on the brain tumor specimen; determining the presence of an ecDNA in the brain tumor specimen by gene alignment based on the whole genome sequencing; identifying the presence of an oncogene present in the ecDNA, wherein the oncogene is an oncogene selected from the group consisting of MET, MET/CAPZA2, MDM2, CDK4, SOX2, PIK3CA, MECOM, PDGFRA, EGFR, MYCN, MYC, TERT, SMARCA4, RP56, FBXW7, CDK6, CCND2, ERBB2, BRCA1, and BAP1; identifying and selecting a first drug candidate targeted against the oncogene, wherein the drug candidate inhibits the function of the oncogene so as to inhibit the tumor growth of the glioma in the human; implanting the brain tumor specimen into a patient-derived xenograft (PDX) mouse, and allowing the glioma cells to grow in the mouse for a predetermined time period; administering the identified first drug candidate into the PDX mouse containing the implanted brain tumor specimen. The method further includes repeating the above steps of identifying and selecting a first drug candidate targeted against the oncogene, wherein the drug candidate inhibits the function of the oncogene so as to inhibit the tumor growth of the glioma in the human; implanting the brain tumor specimen into a patient-derived xenograft (PDX) mouse, and allowing the glioma cells to grow in the mouse for a predetermined time period; and administering the identified first drug candidate into the PDX mouse containing the implanted brain tumor specimen at least once; with a second or more drug candidate targeted against the oncogene, and comparing inhibition of the tumor glioma growth in the PDX mouse; to determine the most effective drug candidate for targeting the ecDNA oncogene in the human.

The present methods also include administering the most effective drug candidate for targeting the ecDNA oncogene in the human, to the human in an amount sufficient to treat glioma in the human.

Also provided herein are methods of diagnosing glioblastoma or recurrent glioblastoma and methods of screening or monitoring for recurrence of glioblastoma. These methods include obtaining a brain tumor specimen from a human subject having a brain tumor, preparing a PDX mouse model as discussed herein, and determining the presence of ecDNA and oncogenes present in the ecDNA if there are ecDNA in the mouse. If ecDNA and oncogenes present in the ecDNA are in the PDX mouse tumor model from a glioblastoma cell line, glioblastoma is diagnosed in the human/patient. According to non-limiting example embodiments, these methods may include preparation of a neurosphere cell culture from the specimen and implanting the neurosphere cells in the mouse.

Other non-limiting example embodiments of the present invention include methods of validating a predicted presence of ecDNA in a brain tumor. Example methods include preparing fluorescence in situ hybridization (FISH) probes from purified BAC clones and fluorescently labeling the probes; obtaining neurosphere cell cultures by a method that includes obtaining a brain tumor specimen from a human subject suffering from a brain tumor; dissociating the brain tumor specimen and placing the dissociated tumor sample in growth medium to culture into neurosphere cell cultures; and snap freezing a portion of each tumor specimen to cryogenically fix the neurosphere cell cultures. The method includes preparing metaphase FISH slides from the cryogenically fixed neurosphere cell cultures; applying the FISH probes to each sample slide; and examining the slides under a fluorescence microscope or acquiring FISH images, and determining from the examination of FISH images if ecDNA amplifications are present in the sample, wherein metaphase FISH on neurosphere cell culture slides validates the presence of ecDNA amplifications. Neurosphere steps may or may not be necessary.

FISH validation of the presence of ecDNA may also be used in a PDX mouse model by obtaining a brain tumor specimen from a human subject suffering from a brain tumor; and obtaining macrodissected xenograft tumor samples by a method that includes either implanting neurospheres that have not been snap frozen, into an immunodeficient mouse or implanting brain tumor cells from the tumor specimen directly into the immunodeficient mouse, and allowing the tumor cell to grow for a predetermined time period, obtaining brain samples of the immunodeficient mouse, freezing the brain samples, and cutting sections of the brain samples having tumor tissue to obtain macrodissected xenograft tumor samples; preparing interphase FISH slides from the macrodissected xenograft tumor samples; applying the FISH probes to each sample slide; and examining the slides under a fluorescence microscope or acquiring FISH images, and determining from the examination of FISH images if ecDNA amplifications are present in the sample.

The following examples are provided to further illustrate various non-limiting embodiments and techniques of the present method, including experiments performed in developing the present method. It should be understood, however, that these examples are meant to be illustrative and do not limit the scope of the claims. As would be apparent to skilled artisans, many variations and modifications are intended to be encompassed within the spirit and scope of the invention.

EXAMPLES

Example 1

Tumor Sample Collection and Cell Culture

The inventors collected resected brain tumor specimens at Henry Ford Hospital (Detroit, MI) with written informed consent from patients, under a protocol approved by the Henry Ford Hospital Institutional Review Board, and graded pathologically according to the WHO criteria. The inventors snap froze and stored a portion of each tumor specimen in liquid nitrogen. was. They used an adjacent portion for cell culture. The inventors dissociated the tumor specimens enzymatically and cultured neurospheres enriched in cancer stem-like cells (CSC). In this study, the inventors adopted the protocol as detailed in Hasselbach, L. A. et al. Optimization of High Grade Glioma Cell Culture from Surgical Specimens for Use in Clinically Relevant Animal Models and 3D immunochemistry, *J Vis Exp* 83, e51088 (2014); and deCarvalho, Gliosarcoma stem cells undergo glial and mesenchymal differentiation in vivo. *Stem Cells* 28, 181-90 (2010). These references are incorporated herein by reference, in their entirety.

After dissociation of the fresh tumor sample, the inventors place tumor cells in growth medium in culture. In particular, dissociated cells were grown in neurosphere medium (NM), composed of DMEM/F-12 supplemented with N2 (Gibco), 0.5 mg/ml BSA (Sigma), 25 µg/ml gentamicin (Gibco), 0.5% antibiotic/antimycotic (Invitrogen), 20 ng/ml basic fibroblast growth factor (bFGF), and 20 ng/ml epidermal growth factor EGF (Peprotech).

After the neurospheres were formed the inventors dissociated the neurospheres and re-plated in 3× the original media volume, this is passage 1. From then on, roughly every 10 days the inventors dissociated the neurospheres and re-plated, being 1 passage older each time. For this work, the inventors used neurosphere cultures that were between 7 and 18 passages.

The inventors serially passaged neurosphere cultures in vitro. No mycoplasma contamination was identified in the subset of samples tested. The inventors used cells with passages between 7 and 18 for mouse implants and molecular analysis, except for those designed "high passage", where the inventors used passage 40.

Example 2

Patient Derived Xenografts (PDX)

Orthotopic xenografts: Following IACUC guidelines in an institutionally approved animal use protocol, the inventors implanted the GBM neurosphere cell suspensions into 8-week old female nude mice (NCRNU, Taconic Farms) (i.e. immunodeficient mice) using the protocol described in Berezovsky, A. D. et al. SOX2 promotes malignancy in glioblastoma by regulating plasticity and astrocytic differentiation, *Neoplasia* 16, 193-206 e25 (2014), which is incorporated herein by reference. It should be noted that other "nude" or "immunodeficient" mice may be used in the present invention, as would be apparent to those skilled in the art. Thus, the present invention is not limited to the specific nude mice used in this experiment. The inventors implanted a minimum of 8 mice with each neurosphere line.

Animals were anesthetized with a mixture of ketamine and xylazine. The inventors injected dissociated neurosphere cells ($3\times10^5$) using a Hamilton syringe at a defined intracranial location: AP+1.0, ML+2.5, DV-3.0. Animals were monitored daily by an observer blinded to the group allocation and sacrificed upon first signs of neurological deficit or weight loss greater than 20%. Brains were harvested, placed in a coronal matrix for 2 mm sections, with the first cut across the implant site. Brain sections were alternately frozen in dry ice and embedded in an optimal cutting temperature (OCT) compound before freezing, for storage at −80° C., or formalin fixed and paraffin embedded (FFPE).

Subcutaneous xenografts: Dissociated neurosphere cells ($1\times10^6$) were injected in the flank of nude nice. Animals were sacrificed and tumors excised when diameter reached 10 mm.

Example 3

Drug Treatment

The inventors treated HF3077 PDXs with capmatinib (purchased from Matrix Scientific Products (Columbia, SC)) suspensions in 0.5% methylcellulose/0.1% Tween 80 were prepared every week and administered by oral gavage using a 20 g×1.5" gavage needle (Cadence) at a dose of 30 mg/kg once a day (5 days/week) until the end of the study. Control animals received vehicle only mock gavage. Forty-five days after implant, animals were randomized to control or treatment groups. Each mouse was followed until death with no censoring and mean survival differences were estimated using a t-distribution to estimate 95% confidence intervals. With a sample size of nine (9) mice per group, a two-sided 95% confidence interval for the difference in mean survival would extend 0.92SD from the observed difference in mean survival, assuming the CI is based on large sample z statistic. Equivalently 80% power was expected to detect a difference in mean survival of 1.4SD, for the common standard deviation, when n=9 animals per group and alpha=0.05. Animals were monitored daily and sacrificed upon first signs of neurological deficit or weight loss greater than 20%. Control animals were administered vehicle. Kaplan-Meier Survival curves were compared by log-rank test.

To evaluate brain penetrance of capmatinib, the inventors drew blood samples two hours after administration of the last capmatinib 30 mg/kg dose, sacrificed the animals, harvested brains, and froze 2 mm coronal sections in OCT. The inventors dissected tumor tissue from the frozen blocks. The inventors determined capmatinib concentration in homogenized tumor tissue and plasma for three treated animals and one control was quantified by LC-MS/MS.

Example 4

Xenograft Tumor Macrodissection of Frozen Tissue

For xenograft tumor microdissection, the inventors used brain samples of 3 randomly selected animals per xenograft line. Frozen 2 mm coronal sections were transferred to a cryostat (Cryotome E, ThermoElectronCorporation) set to −16° C. Six μm sections were cut and stained with hematoxylin, to locate the tumor. Tumor tissue was excised from the frozen block with a scalpel into a pre-chilled microtube and stored at −80° C.

Example 5

Nucleic Acids Isolation

For nucleic acids isolation, the inventors isolated genomic DNA from frozen tumor samples, macrodissected xenograft tumor (3 biological replicates), and neurosphere cultures using QIAamp DNA mini Kit (Qiagen 451304), with on column RNase A digestion, following the manufacturer's instructions. DNA was isolated from blood using a DNA QIAamp Blood kit (Qiagen).

Total RNA was extracted from frozen tumor samples, macrodissected xenograft tumor (3 biological replicates), and neurosphere culture using MirVana (Ambion #AM1560), followed by DNAse treatment using DNA-free (Ambion AM1906).

Example 6

Fluorescence In Situ Hybridization (FISH)

FISH on matching tumor samples/neurospheres/PDX: The inventors prepared FISH probes from purified bacterial artificial chromosome (BAC) clones (BACPAC Resource Center, https://bacpacresources.org). Probes were labeled with Orange-dUTP or with Green-dUTP (Abbott Molecular Inc., Abbott Park, IL), by nick translation.

| Locus | Human BAC Clones: |
|---|---|
| 12q13.3-q14.1 (CDK4 gene) | RP11-181L23, RP11-571M6, RP11-277A02 |
| 7p11.2 (EGFR gene) | RP11-708P5, CTD-2026N22, RP11-148P17 |
| 8q24.21 (MYC gene) | CTD-3056O22 |
| 7q31 (MET gene) | RP11-95I20, RP11-564A14, RP11-39K12 |
| 4q12 (PDGFRA gene) | RP11-58C6 and RP11-977G3 |
| 4q11 (Ch. 4 control) | RP11-365H22 |
| 7q11.22, (Ch 7 control) | RP11-747K2, RP11-668K3 |
| 8q11.21 (Ch. 8 control) | CH17-311E13 and CH17-425G9 |

The inventors prepared metaphase slides from neurosphere cell cultures that were harvested and fixed in methanol:acetic acid (3:1), according to standard cytogenetic procedures. The inventors prepared tumor touch preparations by imprinting thawed tumor tissue onto positively-charged glass slides and fixing them in methanol:acetic acid (3:1) for 30 min then air-dried. The inventors prepared frozen tumor and macrodissected xenograft tumor samples by the protocol described in Graved, C. et al. Activating MET mutations produce unique tumor profiles in mice with selective duplication of the mutant allele. *Proc Natl Acad Sci USA* 101, 17198-203 (2004), which is incorporated herein by reference. The FISH probes were denatured at 75° C. for 5 min and held at 37° C. for 10-30 min until 10 μl of probe was applied to each sample slide. Slides were coverslipped and hybridized overnight at 37° C. in the ThermoBrite hybridization system (Abbott Molecular Inc.). The post-hybridization wash was with 2×SSC/0.2% TWEEN 20 at 73° C. for 3 min followed by a brief water rinse. Slides were air-dried and then counterstained with VECTASHIELD mounting medium with 4'-6-diamidino-2-phenylindole (DAPI) (Vector Laboratories Inc., Burlingame, CA).

The inventors acquired images at 1000× system magnification with a COOL-1300 SpectraCube camera (Applied Spectral Imaging-ASI, Vista, CA) mounted on an Olympus BX43 microscope. The inventors analyzed images using FISHView v7 software (ASI) and scored 100-200 interphase nuclei for each sample in addition to analysis of 50-100 metaphase spreads for each cell line.

FISH on paired primary/recurrent FFPE gliomas: The inventors performed a Fluorescence in situ assay using RPS6/Con 9, CDK4/Con 12, EGFR/con 7, MYC/con 8, PDGFRA/con 4, C-MET/con 7, TERT/Con 5 FISH probes from Empire Genomics (Buffalo, N.Y.). The slides were hybridized with the FISH probes according to the manufacturer's instructions with slight modifications. The slides were then examined under fluorescence microscope (Nikon 80i) equipped with multiple filters and signals were manually counted in 50 cells for each slide. See Table 5.

Example 7

Immunohistochemistry

The inventors deparaffinized sections of formalin fixed, paraffin embedded human glioma surgical samples, tumor xenografts, or multicellular spheroids with xylene and rehydrated through graded alcohol into in phosphate buffered saline. Antigens were unmasked by 10 min incubation in boiling in citrate buffer and sections stained with anti-MET rabbit monoclonal antibody (D1C2) (Cell signaling #8198) or anti-phospho-MET (Tyr1234/1235) rabbit monoclonal antibody (D26) (Cell signaling #3077) and visualized with Betazoid DAB (Biocare BDB2004) and counterstained with Envision Flex Hematoxylin (Dako K8008). Images were captured using an Eclipse E800M microscope equipped with a Nikon DS-Fi2 color digital camera (Nikon).

Example 8

Reverse Transcription and PCR

The inventors prepared cDNA from 1 µg DNAseI-treated total RNA isolated from tumor, neurosphere and xenografts using Superscript III Reverse Transcriptase and oligo dT (Thermo Fisher Scientific). cDNA was used as a template for PCR reaction in a iCycler instrument (BioRad), using Platinum Taq DNA Polymerase (Thermo Fisher Scientific) and the following oligos:Human MET: exon 2 forward (M2F): 5' AGCAATGGGGAGTGTAAAGAGG [SEQ. ID NO. 1] and exon 8 reverse (M8R): 5' GTAAGTAAAGTGC-CACCAGCC [SEQ. ID NO. 2]; Human CAPZA2 exon 1 forward (C1F): 5' GTAAGTAAAGTGCCACCAGCC [SEQ. ID NO. 3]; Human EGFR forward: 5'GCAGC-GATGCGACCCTCCGGG [SEQ. ID NO. 4] and reverse: 5'-CTATTCCGTTACACACTTTGCGG [SEQ. ID NO. 5]; Human b-actin: forward 5' CCGACAG-GATGCAGAAGGAG [SEQ. ID NO. 6] and reverse 5' CATCTGCTGGAAGGTGGACA [SEQ. ID NO. 7].

Example 9

LC-MS/MS Quantitation of Capmatinib and Crizotinib in Mouse Plasma and Tumor For mouse plasma sample analysis, the inventors precipitated 25 µL of each sample with 200 µL of acetonitrile. This suspension was vortexed for 30 min and centrifuged at 4k rpm for 15 min, after which 100 µL of the extract was aliquoted and mixed with 200 µL of acetonitrile/water (1/2, v/v) prior to LC-MS/MS analysis. The extracted plasma samples were analyzed on a Waters Acquity UPLC system coupled with a Waters Xevo TQ-S triple quadrupole mass spectrometer operated at positive mode. The capillary voltage was set to 0.5 kv and collision energy to 32 eV. Capmatinib (purchased from Matrix Scientific Products (Columbia, SC)) and crizotinib (purchased from LC Laboratories (Woburn, MA)) were separated using a Waters Acquity UPLC BEH C18 column (1.7 µm, 2.1×30 mm) and detected by a multiple reaction monitoring transition, m/z 413.04>354.07 for capmatinib and m/z 450.04>260.18 for crizotinib, respectively. The mobile phase A was 0.1% acetic acid/water and B was 0.1% acetic acid/acetonitrile. The LC gradient was 10% B (0-0.3 min), 10-95% B (0.3-1.3 min), 95% B (1.3-1.7 min), 10% B (1.7-2.0 min) and the flow rate was 0.5 mL/min. The column temperature was 40° C. The injection volume was 2 µL. Under these conditions, the retention time was 0.85 min for capmatinib and 0.74 min for crizotinib. The inventors validated the method with an analytical range of 1-1000 ng of capmatinib and crizotinib in untreated CD-1 mouse plasma, respectively.

The inventors homogenized mouse tumor tissue samples in methanol:water (80:20, v/v) to a concentration of 100 mg (tissue)/mL. The homogenates were vortexed for 10 min and centrifuged at 15k rpm for 5 min, then 100 µL of the supernatant was transferred into an HPLC vial for LC-MS/MS analysis. The tissue homogenates were analyzed by using the same method as described above. The method was validated with an analytical range of 1-1000 ng/mL of capmatinib and crizotinib in untreated mouse tumor tissue homogenates, respectively.

Example 10

Sequencing

Whole Exome Sequencing
Library Construction and Sequencing
The sequencing libraries were prepared using the KAPA library prep protocol (catalog number KK8234, KAPA Biosystems, Wilmington, MA). The exomes were captured using the SureSelect XT Human All Exon V5 kit (Agilent Technologies, Santa Clara, CA). Samples were then sequenced 2×100 by to about 340× depth on the Illumina HiSeq 2000.
BAM File Generation
The inventors converted the raw output (BCL) files of an Illumina sequencer to FASTQ files using Illumina's offline basecalling software CASAVA Version 1.8.2. The FASTQ files were then aligned to the reference genome (hg19 for human) using BWA version 0.7.0 using the protocols set forth in Li, H. & Durbin, R. Fast and accurate short read alignment with Burrows-Wheeler transform. *Bioinformatics* 25, 1754-60 (2009) for DNA samples with parameters suitable for a given aligner. The inventors subjected the aligned BAM files to mark duplication, re-alignment, and re-calibration using Picard version 1.112 (http://picard-.sourceforge.net) and GATK version 1.5 using the protocols set forth in McKenna, A. et al. The Genome Analysis Toolkit: a MapReduce framework for analyzing next-generation DNA sequencing data. *Genome Res* 20, 1297-303 (2010)) when applicable before any downstream analysis were conducted. These references are incorporated herein by reference.
Whole Genome Low Pass Sequencing
Library Construction and Sequencing
The Illumina compatible libraries were prepared using KAPA DNA Library preparation kit (Catalog No. KK8232) as per the manufacturer's protocol. In brief, DNA was fragmented to a median size of 200 bp by sonication. The inventors polished fragmented DNA ends and 5'-phosphorylated. After addition of 3'-A to the ends, the inventors ligated indexed Y-adapters and PCT amplified the samples. The inventors quantified and validated the resulting DNA libraries by qPCR, and sequenced on Illumina's HiSeq 2000 in a paired-end read format for 76 cycles. The resulting BCL files containing the sequence data were converted into ".fastq.gz" files and individual sample libraries were demultiplexed using CASAVA version 1.8.2 with no mismatches.

RNA Sequencing

Library Construction and Sequencing

The Illumina compatible libraries were prepared using Illumina's TruSeq RNA Sample Prep kit v2, as per the manufacturer's protocol. In brief, the inventors enriched Poly-A RNA using Oligo-dT beads. Enriched Poly-A RNA was fragmented to a median size of 150 bp using chemical fragmentation and converted into double stranded cDNA. Ends of the double stranded cDNA were polished, 5'-phosphorylated, and 3'-A tailed for ligation of the Y-shaped indexed adapters. Adapter ligated DNA fragments were PCR amplified, quantified and validated by qPCR, and sequenced on Illumina's HiSeq 2000 in a paired-end read format for 76 cycles. The resulting BCL files containing the sequence data were converted into ".fastq.gz" files & individual sample libraries were demultiplexed using CASAVA version 1.8.2 with no mismatches.

BAM File GenerationRNA sequencing BAM files were generated and analyzed using the Pipeline for RNAseq Data Analysis (PRADA) protocol (http://sourceforge.net/projects/prada/) as detailed in Torres-Garcia, W. et al. PRADA: pipeline for RNA sequencing data analysis. *Bioinformatics* 30, 2224-6 (2014)), which is incorporated herein in its entirety. PRADA uses Burroughs-Wheeler alignment, Samtools, and Genome Analysis Toolkit to align RNAseq reads to a reference database composed of whole genome sequences (hg19) and transcriptome sequences (Ensembl64).

Targeted Resequencing

Library Construction and Sequencing

The Illumina compatible libraries were prepared using KAPA DNA Library preparation kit (Catalog No. KK8232) as per the manufacturer's protocol. In brief, the inventors fragmented DNA to a median size of 200 bp by sonication. Fragmented DNA ends were polished and 5'-phosphorylated. After addition of 3'-A to the ends, indexed Y-adapters were ligated and the samples were PCR amplified. The inventors enriched resulting DNA libraries for targeted regions using NimbleGen SeqCap EZ Choice Library 4 RXN (Catalog No. 06740251001) and NimbleGen SeqCap EZ Reagent Kit Plus v2 (Catalog No. 06953247001) as per the manufacturer's protocol. The enriched libraries were quantified and validated by qPCR, and sequenced on Illumina's HiSeq 2000 in a paired-end read format for 76 cycles. The resulting BCL files containing the sequence data were converted into ".fastq.gz" files and individual sample libraries were demultiplexed using CASAVA version 1.8.2 with no mismatches.

BAM File Generation

The inventors aligned Sequencing FASTQ files to the reference genome (hg19 for human) and processed to BAM files by the same pipeline as in whole exome sequencing.

Pacific Biosciences (PacBio) Long Read Sequencing

Library Construction and Sequencing

The DNA libraries were prepared following; the Pacific Biosciences 20 kb Template Preparation Using BluePippin Size-Selection System protocol. No DNA shearing was performed because the samples were already fragmented. The inventors selected sheared DNA on a BluePippin system (Sage Science Inc., Beverly, MA, USA) using a cutoff range of 7 kb to 50 kb. The DNA Damage repair, End repair and SMRT bell ligation steps were performed as described in the template preparation protocol with the SMRTbell Template Prep Kit 1.0 reagents (Pacific Biosciences, Menlo Park, CA, USA). The sequencing primer annealing and the P6 polymerase binding reactions were prepared according to the BindingCalculator (Pacific Biosciences BindingCalculator-master_v2.3.1.1). The libraries were sequenced on a PacBio RSII instrument at a loading concentration (on-plate) of 80 pM, 90 pM and 100 pM using the MagBead OneCellPerWell v1 collection protocol, DNA sequencing kit 4.0, SMRT cells v3 and 4 hours movies.

Filtering the Sequencing Reads

The inventors filtered reads and subreads based on their length and quality values, using smrtpipe.py from the SMRT-Analysis package.

Structural Variation Analysis

In this step, the inventors assembled the filtered PacBio sequence subreads with the parameters suggested for low coverage data using Canu (version 1.2). The protocol is as in Berlin, K. et al. Assembling large genomes with single-molecule sequencing and locality-sensitive hashing. *Nat Biotechnol* 33, 623-30 (2015), which is incorporated herein by reference. The inventors adopted the methods set forth in Belcher, A. L. et al. Alignment of whole genomes. Nucleic Acids Res 27, 2369-76 (1999), and assembled and aligned contigs in, to the human genome reference (hg19) using nucmer (version 3.23). The inventors selected the contigs having sequence fragments aligned to the MET-CAPZA2 region of chromosome 7 for structural variation analysis. For the selected contigs, the inventors performed a blastn search against mouse genome using the sequence fragments aligned to the MET-CAPZA2 region of hg19 in order to make sure that they originated from human (Table 6). The inventors identified sequence fragments shared by two contigs with pairwise alignment of the contigs using the number. Two contigs were considered to be connected only if they shared a sequence fragment which was at least 5,000 bp long with the minimum 99% identity. The high confident shared sequence fragments were used for connecting the contigs into a circular form in the HF3035. In HF3077, only two contigs (tig01141776 and tig01141835) were aligned to MET-CAPZA2 region of chromosome 7, and the two contigs shared 621 bp long sequence with 95.6% identity between the 3' end of tig01141776 and the 5' end of tig01141835.

Example 11

Gene Fusion and Gene Expression Analysis

To detect transcript fusions, PRADA aligned RNAseq reads to a reference database composed of whole genome sequences (hg19) and transcriptome sequences (Ensembl64). Two lines of evidence were required for identification of a gene fusion: 1) a minimum of two discordant read pairs mapping to a candidate gene pair; and 2) a minimum of one junction spanning read mapping to a junction that connected exons between the candidate gene pair, with its pair mate mapping to the either of the two genes. The inventors applied several filters to remove false positives and artifacts, of which the most prominent is based on significant sequence similarity between the two fusion genes (using BLASTN, Expect value=0.01). Gene expression was measured as 'reads per kilobase per million' (RPKM) to normalize for gene length and library size. In this experiment, the inventors adopted the PRADA pipeline, the details of which are described e.g., in Torres-Garcia, W., *Bioinformatics* 30, 2224-6 (2014). The reference is incorporated by reference herein in its entirety.

Example 12

Structural Variant Detection

To detect structural variants, the inventors applied Speed-Seq, the protocol for which is set forth in Chiang, C. et al. SpeedSeq: ultra-fast personal genome analysis and interpretation. *Nat Methods* 12, 966-8 (2015)(with default parameters), to whole genome sequencing from both tumor and matching normal samples. The inventors filtered somatic variants by requiring at least 4 reads supporting evidence in a tumor and no reads in its matching normal.

Example 13

EGFR Intragenic Rearrangement

In this experiment, the inventors searched for EGFR intragenic rearrangements using a Supervised Search for intragenic fusion (GUESS-if), a module of PRADA, the General User protocol of which is defined in Brennan, C. W. et al. The somatic genomic landscape of glioblastoma. *Cell* 155, 462-77 (2013), which is incorporated by reference herein in its entirety. In brief, using the same rationale as in PRADA gene fusion identification, GUESS-if looked for spanning reads for abnormal junctions that were not present in known transcripts. To assure a high accuracy, the inventors obtained at least 10 reads spanning exon 1-8 of EGFR.

Example 14

Validation of Somatic Single Nucleotide Variants

To validate the somatic single nucleotide mutation calls, the inventors performed targeted resequencing at high coverage (>1,400×). The inventors selected 792 unique bases, which had been found to be mutated in tumor, neurosphere, or xenografts but not in all of them. These sites corresponded to 1368 sSNVs. In total, 1287 of 1368 mutations called from the exome sequencing data were detected in the high coverage data, resulting in a true positive validation rate of 94%. Evidence for recovered somatic mutation was observed in 1001 of 2646 wild type nucleotides. The variant allelic fractions (VAFs), i.e. the number of reads harboring the variant allele divided by all reads covering to that base, of exome and validation sequencing were highly correlated (Pearson correlation=0.92).

Example 15

Somatic Single Nucleotide Variant Calling

The inventors detected somatic single nucleotide variants (sSNVs) from tumor and patient-matched normal samples, by using MuTect algorithm (version 1.14) with default parameters, the protocol for which may be found in Cibulskis, K. et al. Sensitive detection of somatic point mutations in impure and heterogeneous cancer samples. *Nat Biotechnol* 31, 213-9 (2013), which is incorporated herein by reference. The search for somatic small insertion/deletions (Indels) was performed by using Pindel, the protocol for which may be found in Ye, K., Schulz, M. H, Long, Q., Apweiler, R. & Ning, Z. Pindel: a pattern growth approach to detect break points of large deletions and medium sized insertions from paired-end short reads. *Bioinformatics* 25, 2865-71 (2009), also incorporated herein by reference, with tumor and patient-matched normal samples. The inventors annotated all sSNVs and small indels by ANNOVAR (version 2012-10-23), the protocol for which may be found in Wang, K., Li, M. & Hakonarson, H. ANNOVAR: functional annotation of genetic variants from high-throughput sequencing data. *Nucleic Acids Res* 38, e164 (2010), incorporated by reference. The inventors selected only exonic or splicing sSNVs for analysis. Mutation counts for individual samples are available in Table 7.

Example 16

Inference of Cellular Frequency and Mutational Clusters

The inventors defined cellular frequency of a mutation as the fraction of cells harboring the mutation. The inventors estimated cellular frequency using PyClone version 0.12.7, the protocol for which may be found in Roth, A. et al. PyClone: statistical inference of clonal population structure in cancer. *Nat Methods* 11, 396-8 (2014), which is incorporated by reference. For each set of patients, neurosphere, and xenograft samples, the inventors ran PyClone on the somatic mutations whose sites were covered over all the samples using multi-sample joint analysis mode with PyClone beta binomial density and parental copy number priors. The inventors estimated allelic copy numbers by applying Sequenza, the protocol for which may be found in Favero, F. et al. Sequenza: allele-specific copy number and mutation profiles from tumor sequencing data. *Ann Oncol* 26, 64-70 (2015), incorporated by reference herein, to exome sequencing data. Default options for PyClone were used. To avoid potential artifacts from sequencing coverage, the analysis was limited to the mutations at the sites covered with at least 50× over all samples from a same patient. PyClone inferred clusters of mutations whose cellular frequencies co-vary over samples. The analysis was limited only to mutation clusters with at least two mutations.

Example 17

Removing Putative Mouse Reads in Short Read Sequencing Data

Sequencing reads derived from xenograft samples were a mixture of reads from human and mouse. The inventors utilized Xenome, the protocol for which may be found in Conway, T. et al. Xenome—a tool for classifying reads from xenograft samples. *Bioinformatics* 28, i172-8 (2012), incorporated herein by reference, to select sequencing reads arising from human. Then, the selected human reads selected were aligned to the human genome using the same pipeline as in patient and neurosphere samples.

Example 18

Identification of Copy Numbers from Low Pass Sequence Data

Regarding DNA copy number prediction, the inventors used NBICSeq version 0.5.2, the protocol for which may be found in Xi, R. et al. Copy number variation detection in whole-genome sequencing data using the Bayesian information criterion, *Proc Natl Acad Sci USA* 108, E1128-36 (2011), incorporated herein by reference, with bin size 1000 bps and BIC penalty 3 to estimate somatic copy number alterations in low pass sequencing data from tumor and patient-matched normal samples.

Example 19

Detecting TERT Promoter Mutations

Whole genome low pass sequencing and whole exome sequencing were evaluated for the presence of TERT mutations in a supervised way using GATK pileup. Minimum 2 variant alleles (combined from WGS and WES) were required for detection of TERT promoter mutations.

| Variant change | Variant site | Patients |
|---|---|---|
| C228T | 5: 1295228-1295228 | 7 |
| C250T | 5: 1295250-1295250 | 5 |

Example 20

Detecting ATRX Indels

The inventors called indels using Pindel (Version 0.2.4t) with the default parameters except maximum allowed mismatch rate being 0.1, the protocol for which may be found in Ye, K., Schulz, et al., *Bioinformatics* 25, 2865-71 (2009), which is incorporated herein by reference. Somatic indels were further filtered to require a minimum 5 supporting tumor reads.

Example 21

Analysis of B-Allele-Frequency Segments

Figure 7:
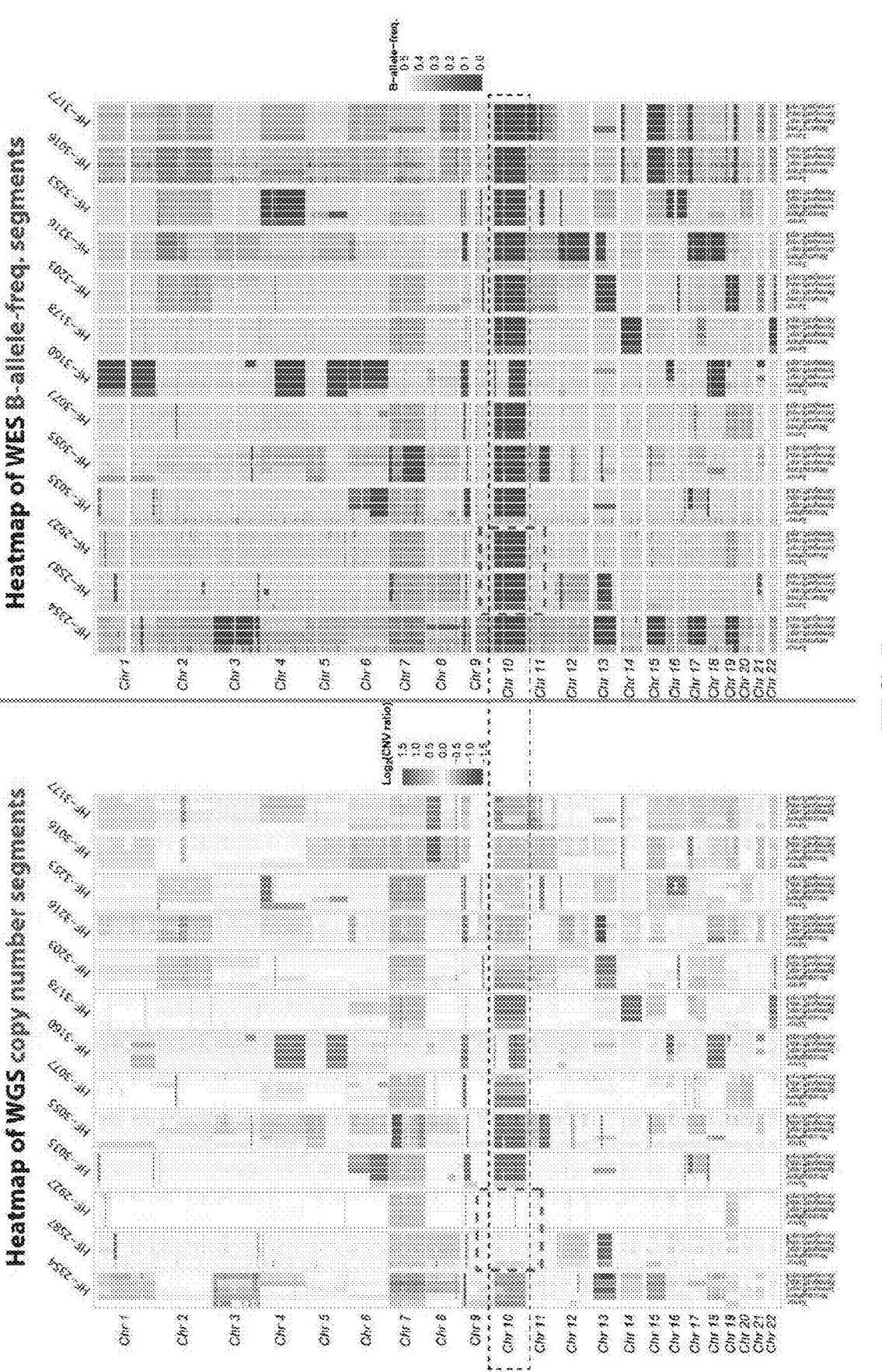
FIG. 7 depicts a comparison of DNA copy number and loss of heterozygosity. Genome wide DNA copy number profiles. Left panel: Copy number increases (red) and decreases (blue) are plotted as a function of distance along the normal genome (vertical axis, divided into chromosomes). Right panel represents segmented B-allele-frequencies at heterozygous germline SNPs, which reflects patterns of loss of heterozygosity. Two cases with diploid but homozygous chromosome 10 are highlighted.

The inventors inferred B-allele-frequency segments by applying Sequenza (Version 2.1.1) the protocol for which may be found in Favero, F. et al., *Ann Oncol* 26, 64-70 (2015), incorporated herein by reference, to whole exome sequencing data with the default parameters. Analysis of B-allele fractions using whole genome sequencing in our sample cohort revealed loss of heterozygosity (LOH) of chromosome 10 in two cases with diploid chromosome 10, suggesting these cases had first lost a single copy of the chromosome which was subsequently duplicated (FIG. 7). FIG. 7 shows a comparison of DNA copy number and loss of heterozygosity. Genome wide DNA copy number profiles. On the left panel in the figure, the copy number increases (red) and decreases (blue) are plotted as a function of distance along the normal genome (vertical axis, divided into chromosomes). The right panel in the figure represents segmented B-allele-frequencies at heterozygous germline SNPs, which reflects patterns of loss of heterozygosity. Two cases with diploid but homozygous chromosome 10 are highlighted in FIG. 7.

Figure 12:
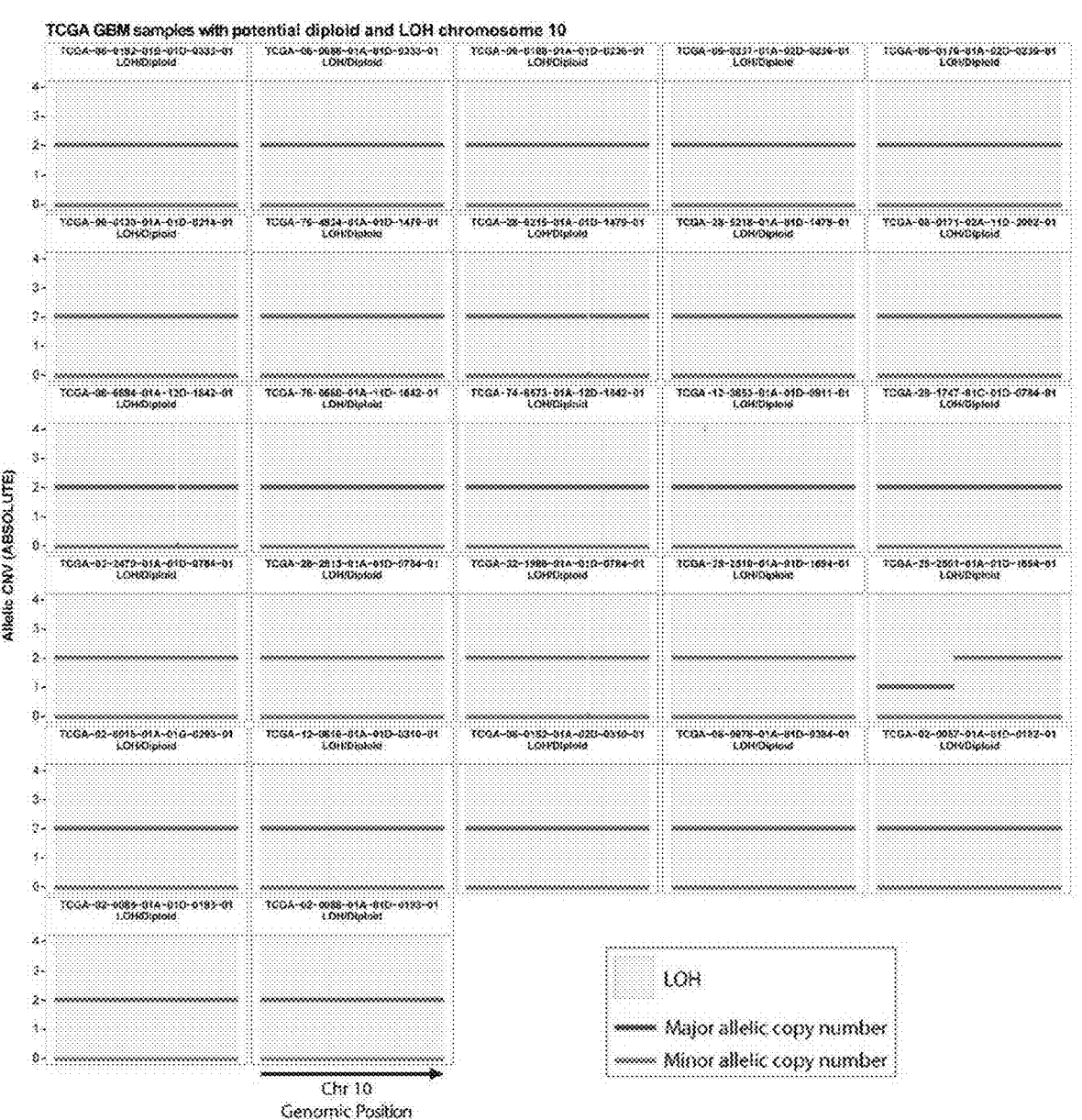
FIG. 12 depicts a comparison of DNA copy number and loss of heterozygosity. TCGA GBMs with diploid and loss of heterozygosity of chromosome 10 (n=27). X axis represents genomic locations on chromosome 10, and Y axis is allelic integer copy numbers, estimated using ABSOLUTE, an algorithm software tool.

The inventors evaluated chromosome 10 LOH using Affymetrix SNP6 profiles from 320 IDH-wildtype TCGA glioblastoma using the protocol of Brennan, C. W. et al., *Cell* 155, 462-77 (2013), incorporated herein by reference, and found that 27 of 52 tumors with diploid chromosome 10 similarly showed LOH, underscoring the importance of aberrations in chromosome 10 in gliomagenesis and evolution (FIG. 12). FIG. 12 depicts a comparison of DNA copy number and loss of heterozygosity. TCGA GBMs with diploid and loss of heterozygosity of chromosome 10 (n=27). The X axis represents genomic locations on chromosome 10, and Y axis is allelic integer copy numbers estimated using the ABSOLUTE software tool. Absolute is the algorithm tool as defined in Carter, et al. Absolute quantification of somatic DNA alterations in human cancer. *Nat Biotechnol.* 2012 Apr. 29. doi: 10.1038/nbt.2203, which is incorporated herein by reference. ABSOLUTE provides information on the absolute cellular copy number of local DNA segments and for point mutations, the number of mutated alleles.

Example 22

Data Used for Longitudinal Analysis in Glioma Patient Tumors

The inventors obtained segmented copy number profiles for thirteen TCGA GBM patients and fourteen TCGA LGG patients from the TCGA portal https://tcga-data.nci.nih.gov/tcga/. Copy number profiles for ten patients from MD Anderson Cancer Center (MDACC) and fourteen patients from either Samsung Medical Center (SMC) or Seoul National University Hospital (SNUH) were previously processed as set forth in Kim, H. et al. Whole-genome and multisector exome sequencing of primary and post-treatment glioblastoma reveals patterns of tumor evolution. *Genome Res* 25, 316-27 (2015); Kim, J. et al. Spatiotemporal Evolution of the Primary Glioblastoma Genome. *Cancer Cell* 28, 318-28 (2015). The inventors generated additional copy number data for seven patients from MD Anderson by applying NBICseq version 0.5.2, the protocol for which may be found in Xi, R. et al., *Proc Natl Acad Sci USA* 108, E1128-36 (2011) to low pass whole genome sequencing. For fusion detection and structural variant calling, the same pipelines as described in the corresponding method subsections of these references, which are hereby incorporated by reference in their entireties, were applied for unaligned RNA sequencing files and whole genome sequencing BAM files from TCGA GBM, TCGA LGG, and MD Anderson patients. The inventors downloaded sequencing data for the TCGA cohort from CGHub. Fusion calls for Samsung Medical Center cohort patients were processed further to Kim, J. et al., *Cancer Cell* 28, 318-28 (2015). Shown below is a summary table (TABLE 1) of data used in the analysis.

TABLE 1

| The number of patients used in the longitudinal analysis | | | |
|---|---|---|---|
| Cohort | CNV | RNASEQ | WGS |
| MDACC | 17 | 9 | 7 |
| SMC/SNUH | 14 | 0 | 0 |
| TCGA GBM | 13 | 6 | 10 |
| TCGA LGG | 14 | 14 | 13 |
| Total | 58 | 29 | 30 |

Note:
Patients do not necessarily have both RNAseq and WGS.

Example 23

Predicting Extrachromosomal DNA (ecDNA) Candidates

After visualizing segmented copy numbers in the Integrative Genomics Viewer (IGV), the protocol for which is set forth in Robinson, J. T. et al. Integrative genomics viewer. *Nat Biotechnol* 29, 24-6 (2011), incorporated herein by reference, the inventors manually scrutinized potential extrachromosomal DNA candidate regions by searching for intermittent patterns of DNA copy number amplification. In cases where structural variations and gene fusions were available, the inventors projected those variation break-points onto the copy number IGV view plots to corroborate the inventors' DNA copy number based predictions to get additional evidence on presence of the inventors' predicted ecDNAs.

To avoid biases of the method, such as the presence of multiple adjacent amplifications in oncogene regions, the inventors applied the Amplicon Architect method that indi-cates extrachromosomal DNA candidates predicted by the Amplicon Architect tool (https://github.com/virajbdesh-pande/AmpliconArchitect) (See Turner, K. M. et al. Extra-chromosomal oncogene amplification drives tumor evolu-tion and genetic heterogeneity. *Nature* (2017), which is incorporated herein by reference, for details of the Amplicon Architect method), to 125 samples with available whole genome sequencing data (65 samples from our hGBM cohort and 60 longitudinal glioma samples) to identify ecDNAs in an unsupervised manner. The inventors pro-cessed forty-six (46) TCGA glioma samples through the Institute for Systems Biology Cancer Genomics Cloud that provides a cloud-based platform for TCGA data analysis. The inventors used processed segmented copy number pro-files (described in the previous section) to identify interval (s) of interest that were required for the input to Amplicon Architect. Default parameters and reference files were used for all other settings. The inventors filtered the ecDNAs predicted by Amplicon Architect by only selecting ampli-cons with at least six amplified amplicon copy count that resulted in relatively balanced numbers of ecDNAs between low pass sequencing cases (a median depth of 6.5×) and TCGA whole genome cases. The Amplicon Architect-pre-dicting ecDNAs further merged with those predicted by the inventors' method in cases where those ecDNAs overlap each other.

Figure 11A:
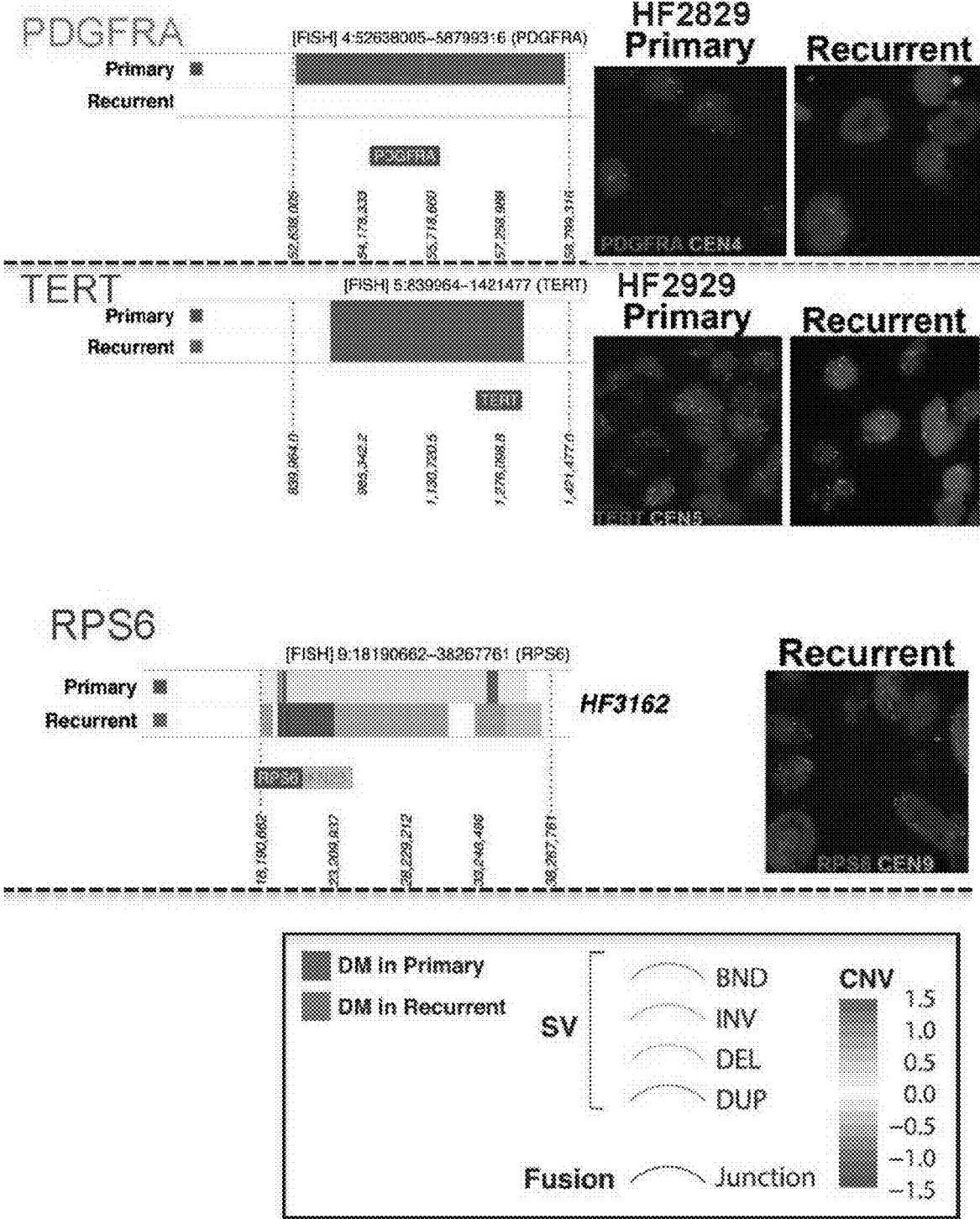
FIG. 11A depicts validation of predicted ecDNA elements in primary and recurrent gliomas using whole genome sequencing, FISH, and DNA copy number profiling. Left panels: Segmented copy numbers, and structural variation (SV) breakpoints/fusion junctions have been visualized for primary and recurrent tumors for each predicted extrachromosomal segment (whose boundaries have been indicated with vertical dots). In cases where one end of a fusion gene junction or SV breakpoint pair does not fall within the predicted ecDNA region, those points have been plotted outside the region. Right panels: shows representative interphase FISH (for tumor and PDX) and metaphase FISH (for neurospheres). Arrows in metaphase FISH images mark extrachromosomal DNA elements.
Figure 11B:
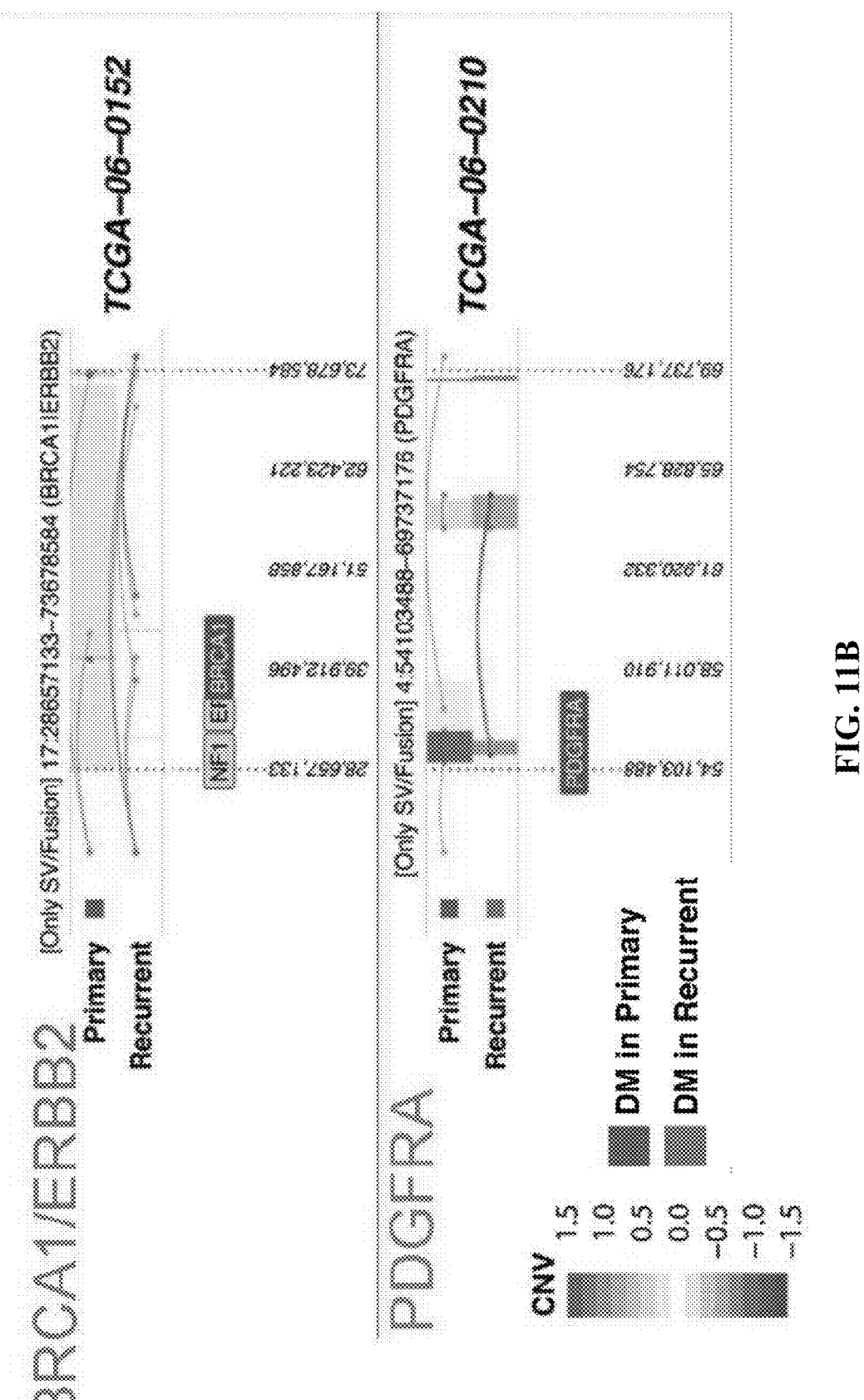
FIG. 11B depicts segmented copy numbers, and structural variation (SV) breakpoints/fusion junctions have been visualized for primary and recurrent tumors for each predicted extrachromosomal segment (whose boundaries have been indicated with vertical dots). In cases where one end of a fusion gene junction or SV breakpoint pair does not fall within the predicted ecDNA region, those points have been plotted outside the region.
Figure 11C:
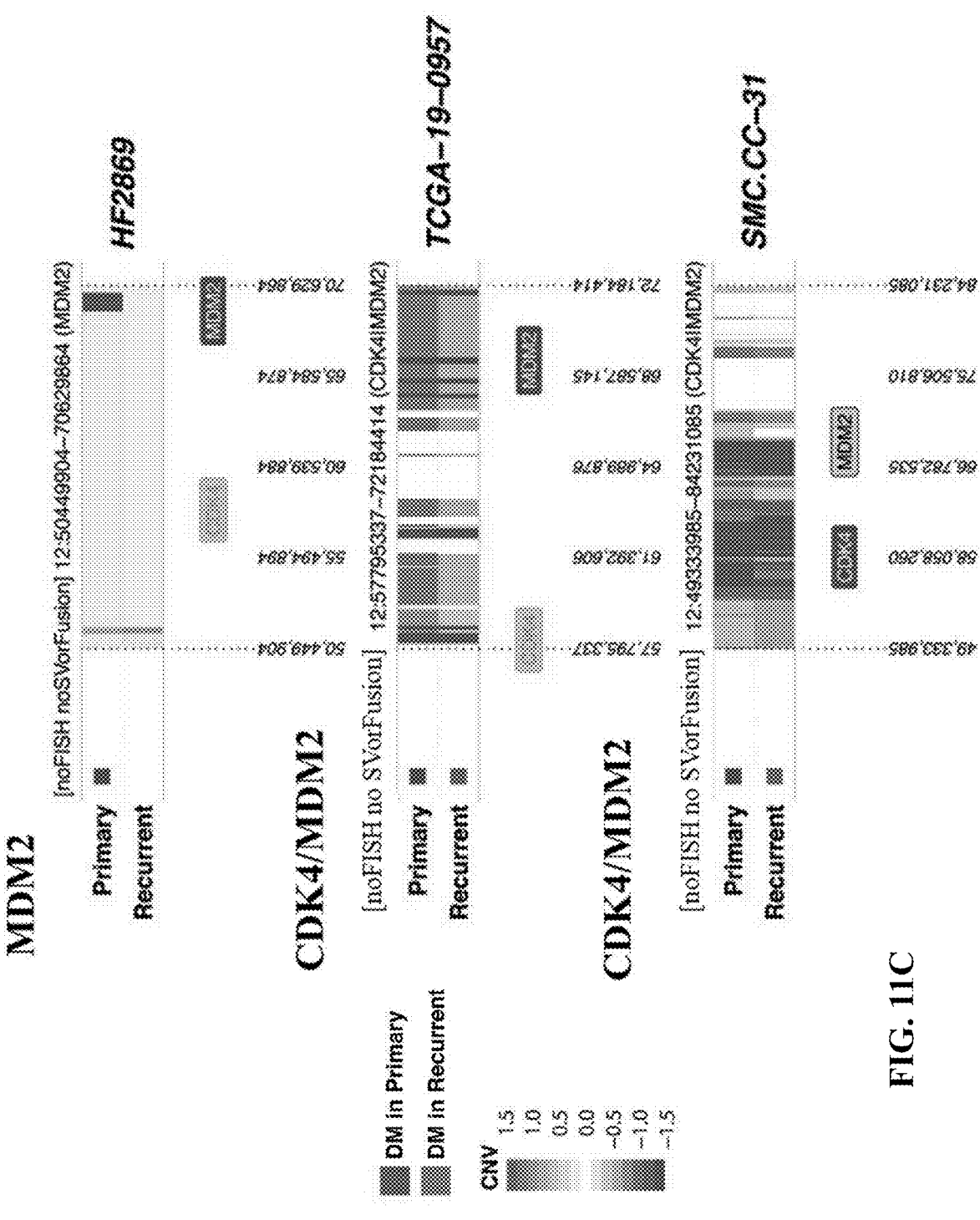
FIG. 11C depicts segmented copy numbers that have been visualized for primary and recurrent tumors for each predicted extrachromosomal segment (whose boundaries have been indicated with vertical dots). In cases where one end of a fusion gene junction or SV breakpoint pair does not fall within the predicted ecDNA region, those points have been plotted outside the region.

FIG. 11C depicts segmented copy numbers that the inven-tors visualized for primary and recurrent tumors for each predicted extrachromosomal segment (whose boundaries have been indicated with vertical dots). In cases where one end of a fusion gene junction or SV breakpoint pair does not fall within the predicted ecDNA region, the inventors have plotted those points outside the region. FIG. 11D depicts validation of predicted ecDNA elements in primary and recurrent gliomas using whole genome sequencing, FISH and DNA copy number profiling. This figure shows days-to-secondary surgery vs. IDH1 status.

To identify tumor driver genes carried by predicted ecD-NAs, the inventors used a list of copy number driver genes (CNA_drivers_per_tumor_type.tsv file) downloaded from http://www.intogen.org/downloads (see Rubio-Perez, C. et al. In silico prescription of anticancer drugs to cohorts of twenty-eight (28) tumor types reveals targeting opportuni-ties. *Cancer Cell* 27, 382-96 (2015)), and glioblastoma frequently-altered genes from the TCGA study (see Bren-nan, C. W. et al., *Cell* 155, 462-77 (2013)). Then the inventors intersected those gene regions with the predicted ecDNA regions. Amplicon Architect also had an internal function on identifying oncogenes (from 522 oncogenes from the COSMIC database (August 2014) Forbes, S. A. et al. COSMIC: exploring the world's knowledge of somatic mutations in human cancer. *Nucleic Acids Res* 43, D805-11 (2015)), covered by the predicted ecDNA, and the inventors included those oncogenes into a list of ecDNA carrying driver genes. Details on how to run Amplicon Architect have been described in Turner, K. M. et al., *Nature* (2017), which is incorporated herein, and its source code depository (https://github.com/virajbdeshpande/AmpliconArchitect)

Statistical Analysis

The inventors conducted all computations with R 3.0.13 and used standard statistical tests as appropriate.

Example 24

CAPZA2-MET Fusion Transcripts

The present study extends the finding of Singh, D. et al. Transforming fusions of FGFR and TACC genes in human glioblastoma. *Science* 337, 1231-5 (2012); Zheng, S. et al. A survey of intragenic breakpoints in glioblastoma identifies a distinct subset associated with poor survival. *Genes Dev* 27, 1462-72 (2013); Bao, Z. S. et al. RNA-seq of 272 gliomas revealed a novel, recurrent PTPRZ1-MET fusion transcript in secondary glioblastomas. *Genome Res* 24, 1765-73 (2014)), and furthers research that chimeric RNA fusions may be therapeutically targetable, in particular when involv-ing receptor tyrosine kinases.

Figure 3A:
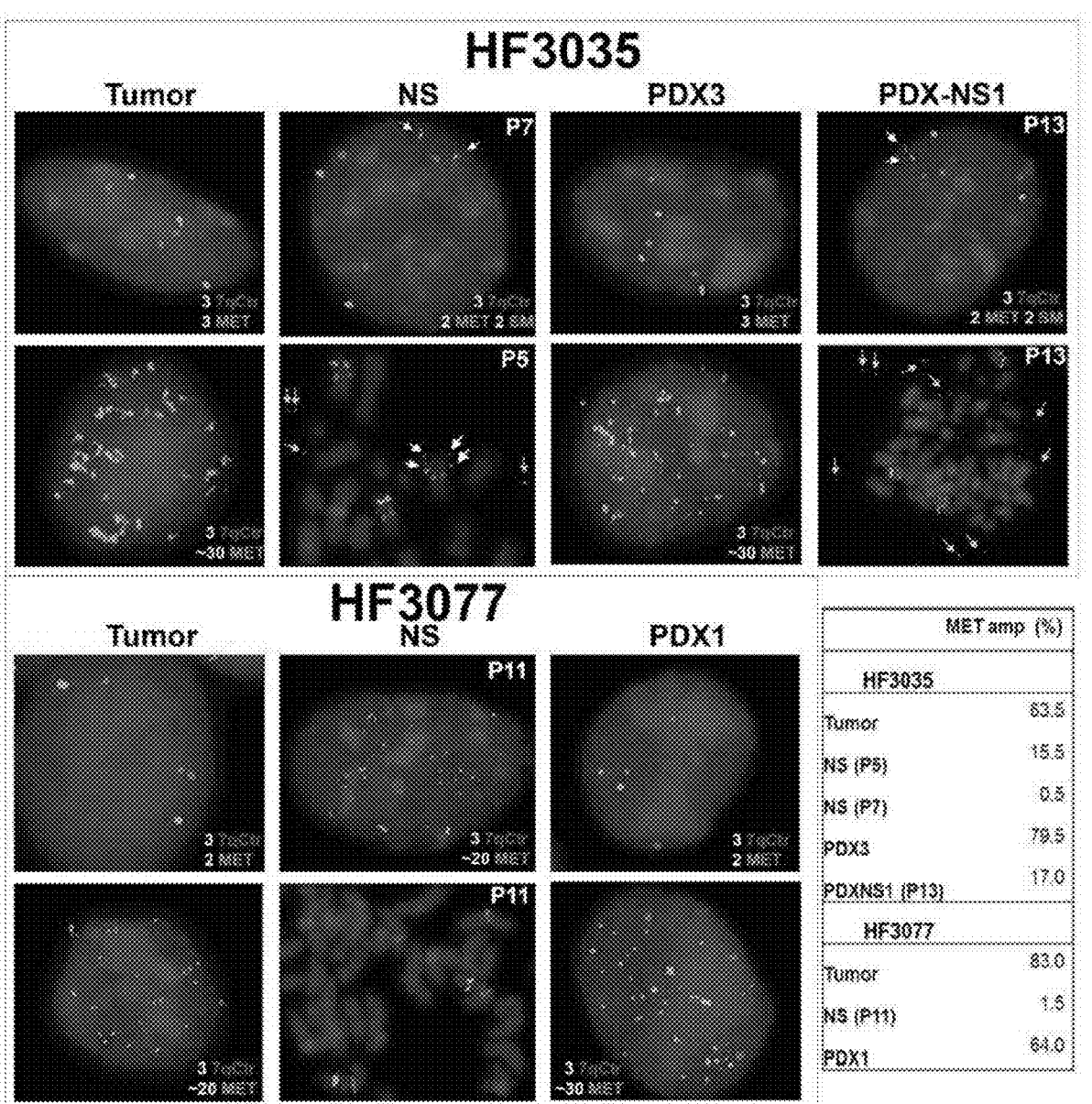
FIG. 3A depicts extrachromosomal MET DNA, Representative FISH images for MET (green) and chromosome 7 control probes (7qCtr, red) labeling of HF3035 and HF3077 tumor, neurosphere (NS), and xenografts (PDX), and neurospheres established from HF3035 xenograft tumors (PDX-NS1). As used herein, "HF" in the tumor identifications throughout this application, stands for specimens collected at Henry Ford Hospital (Detroit, MI). The number after "HF" designates a particular tumor. Interphase FISH was done on tumor and PDX samples, metaphase spread FISH on neurospheres. Passage numbers are indicated for neurosphere cultures. White arrows point to 2 fragmented MET signals in one chromosome in HF3035 samples (2SM). Yellow arrows point to extrachromosomal MET in metaphase nuclei of neurospheres. The percentage of nuclei presenting MET amplification for each sample is shown.
Figure 3B:
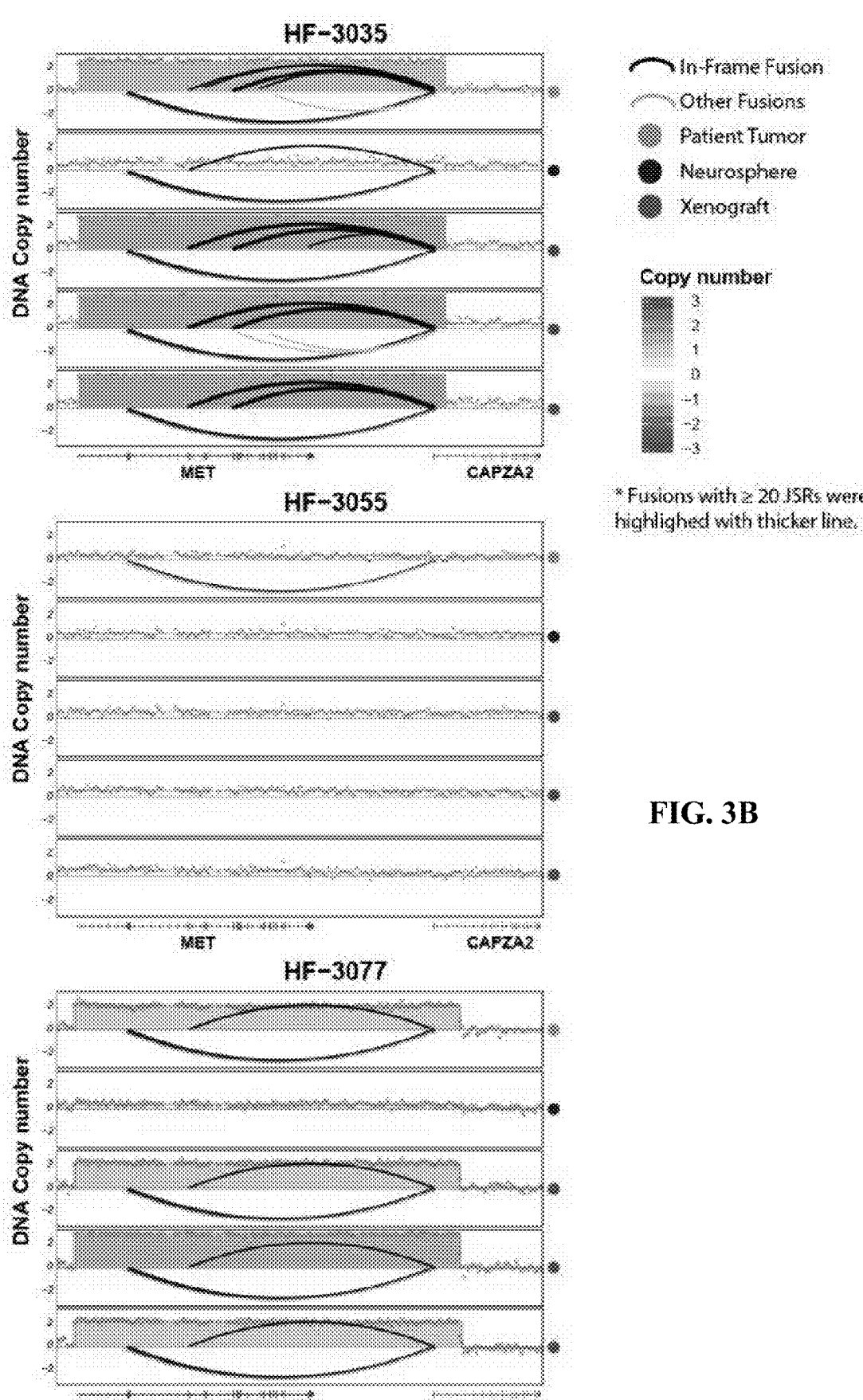
FIG. 3B depicts DNA copy number and chromosomal rearrangement of the 7q31 locus in three sets of GBM tumors and derivate models.

The inventors performed RNA sequencing and detected fusion transcripts in all samples except for a single neuro-sphere line (HF3203) with disqualifying quality control values using the protocol of Torres-Garcia, W. et al., *Bio-informatics* 30, 2224-6 (2014). From this unbiased screen, multiple fusions joining the CAPZA2 coding start with the 5' UTR of MET were identified in the primary tumors of HF3035, HF3077 and HF3055 (FIG. 3B). FIG. 3B depicts DNA copy number and chromosomal rearrangement of the 7q31 locus in three sets of GBM tumors and derivate models.

Figure 13A:
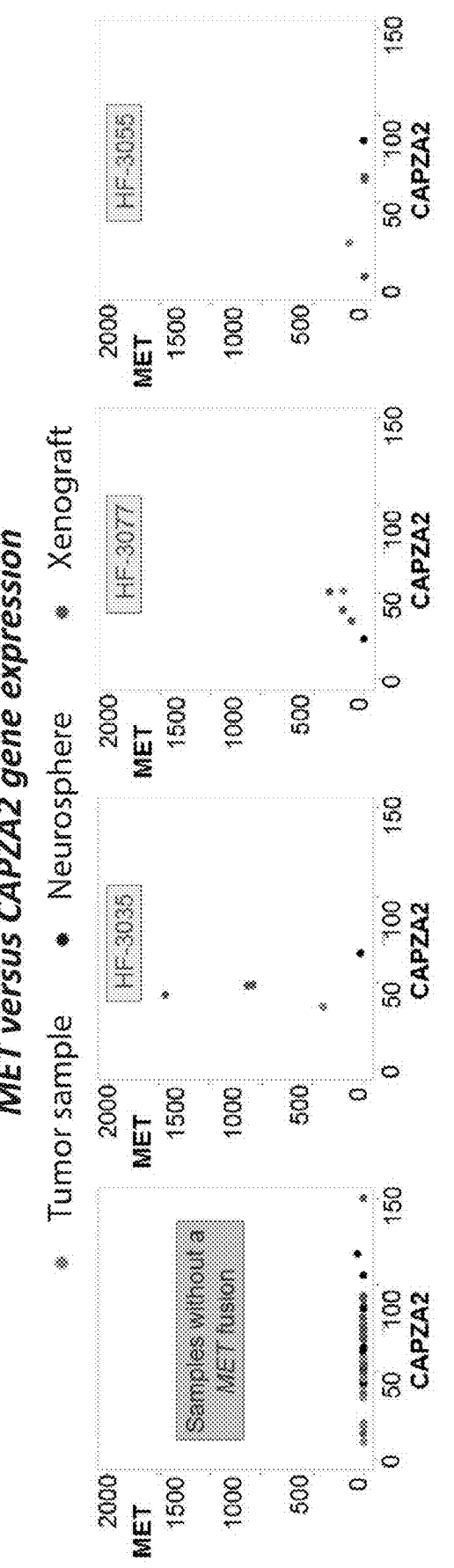
FIG. 13A depicts CAPZA2-MET fusions. The figure shows a comparison of gene expression levels of MET and CAPZA2 in our cohort.

Additional CAPZA2-MET variants resulted in an in-frame transcript consisting of CAPZA2 exon 1 and MET starting from exon 3 (HF3035, HF3077) and exon 6 (HF3035). The CAPZA2-MET fusions associated with out-lier gene expression of MET while CAPZA2 expression was comparable between samples with and without CAPZA2-MET fusions (FIG. 13A). FIG. 13A depicts CAPZA2-MET fusions and comparison of gene expression levels of MET and CAPZA2 in the present cohort.

Figure 13B:
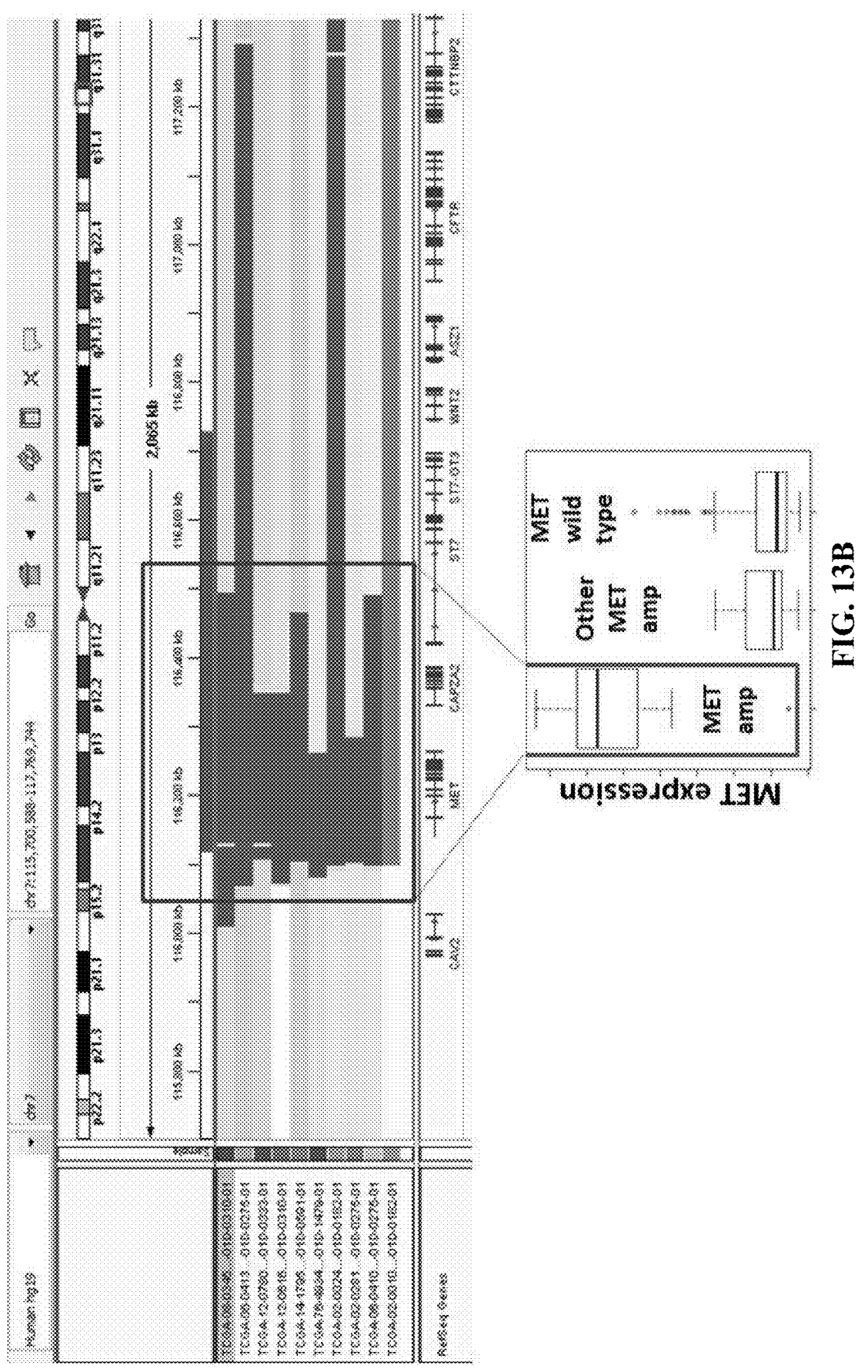
FIG. 13B depicts DNA copy number of MET locus (top) and MET gene expression across different groups (bottom).

The presence of multiple parallel fusion transcripts sug-gested complex chromosomal rearrangements, which asso-ciated with focal amplification of a 200 kb area on 7q31 (FIG. 3B). The present invention extends the findings of Mueller, et al. Identification of an amplified gene cluster in glioma including two novel amplified genes isolated by exon trapping. *Hum Genet* 101, 190-7 (1997), with respect to amplification of the 7q31 genomic area carrying the adjacent CAPZA2 and MET genes. To assess the frequency of MET-activating somatic alterations in glioblastoma, the inventors analyzed the DNA copy number profiles of 486 TCGA IDH wildtype glioblastoma samples. The inventors identified a focal amplification of the MET locus ranging in size from 150 kb to 5.1 Mb which associated with a highly significant increase in expression relative to samples with broad 7q amplification or diploid MET copy number in ten cases (2.1%) (FIG. 13B). FIG. 13B depicts DNA copy number of MET locus (top) and MET gene expression across different groups (see bottom). RNA sequencing data was available for one of the ten TCGA cases and no fusions involving MET were detected in those samples. The present inventors have extended research with respect to CAPZA2-MET fusions in other cancers, as discussed in Kim, H. P. et al. Novel fusion transcripts in human gastric cancer revealed by transcriptome analysis. *Oncogene* 33, 5434-41 (2014); Yoshihara, K. et al. The landscape and therapeutic relevance of cancer-associated transcript fusions. *Oncogene* 34, 4845-54 (2015). The inventors have also extended research with respect to clinical response of a glioblastoma carrying MET amplification to MET and ALK inhibiting agent crizotinib, set forth in Chi, A. S. et al. Rapid radiographic and clinical improvement after treatment of a MET-amplified recurrent glioblastoma with a mesenchymal-epithelial transition inhibitor. *J Clin Oncol* 30, e30-3 (2012).

Figure 9A:
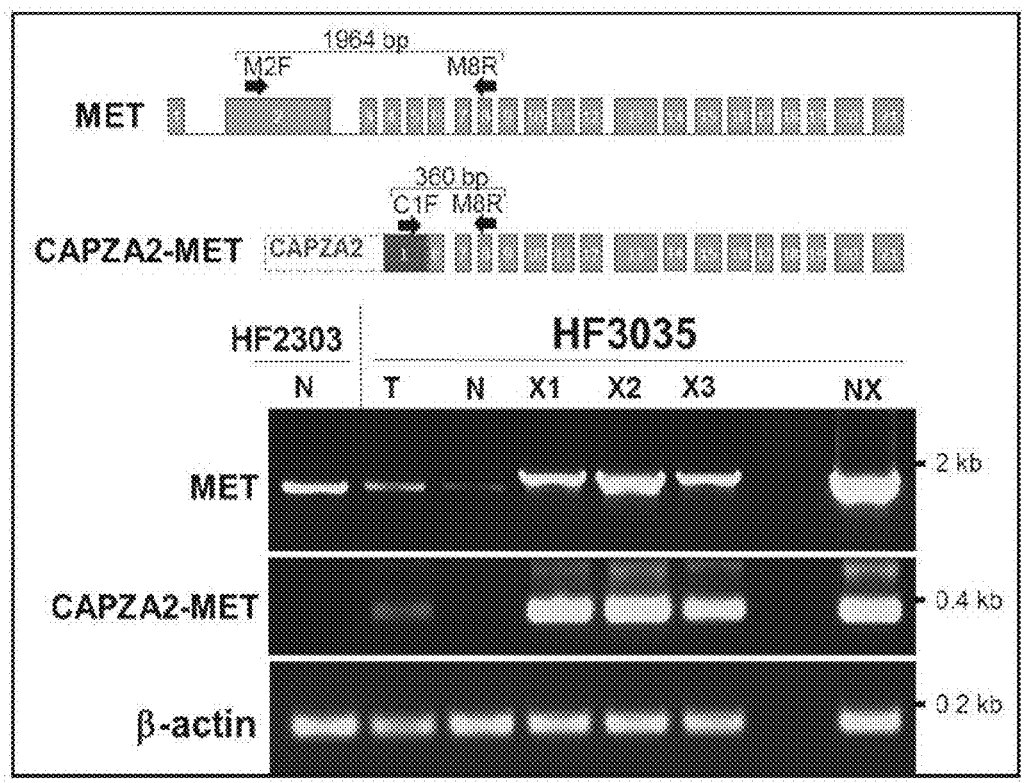
FIG. 9A depicts MET amplification and activation. RT-PCR detection of CAPZA2-MET fusion transcripts in HF3035 samples. Band of predicted size for MET transcript (oligos M2F and M8R) were observed for the HF3035 tumor sample (T), neurosphere cells (N, faint band), three (3) xenografts tumors (X), and neurospheres derived from xenograft tumors (NX). A band of predicted size for the fusion CAPZA2(exon 1)-MET(exon6) transcript was observed for HF3035 T, X and NX samples. HF2303 neurosphere line expressing only wt MET was used as control.
Figure 9B:
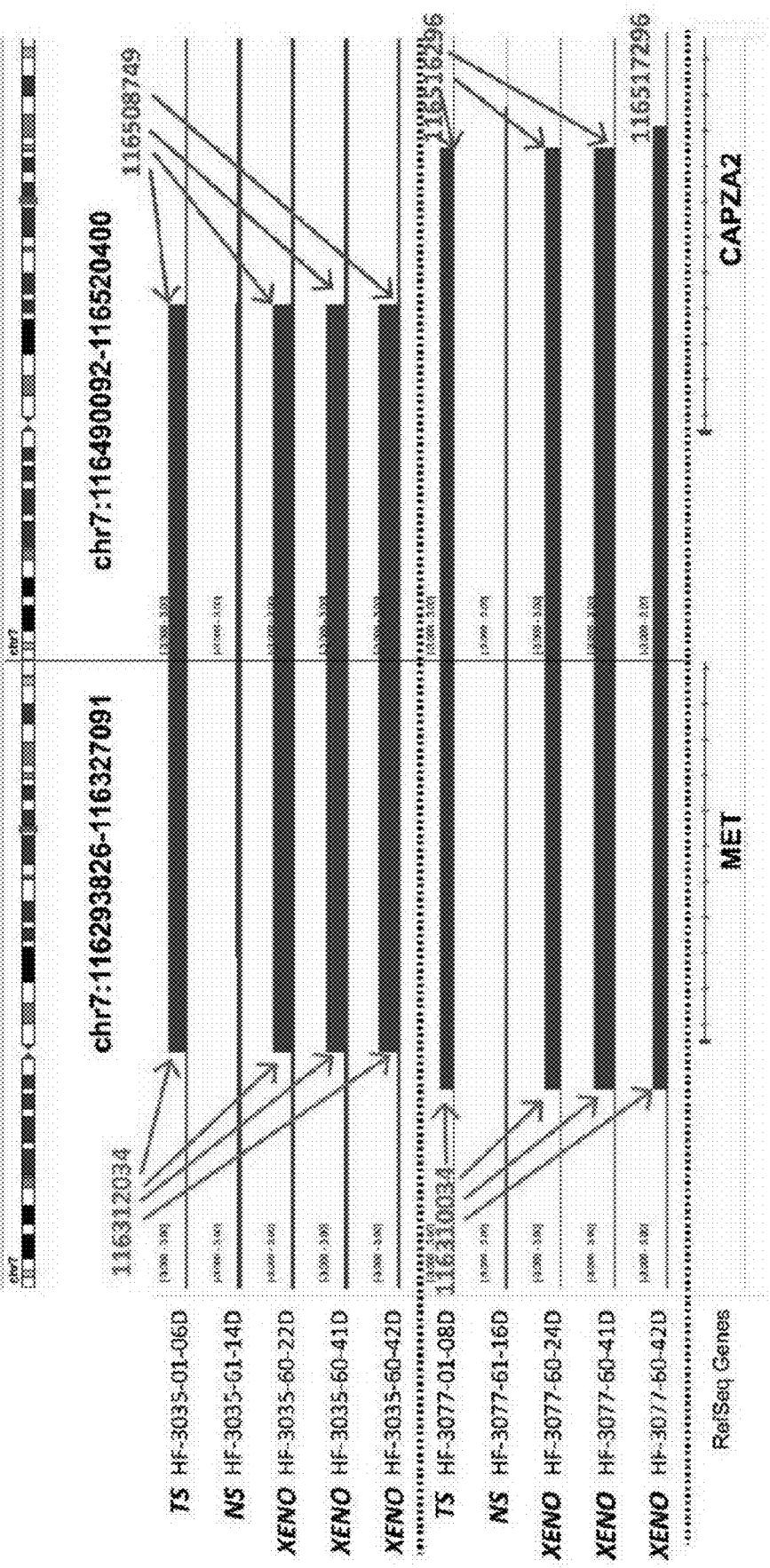
FIG. 9B depicts genomic breakpoints of the 7q31 amplification detected in HF3035 and HF3077 are similar in samples from the same parental tumor.

In spite of convincing evidence supporting fusion events in the GBM samples from HF3035, HF3055 and HF3077, no sequencing reads manifesting the presence of CAPZA2-MET fusion transcripts or the focal 7q31 genomic amplification were identified in the HF3055 and HF3077 neurospheres and only weak support was found in the HF3035 neurosphere. However, identical CAPZA2-MET fusions and 7q31 DNA amplifications resurfaced at high frequency in all xenografts derived from the HF3035 and HF3077 neurospheres, with identical breakpoints (FIG. 9B). FIG. 9B tumor, greatly decreased in the neurospheres, and recovered intracranial and subcutaneous xenografts. MET is activated when expressed, as shown by robust p-MET (Y1234/1235) detection in the orthotopic xenograft. The FISH image shows increased frequency of MET amplification in the subcutaneous tumors, as observed for the intracranial tumors (FIG. 3A). HF3077: MET expression in the tumor, was undetectable in the neurospheres. In orthotopic xenografts, MET and p-MET positive cells can be observed at an early time point (day 56), before a tumor mass has formed, and persists until tumor has grown (day 160). Arrowheads in the figure point to examples of MET or p-MET positive cells. Scale size is indicated in each panel.

Example 25

Genomic Profiling of Glioblastoma, Derived Neurosphere and PDX Samples

The inventors established neurosphere cultures from twelve (12) newly diagnosed and one matched recurrent GBM (see Table 2).

TABLE 2

| Clinical characteristics of GBM patients included in this study. | | | | | | |
|---|---|---|---|---|---|---|
| Sample | Pathology | Age/ Gender | Rx prior to surgery | MGMT | OS (days) | TTP (days) |
| HF2354 | GBM | 61/M | BCNU | U | 196 | 60 |
| HF2587 | GBM | 56/F | Untreated | M | 360 | 232 |
| HF2927 | GBM | 55/F | Untreated | U | 664 | 566 |
| HF3016 | GBM | 45/M | Untreated | U | 649 | 88 |
| HF3177 | rGBM4 | | RT/TMZ/DCVax | U | | |
| HF3035 | GBM | 54/F | Untreated | U | 352 | 196 |
| HF3055 | GBM | 58/M | Untreated | U | 371 | 77 |
| HF3077 | GBM | 56/F | Untreated | U | 465 | 54 |
| HF3160 | GBM | 21/F | Untreated | M | 1018 | 100 |
| HF3178 | GBM | 65/M | Untreated | U | 189 | 138 |
| HF3203 | GBM | 64/M | Untreated | U | 425 | 276 |
| HF3216 | GBM | 76/M | Untreated | U | 94 | |
| HF3253 | GBM | 82/F | Untreated | U | 68 | |

Figure 9C:
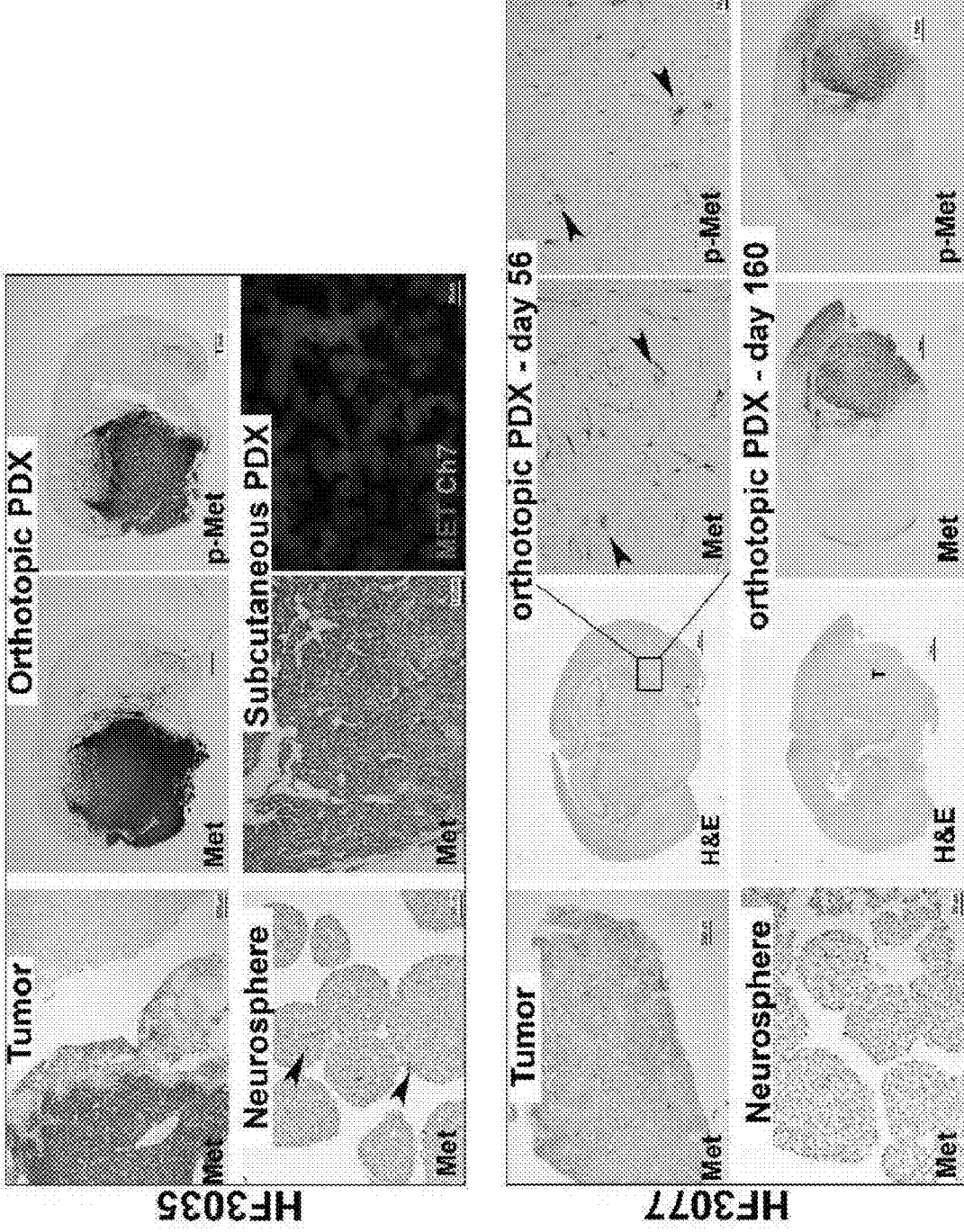
FIG. 9C depicts HF3035: MET protein expression in the tumor, greatly decreased in the neurospheres, and recovered intracranial and subcutaneous xenografts. MET is activated when expressed, as shown by robust p-MET (Y1234/1235) detection in the orthotopic xenograft. The FISH image shows increased frequency of MET amplification in the subcutaneous tumors, as observed for the intracranial tumors (FIG. 3A). HF3077: MET expression in the tumor, was undetectable in the neurospheres. In orthotopic xenografts, MET and p-MET positive cells can be observed at an early time point (day 56), before a tumor mass has formed, and persists until tumor has grown (day 160). Arrowheads point to examples of MET or p-MET positive cells. Scale size is indicated in each panel.

Rx: treatment; MGMT: MGMT gene promoter methylation status, U = unmethylated, M = methylated; OS: overall survival; TTP: time to progression.

depicts Genomic breakpoints of the 7q31 amplification detected in HF3035 and HF3077 were similar in samples from the same parental tumor. None of the HF3055 xenografts carried CAPZA2-MET fusions or 7q31 amplification, in line with the absence of focal 7q31 amplification in the primary HF3055 tumor. To exclude the possibility that the CAPZA2-MET fusion events were artifacts resulting from sequencing, the event in all samples from HF3035 using RT-PCR was validated, which confirmed both wildtype MET and CAPZA2-MET mRNA in the tumor and PDX, but not in the neurosphere (FIGS. 9A and 9B), FIG. 9A depicts MET amplification and activation. RT-PCR detection of CAPZA2-MET fusion transcripts in HF3035 samples. The inventors observed band of predicted size for MET transcript (oligos M2F and M8R) for the HF3035 tumor sample (T), neurosphere cells (N, faint band), 3 xenografts tumors (X), and neurospheres derived from xenograft tumors (NX). The inventors observed a band of predicted size for the fusion CAPZA2(exon1) -MET(exon6) transcript for HF3035 T, X and NX samples. HF2303 neurosphere line expressing only wt MET was used as control. MET protein was abundantly present in the HF3035 and HF3077 tumors as measured using immunohistochemistry, undetectable in the neurospheres, and re-expressed in the PDX (FIG. 9C). FIG. 9C depicts HF3035: MET protein expression in the The inventors used neurosphere cultures between 7 and 18 passages for molecular profiling and engrafting orthotopically into nude (immunodeficient) mice. The sample cohort included one pair of primary (HF3016) and matching recurrent (HF3177) GBM. Following a glioblastoma diagnosis, a patient treated at Henry Ford hospital underwent a craniotomy to remove the tumor. This is the primary tumor, labeled HF3016. As is typical for GBM, the patient relapsed after a number of months in spite of receiving chemo- and radiation therapy. The patient underwent a second craniotomy procedure to remove the recurrent tumor, which was also used in the study, and this tumor sample was labeled HF3177. HF3016 and HF3177 were tumor samples obtained from the same patient at two different timepoints.

A schematic overview of the inventors' study design is presented in FIG. 1A. FIG. 1A depicts a comprehensive comparison of GBM, derived neurospheres and PDX models. The inventors performed genomic and transcriptomic characterization on thirteen patient tumors, their derivative neurospheres and xenograft models. Long read PacBio sequencing was performed on two xenograft tumors.

To determine whether model systems capture the somatic alterations that are thought to drive gliomagenesis, and whether there is selection for specific driver genes, the inventors performed whole genome sequencing at a median depth of 6.5× to determine genome wide DNA copy number as well as exome sequencing on all samples. DNA copy number was generally highly preserved between tumor and derived model systems (FIG. 7). In whole genome sequencing, an entire genome is sequenced, while in whole exome sequencing, an exome enrichment step using exon-specific captures probes is performed prior to sequencing library construction. As a result, all exons/the exome in a genome is preferentially sequenced. A "median depth of 6.5×" in whole genome sequencing means that each genome reference base position is likely to be mapped with between 6 and 7 sequencing reads.

The inventors used model systems which retained whole chromosome 7 gain and chromosome 10 loss when detected in the tumor, which is consistent with their proposed role as canonical GBM lesions (that is, as genes that those skilled in the art in this field are frequently altered in GBM) that occur amongst the earliest events in gliomagenesis. This extends the previous finding in Ozawa, T. et al. Most human non-GCIMP glioblastoma subtypes evolve from a common proneural-like precursor glioma. *Cancer Cell* 26, 288-300 (2014), which is incorporated herein by reference in its entirety. Most human non-GCIMP glioblastoma subtypes evolve from a common proneural-like precursor glioma. The global DNA copy number resemblance between xenografts and the GBM from which they were derived, confirms that PDXs recapitulate the majority of molecular properties found in the original tumor. Thus, the present PDX mouse model is believed to be a good model for diagnosing and predicting treatment of the original tumor.

Figure 1B:
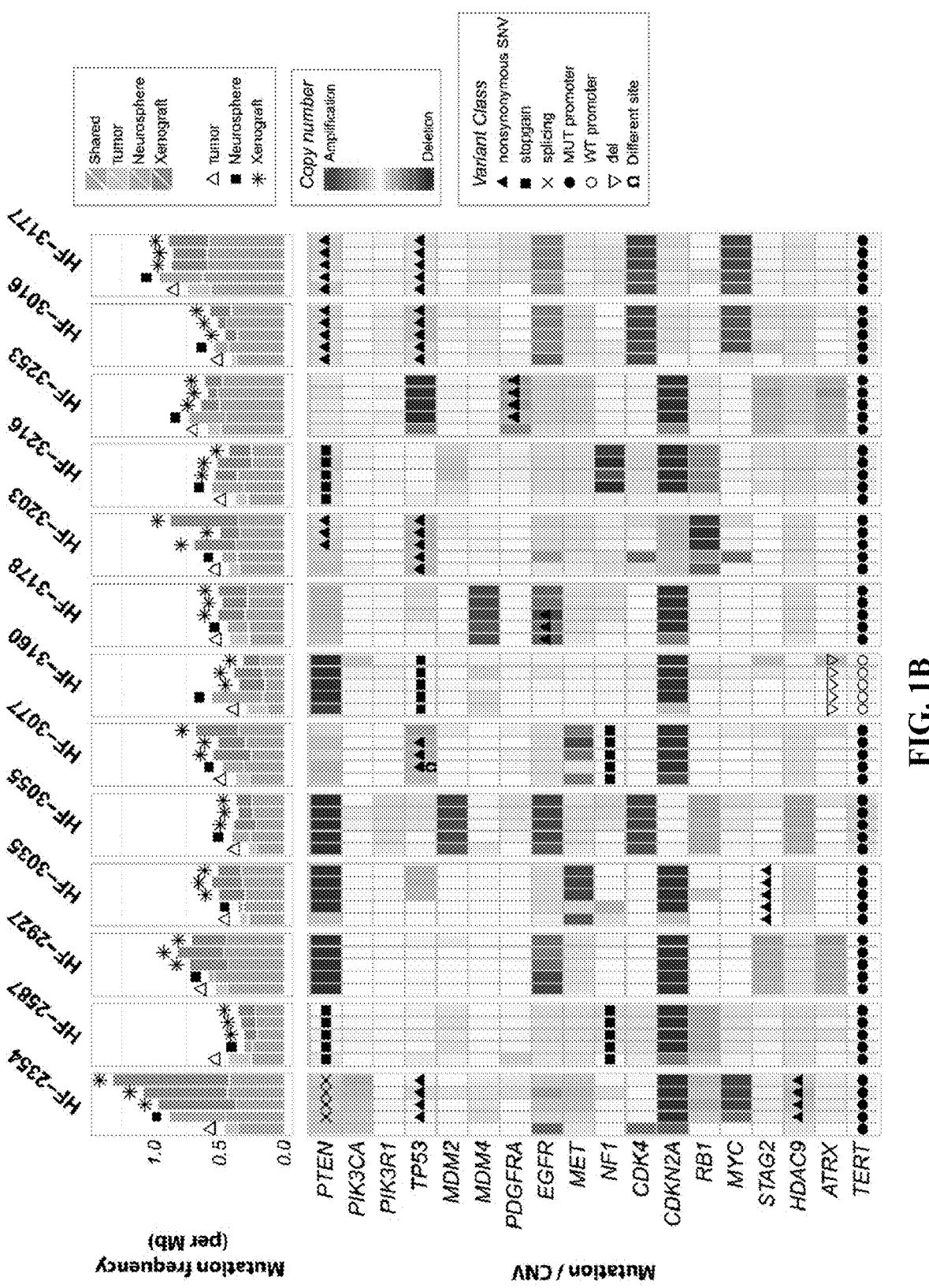
FIG. 1B depicts somatic driver alterations compared between GBM tumors and derivative model systems.

The inventors compared mutation and DNA copy number status of genes previously found to be significantly mutated, gained, or lost in GBM. The present finding extended the previous finding in Ceccarelli, M. et al., *Cell* 164, 550-63 (2016); and Brennan, C. W. et al., *Cell* 155, 462-77 (2013). The inventors further discovered that 100% of homozygous deletions and somatic single nucleotide variants (sSNVs) affecting GBM driver genes in tumor samples were propagated to the neurospheres and xenografts, including non-coding variants in the TERT promoter (FIG. 1B). Genomic amplifications showed greater heterogeneity. In two cases, MYC amplification was not detected in the parental tumor, but presented in the derivative neurospheres and maintained in xenografts, consistent with its role in glioma stem cell maintenance, extending the findings of Wang, J. et al. c-Myc is required for maintenance of glioma cancer stem cells. *PLoS One* 3, e3769 (2008); Annibali, D. et al. Myc inhibition is effective against glioma and reveals a role for Myc in proficient mitosis. *Nat Common* 5, 4632 (2014). Other genes showing variable representation across tumor and model systems included MET in HF3035 and HF3077, and EGFR and PIK3CA (phosphatidylinositol-4,5-bisphosphate 3-kinase catalytic subunit alpha) in HF2354. The HF2354 derived model systems were considerably less similar compared to the primary tumor than other cases which coincided with HF2354 being the only case subjected to neoadjuvant carmustine treatment. Whole chromosome gains of chromosome 1, 14 and 21, and one copy loss of chromosome 3, 8, 13, 15 and 18 were acquired in the neurosphere culture and propagated to the xenograft models (FIG. 7). At the gene level, this resulted in newly detected mutations in PTEN and TP253, focal amplification of MYC (also in HF 3016), and absence of CDK4 and EGFR amplification in the neurosphere and xenografts relative to the tumor sample (FIG.

1B). FIG. 1B depicts Somatic driver alterations compared between GBM tumors and derivative model systems.

Example 26

Extrachromosomal Elements Are Frequently Found in Glioblastoma

The inventors have recognized that DNA in cancer can be amplified as part of chromosomal homogenously staining regions (HSR) and as extrachromomal minute bodies. The inventors searched their data set for complex patterns of DNA copy number amplification and rearrangement that were suggestive of ecDNA elements (FIG. 8). FIG. 8 depicts predicted ecDNA elements in primary tumors, neurospheres, and xenografts using whole genome sequencing.

The inventors' work extends an example of the importance of extrachromosomal DNA elements (ecDNA) in cancer was the discovery of double minutes carrying the oncogene N-MYC in neuroblastoma, set forth in Kohl, N. E. et al. Transposition and amplification of oncogene-related sequences in human neuroblastomas. *Cell* 35, 359-67 (1983). The present work also extends and confirms a recent survey of a compendium of cancer cells and cell lines, which highlighted the frequent presence of ecDNA in glioblastoma, among other cancer types, Turner, K. M. et al.; *Nature* 543, 122-125 (2017), (Sanborn, J. Z. et al., *Cancer Res* 73, 6036-45 (2013), Zheng, S. et al., *Genes Dev* 27, 1462-72 (2013); Nikolaev, S. et al., *Nat Commun* 5, 5690 (2014)).

Segmented copy numbers, structural variation (SV) breakpoints, and fusion junctions have been visualized over patient tumor and its derived model systems for each predicted extrachromosomal region (whose boundaries have been indicated with vertical dots). In cases where one end of a fusion gene junction or SV breakpoint pair does not fall within the predicted ecDNA region, those points have been plotted outside the region.

Figure 2A:
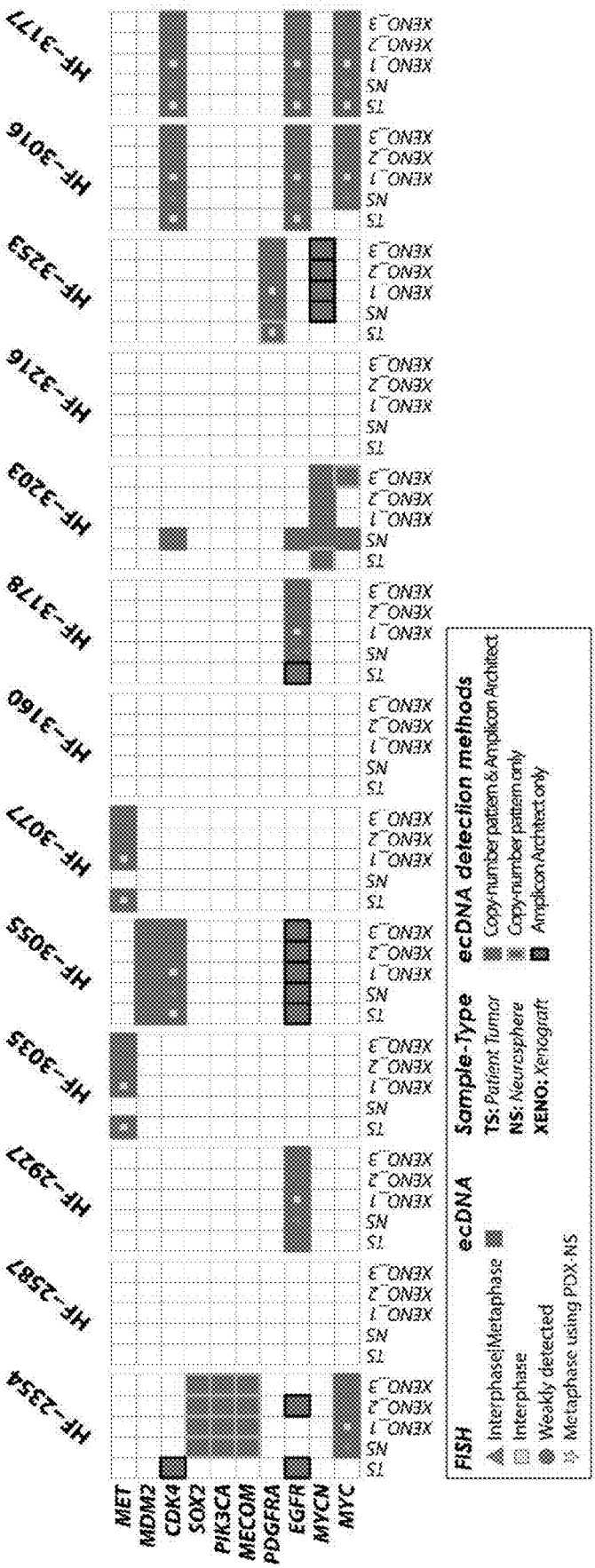
FIG. 2A depicts ecDNA in hGBM samples and FISH validation. Heatmap of samples versus driver genes predicted to reside on extrachromosomal DNA elements that were detected with either copy number based or Amplicon Architect methods. Only ecDNAs with markers were validated using FISH.

On the basis of DNA copy number patterns, the inventors predicted 74 ecDNAs originating from 21 unique genomic loci which were distributed over ten of the thirteen patient tumors and their derived model systems. The predicted ecDNA elements contained oncogenes including MYC, MYCN, EGFR, PDGFRA, MET, the MECOM/PIK3CA/SOX2 gene cluster and the CDK4/MDM2 gene cluster. In total, 19 of the 21 unique oncogene carrying ecDNAs were detected in more than one sample, i.e. in neurospheres and matching PDX or in tumor sample and matching neurosphere or PDX (FIG. 2A). FIG. 2A depicts ecDNA in hGBM samples and FISH validation. Heatmap of samples versus driver genes predicted to reside on extrachromosomal DNA elements that were detected with either copy number based or Amplicon Architect methods. Only ecDNAs with markers were validated using FISH.

The inventors performed interphase FISH on tumor samples and PDX, and metaphase FISH on neurospheres to validate 34 predicted ecDNA amplifications, including of EGFR (HF2927, HF3178, HF3016 and HF3177), MYC (HF2354, HF3016 and HF3177), CDK4 (HF3055, HF3016 and HF3177), MET (HF3035 and HF3077), MDM2 (HF3055) and PDGFRA (HF3253). In all interphase FISH experiments the inventors observed a highly variable number of fluorescent signals per nucleus, ranging from two to 100 (FIG. 2B, Table 3A-3D). FIG. 2B depicts top: DNA copy number and genomic rearrangements at ecDNA loci that were predicted with the copy number based approach. Bottom: Representative FISH images showing amplification of MYC, CDK4, PDGFRA in tumor, neurospheres and PDXs (red) and control chromosomal probes (green), EGFR amplification in neurospheres and PDX (green) and Chr7 control are shown in the figure. Bottom: Representative interphase FISH (Tumor and PDX) and metaphase FISH (neurospheres). Arrows in metaphase FISH images mark extrachromosomally DNA elements. This heterogeneity was strongly suggestive of differences in the number DNA copies of the targeted gene per cell and thereby of an extrachromosomal DNA amplification. Metaphase FISH on neurosphere cells validated the extrachromosomal status in all cases (FIG. 2B). The inventors' analysis showed that oncogene amplification frequently resided on extrachromosomal DNA elements.

Example 27

Extrachromosomal MET DNA Elements Mark a Distinct Tumor Subclone

Figure 3C:
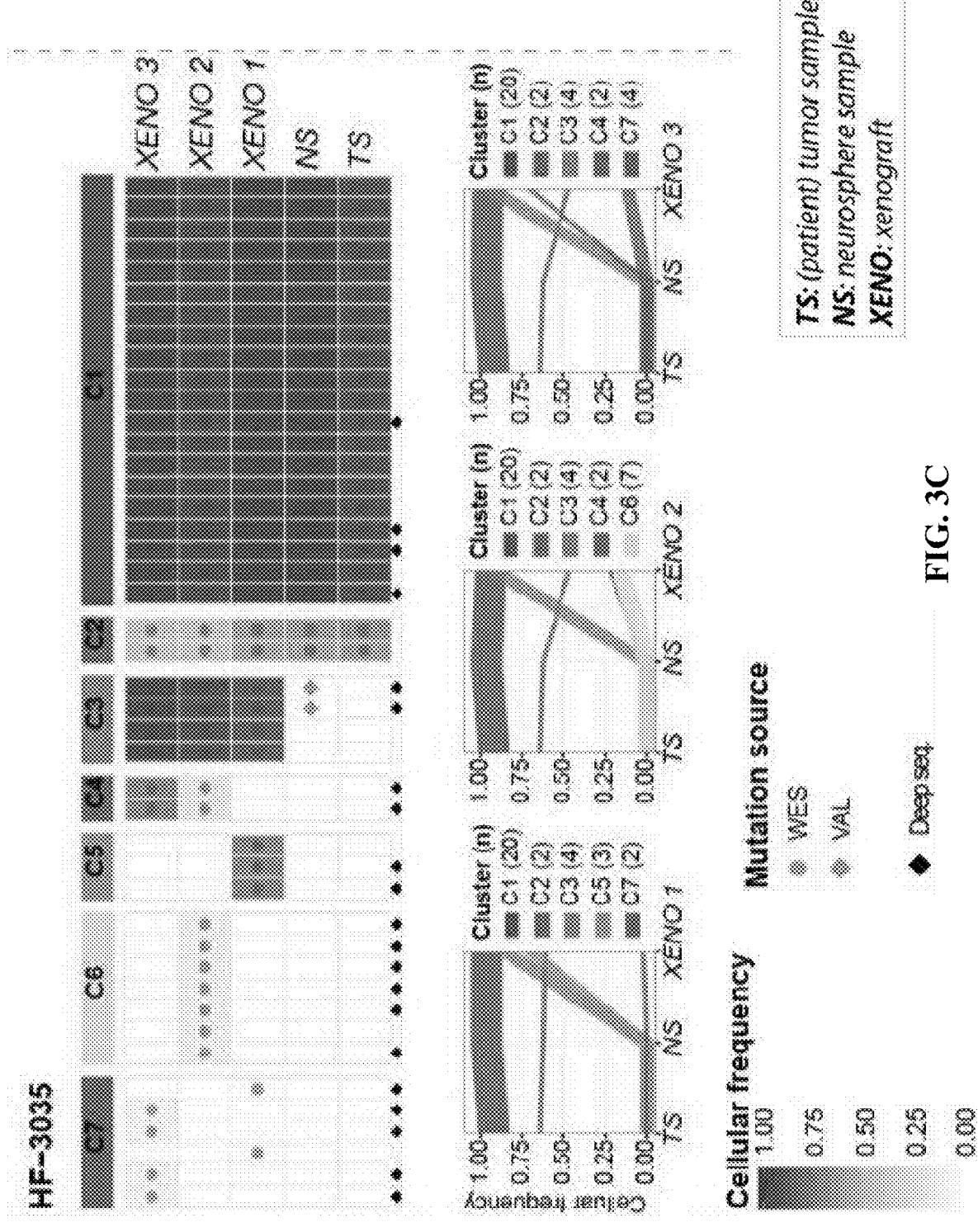
FIG. 3C depicts top panel: Coverage-controlled sSNVs detected using exome and deep validation sequencing. Color reflects cellular frequency estimates. Bottom panel: Clonal tracing from HF3035 and HF3077 parent tumor to neurospheres and xenografts. Each line represents a group of mutations computationally inferred to reflect a subclone.

Among the identified oncogene carrying ecDNA elements, two cases of extrachromosomal MET amplification stood out due to their variable presence across the parental tumor (high frequency), neurosphere (low frequency), and xenograft triplicates (high frequency) (FIG. 3A). FIG. 3A depicts extrachromosomal MET DNA. Representative FISH images for MET (green) and chromosome 7 control probes (7qCtr, red) labeling of HF3035 and HF3077 tumor, neurosphere (NS), and xenografts (PDX), and neurospheres established from HF3035 xenograft tumors (PDX-NS1). The inventors performed interphase FISH on tumor and PDX samples, and metaphase spread FISH on neurospheres. Passage numbers were indicated for neurosphere cultures. White arrows point to 2 fragmented MET signals in one chromosome in HF3035 samples (2SM). Yellow arrows point to extrachromosomal MET in metaphase nuclei of HF3035 neurospheres. The percentage of nuclei presenting MET amplification for each sample is shown. In both cases, the MET amplification associated with a transcript fusion with neighboring gene CAPZA2 (see FIG. 3B, FIG. 9B). The pattern of undetectable and re-appearing MET rearrangements may result from clonal selection of glioblastoma cells with a competitive advantage for proliferation in vivo. This hypothesis is strengthened by the inventors' observation that the breakpoints of the lesions were identical across samples from the same parental origin (FIG. 9B), MET is a growth factor responsive cell surface receptor tyrosine kinase and may provide context dependent proliferative signals. See Organ, S. L. & Tsao, M. S. An overview of the c-MET signaling pathway. *Ther Adv Med Oncol* 3, S7-S19 (2011). The inventors reasoned that evolutionary patterns resulting in such dominant clonal selection would likely be replicated by sSNVs tracing the cells carrying the MET amplicon. To evaluate clonal selection patterns, the inventors determined variant allele fractions of all sSNVs identified across HF3035 and HF3077 samples. To increase sensitivity to detect mutations present in small numbers of cells, the inventors corroborated the exome sequencing data using high coverage (>1,400×) targeted sequencing. All mutations detected in the HF3035 GBM were recovered in the neurosphere and xenografts. The mutational profile of HF3035 suggested that a subclone developed in the xenografts that was not present in parental GBM and neurosphere and revealed a subclone that was present at similar frequencies in all samples (FIG. 3C). FIG. 3C depicts—Top panel: coverage-controlled sSNVs detected using exome and deep validation sequencing color reflects cellular frequency estimates. Bottom panel: clonal tracing from HF3035 and HF3077 parent tumor to neurospheres and xenografts. Each line represents a group of mutations computationally inferred to reflect a subclone. Only a single and very low frequency LAMB1 mutation (variant allele fraction in tumor 0.003) present in the HF3077 primary tumor, but not detected in its derived neurosphere, resurfaced in one of three xenografts with a 0.04 variant allele fraction. A low frequency subclone (C2) developed in the neurosphere which was transmitted to xenografts (FIG. 3C). Subclonal heterogeneity as recovered by the mutation profiles thus suggested a very different clonal selection trend compared to the disappearing and resurfacing MET amplifications and associated transcript fusions. The inventors research is further to prior information that ecDNAs were thought to inherit through random distribution over the two daughter cells (Storlazzi, C. T. et al., *Genome Res* 20, 1198-206 (2010)), possibly through a binomial model (Lundberg, G. et al. Binomial mitotic segregation of MYCN-carrying double minutes in neuroblastoma illustrates the role of randomness in oncogene amplification, *PLoS One* 3, e3099 (2008)), but much is unknown with respect to the propagation of ecDNA through cancer cell populations. The disjointed propagation of chromosomal SNVs and extrachromosomal MET ecDNAs indicate that they were marking different tumor subclones and suggest alternative modes of tumor evolution. While sSNVs were copied to daughter cells during mitosis such that both cells inherit the full spectrum of chromosomal alterations present in the parental cell, ecDNA elements likely randomly segregated and ended up in the daughter cells in uneven numbers.

Figure 3D:
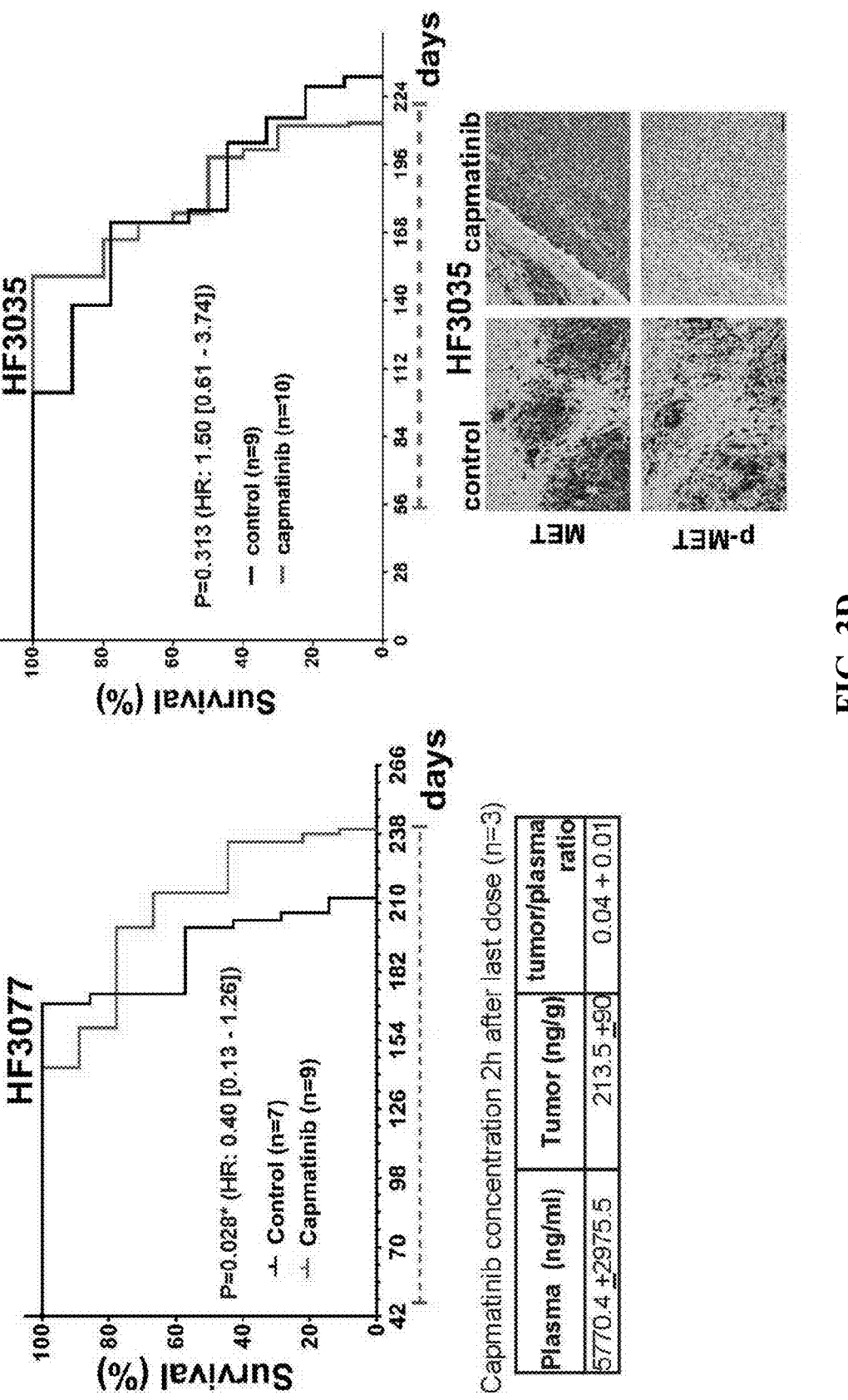
FIG. 3D depicts top panel: Treatment with single agent capmatinib (30 mg/kg, daily oral doses). Capmatinib, also known as INCB28060 and INC280, is an orally bioavailable inhibitor of the proto-oncogene c-MET (hepatocyte growth factor receptor [HGFR]), and increases survival of HF3077 PDX, but not of HF3035. Kaplan-Meier survival curves were compared by log-rank (Mantel-Cox) test, significance set at P<0.05 (*), HR [95% CI], treatment schedule (dotted red line) and number of mice in each arm (n) are shown. Bottom panel, left: Capmatinib concentration in the plasma and tumor tissue collected 2 h after the last dose was determined by LC-MS/MS for HF3077 PDX. Bottom panel, right: MET and p-MET detection by immunohistochemistry of control and capmatinib-treated xenografts show complete inhibition of p-MET, but did not affect MET overexpression in HF3035 PDX. Scale, 40 mm.

MET expressing cells exhibited MET activation and the inventors selected them early during tumor formation in the orthotopic xenografts (FIG. 9C), suggesting that MET activity was driving selection for MET amplified cells in vivo. The inventors treated HF3077 PDX with ATP-competitive MET inhibitor capmatinib (INCB28060) according to the protocol in Liu, X. et al. A novel kinase inhibitor, INCB28060, blocks c-MET-dependent signaling, neoplastic activities, and cross-talk with EGFR and HER-3. *Clin Cancer Res* 17, 7127-38 (2011) at a daily oral dose of 30 mg/kg showed a significant survival benefit, despite the relatively low concentration of drug in the brain tumor as assessed by LC-MS/MS (FIG. 3D). FIG. 3D depicts Top panel: Treatment with single agent capmatinib (30 mg/kg, daily oral doses, capmatinib, also known as INCB28060 and INC280, is an orally bioavailable inhibitor of the proto-oncogene c-MET (hepatocyte growth factor receptor [HGFR])) increases survival of HF3077 PDX, but not of HF3035. Kaplan-Meier survival curves were compared by log-rank (Mantel-Cox) test, significance set at P<0.05 HR [95% CI], treatment schedule (doted red line) and number of mice in each arm (n) are shown in FIG. 3D. Bottom panel, left: Capmatinib concentration in the plasma and tumor tissue collected 2h after the last dose was determined by LC-MS/MS for HF3077 PDX. Bottom panel, right: MET and p-MET detection by immunohistochemistry of control and capmatinib-treated xenografts show complete inhibition of p-MET, but did not affect MET overexpression in HF3035 PDX. Scale, 40 mm.

In contrast, capmatinib treatment of HF3035 PDX did not increase survival nor decrease MET expression but resulted in decrease of phospho-MET in treated tumors. This may reflect MET functions that are independent of the kinase activity in these tumors. These results demonstrate that targeting MET in GBM harboring MET ecDNA amplification has therapeutic potential, but MET amplification alone is not a predictor of response to single agent ATP-competitive inhibitor treatment. Comparable to the orthotopic xeno-grafts, subcutaneous PDX tumors formed from implant of HF3035 neurosphere cells were dominated by MET-ampli-fied cells accompanied by robust MET expression (FIG. 9C). The increase in the frequency of MET-amplification in HF3035 cells in vivo are therefore not dependent on factors uniquely present in the brain microenvironment.

Interphase FISH analysis in the parental HF3077 tumor identified a small percentage of nuclei with 3 copies of chromosome 7 but only 2 copies of MET. The frequency of cells with one deleted copy of MET in Ch 7 increased significantly in HF3077 neurospheres and decreased in the xenografts (Table 3A-D). The observed gene deletion in one copy of chromosome 7 is suggestive of the post-replication segregation-based model of double minute formation, extending the findings of Vogt, N. et al., *Proc Natl Acad Sci USA* 101, 11368-73 (2004). To precisely define the genomic contents and structure of the predicted double minutes, the inventors generated long read (Pacific Biosciences) DNA sequencing from a single xenograft of each HF3035 and HF3077, and performed de novo assembly. In HF3035, the inventors identified seven assembled contigs (range: 6,466~135,621 bp) to have sequence fragments (at least 1,000 bp long) aligned on the MET-CAPZA2 region of hg19 chromosome 7. Interestingly, analysis of the aligned sequence fragments from the seven contigs revealed a more complex structural rearrangement than expected from the analysis of short read sequencing data. For example, the 135 kb tig01170337 contig consisted of 8 sequence fragments that were nonlinearly aligned on alternating strands of the MET-CAPZA2 and CNTNAP2 regions. Other contigs such as tig01170699, tig01170325, and tig00000023 also showed nonlinear alignment, suggesting that these contigs resulted from chromosomal structural variations.

Figure 3E:
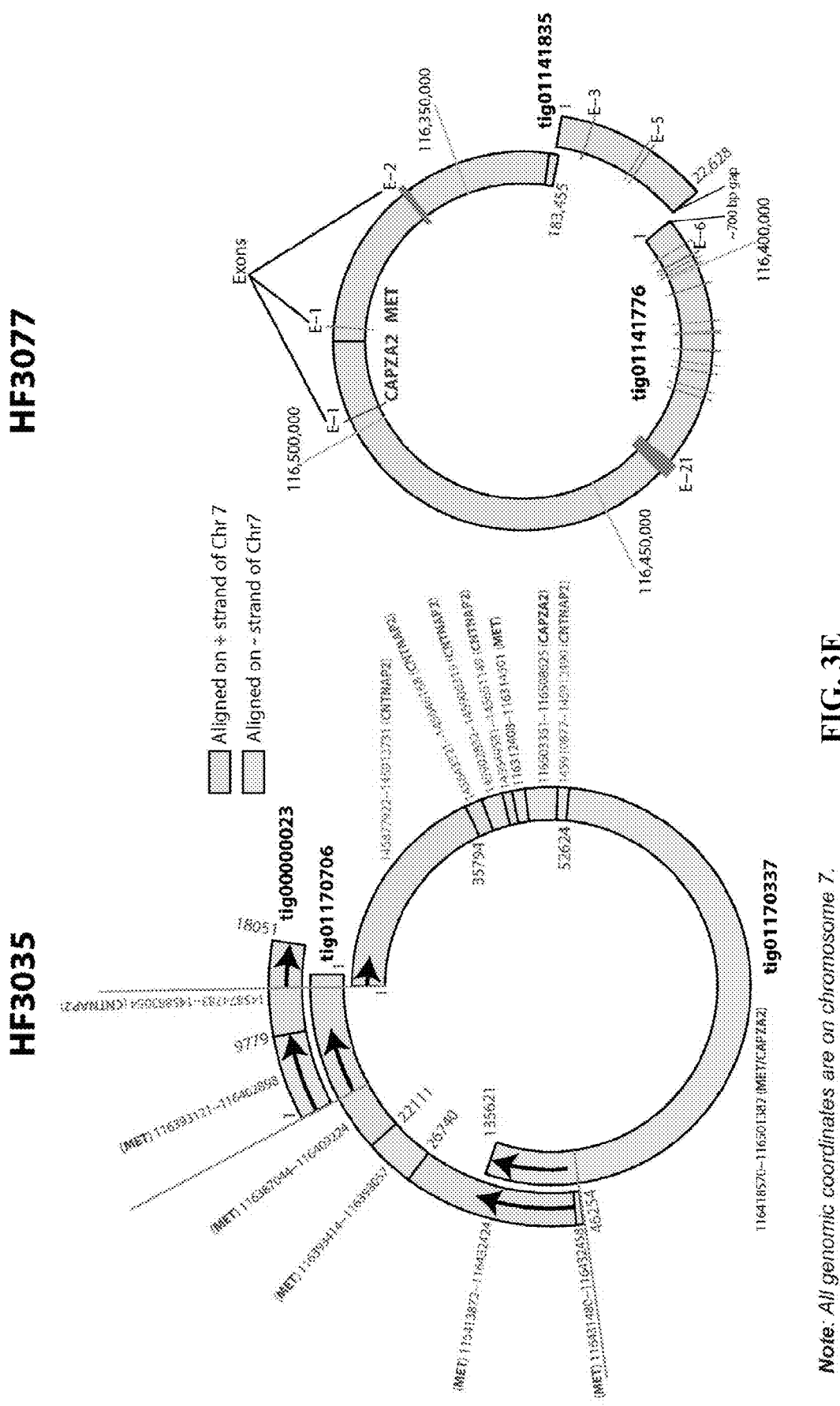
FIG. 3E depicts double minute structures containing the chromosome 7q31 locus including the MET and CAPZA2 genes in HF3035 and HF3077 xenografts, predicted from long read sequencing.
Figure 10A:
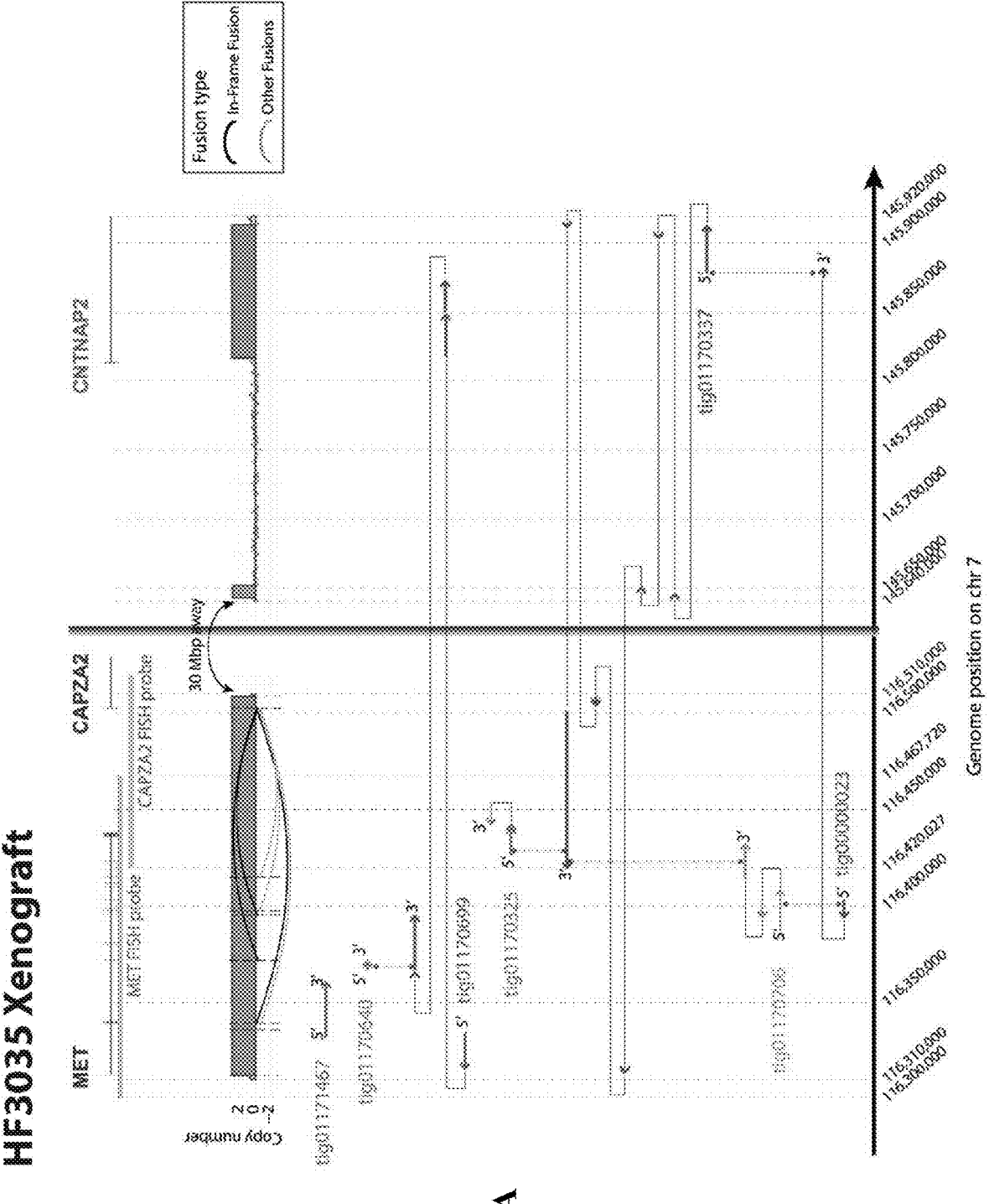
FIG. 10A depicts structural variations detected using PacBio sequencing. Contig sequence fragments of at least 1 kb were aligned to hg19 chr 7. Right and left arrows represent sequence fragments aligned on + and − strands, respectively. A green dotted line between two contigs indicates that the sequence fragment was shared. Copy numbers and fusion junctions are also shown. Red bars represent area of DNA copy number gain.
Figure 10A:
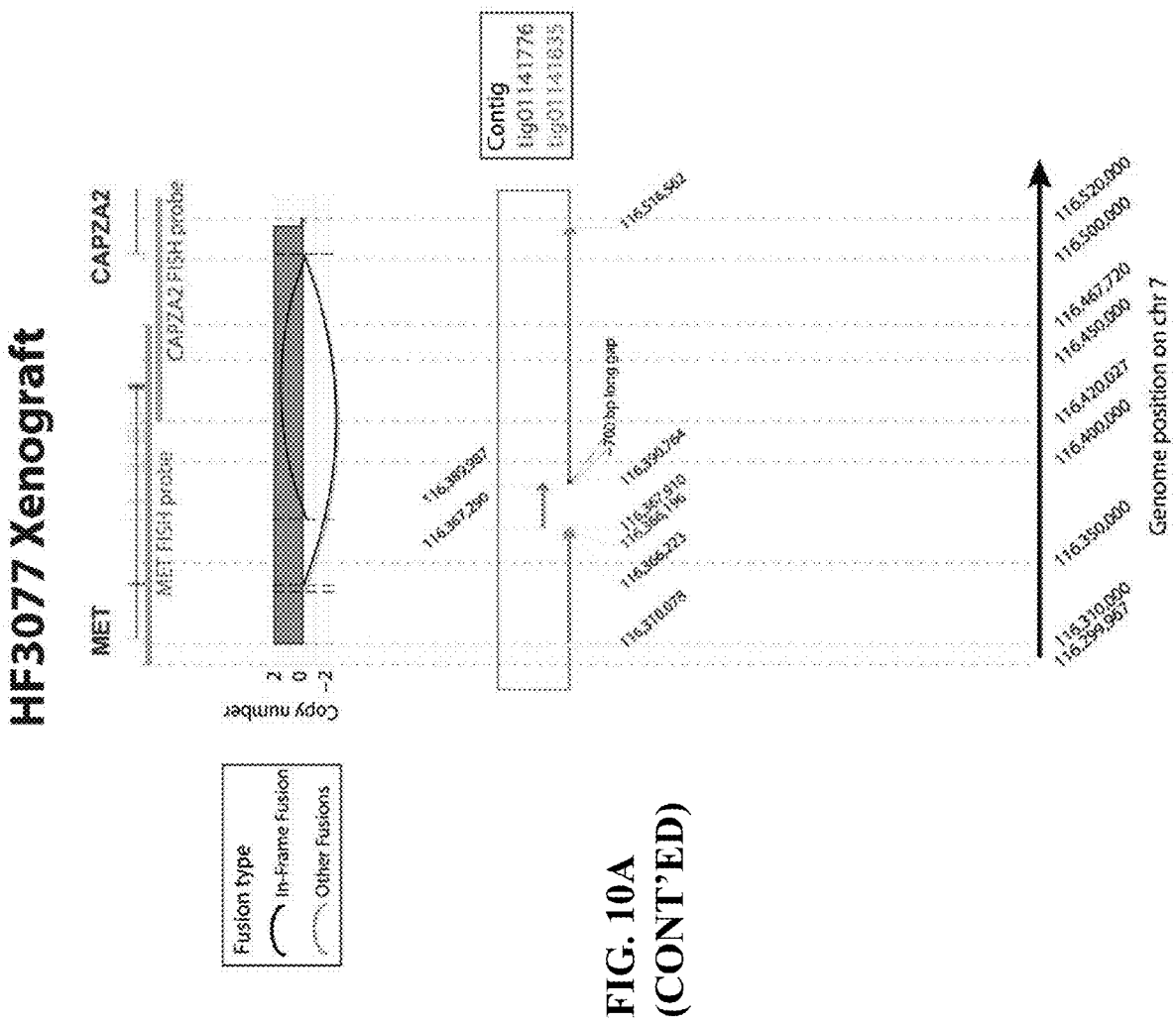

The inventors performed pairwise sequence comparison of the contigs to search for sequence fragments (at least 5,000 bp long) shared among them, and the inventors found four contigs each of which shared sequence fragments with one of the contigs. Interestingly, three of them could be connected in a circular form using the shared sequence fragments (FIG. 3E; FIG. 10A), revealing a circular struc-ture that may represent the full double minute. In HF3077, only two contigs were detected to be aligned on the MET-CAPZA2 region of hg19 chromosome 7 (FIG. 3E; FIG. 10A). FIG. 3E shows double minute structures containing the chromosome 7q31 locus including the MET and CAPZA2 genes in HF3035 and HF3077 xenografts, pre-dicted from long read sequencing. FIG. 10A depicts struc-tural variations detected using PacBio sequencing. Contig sequence fragments of at least 1 kb were aligned to hg19 chr 7. Right and left arrows represent sequence fragments aligned on + and − strands, respectively. A green dotted line between two contigs indicates that the sequence fragment was shared. Copy numbers and fusion junctions are also shown in FIG. 10A. Red bars represent area of DNA copy number gain. Different genetic origins for ecDNA have been postulated, with evidence for post-replicative excision of chromosomal fragments and non-homologous end joining, as discussed in Vogt, N. et al., *Proc Natl Acad Sci USA* 101, 11368-73 (2004).

Figure 10B:
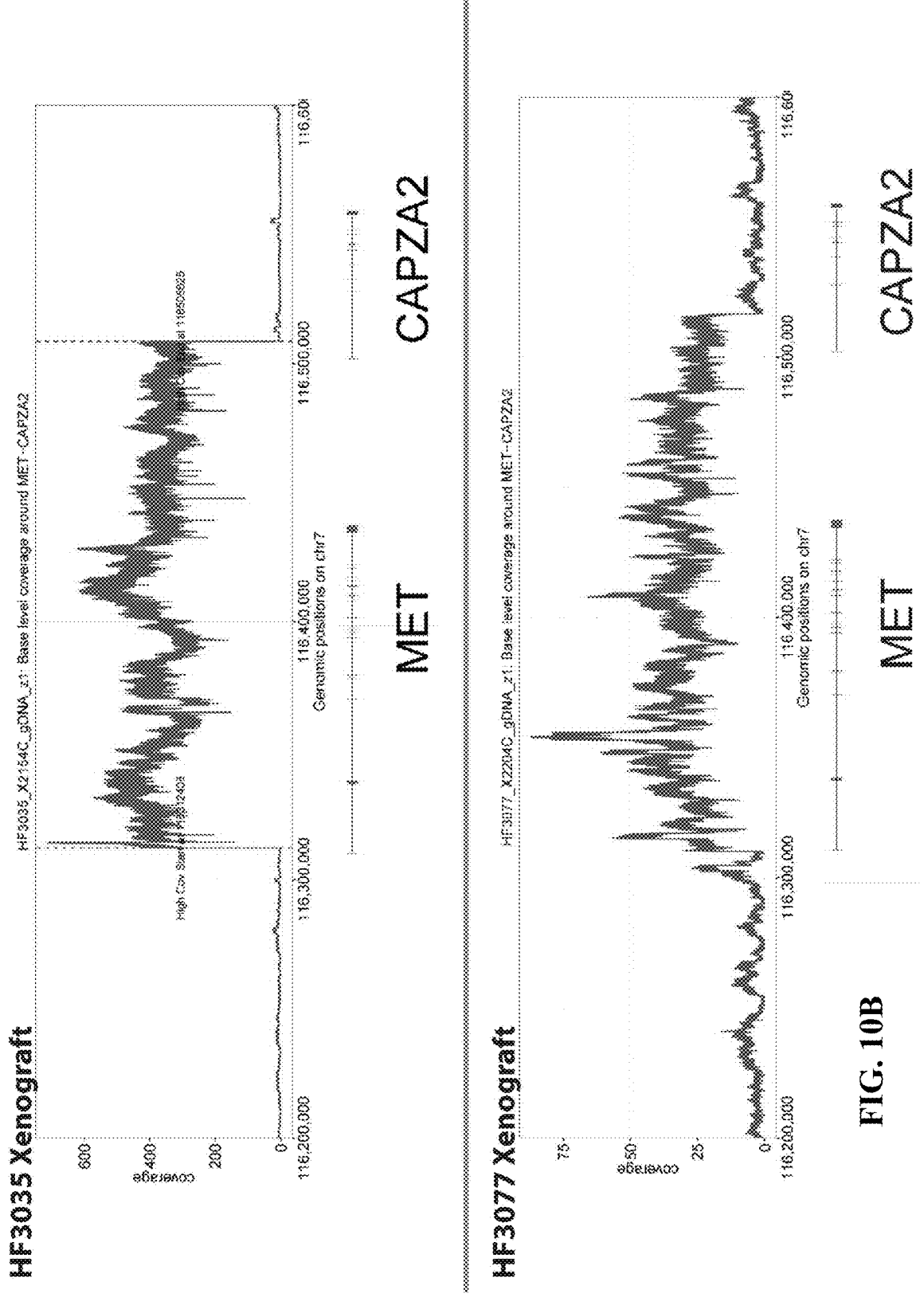
FIG. 10B depicts coverage of the PacBio sequencing reads over the MET-CAPZA2 region.

The presence of only two aligned contigs in HF3077 might be related to the lower sequence coverage of the double minute structure, compared to HF3035 (34× vs 405×, respectively) (FIG. 10B). FIG. 10B depicts coverage of the PacBio sequencing reads over the MET-CAPZA2 region. The longest contig, tig01141776 (183,455 bp long), con-sisted of two segment fragments that were nonlinearly aligned over exon 1 of CAPZA2 and all except exons 3-5 of MET, suggesting that it resulted from structural variations. The second short contig, tig01141835 (22,628 by long), was aligned as a whole over exon 3-5 of MET. Interestingly, connecting the two contigs created a circular DNA segment. Through analysis of PacBio sequencing, the inventors were able to detect and reconstruct the predicted double minute structures.

Example 28

Figures 4A, 4B, 4C, 4D:
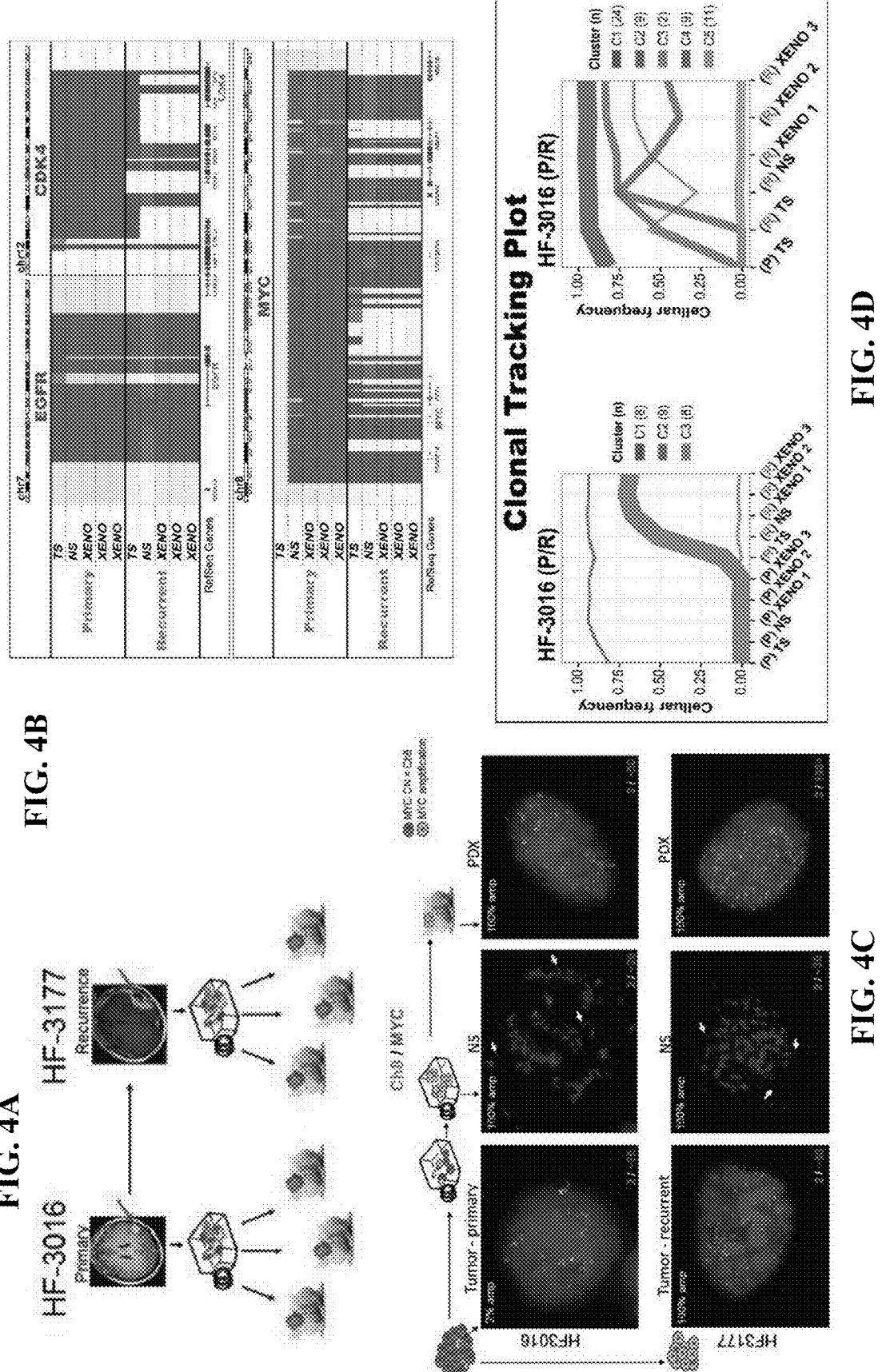
FIG. 4A depicts extrachromosomal DNA marks subclones driving tumor growth in patient tumors and derived model systems, and establishing neurosphere cultures and PDX models from a paired primary/recurrent GBM.
FIG. 4B DNA copy number analysis shows co-amplification of EGFR (chr7)/CDK4 (chr 12) is detected in primary GBM HF3016 which is sustained in both neurosphere and xenografts derived from this primary tumor, as well as the recurrent GBM HF3177, and the neurosphere/xenografts thereof. The HF3016 primary tumor is not MYC amplified. The HF3016 neurosphere, as well as all HF3177 samples, show focal MYC amplification.
FIG. 4C depicts representative FISH images for MYC (red) and Ch8 marker (green) show that a small fraction (2%) of the cells in HF3016 tumor presents MYC amplification, while 100% of nuclei in the remaining samples present MYC amplification, which is clearly extrachromosomal (white arrows) the metaphase spreads (NS).
FIG. 4D depicts clonal tracing of a pair of primary-recurrent GBM, their matching neurospheres, and xenografts. Each line represents a group of mutations computationally inferred to reflect a subclone.
Figure 4E:
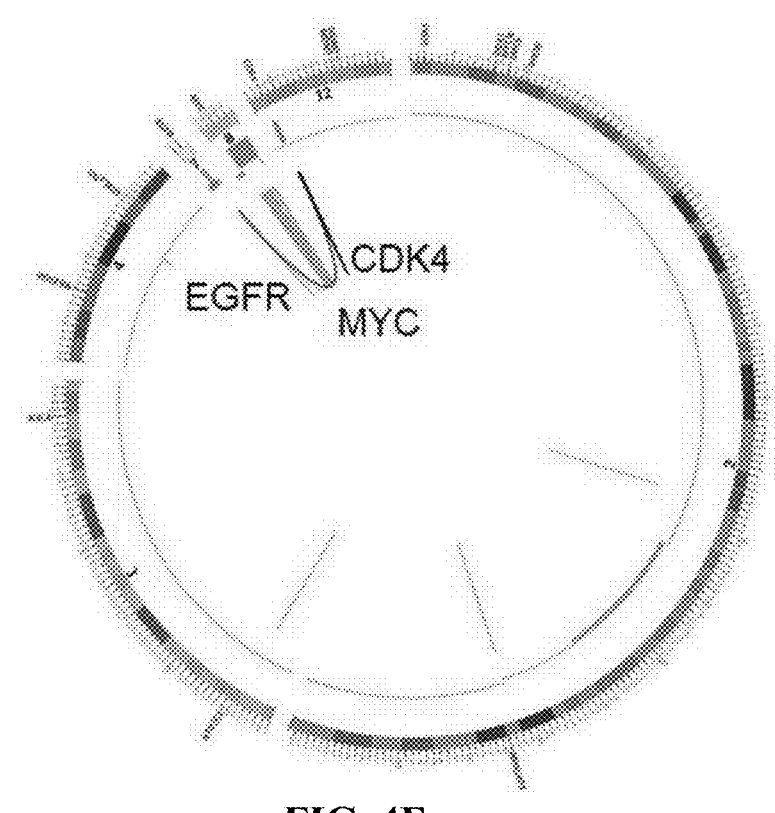
FIG. 4E depicts starting in the neurosphere of the primary tumor, a complex structural variant is identified that connects the CDK4 locus to the EGFR locus. The MYC locus is not part of this variant. The EGFR/CDK4 variant is detected in HF3016 PDXs as well as all HF3177 samples.
Figure 4F:
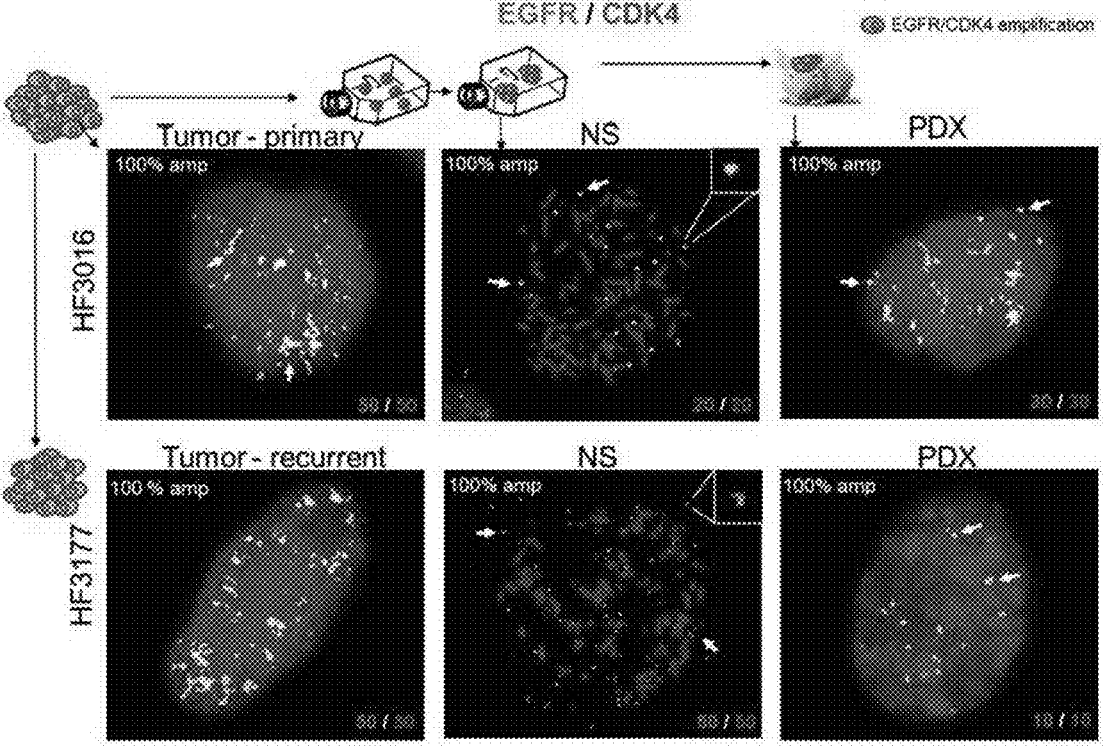
FIG. 4F EGFR (green) and CDK4 (red), detected by FISH, are amplified in 100% of nuclei for every sample from this patient, with identical copy numbers in each nucleus (bottom of the panels). Overlapping dots show that EGFR/CDK4 colocalize (white arrows) and metaphase FISH (NS) shows extrachromosomal co-amplification in the same double minute (inserts).

Multiple ecDNA Elements were Longitudinally Preserved in a Patient GBM and its Derivative Model Systems Analysis of a pair of primary and recurrent GBM included in the inventors' cohort, respectively HF3016 and HF3177, showed that chromosomal and extrachromosomal elements jointly orchestrated complex evolutionary dynamics (FIG. 4A). FIG. 4A depicts Extrachromosomal DNA marks sub-clones driving tumor growth in patient tumors and derived model systems Establishing neurosphere cultures and PDX models from a paired primary/recurrent GBM. Primary and recurrent tumor were globally very similar (FIG. 1B, FIG. 7). While the HF3016 primary tumor showed diploid MYC DNA copy numbers, a focal MYC amplification was detected in the neurosphere and PDXs derived from this tumor, and the same MTV amplification was identified in all samples from the recurrent tumor (FIG. 4B). FIG. 4B depicts DNA copy number analysis shows co-amplification of EGFR (chr7)/CDK4 (chr 12) is detected in primary GBM HF3016 which is sustained in both neurosphere and xeno-grafts derived from this primary tumor, as well as the recurrent GBM HF3177, and the neurosphere/xenografts thereof. The HF3016 primary tumor is not MYC amplified. The HF3016 neurosphere, as well as all HF3177 samples, show focal MYC amplification. Interestingly, FISH analysis showed that MYC amplification was present in low fre-quency (2%) in the initial HF3016 tumor, and was enriched to 100% of nuclei in the neurospheres and in the recurrent tumor (FIG. 4C, Table 3A-3D). FIG. 4C depicts Represen-tative FISH images for MYC (red) and Ch8 marker (green) show that a small fraction (2%) of the cells in HF3016 tumor presents MYC amplification, while 100% of nuclei in the remaining samples present MYC amplification, which is clearly extrachromosomal (white arrows) in the metaphase spreads (NS). Metaphase FISH analysis confirmed extrach-romosomal MYC amplification in both HF3016 and HF3177 neurospheres (FIG. 4C). The sSNV based clonal tracking plots for the paired patient samples identified two subclones in the HF3177 recurrence (FIG. 4D) that were not detected in the HF3016 neurosphere/PDX models, suggest-ing that these were independent of the MYC ecDNA ele-ment. FIG. 4D depicts Clonal tracing of a pair of primary-recurrent GBM, their matching neurospheres, and xenografts. Each line represents a group of mutations com-putationally inferred to reflect a subclone. Of note, a 0.5% cell frequency amplification was also detected in the paren-tal tumor sample of HF2354, which increased to high levels in the derived neurosphere. DNA copy number analysis detected parallel EGFR and CDK4 amplifications in the HF3016 primary GBM that were retained in HF3177 GBM recurrence as well as all model systems. The inventors detected sequencing reads connecting the two amplifications and suggesting a complex structural variant in the HF3016 neurosphere, the HF3016 PDXs, all HF3177 samples, but not the HF3016 primary GBM (FIG. 4E). FIG. 4E depicts starting in the neurosphere of the primary tumor, a complex structural variant is identified that connects the CDK4 locus to the EGFR locus. The MYC locus is not part of this variant. The EGFR/CDK4 variant is detected in HF3016 PDXs as well as all HF 3177 samples. Metaphase FISH on HF3016 neurosphere and HF3177 neurosphere confirmed that the CDK4 and EGFR amplifications were part of the same ecDNA element (FIG. 4F). FIG. 4F depicts EGFR (green) and CDK4 (red), detected by FISH, amplified in 100% of nuclei for every sample from this patient, with identical copy numbers in each nucleus (bottom of the panels). Overlapping dots show that EGFR/CDK4 colocalize (white arrows) and metaphase FISH (NS) shows extrachromosomal co-amplification in the same double minute (inserts). The genomic and extrachromosomal characteristics of these two tumor samples, their derived neurosphere cultures, and xenografts provide an example of how multiple ecDNA elements were able to be preserved during tumor growth and progression while in parallel acquiring new tumor subclones marked by sets of chromosomal sSNVs.

Example 29

Longitudinal Maintenance of Extrachromosomal DNA in Patient Tumors

Figure 5A:
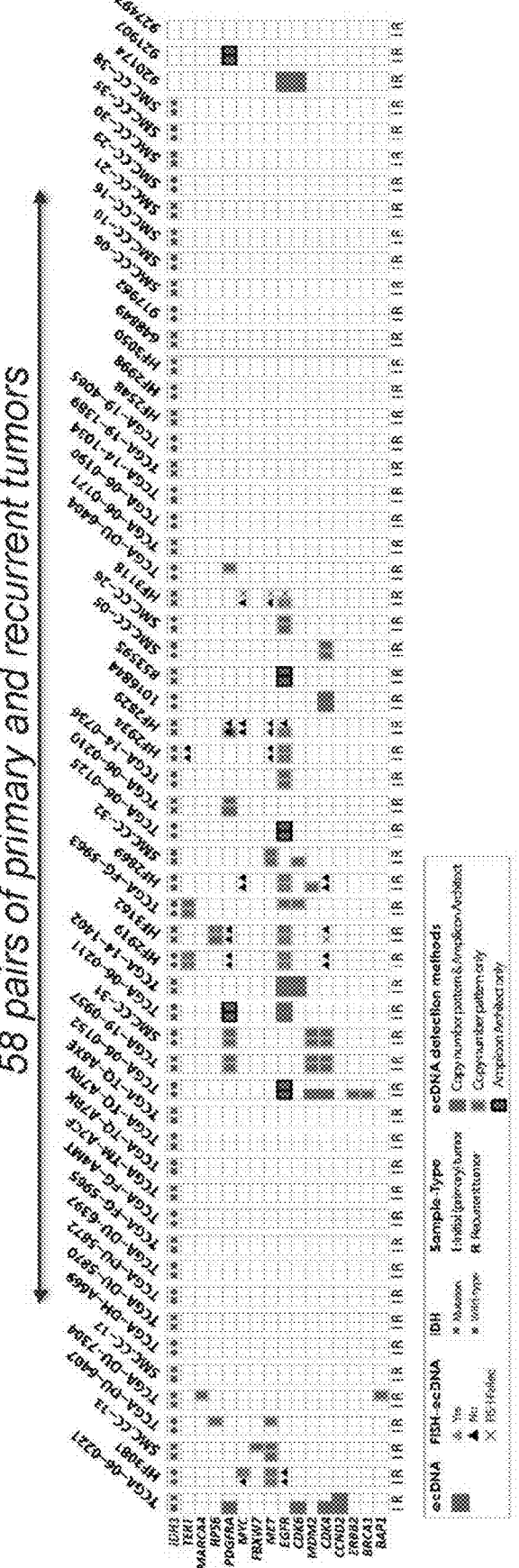
FIG. 5A depicts copy number variant driver genes located on the potential double minute (DM) regions. 66 tumors (33 P, 33 R) from 38 patients were predicted to contain at least one ecDNA that was detected with either copy number based on Amplicon Architect methods. Amongst these, 44 driver gene harboring ecDNAs were predicted in 25 primary tumors, of which 32 were also detected in the matching recurrent tumors.
Figure 5B:
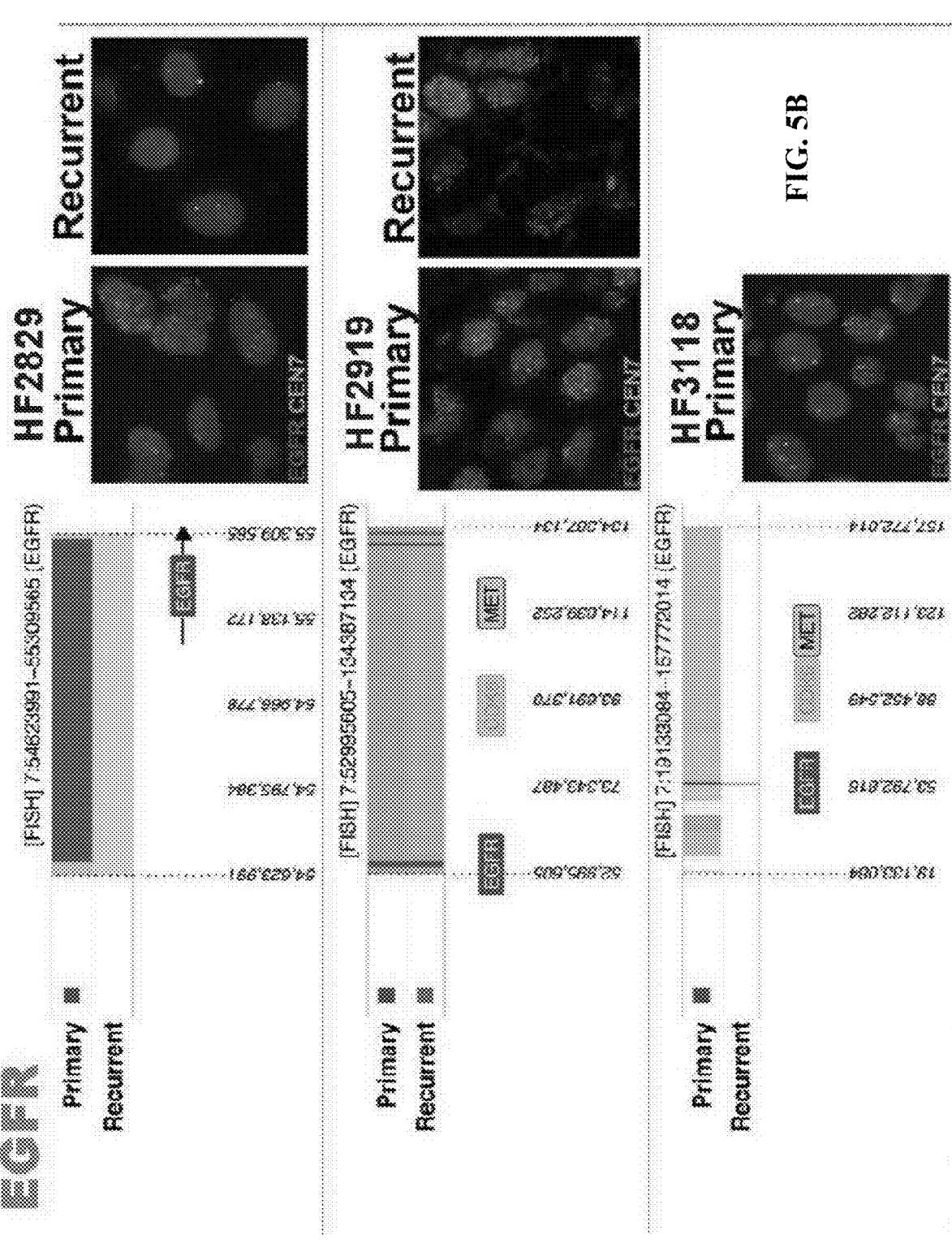
FIG. 5B depicts left panel: DNA copy number and genomic rearrangements at predicted ecDNA loci that were predicted with the copy number based approach. Right panel: Representative FISH images in FFPE tissue sections showing amplification of EGFR, MET and MYC in (red) and control chromosomal probes (green).
Figure 5B:
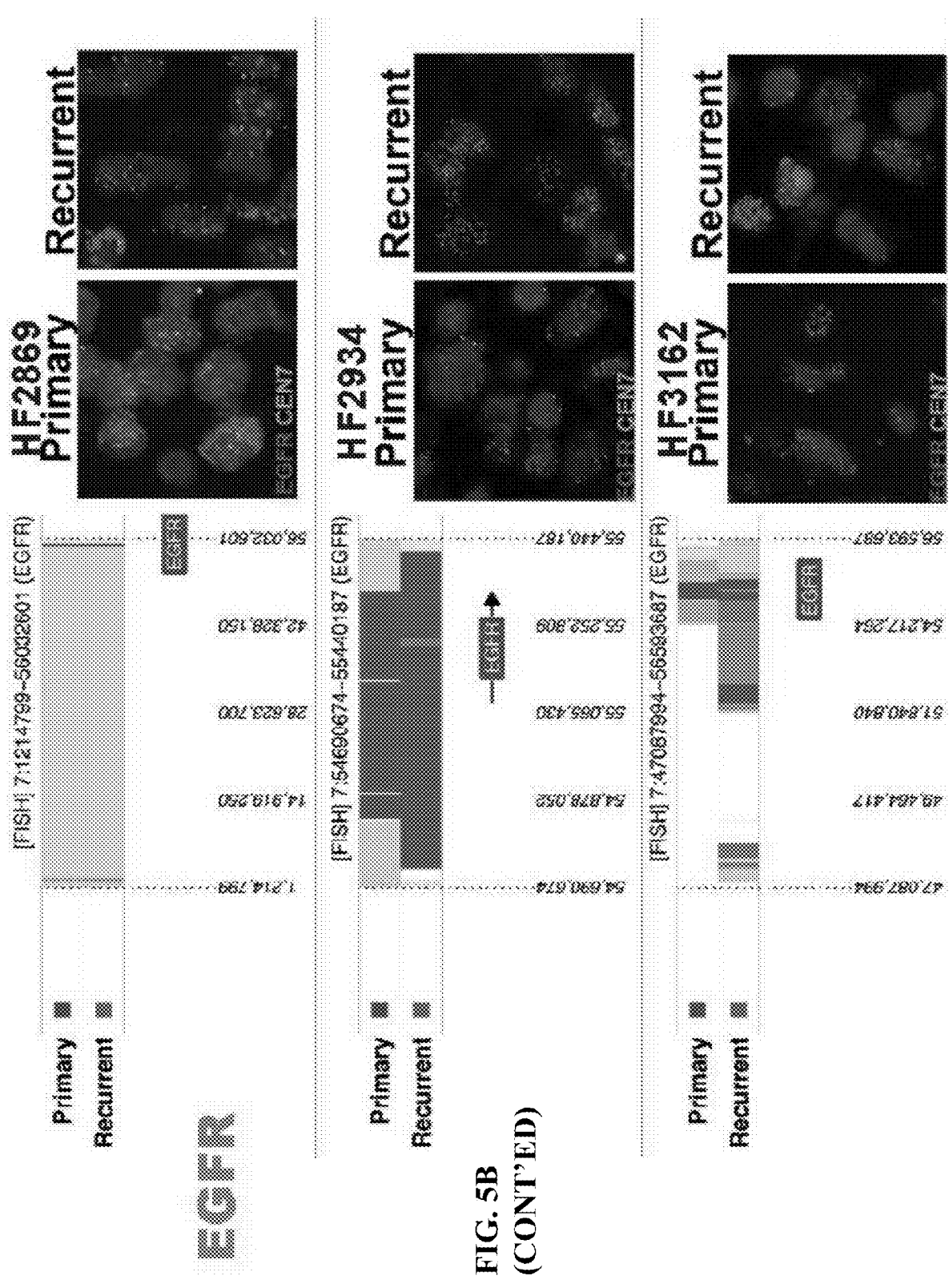
Figure 5B:
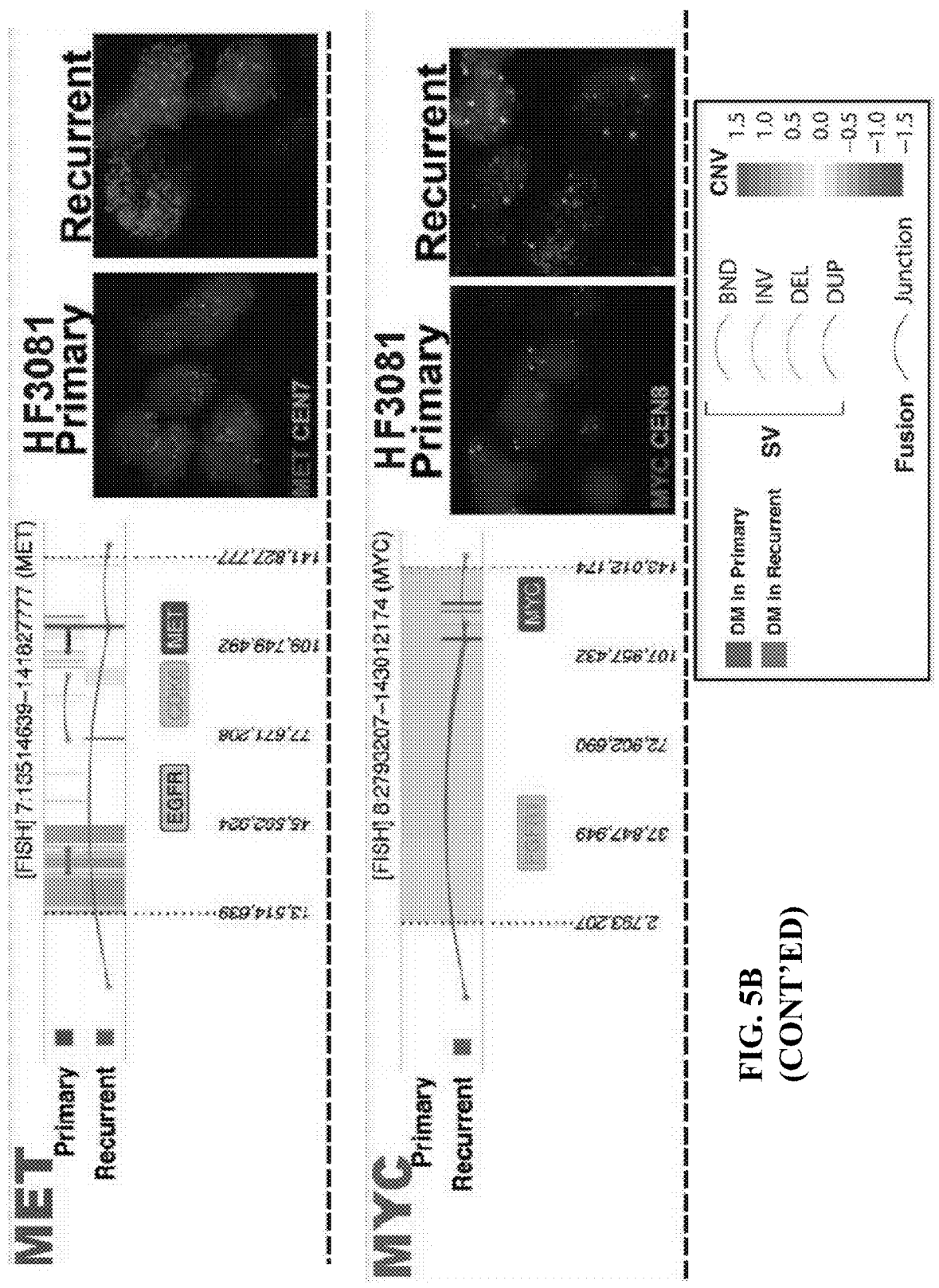

The present study extends findings that large, megabase sized double minutes were frequently found in glioblastoma and can be identified using whole genome sequencing and DNA copy number data. See Sanborn, J. Z. et al., *Cancer Res* 73, 6036-45 (2013); Zheng, S. et al., *Genes Dev* 27, 1462-72 (2013); and Nikolaev, S. et al., *Nat Commun* 5, 5690 (2014). To determine whether extrachromosomal DNA can survive therapeutical barriers, the inventors evaluated the DNA copy number profiles of 58 matching pairs of primary and recurrent glioma for the presence of ecDNAs. (Kim, H. et al., *Genome Res* 25, 316-27 (2015)). In the present study, evidence supporting the presence of ecDNA found in 30 primary and 28 recurrent tumors spanning 34 patients, and of these the inventors predicted ecDNA elements targeting cancer driver genes in 22 primary tumors (FIG. 5A). FIG. 5A depicts copy number variant driver genes located on the potential double minute (DM) regions. 66 tumors (33 P, 33 R) from 38 patients were predicted to contain at least one ecDNA that was detected with either copy number based or Amplicon Architect methods. Amongst these, 44 driver gene harboring ecDNAs were predicted in 25 primary tumors, of which 32 were also detected in the matching recurrent tumors. The most frequently targeted gene was EGFR which was identified by the inventors in 11 primary tumors, which is in agreement with, and extends previous reports in Turner, K. M. et al., *Nature* 543, 122-125 (2017); and Zheng, S. et al., *Genes Dev* 27, 1462-72 (2013). CDK4, PDGFRA were detected in six and five primary tumors, respectively. The inventors corroborated their computational predictions through interphase FISH analyses of 17 predicted ecDNAs and 26 non-altered loci across 6 primary/recurrent tumor pairs. Sixteen out of seventeen genomic amplifications showed the highly variable number of DNA signals that is strongly suggestive of the extrachromosomal nature of the DNA locus (FIG. 5B, FIG. 11A) whereas the 26 control DNA regions predicted to be non-amplified were confirmed as such (Table 4A-4G). EGFR harboring ecDNA was preserved in the recurrent tumor in 4 out 5 pairs, half of which carried EGFRvIII mutation, including the HF2934 recurrent tumor analyzed after treatment with EGFR inhibitor dacomitinib (FIG. 5B, Table 4A-4G). FIG. 5B depicts Left panel: DNA copy number and genomic rearrangements at predicted ecDNA loci that were predicted with the copy number based approach. Right panel: Representative FISH images in FFPE tissue sections showing amplification of EGFR, MET and MYC in (red) and control chromosomal probes (green). This figure depicts validation of predicted ecDNA elements in primary and recurrent gliomas using whole genome sequencing, FISH and DNA copy number profiling. Left panels: Segmented copy numbers, and structural variation (SV) breakpoints/fusion junctions have been visualized for primary and recurrent tumors for each predicted extrachromosomal segment (whose boundaries have been indicated with vertical dots). In cases where one end of a fusion gene junction or SV breakpoint pair does not fall within the predicted ecDNA region, those points have been plotted outside the region. Right panels: Representative interphase FISH (Tumor and PDX) and metaphase FISH (neurospheres). Arrows in metaphase FISH images mark extrachromosomal DNA elements.

Figure 5C:
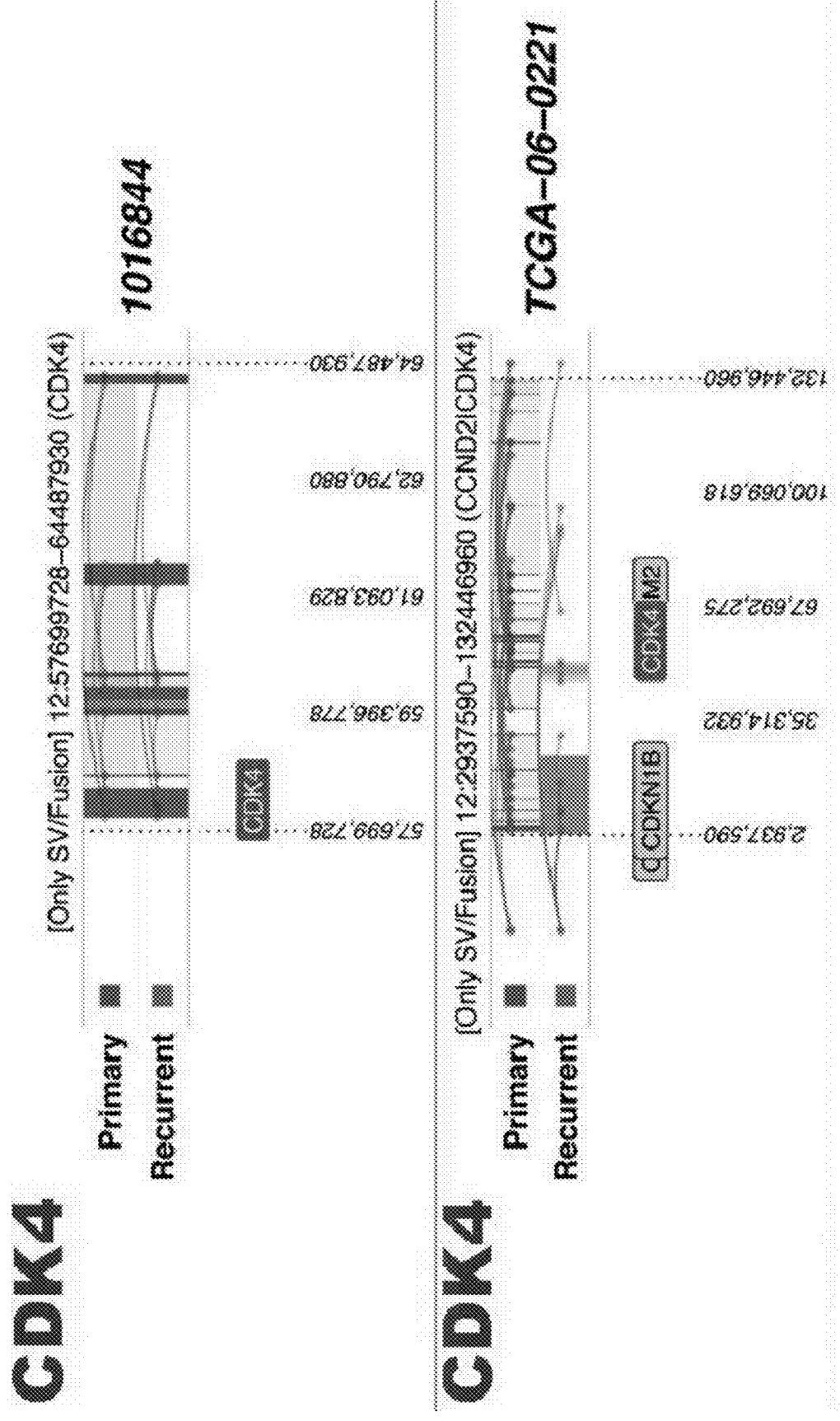
FIG. 5C depicts DNA copy number based predictions of extrachromosomal DNA segments validated using whole genome or RNA sequencing.

One tumor lost EGFR ecDNA and vIII mutation upon recurrence (HF2829), after treatment with the standard of care (radiation and temozolomide). In one case MET ecDNA was present in the primary tumor and maintained in the recurrence, while MYC ecDNA emerged upon recurrence, similar to what the inventors reported above for the HF3016/HF3177 pair. To corroborate 55 DNA copy number predicted ecDNAs, the inventors analyzed whole genome and RNA sequencing data, which identified sequencing reads connecting adjacent focally amplified DNA segments (FIG. 5C and FIG. 11B) supporting the predictions. FIG. 5C depicts DNA copy number based predictions of extrachromosomal DNA segments validated using whole genome or RNA sequencing. FIG. 11C depicts segmented copy numbers, and structural variation (SV) breakpoints/fusion junctions have been visualized for primary and recurrent tumors for each predicted extrachromosomal segment (whose boundaries have been indicated with vertical dots). In cases where one end of a fusion gene junction or SV breakpoint pair does not fall within the predicted ecDNA region, those points have been plotted outside the region.

After disease recurrence, 19 of 22 tumors preserved at least one cancer driver ecDNA, supporting the notion that ecDNA can prevail following the selective pressure imposed by anticancer therapy. The inventors did not detect any significant correlations between somatic mutations and the presence of ecDNA. This analysis was potentially limited by the cohort size and our sensitivity in detecting ecDNA.

In the foregoing specification, the invention has been described with reference to specific embodiments thereof. It will, however, be evident that various modifications and changes may be made thereto without departing from the broader spirit and scope of the invention. Accordingly, it is intended that such changes and modifications fall within the scope of the present invention as defined by the claims appended hereto. The specification and drawings are, accordingly, to be regarded in an illustrative rather than restrictive sense. For example, while example embodiments are described herein with respect to identifying a drug that targets against an oncogene present in ecDNA for treatment of humans, it should be understood that the present methods may be used to treat mammals other than humans. Additionally, although certain drugs are listed, it should be recognized that other drugs may be tested and used, using the protocols and disclosure provided herein, as would be apparent to those skilled in the art. Therefore, the present invention is not limited to the present examples. In view of the teachings provided herein, one having ordinary skill in the art would recognize other applications for which the present invention could be used. One having ordinary skill in the art would be able to use the methods of the present invention in other applications. Accordingly, these alternative uses are intended to be part of the present invention.

55

What is claimed is:

1. A method of treating a primary brain tumor with a drug that targets a subject-specific oncogene present in extrachromosomal DNA (ecDNA) in a subject diagnosed with glioma, comprising:

(a) performing whole genome sequencing on a primary brain tumor specimen collected from the subject, (b) determining that the ecDNA is present in the primary brain tumor specimen based on the whole genome sequencing;

(c) identifying the presence a fused oncogene specific to the subject in the ecDNA;

(d) identifying a drug that targets the fused oncogene;

(e) dissociating the primary brain tumor to produce dissociated tumor cells and growing the cells in vitro to obtain neurospheres;

(f) dissociating the neurospheres into neurosphere cells and implanting the neurosphere cells after 7 to 18 passages into an immunodeficient mouse to generate a patient-derived xenograft (PDX) mouse, and allowing the primary brain tumor-derived neurosphere cells to grow in the PDX mouse for a predetermined time period;

(g) administering the identified drug from step (d) into the PDX mouse;

(h) determining inhibition of tumor growth in the PDX mouse by the drug, wherein inhibition indicates that the identified drug is effective for treating the primary tumor in the subject; and (i) administering the identified drug to treat the primary tumor in the subject, wherein the fused oncogene is CDK4/MDM2, BRCA1/ERBB2, or CCND2/CDK4.

2. The method of claim 1, wherein the glioma is a glioblastoma.

3. The method of claim 2, wherein the subject is an adult human.

4. The method of claim 1, wherein the determining in step (b) is performed by sequence alignment followed by identifying misalignment against a reference genome sequence, wherein the misalignment against a reference genome sequence is indicative of the presence of ecDNA.

5. The method of claim 4, wherein the determination in step (b) is confirmed by one or both of visual inspection and performing amplicon analysis.

6. The method of claim 1, further comprising, identifying in step (c) the presence of more than one fused oncogene specific to the subject, and identifying for each of the identified subject-specific fused oncogenes a drug as targeting against the subject-specific fused oncogene.

7. The method of claim 1, further comprising:

verifying the presence of ecDNA determined in step (b) and the fused oncogene identified in step (c) using fluorescence in situ hybridization (FISH).

8. A method of screening a drug candidate for treatment of a primary brain tumor in a subject diagnosed with glioma, comprising:

(a) performing whole genome sequencing on the primary brain tumor specimen collected from the subject, (b) determining a presence of an ecDNA in the primary brain tumor specimen based on the whole genome sequencing;

(c) identifying a presence of a fused oncogene specific to the subject in the ecDNA;

(d) identifying a drug that targets the fused oncogene;

(e) dissociating the primary brain tumor to produce dissociated tumor cells and growing the cells in vitro to obtain neurospheres;

(f) dissociating the neurospheres into neurosphere cells and implanting the neurosphere cells after 7 to 18 passages into an immunodeficient mouse to generate a patient-derived xenograft (PDX) mouse, and allowing the primary brain tumor-derived neurosphere cells to grow in the PDX mouse for a predetermined time period;

(g) administering the identified drug from step (d) into the PDX mouse; and (h) determining inhibition of the tumor growth in the PDX mouse by the drug, wherein inhibition indicates that the identified drug is effective for treating the primary tumor in the subject, wherein the fused oncogene is CDK4/MDM2, BRCA1/ERBB2, or CCND2/CDK4.

* * * * *